(12) United States Patent
Igawa et al.

(10) Patent No.: US 12,304,960 B2
(45) Date of Patent: May 20, 2025

(54) ANTI-CD137 ANTIGEN-BINDING MOLECULE AND UTILIZATION THEREOF

(71) Applicant: Chugai Seiyaku Kabushiki Kaisha, Tokyo (JP)

(72) Inventors: Tomoyuki Igawa, Singapore (SG); Mika Sakurai, Shizuoka (JP); Shun Shimizu, Shizuoka (JP); Yuji Hori, Shizuoka (JP); Naoka Hironiwa, Singapore (SG); Nasa Savory, Shizuoka (JP); Yoshinori Narita, Kanagawa (JP); Takayuki Kamikawa, Kanagawa (JP); Taro Miyazaki, Tokyo (JP); Shojiro Kadono, Shizuoka (JP); Masami Hasegawa, Kanagawa (JP); Kanako Tatsumi, Shizuoka (JP); Akira Hayasaka, Shizuoka (JP); Takeaki Kawai, Shizuoka (JP); Futa Mimoto, Singapore (SG); Hiroki Kawauchi, Kanagawa (JP); Masaki Kamimura, Kanagawa (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 939 days.

(21) Appl. No.: 17/266,024

(22) PCT Filed: Aug. 9, 2019

(86) PCT No.: PCT/JP2019/031554
§ 371 (c)(1),
(2) Date: Feb. 4, 2021

(87) PCT Pub. No.: WO2020/032230
PCT Pub. Date: Feb. 13, 2020

(65) Prior Publication Data
US 2021/0324099 A1 Oct. 21, 2021

(30) Foreign Application Priority Data
Aug. 10, 2018 (JP) ................................. 2018-152126

(51) Int. Cl.
*C07K 16/28* (2006.01)
*A61K 39/00* (2006.01)
*A61K 47/68* (2017.01)

(52) U.S. Cl.
CPC ...... *C07K 16/2878* (2013.01); *A61K 47/6849* (2017.08); *A61K 2039/505* (2013.01); *C07K 2317/52* (2013.01); *C07K 2317/56* (2013.01); *C07K 2317/75* (2013.01); *C07K 2317/92* (2013.01)

(58) Field of Classification Search
CPC ............ C07K 16/2878; C07K 2317/52; C07K 2317/56; C07K 2317/75; C07K 2317/92; A61K 47/6849; A61K 2039/505
See application file for complete search history.

(56) References Cited

U.S. PATENT DOCUMENTS

| 5,998,588 A | 12/1999 | Hoffman et al. |
| 6,737,056 B1 | 5/2004 | Presta |
| 7,217,797 B2 | 5/2007 | Hinton et al. |
| 7,317,091 B2 | 1/2008 | Lazar et al. |
| 7,662,925 B2 | 2/2010 | Lazar et al. |
| 7,786,270 B2 | 8/2010 | Johnson et al. |
| 7,960,512 B2 | 6/2011 | Stavenhagen et al. |
| 8,063,187 B2 | 11/2011 | Chu et al. |
| 8,101,720 B2 | 1/2012 | Lazar et al. |
| 8,137,667 B2 | 3/2012 | Jure-Kunkel et al. |
| 8,188,231 B2 | 5/2012 | Lazar et al. |

(Continued)

FOREIGN PATENT DOCUMENTS

| AU | 2012222252 A1 | 10/2013 |
| AU | 2012222252 B2 | 8/2016 |

(Continued)

OTHER PUBLICATIONS

Sela-Culang, The structural basis of antibody-antigen recognition, 2013, Frontiers in Immunology, vol. 4, Article 302, pp. 1-13 (Year: 2013).*
Kussie et al., A Single Engineered Amino Acid Substitution Changes Antibody Fine Specificity, 1994, Journal of Immunology, pp. 146-152) (Year: 1994).*
Vajdos et al., Comprehensive Functional Maps of the Antigen binding Site of an Anti-ErbB2 Antibody Obtained with Shotgun Scanning Mutagenesis, 2002, Journal of Molecular Biology, vol. 320, pp. 415-428 (Year: 2002).*
Brown et al., Tolerance to Single, but Not Multiple, Amino Acid Replacements in Antibody Vh, CDR2, 1996, Journal of Immunology, vol. 156, pp. 3285-3291 (Year: 1996).*

(Continued)

*Primary Examiner* — Jeffrey Stucker
*Assistant Examiner* — Brittney E Donoghue
(74) *Attorney, Agent, or Firm* — Nixon & Vanderhye P.C.

(57) ABSTRACT

An objective of the present disclosure is to provide anti-CD137 antigen-binding molecules which have immunocyte-activating effect, cytotoxic activity, or anti-tumor activity, and meanwhile have reduced effect on non-tumor tissues such as normal tissues and produce less side effects, and methods of using the same.
Anti-CD137 antigen-binding molecules which have immunocyte-activating effect, cytotoxic activity, or anti-tumor activity, and meanwhile have reduced effect on non-tumor tissues such as normal tissues and produce less side effects, are provided by discovering and producing CD137 antigen-binding molecules whose binding activity to CD137 depends on various substances (for example, small molecule compounds) in target tissues. Methods of using the same, pharmaceutical formulations, and such are also provided.
The present disclosure also provides an antigen-binding molecule whose binding activity to an antigen varies depending on a small molecule compound, a preparation method thereof, and uses thereof.

27 Claims, 76 Drawing Sheets

Specification includes a Sequence Listing.

(56) References Cited

U.S. PATENT DOCUMENTS

| | | |
|---|---|---|
| 8,193,318 B2 | 6/2012 | Koenig et al. |
| 8,258,263 B2 | 9/2012 | Morrison et al. |
| 8,337,850 B2 | 12/2012 | Ahrens et al. |
| 8,388,955 B2 | 3/2013 | Lazar et al. |
| 8,410,328 B2 | 4/2013 | Chung et al. |
| 8,455,622 B2 | 6/2013 | McDonagh et al. |
| 8,652,466 B2 | 2/2014 | Stavenhagen et al. |
| 8,685,725 B2 | 4/2014 | Beliard et al. |
| 8,735,331 B2 | 5/2014 | Villa |
| 8,735,545 B2 | 5/2014 | Lazar et al. |
| 8,802,820 B2 | 8/2014 | Chamberlain et al. |
| 8,802,823 B2 | 8/2014 | Lazar et al. |
| 8,821,867 B2 | 9/2014 | Ahrens et al. |
| 8,926,976 B2 | 1/2015 | Corbin et al. |
| 9,029,515 B2 | 5/2015 | Pons et al. |
| 9,051,373 B2 | 6/2015 | Lazar et al. |
| 9,079,949 B1 | 7/2015 | Andrien, Jr. et al. |
| 9,107,861 B1 | 8/2015 | Andrien, Jr. et al. |
| 9,334,334 B2 | 5/2016 | McWhirter et al. |
| 9,540,449 B2 | 1/2017 | Yancopoulos et al. |
| 9,644,018 B2 | 5/2017 | Stevis et al. |
| 9,648,856 B2 | 5/2017 | McWhirter et al. |
| 9,790,273 B2 | 10/2017 | Murphy et al. |
| 9,890,218 B2 | 2/2018 | Mimoto et al. |
| 9,920,134 B2 | 3/2018 | Jackson et al. |
| 10,000,560 B2 | 6/2018 | Ruike et al. |
| 10,024,867 B2 | 7/2018 | Igawa et al. |
| 10,111,953 B2 | 10/2018 | Swergold et al. |
| 10,174,122 B2 | 1/2019 | Kwon et al. |
| 10,350,292 B1 | 7/2019 | Bobrowicz et al. |
| 10,556,949 B2 | 2/2020 | Igawa et al. |
| 10,766,960 B2 | 9/2020 | Igawa et al. |
| 10,875,921 B2 | 12/2020 | Akamatsu et al. |
| 10,899,840 B2 | 1/2021 | Davis et al. |
| 10,899,842 B2 | 1/2021 | Wang |
| 10,919,953 B2 | 2/2021 | Katada et al. |
| 10,961,530 B2 | 3/2021 | Igawa et al. |
| 11,319,373 B2 | 5/2022 | Pincetic et al. |
| 11,673,947 B2 | 6/2023 | Igawa et al. |
| 11,702,474 B2 | 7/2023 | Chaparro et al. |
| 11,912,989 B2 | 2/2024 | Igawa et al. |
| 2004/0001822 A1 | 1/2004 | Levanon et al. |
| 2004/0001839 A1 | 1/2004 | Levanon et al. |
| 2004/0002450 A1 | 1/2004 | Lazarovits et al. |
| 2004/0110226 A1 | 6/2004 | Lazar et al. |
| 2005/0032114 A1 | 2/2005 | Hinton et al. |
| 2005/0054832 A1 | 3/2005 | Lazar et al. |
| 2005/0064514 A1 | 3/2005 | Stavenhagen et al. |
| 2005/0260213 A1 | 11/2005 | Koenig et al. |
| 2006/0024298 A1 | 2/2006 | Lazar et al. |
| 2006/0141456 A1 | 6/2006 | Edwards et al. |
| 2007/0003546 A1 | 1/2007 | Lazar et al. |
| 2007/0009523 A1 | 1/2007 | Presta |
| 2007/0231329 A1 | 10/2007 | Lazar et al. |
| 2007/0248602 A1 | 10/2007 | Lazar et al. |
| 2008/0044417 A1 | 2/2008 | Johnson et al. |
| 2008/0138349 A1 | 6/2008 | Stavenhagen et al. |
| 2008/0181890 A1 | 7/2008 | Lazar et al. |
| 2008/0199471 A1 | 8/2008 | Bernett et al. |
| 2008/0292637 A1 | 11/2008 | Fishman |
| 2009/0035836 A1 | 2/2009 | Datta et al. |
| 2009/0041770 A1 | 2/2009 | Chamberlain et al. |
| 2009/0053211 A9 | 2/2009 | Lazar et al. |
| 2009/0053240 A1 | 2/2009 | Lazar et al. |
| 2009/0076251 A1 | 3/2009 | Koenig et al. |
| 2009/0136485 A1 | 5/2009 | Chu et al. |
| 2009/0155255 A1 | 6/2009 | Glaser et al. |
| 2010/0098730 A1 | 4/2010 | Lowman et al. |
| 2010/0158909 A1 | 6/2010 | McDonagh et al. |
| 2010/0172868 A1 | 7/2010 | Morrison et al. |
| 2010/0183621 A1 | 7/2010 | Jure-Kunkel et al. |
| 2010/0184959 A1 | 7/2010 | Guler-Gane et al. |
| 2010/0249482 A1 | 9/2010 | Chung et al. |
| 2011/0021755 A1 | 1/2011 | Lazar et al. |
| 2011/0076284 A1 | 3/2011 | Corbin et al. |
| 2011/0111406 A1 | 5/2011 | Igawa et al. |
| 2011/0223658 A1 | 9/2011 | Beliard et al. |
| 2011/0229489 A1 | 9/2011 | Pons et al. |
| 2011/0236372 A1 | 9/2011 | Villa |
| 2012/0093818 A1 | 4/2012 | Jackson et al. |
| 2012/0237498 A1 | 9/2012 | Ahrens et al. |
| 2013/0078240 A1 | 3/2013 | Ahrens et al. |
| 2013/0085265 A1 | 4/2013 | Jackson et al. |
| 2013/0131319 A1 | 5/2013 | Igawa et al. |
| 2013/0203609 A1 | 8/2013 | Horn |
| 2013/0209457 A1 | 8/2013 | Lazar et al. |
| 2013/0247234 A1 | 9/2013 | McWhirter et al. |
| 2013/0259876 A1 | 10/2013 | Murphy et al. |
| 2014/0044730 A1 | 2/2014 | Yancopoulos et al. |
| 2014/0073768 A1 | 3/2014 | Lazar et al. |
| 2014/0082760 A1 | 3/2014 | McWhirter et al. |
| 2014/0093496 A1 | 4/2014 | Mimoto et al. |
| 2014/0178368 A1 | 6/2014 | Sharp et al. |
| 2014/0199294 A1 | 7/2014 | Mimoto et al. |
| 2014/0234340 A1 | 8/2014 | Igawa et al. |
| 2014/0255398 A1 | 9/2014 | Igawa et al. |
| 2014/0271617 A1 | 9/2014 | Igawa et al. |
| 2014/0335089 A1 | 11/2014 | Igawa et al. |
| 2014/0356371 A1 | 12/2014 | Swergold et al. |
| 2015/0166636 A1 | 6/2015 | Igawa et al. |
| 2015/0166654 A1 | 6/2015 | Igawa et al. |
| 2015/0203577 A1 | 7/2015 | Igawa et al. |
| 2015/0210763 A1 | 7/2015 | Kuramochi et al. |
| 2015/0252107 A1 | 9/2015 | Stevis et al. |
| 2015/0299296 A1 | 10/2015 | Katada et al. |
| 2015/0299313 A1 | 10/2015 | Igawa et al. |
| 2015/0344570 A1 | 12/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0200807 A1 | 7/2016 | Ruike et al. |
| 2016/0304862 A1 | 10/2016 | Igawa et al. |
| 2017/0174773 A1 | 6/2017 | Davis et al. |
| 2018/0258177 A1 | 9/2018 | Kwon et al. |
| 2018/0319877 A1 | 11/2018 | Ruike et al. |
| 2019/0112393 A1 | 4/2019 | Igawa et al. |
| 2019/0194329 A1 | 6/2019 | Akamatsu et al. |
| 2019/0224315 A1 | 7/2019 | Bobrowicz et al. |
| 2019/0284292 A1 | 9/2019 | Wang |
| 2019/0359704 A1 | 11/2019 | Igawa et al. |
| 2019/0359707 A1 | 11/2019 | Pincetic et al. |
| 2021/0179716 A1 | 6/2021 | Chaparro et al. |
| 2021/0180049 A1 | 6/2021 | Igawa et al. |
| 2022/0153875 A1 | 5/2022 | Mizuno et al. |
| 2022/0389118 A1 | 12/2022 | Igawa et al. |
| 2022/0411483 A1 | 12/2022 | Mimoto et al. |
| 2023/0140797 A1 | 5/2023 | Igawa et al. |
| 2023/0174655 A1 | 6/2023 | Mimoto et al. |
| 2023/0272099 A1 | 8/2023 | Sakurai et al. |
| 2023/0279099 A1 | 9/2023 | Igawa et al. |
| 2024/0158785 A1 | 5/2024 | Igawa et al. |

FOREIGN PATENT DOCUMENTS

| | | |
|---|---|---|
| CA | 2827923 A1 | 8/2012 |
| CA | 2850041 A1 | 4/2013 |
| CA | 2850322 A1 | 4/2013 |
| CN | 1763097 A | 4/2006 |
| CN | 101001873 A | 7/2007 |
| CN | 101014619 A | 8/2007 |
| CN | 101098890 A | 1/2008 |
| CN | 101014619 B | 11/2010 |
| CN | 101932593 A | 12/2010 |
| CN | 1763097 B | 4/2011 |
| CN | 102056946 A | 5/2011 |
| CN | 102149729 A | 8/2011 |
| CN | 102405278 A | 4/2012 |
| CN | 101098890 B | 7/2012 |
| CN | 102633880 A | 8/2012 |
| CN | 101001873 B | 3/2013 |
| CN | 103492565 A | 1/2014 |
| CN | 101932593 B | 8/2014 |
| CN | 102149729 B | 8/2014 |
| CN | 104093424 A | 10/2014 |

(56) References Cited

FOREIGN PATENT DOCUMENTS

| | | |
|---|---|---|
| CN | 102633880 B | 2/2015 |
| CN | 104487457 A | 4/2015 |
| CN | 104487457 B | 1/2018 |
| CN | 108463247 A | 8/2018 |
| CN | 108463247 B | 4/2022 |
| EA | 004317 B1 | 2/2004 |
| EP | 2275443 A1 | 1/2011 |
| EP | 2305710 A2 | 4/2011 |
| EP | 2368911 A1 | 9/2011 |
| EP | 2409990 A1 | 1/2012 |
| EP | 2552955 A2 | 2/2013 |
| EP | 2647706 A1 | 10/2013 |
| EP | 2679681 A1 | 1/2014 |
| EP | 2698431 A1 | 2/2014 |
| EP | 2762166 A1 | 8/2014 |
| EP | 2762564 A1 | 8/2014 |
| EP | 2765192 A1 | 8/2014 |
| EP | 2818183 A1 | 12/2014 |
| EP | 2857420 A1 | 4/2015 |
| EP | 2889377 A1 | 7/2015 |
| EP | 2275443 B1 | 12/2015 |
| EP | 3078744 A1 | 10/2016 |
| EP | 3156072 A1 | 4/2017 |
| EP | 2552955 B1 | 5/2017 |
| EP | 3305322 A1 | 4/2018 |
| EP | 3470428 A1 | 4/2019 |
| EP | 2679681 B1 | 8/2019 |
| EP | 2818183 B1 | 4/2020 |
| EP | 3078744 B1 | 8/2020 |
| EP | 2698431 B1 | 9/2020 |
| EP | 3708582 A1 | 9/2020 |
| EP | 3744734 A1 | 12/2020 |
| EP | 3835321 A1 | 6/2021 |
| JP | 2003512019 A | 4/2003 |
| JP | 2006512407 A | 4/2006 |
| JP | 2007531724 A | 11/2007 |
| JP | 2007532139 A | 11/2007 |
| JP | 2008505174 A | 2/2008 |
| JP | 2008511292 A | 4/2008 |
| JP | 2009511067 A | 3/2009 |
| JP | 2010110330 A | 5/2010 |
| JP | 2010514460 A | 5/2010 |
| JP | 4580340 B2 | 11/2010 |
| JP | 2011097869 A | 5/2011 |
| JP | 2011137838 A | 7/2011 |
| JP | 2011184418 A | 9/2011 |
| JP | 2012518613 A | 8/2012 |
| JP | 5055603 B2 | 10/2012 |
| JP | 2013521772 A | 6/2013 |
| JP | 5357778 B2 | 12/2013 |
| JP | 5367982 B2 | 12/2013 |
| JP | 5932670 B2 | 6/2016 |
| JP | 2018517674 A | 7/2018 |
| JP | 2018537473 A | 12/2018 |
| JP | 6718560 B1 | 7/2020 |
| KR | 20110004435 A | 1/2011 |
| RU | 2236222 C2 | 9/2004 |
| RU | 2005112742 A | 1/2006 |
| RU | 2005137578 A | 6/2007 |
| RU | 2325186 C2 | 5/2008 |
| RU | 2337107 C2 | 10/2008 |
| RU | 2008104038 A | 8/2009 |
| RU | 2390527 C2 | 5/2010 |
| RU | 2016129045 A | 1/2018 |
| SG | 192945 A1 | 9/2013 |
| TW | 201202419 A | 1/2012 |
| TW | 201400503 A | 1/2014 |
| TW | 201610247 A | 3/2016 |
| TW | I617578 B | 3/2018 |
| TW | I664331 B | 7/2019 |
| TW | 202005984 A | 2/2020 |
| WO | WO-9734631 A1 | 9/1997 |
| WO | WO-9958572 A1 | 11/1999 |
| WO | WO-0015214 A1 | 3/2000 |
| WO | WO-0042072 A2 | 7/2000 |
| WO | WO-0148480 A1 | 7/2001 |
| WO | WO0170968 A2 | 9/2001 |
| WO | WO-02081646 A2 | 10/2002 |
| WO | WO-03105757 A2 | 12/2003 |
| WO | WO-2004029207 A2 | 4/2004 |
| WO | WO-2004099249 A2 | 11/2004 |
| WO | WO2005035584 A1 | 4/2005 |
| WO | WO-2005047327 A2 | 5/2005 |
| WO | WO-2005056606 A2 | 6/2005 |
| WO | WO-2005059106 A2 | 6/2005 |
| WO | WO2005096706 A2 | 10/2005 |
| WO | WO-2005115452 A2 | 12/2005 |
| WO | WO-2006019447 A1 | 2/2006 |
| WO | WO-2006020114 A2 | 2/2006 |
| WO | WO-2006023403 A2 | 3/2006 |
| WO | WO-2006023420 A2 | 3/2006 |
| WO | WO-2006053301 A2 | 5/2006 |
| WO | WO-2006076594 A2 | 7/2006 |
| WO | WO-2006130834 A2 | 12/2006 |
| WO | WO-2007022520 A2 | 2/2007 |
| WO | WO-2007024249 A2 | 3/2007 |
| WO | WO-2007047578 A2 | 4/2007 |
| WO | WO-2007053718 A1 | 5/2007 |
| WO | WO-2008002933 A2 | 1/2008 |
| WO | WO-2008091954 A2 | 7/2008 |
| WO | WO-2008092117 A2 | 7/2008 |
| WO | WO-2008150494 A1 | 12/2008 |
| WO | WO-2009015284 A2 | 1/2009 |
| WO | WO-2009062083 A2 | 5/2009 |
| WO | WO-2009086320 A1 | 7/2009 |
| WO | WO-2009095235 A1 | 8/2009 |
| WO | WO-2009097017 A2 | 8/2009 |
| WO | WO-2009125825 A1 | 10/2009 |
| WO | WO-2009131702 A2 | 10/2009 |
| WO | WO-2009139822 A1 | 11/2009 |
| WO | WO-2009155513 A2 | 12/2009 |
| WO | WO-2010058860 A1 | 5/2010 |
| WO | WO-2010077854 A1 | 7/2010 |
| WO | WO-2010081173 A2 | 7/2010 |
| WO | WO-2010094698 A2 | 8/2010 |
| WO | WO-2010104821 A1 | 9/2010 |
| WO | WO-2010107109 A1 | 9/2010 |
| WO | WO 2010107110 A1 | 9/2010 |
| WO | WO-2010127284 A2 | 11/2010 |
| WO | WO-2011008517 A2 | 1/2011 |
| WO | WO-2011038302 A2 | 3/2011 |
| WO | WO-2011091078 A2 | 7/2011 |
| WO | WO-2011111007 A2 | 9/2011 |
| WO | WO-2011122011 A2 | 10/2011 |
| WO | WO-2012033953 A1 | 3/2012 |
| WO | WO-2012044831 A1 | 4/2012 |
| WO | WO-2012073992 A1 | 6/2012 |
| WO | WO-2012115241 A1 | 8/2012 |
| WO | WO-2012132067 A1 | 10/2012 |
| WO | WO-2012133782 A1 | 10/2012 |
| WO | WO-2013046722 A1 | 4/2013 |
| WO | WO-2013047729 A1 | 4/2013 |
| WO | WO-2013047748 A1 | 4/2013 |
| WO | WO-2013047752 A1 | 4/2013 |
| WO | WO-2013125667 A1 | 8/2013 |
| WO | WO-2013138681 A1 | 9/2013 |
| WO | WO-2013180200 A1 * | 12/2013 .............. A61P 29/00 |
| WO | WO-2014030728 A1 | 2/2014 |
| WO | WO 2014030750 A1 | 2/2014 |
| WO | WO-2014140366 A1 | 9/2014 |
| WO | WO-2014144080 A2 | 9/2014 |
| WO | WO-2014144577 A1 | 9/2014 |
| WO | WO-2014150983 A2 | 9/2014 |
| WO | WO 2014163101 A1 | 10/2014 |
| WO | WO-2014164959 A2 | 10/2014 |
| WO | WO-2015042250 A1 | 3/2015 |
| WO | WO-2015077491 A1 | 5/2015 |
| WO | WO-2015083764 A1 * | 6/2015 .............. A61P 35/00 |
| WO | WO2015095895 A1 | 6/2015 |
| WO | WO-2015134894 A1 | 9/2015 |
| WO | WO 2015190538 A1 | 12/2015 |
| WO | WO 2016170176 A1 | 10/2016 |
| WO | WO 2016194992 A1 | 12/2016 |
| WO | WO 2017046994 A1 | 3/2017 |

(56) References Cited

FOREIGN PATENT DOCUMENTS

| WO | WO2017074774 A1 | 5/2017 |
| WO | WO2017096165 A1 | 6/2017 |
| WO | WO 2017104783 A1 | 6/2017 |
| WO | WO2018091740 A | 5/2018 |
| WO | WO2019027754 A1 | 2/2019 |
| WO | WO2019036855 A1 | 2/2019 |
| WO | WO2019072870 A1 | 4/2019 |
| WO | WO2019091436 A1 | 5/2019 |
| WO | WO2019109238 A1 | 6/2019 |
| WO | WO2019141268 A1 | 7/2019 |
| WO | WO2020011964 A1 | 1/2020 |
| WO | WO 2020032230 A1 | 2/2020 |
| WO | WO2020189748 A1 | 9/2020 |
| WO | WO2021162020 A1 | 8/2021 |

OTHER PUBLICATIONS

Rudikoff et al., Single amino acid substitution altering antigen-binding specificity, 1982, PNAS, vol. 79, pp. 1979-1983 (Year: 1982).*

Pechmann et al., Interplay between Chaperones and Protein Disorder Promotes the Evolution of Protein Networks, 2014, PLOS Computational Biology, vol. 10, Issue 6, pp. 1-15 (Year: 2014).*

Ascierto, P. A., et al., "Clinical Experiences With Anti-CD137 and Anti-PD1 Therapeutic Antibodies," Semin Oncol., 37:508-516 (2010).

Deluca, L. S. and Gommerman, J. L., "Fine-tuning of dendritic cell biology by the TNF superfamily," Nat Rev Immunol., 12:339-351 (2012).

Dubrot, J., et al., "Treatment with anti-CD137 mAbs causes intense accumulations of liver T cells without selective antitumor immunotherapeutic effects in this organ," Cancer Immunol Immunother., 59:1223-1233 (2010).

Hamid, O., and Carvajal, R. D., "Anti-programmed death-1 and anti-programmed death-ligand 1 antibodies in cancer therapy," Expert Opin Biol Ther., 13(6):847-861 (2013).

Hanahan, D. and Weinberg, R. A., "Hallmarks of Cancer: The Next Generation," Cell, 144:646-674 (2011).

Houot, R., et al., "Therapeutic effect of CD137 immunomodulation in lymphoma and its enhancement by $T_{reg}$ depletion," Blood, 114:3431-3438 (2009).

Li, F. and Ravetch, J. V., "Antitumor activities of agonistic anti-TNFR antibodies require differential FcγRIIB coengagement in vivo," PNAS, 110(48):19501-19506 (2013).

Mimoto, F., et al., "Engineered antibody Fc variant with selectively enhanced FcγRIIb binding over both FcγRIIa$^{R131}$ and FcγRIIa$^{H131}$," Protein Eng Des Sel., 26(10):589-598 (2013).

Misawa, N., et al., "Rapid and High-Sensitivity Cell-Based Assays of Protein-Protein Interactions Using Split Click Beetle Luciferase Complementation: An Approach to the Study of G-Protein-Coupled Receptors," Anal Chem., 82:2552-2560 (2010).

Pace, C. N., et al., "How to measure and predict the molar absorption coefficient of a protein," Protein Sci., 4:2411-2423 (1995).

Prieto, P. A., et al., "CTLA-4 Blockade with Ipilimumab: Long-term Follow-up of 177 Patients with Metastatic Melanoma," Clin Cancer Res., 18(7):2039-2047 (2012).

Schabowsky, R.-H., et al., "A novel form of 4-1BBL has better immunomodulatory activity than an agonistic anti-4-1BB Ab without Ab-associated severe toxicity," Vaccine, 28(2):512-522 (2009).

Vinay, D. S. and Kwon, B. S., "4-1BB signaling beyond T cells," Cell Mol Immunol., 8:281-284 (2011).

U.S. Appl. No. 12/653,137, filed Dec. 9, 2009, Jure-Kunkel et al.

U.S. Appl. No. 13/228,532, filed Sep. 9, 2011, Ahrens et al.

Alley, S.C., et al., "Antibody-Drug Conjugates: Targeted Drug Delivery for Cancer," Current Opinion in Chemical Biology, 14(4):529-537, Elsevier, England (Aug. 2010).

Amigorena, S., et al., "Fc Gamma RII Expression in Resting and Activated B Lymphocytes," European Journal of Immunology, 19(8):1379-1385, Germany, Weinheim Wiley-VCH (Aug. 1989).

Amigorena, S., et al., "Cytoplasmic Domain Heterogeneity and Functions of IgG Fc Receptors in B Lymphocytes," Science, 256(5065):1808-1812, United States, American Association for the Advancement of Science (Jun. 1992).

Armour, K.L, et al., "Differential binding to human FcgammaRIIa and FcγRIIb receptors by human IgG wildtype and mutant antibodies," Molecular Immunology, 40(9):585-593, Pergamon Press, England (Dec. 2003).

Baeuerle, P.A., et al., "BiTE: Teaching Antibodies to Engage T-cells for Cancer Therapy," Current Opinion in Molecular Therapeutics 11(1):22-30, Thomson Reuters (Scientific) Ltd, England (Feb. 2009).

Blank, M., et al., "Decreased Transcription of the Human Fcgr2b Gene Mediated by the -343 G/c Promoter Polymorphism and Association With Systemic Lupus Erythematosus," Human Genetics, 117(2-3):220-227, Springer Verlag, Germany (Jul. 2005).

Bonvin, P., et al., "De Novo Isolation of Antibodies With pH-Dependent Binding Properties," mAbs 7(2):294-302, Taylor & Francis, United States (Mar.-Apr. 2015).

Boruchov, A., et al., "Activating and Inhibitory Igg Fc Receptors on Human Dcs Mediate Opposing Functions," The Journal of Clinical Investigation, 115(10):2914-2923, American Society for Clinical Investigation, United States (Oct. 2005).

Boumpas, T., et al., "A Short Course of Bg9588 (Anti-cd40 Ligand Antibody) Improves Serologic Activity and Decreases Hematuria in Patients With Proliferative Lupus Glomerulonephritis," Arthritis and Rheumatism, 48(3):719-727, United States, Wiley-Blackwell (Mar. 2003).

Bruhns, P., et al., "Specificity and Affinity of Human Fcγ Receptors and Their Polymorphic Variants for Human IgG Subclasses," Blood, 113(16):3716-3725, American Society of Hematology, United States (Apr. 2009).

Bruhns, P., et al., "Properties of Mouse and Human IgG Receptors and Their Contribution to Disease Models," Blood, 119(24):5640-5649, Washington, American Society of Hematology (Jun. 2012).

Burmeister, W.P., et al., "Crystal Structure of the Complex of Rat Neonatal Fc Receptor With Fc," Nature, 372: 379-383, England, Nature Publishing Group (Nov. 1994).

Carreno, R., et al., "2E8 Binds to the High Affinity I-domain in a Metal Ion-dependent Manner: A Second Generation Monoclonal Antibody Selectively Targeting Activated LFA-1," The Journal of Biological Chemistry 285(43):32860-32868 (Oct. 2010).

Cartron, et al., "Therapeutic Activity of Humanized Anti-cCD20 Monoclonal Antibody and Polymorphism in IgG Fc Receptor FcγRIIIa Gene," Blood, 99(3):754-758, United States, American Society of Hematology (Feb. 2002).

Cemerski, et al., "Suppression of Mast Cell Degranulation Through a Dual-targeting Tandem IgE-igg Fc Domain Biologic Engineered to Bind With High Affinity to FcγRIIb," Immunology Letters, 143(1):34-43, Netherlands, Elsevier/North-Holland Biomedical Press (Mar. 2012).

Chaparro-Riggers, J., et al., "Increasing Serum Half-life and Extending Cholesterol Lowering in Vivo by Engineering Antibody With pH-sensitive Binding in PCSK9," The Journal of biological chemistry 287(14):11090-11097, American Society for Biochemistry and Molecular Biology, United States (Mar. 2012).

Chen, J.Y., et al., "Association of a transmembrane polymorphism of Fcγ receptor IIb (FCGR2B) with systemic lupus erythematosus in Taiwanese patients," Arthritis and Rheumatology, 54(12):3908-3917, Wiley-Blackwell, United States (Dec. 2006).

Chen, Y. and Guillemin, G.J., "Kynurenine Pathway Metabolites in Humans: Disease and Healthy States," International Journal of Tryptophan Research 2:1-19 (2009).

Chockalingam, K., et al., "Design and Application of Stimulus-responsive Peptide Systems," Protein Engineering, Design & Selection 20(4):155-161 (Apr. 2007).

Chu, et al., "Inhibition of B Cell Receptor-Mediated Activation of Primary Human B Cells by Coengagement of CD19 and FcγRIIb With Fc-engineered Antibodies," Molecular Immunology, 45(15):3926-3933, England, Pergamon Press (Sep. 2008).

Chu, S.Y., et al., "Reduction of Total IgE by Targeted Coengagement of IgE B-Cell Receptor and FcγRIIb with Fc-Engineered Antibody," The Journal of Allergy and Clinical Immunology, 129(4):1102-1115, United States, St Louis, Mosby (Apr. 2012).

(56) References Cited

OTHER PUBLICATIONS

Chuntharapai, A., et al., "Isotype-dependent Inhibition of Tumor Growth in Vivo by Monoclonal Antibodies to Death Receptor 4," Journal of Immunology, 166(8):4891-4898, American Association of Immunologists, United States (Apr. 2001).
Clark, R., "IgG Effector Mechanisms," Chemical Immunology, 65:88-110, Switzerland, Karger [c1989]-2002 (1997).
Clayton, A., et al., "Cancer Exosomes Express CD39 and CD73, Which Suppress T Cells Through Adenosine Production," Journal of Immunology 187(2):676-683 (Jul. 2011).
Clynes, R., et al., "Fc Receptors Are Required in Passive and Active Immunity to Melanoma," Proceedings of the National Academy of Sciences of the United States of America 95(2):652-656, National Academy of Sciences, United States (Jan. 1998).
Clynes, R.A., et al., "Inhibitory Fc Receptors Modulate in Vivo Cytotoxicity Against Tumor Targets," Nature Medicine 6(4):443-446, Nature Publishing Company, United States (Apr. 2000).
Dall'Acqua, W.F., et al., "Increasing the Affinity of a Human IgG1 for the Neonatal Fc Receptor: Biological Consequences," Journal of Immunology 169(9):5171-5180, American Association of Immunologists, United States (Nov. 2002).
Dall'Acqua, W.F., et al., "Properties of Human IgG1s Engineered for Enhanced Binding to the Neonatal Fc Receptor (FcRn)," The Journal of Biological Chemistry 281(33):23514-23524, American Society for Biochemistry and Molecular Biology, United States (Aug. 2006).
Datta-Mannan, A., et al., "Monoclonal Antibody Clearance. Impact of Modulating the Interaction of IgG With the Neonatal Fc Receptor," The Journal of Biological Chemistry 282(3):1709-1717, American Society for Biochemistry and Molecular Biology, United States (Jan. 2007).
De Bono, J.S., et al., "ING-1, A Monoclonal Antibody Targeting Ep-CAM in Patients With Advanced Adenocarcinomas," Clinical Cancer Research 10(22):7555-7565, The Association, United States (Nov. 2004).
Desai, D.D., et al., "Fc Gamma Receptor IIB on Dendritic Cells Enforces Peripheral Tolerance by Inhibiting Effector T Cell Responses," Journal of Immunology 178(10):6217-6226, American Association of Immunologists, United States (May 2007).
Desjarlais, J.R., et al., "Optimizing Engagement of the Immune System by Anti-Tumor Antibodies: An Engineer's Perspective," Drug Discovery Today 12(21-22):898-910, Elsevier Science Ltd., England (Nov. 2007).
Dhodapkar, K., et al., "Selective Blockade of Inhibitory Fcgamma Receptor Enables Human Dendritic Cell Maturation With IL-12p70 Production and Immunity to Antibody-coated Tumor Cells," Proceedings of the National Academy of Sciences of the United States of America, 102(8):2910-2915, National Academy of Sciences, United States (Feb. 2005).
Diamond, B. and Scharff, M. D., "Somatic Mutation of the T15 Heavy Chain Gives Rise to an Antibody With Autoantibody Specificity," Proceedings of the National Academy of Sciences of the United States of America, 81(18):5841-5844, United States, National Academy of Sciences (Sep. 1984).
Duffau, P., et al., "Platelet CD154 Potentiates Interferon-alpha Secretion by Plasmacytoid Dendritic Cells in Systemic Lupus Erythematosus," Science Translational Medicine, 2(47):47ra63, American Association for the Advancement of Science, United States (Sep. 2010).
Edwards, B.M., et al., "The Remarkable Flexibility of the Human Antibody Repertoire; Isolation of Over One Thousand Different Antibodies to a Single Protein, BLyS," Journal of Molecular Biology 334(1):103-118, Elsevier, England (Nov. 2003).
Examination report for AU application No. AU2013306700 issued on Jun. 7, 2018.
Fanning, S.W., et al., "A Combinatorial Approach to Engineering a Dual-specific Metal Switch Antibody," Biochemistry 50(23):5093-5095 (Jun. 2011).
Fanning, S.W., et al., "Structural Basis of an Engineered Dual-specific Antibody: Conformational Diversity Leads to a Hypervariable Loop Metal-binding Site," Protein Engineering, Design & Selection 27(10):391-397 (Oct. 2014).
Fillipovic, Biochemical basis of human life activity, VLADOS, 38-43 (2005).
Fillipovich, Biochemical basis of human life, VLADOS, 49-50 (2005).
Finkelstein, A. V. and Ptitsyn, O. B., Protein physics. Lecture course with colored and stereoscope illustrations and tasks: study guide. $4^{th}$ ed., Moscow, KDU, 23 (2012).
Flores, M., et al., "Dominant Expression of the Inhibitory FcγRIIB Prevents Antigen Presentation by Murine Plasmacytoid Dendritic Cells," Journal of immunology 183(11):7129-7139, American Association of Immunologists, United States (Dec. 2009).
Floto, R.A., et al., "Loss of Function of a Lupus-associated FcγRIIb Polymorphism Through Exclusion From Lipid Rafts," Nature Medicine, 11(10):1056-1058, Nature Publishing Company, United States (Oct. 2005).
Forster, A.C., et al., "Programming Peptidomimetic Syntheses by Translating Genetic Codes Designed De Novo," Proceedings of the National Academy of Sciences of the United States of America 100(11):6353-6357 (May 2003).
Fournier, E., et al., "Activation of Human Peripheral IgM+ B Cells Is Transiently Inhibited by BCR-Independent Aggregation of FcγRIIB," Journal of Immunology, 181(8):5350-5359, American Association of Immunologists, United States (Oct. 2008).
Ghetie, V., et al., "Increasing the Serum Persistence of an IgG Fragment by Random Mutagenesis," Nature Biotechnology 15(7):637-640, Nature America Publishing, United States (Jul. 1997).
Greenwood, J., et al., "Structural Motifs Involved in Human IgG Antibody Effector Functions," European Journal of Immunology, 23(5):1098-1104, Germany, Wiley-VCH Verlag (May 1993).
Hanson, et al., "Catalytic Antibodies and Their Applications," Biotechnology Letters, 16:631-636 (Dec. 2005).
Hardie, G. and Van Regenmortel, M.H., "Isolation of Specific Antibody Under Conditions of Low Ionic Strength," Journal of Immunological Methods, 15(4):305-314 (1977).
Hasemann, C.A., et al., "Mutational analysis of arsonate binding by a CRIA+ antibody. VH and VL junctional diversity are essential for binding activity," Journal of Biological Chemistry, 266(12):7626-7632, American Society for Biochemistry and Molecular Biology, United States (Apr. 1991).
Heyman, B., "Feedback Regulation by IgG Antibodies," Immunology Letters, 88(2): 157-161, Elsevier/North-Holland Biomedical Press, Netherlands (Aug. 2003).
Hinton, P.R., et al., "An Engineered Human IgG1 Antibody With Longer Serum Half-life," Journal of Immunology 176(1):346-356, American Association of Immunologists, United States (Jan. 2006).
Hjelm, F., et al., "Antibody-mediated Regulation of the Immune Response," Scandinavian Journal of Immunology, 64(3):177-84, England, Blackwell Scientific Publications (Sep. 2006).
Hogenesch, H. and Nikitin, A.Y., "Challenges in Pre-clinical Testing of Anti-cancer Drugs in Cell Culture and in Animal Models," Journal of Controlled Release 164(2):183-186 (Dec. 2012).
Horton, H.M., et al., "Potent in vitro and in vivo activity of an Fc-engineered anti-CD19 monoclonal antibody against lymphoma and leukemia," Cancer Research, 68(19):8049-8057, American Association for Cancer Research, United States (Oct. 2008).
Howard, G. C. and Kaser, M. R., editors, "Making and Using Antibodies: A Practical Handbook," CRC Press, 157-177 (2006).
Hu, X., et al., "Combinatorial Libraries Against Libraries for Selecting Neoepitope Activation-specific Antibodies," Proceedings of the National Academy of Sciences of the United States of America 107(14):6252-6257 (Apr. 2010).
Idusogie, E. E., et al., "Engineered Antibodies with Increased Activity to Recruit Complement," Journal of Immunology 166(4):2571-2575, American Association of Immunologists, United States (Feb. 2001).
Idusogie, E.E., et al., "Mapping of the C1q Binding Site on Rituxan, a Chimeric Antibody With a Human IgG1 Fc," Journal of Immunology 164(8):4178-4184, American Association of Immunologists, United States (Apr. 2000).

(56) References Cited

OTHER PUBLICATIONS

Igawa, T., et al., "Antibody Recycling by Engineered pH-Dependent Antigen Binding Improves the Duration of Antigen Neutralization," Nature Biotechnology 28(11):1203-1207, Nature America Publishing, United States (Nov. 2010).

Igawa, T., et al., "Reduced Elimination of IgG Antibodies by Engineering the Variable Region," Protein Engineering, Design & Selection, 23(5):385-392, Oxford University Press, England (May 2010).

Ito, W., et al., "The His-probe Method: Effects of Histidine Residues Introduced Into the Complementarity-Determining Regions of Antibodies on Antigen-antibody Interactions at Different Ph Values," FEBS letters, 309(1):85-88, John Wiley & Sons Ltd., England (Aug. 31, 1992).

Jaeger, "Clinical Immunology and Allergology," 2nd edition, M.: Medicina, 2:484-5 (1990).

Janeway, et al., Immunobiology, 3rd Edition, Garland Press, 3:1-3:11 (1997).

Jefferis, R and Lund, J., "Interaction Sites on Human IgG-fc for Fcgammar: Current Models," Immunology Letters 82(1-2):57-65, Elsevier, Netherlands (Jun. 2002).

Juszczak, A., et al., "Ipilimumab: A Novel Immunomodulating Therapy Causing Autoimmune Hypophysitis: A Case Report and Review," European Journal of Endocrinology 167(1):1-5, BioScientifica Ltd., England (Jul. 2012).

Kabat, et al., "Sequences of proteins of immunological interest," DIANE publishing, 5th ed., 1:679-687 (1991).

Kamata, N., et al., "Comparison of pH and Ionic Strength Dependence of Interactions Between Monoclonal Antibodies and Bovine Beta-Lactoglobulin," Bioscience, Biotechnology, and Biochemistry, 60(1):25-29, Taylor & Francis, United States (Jan. 1996).

Kim, S.J., et al., "Antibody Engineering for the Development of Therapeutic Antibodies," Molecules and Cells 20(1):17-29, Korean Society for Molecular and Cellular Biology, Korea (Aug. 2005).

King, D.J., "Applications and Engineering of Monoclonal Antibodies," Taylor & Francis, 151-159, 162-164 (2005).

King, D.J., "Applications and Engineering of Monoclonal Antibodies," 2, 13-4, CRC Press (Nov. 1998).

Kohrt, H., et al., "Stimulation of Natural Killer Cells With a CD137-specific Antibody Enhances Trastuzumab Efficacy in Xenotransplant Models of Breast Cancer," The Journal of Clinical Investigation, 122(3):1066-1075, American Society for Clinical Investigation, United States (Mar. 2012).

Kunkel, T.A., "Rapid and Efficient Site-specific Mutagenesis Without Phenotypic Selection," Proceedings of the National Academy of Sciences of the United States of America 82(2):488- 492, National Academy of Sciences, United States (Jan. 1985).

Lazar, G.A., et al., "Engineered Antibody Fc Variants With Enhanced Effector Function," Proceedings of the National Academy of Sciences of the United States of America, 103(11):4005-4010, National Academy of Sciences, United States (Mar. 2006).

Lewis, G.D., et al., "Differential Responses of Human Tumor Cell Lines to Anti-p185HER2 Monoclonal Antibodies," Cancer Immunology, Immunotherapy 37(4):255-263, Springer Verlag, Germany (Sep. 1993).

Li, et al., "CD72 Down-modulates BCR-induced Signal Transduction and Diminishes Survival in Primary Mature B Lymphocytes," Journal of Immunology (Baltimore, Md.: 1950), 176(9):5321-5328, United States, American Association of Immunologists (May 2006).

Li, F. and Ravetch, J.V., "Apoptotic and Antitumor Activity of Death Receptor Antibodies Require Inhibitory Fcγ Receptor Engagement," Proceedings of the National Academy of Sciences of the United States of America 109(27):10966-10971, National Academy of Sciences, United States (Jul. 2012).

Li, F., et al., "Inhibitory Fcγ Receptor Engagement Drives Adjuvant and Anti-Tumor Activities of Agonistic CD40 Antibodies," Science, 333(6045):1030-1034, United States, American Association for the Advancement of Science (Aug. 2011).

Liberti, P. A., et al., "Antigenicity of Polypeptides (Poly-alpha-amino Acids). Physicochemical Studies of a Calcium-dependent Antigen-antibody Reaction," Biochemistry 10(9):1632-1639, American Chemical Society, United States (Apr. 1971).

Lloyd, C., et al., "Modelling the Human Immune Response: Performance of a 1011 Human Antibody Repertoire Against a Broad Panel of Therapeutically Relevant Antigens," Protein Engineering, Design & Selection 22(3):159-168, Oxford University Press, England (Mar. 2009).

Lowder, J.N. and Levy, R., "Monoclonal Antibodies—therapeutic and Diagnostic Uses in Malignancy," The Western Journal of Medicine 143(6):810-818 (Dec. 1985).

Lukashev, D., et al., "Hypoxia-dependent Anti-inflammatory Pathways in Protection of Cancerous Tissues," Cancer Metastasis Reviews 26(2):273-279 (Jun. 2007).

Lutterbuese, R., et al., "T Cell-Engaging BiTE Antibodies Specific for EGFR Potently Eliminate KRAS- and BRAF-Mutated Colorectal Cancer Cells," Proceedings of the National Academy of Sciences of the United States of America 107(28):12605-12610, National Academy of Sciences, United States (Jul. 2010).

Luttrell, B.M. and Henniker, A.J., "Reaction Coupling of Chelation and Antigen Binding in the Calcium Ion-dependent Antibody Binding of Cyclic AMP," The Journal of Biological Chemistry 266(32):21626-21630 (Nov. 1991).

MacCallum, R.M., et al., "Antibody-antigen Interactions: Contact Analysis and Binding Site Topography," Journal of Molecular Biology 262(5):732-745, Academic Press, England (Oct. 1996).

Mackay, M., et al., "Selective Dysregulation of the FcγIIB Receptor on Memory B Cells in SLE," The Journal of Experimental Medicine, 203(9):2157-2164, New York, Rockefeller University Press (Sep. 2006).

Malbec, O., et al., "Antibodies against growth factor receptors can inhibit the proliferation of transformed cells via a cis-interaction with inhibitory FcR," Immunology Letters, 143(1):28-33, Elsevier (Mar. 2012).

Manger, et al., "FcγReceptor IIa Polymorphism in Caucasian Patients With Systemic Lupus Erythematosus Association With Clinical Symptoms," Arthritis and Rheumatism, 41(7):1181-1189, United States, Wiley-Blackwell (Jul. 1998).

Matsumiya, S., et al., "Structural Comparison of Fucosylated and Nonfucosylated Fc Fragments of Human Immunoglobulin G1," Journal of Molecular Biology, 368(3):767-779, Amsterdam, Elsevier (May 2007).

Maurer, P., et al., "Antigenicity of Polypeptides (Poly Alpha Amino Acids): Calcium-dependent and Independent Antibodies," Journal of Immunology, 105(3):567-573, American Association of Immunologists, United States (Sep. 1970).

Maxfield, F.R. and McGraw, T.E., "Endocytic Recycling," Nature Reviews Molecular Cell Biology 5(2):121-132, Nature Pub. Group, England (Feb. 2004).

Maxwell, K.F., et al., "Crystal Structure of the Human Leukocyte Fc Receptor, FcγRIIa," Nature Structural Biology, 6(5):437-442, Nature Pub. Co., United States (May 1999).

Mendez-Fernandez, Y. V., et al., "The Inhibitory FcγRIIb Modulates the Inflammatory Response and Influences Atherosclerosis in Male apoE(-/-) Mice," Atherosclerosis 214(1):73-80, Elsevier, Ireland (Jan. 2011).

Meyer, T., et al., "Bevacizumab immune complexes activate platelets and induce thrombosis in FCGR2A transgenic mice," Journal of Thrombosis and Haemostasis, 7(1):171-181, Blackwell Pub, England (Jan. 2009).

Mi, W., et al., "Targeting the Neonatal Fc Receptor for Antigen Delivery Using Engineered Fc Fragments," Journal of Immunology, 181(11):7550-7561, United States, American Association of Immunologists (Dec. 2008).

Moore, G.L., et al., "Engineered Fc Variant Antibodies With Enhanced Ability to Recruit Complement and Mediate Effector Functions," mAbs 2(2):181-189, Taylor & Francis, United States (Mar.-Apr. 2010).

Morgan, A., et al., "The N-Terminal End of the CH2 Domain of Chimeric Human IgG1 Anti-HLA-DR is Necessary for C1q, Fc Gamma RI and Fc Gamma RIII Binding," Immunology, 86(2):319-324, England, Blackwell Scientific Publications (Oct. 1995).

(56) References Cited

OTHER PUBLICATIONS

Murtaugh, M.L., et al., "A Combinatorial Histidine Scanning Library Approach to EngineerHighly pH-Dependent Protein Switches," Protein Science 20(9):1619-1631, Cold Spring Harbor Laboratory Press, United States (Sep. 2011).

Muta, et al., "A 13-Amino-Acid Motif in the Cytoplasmic Domain of Fc Gamma RIIB Modulates B-cell Receptor Signalling," Nature, 368(6466):70-73, England, Nature Publishing Group (Mar. 1994).

Nagaoka, M. and Akaike, T., "Single Amino Acid Substitution in the Mouse IgG1 Fc Region Induces Drastic Enhancement of the Affinity to Protein A," Protein Engineering 16(4):243-245, Oxford University Press, England (Apr. 2003).

Nakamura, A., et al., "Fcγ Receptor IIB-deficient Mice Develop Goodpasture's Syndrome Upon Immunization With Type IV Collagen: a Novel Murine Model for Autoimmune Glomerular Basement Membrane Disease," The Journal of Experimental Medicine, 191(5):899-906, United States, Rockefeller University Press (Mar. 2000).

Nam, J.L., et al., "Current Evidence for the Management of Rheumatoid Arthritis With Biological Disease-modifying Antirheumatic Drugs: a Systematic Literature Review Informing the EULAR Recommendations for the Management of RA," Annals of the Rheumatic Diseases 69(6):976-986, BMJ, England (Jun. 2010).

Nicholas, R., et al., "Regulation of the immune response. I. Reduction in ability of specific antibody to inhibit long-lasting IgG immunological priming after removal of the Fc fragment," Journal of Experimental Medicine, 129(6):1183-1201, Rockefeller University Press, United States (Jun. 1969).

Nimmerjahn, F and Ravetch, J.V., "Fcγ Receptors as Regulators of Immune Responses," Nature Reviews. Immunology, 8(1):34-47, Nature Publishing Group, England (Jan. 2008).

Nimmerjahn, F., et al., "Divergent Immunoglobulin G Subclass Activity Through Selective Fc Receptor Binding," Science, 310(5753):1510-1512, United States, American Association for the Advancement of Science (Dec. 2005).

Ohno et al., "Antigen-Binding Specificities of Antibodies Are Primarily Determined by Seven Residues of VH," Proceedings of the National Academy of Sciences U.S.A., 82(9):2945-9 (May 1985).

Olferiev., et al., "The Role of Activating Protein 1 in the Transcriptional Regulation of the Human FCGR2B Promoter Mediated by the -343 G—C Polymorphism Associated With Systemic Lupus Erythematosus," The Journal of Biological Chemistry, 282(3):1738-1746, United States, American Society for Biochemistry and Molecular Biology (Jan. 2007).

Patentee submission dated Jul. 16, 2015 (Response to Search Report filed on Jul. 16, 2015)(document submitted by the Opponent on May 6, 2020 in the Opposition of EP2679681).

Paul, W. E., editor, Immunology. Moscow, Mir, 3; 6-10 (1987-1989), with English translation, Paul, W.E., Fundamental Immunology, Editor William E. Paul, M. D., Chapter 12: 421-424, Laboratory of Immunology National Institute of Allergy and Infectious Diseases National Institutes of Health Bethesda, Maryland, Raven Press New York (1984).

Pavlou, A.K and Belsey, M.J, "The Therapeutic Antibodies Market to 2008," European Journal of Pharmaceutics and Biopharmaceutics, 59(3):389-396, Elsevier Science, Netherlands (Apr. 2005).

Pedroza, M., et al., "Interleukin-6 Contributes to Inflammation and Remodeling in a Model of Adenosine Mediated Lung Injury," PloS One 6(7):e22667 (2011).

Petkova, S.B., et al., "Enhanced Half-life of Genetically Engineered Human IgG1 Antibodies in a Humanized Fcrn Mouse Model: Potential Application in Humorally Mediated Autoimmune Disease," International Immunology 18(12):1759-1769, Oxford University Press, England (Dec. 2006).

Poosarla, V. G., et al., "Computational de Novo Design of Antibodies binding to a Peptide with High Affinity," Biotechnology and Bioengineering 114(6):1331-1342, Wiley, United States (Jun. 2017).

Radaev, S., et al., "Recognition of IgG by Fcγ Receptor. The Role of Fc Glycosylation and the Binding of Peptide Inhibitors," The Journal of Biological Chemistry, 276(19):16478-16483, American Society for Biochemistry and Molecular Biology, United States (May 2001).

Radaev, S., et al., "The Structure of a Human Type Iii Fcγ Receptor in Complex With Fc," The Journal of Biological Chemistry, 276(19):16469-16477, American Society for Biochemistry and Molecular Biology, United States (May 2001).

Rajpal, A., et al., "A General Method for Greatly Improving the Affinity of Antibodies by Using Combinatorial Libraries," Proceedings of the National Academy of Sciences of the United States of America 102(24):8466-8471, National Academy of Sciences, United States (Jun. 2005).

Rathanaswami, P., et al., "Demonstration of an in Vivo Generated Sub-picomolar Affinity Fully Human Monoclonal Antibody to Interleukin-8," Biochemical and Biophysical Research Communications, 334(4):1004-1013, Elsevier, United States (Sep. 2005).

Ravetch, et al., "Immune Inhibitory Receptors," Science, 290(5489):84-89, United States, American Association for the Advancement of Science (Oct. 2000).

Reichert, J.M., et al., "Monoclonal Antibody Successes in the Clinic," Nature Biotechnology, 23(9):1073-1078, Nature America Publishing, United States (Sep. 2005).

Reverberi, R. and Reverberi, L., "Factors Affecting the Antigen-Antibody reaction," Blood Transfusion 5:227-240, SIMTI servizi, Italy (Nov. 2007).

Richard, C.L., et al., "Adenosine Upregulates CXCR4 and Enhances the Proliferative and Migratory Responses of Human Carcinoma Cells to CXCL12/SDF-1alpha," International Journal of Cancer 119(9):2044-2053 (Nov. 2006).

Richards, J.O., et al., "Optimization of Antibody Binding to FcγRIIa Enhances Macrophage Phagocytosis of Tumor Cells," Molecular Cancer Therapeutics, 7(8):2517-2527, Philadelphia, American Association for Cancer Research (Aug. 2008).

Riechelmann, H., et al., "Phase I Trial With the CD44v6-Targeting Immunoconjugate Bivatuzumab Mertansine in Head and Neck Squamous Cell Carcinoma," Oral Oncology 44(9):823-829, Elsevier, England (Sep. 2008).

Robles-Carrillo, L., et al., "Anti-CD40L Immune Complexes Potently Activate Platelets in Vitro and Cause Thrombosis in FCGR2A Transgenic Mice," Journal of Immunology, 185(3):1577-1583, United States, American Association of Immunologists (Aug. 2010).

Roitt., et al., Immunology, Moscow, Mir, 110 (2000).

Roitt., et al., Immunology. Moscow, Mir, 9 (2000).

Roitt et al., Immunology, Moscow: Mir, 373-374 (2000).

Roopenian, D.C., et al., "FcRn: the Neonatal Fc Receptor Comes of Age," Nature reviews. Immunology, 7(9):715-725, Nature Pub. Group, [c2001-, England (Sep. 2007).

Rudikoff, S., et al., "Single Amino Acid Substitution Altering Antigen-Binding Specificity," Proceedings of the National Academy of Sciences of the United States of America, 79(6):1979-1983, National Academy of Sciences, Washington (Mar. 1982).

Safdari, Y., et al., "Antibody Humanization Methods—A Review and Update," Biotechnology & Genetic Engineering Reviews, 29(2):175-186, England, Taylor & Francis (2013).

Salmon, J.E., et al., "Fc Gamma RIIA Alleles are Heritable Risk Factors for Lupus Nephritis in African Americans," The Journal of Clinical Investigation, 97(5):1348-1354, United States, American Society for Clinical Investigation (Mar. 1996).

Satoh, M., et al., "Non-Fucosylated Therapeutic Antibodies as Next-Generation Therapeutic Antibodies," Expert Opinion on Biological Therapy 6(11):1161-1173, Taylor & Francis, London (Nov. 2006).

Sazinsky, S.L., et al., "Aglycosylated Immunoglobulin G1 Variants Productively Engage Activating Fc Receptors," Proceedings of the National Academy of Sciences of the United States of America 105(51):20167-20172, National Academy of Sciences, United States (Dec. 2008).

Scappaticci, F.A., et al., "Arterial Thromboembolic Events in Patients With Metastatic Carcinoma Treated With Chemotherapy and Bevacizumab," Journal of the National Cancer Institute 99(16):1232-1239, Oxford University Press, United States (Aug. 2007).

Schlothauer, T., et al., "Novel Human IgG1 and IgG4 Fc-engineered Antibodies With Completely Abolished Immune Effector Func-

(56) References Cited

OTHER PUBLICATIONS tions," Protein Engineering, Design & Selection: PEDS, 29(10):457-466, Oxford University Press, England (Oct. 2016).

Schröter, C., et al., "A Generic Approach to Engineer Antibody Ph-switches Using Combinatorial Histidine Scanning Libraries and Yeast Display," mAbs 7(1): 138-151, Taylor & Francis, United States (Jan.-Feb. 2015).

Shields, R. L., et al., "High Resolution Mapping of the Binding Site on Human IgG1 for Fc Gamma RI, Fc Gamma RIII, Fc Gamma RIII, and FcRn and Design of Igg1 Variants With Improved Binding to the Fc Gamma R," The Journal of Biological Chemistry, 276(9):6591-6604, American Society for Biochemistry and Molecular Biology, United States (Mar. 2001).

Shinkawa, T., et al., "The Absence of Fucose but Not the Presence of Galactose or Bisecting N-acetylglucosamine of Human IgG1 Complex-type Oligosaccharides Shows the Critical Role of Enhancing Antibody-dependent Cellular Cytotoxicity," The Journal of Biological Chemistry 278(5):3466-3473, American Society for Biochemistry and Molecular Biology, United States (Jan. 2003).

Siberil, et al., "Molecular Aspects of Human FcγR Interactions With IgG Functional and Therapeutic Consequences," Immunology Letters, 106(2):111-118, Netherlands, Elsevier/North-Holland Biomedical Press (Aug. 2006).

Singer, et al., Genes & Genomes, 1:63-64 (1998).

Singer, et al., Genes & Genomes, Moscow: Mir, 115-188 (1998).

Smith, K., et al., "FcγRIIB in Autoimmunity and Infection: Evolutionary and Therapeutic Implications," Nature Reviews. Immunology, 10(5):328-343, Nature Pub. Group, England (May 2010).

Sondermann, P., et al., "Crystal Structure of the Soluble Form of the Human Fcγ-receptor IIb: a New Member of the Immunoglobulin Superfamily at 1.7 a Resolution," The EMBO Journal, 18(5):1095-1103, Wiley Blackwell, England (Mar. 1999).

Sondermann, P., et al., "Molecular basis for immune complex recognition: a comparison of Fc-receptor structures," Journal of Molecular Biology, 309(3):737-749, Elsevier, England (Jun. 2001).

Sondermann, P., et al., "The 3.2-A crystal structure of the human IgG1 Fc fragment-FcγRIII complex," Nature, 406(6793):267-273, Nature Publishing Group, England (Jul. 2000).

Stepanov, Molecular biology. Structure and functions of proteins. Moscow, Nauka, 61-62 (2005).

Stepanov, Molecular biology. Structure and functions of proteins. Moscow, Nauka, pp. 144-146 (2005).

Su, K., et al., "Expression Profile of FcgammaRIIb on Leukocytes and Its Dysregulation in Systemic Lupus Erythematosus," Journal of Immunology, 178(5):3272-3280, United States, American Association of Immunologists (Mar. 2007).

Suzuki, "Research and Development of Antibody Pharmaceuticals," NIBS Letter 56(4):45-51 (2010).

Suzuki, T., et al., "Importance of Neonatal Fcr in Regulating the Serum Half-life of Therapeutic Proteins Containing the Fc Domain of Human Igg1: a Comparative Study of the Affinity of Monoclonal Antibodies and Fc-fusion Proteins to Human Neonatal Fcr," Journal of Immunology, 184(4):1968-1976, American Association of Immunologists, United States (Feb. 2010).

Tackenberg, B., et al., "Impaired Inhibitory Fcgamma Receptor IIB Expression on B Cells in Chronic Inflammatory Demyelinating Polyneuropathy," Proceedings of the National Academy of Sciences of the United States of America 106(12):4788-4792, National Academy of Sciences, United States (Mar. 2009).

Takeuchi, T. and Kameda, H., "The Japanese Experience With Biologic Therapies for Rheumatoid Arthritis," Nature Reviews. Rheumatology 6(11):644-652, Nature Pub. Group, United States (Nov. 2010).

Tang, H., et al., "Immunotherapy and Tumor Microenvironment," Cancer Letters 370(1):85-90 (Jan. 2016).

Torres, M. and Casadevall, A., "The Immunoglobulin Constant Region Contributes to Affinity and Specificity," Trends in Immunology 29(2):91-97, Elsevier Science Ltd., England (Feb. 2008).

Travis, J., et al., "Isolation of Albumin from Whole Human Plasma and Fractionation of Albumin-Depleted Plasma," Biochemical Journal 157(2):301-306, Portland Press, England (Aug. 1976).

Trinh, V.A. and Hwu, W.-J., "Ipilimumab in the Treatment of Melanoma," Expert Opinion on Biological Therapy 12(6):773-782, Taylor & Francis, England (Jun. 2012).

Vaccaro, C., et al., "Engineering the Fc Region of Immunoglobulin G to Modulate in Vivo Antibody Levels," Nature Biotechnology 23(10):1283-1288, Nature America Publishing, United States (Oct. 2005).

Vajdos, F.F et al., "Comprehensive Functional Maps of the Antigen-binding Site of an Anti-ErbB2 Antibody Obtained With Shotgun Scanning Mutagenesis," Journal of Molecular Biology, 320(2):415-428, Elsevier, England (Jul. 2002).

Vengelen-Tyler, V., et al., "Two Examples of Antibodies Dependent Upon the Presence of Inosine," Transfusion 21(3):315-319 (May-Jun. 1981).

Veri, M., et al., "Monoclonal Antibodies Capable of Discriminating the Human Inhibitory Fcγ-receptor IIb (Cd32b) From the Activating Fcγ-receptor IIa (Cd32a): Biochemical, Biological and Functional Characterization," Immunology, 121(3):392-404, Blackwell Scientific Publications, England (Jul. 2007).

Veri, M.C., et al., "Therapeutic control of B cell activation via recruitment of Fcγ receptor IIb (CD32B) inhibitory function with a novel bispecific antibody scaffold," Arthritis and Rheumatology, 62(7):1933-1943, Wiley-Blackwell, United States (Jul. 2010).

Wang, et al., "Monoclonal Antibodies With Identical Fc Sequences Can Bind to FcRn Differentially With Pharmacokinetic Consequences," Drug Metabolism and Disposition the Biological Fate of Chemicals, 39(9):1469-1477, United States, American Society for Pharmacology and Experimental Therapeutics (Sep. 2011).

Wang, L., et al., "Expanding the Genetic Code," Annual Review of Biophysics and Biomolecular Structure 35:225-249 (2006).

Warmerdam, P. A., et al., "The Human Low Affinity Immunoglobulin G Fc Receptor IIC Gene is a Result of an Unequal Crossover Event," The Journal of Biological Chemistry 268(10):7346-7349, Elsevier Inc., United States (Apr. 1993).

Warmerdam, P.A., et al., "Molecular Basis for a Polymorphism of Human Fc Gamma Receptor II (CD32)," Journal of Experimental Medicine 172(1):19-25, Rockefeller University Press, United States (Jul. 1990).

Weiner, L.M., et al., "Monoclonal Antibodies: Versatile Platforms for Cancer Immunotherapy," Nature Reviews. Immunology, 10(5):317-327, Nature Publishing Group, England (May 2010).

Weiss, G.A., et al., "Rapid Mapping of Protein Functional Epitopes by Combinatorial Alanine Scanning," Proceedings of the National Academy of Sciences of the United States of America 97(16):8950-8954, National Academy of Sciences, United States (Aug. 2000).

Wenink, H., et al., "The Inhibitory Fcγ IIb Receptor Dampens TLR4-mediated Immune Responses and is Selectively Up-regulated on Dendritic Cells From Rheumatoid Arthritis Patients With Quiescent Disease," Journal of Immunology, 183(7):4509-4520, United States, American Association of Immunologists (Oct. 2009).

Wernersson, S., et al., "IgG-mediated Enhancement of Antibody Responses is Low in Fc Receptor Gamma Chain-deficient Mice and Increased in Fcγ RII-deficient Mice," Journal of Immunology, 163(2):618-622, American Association of Immunologists, United States (Jul. 1999).

Wilson, N.S., et al., "An Fcγ Receptor-Dependent Mechanism Drives Antibody-Mediated Target-Receptor Signaling in Cancer Cells," Cancer Cell, 19(1):101-113, Cambridge, Mass: Cell Press (Jan. 2011).

Wu, H., et al., "Development of Motavizumab, an Ultra-potent Antibody for the Prevention of Respiratory Syncytial Virus Infection in the Upper and Lower Respiratory Tract," Journal of Molecular Biology 368:652-665, Elsevier, England (May 2007).

Xu, Y., et al., "Fc Gamma Rs Modulate Cytotoxicity of anti-Fas Antibodies: Implications for Agonistic Antibody-based Therapeutics," Journal of Immunology, 171(2):562-568, American Association of Immunologists, United States (Jul. 2003).

Yarilin, A. A., Fundamentals of Immunology (Osnovy immunologii), Moscow, Medicina, 171 (1999).

(56) References Cited

OTHER PUBLICATIONS

Yarilin, A., "Osnovy Immunologii," M.: Meditsina, 169-172, 354-358/Fundamentals of Immunology. M: Medicina, 169-172, 354-358 (1999).
Yarilin, A., "Osnovy Immunologii," M.: Meditsina, 172-174/Fundamentals of Immunology. M: Medicina, 172-174 (1999).
Yarilin, "Osnovy immunologii," M. Meditsina, 181-184 (1999).
Yeung, Y.A., et al., "Engineering Human IgG1 Affinity to Human Neonatal Fc Receptor: Impact of Affinity Improvement on Pharmacokinetics in Primates," Journal of Immunology 182(12):7663-7671, American Association of Immunologists, United States (Jun. 2009).
Yuasa, T., et al., "Deletion of Fcγ Receptor IIB renders H-2(b) Mice Susceptible to Collagen-induced Arthritis," The Journal of Experimental Medicine, 189(1):187-194, Rockefeller University Press, United States (Jan. 1999).
Zalevsky, J., et al., "Enhanced Antibody Half-life Improves in Vivo Activity," Nature Biotechnology 28(2):157-159, Nature America Publishing, United States (Feb. 2010).
Zalevsky, J, et al., "The Impact of Fc Engineering on an Anti-cd19 Antibody: Increased Fcγ Receptor Affinity Enhances B-cell Clearing in Nonhuman Primates," Blood, 113(16):3735-3743, American Society of Hematology, United States (Apr. 2009).
Zhang, et al., "Immune Complex/Ig Negatively Regulate TLR4-Triggered Inflammatory Response in Macrophages Through Fcγ RIIb-Dependent PGE2 Production," Journal of Immunology, 182(1):554-562, United States, American Association of Immunologists (Jan. 2009).
Zhang, M., et al., "Effective Therapy for a Murine Model of Human Anaplastic Large-Cell Lymphoma with the Anti-CD30 Monoclonal Antibody, HeFi-1, Does Not Require Activating Fc Receptors," Blood, 108(2):705-710, United States, American Society of Hematology (Jul. 2006).
U.S. Appl. No. 08/697,904, filed Aug. 30, 1996, Hoffman, et al.
U.S. Appl. No. 09/483,588, filed Jan. 14, 2000, Presta.
U.S. Appl. No. 10/029,988, filed Dec. 31, 2001, Levanon, et al.
U.S. Appl. No. 10/032,037, filed Dec. 31, 2001, Levanon, et al.
U.S. Appl. No. 10/032,423, filed Dec. 31, 2001, Lazarovitis, et al.
U.S. Appl. No. 10/379,392, filed Mar. 3, 2003, Lazar, et al.
U.S. Appl. No. 10/514,516, filed Oct. 28, 2005, Edwards, et al.
U.S. Appl. No. 10/687,118, filed Oct. 15, 2003, Hinton, et al.
U.S. Appl. No. 10/822,231, filed Mar. 26, 2004, Lazar, et al.
U.S. Appl. No. 10/902,588, filed Jul. 28, 2004, Stavenhagen, et al.
U.S. Appl. No. 11/108,135, filed Apr. 15, 2005, Koenig, et al.
U.S. Appl. No. 11/124,620, filed May 5, 2005, Lazar, et al.
U.S. Appl. No. 11/483,250, filed Jul. 7, 2006, Lazar, et al.
U.S. Appl. No. 11/520,121, filed Sep. 13, 2006, Presta.
U.S. Appl. No. 11/632,898, filed Jan. 19, 2007, Fishman.
U.S. Appl. No. 11/754,015, filed May 25, 2007, Johnson, et al.
U.S. Appl. No. 11/764,001, filed Jun. 15, 2007, Lazar, et al.
U.S. Appl. No. 11/765,353, filed Jun. 19, 2007, Lazar, et al.
U.S. Appl. No. 11/929,742, filed Oct. 30, 2007, Lazar, et al.
U.S. Appl. No. 11/932,151, filed Oct. 31, 2007, Chamberlain, et al.
U.S. Appl. No. 11/952,568, filed Dec. 7, 2007, Stavenhagen, et al.
U.S. Appl. No. 12/018,754, filed Jan. 23, 2008, Bernett, et al.
U.S. Appl. No. 12/020,443, filed Jan. 25, 2008, Lazar, et al.
U.S. Appl. No. 12/147,379, filed Jun. 26, 2008, Datta, et al.
U.S. Appl. No. 12/156,183, filed May 30, 2008, Chu Seung, et al.
U.S. Appl. No. 12/186,058, filed Aug. 5, 2008, Koenig, et al.
U.S. Appl. No. 12/240,880, filed Sep. 29, 2008, Glaser, et al.
U.S. Appl. No. 12/516,914, filed Feb. 12, 2010, McDonagh, et al.
U.S. Appl. No. 12/532,022, filed Mar. 19, 2008, Guler-Gane, et al.
U.S. Appl. No. 12/577,967, filed Oct. 13, 2009, Lowman, et al.
U.S. Appl. No. 12/650,329, filed Dec. 30, 2009, Morrison, et al.
U.S. Appl. No. 12/733,865, filed Aug. 24, 2008, Chung, et al.
U.S. Appl. No. 12/890,598, filed Sep. 24, 2010, Corbin, et al.
U.S. Appl. No. 12/896,610, filed Oct. 1, 2010, Lazar, et al.
U.S. Appl. No. 12/936,587, filed Apr. 10, 2009, Igawa, et al.
U.S. Appl. No. 13/045,345, filed Mar. 10, 2011, Pons, et al.
U.S. Appl. No. 13/063,123, filed Mar. 9, 2011, Villa, et al.
U.S. Appl. No. 13/077,644, filed Mar. 31, 2011, Beliard, et al.
U.S. Appl. No. 13/174,423, filed Jun. 30, 2011, Jackson, et al.
U.S. Appl. No. 13/422,887, filed Mar. 16, 2012, Jackson, et al.
U.S. Appl. No. 13/637,415, filed Mar. 30, 2011, Igawa, et al.
U.S. Appl. No. 13/764,693, filed Feb. 11, 2013, Lazar, et al.
U.S. Appl. No. 13/832,247, filed Mar. 15, 2013, McWhirter, et al.
U.S. Appl. No. 13/848,547, filed Mar. 21, 2013, Horn.
U.S. Appl. No. 13/855,448, filed Apr. 2, 2013, Murphy, et al.
U.S. Appl. No. 13/964,159, filed Aug. 12, 2013, Yancopoulos, et al.
U.S. Appl. No. 13/990,158, filed Nov. 30, 2011, Igawa, et al.
U.S. Appl. No. 14/078,501, filed Nov. 12, 2013, Lazar, et al.
U.S. Appl. No. 14/085,424, filed Nov. 20, 2013, McWhirter, et al.
U.S. Appl. No. 14/127,576, filed Jun. 29, 2012, Mimoto, et al.
U.S. Appl. No. 14/290,544, filed May 29, 2014, Swergold, et al.
U.S. Appl. No. 14/347,448, filed Mar. 26, 2014, Igawa, et al.
U.S. Appl. No. 14/348,511, filed Mar. 28, 2014, IGAWA, et al.
U.S. Appl. No. 14/349,884, filed Oct. 5, 2012, IGAWA, et al.
U.S. Appl. No. 14/377,556, filed Feb. 8, 2013, KURAMOCHI, et al.
U.S. Appl. No. 14/404,051, filed May 30, 2013, IGAWA, et al.
U.S. Appl. No. 14/406,232, filed Jun. 14, 2013, IGAWA, et al.
U.S. Appl. No. 14/422,207, filed Aug. 23, 2013, IGAWA, et al.
U.S. Appl. No. 14/641,026, filed Mar. 6, 2015, ANDRIEN, et al.
U.S. Appl. No. 14/654,895, filed Dec. 26, 2013, IGAWA, et al.
U.S. Appl. No. 14/717,914, filed May 20, 2015, STEVIS, et al.
U.S. Appl. No. 14/727,313, filed Jun. 1, 2015, ANDRIEN, et al.
U.S. Appl. No. 14/974,488, filed Dec. 18, 2015, RUIKE, et al.
U.S. Appl. No. 17/266,024, filed Feb. 4, 2021, Igawa, et al., related application.
Crowe, J. S., et al., "Humanized monoclonal antibody CAMPATH-1H: myeloma cell expression of genomic constructs, nucleotide sequence of cDNA constructs and comparison of effector mechanisms of myeloma and Chinese hamster ovary cell-derived material," Clin Exp Immunol., 87:105-110 (1992).
Enomoto, K., et al., "Development of high-throughput spermidine synthase activity assay using homogenous time-resolved fluorescence," Anal Biochem., 351:229-240 (2006).
Final Office Action dated Jul. 12, 2022 in U.S. Appl. No. 16/539,765, filed Aug. 13, 2019, Igawa et al.
James, L. C., et al., "1.9 Å Structure of the Therapeutic Antibody CAMPATH-1H Fab in Complex with a Synthetic Peptide Antigen," J Mol Biol., 289:293-301 (1999).
Kamata-Sakurai, M., "Antibody to CD137 Activated by Extracellular Adenosine Triphosphate Is Tumor Selective and Broadly Effective In Vivo without Systemic Immune Activation," Cancer Discov., 11(1):158-175 (2021).
Kamata-Sakurai, M., "Supplementary Data—Antibody to CD137 Activated by Extracellular Adenosine Triphosphate Is Tumor Selective and Broadly Effective In Vivo without Systemic Immune Activation," Cancer Discov., 11(1):158-175 (2021).
Larkin, J., et al., "Combined Nivolumab and Ipilimumab or Monotherapy in Untreated Melanoma," N Engl J Med., 373:23-34 (2015).
Limm, K., et al., "The metabolite 5'-methylthioadenosine signals through the adenosine receptor A2B in melanoma," Eur J Cancer, 50:2714-2724 (2014).
Mariuzza, R. A., et al., "The Structural Basis of Antigen-Antibody Recognition," Ann Rev Biophys Chem., 16:139-159 (1987).
Office Action dated Nov. 18, 2021 in U.S. Appl. No. 16/539,765, filed Aug. 13, 2019, Igawa et al.
Pakula, A. A. and Sauer, R. T., "Genetic Analysis of Protein Stability and Function," Annu Rev Genet., 23:289-310 (1989).
Qu, Y.-H. and Li, Y., "Progress of Study on Antitum or Effects of Antibody Dependent Cell Mediated Cytotoxicity," J Exp Hematol., 18(5):1370-1375 (2010).
Roitt, I., et al., "Immunology," Mir, 110-111 (2000).
Roitt, I., et al., "Immunology," Mir, 110-111, 132 (2000).
Stevens, A. P., et al., "Quantitative analysis of 5'-deoxy-5'-methylthioadenosine in melanoma cells by liquid chromatography-stable isotope ration tandem mass spectrometry," J Chromatogr B., 876:123-128 (2008).
Wines, B. D., et al., "The IgG Fc Contains Distinct Fc Receptor (FcR) Binding Sites: The Leukocyte Receptors Fc$_\gamma$RI and Fc$_\gamma$RIIa

(56) References Cited

OTHER PUBLICATIONS

Bind to a Region in the Fc Distinct from That Recognized by Neonatal FcR and Protein A," J Immunol., 164:5313-5318 (2000).
U.S. Appl. No. 14/001,218, filed Dec. 2, 2013, Mimoto et al., related application.
U.S. Appl. No. 14/347,321, filed Sep. 28, 2012, Igawa et al., related application.
U.S. Appl. No. 14/379,825, filed Feb. 22, 2013, Igawa et al., related application.
U.S. Appl. No. 14/402,574, filed May 30, 2013, Igawa et al., related application.
U.S. Appl. No. 14/423,269, filed Aug. 23, 2013, Katada et al., related application.
U.S. Appl. No. 14/781,069, filed Apr. 2, 2014, Mimoto et al., related application.
U.S. Appl. No. 15/100,934, filed Jun. 1, 2016, Igawa et al., related application.
U.S. Appl. No. 15/963,455, filed Apr. 26, 2018, Ruike et al.
U.S. Appl. No. 15/977,757, filed May 11, 2018, Igawa et al., related application.
U.S. Appl. No. 16/539,765, filed Aug. 13, 2019, Igawa et al., related application.
U.S. Appl. No. 17/028,210, filed Sep. 22, 2020, Katada et al., related application.
U.S. Appl. No. 17/182,331, filed Feb. 23, 2021, Igawa et al., related application.
U.S. Appl. No. 17/438,993, filed Sep. 14, 2021, Mizuno et al., related application.
U.S. Appl. No. 17/561,207, filed Dec. 23, 2021, Igawa et al., related application.
U.S. Appl. No. 17/671,185, filed Feb. 14, 2022, Mimoto et al., related application.
U.S. Appl. No. 17/798,686, filed Aug. 10, 2022, Sakurai et al., related application.
U.S. Appl. No. 17/846,672, filed Jun. 22, 2022, Mimoto et al., related application.
U.S. Appl. No. 17/854,023, filed Jun. 30, 2022, Igawa et al., related application.
U.S. Appl. No. 18/138,888, filed Apr. 25, 2023, Igawa et al., related application.
U.S. Appl. No. 18/411,929, filed Jan. 12, 2024, Igawa et al., related application.
Liu, et al., Chinese Journal of Cancer Biotherapy, 15(2):193-196, 200 (2008), with English abstract.

* cited by examiner shIL6R

| 11 | | | | | | | | | | 12 | | | | | | | | | | 13 | | | | | | | | | |
|---|---|---|---|---|---|---|---|---|---|---|---|---|---|---|---|---|---|---|---|---|---|---|---|---|---|---|---|---|---|
| 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 | |
| D | V | P | P | E | E | P | Q | L | S | C | F | R | K | S | P | L | S | N | V | V | C | E | W | G | P | R | S | T | |

| 14 | | | | | | | | | | 15 | | | | | | | | | | 16 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| P | S | L | T | T | K | A | V | L | L | V | R | K | F | Q | N | S | P | A | E | D | F | Q | E | P | C | Q | Y | S | Q |

| 17 | | | | | | | | | | 18 | | | | | | | | | | 19 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| E | S | Q | K | F | S | C | Q | L | A | V | P | E | G | D | S | S | F | Y | I | V | S | M | S | V | A | S | S | V | G |

| 20 | | | | | | | | | | 21 | | | | | | | | | | 22 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| S | K | F | S | K | T | Q | T | F | Q | G | C | G | I | L | Q | P | D | P | P | A | N | I | T | V | T | A | V | A | R |

| 23 | | | | | | | | | | 24 | | | | | | | | | | 25 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| N | P | R | W | L | S | V | T | W | Q | D | P | H | S | W | N | S | S | F | Y | R | L | R | F | E | L | R | Y | R | A |

| 26 | | | | | | | | | | 27 | | | | | | | | | | 28 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| E | R | S | K | T | F | T | T | W | M | V | K | D | L | Q | H | H | C | V | I | H | D | A | W | S | G | L | R | H | V |

| 29 | | | | | | | | | | 30 | | | | | | | | | | 31 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| V | Q | L | R | A | Q | E | E | F | G | Q | G | E | W | S | E | W | S | P | E | A | M | G | T | P | W | T | E | S | R |

| 32 | | | | | | | | | | 30 | | | | | | | | | | 31 | | | | | | | | | |
|---|---|---|---|---|---|---|---|---|---|---|---|---|---|---|---|---|---|---|---|---|---|---|---|---|---|---|---|---|---|
| 0 | 1 | 2 | 3 | 4 | 5 | 6 | 7 | 8 | 9 | 0 | 1 | 2 | 3 | 4 | 5 | 6 | 7 | 8 | 9 | 0 | 1 | 2 | 3 | 4 | 5 | 6 | 7 | 8 | 9 |
| S | | | | | | | | | | | | | | | | | | | | | | | | | | | | | |

▓ Epitope residue

FIG. 85

Mean±SD (3 cases)

```
                        SEQUENCE LISTING

<160> NUMBER OF SEQ ID NOS: 225

<210> SEQ ID NO 1
<211> LENGTH: 255
<212> TYPE: PRT
<213> ORGANISM: Homo sapiens

<400> SEQUENCE: 1

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255

<210> SEQ ID NO 2
<211> LENGTH: 164
<212> TYPE: PRT
<213> ORGANISM: Homo sapiens

<400> SEQUENCE: 2

Ser Leu Gln Asp Pro Cys Ser Asn Cys Pro Ala Gly Thr Phe Cys Asp
1               5                   10                  15

Asn Asn Arg Asn Gln Ile Cys Ser Pro Cys Pro Pro Asn Ser Phe Ser
            20                  25                  30

Ser Ala Gly Gly Gln Arg Thr Cys Asp Ile Cys Arg Gln Cys Lys Gly
```

```
                35                  40                  45
Val Phe Arg Thr Arg Lys Glu Cys Ser Ser Thr Ser Asn Ala Glu Cys
 50                  55                  60

Asp Cys Thr Pro Gly Phe His Cys Leu Gly Ala Gly Cys Ser Met Cys
 65                  70                  75                  80

Glu Gln Asp Cys Lys Gln Gly Gln Glu Leu Thr Lys Lys Gly Cys Lys
                 85                  90                  95

Asp Cys Cys Phe Gly Thr Phe Asn Asp Gln Lys Arg Gly Ile Cys Arg
                100                 105                 110

Pro Trp Thr Asn Cys Ser Leu Asp Gly Lys Ser Val Leu Val Asn Gly
                115                 120                 125

Thr Lys Glu Arg Asp Val Val Cys Gly Pro Ser Pro Ala Asp Leu Ser
                130                 135                 140

Pro Gly Ala Ser Ser Val Thr Pro Pro Ala Pro Ala Arg Glu Pro Gly
145                 150                 155                 160

His Ser Pro Gln

<210> SEQ ID NO 3
<211> LENGTH: 256
<212> TYPE: PRT
<213> ORGANISM: Mus musculus

<400> SEQUENCE: 3

Met Gly Asn Asn Cys Tyr Asn Val Val Ile Val Leu Leu Leu Val
  1               5                  10                  15

Gly Cys Glu Lys Val Gly Ala Val Gln Asn Ser Cys Asp Asn Cys Gln
                 20                  25                  30

Pro Gly Thr Phe Cys Arg Lys Tyr Asn Pro Val Cys Lys Ser Cys Pro
                 35                  40                  45

Pro Ser Thr Phe Ser Ser Ile Gly Gly Gln Pro Asn Cys Asn Ile Cys
 50                  55                  60

Arg Val Cys Ala Gly Tyr Phe Arg Phe Lys Lys Phe Cys Ser Ser Thr
 65                  70                  75                  80

His Asn Ala Glu Cys Glu Cys Ile Glu Gly Phe His Cys Leu Gly Pro
                 85                  90                  95

Gln Cys Thr Arg Cys Glu Lys Asp Cys Arg Pro Gly Gln Glu Leu Thr
                100                 105                 110

Lys Gln Gly Cys Lys Thr Cys Ser Leu Gly Thr Phe Asn Asp Gln Asn
                115                 120                 125

Gly Thr Gly Val Cys Arg Pro Trp Thr Asn Cys Ser Leu Asp Gly Arg
                130                 135                 140

Ser Val Leu Lys Thr Gly Thr Thr Glu Lys Asp Val Val Cys Gly Pro
145                 150                 155                 160

Pro Val Val Ser Phe Ser Pro Ser Thr Thr Ile Ser Val Thr Pro Glu
                165                 170                 175

Gly Gly Pro Gly Gly His Ser Leu Gln Val Leu Thr Leu Phe Leu Ala
                180                 185                 190

Leu Thr Ser Ala Leu Leu Leu Ala Leu Ile Phe Ile Thr Leu Leu Phe
                195                 200                 205

Ser Val Leu Lys Trp Ile Arg Lys Lys Phe Pro His Ile Phe Lys Gln
                210                 215                 220

Pro Phe Lys Lys Thr Thr Gly Ala Ala Gln Glu Glu Asp Ala Cys Ser
225                 230                 235                 240

Cys Arg Cys Pro Gln Glu Glu Glu Gly Gly Gly Gly Gly Tyr Glu Leu
```

<210> SEQ ID NO 4
<211> LENGTH: 165
<212> TYPE: PRT
<213> ORGANISM: Mus musculus

<400> SEQUENCE: 4

```
Ala Val Gln Asn Ser Cys Asp Asn Cys Gln Pro Gly Thr Phe Cys Arg
1               5                   10                  15

Lys Tyr Asn Pro Val Cys Lys Ser Cys Pro Pro Ser Thr Phe Ser Ser
            20                  25                  30

Ile Gly Gly Gln Pro Asn Cys Asn Ile Cys Arg Val Cys Ala Gly Tyr
        35                  40                  45

Phe Arg Phe Lys Lys Phe Cys Ser Ser Thr His Asn Ala Glu Cys Glu
    50                  55                  60

Cys Ile Glu Gly Phe His Cys Leu Gly Pro Gln Cys Thr Arg Cys Glu
65                  70                  75                  80

Lys Asp Cys Arg Pro Gly Gln Glu Leu Thr Lys Gln Gly Cys Lys Thr
                85                  90                  95

Cys Ser Leu Gly Thr Phe Asn Asp Gln Asn Gly Thr Gly Val Cys Arg
            100                 105                 110

Pro Trp Thr Asn Cys Ser Leu Asp Gly Arg Ser Val Leu Lys Thr Gly
        115                 120                 125

Thr Thr Glu Lys Asp Val Val Cys Gly Pro Pro Val Val Ser Phe Ser
130                 135                 140

Pro Ser Thr Thr Ile Ser Val Thr Pro Glu Gly Gly Pro Gly Gly His
145                 150                 155                 160

Ser Leu Gln Val Leu
                165
```

<210> SEQ ID NO 5
<211> LENGTH: 254
<212> TYPE: PRT
<213> ORGANISM: Macaca fascicularis

<400> SEQUENCE: 5

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
                85                  90                  95

Ala Glu Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
```

-continued

```
               145                 150                 155                 160
Ser Pro Ala Asp Leu Ser Pro Gly Ala Ser Ala Thr Pro Ala
                165                 170                 175

Pro Ala Arg Glu Pro Gly His Ser Pro Gln Ile Ile Phe Leu Ala
                180                 185                 190

Leu Thr Ser Thr Val Val Leu Phe Leu Phe Phe Leu Val Leu Arg
                195                 200                 205

Phe Ser Val Val Lys Arg Ser Arg Lys Lys Leu Leu Tyr Ile Phe Lys
210                 215                 220

Gln Pro Phe Met Arg Pro Val Gln Thr Thr Gln Glu Glu Asp Gly Cys
225                 230                 235                 240

Ser Cys Arg Phe Pro Glu Glu Glu Glu Gly Gly Cys Glu Leu
                245                 250

<210> SEQ ID NO 6
<211> LENGTH: 165
<212> TYPE: PRT
<213> ORGANISM: Macaca fascicularis

<400> SEQUENCE: 6

Ser Leu Gln Asp Leu Cys Ser Asn Cys Pro Ala Gly Thr Phe Cys Asp
1               5                   10                  15

Asn Asn Arg Ser Gln Ile Cys Ser Pro Cys Pro Pro Asn Ser Phe Ser
                20                  25                  30

Ser Ala Gly Gly Gln Arg Thr Cys Asp Ile Cys Arg Gln Cys Lys Gly
            35                  40                  45

Val Phe Lys Thr Arg Lys Glu Cys Ser Ser Thr Ser Asn Ala Glu Cys
50                  55                  60

Asp Cys Ile Ser Gly Tyr His Cys Leu Gly Ala Glu Cys Ser Met Cys
65                  70                  75                  80

Glu Gln Asp Cys Lys Gln Gly Gln Glu Leu Thr Lys Lys Gly Cys Lys
                85                  90                  95

Asp Cys Cys Phe Gly Thr Phe Asn Asp Gln Lys Arg Gly Ile Cys Arg
                100                 105                 110

Pro Trp Thr Asn Cys Ser Leu Asp Gly Lys Ser Val Leu Val Asn Gly
            115                 120                 125

Thr Lys Glu Arg Asp Val Val Cys Gly Pro Ser Pro Ala Asp Leu Ser
130                 135                 140

Pro Gly Ala Ser Ser Ala Thr Pro Pro Ala Pro Ala Arg Glu Pro Gly
145                 150                 155                 160

His Ser Pro Gln Ile
                165

<210> SEQ ID NO 7
<211> LENGTH: 5
<212> TYPE: PRT
<213> ORGANISM: Artificial Sequence
<220> FEATURE:
<223> OTHER INFORMATION: An artificially synthesized sequence

<400> SEQUENCE: 7

Thr Phe Thr Met Asn
1               5

<210> SEQ ID NO 8
<211> LENGTH: 17
<212> TYPE: PRT
<213> ORGANISM: Artificial Sequence
```

<220> FEATURE:
<223> OTHER INFORMATION: An artificially synthesized sequence

<400> SEQUENCE: 8

Ser Ile Ser Ser Lys Ser Thr Tyr Ile Glu Tyr Ala Asp Ser Phe Lys
1               5                   10                  15

Val

<210> SEQ ID NO 9
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 9

Ser Ile Ser Ser His Ser Ser Tyr Ile Glu Tyr Ala Asp Ser Phe Lys
1               5                   10                  15

Val

<210> SEQ ID NO 10
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 10

Ser Ile Ser Ser Ser Ser Ser Tyr Ile Glu Tyr Ala Asp Ser Phe Lys
1               5                   10                  15

Gly

<210> SEQ ID NO 11
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 11

Ser Ile Ser Ser Lys Ser Ser Tyr Ile Glu Tyr Ala Asp Ser Phe Lys
1               5                   10                  15

Val

<210> SEQ ID NO 12
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 12

Ser Ile Ser Ser Ser Ser Ser Tyr Ile Glu Tyr Ala Asp Ser Phe Lys
1               5                   10                  15

Leu

<210> SEQ ID NO 13
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 13

```
Ser Ile Ser Ser Lys Ser Ser Tyr Ile Tyr Tyr Ala Asp Ser Phe Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 14

Ser Ile Ser Ser Lys Gly Ser Tyr Ile Glu Tyr Ala Glu Gln Phe Lys
1               5                   10                  15

Val

<210> SEQ ID NO 15
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 15

Ser Ile Ser Ser Lys Gly Ser Tyr Ile Glu Tyr Ala Glu Ser Phe Lys
1               5                   10                  15

Val

<210> SEQ ID NO 16
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 16

Ser Ile Ser Ser Lys Gly Ser Tyr Ile Glu Tyr Ala Asp Ser Phe Lys
1               5                   10                  15

Val

<210> SEQ ID NO 17
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 17

Tyr Gly Ala Lys Asn Phe Leu Asn Trp Val Phe Asp Tyr
1               5                   10

<210> SEQ ID NO 18
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 18

Tyr Gly Pro Lys Asn Glu Leu Asn Trp Val Phe Asp Tyr
1               5                   10

<210> SEQ ID NO 19
```

```
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 19

Tyr Gly Lys Lys Asn Glu Leu Asn Trp Val Phe Asp Tyr
1               5                   10

<210> SEQ ID NO 20
<211> LENGTH: 13
<212> TYPE: PRT
<213> ORGANISM: Artificial Sequence
<220> FEATURE:
<223> OTHER INFORMATION: An artificially synthesized sequence

<400> SEQUENCE: 20

Tyr Gly Ile Lys Asn Glu Leu Asn Trp Val Phe Asp Tyr
1               5                   10

<210> SEQ ID NO 21
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 21

Thr Gly Thr Arg Tyr Asp Val Gly Tyr Tyr Glu Tyr Val Ser
1               5                   10

<210> SEQ ID NO 22
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 22

Thr Gly Thr Ser Thr Asp Val Gly Phe Tyr Asn Tyr Val Ser
1               5                   10

<210> SEQ ID NO 23
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 23

Thr Gly Thr Arg Thr Asp Val Gly Phe Tyr Glu Tyr Val Ser
1               5                   10

<210> SEQ ID NO 24
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 24

Thr Gly Thr Ser Thr Asp Val Gly Phe Tyr Glu Tyr Val Ser
1               5                   10

<210> SEQ ID NO 25
<211> LENGTH: 14
```

```
<212> TYPE: PRT
<213> ORGANISM: Artificial Sequence
<220> FEATURE:
<223> OTHER INFORMATION: An artificially synthesized sequence

<400> SEQUENCE: 25

Thr Gly Thr Ser Thr Asp Val Gly Tyr Tyr Glu Tyr Val Ser
1               5                   10

<210> SEQ ID NO 26
<211> LENGTH: 7
<212> TYPE: PRT
<213> ORGANISM: Artificial Sequence
<220> FEATURE:
<223> OTHER INFORMATION: An artificially synthesized sequence

<400> SEQUENCE: 26

Glu Thr Ser Lys Arg Leu Ser
1               5

<210> SEQ ID NO 27
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 27

Ser Ser Tyr Arg Tyr Glu His Gln Val Ser
1               5                   10

<210> SEQ ID NO 28
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 28

Ser Ser Tyr Arg Tyr Pro His Ile Val Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 29

Ser Ser Tyr Arg Tyr Glu Ala Gln Val Ser
1               5                   10

<210> SEQ ID NO 30
<211> LENGTH: 17
<212> TYPE: PRT
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: (5)..(5)
<223> OTHER INFORMATION: Xaa can be Lys, His or Ser
<220> FEATURE:
<221> NAME/KEY: misc_feature
<222> LOCATION: (6)..(6)
<223> OTHER INFORMATION: Xaa can be Ser or Gly
<220> FEATURE:
<221> NAME/KEY: misc_feature
```

```
<222> LOCATION: (7)..(7)
<223> OTHER INFORMATION: Xaa can be Thr or Ser
<220> FEATURE:
<221> NAME/KEY: misc_feature
<222> LOCATION: (10)..(10)
<223> OTHER INFORMATION: Xaa can Glu or Tyr
<220> FEATURE:
<221> NAME/KEY: misc_feature
<222> LOCATION: (13)..(13)
<223> OTHER INFORMATION: Xaa can be Asp or Glu
<220> FEATURE:
<221> NAME/KEY: misc_feature
<222> LOCATION: (14)..(14)
<223> OTHER INFORMATION: Xaa can be Ser or Gln
<220> FEATURE:
<221> NAME/KEY: misc_feature
<222> LOCATION: (17)..(17)
<223> OTHER INFORMATION: Xaa can be Val, Gly or Leu

<400> SEQUENCE: 30

Ser Ile Ser Ser Xaa Xaa Xaa Tyr Ile Xaa Tyr Ala Xaa Xaa Phe Lys
1               5                   10                  15

Xaa

<210> SEQ ID NO 31
<211> LENGTH: 13
<212> TYPE: PRT
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: (3)..(3)
<223> OTHER INFORMATION: Xaa can be Ala, Pro, Lys or Ile
<220> FEATURE:
<221> NAME/KEY: misc_feature
<222> LOCATION: (6)..(6)
<223> OTHER INFORMATION: Xaa can be Phe or Glu

<400> SEQUENCE: 31

Tyr Gly Xaa Lys Asn Xaa Leu Asn Trp Val Phe Asp Tyr
1               5                   10

<210> SEQ ID NO 32
<211> LENGTH: 14
<212> TYPE: PRT
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: (4)..(4)
<223> OTHER INFORMATION: Xaa can be Arg or Ser
<220> FEATURE:
<221> NAME/KEY: misc_feature
<222> LOCATION: (5)..(5)
<223> OTHER INFORMATION: Xaa can be Tyr or Thr
<220> FEATURE:
<221> NAME/KEY: misc_feature
<222> LOCATION: (9)..(9)
<223> OTHER INFORMATION: Xaa can be Tyr or Phe
<220> FEATURE:
<221> NAME/KEY: misc_feature
<222> LOCATION: (11)..(11)
<223> OTHER INFORMATION: Xaa can be Glu or Asn

<400> SEQUENCE: 32

Thr Gly Thr Xaa Xaa Asp Val Gly Xaa Tyr Xaa Tyr Val Ser
1               5                   10

<210> SEQ ID NO 33
<211> LENGTH: 10
```

```
<212> TYPE: PRT
<213> ORGANISM: Artificial Sequence
<220> FEATURE:
<223> OTHER INFORMATION: An artificially synthesized sequence
<220> FEATURE:
<221> NAME/KEY: misc_feature
<222> LOCATION: (6)..(6)
<223> OTHER INFORMATION: Xaa can be Glu or Pro
<220> FEATURE:
<221> NAME/KEY: misc_feature
<222> LOCATION: (7)..(7)
<223> OTHER INFORMATION: Xaa can be His or Ala
<220> FEATURE:
<221> NAME/KEY: misc_feature
<222> LOCATION: (8)..(8)
<223> OTHER INFORMATION: Xaa can be Gln or Ile

<400> SEQUENCE: 33

Ser Ser Tyr Arg Tyr Xaa Xaa Xaa Val Ser
1               5                   10

<210> SEQ ID NO 34
<211> LENGTH: 17
<212> TYPE: PRT
<213> ORGANISM: Artificial Sequence
<220> FEATURE:
<223> OTHER INFORMATION: An artificially synthesized sequence

<400> SEQUENCE: 34

Ser Ile Ser Ser Arg Ser Asn Tyr Lys Glu Tyr Ala Asp Ser Val Lys
1               5                   10                  15

Gly

<210> SEQ ID NO 35
<211> LENGTH: 30
<212> TYPE: PRT
<213> ORGANISM: Artificial Sequence
<220> FEATURE:
<223> OTHER INFORMATION: An artificially synthesized sequence

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 36
<211> LENGTH: 14
<212> TYPE: PRT
<213> ORGANISM: Artificial Sequence
<220> FEATURE:
<223> OTHER INFORMATION: An artificially synthesized sequence

<400> SEQUENCE: 36

Trp Val Arg Gln Ala Pro Gly Lys Gly Leu Glu Trp Val Ser
1               5                   10

<210> SEQ ID NO 37
<211> LENGTH: 32
<212> TYPE: PRT
<213> ORGANISM: Artificial Sequence
<220> FEATURE:
<223> OTHER INFORMATION: An artificially synthesized sequence

<400> SEQUENCE: 37

Arg Phe Thr Ile Ser Arg Asp Asn Ala Lys Asn Ser Leu Tyr Leu Gln
1               5                   10                  15
```

Met Asn Ser Leu Arg Ala Glu Asp Thr Ala Val Tyr Tyr Cys Ala Arg
            20                  25                  30

<210> SEQ ID NO 38
<211> LENGTH: 11
<212> TYPE: PRT
<213> ORGANISM: Artificial Sequence
<220> FEATURE:
<223> OTHER INFORMATION: An artificially synthesized sequence

<400> SEQUENCE: 38

Trp Gly Gln Gly Thr Leu Val Thr Val Ser Ser
1               5                   10

<210> SEQ ID NO 39
<211> LENGTH: 22
<212> TYPE: PRT
<213> ORGANISM: Artificial Sequence
<220> FEATURE:
<223> OTHER INFORMATION: An artificially synthesized sequence

<400> SEQUENCE: 39

Gln Ser Ala Leu Thr Gln Pro Pro Ser Ala Ser Gly Ser Pro Gly Gln
1               5                   10                  15

Thr Val Thr Ile Ser Cys
            20

<210> SEQ ID NO 40
<211> LENGTH: 15
<212> TYPE: PRT
<213> ORGANISM: Artificial Sequence
<220> FEATURE:
<223> OTHER INFORMATION: An artificially synthesized sequence

<400> SEQUENCE: 40

Trp Tyr Gln Gln His Pro Gly Lys Ala Pro Lys Leu Met Ile Tyr
1               5                   10                  15

<210> SEQ ID NO 41
<211> LENGTH: 32
<212> TYPE: PRT
<213> ORGANISM: Artificial Sequence
<220> FEATURE:
<223> OTHER INFORMATION: An artificially synthesized sequence

<400> SEQUENCE: 41

Gly Val Pro Asp Arg Phe Ser Gly Ser Lys Ser Gly Asn Thr Ala Ser
1               5                   10                  15

Leu Thr Val Ser Gly Leu Gln Ala Glu Asp Glu Ala Asp Tyr Tyr Cys
            20                  25                  30

<210> SEQ ID NO 42
<211> LENGTH: 10
<212> TYPE: PRT
<213> ORGANISM: Artificial Sequence
<220> FEATURE:
<223> OTHER INFORMATION: An artificially synthesized sequence

<400> SEQUENCE: 42

Phe Gly Gly Gly Thr Lys Leu Thr Val Leu
1               5                   10

<210> SEQ ID NO 43
<211> LENGTH: 122
<212> TYPE: PRT
<213> ORGANISM: Artificial Sequence

```
<220> FEATURE:
<223> OTHER INFORMATION: An artificially synthesized sequence

<400> SEQUENCE: 43

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Lys Ser Thr Tyr Ile Glu Tyr Ala Asp Ser Phe
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Phe Leu Asn Trp Val Phe Asp Tyr Trp
                100                 105                 110

Gly Gln Gly Thr Leu Val Thr Val Ser Ser
            115                 120

<210> SEQ ID NO 44
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 44

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser His Ser Ser Tyr Ile Glu Tyr Ala Asp Ser Phe
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Phe Leu Asn Trp Val Phe Asp Tyr Trp
                100                 105                 110

Gly Gln Gly Thr Leu Val Thr Val Ser Ser
            115                 120

<210> SEQ ID NO 45
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 45

Glu Val Gln Leu Val Glu Ser Gly Gly Gly Leu Val Lys Pro Gly Gly
1               5                   10                  15

Ser Leu Arg Leu Ser Cys Ala Ser Gly Phe Thr Phe Ser Thr Phe
            20                  25                  30
```

```
Thr Met Asn Trp Val Arg Gln Ala Pro Gly Lys Gly Leu Glu Trp Val
            35                  40                  45

Ser Ser Ile Ser Ser Ser Ser Tyr Ile Glu Tyr Ala Asp Ser Phe
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Ala Lys Asn Phe Leu Asn Trp Val Phe Asp Tyr Trp
                100                 105                 110

Gly Gln Gly Thr Leu Val Thr Val Ser Ser
            115                 120

<210> SEQ ID NO 46
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 46

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Phe
                 20                  25                  30

Thr Met Asn Trp Val Arg Gln Ala Pro Gly Lys Gly Leu Glu Trp Val
            35                  40                  45

Ser Ser Ile Ser Ser Lys Ser Ser Tyr Ile Glu Tyr Ala Asp Ser Phe
 50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Tyr Gly Pro Lys Asn Glu Leu Asn Trp Val Phe Asp Tyr Trp
                100                 105                 110

Gly Gln Gly Thr Leu Val Thr Val Ser Ser
            115                 120

<210> SEQ ID NO 47
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 47

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Thr Phe
                 20                  25                  30

Thr Met Asn Trp Val Arg Gln Ala Pro Gly Lys Gly Leu Glu Trp Val
            35                  40                  45

Ser Ser Ile Ser Ser Lys Ser Thr Tyr Ile Glu Tyr Ala Asp Ser Phe
 50                  55                  60

Lys Val Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

-continued

Ala Arg Tyr Gly Pro Lys Asn Glu Leu Asn Trp Val Phe Asp Tyr Trp
          100                 105                 110

Gly Gln Gly Thr Leu Val Thr Val Ser Ser
          115                 120

<210> SEQ ID NO 48
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 48

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Ser Ser Tyr Ile Glu Tyr Ala Asp Ser Phe
    50                  55                  60

Lys Leu Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Pro Lys Asn Glu Leu Asn Trp Val Phe Asp Tyr Trp
          100                 105                 110

Gly Gln Gly Thr Leu Val Thr Val Ser Ser
          115                 120

<210> SEQ ID NO 49
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 49

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Lys Ser Ser Tyr Ile Tyr Tyr Ala Asp Ser Phe
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Pro Lys Asn Glu Leu Asn Trp Val Phe Asp Tyr Trp
          100                 105                 110

Gly Gln Gly Thr Leu Val Thr Val Ser Ser
          115                 120

<210> SEQ ID NO 50
<211> LENGTH: 122
<212> TYPE: PRT

```
<213> ORGANISM: Artificial Sequence
<220> FEATURE:
<223> OTHER INFORMATION: An artificially synthesized sequence

<400> SEQUENCE: 50

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Lys Gly Ser Tyr Ile Glu Tyr Ala Glu Gln Phe
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Tyr Gly Lys Lys Asn Glu Leu Asn Trp Val Phe Asp Tyr Trp
            100                 105                 110

Gly Gln Gly Thr Leu Val Thr Val Ser Ser
        115                 120

<210> SEQ ID NO 51
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 51

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Lys Gly Ser Tyr Ile Glu Tyr Ala Glu Ser Phe
    50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Tyr Gly Ile Lys Asn Glu Leu Asn Trp Val Phe Asp Tyr Trp
            100                 105                 110

Gly Gln Gly Thr Leu Val Thr Val Ser Ser
        115                 120

<210> SEQ ID NO 52
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 52

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30
```

Thr Met Asn Trp Val Arg Gln Ala Pro Gly Lys Gly Leu Glu Trp Val
        35                  40                  45

Ser Ser Ile Ser Ser Lys Gly Ser Tyr Ile Glu Tyr Ala Asp Ser Phe
 50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Tyr Gly Ile Lys Asn Glu Leu Asn Trp Val Phe Asp Tyr Trp
                100                 105                 110

Gly Gln Gly Thr Leu Val Thr Val Ser Ser
            115                 120

<210> SEQ ID NO 53
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 53

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Lys Gly Ser Tyr Ile Glu Tyr Ala Glu Gln Phe
 50                  55                  60

Lys Val Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Tyr Gly Ala Lys Asn Phe Leu Asn Trp Val Phe Asp Tyr Trp
                100                 105                 110

Gly Gln Gly Thr Leu Val Thr Val Ser Ser
            115                 120

<210> SEQ ID NO 54
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 54

Gln Ser Ala Leu Thr Gln Pro Pro Ser Ala Ser Gly Ser Pro Gly Gln
1               5                   10                  15

Thr Val Thr Ile Ser Cys Thr Gly Thr Arg Tyr Asp Val Gly Tyr Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
 50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu

```
                85                  90                  95
His Gln Val Ser Phe Gly Gly Gly Thr Lys Leu Thr Val Leu
            100                 105                 110

<210> SEQ ID NO 55
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 55

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu
            100                 105                 110

<210> SEQ ID NO 56
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 56

Gln Ser Ala Leu Thr Gln Pro Pro Ser Ala Ser Gly Ser Pro Gly Gln
1               5                   10                  15

Thr Val Thr Ile Ser Cys Thr Gly Thr Arg Tyr Asp Val Gly Tyr Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Pro
                85                  90                  95

His Ile Val Ser Phe Gly Gly Gly Thr Lys Leu Thr Val Leu
            100                 105                 110

<210> SEQ ID NO 57
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 57

Gln Ser Ala Leu Thr Gln Pro Pro Ser Ala Ser Gly Ser Pro Gly Gln
1               5                   10                  15
```

Thr Val Thr Ile Ser Cys Thr Gly Thr Arg Tyr Asp Val Gly Tyr Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

Ala Gln Val Ser Phe Gly Gly Gly Thr Lys Leu Thr Val Leu
            100                 105                 110

<210> SEQ ID NO 58
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 58

Gln Ser Ala Leu Thr Gln Pro Pro Ser Ala Ser Gly Ser Pro Gly Gln
1               5                   10                  15

Thr Val Thr Ile Ser Cys Thr Gly Thr Arg Thr Asp Val Gly Phe Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu
            100                 105                 110

<210> SEQ ID NO 59
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 59

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu

-continued

```
                100                 105                 110
```

<210> SEQ ID NO 60
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 60

```
Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Tyr Tyr
            20                  25                  30

Glu Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu
            100                 105                 110
```

<210> SEQ ID NO 61
<211> LENGTH: 330
<212> TYPE: PRT
<213> ORGANISM: Homo sapiens

<400> SEQUENCE: 61

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 62
<211> LENGTH: 330
<212> TYPE: PRT
<213> ORGANISM: Homo sapiens

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                    245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 63
<211> LENGTH: 106
<212> TYPE: PRT
<213> ORGANISM: Homo sapiens

<400> SEQUENCE: 63

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 64
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125
```

```
Lys Pro Lys Asp Thr Leu Met Ile Ser Arg Thr Pro Glu Val Thr Cys
        130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Thr Ala Leu Pro Lys Pro Ile Glu Lys Thr Ile Ser Lys Ala Lys Gly
    210                 215                 220

Gln Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 65
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
                165                 170                 175
Glu Leu Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Thr Ala Leu Pro Lys Pro Ile Glu Lys Thr Ile Ser Lys Ala Lys Gly
    210                 215                 220
Gln Arg Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro
                325
```

<210> SEQ ID NO 66
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 66

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Tyr Leu Gly Gly Asp Ser Val Phe Leu Phe Pro Pro
        115                 120                 125
Lys Pro Lys Asp Val Leu Met Ile Ser Arg Thr Pro Glu Val Thr Cys
    130                 135                 140
Val Val Ile Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Pro Val Leu
            180                 185                 190
```

```
His Gln Asp Trp Leu Asn Gly Lys Glu Tyr Lys Cys Lys Val Ser Asn
            195                 200                 205

Lys Ala Leu Pro Lys Pro Ile Glu Lys Thr Ile Ser Lys Ala Lys Gly
        210                 215                 220

Gln Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 67
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 67

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Asp Asp Ser Val Phe Leu Phe Pro Pro
        115                 120                 125

Lys Pro Lys Asp Val Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220
```

```
Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 68
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
        195                 200                 205

Thr Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255
```

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 69
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 69

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Gly Asp Ser Val Phe Leu Phe Pro Pro
            115                 120                 125

Lys Pro Lys Asp Val Leu Met Ile Ser Arg Thr Pro Glu Val Thr Cys
130                 135                 140

Val Val Ile Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
            180                 185                 190

His Arg Asp Trp Leu Asn Gly Lys Glu Tyr Lys Cys Lys Val Ser Asn
            195                 200                 205

Lys Ala Leu Pro Lys Pro Ile Glu Lys Thr Ile Ser Lys Ala Lys Gly
        210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 70
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 70

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Asp Asp Ser Val Phe Leu Phe Pro Pro
        115                 120                 125

Lys Pro Lys Asp Val Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 71
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 71

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Thr Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 72

<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 72

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Thr Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 73
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Thr Ala Leu Pro Lys Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 74
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 74

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 75
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val Glu Pro Lys Ser Cys Asp Lys Thr His Thr Cys Pro Pro Cys
                100                 105                 110

Pro Ala Pro Glu Leu Trp Asn Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 76
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 76

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
```

```
                    85                  90                  95
Arg Val Glu Pro Lys Ser Cys Asp Lys Thr His Thr Cys Pro Pro Cys
                100                 105                 110

Pro Ala Pro Glu Leu Leu Asn Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 77
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 77

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Asn Gly Pro Ser Val Phe Leu Phe Pro Pro
```

```
                 115                 120                 125
Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 78
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75              80

Tyr Ile Cys Asn Val Asn His Lys Pro Ser Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
```

145                 150                 155                 160
Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Lys Pro Ile Glu Lys Thr Ile Ser Lys Ala Lys Gly
        210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255

Pro Ser Asp Ile Ala Val Glu Trp Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Lys Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                    325

<210> SEQ ID NO 79
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Leu Leu Asn Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu

```
                180                 185                 190
His Arg Asp Trp Leu Asn Gly Lys Glu Tyr Lys Cys Lys Val Ser Asn
            195                 200                 205
Lys Ala Leu Pro Lys Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 80
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 80

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Trp Asn Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser Asp Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Arg Asp Trp Leu Asn Gly Lys Glu Tyr Lys Cys Lys Val Ser Asn
            195                 200                 205
Lys Ala Leu Pro Lys Pro Ile Glu Lys Thr Ile Ser Lys Ala Lys Gly
```

```
                    210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 81
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 81

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                        245                 250                 255
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325

<210> SEQ ID NO 82
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 82

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Arg Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
            275                 280                 285
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 83
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 83

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
```

Gln Lys Ser Leu Ser Leu Ser Pro
            325

<210> SEQ ID NO 84
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 84

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Lys Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
            325

```
<210> SEQ ID NO 85
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 85

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
            180                 185                 190

His Arg Asp Trp Leu Asn Gly Lys Glu Tyr Lys Cys Lys Val Ser Asn
        195                 200                 205

Thr Ala Leu Pro Lys Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 86
<211> LENGTH: 15
<212> TYPE: PRT
<213> ORGANISM: Artificial Sequence
<220> FEATURE:
<223> OTHER INFORMATION: An artificially synthesized sequence
```

-continued

<400> SEQUENCE: 86

Gly Leu Asn Asp Ile Phe Glu Ala Gln Lys Ile Glu Trp His Glu
1               5                   10                  15

<210> SEQ ID NO 87
<211> LENGTH: 212
<212> TYPE: PRT
<213> ORGANISM: Artificial Sequence
<220> FEATURE:
<223> OTHER INFORMATION: An artificially synthesized sequence

<400> SEQUENCE: 87

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln His His His His His His
            180                 185                 190

Gly Gly Gly Gly Ser Gly Leu Asn Asp Ile Phe Glu Ala Gln Lys Ile
        195                 200                 205

Glu Trp His Glu
    210

<210> SEQ ID NO 88
<211> LENGTH: 641
<212> TYPE: PRT
<213> ORGANISM: Human gammaherpesvirus 4

<400> SEQUENCE: 88

Met Ser Asp Glu Gly Pro Gly Thr Gly Pro Gly Asn Gly Leu Gly Glu
1               5                   10                  15

Lys Gly Asp Thr Ser Gly Pro Glu Gly Ser Gly Gly Ser Gly Pro Gln
            20                  25                  30

Arg Arg Gly Gly Asp Asn His Gly Arg Gly Arg Gly Arg Gly Arg Gly
        35                  40                  45

Arg Gly Gly Gly Arg Pro Gly Ala Pro Gly Gly Ser Gly Ser Gly Pro
    50                  55                  60

Arg His Arg Asp Gly Val Arg Arg Pro Gln Lys Arg Pro Ser Cys Ile

-continued

```
                65                  70                  75                  80
        Gly Cys Lys Gly Thr His Gly Thr Gly Ala Gly Ala Gly Ala Gly
                        85                  90                  95
        Gly Ala Gly Ala Gly Gly Ala Gly Ala Gly Gly Gly Ala Gly Ala Gly
                        100                 105                 110
        Gly Gly Ala Gly Gly Ala Gly Gly Ala Gly Gly Ala Gly Ala Gly Gly
                        115                 120                 125
        Gly Ala Gly Ala Gly Gly Ala Gly Gly Ala Gly Gly Ala Gly Ala
                        130                 135                 140
        Gly Gly Gly Ala Gly Ala Gly Gly Ala Gly Gly Ala Gly Ala Gly
        145                 150                 155                 160
        Gly Gly Ala Gly Gly Ala Gly Gly Ala Gly Ala Gly Gly Ala Gly
                        165                 170                 175
        Ala Gly Gly Gly Ala Gly Gly Ala Gly Ala Gly Gly Gly Ala Gly Gly
                        180                 185                 190
        Ala Gly Gly Ala Gly Ala Gly Gly Ala Gly Ala Gly Gly Ala Gly
                        195                 200                 205
        Gly Ala Gly Gly Ala Gly Ala Gly Gly Ala Gly Ala Gly Gly Ala
                        210                 215                 220
        Gly Gly Ala Gly Gly Ala Gly Ala Gly Gly Ala Gly Ala Gly Gly Ala
        225                 230                 235                 240
        Gly Ala Gly Gly Ala Gly Ala Gly Gly Ala Gly Gly Ala Gly Ala Gly
                        245                 250                 255
        Gly Ala Gly Gly Ala Gly Ala Gly Gly Ala Gly Gly Ala Gly Ala Gly
                        260                 265                 270
        Gly Gly Ala Gly Gly Ala Gly Ala Gly Gly Ala Gly Gly Ala Gly
                        275                 280                 285
        Ala Gly Gly Ala Gly Gly Ala Gly Ala Gly Gly Ala Gly Gly Ala Gly
                        290                 295                 300
        Ala Gly Gly Ala Gly Gly Ala Gly Ala Gly Gly Ala Gly Gly Ala Gly
        305                 310                 315                 320
        Gly Ala Gly Ala Gly Gly Gly Gly Arg Gly Arg Gly Gly Ser Gly Gly
                        325                 330                 335
        Arg Gly Arg Gly Gly Ser Gly Gly Arg Gly Arg Gly Gly Ser Gly Gly
                        340                 345                 350
        Arg Arg Gly Arg Gly Arg Glu Arg Ala Arg Gly Gly Ser Arg Glu Arg
                        355                 360                 365
        Ala Arg Gly Arg Gly Arg Gly Arg Gly Glu Lys Arg Pro Arg Ser Pro
                        370                 375                 380
        Ser Ser Gln Ser Ser Ser Gly Ser Pro Pro Arg Arg Pro Pro Pro
        385                 390                 395                 400
        Gly Arg Arg Pro Phe Phe His Pro Val Gly Glu Ala Asp Tyr Phe Glu
                        405                 410                 415
        Tyr His Gln Glu Gly Gly Pro Asp Gly Glu Pro Asp Val Pro Pro Gly
                        420                 425                 430
        Ala Ile Glu Gln Gly Pro Ala Asp Asp Pro Gly Glu Gly Pro Ser Thr
                        435                 440                 445
        Gly Pro Arg Gly Gln Gly Asp Gly Gly Arg Arg Lys Lys Gly Gly Trp
                        450                 455                 460
        Phe Gly Lys His Arg Gly Gln Gly Gly Ser Asn Pro Lys Phe Glu Asn
        465                 470                 475                 480
        Ile Ala Glu Gly Leu Arg Ala Leu Leu Ala Arg Ser His Val Glu Arg
                        485                 490                 495
```

Thr Thr Asp Glu Gly Thr Trp Val Ala Gly Val Phe Val Tyr Gly Gly
                500                 505                 510

Ser Lys Thr Ser Leu Tyr Asn Leu Arg Arg Gly Thr Ala Leu Ala Ile
            515                 520                 525

Pro Gln Cys Arg Leu Thr Pro Leu Ser Arg Leu Pro Phe Gly Met Ala
        530                 535                 540

Pro Gly Pro Gly Pro Gln Pro Gly Pro Leu Arg Glu Ser Ile Val Cys
545                 550                 555                 560

Tyr Phe Met Val Phe Leu Gln Thr His Ile Phe Ala Glu Val Leu Lys
                565                 570                 575

Asp Ala Ile Lys Asp Leu Val Met Thr Lys Pro Ala Pro Thr Cys Asn
            580                 585                 590

Ile Arg Val Thr Val Cys Ser Phe Asp Asp Gly Val Asp Leu Pro Pro
        595                 600                 605

Trp Phe Pro Pro Met Val Glu Gly Ala Ala Glu Gly Asp Asp Gly
    610                 615                 620

Asp Asp Gly Asp Glu Gly Gly Asp Gly Asp Glu Gly Glu Glu Gly Gln
625                 630                 635                 640

Glu

<210> SEQ ID NO 89
<211> LENGTH: 399
<212> TYPE: PRT
<213> ORGANISM: Artificial Sequence
<220> FEATURE:
<223> OTHER INFORMATION: An artificially synthesized sequence

<400> SEQUENCE: 89

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Asp Ile Glu Gly Arg Met Asp Pro Lys Ser Cys Asp Lys
                165                 170                 175

Thr His Thr Cys Pro Pro Cys Pro Ala Pro Glu Leu Leu Gly Gly Pro
            180                 185                 190

Ser Val Phe Leu Phe Pro Pro Lys Pro Lys Asp Thr Leu Met Ile Ser
        195                 200                 205

```
Arg Thr Pro Glu Val Thr Cys Val Val Asp Val Ser His Glu Asp
            210                 215                 220

Pro Glu Val Lys Phe Asn Trp Tyr Val Asp Gly Val Glu Val His Asn
225                 230                 235                 240

Ala Lys Thr Lys Pro Arg Glu Glu Gln Tyr Asn Ser Thr Tyr Arg Val
                245                 250                 255

Val Ser Val Leu Thr Val Leu His Gln Asp Trp Leu Asn Gly Lys Glu
            260                 265                 270

Tyr Lys Cys Lys Val Ser Asn Lys Ala Leu Pro Ala Pro Ile Glu Lys
            275                 280                 285

Thr Ile Ser Lys Ala Lys Gly Gln Pro Arg Glu Pro Gln Val Tyr Thr
290                 295                 300

Leu Pro Pro Ser Arg Asp Glu Leu Thr Lys Asn Gln Val Ser Leu Thr
305                 310                 315                 320

Cys Leu Val Lys Gly Phe Tyr Pro Ser Asp Ile Ala Val Glu Trp Glu
                325                 330                 335

Ser Asn Gly Gln Pro Glu Asn Asn Tyr Lys Thr Thr Pro Pro Val Leu
            340                 345                 350

Asp Ser Asp Gly Ser Phe Phe Leu Tyr Ser Lys Leu Thr Val Asp Lys
            355                 360                 365

Ser Arg Trp Gln Gln Gly Asn Val Phe Ser Cys Ser Val Met His Glu
370                 375                 380

Ala Leu His Asn His Tyr Thr Gln Lys Ser Leu Ser Leu Ser Pro
385                 390                 395

<210> SEQ ID NO 90
<211> LENGTH: 442
<212> TYPE: PRT
<213> ORGANISM: Artificial Sequence
<220> FEATURE:
<223> OTHER INFORMATION: An artificially synthesized sequence

<400> SEQUENCE: 90

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175
```

Pro Ala Arg Glu Pro Gly His Ser Pro Gln Asp Ile Glu Gly Arg Met
                180                 185                 190

Asp Pro Lys Ser Cys Asp Lys Thr His Thr Cys Pro Pro Cys Pro Ala
            195                 200                 205

Pro Glu Leu Leu Gly Gly Pro Ser Val Phe Leu Phe Pro Pro Lys Pro
        210                 215                 220

Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
                245                 250                 255

Asp Gly Val Glu Val His Asn Ala Lys Thr Lys Pro Arg Glu Glu Gln
            260                 265                 270

Tyr Asn Ser Thr Tyr Arg Val Val Ser Val Leu Thr Val Leu His Gln
        275                 280                 285

Asp Trp Leu Asn Gly Lys Glu Tyr Lys Cys Lys Val Ser Asn Lys Ala
    290                 295                 300

Leu Pro Ala Pro Ile Glu Lys Thr Ile Ser Lys Ala Lys Gly Gln Pro
305                 310                 315                 320

Arg Glu Pro Gln Val Tyr Thr Leu Pro Pro Ser Arg Glu Glu Met Thr
                325                 330                 335

Lys Asn Gln Val Ser Leu Thr Cys Leu Val Lys Gly Phe Tyr Pro Ser
            340                 345                 350

Asp Ile Ala Val Glu Trp Glu Ser Asn Gly Gln Pro Glu Asn Asn Tyr
        355                 360                 365

Lys Thr Thr Pro Pro Val Leu Asp Ser Asp Gly Ser Phe Phe Leu Tyr
    370                 375                 380

Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
                405                 410                 415

Ser Leu Ser Leu Ser Pro Gly Gly Gly Gly Ser Gly Leu Asn Asp Ile
            420                 425                 430

Phe Glu Ala Gln Lys Ile Glu Trp His Glu
        435                 440

<210> SEQ ID NO 91
<211> LENGTH: 347
<212> TYPE: PRT
<213> ORGANISM: Artificial Sequence
<220> FEATURE:
<223> OTHER INFORMATION: An artificially synthesized sequence

<400> SEQUENCE: 91

Met Val Leu Ala Ser Ser Thr Thr Ser Ile His Thr Met Leu Leu Leu
1               5                   10                  15

Leu Leu Met Leu Ala Gln Pro Ala Met Ala Met Lys Asp Asn Thr Val
                20                  25                  30

Pro Leu Lys Leu Ile Ala Leu Leu Ala Asn Gly Glu Phe His Ser Gly
            35                  40                  45

Glu Gln Leu Gly Glu Thr Leu Gly Met Ser Arg Ala Ala Ile Asn Lys
        50                  55                  60

His Ile Gln Thr Leu Arg Asp Trp Gly Val Asp Val Phe Thr Val Pro
65                  70                  75                  80

Gly Lys Gly Tyr Ser Leu Pro Glu Pro Ile Gln Leu Leu Asn Ala Lys
                85                  90                  95

```
Gln Ile Leu Gly Gln Leu Asp Gly Gly Ser Val Ala Val Leu Pro Val
                100                 105                 110

Ile Asp Ser Thr Asn Gln Tyr Leu Leu Asp Arg Ile Gly Glu Leu Lys
            115                 120                 125

Ser Gly Asp Ala Cys Ile Ala Glu Tyr Gln Gln Ala Gly Arg Gly Arg
        130                 135                 140

Arg Gly Arg Lys Trp Phe Ser Pro Phe Gly Ala Asn Leu Tyr Leu Ser
145                 150                 155                 160

Met Phe Trp Arg Leu Glu Gln Gly Pro Ala Ala Ile Gly Leu Ser
                165                 170                 175

Leu Val Ile Gly Ile Val Met Ala Glu Val Leu Arg Lys Leu Gly Ala
                180                 185                 190

Asp Lys Val Arg Val Lys Trp Pro Asn Asp Leu Tyr Leu Gln Asp Arg
            195                 200                 205

Lys Leu Ala Gly Ile Leu Val Glu Leu Thr Gly Lys Thr Gly Asp Ala
        210                 215                 220

Ala Gln Ile Val Ile Gly Ala Gly Ile Asn Met Ala Met Arg Arg Val
225                 230                 235                 240

Glu Glu Ser Val Val Asn Gln Gly Trp Ile Thr Leu Gln Glu Ala Gly
                245                 250                 255

Ile Asn Leu Asp Arg Asn Thr Leu Ala Ala Met Leu Ile Arg Glu Leu
            260                 265                 270

Arg Ala Ala Leu Glu Leu Phe Glu Gln Glu Gly Leu Ala Pro Tyr Leu
        275                 280                 285

Ser Arg Trp Glu Lys Leu Asp Asn Phe Ile Asn Arg Pro Val Lys Leu
290                 295                 300

Ile Ile Gly Asp Lys Glu Ile Phe Gly Ile Ser Arg Gly Ile Asp Lys
                305                 310                 315                 320

Gln Gly Ala Leu Leu Leu Glu Gln Asp Gly Ile Ile Lys Pro Trp Met
            325                 330                 335

Gly Gly Glu Ile Ser Leu Arg Ser Ala Glu Lys
        340                 345

<210> SEQ ID NO 92
<211> LENGTH: 442
<212> TYPE: PRT
<213> ORGANISM: Artificial Sequence
<220> FEATURE:
<223> OTHER INFORMATION: An artificially synthesized sequence

<400> SEQUENCE: 92

Met Gly Asn Ser Cys Tyr Asn Ile Val Ala Thr Leu Leu Leu Val Leu
1               5                   10                  15

Asn Phe Glu Arg Thr Arg Ser Leu Gln Asp Leu Cys Ser Asn Cys Pro
            20                  25                  30

Ala Gly Thr Phe Cys Asp Asn Asn Arg Ser Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Lys Thr Arg Lys Glu Cys Ser Ser
65                  70                  75                  80

Thr Ser Asn Ala Glu Cys Asp Cys Ile Ser Gly Tyr His Cys Leu Gly
                85                  90                  95

Ala Glu Cys Ser Met Cys Glu Gln Asp Cys Lys Gln Gly Gln Glu Leu
            100                 105                 110
```

```
Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Ala Thr Pro Pro Ala
                165                 170                 175

Pro Ala Arg Glu Pro Gly His Ser Pro Gln Asp Ile Glu Gly Arg Met
            180                 185                 190

Asp Pro Lys Ser Cys Asp Lys Thr His Thr Cys Pro Pro Cys Pro Ala
            195                 200                 205

Pro Glu Leu Leu Gly Gly Pro Ser Val Phe Leu Phe Pro Pro Lys Pro
210                 215                 220

Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
                245                 250                 255

Asp Gly Val Glu Val His Asn Ala Lys Thr Lys Pro Arg Glu Glu Gln
            260                 265                 270

Tyr Asn Ser Thr Tyr Arg Val Val Ser Val Leu Thr Val Leu His Gln
        275                 280                 285

Asp Trp Leu Asn Gly Lys Glu Tyr Lys Cys Lys Val Ser Asn Lys Ala
            290                 295                 300

Leu Pro Ala Pro Ile Glu Lys Thr Ile Ser Lys Ala Lys Gly Gln Pro
305                 310                 315                 320

Arg Glu Pro Gln Val Tyr Thr Leu Pro Pro Ser Arg Glu Glu Met Thr
                325                 330                 335

Lys Asn Gln Val Ser Leu Thr Cys Leu Val Lys Gly Phe Tyr Pro Ser
            340                 345                 350

Asp Ile Ala Val Glu Trp Glu Ser Asn Gly Gln Pro Glu Asn Asn Tyr
        355                 360                 365

Lys Thr Thr Pro Pro Val Leu Asp Ser Asp Gly Ser Phe Phe Leu Tyr
370                 375                 380

Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
                405                 410                 415

Ser Leu Ser Leu Ser Pro Gly Gly Gly Gly Ser Gly Leu Asn Asp Ile
            420                 425                 430

Phe Glu Ala Gln Lys Ile Glu Trp His Glu
        435                 440

<210> SEQ ID NO 93
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 94
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 94

Glu Val Gln Leu Val Glu Ser Gly Gly Asp Leu Val Lys Pro Gly Gly
 1               5                  10                  15

Gly Leu Arg Leu Ser Cys Ala Ala Ser Gly Phe Thr Phe Ser Gly Tyr
             20                  25                  30

Thr Met Asn Trp Val Arg Gln Ala Pro Gly Lys Gly Leu Glu Trp Val
         35                  40                  45

Ser Ser Ile Ser Ser Arg Ser Asn Tyr Ala His Tyr Ala Asp Ser Val
     50                  55                  60
```

-continued

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Phe Gly Leu Lys Asn Phe Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 95
<211> LENGTH: 452
<212> TYPE: PRT
```

<213> ORGANISM: Artificial Sequence
<220> FEATURE:
<223> OTHER INFORMATION: An artificially synthesized sequence

<400> SEQUENCE: 95

```
Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser His
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Met Lys Asn Lys Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

-continued

```
                385                 390                 395                 400
Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
                435                 440                 445

Ser Pro Gly Lys
        450

<210> SEQ ID NO 96
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 96

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Thr Tyr Ala Thr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Leu Lys Asn Ser Leu Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
```

```
                290                 295                 300
Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 97
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 97

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
                20                  25                  30

Thr Met Asn Trp Val Arg Gln Ala Pro Gly Lys Gly Leu Glu Trp Val
                35                  40                  45

Ser Ser Ile Ser Ser Arg Ser Asn Tyr Lys Tyr Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Thr Lys Asn Ser Arg Asn Trp Val Phe Asp Tyr Trp
                100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
```

```
                195                 200                 205
His Lys Pro Ser Asn Thr Lys Val Asp Lys Val Glu Pro Lys Ser
    210                 215                 220

Cys Asp Lys Thr His Thr Cys Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 98
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 98

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Arg Tyr Ile Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Lys Lys Asn Tyr His Asn Trp Val Phe Asp Tyr Trp
```

100                 105                 110
Gly Gln Gly Thr Leu Val Thr Val Ser Ser Ala Ser Thr Lys Gly Pro
            115                 120                 125
Ser Val Phe Pro Leu Ala Pro Ser Ser Lys Ser Thr Ser Gly Gly Thr
        130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Glu
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Phe Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 99
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 99

Glu Val Gln Leu Val Glu Ser Gly Gly Asp Leu Val Lys Pro Gly Gly

-continued

```
1               5               10              15
Gly Leu Arg Leu Ser Cys Ala Ala Ser Gly Phe Thr Phe Ser Ser His
                20                  25                  30

Thr Met Asn Trp Val Arg Gln Ala Pro Gly Lys Gly Leu Glu Trp Val
                35                  40                  45

Ser Ser Ile Ser Ser Arg Ser Asn Tyr Lys Asp Tyr Ala Asp Ser Val
            50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Ile Lys Asn His Met Asn Trp Val Phe Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val
            260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430
```

```
Met His Glu Ala Leu His Asn His Tyr Thr Gln Lys Ser Leu Ser Leu
        435                 440                 445
Ser Pro Gly Lys
    450

<210> SEQ ID NO 100
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 100

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Thr Tyr Ala Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Lys Lys Asn Met Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335
```

```
Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
        450

<210> SEQ ID NO 101
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 101

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Leu Lys Asn Ser Leu Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240
```

```
Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
    450

<210> SEQ ID NO 102
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 102

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser His
            20                  25                  30

Thr Met Asn Trp Val Arg Gln Ala Pro Gly Lys Gly Leu Glu Trp Ile
            35                  40                  45

Ser Ser Ile Ser Ser Arg Ser Asn Tyr Lys Ser Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly His Lys Asn Met His Asn Trp Val Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
        130                 135                 140
```

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Glu
        260                 265                 270

His Glu Asp Pro Glu Val Lys Phe Asn Trp Tyr Val Asp Gly Val Glu
    275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys
    450

<210> SEQ ID NO 103
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 103

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

```
Ser Ser Ile Ser Ser Arg Ser Asn Tyr Ile Tyr Tyr Ala Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Phe Gly Leu Lys Asn Glu Met Asn Trp Val Phe Asp Tyr Trp
                100                 105                 110

Gly Gln Gly Thr Leu Val Thr Val Ser Ser Ala Ser Thr Lys Gly Pro
                115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
            370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450
```

<210> SEQ ID NO 104
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 104

```
Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ile Lys Asn Glu Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365
```

```
Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 105
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 105

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Arg Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Tyr Gly Gly Lys Asn Ile Leu Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
            165                 170                 175

Ala Val Leu Gln Ser Ser Gly Leu Tyr Ser Leu Ser Ser Val Val Thr
        180                 185                 190

Val Pro Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270
```

```
His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 106
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 106

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Lys Lys Asn Asp Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 107
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 107

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Lys Phe Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95
Ala Arg Phe Gly Val Lys Asn Asn Met Asn Trp Val Phe Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Glu
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Phe Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
Ser Pro Gly Lys
    450

<210> SEQ ID NO 108
<211> LENGTH: 452
<212> TYPE: PRT
<213> ORGANISM: Artificial Sequence
<220> FEATURE:
<223> OTHER INFORMATION: An artificially synthesized sequence
```

<400> SEQUENCE: 108

```
Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Gly Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Ala Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Val Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
```

```
                    405                 410                 415
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 109
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 109

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Lys Ser Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Phe Met Asn Trp Val Phe Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

```
              305                 310                 315                 320
    Gly Lys Glu Tyr Lys Cys Lys Val Ser Asn Lys Ala Phe Pro Ala Pro
                    325                 330                 335

Ile Glu Lys Thr Ile Ser Lys Ala Lys Gly Gln Pro Arg Glu Pro Gln
                    340                 345                 350

Val Tyr Thr Leu Pro Pro Ser Arg Asp Glu Leu Thr Lys Asn Gln Val
                    355                 360                 365

Ser Leu Thr Cys Leu Val Lys Gly Phe Tyr Pro Ser Asp Ile Ala Val
                    370                 375                 380

Glu Trp Glu Ser Asn Gly Gln Pro Glu Asn Asn Tyr Lys Thr Thr Pro
    385                 390                 395                 400

Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                    420                 425                 430

Met His Glu Ala Leu His Asn His Tyr Thr Gln Lys Ser Leu Ser Leu
                    435                 440                 445

Ser Pro Gly Lys
                450

<210> SEQ ID NO 110
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 110

Glu Val Gln Leu Val Glu Ser Gly Gly Asp Leu Val Lys Pro Gly Gly
    1               5                   10                  15

Gly Leu Arg Leu Ser Cys Ala Ala Ser Gly Phe Thr Phe Ser Gly Tyr
                    20                  25                  30

Thr Met Asn Trp Val Arg Gln Ala Pro Gly Lys Gly Leu Glu Trp Val
                    35                  40                  45

Ser Ser Ile Ser Ser Arg Ser Asn Tyr Lys His Tyr Ala Asp Ser Val
    50                  55                  60

Lys Gly Arg Phe Thr Ile Ser Arg Asp Asn Ala Lys Asn Ser Leu Tyr
    65                  70                  75                  80

Leu Gln Met Asn Ser Leu Arg Ala Glu Asp Thr Ala Val Tyr Tyr Cys
                    85                  90                  95

Ala Arg Phe Gly Leu Lys Asn Glu Arg Asn Trp Val Phe Asp Tyr Trp
                    100                 105                 110

Gly Gln Gly Thr Leu Val Thr Val Ser Ser Ala Ser Thr Lys Gly Pro
                    115                 120                 125

Ser Val Phe Pro Leu Ala Pro Ser Ser Lys Ser Thr Ser Gly Gly Thr
                    130                 135                 140

Ala Ala Leu Gly Cys Leu Val Lys Asp Tyr Phe Pro Glu Pro Val Thr
    145                 150                 155                 160

Val Ser Trp Asn Ser Gly Ala Leu Thr Ser Gly Val His Thr Phe Pro
                    165                 170                 175

Ala Val Leu Gln Ser Ser Gly Leu Tyr Ser Leu Ser Ser Val Val Thr
                    180                 185                 190

Val Pro Ser Ser Ser Leu Gly Thr Gln Thr Tyr Ile Cys Asn Val Asn
                    195                 200                 205

His Lys Pro Ser Asn Thr Lys Val Asp Lys Lys Val Glu Pro Lys Ser
```

```
            210                 215                 220
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
                260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly Lys
    450

<210> SEQ ID NO 111
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 111

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Thr Tyr
                20                  25                  30

Thr Met Asn Trp Val Arg Gln Ala Pro Gly Lys Gly Leu Glu Trp Val
                35                  40                  45

Ser Ser Ile Ser Ser Arg Ser Asn Tyr Lys Phe Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Phe Gly Gly Lys Asn Asn Met Asn Trp Val Phe Asp Tyr Trp
                100                 105                 110

Gly Gln Gly Thr Leu Val Thr Val Ser Ser Ala Ser Thr Lys Gly Pro
```

```
            115                 120                 125
Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Glu
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
            290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys
    450

<210> SEQ ID NO 112
<211> LENGTH: 452
<212> TYPE: PRT
<213> ORGANISM: Artificial Sequence
<220> FEATURE:
<223> OTHER INFORMATION: An artificially synthesized sequence

<400> SEQUENCE: 112

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
```

-continued

```
                20                  25                  30
Thr Met Asn Trp Val Arg Gln Ala Pro Gly Lys Gly Leu Glu Trp Val
            35                  40                  45
Ser Ser Ile Ser Ser Arg Ser Asn Tyr Ala Asp Tyr Ala Asp Ser Val
        50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Tyr Gly Ala Lys Asn Glu Met Asn Trp Val Phe Asp Tyr Trp
            100                 105                 110
Gly Gln Gly Thr Leu Val Thr Val Ser Ser Ala Ser Thr Lys Gly Pro
        115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Ile Cys Asn Val Asn
        195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Glu
            260                 265                 270
His Glu Asp Pro Glu Val Lys Phe Asn Trp Tyr Val Asp Gly Val Glu
        275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Phe Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Asp Glu Leu Thr Lys Asn Gln Val
        355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
        435                 440                 445
```

```
Ser Pro Gly Lys
    450

<210> SEQ ID NO 113
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 113

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Gly Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ala Tyr Asp
                85                  90                  95

Ala Gln Leu Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 114
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 114

Gln Ser Ala Leu Thr Gln Pro Pro Ser Ala Ser Gly Ser Pro Gly Gln
1               5                   10                  15

Thr Val Asn Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
```

```
                65                  70                  75                  80
Gln Ala Glu Asp Glu Ala Asp Tyr Phe Cys Ser Thr Tyr Arg Tyr Asn
                    85                  90                  95

Asn Leu Leu Ala Phe Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                    165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
            210                 215

<210> SEQ ID NO 115
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 115

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Lys Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Tyr Ser Tyr Asp
                    85                  90                  95

Glu Ser Val Ala Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
                115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Pro Ser Lys Gln Ser Asn Asn Lys Tyr
                    165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Thr Glu Cys Ser
```

<210> SEQ ID NO 116
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 116

```
Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ala Tyr Thr
                85                  90                  95

Lys Asn Val Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 117
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 117

```
Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80
```

```
Gln Ala Glu Asp Glu Ala Asp Tyr Phe Cys Ser Val Tyr Arg Tyr Asn
                85                  90                  95

Asp Gln Val Ala Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 118
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 118

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
                20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65              70                  75                  80

Gln Ala Glu Asp Glu Ala Asp Tyr Phe Cys Ser Thr Tyr Ala Tyr Ser
                85                  90                  95

Thr Ile Val Met Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215
```

<210> SEQ ID NO 119
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 119

```
Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Tyr Arg Tyr Arg
                85                  90                  95

Asp Tyr Val Gly Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 120
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 120

```
Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ser Gly Ala
                85                  90                  95
```

```
Ser Ile Leu Leu Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 121
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 121

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Tyr Arg Tyr Asp
                85                  90                  95

Gln Asn Val Ala Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 122
```

```
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 122

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Val Tyr Ser Tyr Ile
                85                  90                  95

Tyr Tyr Val Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 123
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 123

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Val Tyr Arg Tyr Ser
                85                  90                  95

Leu Gly Val Gly Phe Gly Gly Gly Thr Lys Leu Thr Val Leu Gly Gln
```

```
                  100                 105                 110
Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 124
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 124

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ser Ser Asp
                85                  90                  95

Thr His Val Gly Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 125
<211> LENGTH: 216
<212> TYPE: PRT
```

<213> ORGANISM: Artificial Sequence
<220> FEATURE:
<223> OTHER INFORMATION: An artificially synthesized sequence

<400> SEQUENCE: 125

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Glu Tyr Thr
                85                  90                  95

Glu Ser Val Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 126
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 126

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Glu Tyr Ile
                85                  90                  95

Glu Ser Val Leu Phe Gly Gly Gly Thr Lys Leu Thr Val Leu Gly Gln
            100                 105                 110

```
Pro Lys Ala Ala Pro Ser Val Thr Leu Phe Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 127
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 127

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Gly Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Ala Tyr Thr
                85                  90                  95

Lys Asn Val Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 128
<211> LENGTH: 216
<212> TYPE: PRT
<213> ORGANISM: Artificial Sequence
<220> FEATURE:
```

<223> OTHER INFORMATION: An artificially synthesized sequence

<400> SEQUENCE: 128

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Asp Val Gly Phe Tyr
            20                  25                  30

Asn Tyr Val Ser Trp Tyr Gln Gln His Pro Gly Lys Ala Pro Lys Leu
            35                  40                  45

Met Ile Tyr Tyr Thr Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Arg Tyr Asp
                85                  90                  95

His Gln Val Ser Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 129
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 129

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Asp Val Gly Phe Tyr
            20                  25                  30

Asn Tyr Val Ser Trp Tyr Gln Gln His Pro Gly Lys Ala Pro Lys Leu
            35                  40                  45

Met Ile Tyr Glu Val Ser Lys Arg Pro Ser Gly Val Pro Asp Arg Phe
        50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Tyr Thr Tyr Asn
                85                  90                  95

Ala Leu Leu Ala Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

```
Leu Gln Ala Asn Lys Ala Thr Leu Val Cys Leu Ile Ser Asp Phe Tyr
        130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 130
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 130

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Ser Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Glu Tyr Ile
                85                  90                  95

Glu Ser Val Leu Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
        210                 215

<210> SEQ ID NO 131
<211> LENGTH: 216
<212> TYPE: PRT
<213> ORGANISM: Artificial Sequence
<220> FEATURE:
<223> OTHER INFORMATION: An artificially synthesized sequence
```

<400> SEQUENCE: 131

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Ser Tyr Thr Tyr Asp
                85                  90                  95

Gln Gln Leu Met Phe Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 132
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 132

Glu Val Gln Leu Val Glu Ser Gly Gly Gly Leu Val Lys Pro Gly Gly
1               5                   10                  15

Ser Leu Arg Leu Ser Cys Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Lys Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Phe Leu Asn Trp Val Phe Asp Tyr Trp
            100                 105                 110

Gly Gln Gly Thr Leu Val Thr Val Ser Ser
        115                 120

```
<210> SEQ ID NO 133
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 133
```

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Asp Val Gly Phe Tyr
            20                  25                  30

Asn Tyr Val Ser Trp Tyr Gln Gln His Pro Gly Lys Ala Pro Lys Leu
            35                  40                  45

Met Ile Tyr Tyr Thr Ser Lys Arg Pro Ser Gly Val Pro Asp Arg Phe
50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu
            100                 105                 110

```
<210> SEQ ID NO 134
<211> LENGTH: 450
<212> TYPE: PRT
<213> ORGANISM: Artificial Sequence
<220> FEATURE:
<223> OTHER INFORMATION: An artificially synthesized sequence

<400> SEQUENCE: 134
```

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
            35                  40                  45

Ser Ser Ile Ser Ser Arg Ser Asn Tyr Lys Glu Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Phe Leu Asn Trp Val Phe Asp Tyr Trp
            100                 105                 110

Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Glu
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Phe Pro Ala Pro
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro
    450

<210> SEQ ID NO 135
<211> LENGTH: 216
<212> TYPE: PRT
<213> ORGANISM: Artificial Sequence
<220> FEATURE:
<223> OTHER INFORMATION: An artificially synthesized sequence

<400> SEQUENCE: 135

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu Gly Gln
            100                 105                 110

Pro Lys Ala Ala Pro Ser Val Thr Leu Phe Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 136
<211> LENGTH: 122
<212> TYPE: PRT
<213> ORGANISM: Artificial Sequence
<220> FEATURE:
<223> OTHER INFORMATION: An artificially synthesized sequence

<400> SEQUENCE: 136

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Thr Phe
            20                  25                  30

Thr Met Asn Trp Val Arg Gln Ala Pro Gly Lys Gly Leu Glu Trp Val
        35                  40                  45

Ser Ser Ile Ser Ser Arg Ser Asn Tyr Lys Glu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Ala Lys Asn Phe Leu Asn Trp Val Phe Asp Tyr Trp
            100                 105                 110

Gly Gln Gly Thr Leu Val Thr Val Ser Ser
            115                 120

<210> SEQ ID NO 137
<211> LENGTH: 110
<212> TYPE: PRT
<213> ORGANISM: Artificial Sequence
<220> FEATURE:
<223> OTHER INFORMATION: An artificially synthesized sequence

<400> SEQUENCE: 137

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Phe Tyr
            20                  25                  30

Asn Tyr Val Ser Trp Tyr Gln Gln His Pro Gly Lys Ala Pro Lys Leu
        35                  40                  45

Met Ile Tyr Glu Thr Ser Lys Arg Leu Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Arg Tyr Glu
                85                  90                  95

His Gln Val Ser Phe Gly Gly Gly Thr Lys Leu Thr Val Leu
            100                 105                 110

<210> SEQ ID NO 138
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 138

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Glu Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 139
<211> LENGTH: 121
<212> TYPE: PRT
<213> ORGANISM: Artificial Sequence
<220> FEATURE:
<223> OTHER INFORMATION: An artificially synthesized sequence

<400> SEQUENCE: 139

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser
        115                 120
```

<210> SEQ ID NO 140
<211> LENGTH: 109
<212> TYPE: PRT
<213> ORGANISM: Artificial Sequence
<220> FEATURE:
<223> OTHER INFORMATION: An artificially synthesized sequence

<400> SEQUENCE: 140

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105
```

<210> SEQ ID NO 141
<211> LENGTH: 107
<212> TYPE: PRT
<213> ORGANISM: Homo sapiens

<400> SEQUENCE: 141

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 142
<211> LENGTH: 116
<212> TYPE: PRT
<213> ORGANISM: Artificial Sequence
<220> FEATURE:
<223> OTHER INFORMATION: An artificially synthesized sequence

<400> SEQUENCE: 142

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Ser Thr Tyr
                20                  25                  30

Trp Ile Ser Trp Val Arg Gln Met Pro Gly Lys Gly Leu Glu Trp Met
            35                  40                  45

Gly Lys Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Gly Ile Phe Asp Tyr Trp Gly Gln Gly Thr Leu Val
                100                 105                 110

Thr Val Ser Ser
            115

<210> SEQ ID NO 143
<211> LENGTH: 108
<212> TYPE: PRT
<213> ORGANISM: Artificial Sequence
<220> FEATURE:
<223> OTHER INFORMATION: An artificially synthesized sequence

<400> SEQUENCE: 143

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
                20                  25                  30

His Trp Tyr Gln Gln Lys Pro Gly Gln Ser Pro Val Leu Val Ile Tyr
            35                  40                  45

Gln Asp Lys Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu
```

<210> SEQ ID NO 144
<211> LENGTH: 324
<212> TYPE: PRT
<213> ORGANISM: Mus musculus

<400> SEQUENCE: 144

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 145
<211> LENGTH: 324
<212> TYPE: PRT
<213> ORGANISM: Artificial Sequence
<220> FEATURE:
<223> OTHER INFORMATION: An artificially synthesized sequence

<400> SEQUENCE: 145

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Asp Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 146
<211> LENGTH: 324
<212> TYPE: PRT
<213> ORGANISM: Artificial Sequence
<220> FEATURE:
<223> OTHER INFORMATION: An artificially synthesized sequence

<400> SEQUENCE: 146

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr

```
                    20                  25                  30
Phe Pro Glu Pro Val Thr Val Thr Trp Asn Ser Gly Ser Leu Ser Ser
                35                  40                  45

Gly Val His Thr Phe Pro Ala Val Leu Gln Ser Asp Leu Tyr Thr Leu
            50                  55                  60

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Glu Pro Asn
            100                 105                 110

Glu Val Glu Asp Val Phe Ile Phe Pro Pro Lys Pro Lys Asp Val Leu
        115                 120                 125

Thr Ile Thr Leu Thr Pro Lys Val Thr Cys Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asp Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 147
<211> LENGTH: 107
<212> TYPE: PRT
<213> ORGANISM: Mus musculus

<400> SEQUENCE: 147

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
```

```
                65                  70                  75                  80
Arg His Asn Ser Tyr Thr Cys Glu Ala Thr His Lys Thr Ser Thr Ser
                85                  90                  95
Pro Ile Val Lys Ser Phe Asn Arg Asn Glu Cys
            100                 105

<210> SEQ ID NO 148
<211> LENGTH: 106
<212> TYPE: PRT
<213> ORGANISM: Mus musculus

<400> SEQUENCE: 148

Gly Gln Pro Lys Ser Ser Pro Ser Val Thr Leu Phe Pro Pro Ser Ser
1               5                   10                  15
Glu Glu Leu Glu Thr Asn Lys Ala Thr Leu Val Cys Thr Ile Thr Asp
            20                  25                  30
Phe Tyr Pro Gly Val Val Thr Val Asp Trp Lys Val Asp Gly Thr Pro
        35                  40                  45
Val Thr Gln Gly Met Glu Thr Thr Gln Pro Ser Lys Gln Ser Asn Asn
    50                  55                  60
Lys Tyr Met Ala Ser Ser Tyr Leu Thr Leu Thr Ala Arg Ala Trp Glu
65                  70                  75                  80
Arg His Ser Ser Tyr Ser Cys Gln Val Thr His Glu Gly His Thr Val
                85                  90                  95
Glu Lys Ser Leu Ser Arg Ala Asp Cys Ser
            100                 105

<210> SEQ ID NO 149
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 149

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Tyr Leu Gly Gly Asp Ser Val Phe Leu Phe Pro Pro
        115                 120                 125
Lys Pro Lys Asp Val Leu Met Ile Ser Arg Thr Pro Glu Val Thr Cys
    130                 135                 140
Val Val Ile Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Pro Val Leu
                180                 185                 190

His Gln Asp Trp Leu Asn Gly Lys Glu Tyr Lys Cys Lys Val Ser Asn
            195                 200                 205

Lys Ala Leu Pro Lys Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 150
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 150

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Tyr Leu Gly Asp Asp Ser Val Phe Leu Phe Pro Pro
        115                 120                 125

Lys Pro Lys Asp Val Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Pro Val Leu
            180                 185                 190

His Gln Asp Trp Leu Asn Gly Lys Glu Tyr Lys Cys Lys Val Ser Asn
        195                 200                 205
```

```
Lys Ala Leu Pro Lys Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
            325
```

<210> SEQ ID NO 151
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 151

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Asp Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Ile Asp Val Ala Glu Glu Asp Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240
```

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 152
<211> LENGTH: 116
<212> TYPE: PRT
<213> ORGANISM: Artificial Sequence
<220> FEATURE:
<223> OTHER INFORMATION: An artificially synthesized sequence

<400> SEQUENCE: 152

Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ser Tyr
            20                  25                  30

Trp Met His Trp Val Asn Gln Arg Pro Gly Gln Gly Leu Glu Trp Ile
        35                  40                  45

Gly Met Ile Asp Pro Ser Tyr Ser Glu Thr Arg Leu Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Leu Tyr Gly Asn Tyr Phe Asp Tyr Trp Gly Gln Gly Thr Thr Leu
            100                 105                 110

Thr Val Ser Ser
        115

<210> SEQ ID NO 153
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 153

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                    85                  90                  95
Lys Val Glu Pro Lys Ser Cys Asp Lys Thr His Thr Cys Pro Pro Cys
                100                 105                 110

Pro Ala Pro Glu Leu Leu Asn Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 154
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 154

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
```

```
                115                 120                 125
Lys Pro Lys Asp Thr Leu Met Ile Ser Arg Thr Pro Glu Val Thr Cys
130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Leu Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Thr Ala Leu Pro Lys Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 155
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 155

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Asn Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Asp Glu Asp Pro Glu Val Lys Phe Asn Trp
```

```
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Pro Lys Pro Ile Glu Lys Thr Ile Ser Lys Ala Lys Gly
210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro
                325

<210> SEQ ID NO 156
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 156

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
                100                 105                 110
Pro Ala Pro Glu Leu Trp Asn Gly Pro Ser Val Phe Leu Phe Pro Pro
                115                 120                 125
Lys Pro Lys Asp Thr Leu Met Ile Ser Arg Thr Pro Glu Val Thr Cys
                130                 135                 140
Val Val Val Asp Val Ser Asp Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Leu Tyr Asn Ser Thr Tyr Arg Val Val Ser Val Leu Thr Val Leu
```

```
                 180                 185                 190
His Gln Asp Trp Leu Asn Gly Lys Glu Tyr Lys Cys Lys Val Ser Asn
            195                 200                 205

Thr Ala Leu Pro Lys Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 157
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 157

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Trp Asn Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser Asp Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Lys Pro Ile Glu Lys Thr Ile Ser Lys Ala Lys Gly
    210                 215                 220
```

```
                   210                 215                 220
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro
                325
```

<210> SEQ ID NO 158
<211> LENGTH: 107
<212> TYPE: PRT
<213> ORGANISM: Artificial Sequence
<220> FEATURE:
<223> OTHER INFORMATION: An artificially synthesized sequence

<400> SEQUENCE: 158

```
Asp Ile Gln Met Thr Gln Ser Ser Ser Phe Ser Val Ser Leu Gly
1               5                   10                  15

Asp Arg Val Thr Ile Thr Cys Lys Ala Ser Glu Asp Ile Tyr Asn Arg
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Tyr
                85                  90                  95

Thr Phe Gly Gly Gly Thr Lys Leu Glu Val Lys
            100                 105
```

<210> SEQ ID NO 159
<211> LENGTH: 325
<212> TYPE: PRT
<213> ORGANISM: Artificial Sequence
<220> FEATURE:
<223> OTHER INFORMATION: An artificially synthesized sequence

<400> SEQUENCE: 159

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80
```

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu
                325

<210> SEQ ID NO 160
<211> LENGTH: 319
<212> TYPE: PRT
<213> ORGANISM: Artificial Sequence
<220> FEATURE:
<223> OTHER INFORMATION: An artificially synthesized sequence

<400> SEQUENCE: 160

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Ile Glu Gly Arg Met Asp Pro Lys Ser Cys Asp Lys Thr His Thr Cys
65                  70                  75                  80

Pro Pro Cys Pro Ala Pro Glu Leu Leu Gly Gly Pro Ser Val Phe Leu
                85                  90                  95

Phe Pro Pro Lys Pro Lys Asp Thr Leu Met Ile Ser Arg Thr Pro Glu
            100                 105                 110

```
Val Thr Cys Val Val Asp Val Ser His Glu Asp Pro Glu Val Lys
            115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
    195                 200                 205

Arg Glu Glu Met Thr Lys Asn Gln Val Ser Leu Thr Cys Leu Val Lys
210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
    275                 280                 285

His Tyr Thr Gln Lys Ser Leu Ser Leu Ser Pro Gly Gly Gly Gly Ser
290                 295                 300

Gly Leu Asn Asp Ile Phe Glu Ala Gln Lys Ile Glu Trp His Glu
305                 310                 315

<210> SEQ ID NO 161
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 161

Gln Val Gln Leu Val Gln Ser Gly Ala Glu Val Lys Lys Pro Gly Ser
1               5                   10                  15

Ser Val Lys Val Ser Cys Lys Ala Ser Gly Gly Glu Phe Ser Asn Tyr
            20                  25                  30

Phe Ile Ser Trp Val Arg Gln Ala Pro Gly Gln Gly Leu Glu Trp Met
        35                  40                  45

Gly Met Val His Pro Ile Glu Gly Trp Ala Val Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Pro Val Phe Cys Cys Pro Arg Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160
```

```
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Glu His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Phe Pro Ala
                325                 330                 335
Pro Ile Glu Lys Thr Ile Ser Lys Ala Lys Gly Gln Pro Arg Glu Pro
            340                 345                 350
Gln Val Tyr Thr Leu Pro Pro Ser Arg Asp Glu Leu Thr Lys Asn Gln
        355                 360                 365
Val Ser Leu Thr Cys Leu Val Lys Gly Phe Tyr Pro Ser Asp Ile Ala
    370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Pro
    450

<210> SEQ ID NO 162
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 162

Gln Val Gln Leu Val Gln Ser Gly Ala Glu Val Lys Lys Pro Gly Ser
1               5                   10                  15
Ser Val Lys Val Ser Cys Lys Ala Ser Gly Gly Phe Ser Ser Tyr
            20                  25                  30
Gly Ile Ser Trp Val Arg Gln Ala Pro Gly Gln Gly Leu Glu Trp Met
        35                  40                  45
Gly Ala Leu Phe Pro Ile Ser Ser Gln Ala Ser Tyr Ala Gln Lys Phe
    50                  55                  60
```

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Arg Pro Val Asp Tyr Val Pro His Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Glu His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 163
<211> LENGTH: 451
<212> TYPE: PRT
```

<213> ORGANISM: Artificial Sequence
<220> FEATURE:
<223> OTHER INFORMATION: An artificially synthesized sequence

<400> SEQUENCE: 163

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Trp Phe Ser Tyr Tyr
            20                  25                  30

Met Ile Ser Trp Val Arg Gln Ala Pro Gly Gln Gly Leu Glu Trp Met
        35                  40                  45

Gly Val Ile Val Pro Ile Asn Gly Ala Ala Gln Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Pro Val Trp Arg Thr Pro Arg Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Glu His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                385                 390                 395                 400
Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro
        450

<210> SEQ ID NO 164
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 164

Gln Val Gln Leu Val Gln Ser Gly Ala Glu Val Lys Lys Pro Gly Ser
1               5                   10                  15

Ser Val Lys Val Ser Cys Lys Ala Ser Gly Gly Asp Phe Ser Asn Tyr
            20                  25                  30

Val Ile Ser Trp Val Arg Gln Ala Pro Gly Gln Gly Leu Glu Trp Met
        35                  40                  45

Gly Phe Ile Asn Pro Ile Tyr Gly Ala Ala Gly Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Glu Pro Val Ala Ser Leu Pro His Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
```

```
                290                 295                 300
Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro
    450

<210> SEQ ID NO 165
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 165

Gln Val Gln Leu Val Gln Ser Gly Ala Glu Val Lys Lys Pro Gly Ser
1               5                   10                  15

Ser Val Lys Val Ser Cys Lys Ala Ser Gly Gly Trp Phe Ser His Tyr
                20                  25                  30

Ser Ile Ser Trp Val Arg Gln Ala Pro Gly Gln Gly Leu Glu Trp Met
                35                  40                  45

Gly Val Val Trp Pro Ile Arg Ser Phe Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Asn Pro Val Thr Ser Trp Pro His Gly Ala Phe Asp Ile
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
```

```
                195                 200                 205
Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Glu His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 166
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 166

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ala Phe Ser Tyr Tyr
            20                  25                  30

Leu Ile Ser Trp Val Arg Gln Ala Pro Gly Gln Gly Leu Glu Trp Met
        35                  40                  45

Gly Phe Val Asp Pro Ile Arg Gly Gly Ala Phe Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Arg Pro Val Asn Ala Ala Pro Arg Gly Ala Phe Asp Ile
```

```
            100                 105                 110
Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Glu His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 167
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 167

Gln Val Gln Leu Val Gln Ser Gly Ala Glu Val Lys Lys Pro Gly Ser
```

-continued

```
1               5                   10                  15
Ser Val Lys Val Ser Cys Lys Ala Ser Gly Gly Ala Phe Ser Tyr Tyr
                20                  25                  30
Leu Ile Ser Trp Val Arg Gln Ala Pro Gly Gln Gly Leu Glu Trp Met
                35                  40                  45
Gly Phe Val Asp Pro Ile Arg Gly Gly Ala Phe Tyr Ala Gln Lys Phe
            50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Asp Arg Pro Val Asn Ala Ala Pro Arg Gly Ala Phe Asp Ile
                100                 105                 110
Trp Gly Gln Gly Thr Leu Val Thr Val Ser Ser Ala Ser Thr Lys Gly
                115                 120                 125
Pro Ser Val Phe Pro Leu Ala Pro Ser Ser Lys Ser Thr Ser Gly Gly
            130                 135                 140
Thr Ala Ala Leu Gly Cys Leu Val Lys Asp Tyr Phe Pro Glu Pro Val
145                 150                 155                 160
Thr Val Ser Trp Asn Ser Gly Ala Leu Thr Ser Gly Val His Thr Phe
                165                 170                 175
Pro Ala Val Leu Gln Ser Ser Gly Leu Tyr Ser Leu Ser Ser Val Val
                180                 185                 190
Thr Val Pro Ser Ser Ser Leu Gly Thr Gln Thr Tyr Ile Cys Asn Val
                195                 200                 205
Asn His Lys Pro Ser Asn Thr Lys Val Asp Lys Lys Val Glu Pro Lys
                210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
                260                 265                 270
Ser His Glu Asp Pro Glu Val Lys Phe Asn Trp Tyr Val Asp Gly Val
                275                 280                 285
Glu Val His Asn Ala Lys Thr Lys Pro Arg Glu Glu Gln Tyr Asn Ser
                290                 295                 300
Thr Tyr Arg Val Val Ser Val Leu Thr Val Leu His Gln Asp Trp Leu
305                 310                 315                 320
Asn Gly Lys Glu Tyr Lys Cys Lys Val Ser Asn Lys Ala Phe Pro Ala
                325                 330                 335
Pro Ile Glu Lys Thr Ile Ser Lys Ala Lys Gly Gln Pro Arg Glu Pro
                340                 345                 350
Gln Val Tyr Thr Leu Pro Pro Ser Arg Asp Glu Leu Thr Lys Asn Gln
                355                 360                 365
Val Ser Leu Thr Cys Leu Val Lys Gly Phe Tyr Pro Ser Asp Ile Ala
                370                 375                 380
Val Glu Trp Glu Ser Asn Gly Gln Pro Glu Asn Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
                420                 425                 430
```

Val Met His Glu Ala Leu His Asn His Tyr Thr Gln Lys Ser Leu Ser
            435                 440                 445

Leu Ser Pro
        450

<210> SEQ ID NO 168
<211> LENGTH: 451
<212> TYPE: PRT
<213> ORGANISM: Artificial Sequence
<220> FEATURE:
<223> OTHER INFORMATION: An artificially synthesized sequence

<400> SEQUENCE: 168

Gln Val Gln Leu Val Gln Ser Gly Ala Glu Val Lys Lys Pro Gly Ser
1               5                   10                  15

Ser Val Lys Val Ser Cys Lys Ala Ser Gly Gly Trp Phe Ser Arg Tyr
            20                  25                  30

Ile Ile Ser Trp Val Arg Gln Ala Pro Gly Gln Gly Leu Glu Trp Met
        35                  40                  45

Gly Thr Ile Asn Pro Ile Tyr Gly Val Ala Leu Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ala Pro Val Asn Asp Met Pro Arg Gly Ala Phe Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Glu His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Phe Pro Ala
                325                 330                 335

```
Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro
    450

<210> SEQ ID NO 169
<211> LENGTH: 219
<212> TYPE: PRT
<213> ORGANISM: Artificial Sequence
<220> FEATURE:
<223> OTHER INFORMATION: An artificially synthesized sequence

<400> SEQUENCE: 169

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Pro
            20                  25                  30

Gly Asp Asn Thr Phe Leu Ser Trp Tyr Leu Gln Lys Pro Gly Gln Ser
        35                  40                  45

Pro Gln Leu Leu Ile Tyr Glu Ile Glu Arg Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Thr Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 170
```

<211> LENGTH: 219
<212> TYPE: PRT
<213> ORGANISM: Artificial Sequence
<220> FEATURE:
<223> OTHER INFORMATION: An artificially synthesized sequence

<400> SEQUENCE: 170

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Ser Pro
            20                  25                  30

Gly Asp Asn Thr Phe Leu Ser Trp Tyr Leu Gln Lys Pro Gly Gln Ser
        35                  40                  45

Pro Gln Leu Leu Ile Tyr Glu Ile Glu Arg Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Thr Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 171
<211> LENGTH: 219
<212> TYPE: PRT
<213> ORGANISM: Artificial Sequence
<220> FEATURE:
<223> OTHER INFORMATION: An artificially synthesized sequence

<400> SEQUENCE: 171

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Asp Ser
            20                  25                  30

Asn Met Asn Thr Phe Leu Ser Trp Tyr Leu Gln Lys Pro Gly Gln Ser
        35                  40                  45

Pro Gln Leu Leu Ile Tyr Glu Ile Gln His Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Met Gly Phe Pro Arg Thr Phe Gly Gln Gly Thr Lys Val Glu Ile Lys

```
            100             105             110
Arg Thr Val Ala Ala Pro Ser Val Phe Ile Phe Pro Pro Ser Asp Glu
        115             120             125

Gln Leu Lys Ser Gly Thr Ala Ser Val Val Cys Leu Leu Asn Asn Phe
    130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
        180             185             190

Lys His Lys Val Tyr Ala Cys Glu Val Thr His Gln Gly Leu Ser Ser
    195             200             205

Pro Val Thr Lys Ser Phe Asn Arg Gly Glu Cys
    210             215
```

<210> SEQ ID NO 172
<211> LENGTH: 219
<212> TYPE: PRT
<213> ORGANISM: Artificial Sequence
<220> FEATURE:
<223> OTHER INFORMATION: An artificially synthesized sequence

<400> SEQUENCE: 172

```
Asp Ile Val Met Thr Gln Ser Pro Leu Ser Leu Pro Val Thr Pro Gly
1               5               10              15

Glu Pro Ala Ser Ile Ser Cys Arg Ser Ser Gln Ser Leu Val Asp Pro
            20              25              30

Trp Gly Asn Thr Phe Leu Ser Trp Tyr Leu Gln Lys Pro Gly Gln Ser
        35              40              45

Pro Gln Leu Leu Ile Tyr Glu Ile Ser Asn Arg Phe Tyr Gly Val Pro
    50              55              60

Asp Arg Phe Ser Gly Ser Gly Ser Gly Thr Asp Phe Thr Leu Lys Ile
65              70              75              80

Ser Arg Val Glu Ala Glu Asp Val Gly Val Tyr Tyr Cys Met Gln Ala
            85              90              95

Lys Asp Phe Pro Arg Thr Phe Gly Pro Gly Thr Lys Val Glu Ile Lys
        100             105             110

Arg Thr Val Ala Ala Pro Ser Val Phe Ile Phe Pro Pro Ser Asp Glu
    115             120             125

Gln Leu Lys Ser Gly Thr Ala Ser Val Val Cys Leu Leu Asn Asn Phe
130             135             140

Tyr Pro Arg Glu Ala Lys Val Gln Trp Lys Val Asp Asn Ala Leu Gln
145             150             155             160

Ser Gly Asn Ser Gln Glu Ser Val Thr Glu Gln Asp Ser Lys Asp Ser
            165             170             175

Thr Tyr Ser Leu Ser Ser Thr Leu Thr Leu Ser Lys Ala Asp Tyr Glu
        180             185             190

Lys His Lys Val Tyr Ala Cys Glu Val Thr His Gln Gly Leu Ser Ser
    195             200             205

Pro Val Thr Lys Ser Phe Asn Arg Gly Glu Cys
    210             215
```

<210> SEQ ID NO 173
<211> LENGTH: 219
<212> TYPE: PRT

<213> ORGANISM: Artificial Sequence
<220> FEATURE:
<223> OTHER INFORMATION: An artificially synthesized sequence

<400> SEQUENCE: 173

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Arg Pro
            20                  25                  30

Phe Gly Asn Thr Phe Leu Ser Trp Tyr Leu Gln Lys Pro Gly Gln Ser
        35                  40                  45

Pro Gln Leu Leu Ile Tyr Glu Ile Ser Thr Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

His Gln Phe Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 174
<211> LENGTH: 219
<212> TYPE: PRT
<213> ORGANISM: Artificial Sequence
<220> FEATURE:
<223> OTHER INFORMATION: An artificially synthesized sequence

<400> SEQUENCE: 174

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Gly Asp
            20                  25                  30

Arg Gly Asn Thr Tyr Leu Ser Trp Tyr Leu Gln Lys Pro Gly Gln Ser
        35                  40                  45

Pro Gln Leu Leu Ile Tyr Glu Ile Gly Ser Ile Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ala Glu Phe Pro Arg Thr Phe Gly Gln Gly Thr Lys Val Glu Ile Lys
            100                 105                 110

```
Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 175
<211> LENGTH: 219
<212> TYPE: PRT
<213> ORGANISM: Artificial Sequence
<220> FEATURE:
<223> OTHER INFORMATION: An artificially synthesized sequence

<400> SEQUENCE: 175

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Trp Asn
            20                  25                  30

Asp Arg Asn Thr Phe Leu Ser Trp Tyr Leu Gln Lys Pro Gly Gln Ser
        35                  40                  45

Pro Gln Leu Leu Ile Tyr Glu Ile Arg Lys Arg Phe Tyr Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Gln Asp Phe Pro Arg Thr Phe Gly Gln Gly Thr Lys Val Glu Ile Lys
            100                 105                 110

Arg Thr Val Ala Ala Pro Ser Val Phe Ile Phe Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 176
<211> LENGTH: 219
<212> TYPE: PRT
<213> ORGANISM: Artificial Sequence
<220> FEATURE:
```

<223> OTHER INFORMATION: An artificially synthesized sequence

<400> SEQUENCE: 176

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val Asp Gly
            20                  25                  30
Phe Gly Asn Thr Phe Leu Ser Trp Tyr Leu Gln Lys Pro Gly Gln Ser
        35                  40                  45
Pro Gln Leu Leu Ile Tyr Glu Ile Arg Lys Arg Phe Tyr Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Met Gln Ala
                85                  90                  95
Phe Ala Phe Pro Arg Thr Phe Gly Gln Gly Thr Lys Val Glu Ile Lys
            100                 105                 110
Arg Thr Val Ala Ala Pro Ser Val Phe Ile Phe Pro Pro Ser Asp Glu
        115                 120                 125
Gln Leu Lys Ser Gly Thr Ala Ser Val Val Cys Leu Leu Asn Asn Phe
    130                 135                 140
Tyr Pro Arg Glu Ala Lys Val Gln Trp Lys Val Asp Asn Ala Leu Gln
145                 150                 155                 160
Ser Gly Asn Ser Gln Glu Ser Val Thr Glu Gln Asp Ser Lys Asp Ser
                165                 170                 175
Thr Tyr Ser Leu Ser Ser Thr Leu Thr Leu Ser Lys Ala Asp Tyr Glu
            180                 185                 190
Lys His Lys Val Tyr Ala Cys Glu Val Thr His Gln Gly Leu Ser Ser
        195                 200                 205
Pro Val Thr Lys Ser Phe Asn Arg Gly Glu Cys
    210                 215
```

<210> SEQ ID NO 177
<211> LENGTH: 258
<212> TYPE: PRT
<213> ORGANISM: Artificial Sequence
<220> FEATURE:
<223> OTHER INFORMATION: An artificially synthesized sequence

<400> SEQUENCE: 177

```
Leu Gln Asp Pro Cys Ser Asn Cys Pro Ala Gly Thr Phe Cys Asp Asn
1               5                   10                  15
Asn Arg Asn Gln Ile Cys Asp Ile Glu Gly Arg Met Asp Pro Lys Ser
            20                  25                  30
Cys Asp Lys Thr His Thr Cys Pro Pro Cys Pro Ala Pro Glu Leu Leu
        35                  40                  45
Gly Gly Pro Ser Val Phe Leu Phe Pro Pro Lys Pro Lys Asp Thr Leu
    50                  55                  60
Met Ile Ser Arg Thr Pro Glu Val Thr Cys Val Val Val Asp Val Ser
65                  70                  75                  80
His Glu Asp Pro Glu Val Lys Phe Asn Trp Tyr Val Asp Gly Val Glu
                85                  90                  95
Val His Asn Ala Lys Thr Lys Pro Arg Glu Glu Gln Tyr Asn Ser Thr
            100                 105                 110
Tyr Arg Val Val Ser Val Leu Thr Val Leu His Gln Asp Trp Leu Asn
        115                 120                 125
```

```
Gly Lys Glu Tyr Lys Cys Lys Val Ser Asn Lys Ala Leu Pro Ala Pro
            130                 135                 140

Ile Glu Lys Thr Ile Ser Lys Ala Lys Gly Gln Pro Arg Glu Pro Gln
145                 150                 155                 160

Val Tyr Thr Leu Pro Pro Ser Arg Asp Glu Leu Thr Lys Asn Gln Val
                165                 170                 175

Ser Leu Thr Cys Leu Val Lys Gly Phe Tyr Pro Ser Asp Ile Ala Val
            180                 185                 190

Glu Trp Glu Ser Asn Gly Gln Pro Glu Asn Asn Tyr Lys Thr Thr Pro
            195                 200                 205

Pro Val Leu Asp Ser Asp Gly Ser Phe Phe Leu Tyr Ser Lys Leu Thr
            210                 215                 220

Val Asp Lys Ser Arg Trp Gln Gln Gly Asn Val Phe Ser Cys Ser Val
225                 230                 235                 240

Met His Glu Ala Leu His Asn His Tyr Thr Gln Lys Ser Leu Ser Leu
                245                 250                 255

Ser Pro

<210> SEQ ID NO 178
<211> LENGTH: 299
<212> TYPE: PRT
<213> ORGANISM: Artificial Sequence
<220> FEATURE:
<223> OTHER INFORMATION: An artificially synthesized sequence

<400> SEQUENCE: 178

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
                20                  25                  30

Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
    50                  55                  60

Ile Glu Gly Arg Met Asp Pro Lys Ser Cys Asp Lys Thr His Thr Cys
65                  70                  75                  80

Pro Pro Cys Pro Ala Pro Glu Leu Leu Gly Gly Pro Ser Val Phe Leu
                85                  90                  95

Phe Pro Pro Lys Pro Lys Asp Thr Leu Met Ile Ser Arg Thr Pro Glu
            100                 105                 110

Val Thr Cys Val Val Val Asp Val Ser His Glu Asp Pro Glu Val Lys
        115                 120                 125

Phe Asn Trp Tyr Val Asp Gly Val Glu Val His Asn Ala Lys Thr Lys
    130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Asp Glu Leu Thr Lys Asn Gln Val Ser Leu Thr Cys Leu Val Lys
    210                 215                 220
```

```
Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro
    290                 295

<210> SEQ ID NO 179
<211> LENGTH: 377
<212> TYPE: PRT
<213> ORGANISM: Artificial Sequence
<220> FEATURE:
<223> OTHER INFORMATION: An artificially synthesized sequence

<400> SEQUENCE: 179

Ser Pro Cys Pro Pro Asn Ser Phe Ser Ser Ala Gly Gly Gln Arg Thr
1               5                   10                  15

Cys Asp Ile Cys Arg Gln Cys Lys Gly Val Phe Arg Thr Arg Lys Glu
            20                  25                  30

Cys Ser Ser Thr Ser Asn Ala Glu Cys Asp Cys Thr Pro Gly Phe His
        35                  40                  45

Cys Leu Gly Ala Gly Cys Ser Met Cys Glu Gln Asp Cys Lys Gln Gly
    50                  55                  60

Gln Glu Leu Thr Lys Lys Gly Cys Lys Asp Cys Cys Phe Gly Thr Phe
65                  70                  75                  80

Asn Asp Gln Lys Arg Gly Ile Cys Arg Pro Trp Thr Asn Cys Ser Leu
                85                  90                  95

Asp Gly Lys Ser Val Leu Val Asn Gly Thr Lys Glu Arg Asp Val Val
            100                 105                 110

Cys Gly Pro Ser Pro Ala Asp Leu Ser Pro Gly Ala Ser Ser Val Thr
        115                 120                 125

Pro Pro Ala Pro Ala Arg Glu Pro Gly His Ser Pro Gln Asp Ile Glu
    130                 135                 140

Gly Arg Met Asp Pro Lys Ser Cys Asp Lys Thr His Thr Cys Pro Pro
145                 150                 155                 160

Cys Pro Ala Pro Glu Leu Leu Gly Gly Pro Ser Val Phe Leu Phe Pro
                165                 170                 175

Pro Lys Pro Lys Asp Thr Leu Met Ile Ser Arg Thr Pro Glu Val Thr
            180                 185                 190

Cys Val Val Val Asp Val Ser His Glu Asp Pro Glu Val Lys Phe Asn
        195                 200                 205

Trp Tyr Val Asp Gly Val Glu Val His Asn Ala Lys Thr Lys Pro Arg
    210                 215                 220

Glu Glu Gln Tyr Asn Ser Thr Tyr Arg Val Val Ser Val Leu Thr Val
225                 230                 235                 240

Leu His Gln Asp Trp Leu Asn Gly Lys Glu Tyr Lys Cys Lys Val Ser
                245                 250                 255

Asn Lys Ala Leu Pro Ala Pro Ile Glu Lys Thr Ile Ser Lys Ala Lys
            260                 265                 270

Gly Gln Pro Arg Glu Pro Gln Val Tyr Thr Leu Pro Pro Ser Arg Asp
        275                 280                 285
```

```
Glu Leu Thr Lys Asn Gln Val Ser Leu Thr Cys Leu Val Lys Gly Phe
    290                 295                 300
Tyr Pro Ser Asp Ile Ala Val Glu Trp Glu Ser Asn Gly Gln Pro Glu
305                 310                 315                 320
Asn Asn Tyr Lys Thr Thr Pro Pro Val Leu Asp Ser Asp Gly Ser Phe
                325                 330                 335
Phe Leu Tyr Ser Lys Leu Thr Val Asp Lys Ser Arg Trp Gln Gln Gly
            340                 345                 350
Asn Val Phe Ser Cys Ser Val Met His Glu Ala Leu His Asn His Tyr
        355                 360                 365
Thr Gln Lys Ser Leu Ser Leu Ser Pro
    370                 375

<210> SEQ ID NO 180
<211> LENGTH: 308
<212> TYPE: PRT
<213> ORGANISM: Artificial Sequence
<220> FEATURE:
<223> OTHER INFORMATION: An artificially synthesized sequence

<400> SEQUENCE: 180

Ser Pro Cys Pro Pro Asn Ser Phe Ser Ser Ala Gly Gly Gln Arg Thr
1               5                   10                  15
Cys Asp Ile Cys Arg Gln Cys Lys Gly Val Phe Arg Thr Arg Lys Glu
            20                  25                  30
Cys Ser Ser Thr Ser Asn Ala Glu Cys Asp Cys Thr Pro Gly Phe His
        35                  40                  45
Cys Leu Gly Ala Gly Cys Ser Met Cys Glu Gln Asp Cys Lys Gln Gly
    50                  55                  60
Gln Glu Leu Thr Lys Lys Gly Cys Asp Ile Glu Gly Arg Met Asp Pro
65                  70                  75                  80
Lys Ser Cys Asp Lys Thr His Thr Cys Pro Pro Cys Pro Ala Pro Glu
                85                  90                  95
Leu Leu Gly Gly Pro Ser Val Phe Leu Phe Pro Pro Lys Pro Lys Asp
            100                 105                 110
Thr Leu Met Ile Ser Arg Thr Pro Glu Val Thr Cys Val Val Val Asp
        115                 120                 125
Val Ser His Glu Asp Pro Glu Val Lys Phe Asn Trp Tyr Val Asp Gly
130                 135                 140
Val Glu Val His Asn Ala Lys Thr Lys Pro Arg Glu Glu Gln Tyr Asn
145                 150                 155                 160
Ser Thr Tyr Arg Val Val Ser Val Leu Thr Val Leu His Gln Asp Trp
                165                 170                 175
Leu Asn Gly Lys Glu Tyr Lys Cys Lys Val Ser Asn Lys Ala Leu Pro
            180                 185                 190
Ala Pro Ile Glu Lys Thr Ile Ser Lys Ala Lys Gly Gln Pro Arg Glu
        195                 200                 205
Pro Gln Val Tyr Thr Leu Pro Pro Ser Arg Asp Glu Leu Thr Lys Asn
    210                 215                 220
Gln Val Ser Leu Thr Cys Leu Val Lys Gly Phe Tyr Pro Ser Asp Ile
225                 230                 235                 240
Ala Val Glu Trp Glu Ser Asn Gly Gln Pro Glu Asn Asn Tyr Lys Thr
                245                 250                 255
Thr Pro Pro Val Leu Asp Ser Asp Gly Ser Phe Phe Leu Tyr Ser Lys
            260                 265                 270
```

Leu Thr Val Asp Lys Ser Arg Trp Gln Gln Gly Asn Val Phe Ser Cys
            275                 280                 285

Ser Val Met His Glu Ala Leu His Asn His Tyr Thr Gln Lys Ser Leu
    290                 295                 300

Ser Leu Ser Pro
305

<210> SEQ ID NO 181
<211> LENGTH: 336
<212> TYPE: PRT
<213> ORGANISM: Artificial Sequence
<220> FEATURE:
<223> OTHER INFORMATION: An artificially synthesized sequence

<400> SEQUENCE: 181

Asp Cys Thr Pro Gly Phe His Cys Leu Gly Ala Gly Cys Ser Met Cys
1               5                   10                  15

Glu Gln Asp Cys Lys Gln Gly Gln Glu Leu Thr Lys Lys Gly Cys Lys
            20                  25                  30

Asp Cys Cys Phe Gly Thr Phe Asn Asp Gln Lys Arg Gly Ile Cys Arg
        35                  40                  45

Pro Trp Thr Asn Cys Ser Leu Asp Gly Lys Ser Val Leu Val Asn Gly
50                  55                  60

Thr Lys Glu Arg Asp Val Val Cys Gly Pro Ser Pro Ala Asp Leu Ser
65                  70                  75                  80

Pro Gly Ala Ser Ser Val Thr Pro Pro Ala Pro Ala Arg Glu Pro Gly
                85                  90                  95

His Ser Pro Gln Asp Ile Glu Gly Arg Met Asp Pro Lys Ser Cys Asp
            100                 105                 110

Lys Thr His Thr Cys Pro Pro Cys Pro Ala Pro Glu Leu Leu Gly Gly
        115                 120                 125

Pro Ser Val Phe Leu Phe Pro Pro Lys Pro Lys Asp Thr Leu Met Ile
130                 135                 140

Ser Arg Thr Pro Glu Val Thr Cys Val Val Val Asp Val Ser His Glu
145                 150                 155                 160

Asp Pro Glu Val Lys Phe Asn Trp Tyr Val Asp Gly Val Glu Val His
                165                 170                 175

Asn Ala Lys Thr Lys Pro Arg Glu Glu Gln Tyr Asn Ser Thr Tyr Arg
            180                 185                 190

Val Val Ser Val Leu Thr Val Leu His Gln Asp Trp Leu Asn Gly Lys
        195                 200                 205

Glu Tyr Lys Cys Lys Val Ser Asn Lys Ala Leu Pro Ala Pro Ile Glu
210                 215                 220

Lys Thr Ile Ser Lys Ala Lys Gly Gln Pro Arg Glu Pro Gln Val Tyr
225                 230                 235                 240

Thr Leu Pro Pro Ser Arg Asp Glu Leu Thr Lys Asn Gln Val Ser Leu
                245                 250                 255

Thr Cys Leu Val Lys Gly Phe Tyr Pro Ser Asp Ile Ala Val Glu Trp
            260                 265                 270

Glu Ser Asn Gly Gln Pro Glu Asn Asn Tyr Lys Thr Thr Pro Pro Val
        275                 280                 285

Leu Asp Ser Asp Gly Ser Phe Phe Leu Tyr Ser Lys Leu Thr Val Asp
290                 295                 300

Lys Ser Arg Trp Gln Gln Gly Asn Val Phe Ser Cys Ser Val Met His
305                 310                 315                 320

```
Glu Ala Leu His Asn His Tyr Thr Gln Lys Ser Leu Ser Leu Ser Pro
                325                 330                 335

<210> SEQ ID NO 182
<211> LENGTH: 328
<212> TYPE: PRT
<213> ORGANISM: Artificial Sequence
<220> FEATURE:
<223> OTHER INFORMATION: An artificially synthesized sequence

<400> SEQUENCE: 182

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 183
<211> LENGTH: 189
```

```
<212> TYPE: PRT
<213> ORGANISM: Homo sapiens

<400> SEQUENCE: 183

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
130                 135                 140

Gly Ala Ser Ser Val Thr Pro Pro Ala Pro Ala Arg Glu Pro Gly His
145                 150                 155                 160

Ser Pro Gln His His His His His His Gly Gly Gly Ser Gly Leu
                165                 170                 175

Asn Asp Ile Phe Glu Ala Gln Lys Ile Glu Trp His Glu
            180                 185

<210> SEQ ID NO 184
<211> LENGTH: 330
<212> TYPE: PRT
<213> ORGANISM: Mus musculus

<400> SEQUENCE: 184

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Asp Val Phe Ile Phe Pro Pro
        115                 120                 125

Lys Ile Lys Asp Val Leu Met Ile Ser Leu Ser Pro Ile Val Thr Cys
    130                 135                 140

Val Val Val Asp Val Ser Glu Asp Asp Pro Asp Val Gln Ile Ser Trp
145                 150                 155                 160
```

```
Phe Val Asn Asn Val Glu Val His Thr Ala Gln Thr Gln Thr His Arg
            165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
            210                 215                 220

Ser Val Arg Ala Pro Gln Val Tyr Val Leu Pro Pro Glu Glu Glu
225                 230                 235                 240

Met Thr Lys Lys Gln Val Thr Leu Thr Cys Met Val Thr Asp Phe Met
            245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
            290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
            325                 330

<210> SEQ ID NO 185
<211> LENGTH: 107
<212> TYPE: PRT
<213> ORGANISM: Mus musculus

<400> SEQUENCE: 185

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
            85                  90                  95

Pro Ile Val Lys Ser Phe Asn Arg Asn Glu Cys
            100                 105

<210> SEQ ID NO 186
<211> LENGTH: 107
<212> TYPE: PRT
<213> ORGANISM: Homo sapiens

<400> SEQUENCE: 186

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45
```

-continued

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 187
<211> LENGTH: 116
<212> TYPE: PRT
<213> ORGANISM: Artificial Sequence
<220> FEATURE:
<223> OTHER INFORMATION: IC17Hdk

<400> SEQUENCE: 187

Gln Val Gln Leu Gln Gln Ser Gly Pro Gln Leu Val Arg Pro Gly Ala
 1               5                  10                  15

Ser Val Lys Ile Ser Cys Lys Ala Ser Gly Tyr Ser Phe Thr Ser Tyr
                 20                  25                  30

Trp Met His Trp Val Asn Gln Arg Pro Gly Gln Gly Leu Glu Trp Ile
             35                  40                  45

Gly Met Ile Asp Pro Ser Tyr Ser Glu Thr Arg Leu Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Leu Tyr Gly Asn Tyr Phe Asp Tyr Trp Gly Gln Gly Thr Thr Leu
            100                 105                 110

Thr Val Ser Ser
        115

<210> SEQ ID NO 188
<211> LENGTH: 107
<212> TYPE: PRT
<213> ORGANISM: Artificial Sequence
<220> FEATURE:
<223> OTHER INFORMATION: IC17VL

<400> SEQUENCE: 188

Asp Ile Gln Met Thr Gln Ser Ser Ser Phe Ser Val Ser Leu Gly
 1               5                  10                  15

Asp Arg Val Thr Ile Thr Cys Lys Ala Ser Glu Asp Ile Tyr Asn Arg
                 20                  25                  30

Leu Ala Trp Tyr Gln Gln Lys Pro Gly Asn Ala Pro Arg Leu Leu Ile
             35                  40                  45

Ser Gly Ala Thr Ser Leu Glu Thr Gly Val Pro Ser Arg Phe Ser Gly
 50                  55                  60

Ser Gly Ser Gly Lys Asp Tyr Thr Leu Ser Ile Thr Ser Leu Gln Thr
 65                  70                  75                  80

Glu Asp Val Ala Thr Tyr Tyr Cys Gln Gln Tyr Trp Ser Thr Pro Tyr
                 85                  90                  95

Thr Phe Gly Gly Gly Thr Lys Leu Glu Val Lys
            100                 105

<210> SEQ ID NO 189

<211> LENGTH: 106
<212> TYPE: PRT
<213> ORGANISM: Artificial Sequence
<220> FEATURE:
<223> OTHER INFORMATION: lam1

<400> SEQUENCE: 189

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 190
<211> LENGTH: 119
<212> TYPE: PRT
<213> ORGANISM: Artificial Sequence
<220> FEATURE:
<223> OTHER INFORMATION: MRAH

<400> SEQUENCE: 190

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
        115

<210> SEQ ID NO 191
<211> LENGTH: 107
<212> TYPE: PRT
<213> ORGANISM: Artificial Sequence
<220> FEATURE:
<223> OTHER INFORMATION: MRAL

<400> SEQUENCE: 191

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

```
Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
 50                      55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Asn Thr Leu Pro Tyr
                    85                  90                  95

Thr Phe Gly Gln Gly Thr Lys Val Glu Ile Lys
                100                 105
```

<210> SEQ ID NO 192
<211> LENGTH: 122
<212> TYPE: PRT
<213> ORGANISM: Artificial Sequence
<220> FEATURE:
<223> OTHER INFORMATION: H0002

<400> SEQUENCE: 192

```
Glu Val Gln Leu Val Glu Ser Gly Gly Asp Leu Val Lys Pro Gly Gly
 1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Tyr His Ala Tyr Tyr Ala Asp Ser Val
 50                      55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Ala Arg Tyr Gly Lys Leu Tyr Ser Leu Asn Trp Val Phe Asp Tyr Trp
                100                 105                 110

Gly Gln Gly Thr Leu Val Thr Val Ser Ser
            115                 120
```

<210> SEQ ID NO 193
<211> LENGTH: 110
<212> TYPE: PRT
<213> ORGANISM: Artificial Sequence
<220> FEATURE:
<223> OTHER INFORMATION: L1058

<400> SEQUENCE: 193

```
Gln Ser Ala Leu Thr Gln Pro Pro Ser Ala Ser Gly Ser Pro Gly Gln
 1               5                   10                  15

Thr Val Thr Ile Ser Cys Thr Gly Thr Ser Thr Asp Val Gly Asp Tyr
            20                  25                  30

Asn Tyr Val Ser Trp Tyr Gln Gln His Pro Gly Lys Ala Pro Lys Leu
        35                  40                  45

Met Ile Tyr Glu Val Val Lys Lys Pro Ser Gly Val Pro Asp Arg Phe
 50                      55                  60

Ser Gly Ser Lys Ser Gly Asn Thr Ala Ser Leu Thr Ser Gly Leu
 65                  70                  75                  80

Gln Ala Glu Asp Glu Ala Asp Tyr Phe Cys Ser Leu Arg Ser Ala Gly
                    85                  90                  95

Pro Tyr Pro Leu Phe Gly Gly Thr Lys Leu Thr Val Leu
                100                 105                 110
```

<210> SEQ ID NO 194
<211> LENGTH: 122
<212> TYPE: PRT
<213> ORGANISM: Artificial Sequence
<220> FEATURE:
<223> OTHER INFORMATION: H0041

<400> SEQUENCE: 194

Glu Val Gln Leu Val Glu Ser Gly Gly Asp Leu Val Lys Pro Gly Gly
1               5                   10                  15

Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Gln Ser Tyr His Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Lys Leu Tyr Ser Leu Asn Trp Val Phe Asp Tyr Trp
            100                 105                 110

Gly Gln Gly Thr Leu Val Thr Val Ser Ser
        115                 120

<210> SEQ ID NO 195
<211> LENGTH: 110
<212> TYPE: PRT
<213> ORGANISM: Artificial Sequence
<220> FEATURE:
<223> OTHER INFORMATION: L1088

<400> SEQUENCE: 195

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Ala Tyr Val Ser Trp Tyr Gln Gln His Pro Gly Lys Ala Pro Lys Leu
        35                  40                  45

Met Ile Tyr Tyr Val Ser Lys Lys Pro Asp Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Leu Arg Ser Pro Gly
                85                  90                  95

Pro Tyr Pro Leu Phe Gly Gly Gly Thr Lys Leu Thr Val Leu
            100                 105                 110

<210> SEQ ID NO 196
<211> LENGTH: 122
<212> TYPE: PRT
<213> ORGANISM: Artificial Sequence
<220> FEATURE:
<223> OTHER INFORMATION: H0052

<400> SEQUENCE: 196

Glu Val Gln Leu Val Glu Ser Gly Gly Asp Leu Val Lys Pro Gly Gly
1               5                   10                  15

-continued

```
Gly Leu Arg Leu Ser Cys Ala Ala Ser Gly Phe Thr Phe Ser Ser Tyr
            20                  25                  30

Thr Met Asn Trp Val Arg Gln Ala Pro Gly Lys Gly Leu Glu Trp Val
        35                  40                  45

Ser Ser Ile Ser Ser Arg Ser Tyr His Ile Tyr Tyr Ala Asp Ser Val
    50                  55                  60

Asp Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Lys Leu Tyr Ser Leu Asn Trp Val Phe Asp Tyr Trp
            100                 105                 110

Gly Gln Gly Thr Leu Val Thr Val Ser Ser
            115                 120

<210> SEQ ID NO 197
<211> LENGTH: 110
<212> TYPE: PRT
<213> ORGANISM: Artificial Sequence
<220> FEATURE:
<223> OTHER INFORMATION: L1083

<400> SEQUENCE: 197

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Asp Val Gly Asp Tyr
            20                  25                  30

Ala Tyr Val Ser Trp Tyr Gln Gln His Pro Gly Lys Ala Pro Lys Leu
        35                  40                  45

Met Ile Tyr Tyr Val Asp Lys Lys Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Leu Arg Ser Pro Gly
                85                  90                  95

Pro Tyr Pro Leu Phe Gly Gly Gly Thr Lys Leu Thr Val Leu
            100                 105                 110

<210> SEQ ID NO 198
<211> LENGTH: 325
<212> TYPE: PRT
<213> ORGANISM: Artificial Sequence
<220> FEATURE:
<223> OTHER INFORMATION: G4T1

<400> SEQUENCE: 198

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95
```

```
Arg Val Glu Ser Lys Tyr Gly Pro Pro Cys Pro Pro Cys Pro Ala Pro
            100                 105                 110

Glu Phe Arg Arg Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro
                325

<210> SEQ ID NO 199
<211> LENGTH: 107
<212> TYPE: PRT
<213> ORGANISM: Artificial Sequence
<220> FEATURE:
<223> OTHER INFORMATION: k0

<400> SEQUENCE: 199

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 200
```

```
<211> LENGTH: 338
<212> TYPE: PRT
<213> ORGANISM: Homo sapiens

<400> SEQUENCE: 200
```

| | | | | | | | | | | | | | | |
|---|---|---|---|---|---|---|---|---|---|---|---|---|---|---|
|Leu|Ala|Pro|Arg|Arg|Cys|Pro|Ala|Gln|Glu|Val|Ala|Arg|Gly|Val|Leu|
|1| | | |5| | | | |10| | | | |15|

Thr Ser Leu Pro Gly Asp Ser Val Thr Leu Thr Cys Pro Gly Val Glu
           20                  25                  30

Pro Glu Asp Asn Ala Thr Val His Trp Val Leu Arg Lys Pro Ala Ala
         35                  40                  45

Gly Ser His Pro Ser Arg Trp Ala Gly Met Gly Arg Arg Leu Leu Leu
     50                  55                  60

Arg Ser Val Gln Leu His Asp Ser Gly Asn Tyr Ser Cys Tyr Arg Ala
65                  70                  75                  80

Gly Arg Pro Ala Gly Thr Val His Leu Leu Val Asp Val Pro Pro Glu
                 85                  90                  95

Glu Pro Gln Leu Ser Cys Phe Arg Lys Ser Pro Leu Ser Asn Val Val
            100                 105                 110

Cys Glu Trp Gly Pro Arg Ser Thr Pro Ser Leu Thr Thr Lys Ala Val
        115                 120                 125

Leu Leu Val Arg Lys Phe Gln Asn Ser Pro Ala Glu Asp Phe Gln Glu
130                 135                 140

Pro Cys Gln Tyr Ser Gln Glu Ser Gln Lys Phe Ser Cys Gln Leu Ala
145                 150                 155                 160

Val Pro Glu Gly Asp Ser Ser Phe Tyr Ile Val Ser Met Cys Val Ala
                165                 170                 175

Ser Ser Val Gly Ser Lys Phe Ser Lys Thr Gln Thr Phe Gln Gly Cys
            180                 185                 190

Gly Ile Leu Gln Pro Asp Pro Pro Ala Asn Ile Thr Val Thr Ala Val
        195                 200                 205

Ala Arg Asn Pro Arg Trp Leu Ser Val Thr Trp Gln Asp Pro His Ser
210                 215                 220

Trp Asn Ser Ser Phe Tyr Arg Leu Arg Phe Glu Leu Arg Tyr Arg Ala
225                 230                 235                 240

Glu Arg Ser Lys Thr Phe Thr Thr Trp Met Val Lys Asp Leu Gln His
                245                 250                 255

His Cys Val Ile His Asp Ala Trp Ser Gly Leu Arg His Val Val Gln
            260                 265                 270

Leu Arg Ala Gln Glu Glu Phe Gly Gln Gly Glu Trp Ser Glu Trp Ser
        275                 280                 285

Pro Glu Ala Met Gly Thr Pro Trp Thr Glu Ser Arg Ser Pro Pro Ala
290                 295                 300

Glu Asn Glu Val Ser Thr Pro Met Gln Ala Leu Thr Thr Asn Lys Asp
305                 310                 315                 320

Asp Asp Asn Ile Leu Phe Arg Asp Ser Ala Asn Ala Thr Ser Leu Pro
                325                 330                 335

Val Gln

```
<210> SEQ ID NO 201
<211> LENGTH: 118
<212> TYPE: PRT
<213> ORGANISM: Artificial Sequence
<220> FEATURE:
<223> OTHER INFORMATION: mPD1F2VH
```

```
<400> SEQUENCE: 201

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Trp Gly Ser Tyr Phe Asp Leu Trp Gly Gln Gly Thr
            100                 105                 110

Thr Val Thr Val Ser Ser
            115

<210> SEQ ID NO 202
<211> LENGTH: 107
<212> TYPE: PRT
<213> ORGANISM: Artificial Sequence
<220> FEATURE:
<223> OTHER INFORMATION: mPD1F2VL

<400> SEQUENCE: 202

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys
            100                 105

<210> SEQ ID NO 203
<211> LENGTH: 324
<212> TYPE: PRT
<213> ORGANISM: Mus musculus

<400> SEQUENCE: 203

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Thr Trp Pro Ser Glu Thr Val
65                  70                  75                  80
```

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Lys
            100                 105                 110

Glu Val Ser Lys Val Phe Ile Phe Pro Pro Lys Pro Lys Asp Val Leu
        115                 120                 125

Thr Ile Thr Leu Thr Pro Lys Val Thr Cys Val Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255

Glu Trp Gln Trp Asn Gly Gln Pro Ala Glu Asn Tyr Lys Asn Thr Gln
            260                 265                 270

Pro Ile Met Asp Thr Asp Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 204
<211> LENGTH: 122
<212> TYPE: PRT
<213> ORGANISM: Artificial Sequence
<220> FEATURE:
<223> OTHER INFORMATION: H5029

<400> SEQUENCE: 204

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Thr Met His Trp Val Arg Gln Ala Pro Gly Lys Gly Leu Glu Trp Val
        35                  40                  45

Ser Ser Ile Ser Ser Ser Ser Arg His Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Pro Phe Glu Leu Leu Trp Val Leu Asp Tyr Trp
            100                 105                 110

```
Gly Gln Gly Thr Leu Val Thr Val Ser Ser
        115                 120

<210> SEQ ID NO 205
<211> LENGTH: 110
<212> TYPE: PRT
<213> ORGANISM: Artificial Sequence
<220> FEATURE:
<223> OTHER INFORMATION: L3021

<400> SEQUENCE: 205

Gln Ser Ala Leu Thr Gln Pro Pro Ser Ala Ser Gly Ser Pro Gly Gln
1               5                   10                  15

Thr Val Thr Ile Ser Cys Thr Gly Thr Ser Thr Pro Ser Gly Ala Trp
            20                  25                  30

Asp Tyr Val Ser Trp Tyr Gln Gln His Pro Gly Lys Ala Pro Lys Leu
        35                  40                  45

Met Ile Tyr Gln Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Phe Cys Ser Thr Thr Ser Ser Ala
                85                  90                  95

Trp Asp Pro Asp Phe Gly Gly Gly Thr Lys Leu Thr Val Leu
            100                 105                 110

<210> SEQ ID NO 206
<211> LENGTH: 122
<212> TYPE: PRT
<213> ORGANISM: Artificial Sequence
<220> FEATURE:
<223> OTHER INFORMATION: H5041

<400> SEQUENCE: 206

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Thr Tyr
            20                  25                  30

Thr Met His Trp Val Arg Gln Ala Pro Gly Lys Gly Leu Glu Trp Val
        35                  40                  45

Ser Ser Ile Ser Ser Ser Ser Lys His Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Pro Trp Glu Leu Leu Trp Val Leu Asp Tyr Trp
            100                 105                 110

Gly Gln Gly Thr Leu Val Thr Val Ser Ser
        115                 120

<210> SEQ ID NO 207
<211> LENGTH: 110
<212> TYPE: PRT
<213> ORGANISM: Artificial Sequence
<220> FEATURE:
<223> OTHER INFORMATION: L3023

<400> SEQUENCE: 207

Gln Ser Ala Leu Thr Gln Pro Pro Ser Ala Ser Gly Ser Pro Gly Gln
```

-continued

```
            1               5                   10                  15
          Thr Val Thr Ile Ser Cys Thr Gly Thr Ser Thr Pro Ser Gly Ala Tyr
                          20                  25                  30

Asp Tyr Val Ser Trp Tyr Gln Gln His Pro Gly Lys Ala Pro Lys Leu
                          35                  40                  45

Met Ile Tyr Gln Val Ser Lys Arg Pro Ser Gly Val Pro Asp Arg Phe
                          50                  55                  60

Ser Gly Ser Lys Ser Gly Asn Thr Ala Ser Leu Thr Val Ser Gly Leu
           65                  70                  75                  80

Gln Ala Glu Asp Glu Ala Asp Tyr Phe Cys Ser Thr Thr Asn Ser Ala
                          85                  90                  95

Trp Asp Pro Asp Phe Gly Gly Gly Thr Lys Leu Thr Val Leu
                          100                 105                 110

<210> SEQ ID NO 208
<211> LENGTH: 330
<212> TYPE: PRT
<213> ORGANISM: Artificial Sequence
<220> FEATURE:
<223> OTHER INFORMATION: mFa31

<400> SEQUENCE: 208

Ala Lys Thr Thr Ala Pro Ser Val Tyr Pro Leu Ala Pro Val Cys Gly
           1               5                   10                  15

Asp Thr Thr Gly Ser Ser Val Thr Leu Gly Cys Leu Val Lys Gly Tyr
                          20                  25                  30

Phe Pro Glu Pro Val Thr Leu Thr Trp Asn Ser Gly Ser Leu Ser Ser
                          35                  40                  45

Gly Val His Thr Phe Pro Ala Val Leu Gln Ser Asp Leu Tyr Thr Leu
                          50                  55                  60

Ser Ser Ser Val Thr Val Thr Ser Ser Thr Trp Pro Ser Gln Ser Ile
           65                  70                  75                  80

Thr Cys Asn Val Ala His Pro Ala Ser Ser Thr Lys Val Asp Lys Lys
                          85                  90                  95

Ile Glu Pro Arg Gly Pro Thr Ile Lys Pro Cys Pro Pro Cys Lys Cys
                          100                 105                 110

Pro Ala Pro Asn Leu Arg Arg Gly Pro Lys Val Phe Ile Phe Pro Pro
                          115                 120                 125

Lys Ile Lys Asp Val Leu Met Ile Ser Leu Ser Pro Ile Val Thr Cys
                          130                 135                 140

Val Val Val Asp Val Ser Glu Asp Asp Pro Asp Val Gln Ile Ser Trp
          145                 150                 155                 160

Phe Val Asn Asn Val Glu Val His Thr Ala Gln Thr Gln Thr His Arg
                          165                 170                 175

Glu Asp Tyr Asn Ser Thr Leu Arg Val Val Ser Ala Leu Pro Ile Gln
                          180                 185                 190

His Gln Asp Trp Met Ser Gly Lys Glu Phe Lys Cys Lys Val Asn Asn
                          195                 200                 205

Lys Asp Leu Pro Ala Pro Ile Glu Arg Thr Ile Ser Lys Pro Lys Gly
                          210                 215                 220

Ser Val Arg Ala Pro Gln Val Tyr Val Leu Pro Pro Glu Glu Glu
          225                 230                 235                 240

Met Thr Lys Lys Gln Val Thr Leu Thr Cys Met Val Thr Asp Phe Met
                          245                 250                 255

Pro Glu Asp Ile Tyr Val Glu Trp Thr Asn Asn Gly Lys Thr Glu Leu
```

```
                260             265             270
Asn Tyr Lys Asn Thr Glu Pro Val Leu Asp Ser Asp Gly Ser Tyr Phe
            275                 280                 285
Met Tyr Ser Lys Leu Arg Val Glu Lys Lys Asn Trp Val Glu Arg Asn
        290                 295                 300
Ser Tyr Ser Cys Ser Val Val His Glu Gly Leu His Asn His His Thr
305                 310                 315                 320
Thr Lys Ser Phe Ser Arg Thr Pro Gly Lys
            325                 330

<210> SEQ ID NO 209
<211> LENGTH: 402
<212> TYPE: PRT
<213> ORGANISM: Artificial Sequence
<220> FEATURE:
<223> OTHER INFORMATION: mPD1-G1CH2

<400> SEQUENCE: 209

Trp Val Arg Gln Val Pro Trp Ser Phe Thr Trp Ala Val Leu Gln Leu
1               5                   10                  15
Ser Trp Gln Ser Gly Trp Leu Leu Glu Val Pro Asn Gly Pro Trp Arg
            20                  25                  30
Ser Leu Thr Phe Tyr Pro Ala Trp Leu Thr Val Ser Glu Gly Ala Asn
        35                  40                  45
Ala Thr Phe Thr Cys Ser Leu Ser Asn Trp Ser Glu Asp Leu Met Leu
    50                  55                  60
Asn Trp Asn Arg Leu Ser Pro Ser Asn Gln Thr Glu Lys Gln Ala Ala
65                  70                  75                  80
Phe Ser Asn Gly Leu Ser Gln Pro Val Gln Asp Ala Arg Phe Gln Ile
                85                  90                  95
Ile Gln Leu Pro Asn Arg His Asp Phe His Met Asn Ile Leu Asp Thr
            100                 105                 110
Arg Arg Asn Asp Ser Gly Ile Tyr Leu Cys Gly Ala Ile Ser Leu His
        115                 120                 125
Pro Lys Ala Lys Ile Glu Glu Ser Pro Gly Ala Glu Leu Val Val Thr
    130                 135                 140
Glu Arg Ile Leu Glu Thr Ser Thr Arg Tyr Pro Ser Pro Ser Pro Lys
145                 150                 155                 160
Pro Glu Gly Arg Phe Gln Asp Ile Glu Gly Arg Met Asp Pro Lys Ser
                165                 170                 175
Cys Asp Lys Thr His Thr Cys Pro Pro Cys Pro Ala Pro Glu Leu Leu
            180                 185                 190
Gly Gly Pro Ser Val Phe Leu Phe Pro Pro Lys Pro Lys Asp Thr Leu
        195                 200                 205
Met Ile Ser Arg Thr Pro Glu Val Thr Cys Val Val Val Asp Val Ser
    210                 215                 220
His Glu Asp Pro Glu Val Lys Phe Asn Trp Tyr Val Asp Gly Val Glu
225                 230                 235                 240
Val His Asn Ala Lys Thr Lys Pro Arg Glu Glu Gln Tyr Asn Ser Thr
                245                 250                 255
Tyr Arg Val Val Ser Val Leu Thr Val Leu His Gln Asp Trp Leu Asn
            260                 265                 270
Gly Lys Glu Tyr Lys Cys Lys Val Ser Asn Lys Ala Leu Pro Ala Pro
        275                 280                 285
Ile Glu Lys Thr Ile Ser Lys Ala Lys Gly Gln Pro Arg Glu Pro Gln
```

```
                        290                 295                 300
Val Tyr Thr Leu Pro Pro Ser Arg Asp Glu Leu Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
            340                 345                 350

Pro Val Leu Asp Ser Asp Gly Ser Phe Phe Leu Tyr Ser Lys Leu Thr
        355                 360                 365

Val Asp Lys Ser Arg Trp Gln Gln Gly Asn Val Phe Ser Cys Ser Val
    370                 375                 380

Met His Glu Ala Leu His Asn His Tyr Thr Gln Lys Ser Leu Ser Leu
385                 390                 395                 400

Ser Pro

<210> SEQ ID NO 210
<211> LENGTH: 463
<212> TYPE: PRT
<213> ORGANISM: Artificial Sequence
<220> FEATURE:
<223> OTHER INFORMATION: mPDL1-G1dCH2His

<400> SEQUENCE: 210

Phe Thr Ile Thr Ala Pro Lys Asp Leu Tyr Val Val Glu Tyr Gly Ser
1               5                   10                  15

Asn Val Thr Met Glu Cys Arg Phe Pro Val Glu Arg Glu Leu Asp Leu
                20                  25                  30

Leu Ala Leu Val Val Tyr Trp Glu Lys Glu Asp Glu Gln Val Ile Gln
            35                  40                  45

Phe Val Ala Gly Glu Glu Asp Leu Lys Pro Gln His Ser Asn Phe Arg
        50                  55                  60

Gly Arg Ala Ser Leu Pro Lys Asp Gln Leu Leu Lys Gly Asn Ala Ala
65                  70                  75                  80

Leu Gln Ile Thr Asp Val Lys Leu Gln Asp Ala Gly Val Tyr Cys Cys
                85                  90                  95

Ile Ile Ser Tyr Gly Gly Ala Asp Tyr Lys Arg Ile Thr Leu Lys Val
            100                 105                 110

Asn Ala Pro Tyr Arg Lys Ile Asn Gln Arg Ile Ser Val Asp Pro Ala
        115                 120                 125

Thr Ser Glu His Glu Leu Ile Cys Gln Ala Glu Gly Tyr Pro Glu Ala
130                 135                 140

Glu Val Ile Trp Thr Asn Ser Asp His Gln Pro Val Ser Gly Lys Arg
145                 150                 155                 160

Ser Val Thr Thr Ser Arg Thr Glu Gly Met Leu Leu Asn Val Thr Ser
                165                 170                 175

Ser Leu Arg Val Asn Ala Thr Ala Asn Asp Val Phe Tyr Cys Thr Phe
            180                 185                 190

Trp Arg Ser Gln Pro Gly Gln Asn His Thr Ala Glu Leu Ile Ile Pro
        195                 200                 205

Glu Leu Pro Ala Thr His Pro Pro Gln Asn Arg Thr His Ile Glu Gly
    210                 215                 220

Arg Met Asp Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255
```

```
Pro Lys Pro Lys Asp Thr Leu Met Ile Ser Arg Thr Pro Glu Val Thr
            260                 265                 270

Cys Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
                340                 345                 350

Gly Gln Pro Arg Glu Pro Gln Val Tyr Thr Leu Pro Pro Ser Arg Asp
                355                 360                 365

Glu Leu Thr Lys Asn Gln Val Ser Leu Thr Cys Leu Val Lys Gly Phe
        370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
            435                 440                 445

Thr Gln Lys Ser Leu Ser Leu Ser Pro His His His His His His
        450                 455                 460

<210> SEQ ID NO 211
<211> LENGTH: 107
<212> TYPE: PRT
<213> ORGANISM: Artificial Sequence
<220> FEATURE:
<223> OTHER INFORMATION: mk0

<400> SEQUENCE: 211

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 212
<211> LENGTH: 105
<212> TYPE: PRT
<213> ORGANISM: Artificial Sequence
<220> FEATURE:
<223> OTHER INFORMATION: ml0
```

-continued

<400> SEQUENCE: 212

```
Gln Pro Lys Ser Ser Pro Ser Val Thr Leu Phe Pro Pro Ser Ser Glu
1               5                   10                  15

Glu Leu Glu Thr Asn Lys Ala Thr Leu Val Cys Thr Ile Thr Asp Phe
            20                  25                  30

Tyr Pro Gly Val Val Thr Val Asp Trp Lys Val Asp Gly Thr Pro Val
        35                  40                  45

Thr Gln Gly Met Glu Thr Thr Gln Pro Ser Lys Gln Ser Asn Asn Lys
    50                  55                  60

Tyr Met Ala Ser Ser Tyr Leu Thr Leu Thr Ala Arg Ala Trp Glu Arg
65                  70                  75                  80

His Ser Ser Tyr Ser Cys Gln Val Thr His Glu Gly His Thr Val Glu
                85                  90                  95

Lys Ser Leu Ser Arg Ala Asp Cys Ser
            100                 105
```

<210> SEQ ID NO 213
<211> LENGTH: 468
<212> TYPE: PRT
<213> ORGANISM: Artificial Sequence
<220> FEATURE:
<223> OTHER INFORMATION: hIL6R

<400> SEQUENCE: 213

```
Met Leu Ala Val Gly Cys Ala Leu Leu Ala Ala Leu Leu Ala Ala Pro
1               5                   10                  15

Gly Ala Ala Leu Ala Pro Arg Arg Cys Pro Ala Gln Glu Val Ala Arg
            20                  25                  30

Gly Val Leu Thr Ser Leu Pro Gly Asp Ser Val Thr Leu Thr Cys Pro
        35                  40                  45

Gly Val Glu Pro Glu Asp Asn Ala Thr Val His Trp Val Leu Arg Lys
    50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
            100                 105                 110

Pro Pro Glu Glu Pro Gln Leu Ser Cys Phe Arg Lys Ser Pro Leu Ser
        115                 120                 125

Asn Val Val Cys Glu Trp Gly Pro Arg Ser Thr Pro Ser Leu Thr Thr
    130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
            180                 185                 190

Cys Val Ala Ser Ser Val Gly Ser Lys Phe Ser Lys Thr Gln Thr Phe
        195                 200                 205

Gln Gly Cys Gly Ile Leu Gln Pro Asp Pro Ala Asn Ile Thr Val
    210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
```

```
                    245                 250                 255
Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
            275                 280                 285

Val Val Gln Leu Arg Ala Gln Glu Phe Gly Gln Gly Glu Trp Ser
        290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350

Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
        370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
            435                 440                 445

Asp Ala Arg Asp Pro Arg Ser Pro Tyr Asp Ile Ser Asn Thr Asp Tyr
        450                 455                 460

Phe Phe Pro Arg
465

<210> SEQ ID NO 214
<211> LENGTH: 288
<212> TYPE: PRT
<213> ORGANISM: Mus musculus

<400> SEQUENCE: 214

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140
```

-continued

```
Thr Glu Arg Ile Leu Glu Thr Ser Thr Arg Tyr Pro Ser Pro Ser Pro
145                 150                 155                 160

Lys Pro Glu Gly Arg Phe Gln Gly Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

<210> SEQ ID NO 215
<211> LENGTH: 328
<212> TYPE: PRT
<213> ORGANISM: Artificial Sequence
<220> FEATURE:
<223> OTHER INFORMATION: G1m

<400> SEQUENCE: 215

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 216
<211> LENGTH: 106
<212> TYPE: PRT
<213> ORGANISM: Artificial Sequence
<220> FEATURE:
<223> OTHER INFORMATION: lam1

<400> SEQUENCE: 216

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 217
<211> LENGTH: 328
<212> TYPE: PRT
<213> ORGANISM: Artificial Sequence
<220> FEATURE:
<223> OTHER INFORMATION: G1d

<400> SEQUENCE: 217

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 218
<211> LENGTH: 107
<212> TYPE: PRT
<213> ORGANISM: Artificial Sequence
<220> FEATURE:
<223> OTHER INFORMATION: k0

<400> SEQUENCE: 218

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 219
```

```
<211> LENGTH: 330
<212> TYPE: PRT
<213> ORGANISM: Homo sapiens

<400> SEQUENCE: 219

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 220
<211> LENGTH: 326
<212> TYPE: PRT
<213> ORGANISM: Homo sapiens

<400> SEQUENCE: 220

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 221
<211> LENGTH: 377
<212> TYPE: PRT
<213> ORGANISM: Homo sapiens

<400> SEQUENCE: 221

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
            50                  55                  60
Leu Ser Ser Val Thr Val Pro Ser Ser Leu Gly Thr Gln Thr
 65                  70                  75                  80

Tyr Thr Cys Asn Val Asn His Lys Pro Ser Asn Thr Lys Val Asp Lys
                     85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Cys Pro Arg
            115                 120                 125

Cys Pro Glu Pro Lys Ser Cys Asp Thr Pro Pro Cys Pro Arg Cys
130                 135                 140

Pro Glu Pro Lys Ser Cys Asp Thr Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
                195                 200                 205

Val Asp Gly Val Glu Val His Asn Ala Lys Thr Lys Pro Arg Glu Glu
                210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
                275                 280                 285

Thr Lys Asn Gln Val Ser Leu Thr Cys Leu Val Lys Gly Phe Tyr Pro
                290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
                340                 345                 350

Phe Ser Cys Ser Val Met His Glu Ala Leu His Asn Arg Phe Thr Gln
                355                 360                 365

Lys Ser Leu Ser Leu Ser Pro Gly Lys
                370                 375

<210> SEQ ID NO 222
<211> LENGTH: 327
<212> TYPE: PRT
<213> ORGANISM: Homo sapiens

<400> SEQUENCE: 222

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45
```

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 223
<211> LENGTH: 328
<212> TYPE: PRT
<213> ORGANISM: Artificial Sequence
<220> FEATURE:
<223> OTHER INFORMATION: G1T6

<400> SEQUENCE: 223

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Ser Asn Gly Gln Pro Glu Asn
            260                 265                 270    Asn

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro
                325

<210> SEQ ID NO 224
<211> LENGTH: 122
<212> TYPE: PRT
<213> ORGANISM: Artificial Sequence
<220> FEATURE:
<223> OTHER INFORMATION: TR01H113

<400> SEQUENCE: 224

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Asn Ala
            20                  25                  30

Trp Met His Trp Val Arg Gln Ala Pro Gly Lys Gly Leu Glu Trp Val
        35                  40                  45

Ala Gln Ile Lys Asp Lys Ser Gln Asn Tyr Ala Thr Tyr Val Ala Glu
    50                  55                  60

Ser Val Lys Gly Arg Phe Thr Ile Ser Arg Ala Asp Ser Lys Asn Ser
65                  70                  75                  80

Ile Tyr Leu Gln Met Asn Ser Leu Lys Thr Glu Asp Thr Ala Val Tyr
                85                  90                  95

Tyr Cys Arg Tyr Val His Tyr Ala Ala Gly Tyr Gly Val Asp Ile Trp
            100                 105                 110
```

-continued

```
Gly Gln Gly Thr Thr Val Thr Val Ser Ser
        115                 120

<210> SEQ ID NO 225
<211> LENGTH: 219
<212> TYPE: PRT
<213> ORGANISM: Artificial Sequence
<220> FEATURE:
<223> OTHER INFORMATION: L0011-k0

<400> SEQUENCE: 225

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Pro Leu Val His Ser
            20                  25                  30

Asn Arg Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Val Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

ANTI-CD137 ANTIGEN-BINDING MOLECULE AND UTILIZATION THEREOF

CROSS-REFERENCE TO RELATED APPLICATIONS

This application is a U.S. National Phase of PCT Application No. PCT/JP2019/031554, filed Aug. 9, 2019, which claims the benefit of Japanese Patent Application No. 2018-152126, filed Aug. 10, 2018, each of which is incorporated herein by reference in its entirety.

Reference to Sequence Listing Submitted Electronically

The content of the electronically submitted sequence listing (Name: 6663 0167 Sequence Listing. txt; Size: 445 kilobytes; and Date of Creation: Feb. 1, 2021) filed with the application is incorporated herein by reference in its entirety.

The present disclosure relates to anti-CD137 antigen-binding molecules and methods of using the same.

BACKGROUND ART

Cancer is a fatal disease that is difficult to cure completely except for some cases. The outcome of treatment with chemotherapeutic agents, which is the main therapeutic method, is by no means good. It has been suggested that not only the heterogeneity of cancer cells themselves but the tumor microenvironment plays a significant role as a factor making cancer treatment difficult (NPL 1). Recently, unresectable malignant melanoma and such were shown to be potentially curable with an anti-CTLA-4 antibody, which suppresses the immunosuppressive function of CTLA-4 and thereby promotes activation of T cells (NPL 2). In the year 2011, an anti-human CTLA-4 monoclonal antibody (ipilimumab) was approved by the U.S. Food and Drug Administration (FDA) as the first immune-activating antibody drug in the world. Furthermore, inhibitory antibodies against PD-1 and PD-L1, other immune checkpoint molecules than CTLA-4, have also been reported to have therapeutic effects (NPL 3), and approved by FDA.

It is understood that T cells, which have important roles in tumor immunity, are activated by two signals: 1) binding of a T cell receptor (TCR) to an antigenic peptide presented by major histocompatibility complex (MHC) class I molecules and activation of the TCR; and 2) binding of a costimulatory molecule on the surface of T cells to its ligands on the antigen-presenting cells and activation of the costimulatory molecule. In addition, activation of costimulatory molecules belonging to the tumor necrosis factor receptor superfamily (TNFRSF), including CD137 (4-1BB), on the surface of T cells has been described as important for T cell activation (NPL 4).

TNFRSF includes CD137, CD40, OX40, RANK, GITR, and such molecules. CD137 is reportedly expressed not only on the surface of T cells but also on the surface of other immune cells such as dendritic cells (DC), B cells, NK cells, macrophages, and neutrophils (NPL 5).

CD137 agonist antibody has already been demonstrated to show antitumor effect in a mouse model, and this has been shown to result mainly from activation of CD8-positive T cells and NK cells by the mouse model experiments (NPL 6). However, side effects due to the nonspecific hepatotoxicity of CD137 agonist antibody have become clinical and non-clinical problems, hindering the desired progress of drug development (NPL 7, NPL 8). It is suggested that the side effects are caused mainly by activation of immune cells in non-tumor, non-immune tissues such as liver which involves binding of the antibody to the Fcγ receptor via the antibody constant region (NPL 9). On the other hand, it has been reported that in order for agonistic anti-TNF receptor superfamily member antibodies to exhibit agonistic activity in vivo, the antibody needs to be cross-linked by Fcγ receptor-expressing cells (FcγRII-expressing cells) (NPL 10). That is, binding of CD137 agonist antibody to Fcγ receptor is involved in both the drug efficacy of the antitumor effect of the antibody and its side effects such as hepatotoxicity. Thus, increasing the binding between the antibody and the Fcγ receptor is expected to enhance the drug efficacy but may also increase hepatotoxic side effects, and reducing the binding between the antibody and the Fcγ receptor may reduce the side effects but also reduce the drug efficacy. There has been no report so far of a CD137 agonist antibody whose drug efficacy and side effects are separated. Moreover, the antitumor effect of CD137 agonist antibody itself is by no means clinically potent, and further enhancement of the drug efficacy is wanted along with avoidance of the toxicity. Accordingly, a new drug is desired to be developed that is capable of inducing antitumor immune responses while reducing those side effects.

When a therapeutic antibody is administered into a living body, it is desirable that its target antigen be expressed specifically at the site of lesion only. However, in many cases, the same antigen is also expressed in non-lesion sites, i.e. normal tissues, and this could be a cause of side effects unwanted from the viewpoint of treatment. For example, while antibodies against tumor antigens can exhibit cytotoxic activity on tumor cells by ADCC etc., they could also damage normal cells if the same antigen is expressed in normal cells. In order to solve the above-mentioned problems, a focus was placed on the phenomenon in which certain compounds are abundantly present in target tissues (e.g. tumor tissues), and a technology to search for antigen-binding molecules with varying antigen-binding activity depending on the concentration of such compounds was developed (for example, PTL 1).

CITATION LIST

Patent Literature

[PTL 1] WO2013/180200

Non Patent Literature

[NPL 1] Hanahan, Cell, 2011, 144, 646-74
[NPL 2] Prieto, Clin Cancer Res. 2012, 18, 2039-47
[NPL 3] Hamid, Expert Opin. Biol. Ther., 2013, 6, 847-61
[NPL 4] Summers, Nat Rev Immunol, 2012, 12, 339-51
[NPL 5] Vinay, Cellular & Molecular Immunology, 2011, 8, 281-284
[NPL 6] Houot, Blood, 2009, 114, 3431-8
[NPL 7] Ascierto, Semin Oncol, 2010, 37, 508-16
[NPL 8] Dubrot, Cancer Immunol Immunother, 2010, 59, 1223-33
[NPL 9] Schabowsky, Vaccine, 2009, 28, 512-22
[NPL 10] Li, Proc Natl Acad Sci USA. 2013, 110(48), 19501-6

SUMMARY OF INVENTION

Technical Problem

The present disclosure relates to anti-CD137 antigen-binding molecules and methods of using the same.

Solution to Problem

In order to provide anti-CD137 antigen-binding molecules which have immunocyte-activating effect, cytotoxic activity, or antitumor activity and meanwhile have reduced effect on non-tumor tissues such as normal tissues and have less side effects, and provide methods of using the same, the present disclosure provides anti-CD137 antigen-binding molecules characterized in that their binding activity to CD137 varies depending on various compounds (e.g. small molecule compounds) in target tissues (e.g. tumor tissues), and provides methods of using the same, pharmaceutical formulations, and such. In one embodiment, the anti-CD137 antigen-binding molecules of the present disclosure have low side effects, and thus the dosage can be increased without concerns about side effects, and as a result, they can exhibit stronger drug efficacy (cytotoxic activity or antitumor activity).

Specifically, the present disclosure provides anti-CD137 antigen-binding molecules, methods of using the same, pharmaceutical formulations, and such, as exemplarily described below.

[1] An anti-CD137 antigen-binding molecule which has CD137-binding activity dependent on a small molecule compound.

[2] The anti-CD137 antigen-binding molecule of [1], wherein the binding activity to CD137 in the presence of 10 μM, 50 μM, 100 μM, 150 μM, 200 μM, or 250 μM of the small molecule compound is twice or more higher than the binding activity to CD137 in the absence of the small molecule compound.

[2.1] The anti-CD137 antigen-binding molecule of [1] or [2], wherein the binding activity to CD137 in the presence of 10 μM or more of the small molecule compound is twice or more higher than the binding activity to CD137 in the absence of the small molecule compound.

[2.2] The anti-CD137 antigen-binding molecule of any one of [1] to [2.1], wherein the KD value for CD137 in the presence of 10 μM or more of the small molecule compound is $5 \times 10^{-7}$ M or less.

[2.3] The anti-CD137 antigen-binding molecule of any one of [1] to [2.2], wherein the KD value for CD137 in the absence of the small molecule compound is $1 \times 10^{-6}$ M or more.

[2.4] The anti-CD137 antigen-binding molecule of [1], wherein the KD value for CD137 in a solution that is prepared such that the concentration of the small molecule compound is 10 μM or more is $5 \times 10^{-7}$ M or less, and the KD value for CD137 in a solution to which the small molecule compound is not added is $1 \times 10^{-6}$ M or more.

[2.5] The anti-CD137 antigen-binding molecule of [1], wherein the KD value for CD137 in a solution that is prepared such that the concentration of the small molecule compound is 10 μM or more, and the KD value for CD137 in a solution to which the small molecule compound is not added, are each measured by a Biacore assay within 24 hours after CD137 and the anti-CD137 antigen-binding molecule are contacted in the solution.

[2.6] The anti-CD137 antigen-binding molecule of any one of [1] to [2.5], which forms a trimolecular complex with the small molecule compound and CD137.

[2.7] The anti-CD137 antigen-binding molecule of any one of [1] to [2.6], which binds to CD137 derived from human and monkey.

[2.8] The anti-CD137 antigen-binding molecule of any one of [1] to [2.7], wherein the small molecule compound is an adenosine-containing compound.

[2.9] The anti-CD137 antigen-binding molecule of any one of [1] to [2.8], wherein the small molecule compound is ATP.

[3] The anti-CD137 antigen-binding molecule of any one of [1] to [2.9], which comprises any combination of HVR-H1, HVR-H2, and HVR-H3 selected from (a) to (k) below:
  (a) HVR-H1 comprising the amino acid sequence of SEQ ID NO: 7, HVR-H2 comprising the amino acid sequence of SEQ ID NO: 8, and HVR-H3 comprising the amino acid sequence of SEQ ID NO: 17;
  (b) HVR-H1 comprising the amino acid sequence of SEQ ID NO: 7, HVR-H2 comprising the amino acid sequence of SEQ ID NO: 9, and HVR-H3 comprising the amino acid sequence of SEQ ID NO: 17;
  (c) HVR-H1 comprising the amino acid sequence of SEQ ID NO: 7, HVR-H2 comprising the amino acid sequence of SEQ ID NO: 10, and HVR-H3 comprising the amino acid sequence of SEQ ID NO: 17;
  (d) HVR-H1 comprising the amino acid sequence of SEQ ID NO: 7, HVR-H2 comprising the amino acid sequence of SEQ ID NO: 11, and HVR-H3 comprising the amino acid sequence of SEQ ID NO: 18;
  (e) HVR-H1 comprising the amino acid sequence of SEQ ID NO: 7, HVR-H2 comprising the amino acid sequence of SEQ ID NO: 8, and HVR-H3 comprising the amino acid sequence of SEQ ID NO: 18;
  (f) HVR-H1 comprising the amino acid sequence of SEQ ID NO: 7, HVR-H2 comprising the amino acid sequence of SEQ ID NO: 12, and HVR-H3 comprising the amino acid sequence of SEQ ID NO: 18;
  (g) HVR-H1 comprising the amino acid sequence of SEQ ID NO: 7, HVR-H2 comprising the amino acid sequence of SEQ ID NO: 13, and HVR-H3 comprising the amino acid sequence of SEQ ID NO: 18;
  (h) HVR-H1 comprising the amino acid sequence of SEQ ID NO: 7, HVR-H2 comprising the amino acid sequence of SEQ ID NO: 14, and HVR-H3 comprising the amino acid sequence of SEQ ID NO: 19;
  (i) HVR-H1 comprising the amino acid sequence of SEQ ID NO: 7, HVR-H2 comprising the amino acid sequence of SEQ ID NO: 15, and HVR-H3 comprising the amino acid sequence of SEQ ID NO: 20;
  (j) HVR-H1 comprising the amino acid sequence of SEQ ID NO: 7, HVR-H2 comprising the amino acid sequence of SEQ ID NO: 16, and HVR-H3 comprising the amino acid sequence of SEQ ID NO: 20; and
  (k) HVR-H1 comprising the amino acid sequence of SEQ ID NO: 7, HVR-H2 comprising the amino acid sequence of SEQ ID NO: 14, and HVR-H3 comprising the amino acid sequence of SEQ ID NO: 17.

[3.1] The anti-CD137 antigen-binding molecule of any one of [1] to [3], which comprises any combination of HVR-L1, HVR-L2, and HVR-L3 selected from (a) to (g) below:
  (a) HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;
  (b) HVR-L1 comprising the amino acid sequence of SEQ ID NO: 22, HVR-L2 comprising the amino acid sequence of SEQ ID NO: 26, and HVR-L3 comprising the amino acid sequence of SEQ ID NO: 27;

(c) HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 28;

(d) HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 29;

(e) HVR-L1 comprising the amino acid sequence of SEQ ID NO: 23, HVR-L2 comprising the amino acid sequence of SEQ ID NO: 26, and HVR-L3 comprising the amino acid sequence of SEQ ID NO: 27;

(f) HVR-L1 comprising the amino acid sequence of SEQ ID NO: 24, HVR-L2 comprising the amino acid sequence of SEQ ID NO: 26, and HVR-L3 comprising the amino acid sequence of SEQ ID NO: 27; and (g) HVR-L1 comprising the amino acid sequence of SEQ ID NO: 25, HVR-L2 comprising the amino acid sequence of SEQ ID NO: 26, and HVR-L3 comprising the amino acid sequence of SEQ ID NO: 27.

[4] An anti-CD137 antigen-binding molecule comprising any combination of HVR-H1, HVR-H2, HVR-H3, HVR-L1, HVR-L2, and HVR-L3 selected from (a) to (m) below:

(a) HVR-H1 comprising the amino acid sequence of SEQ ID NO: 7, HVR-H2 comprising the amino acid sequence of SEQ ID NO: 8, HVR-H3 comprising the amino acid sequence of SEQ ID NO: 17, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;

(b) HVR-H1 comprising the amino acid sequence of SEQ ID NO: 7, HVR-H2 comprising the amino acid sequence of SEQ ID NO: 9, HVR-H3 comprising the amino acid sequence of SEQ ID NO: 17, HVR-L1 comprising the amino acid sequence of SEQ ID NO: 22, HVR-L2 comprising the amino acid sequence of SEQ ID NO: 26, and HVR-L3 comprising the amino acid sequence of SEQ ID NO: 27;

(c) HVR-H1 comprising the amino acid sequence of SEQ ID NO: 7, HVR-H2 comprising the amino acid sequence of SEQ ID NO: 10, HVR-H3 comprising the amino acid sequence of SEQ ID NO: 17, HVR-L1 comprising the amino acid sequence of SEQ ID NO: 22, HVR-L2 comprising the amino acid sequence of SEQ ID NO: 26, and HVR-L3 comprising the amino acid sequence of SEQ ID NO: 27;

(d) HVR-H1 comprising the amino acid sequence of SEQ ID NO: 7, HVR-H2 comprising the amino acid sequence of SEQ ID NO: 11, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;

(e) HVR-H1 comprising the amino acid sequence of SEQ ID NO: 7, HVR-H2 comprising the amino acid sequence of SEQ ID NO: 8, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;

(f) HVR-H1 comprising the amino acid sequence of SEQ ID NO: 7, HVR-H2 comprising the amino acid sequence of SEQ ID NO: 12, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 28;

(g) HVR-H1 comprising the amino acid sequence of SEQ ID NO: 7, HVR-H2 comprising the amino acid sequence of SEQ ID NO: 13, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 29;

(h) HVR-H1 comprising the amino acid sequence of SEQ ID NO: 7, HVR-H2 comprising the amino acid sequence of SEQ ID NO: 14, HVR-H3 comprising the amino acid sequence of SEQ ID NO: 19, HVR-L1 comprising the amino acid sequence of SEQ ID NO: 23, HVR-L2 comprising the amino acid sequence of SEQ ID NO: 26, and HVR-L3 comprising the amino acid sequence of SEQ ID NO: 27;

(i) HVR-H1 comprising the amino acid sequence of SEQ ID NO: 7, HVR-H2 comprising the amino acid sequence of SEQ ID NO: 15, HVR-H3 comprising the amino acid sequence of SEQ ID NO: 20, HVR-L1 comprising the amino acid sequence of SEQ ID NO: 24, HVR-L2 comprising the amino acid sequence of SEQ ID NO: 26, and HVR-L3 comprising the amino acid sequence of SEQ ID NO: 27;

(j) HVR-H1 comprising the amino acid sequence of SEQ ID NO: 7, HVR-H2 comprising the amino acid sequence of SEQ ID NO: 15, HVR-H3 comprising the amino acid sequence of SEQ ID NO: 20, HVR-L1 comprising the amino acid sequence of SEQ ID NO: 25, HVR-L2 comprising the amino acid sequence of SEQ ID NO: 26, and HVR-L3 comprising the amino acid sequence of SEQ ID NO: 27;

(k) HVR-H1 comprising the amino acid sequence of SEQ ID NO: 7, HVR-H2 comprising the amino acid sequence of SEQ ID NO: 16, HVR-H3 comprising the amino acid sequence of SEQ ID NO: 20, HVR-L1 comprising the amino acid sequence of SEQ ID NO: 25, HVR-L2 comprising the amino acid sequence of SEQ ID NO: 26, and HVR-L3 comprising the amino acid sequence of SEQ ID NO: 27;

(l) HVR-H1 comprising the amino acid sequence of SEQ ID NO: 7, HVR-H2 comprising the amino acid sequence of SEQ ID NO: 14, HVR-H3 comprising the amino acid sequence of SEQ ID NO: 19, HVR-L1 comprising the amino acid sequence of SEQ ID NO: 24, HVR-L2 comprising the amino acid sequence of SEQ ID NO: 26, and HVR-L3 comprising the amino acid sequence of SEQ ID NO: 27; and (m) HVR-H1 comprising the amino acid sequence of SEQ ID NO: 7, HVR-H2 comprising the amino acid sequence of SEQ ID NO: 14, HVR-H3 comprising the amino acid sequence of SEQ ID NO: 17, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27.

[5] An anti-CD137 antigen-binding molecule comprising:

(a) a VH having at least 95% sequence identity with any one of the amino acid sequences of SEQ ID NOs: 43 to 53; or (b) a VL having at least 95% sequence identity with any one of the amino acid sequences of SEQ ID NOs: 54 to 60.

[5.1] An anti-CD137 antigen-binding molecule, which comprises any combination of VH and VL selected from (a) to (m) below:
- (a) a VH having at least 95% sequence identity with the amino acid sequence of SEQ ID NO: 43, and a VL having at least 95% sequence identity with the amino acid sequence of SEQ ID NO: 54;
- (b) a VH having at least 95% sequence identity with the amino acid sequence of SEQ ID NO: 44, and a VL having at least 95% sequence identity with the amino acid sequence of SEQ ID NO: 55;
- (c) a VH having at least 95% sequence identity with the amino acid sequence of SEQ ID NO: 45, and a VL having at least 95% sequence identity with the amino acid sequence of SEQ ID NO: 55;
- (d) a VH having at least 95% sequence identity with the amino acid sequence of SEQ ID NO: 46, and a VL having at least 95% sequence identity with the amino acid sequence of SEQ ID NO: 54;
- (e) a VH having at least 95% sequence identity with the amino acid sequence of SEQ ID NO: 47, and a VL having at least 95% sequence identity with the amino acid sequence of SEQ ID NO: 54;
- (f) a VH having at least 95% sequence identity with the amino acid sequence of SEQ ID NO: 48, and a VL having at least 95% sequence identity with the amino acid sequence of SEQ ID NO: 56;
- (g) a VH having at least 95% sequence identity with the amino acid sequence of SEQ ID NO: 49, and a VL having at least 95% sequence identity with the amino acid sequence of SEQ ID NO: 57;
- (h) a VH having at least 95% sequence identity with the amino acid sequence of SEQ ID NO: 50, and a VL having at least 95% sequence identity with the amino acid sequence of SEQ ID NO: 58;
- (i) a VH having at least 95% sequence identity with the amino acid sequence of SEQ ID NO: 51, and a VL having at least 95% sequence identity with the amino acid sequence of SEQ ID NO: 59;
- (j) a VH having at least 95% sequence identity with the amino acid sequence of SEQ ID NO: 51, and a VL having at least 95% sequence identity with the amino acid sequence of SEQ ID NO: 60;
- (k) a VH having at least 95% sequence identity with the amino acid sequence of SEQ ID NO: 52, and a VL having at least 95% sequence identity with the amino acid sequence of SEQ ID NO: 60;
- (l) a VH having at least 95% sequence identity with the amino acid sequence of SEQ ID NO: 50, and a VL having at least 95% sequence identity with the amino acid sequence of SEQ ID NO: 59; and
- (m) a VH having at least 95% sequence identity with the amino acid sequence of SEQ ID NO: 53, and a VL having at least 95% sequence identity with the amino acid sequence of SEQ ID NO: 54.

[5.2] An anti-CD137 antigen-binding molecule, which comprises any combination of VH and VL selected from (a) to (m) below:
- (a) a VH comprising the amino acid sequence of SEQ ID NO: 43, and a VL comprising the amino acid sequence of SEQ ID NO: 54;
- (b) a VH comprising the amino acid sequence of SEQ ID NO: 44, and a VL comprising the amino acid sequence of SEQ ID NO: 55;
- (c) a VH comprising the amino acid sequence of SEQ ID NO: 45, and a VL comprising the amino acid sequence of SEQ ID NO: 55;
- (d) a VH comprising the amino acid sequence of SEQ ID NO: 46, and a VL comprising the amino acid sequence of SEQ ID NO: 54;
- (e) a VH comprising the amino acid sequence of SEQ ID NO: 47, and a VL comprising the amino acid sequence of SEQ ID NO: 54;
- (f) a VH comprising the amino acid sequence of SEQ ID NO: 48, and a VL comprising the amino acid sequence of SEQ ID NO: 56;
- (g) a VH comprising the amino acid sequence of SEQ ID NO: 49, and a VL comprising the amino acid sequence of SEQ ID NO: 57;
- (h) a VH comprising the amino acid sequence of SEQ ID NO: 50, and a VL comprising the amino acid sequence of SEQ ID NO: 58;
- (i) a VH comprising the amino acid sequence of SEQ ID NO: 51, and a VL comprising the amino acid sequence of SEQ ID NO: 59;
- (j) a VH comprising the amino acid sequence of SEQ ID NO: 51, and a VL comprising the amino acid sequence of SEQ ID NO: 60;
- (k) a VH comprising the amino acid sequence of SEQ ID NO: 52, and a VL comprising the amino acid sequence of SEQ ID NO: 60;
- (l) a VH comprising the amino acid sequence of SEQ ID NO: 50, and a VL comprising the amino acid sequence of SEQ ID NO: 59; and
- (m) a VH comprising the amino acid sequence of SEQ ID NO: 53, and a VL comprising the amino acid sequence of SEQ ID NO: 54.

[5.3] An anti-CD137 antigen-binding molecule whose value of [binding activity (binding amount) to CD137 in the presence of 10 µM or more of a small molecule compound]/[binding activity (binding amount) to CD137 in the absence of the small molecule compound] is equal to or greater than that of a reference antigen-binding molecule, wherein the reference antigen-binding molecule is an anti-CD137 antigen-binding molecule comprising a combination of HVR-H1 comprising the amino acid sequence of SEQ ID NO: 7, HVR-H2 comprising the amino acid sequence of SEQ ID NO: 8, HVR-H3 comprising the amino acid sequence of SEQ ID NO: 17, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27.

[5.4] The anti-CD137 antigen-binding molecule of [5.3], wherein the reference antigen-binding molecule is an anti-CD137 antigen-binding molecule comprising a combination of a VH comprising the amino acid sequence of SEQ ID NO: 43 and a VL comprising the amino acid sequence of SEQ ID NO: 54.

[5.5] An anti-CD137 antigen-binding molecule whose value of [binding activity (KD) to CD137 in the presence of 1 µM of a small molecule compound]/[binding activity (KD) to CD137 in the presence of 10 µM or more of the small molecule compound is equal to or greater than that of a reference antigen-binding molecule,
wherein the reference antigen-binding molecule is an anti-CD137 antigen-binding molecule comprising a combination of HVR-H1 comprising the amino acid sequence of SEQ ID NO: 7, HVR-H2 comprising the amino acid sequence of SEQ ID NO: 8, HVR-H3 comprising the amino acid sequence of SEQ ID NO: 17, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27.

[5.6] The anti-CD137 antigen-binding molecule of [5.5], wherein the reference antigen-binding molecule is an anti-CD137 antigen-binding molecule comprising a combination of a VH comprising the amino acid sequence of SEQ ID NO: 43 and a VL comprising the amino acid sequence of SEQ ID NO: 54.

[5.7] An anti-CD137 antigen-binding molecule which has CD137-binding activity dependent on a small molecule compound, wherein the anti-CD137 antigen-binding molecule competes with the antigen binding molecule of any one of [3] to [5.2] for binding to CD137 in the presence of 10 μM or more, 50 μM or more, 100 μM or more, 150 μM or more, 200 μM or more, or 250 μM or more of the small molecule compound.

[5.8] An anti-CD137 antigen-binding molecule which has CD137-binding activity dependent on a small molecule compound, wherein the anti-CD137 antigen-binding molecule binds to the same epitope of CD137 bound by the antigen binding molecule of any one of [3] to [5.2] in the presence of 10 μM or more, 50 μM or more, 100 μM or more, 150 μM or more, 200 μM or more, or 250 μM or more of the small molecule compound.

[5.8A] The anti-CD137 antigen-binding molecule of any one of [5.3] to [5.8], wherein the small molecule compound is an adenosine-containing compound.

[5.8B] The anti-CD137 antigen-binding molecule of any one of [5.3] to [5.8A], wherein the small molecule compound is ATP.

[5.9] The anti-CD137 antigen-binding molecule of any one of [1] to [5.8B], which is a monoclonal antibody or an antigen-binding fragment thereof.

[5.10] The anti-CD137 antigen-binding molecule of any one of [1] to [5.9], which is a human antibody, humanized antibody, or chimeric antibody, or an antigen-binding fragment thereof.

[5.11] The anti-CD137 antigen-binding molecule of any one of [1] to [5.10], which is a full-length IgG1 antibody.

[5.12] The anti-CD137 antigen-binding molecule of any one of [1] to [5.11], which comprises an altered Fc region in which at least one amino acid is altered, wherein the altered Fc region has increased binding activity to FcγRIIb as compared to a parent Fc region which does not comprise the amino acid alteration.

[5.13] The anti-CD137 antigen-binding molecule of [5.12], wherein the binding activity of the altered Fc to FcγRIIb is equal to or higher than that of a reference Fc region, wherein the reference Fc is a human IgG1 Fc region comprising a combination of amino acid substitutions G236N/H268D/A330K according to EU numbering.

[5.14] The anti-CD137 antigen-binding molecule of [5.12] or [5.13], wherein the reference Fc region comprises the amino acid sequence of SEQ ID NO: 153.

[5.15] The anti-CD137 antigen-binding molecule of [5.12], wherein the at least one amino acid alteration is at least one amino acid substitution selected from the group consisting of G236N, H268D, and A330K according to EU numbering.

[5.16] The anti-CD137 antigen-binding molecule of [5.12] or [5.15], wherein the at least one amino acid alteration is a combination of amino acid substitutions G236N/H268D/A330K according to EU numbering.

[5.17] The anti-CD137 antigen-binding molecule of any one of [5.12] to [5.16], wherein the parent Fc region is derived from a human IgG1 Fc region.

[5.18] The anti-CD137 antigen-binding molecule of any one of [1] to [5.17], which comprises an altered Fc region in which at least one amino acid is altered, wherein the anti-CD137 antigen-binding molecule has an increased isoelectric point (pI) as compared to that of a parent anti-CD137 antigen-binding molecule comprising a parent Fc region that does not comprise the amino acid alteration.

[5.19] The anti-CD137 antigen-binding molecule of [5.18], wherein the at least one amino acid alteration is an alteration of an amino acid residue that can be exposed on the surface of the parent Fc region.

[5.20] The anti-CD137 antigen-binding molecule of [5.18] or [5.19], wherein the at least one amino acid alteration is:
  (i) substitution of at least one amino acid residue having a negative charge on the side chain in the parent Fc region with an amino acid residue having no charge on the side chain,
  (ii) substitution of at least one amino acid residue having no charge on the side chain in the parent Fc region with an amino acid residue having a positive charge on the side chain, and/or
  (iii) substitution of at least one amino acid residue having a negative charge on the side chain in the parent Fc region with an amino acid residue having a positive charge on the side chain.

[5.21] The anti-CD137 antigen-binding molecule of any one of [5.18] to [5.20], wherein the at least one amino acid alteration is a combination of amino acid substitutions, and wherein the amino acid substitutions are located at positions that are conformationally close to one another.

[5.22] The anti-CD137 antigen-binding molecule of any one of [5.18] to [5.21], wherein the binding activity of the altered Fc region to an Fcγ receptor (FcγR) is not substantially reduced as compared to that of the parent Fc region.

[5.23] The anti-CD137 antigen-binding molecule of [5.22], wherein the Fcγ receptor (FcγR) is FcγRIIb.

[5.24] The anti-CD137 antigen-binding molecule of any one of [5.18] to [5.23], wherein the at least one amino acid alteration is at least one amino acid substitution selected from the group consisting of Q311R, P343R, and D413K according to EU numbering.

[5.25] The anti-CD137 antigen-binding molecule of any one of [5.18] to [5.24], wherein the at least one amino acid alteration is (i) amino acid substitution P343R, (ii) a combination of amino acid substitutions Q311R/P343R, or (iii) a combination of amino acid substitutions Q311R/D413K, according to EU numbering.

[6] The anti-CD137 antigen-binding molecule of any one of [1] to [5.25], which comprises an altered Fc region, wherein the altered Fc region comprises any one combination of amino acid alterations selected from the following:
  L235W/G236N/H268D/Q295L/K326T/A330K/P343R/D413K;
  K214R/L235W/G236N/H268D/Q295L/K326T/A330K/P343R/D413K;
  L234Y/P238D/T250V/V264I/T307P/A330K/P343R/D413K;
  L234Y/P238D/V264I/A330K/P343R/D413K;
  L234Y/G237D/P238D/T250V/T307P/A330K/P343R/D413K;
  L234Y/G237D/P238D/A330K/P343R/D413K;
  L235W/G236N/H268D/Q295L/K326T/A330K/Q311R/P343R;
  L234Y/P238D/T250V/V264I/T307P/A330K/Q311R/P343R;
  L234Y/P238D/V264I/A330K/Q311R/P343R;

L234Y/G237D/P238D/T250V/T307P/A330K/Q311R/ P343R;
L234Y/G237D/P238D/A330K/Q311R/P343R;
L235W/G236N/H268D/Q295L/K326T/A330K/P343R;
K214R/L235W/G236N/H268D/Q295L/K326T/A330K/ P343R;
L235W/G236N/H268D/Q295L/K326T/A330K/D413K;
K214R/G236N/H268D/A330K/P343R;
K214R/L235W/G236N/H268D/A330K/P343R;
K214R/G236N/H268D/A330K/D413K;
K214R/G236N/H268D/A330K/P343R/D413K;
K214R/L235W/G236N/H268D/A330K/P343R/D413K;
K214R/G236N/H268D/A330K/Q311R;
K214R/L235W/G236N/H268D/A330K/Q311R;
K214R/G236N/H268D/A330K/Q311R/P343R;
K214R/L235W/G236N/H268D/A330K/Q311R/P343R;
K214R/G236N/H268D/A330K/Q311R/D413K;
K214R/L235W/G236N/H268D/A330K/Q311R/D413K; and
K214R/L235W/G236N/H268D/Q295L/K326T/A330K/ Q311R,
according to EU numbering.

[6.1] The anti-CD137 antigen-binding molecule of any one of [1] to [6], wherein the altered Fc region is derived from a human IgG1 Fc region.

[6.2] The anti-CD137 antigen-binding molecule of any one of [1] to [6.1], wherein the altered Fc region further comprises deletions at positions 446 and 447 according to EU numbering.

[7] The anti-CD137 antigen-binding molecule of any one of [1] to [6.2], which comprises a heavy chain constant region comprising any one of the amino acid sequences of SEQ ID NOs: 64 to 85.

[7.1] An anti-CD137 antigen-binding molecule comprising any combination of VH, VL, CH, and CL selected from (i) to (xxxviii) below:

(i) VH comprising the amino acid sequence of SEQ ID NO: 43, CH comprising the amino acid sequence of SEQ ID NO: 64, VL comprising the amino acid sequence of SEQ ID NO: 54, and CL comprising the amino acid sequence of SEQ ID NO: 63;

(ii) VH comprising the amino acid sequence of SEQ ID NO: 43, CH comprising the amino acid sequence of SEQ ID NO: 66, VL comprising the amino acid sequence of SEQ ID NO: 54, and CL comprising the amino acid sequence of SEQ ID NO: 63;

(iii) VH comprising the amino acid sequence of SEQ ID NO: 43, CH comprising the amino acid sequence of SEQ ID NO: 67, VL comprising the amino acid sequence of SEQ ID NO: 54, and CL comprising the amino acid sequence of SEQ ID NO: 63;

(iv) VH comprising the amino acid sequence of SEQ ID NO: 43, CH comprising the amino acid sequence of SEQ ID NO: 68, VL comprising the amino acid sequence of SEQ ID NO: 54, and CL comprising the amino acid sequence of SEQ ID NO: 63;

(v) VH comprising the amino acid sequence of SEQ ID NO: 43, CH comprising the amino acid sequence of SEQ ID NO: 69, VL comprising the amino acid sequence of SEQ ID NO: 54, and CL comprising the amino acid sequence of SEQ ID NO: 63;

(vi) VH comprising the amino acid sequence of SEQ ID NO: 43, CH comprising the amino acid sequence of SEQ ID NO: 70, VL comprising the amino acid sequence of SEQ ID NO: 54, and CL comprising the amino acid sequence of SEQ ID NO: 63;

(vii) VH comprising the amino acid sequence of SEQ ID NO: 43, CH comprising the amino acid sequence of SEQ ID NO: 71, VL comprising the amino acid sequence of SEQ ID NO: 54, and CL comprising the amino acid sequence of SEQ ID NO: 63;

(viii) VH comprising the amino acid sequence of SEQ ID NO: 43, CH comprising the amino acid sequence of SEQ ID NO: 73, VL comprising the amino acid sequence of SEQ ID NO: 54, and CL comprising the amino acid sequence of SEQ ID NO: 63;

(ix) VH comprising the amino acid sequence of SEQ ID NO: 43, CH comprising the amino acid sequence of SEQ ID NO: 75, VL comprising the amino acid sequence of SEQ ID NO: 54, and CL comprising the amino acid sequence of SEQ ID NO: 63;

(x) VH comprising the amino acid sequence of SEQ ID NO: 43, CH comprising the amino acid sequence of SEQ ID NO: 78, VL comprising the amino acid sequence of SEQ ID NO: 54, and CL comprising the amino acid sequence of SEQ ID NO: 63;

(xi) VH comprising the amino acid sequence of SEQ ID NO: 43, CH comprising the amino acid sequence of SEQ ID NO: 80, VL comprising the amino acid sequence of SEQ ID NO: 54, and CL comprising the amino acid sequence of SEQ ID NO: 63;

(xii) VH comprising the amino acid sequence of SEQ ID NO: 43, CH comprising the amino acid sequence of SEQ ID NO: 82, VL comprising the amino acid sequence of SEQ ID NO: 54, and CL comprising the amino acid sequence of SEQ ID NO: 63;

(xiii) VH comprising the amino acid sequence of SEQ ID NO: 43, CH comprising the amino acid sequence of SEQ ID NO: 84, VL comprising the amino acid sequence of SEQ ID NO: 54, and CL comprising the amino acid sequence of SEQ ID NO: 63;

(xiv) VH comprising the amino acid sequence of SEQ ID NO: 43, CH comprising the amino acid sequence of SEQ ID NO: 85, VL comprising the amino acid sequence of SEQ ID NO: 54, and CL comprising the amino acid sequence of SEQ ID NO: 63;

(xv) VH comprising the amino acid sequence of SEQ ID NO: 51, CH comprising the amino acid sequence of SEQ ID NO: 65, VL comprising the amino acid sequence of SEQ ID NO: 59, and CL comprising the amino acid sequence of SEQ ID NO: 63;

(xvi) VH comprising the amino acid sequence of SEQ ID NO: 51, CH comprising the amino acid sequence of SEQ ID NO: 72, VL comprising the amino acid sequence of SEQ ID NO: 59, and CL comprising the amino acid sequence of SEQ ID NO: 63;

(xvii) VH comprising the amino acid sequence of SEQ ID NO: 51, CH comprising the amino acid sequence of SEQ ID NO: 74, VL comprising the amino acid sequence of SEQ ID NO: 59, and CL comprising the amino acid sequence of SEQ ID NO: 63;

(xviii) VH comprising the amino acid sequence of SEQ ID NO: 51, CH comprising the amino acid sequence of SEQ ID NO: 75, VL comprising the amino acid sequence of SEQ ID NO: 59, and CL comprising the amino acid sequence of SEQ ID NO: 63;

(xix) VH comprising the amino acid sequence of SEQ ID NO: 51, CH comprising the amino acid sequence of SEQ ID NO: 77, VL comprising the amino acid sequence of SEQ ID NO: 59, and CL comprising the amino acid sequence of SEQ ID NO: 63;

(xx) VH comprising the amino acid sequence of SEQ ID NO: 51, CH comprising the amino acid sequence of SEQ ID NO: 78, VL comprising the amino acid sequence of SEQ ID NO: 59, and CL comprising the amino acid sequence of SEQ ID NO: 63;

(xxi) VH comprising the amino acid sequence of SEQ ID NO: 51, CH comprising the amino acid sequence of SEQ ID NO: 79, VL comprising the amino acid sequence of SEQ ID NO: 59, and CL comprising the amino acid sequence of SEQ ID NO: 63;

(xxii) VH comprising the amino acid sequence of SEQ ID NO: 51, CH comprising the amino acid sequence of SEQ ID NO: 80, VL comprising the amino acid sequence of SEQ ID NO: 59, and CL comprising the amino acid sequence of SEQ ID NO: 63;

(xxiii) VH comprising the amino acid sequence of SEQ ID NO: 51, CH comprising the amino acid sequence of SEQ ID NO: 81, VL comprising the amino acid sequence of SEQ ID NO: 59, and CL comprising the amino acid sequence of SEQ ID NO: 63;

(xxiv) VH comprising the amino acid sequence of SEQ ID NO: 51, CH comprising the amino acid sequence of SEQ ID NO: 82, VL comprising the amino acid sequence of SEQ ID NO: 59, and CL comprising the amino acid sequence of SEQ ID NO: 63;

(xxv) VH comprising the amino acid sequence of SEQ ID NO: 51, CH comprising the amino acid sequence of SEQ ID NO: 83, VL comprising the amino acid sequence of SEQ ID NO: 59, and CL comprising the amino acid sequence of SEQ ID NO: 63;

(xxvi) VH comprising the amino acid sequence of SEQ ID NO: 51, CH comprising the amino acid sequence of SEQ ID NO: 84, VL comprising the amino acid sequence of SEQ ID NO: 59, and CL comprising the amino acid sequence of SEQ ID NO: 63;

(xxvii) VH comprising the amino acid sequence of SEQ ID NO: 51, CH comprising the amino acid sequence of SEQ ID NO: 72, VL comprising the amino acid sequence of SEQ ID NO: 60, and CL comprising the amino acid sequence of SEQ ID NO: 63;

(xxviii) VH comprising the amino acid sequence of SEQ ID NO: 51, CH comprising the amino acid sequence of SEQ ID NO: 74, VL comprising the amino acid sequence of SEQ ID NO: 60, and CL comprising the amino acid sequence of SEQ ID NO: 63;

(xxix) VH comprising the amino acid sequence of SEQ ID NO: 51, CH comprising the amino acid sequence of SEQ ID NO: 75, VL comprising the amino acid sequence of SEQ ID NO: 60, and CL comprising the amino acid sequence of SEQ ID NO: 63;

(xxx) VH comprising the amino acid sequence of SEQ ID NO: 51, CH comprising the amino acid sequence of SEQ ID NO: 77, VL comprising the amino acid sequence of SEQ ID NO: 60, and CL comprising the amino acid sequence of SEQ ID NO: 63;

(xxxi) VH comprising the amino acid sequence of SEQ ID NO: 51, CH comprising the amino acid sequence of SEQ ID NO: 78, VL comprising the amino acid sequence of SEQ ID NO: 60, and CL comprising the amino acid sequence of SEQ ID NO: 63;

(xxxii) VH comprising the amino acid sequence of SEQ ID NO: 51, CH comprising the amino acid sequence of SEQ ID NO: 79, VL comprising the amino acid sequence of SEQ ID NO: 60, and CL comprising the amino acid sequence of SEQ ID NO: 63;

(xxxiii) VH comprising the amino acid sequence of SEQ ID NO: 51, CH comprising the amino acid sequence of SEQ ID NO: 80, VL comprising the amino acid sequence of SEQ ID NO: 60, and CL comprising the amino acid sequence of SEQ ID NO: 63;

(xxxiv) VH comprising the amino acid sequence of SEQ ID NO: 51, CH comprising the amino acid sequence of SEQ ID NO: 81, VL comprising the amino acid sequence of SEQ ID NO: 60, and CL comprising the amino acid sequence of SEQ ID NO: 63;

(xxxv) VH comprising the amino acid sequence of SEQ ID NO: 51, CH comprising the amino acid sequence of SEQ ID NO: 82, VL comprising the amino acid sequence of SEQ ID NO: 60, and CL comprising the amino acid sequence of SEQ ID NO: 63;

(xxxvi) VH comprising the amino acid sequence of SEQ ID NO: 51, CH comprising the amino acid sequence of SEQ ID NO: 83, VL comprising the amino acid sequence of SEQ ID NO: 60, and CL comprising the amino acid sequence of SEQ ID NO: 63;

(xxxvii) VH comprising the amino acid sequence of SEQ ID NO: 51, CH comprising the amino acid sequence of SEQ ID NO: 84, VL comprising the amino acid sequence of SEQ ID NO: 60, and CL comprising the amino acid sequence of SEQ ID NO: 63; and (xxxviii) VH comprising the amino acid sequence of SEQ ID NO: 51, CH comprising the amino acid sequence of SEQ ID NO: 85, VL comprising the amino acid sequence of SEQ ID NO: 60, and CL comprising the amino acid sequence of SEQ ID NO: 63.

[8] An isolated nucleic acid encoding the anti-CD137 antigen-binding molecule of any one of [1] to [7.1].

[9] A vector comprising the nucleic acid of [8].

[10] A host cell comprising the nucleic acid of [8] or the vector of [9].

[11] A method for producing an anti-CD137 antigen-binding molecule, which comprises culturing the host cell of [10] such that the anti-CD137 antigen-binding molecule is produced.

[12] An immunoconjugate comprising the anti-CD137 antigen-binding molecule of any one of [1] to [7.1] and a cytotoxic agent.

[13] A pharmaceutical formulation comprising the anti-CD137 antigen-binding molecule of any one of [1] to [7.1] or the immunoconjugate of [12]; and a pharmaceutically acceptable carrier.

[14] The anti-CD137 antigen-binding molecule of any one of [1] to [7.1] or the immunoconjugate of [12], which is for use as a pharmaceutical.

[14.1] The anti-CD137 antigen-binding molecule of any one of [1] to [7.1], the immunoconjugate of [12], or the pharmaceutical formulation of [13], which is for use in treating a tumor.

[14.2] The anti-CD137 antigen-binding molecule, immunoconjugate, or pharmaceutical formulation of [14.1], wherein the tumor is a solid tumor infiltrated by a B cell, a dendritic cell, a natural killer cell, a macrophage, and/or a CD8-positive T cell.

[14.3] The anti-CD137 antigen-binding molecule, immunoconjugate, or pharmaceutical formulation of [14.1], wherein the tumor is a solid tumor infiltrated by a regulatory T (Treg) cell.

[15] The anti-CD137 antigen-binding molecule of any one of [1] to [7.1], the immunoconjugate of [12], or the pharmaceutical formulation of [13], which is for use in activating an immune cell.

[15.1] The anti-CD137 antigen-binding molecule, immunoconjugate, or pharmaceutical formulation of [15], wherein the immune cell is a B cell, a dendritic cell, a natural killer cell, a macrophage, and/or a T cell.

[15.2] The anti-CD137 antigen-binding molecule of any one of [1] to [7.1], or the pharmaceutical formulation of [13], which is for activating an immune cell in a tumor tissue.
[15.3] The anti-CD137 antigen-binding molecule or pharmaceutical formulation of [15.2], wherein the immune cell is a B cell, a dendritic cell, a natural killer cell, a macrophage, and/or a T cell.
[15.4] The anti-CD137 antigen-binding molecule of any one of [1] to [7.1], the immunoconjugate of [12], or the pharmaceutical formulation of [13], which is for use in damaging a cell.
[16] The anti-CD137 antigen-binding molecule of any one of [1] to [7.1], the immunoconjugate of [12], or the pharmaceutical formulation of [13], whose level of activation of immunity in a non-tumor tissue is lower than that of an anti-CD137 antigen-binding molecule that does not have CD137-binding activity dependent on a small molecule compound.
[16.1] The anti-CD137 antigen-binding molecule, immunoconjugate, or pharmaceutical formulation of [16], wherein the non-tumor tissue is a lymph node, spleen, and/or liver.
[16.2] The anti-CD137 antigen-binding molecule of any one of [1] to [7.1] or the immunoconjugate of [12], which does not substantially bind to CD137 expressed in a non-tumor tissue.
[16.3] The anti-CD137 antigen-binding molecule of any one of ['] to [7.1] or the immunoconjugate of [12], which has a longer blood half-life than that of an anti-CD137 antigen-binding molecule that does not have CD137-binding activity dependent on a small molecule compound.
[17] The anti-CD137 antigen-binding molecule of any one of [1] to [7.1], the immunoconjugate of [12], or the pharmaceutical formulation of [13], which has a lower level of side effect than an anti-CD137 antigen-binding molecule that does not have CD137-binding activity dependent on a small molecule compound.
[17.1] The anti-CD137 antigen-binding molecule, immunoconjugate, or pharmaceutical formulation of [17], wherein the side effect is increased AST, increased ALT, fever, nausea, acute hepatitis, hepatopathy, splenomegaly, enteritis, purulent inflammation of skin, reduction of neutrophils, reduction of lymphocytes, reduction of platelets, expression of transaminase, and/or hyperbilirubinemia.
[18] An anti-CD137 antigen-binding molecule which has CD137 agonist activity dependent on a small molecule compound.
[18.1] The anti-CD137 antigen-binding molecule of [18], wherein the agonist activity for CD137 in the presence of 10 μM, 50 μM, 100 μM, 150 μM, 200 μM, or 250 μM of the small molecule compound is twice or more higher than the agonist activity for CD137 in the absence of the small molecule compound.
[18.2] The anti-CD137 antigen-binding molecule of [18] or [18.1], wherein the agonist activity for CD137 in the presence of 10 μM or more of the small molecule compound is twice or more higher than the agonist activity for CD137 in the absence of the small molecule compound.
[18.3] The anti-CD137 antigen-binding molecule of [18] or [18.1], wherein the agonist activity for CD137 in the presence of 50 μM or more of the small molecule compound is twice or more higher than the agonist activity for CD137 in the absence of the small molecule compound.
[18.4] The anti-CD137 antigen-binding molecule of [18] or [18.1], wherein the agonist activity for CD137 in the presence of 250 μM or more of the small molecule compound is twice or more higher than the agonist activity for CD137 in the absence of the small molecule compound.
[18.5] The anti-CD137 antigen-binding molecule of any one of [18] to [18.4], wherein the agonist activity for CD137 is evaluated with the amount of IL-2 and/or IFN-γ produced by a CD137-expressing cell.
[18.6] The anti-CD137 antigen-binding molecule of [18.5], wherein the CD137-expressing cell is an isolated human peripheral blood mononuclear cell (PBMC) or a human PBMC-derived T cell.
[18.7] The anti-CD137 antigen-binding molecule of any one of [18] to [18.4], wherein the agonist activity for CD137 is evaluated by a reporter gene assay.
[18.8] The anti-CD137 antigen-binding molecule of [18], which exhibits agonist activity for CD137 in a solution that is prepared such that the final concentration of a small molecule compound is 50 μM or more, and does not substantially exhibit agonist activity for CD137 in a solution to which the small molecule compound is not added.
[18.9] The anti-CD137 antigen-binding molecule of [18.8], wherein the agonist activity for CD137 in a solution that is prepared such that the final concentration of a small molecule compound is 50 μM or more, and the agonist activity for CD137 in a solution to which the small molecule compound is not added, are each evaluated with the amount of IL-2, IFN-γ, and/or IL-6 measured within 72 hours after a CD137-expressing cell and the anti-CD137 antigen-binding molecule are contacted in the solution.
[18.10] The anti-CD137 antigen-binding molecule of [18.8], wherein the agonist activity for CD137 in a solution that is prepared such that the final concentration of a small molecule compound is 50 μM or more, and the agonist activity for CD137 in a solution to which the small molecule compound is not added, are each evaluated with a luciferase luminescence signal that is measured within 6 hours after a T cell expressing a NF-kappaB-luciferase reporter construct and CD137 is contacted with the anti-CD137 antigen-binding molecule.
[18.11] The anti-CD137 antigen-binding molecule of any one of [18] to [18.10], wherein the small molecule compound is an adenosine-containing compound.
[18.12] The anti-CD137 antigen-binding molecule of any one of [18] to [18.11], wherein the small molecule compound is ATP.
[19] The anti-CD137 antigen-binding molecule of any one of [1] to [7.1], which has CD137 agonist activity dependent on a small molecule compound.
[19.1] The anti-CD137 antigen-binding molecule of [19], wherein the agonist activity for CD137 in the presence of 10 μM, 50 μM, 100 μM, 150 μM, 200 μM, or 250 μM of the small molecule compound is twice or more higher than the agonist activity for CD137 in the absence of the small molecule compound.
[19.2] The anti-CD137 antigen-binding molecule of [19] or [19.1], wherein the agonist activity for CD137 in the presence of 10 μM or more of the small molecule compound is twice or more higher than the agonist activity for CD137 in the absence of the small molecule compound.
[19.3] The anti-CD137 antigen-binding molecule of [19] or [19.1], wherein the agonist activity for CD137 in the presence of 50 μM or more of the small molecule compound is twice or more higher than the agonist activity for CD137 in the absence of the small molecule compound.
[19.4] The anti-CD137 antigen-binding molecule of [19] or [19.1], wherein the agonist activity for CD137 in the presence of 250 μM or more of the small molecule compound is twice or more higher than the agonist activity for CD137 in the absence of the small molecule compound.

[19.5] The anti-CD137 antigen-binding molecule of any one of [19] to [19.4], wherein the agonist activity for CD137 is evaluated with the amount of IL-2 and/or IFN-γ produced by a CD137-expressing cell.

[19.6] The anti-CD137 antigen-binding molecule of [19.5], wherein the CD137-expressing cell is an isolated human peripheral blood mononuclear cell (PBMC) or a human PBMC-derived T cell.

[19.7] The anti-CD137 antigen-binding molecule of any one of [19] to [19.4], wherein the agonist activity for CD137 is evaluated by a reporter gene assay.

[19.8] The anti-CD137 antigen-binding molecule of [19], which exhibits agonist activity for CD137 in a solution that is prepared such that the final concentration of a small molecule compound is 50 μM or more, and does not substantially exhibit agonist activity for CD137 in a solution to which the small molecule compound is not added.

[19.9] The anti-CD137 antigen-binding molecule of [19.8], wherein the agonist activity for CD137 in a solution that is prepared such that the final concentration of a small molecule compound is 50 μM or more, and the agonist activity for CD137 in a solution to which the small molecule compound is not added, are each evaluated with the amount of IL-2, IFN-γ, and/or IL-6 measured within 72 hours after a CD137-expressing cell and the anti-CD137 antigen-binding molecule are contacted in the solution.

[19.10] The anti-CD137 antigen-binding molecule of [19.8], wherein the agonist activity for CD137 in a solution that is prepared such that the final concentration of a small molecule compound is 50 μM or more, and the agonist activity for CD137 in a solution to which the small molecule compound is not added, are each evaluated with a luciferase luminescence signal that is measured within 6 hours after a T cell expressing a NF-kappaB-luciferase reporter construct and CD137 is contacted with the anti-CD137 antigen-binding molecule.

[19.11] The anti-CD137 antigen-binding molecule of any one of [19] to [19.10], wherein the small molecule compound is an adenosine-containing compound.

[19.12] The anti-CD137 antigen-binding molecule of any one of [19] to [19.11], wherein the small molecule compound is ATP.

[20] An agonist antigen-binding molecule comprising an altered Fc region, wherein the altered Fc region comprises at least one amino acid alteration that leads to an increased isoelectric point (pI) as compared to that of a parent agonist antigen-binding molecule comprising a parent Fc region, and wherein the agonist antigen-binding molecule has increased agonist activity as compared to that of the parent agonist antigen-binding molecule.

[20.1] The agonist antigen-binding molecule of [20], wherein the at least one amino acid alteration is an alteration of an amino acid residue that can be exposed on the surface of the parent Fc region.

[20.2] The agonist antigen-binding antibody of [20] or [20.1], wherein the at least one amino acid alteration is:
  (i) substitution of at least one amino acid residue having a negative charge on the side chain in the parent Fc region with an amino acid residue having no charge on the side chain,
  (ii) substitution of at least one amino acid residue having no charge on the side chain in the parent Fc region with an amino acid residue having a positive charge on the side chain, and/or
  (iii) substitution of at least one amino acid residue having a negative charge on the side chain in the parent Fc region with an amino acid residue having a positive charge on the side chain.

[20.3] The agonist antigen-binding molecule of any one of [20] to [20.2], wherein the at least one amino acid alteration is a combination of amino acid substitutions, and wherein the amino acid substitutions are located at positions that are conformationally close to one another.

[20.4] The agonist antigen-binding molecule of any one of [20] to [20.3], wherein the binding activity of the altered Fc region to an Fcγ receptor is not substantially reduced as compared to that of the parent Fc region.

[20.5] The agonist antigen-binding molecule of [20.4], wherein the Fcγ receptor is FcγRIIb.

[20.6] The agonist antigen-binding molecule of any one of [20] to [20.4], wherein the at least one amino acid alteration is at least one amino acid substitution selected from the group consisting of Q311R, P343R, and D413K, according to EU numbering.

[20.7] The agonist antigen-binding molecule of any one of [20] to [20.6], wherein the at least one amino acid alteration is amino acid alteration of (i) P343R/D413K, (ii) Q311R/P343R, (iii) P343R, (iv) D413K, (v) Q311R, or (vi) Q311R/D413K or a combination thereof, according to EU numbering.

[20.8] The agonist antigen-binding molecule of any one of [20] to [20.7], which is an anti-CD137 antigen-binding molecule.

[20.9] The agonist antigen-binding molecule of any one of [20] to [20.8], which is an anti-CD137 antibody.

[21] A method for producing an agonist antigen-binding molecule comprising an altered Fc region, wherein the method comprises:
introducing into a parent Fc at least one amino acid alteration that leads to an increased isoelectric point (pI) as compared to that of a parent agonist antigen-binding molecule comprising the parent Fc region,
  wherein the agonist activity of the agonist antigen-binding molecule comprising the altered Fc region is increased as compared to that of the parent agonist antigen-binding molecule.

[21.1] The method of [21], wherein the agonist activity of the agonist antigen-binding molecule for the antigen in the presence of 10 μM, 50 μM, 100 μM, 150 μM, 200 μM, or 250 μM of a small molecule compound is twice or more higher than the agonist activity for the antigen in the absence of the small molecule compound.

[21.2] The method of [21] or [21.1], wherein the agonist activity of the agonist antigen-binding molecule for the antigen in the presence of 10 μM or more of a small molecule compound is twice or more higher than the agonist activity for the antigen in the absence of the small molecule compound.

[21.3] The method of [21] or [21.1], wherein the agonist activity of the agonist antigen-binding molecule for the antigen in the presence of 50 μM or more of a small molecule compound is twice or more higher than the agonist activity for the antigen in the absence of the small molecule compound.

[21.4] The method of [21] or [21.1], wherein the agonist activity of the agonist antigen-binding molecule for the antigen in the presence of 250 μM or more of a small molecule compound is twice or more higher than the agonist activity for the antigen in the absence of the small molecule compound.

[21.5] The method of any one of [21] to [21.4], wherein the agonist activity for the antigen is evaluated with the amount of IL-2 and/or IFN-γ produced by an antigen-expressing cell.

[21.6] The method of [21.5], wherein the antigen-expressing cell is an isolated human peripheral blood mononuclear cell (PBMC) or a human PBMC-derived T cell.

[21.7] The method of any one of [21] to [21.4], wherein the agonist activity for the antigen is evaluated by a reporter gene assay.

[21.8] The method of any one of [21] to [21.7], further comprising:
(i) obtaining an expression vector which comprises an appropriate promoter operably linked with a gene encoding the agonist antigen-binding molecule produced by the method of any one of [21] to [21.7],
(ii) introducing the vector into a host cell and culturing the host cell to produce the agonist antigen-binding molecule, and
(iii) collecting the agonist antigen-binding molecule from the host cell culture.

[21.9] The method of any one of [21] to [21.8], which is an anti-CD137 antigen-binding molecule.

[21.10] The method of any one of [21] to [21.9], which is an anti-CD137 antibody.

[21.11] The method of any one of [21.1] to [21.10], wherein the small molecule compound is an adenosine-containing compound.

[21.12] The method of any one of [21.1] to [21.11], wherein the small molecule compound is ATP.

[22] A method for increasing the agonist activity of an agonist antigen-binding molecule comprising an Fc region, wherein the method comprises introducing into the Fc region at least one amino acid alteration that leads to an increased isoelectric point (pI) as compared to that of a parent agonist antigen-binding molecule comprising a parent Fc region.

[22.1] The method of [22], wherein the agonist activity of the agonist antigen-binding molecule for the antigen in the presence of 10 μM, 50 μM, 100 μM, 150 μM, 200 μM, or 250 μM of a small molecule compound is twice or more higher than the agonist activity for the antigen in the absence of the small molecule compound.

[22.2] The method of [22] or [22.1], wherein the agonist activity of the agonist antigen-binding molecule for the antigen in the presence of 10 μM or more of a small molecule compound is twice or more higher than the agonist activity for the antigen in the absence of the small molecule compound.

[22.3] The method of [22] or [22.1], wherein the agonist activity of the agonist antigen-binding molecule for the antigen in the presence of 50 μM or more of a small molecule compound is twice or more higher than the agonist activity for the antigen in the absence of the small molecule compound.

[22.4] The method of [22] or [22.1], wherein the agonist activity of the agonist antigen-binding molecule for the antigen in the presence of 250 μM or more of the small molecule compound is twice or more higher than the agonist activity for the antigen in the absence of the small molecule compound.

[22.5] The method of any one of [22] to [22.4], wherein the agonist activity for the antigen is evaluated with the amount of IL-2 and/or IFN-γ produced by an antigen-expressing cell.

[22.6] The method of [22.5], wherein the antigen-expressing cell is an isolated human peripheral blood mononuclear cell (PBMC) or a human PBMC-derived T cell.

[22.7] The method of any one of [22] to [22.4], wherein the agonist activity for the antigen is evaluated by a reporter gene assay.

[22.8] The method of any one of [22] to [22.7], which is an anti-CD137 antigen-binding molecule.

[22.9] The method of any one of [22] to [22.8], which is an anti-CD137 antibody.

[22.10] The method of any one of [22.1] to [22.9], wherein the small molecule compound is an adenosine-containing compound.

[21.11] The method of any one of [22.1] to [22.10], wherein the small molecule compound is ATP.

[23] A method of use of at least one amino acid alteration for increasing the agonist activity of an agonist antigen-binding molecule comprising an Fc region, wherein the amino acid alteration leads to an increased isoelectric point (pI) as compared to that of a parent agonist antigen-binding molecule comprising a parent Fc region.

[23.1] The method of [23], wherein the agonist activity of the agonist antigen-binding molecule for the antigen in the presence of 10 μM, 50 μM, 100 μM, 150 μM, 200 μM, or 250 μM of a small molecule compound is twice or more higher than the agonist activity for the antigen in the absence of the small molecule compound.

[23.2] The method of [23] or [23.1], wherein the agonist activity of the agonist antigen-binding molecule for the antigen in the presence of 10 μM or more of a small molecule compound is twice or more higher than the agonist activity for the antigen in the absence of the small molecule compound.

[23.3] The method of [23] or [23.1], wherein the agonist activity of the agonist antigen-binding molecule for the antigen in the presence of 50 μM or more of a small molecule compound is twice or more higher than the agonist activity for the antigen in the absence of the small molecule compound.

[23.4] The method of [23] or [23.1], wherein the agonist activity of the agonist antigen-binding molecule for the antigen in the presence of 250 μM or more of a small molecule compound is twice or more higher than the agonist activity for the antigen in the absence of the small molecule compound.

[23.5] The method of any one of [23] to [23.4], wherein the agonist activity for the antigen is evaluated with the amount of IL-2 and/or IFN-γ produced by an antigen-expressing cell.

[23.6] The method of [23.5], wherein the antigen-expressing cell is an isolated human peripheral blood mononuclear cell (PBMC) or a human PBMC-derived T cell.

[23.7] The method of any one of [23] to [23.4], wherein the agonist activity for the antigen is evaluated by a reporter gene assay.

[23.8] The method of any one of [23] to [23.7], which is an anti-CD137 antigen-binding molecule.

[23.9] The method of any one of [23] to [23.8], which is an anti-CD137 antibody.

[23.10] The method of any one of [23.1] to [23.9], wherein the small molecule compound is an adenosine-containing compound.

[23.11] The method of any one of [23.1] to [23.10], wherein the small molecule compound is ATP.

[24] A method of screening for an antigen-binding domain or antigen-binding molecule which has antigen-binding activity dependent on a small molecule compound, wherein the method comprises:
  (a) contacting an antigen-binding domain or antigen-binding molecule or a library of antigen-binding domains or antigen-binding molecules with a fusion molecule in the presence of a small molecule compound, wherein in the fusion molecule two or more units of an antigen are fused to one unit of a fusion partner,
  (b) placing an antigen-binding domain or antigen-binding molecule bound with the antigen within the fusion molecule in step (a) in the absence of, or in the presence of a low concentration of, the small molecule compound, and
  (c) isolating an antigen-binding domain or antigen-binding molecule dissociated in step (b).

[24.1] The method of [24], wherein the fusion partner molecule is a dimer Fc region.

[24.2] The method of [24.1], wherein the Fc region comprises a first Fc subunit and a second Fc subunit, and wherein one unit of the antigen is fused to each of the first and second Fc subunits.

[24.3] The method of [24.1] or [24.2], wherein one unit of the antigen is fused to the N terminus of each of the first and second Fc subunits.

[24.4] The method of any one of [24] to [24.3], wherein the library of antigen-binding domains or antigen-binding molecules is a phage library.

[24.5] The method of any one of [24] to [24.4], wherein the phages included in the phage library are phages presenting on their surface two or more antigen-binding domains or antigen-binding molecules.

[24.6] The method of any one of [24] to [24.5], wherein the phages included in the phage library are phages having a defect in the helper phage-derived pIII gene.

[25] A method of screening for an antigen-binding domain or antigen-binding molecule which has antigen-binding activity dependent on two or more different small molecule compounds, wherein the method comprises:
  (a) contacting an antigen-binding domain or antigen-binding molecule or a library of antigen-binding domains or antigen-binding molecules with an antigen in the presence of a first small molecule compound,
  (b) placing an antigen-binding domain or antigen-binding molecule bound with the antigen in step (a) in the absence of, or in the presence of a low concentration of, the first small molecule compound,
  (c) isolating an antigen-binding domain or antigen-binding molecule dissociated in step (b),
  (d) contacting an antigen-binding domain or antigen-binding molecule isolated in step (c) with the antigen in the presence of a second small molecule compound,
  (e) placing an antigen-binding domain or antigen-binding molecule bound with the antigen in step (d) in the absence of, or in the presence of a low concentration of, the second small molecule compound, and
  (f) isolating an antigen-binding domain or antigen-binding molecule dissociated in step (e), wherein the method does not comprise, between steps (c) and (d), amplifying a gene encoding the antigen-binding domain or antigen-binding molecule isolated in step (c).

[25.1] The method of [25], wherein the library of antigen-binding domains or antigen-binding molecules is a phage library.

[26] A method of screening for an antigen-binding domain or antigen-binding molecule which has antigen-binding activity dependent on a small molecule compound, wherein the method comprises:
  (a) contacting a naive library of antigen-binding domains or antigen-binding molecules with an antigen in the presence of a small molecule compound,
  (b) placing an antigen-binding domain or antigen-binding molecule bound with the antigen in step (a) in the absence of, or the presence of a low concentration of, the small molecule compound, and
  (c) isolating an antigen-binding domain or antigen-binding molecule dissociated in step (b),
    wherein the naive library is a phage library including phages presenting on their surface two or more antigen-binding domains or antigen-binding molecules.

[27] A method of screening for an antigen-binding domain or antigen-binding molecule which has antigen-binding activity dependent on a small molecule compound, wherein the method comprises:
  (a) contacting a library of antigen-binding domains or antigen-binding molecules with an antigen in the presence of a small molecule compound,
  (b) placing an antigen-binding domain or antigen-binding molecule bound with the antigen in step (a) in the absence of, or the presence of a low concentration of, the small molecule compound, and
  (c) isolating an antigen-binding domain or antigen-binding molecule dissociated in step (b),
    wherein the library is a library including phages having a defect in the helper phage-derived pIII gene.

[28] A method of screening for an antigen-binding domain or antigen-binding molecule which has antigen-binding activity dependent on a small molecule compound, wherein the method comprises:
  (a) contacting a library of antigen-binding domains or antigen-binding molecules with an antigen in the presence of a small molecule compound,
  (b) placing an antigen-binding domain or antigen-binding molecule bound with the antigen in step (a) in the absence of, or the presence of a low concentration of, the small molecule compound, and
  (c) isolating an antigen-binding domain or antigen-binding molecule dissociated in step (b),
    wherein the library is a library including phages prepared by increasing the expression of the antigen-binding domain or antigen-binding molecule with a small molecule additive that increases the level of expression from the promoter regulating the expression of the antigen-binding domain or antigen-binding molecule.

[28.1] The screening method of [28], wherein the small molecule additive is isopropyl-β-thiogalactopyranoside or arabinose.

[28.2] The method of any one of [24] to [28.1], wherein the small molecule compound is an adenosine-containing compound.

[28.3] The method of any one of [24] to [28.2], wherein the small molecule compound is ATP.

[29] An antigen-binding molecule which has antigen-binding activity dependent on the concentration of a tumor tissue-specific compound, wherein the antigen-binding activity in the presence of 100 μM of the compound is twice or more higher than the antigen-binding activity in the absence of the compound.

[29.1] The antigen-binding molecule of [29], wherein the KD value in the presence of 100 μM of the compound is 5×10-7 M or less.
[29.2] The antigen-binding molecule of [29] or [29.1], wherein the KD value in the absence of the compound is 1×10-6 M or more.
[29.3] The antigen-binding molecule of any one of [29] to [29.2], which has neutralizing activity against the antigen.
[29.4] The antigen-binding molecule of any one of [29] to [29.3], which has cytotoxic activity against a cell expressing the antigen.
[29.5] The antigen-binding molecule of any one of [29] to [29.4], wherein the antigen is an antigen expressed or secreted by any of a tumor cell, immune cell, and stromal cell in a tumor tissue.
[29.6] The antigen-binding molecule of any one of [29] to [29.5], wherein the compound is an adenosine-containing compound.
[29.7] The antigen-binding molecule of any one of [29] to [29.6], which comprises an Fc region.
[29.8] The antigen-binding molecule of [29.7], wherein the Fc region is a mutated Fc region comprising an amino acid alteration, wherein the mutated Fc region has enhanced binding activity to at least one Fcγ receptor selected from the group consisting of FcγRIa, FcγRIIa, FcγRIIb, and FcγRIIIa, as compared to a wild-type Fc region.
[29.9] The antigen-binding molecule of any one of [29] to [29.8], wherein the antigen-binding molecule is an antibody or an antibody fragment.
[30] A pharmaceutical formulation comprising the antigen-binding molecule of any one of
[29] to [29.9] and a pharmaceutically acceptable carrier.
[30.1] The pharmaceutical formulation of [30], which is for use in treatment of a tumor.
[30.2] The pharmaceutical formulation of [30.1], which has lower cytotoxic activity in a non-tumor tissue than a pharmaceutical formulation comprising a control antigen-binding molecule.
[30.3] The pharmaceutical formulation of [30.1] or [30.2], which has a lower side effect level than a pharmaceutical formulation comprising a control antigen-binding molecule.
[30.4] The pharmaceutical formulation of [30.2] or [30.3], wherein the control antigen-binding molecule is an antigen-binding molecule which does not have antigen-binding activity dependent on the concentration of a tumor tissue-specific compound.
[31] A method for producing an antigen-binding molecule for use in treatment of a tumor, wherein the method comprises the step of selecting an antigen-binding molecule whose antigen-binding activity in the presence of 100 μM of a tumor tissue-specific compound is twice or more higher than the antigen-binding activity in the absence of the compound.
[32] A method for producing a pharmaceutical formulation for use in treatment of a tumor, wherein the method comprises the step of mixing the antigen-binding molecule of any one of
[29] to [29.9] with a pharmaceutically acceptable carrier.
[33] An antigen-binding molecule which has antigen-binding activity dependent on the concentration of a target tissue-specific compound, wherein the antigen-binding activity in the presence of 1 μM of the compound is twice or more lower than the antigen-binding activity in the presence of a sufficient amount of the compound.
[33.1] The antigen-binding molecule of [33], wherein the KD value in the presence of 1 μM of the compound is $2\times10^{-7}$ M or more.
[33.2] The antigen-binding molecule of [33] or [33.1], wherein the KD value in the presence of a sufficient amount of the compound is $1\times10^{-7}$ M or less.
[33.3] The antigen-binding molecule of any one of [33] to [33.2], wherein the compound is a tumor tissue-specific compound.
[33.4] The antigen-binding molecule of [33.3], wherein the compound is an adenosine-containing compound.
[33.5] The antigen-binding molecule of any one of [33] to [33.4], which has higher retentivity in plasma and/or has lower ability of antigen accumulation in plasma than a control antigen-binding molecule.
[33.6] The antigen-binding molecule of [33.5], wherein the control antigen-binding molecule is an antigen-binding molecule which does not have antigen-binding activity dependent on the concentration of a target tissue-specific compound.
[33.7] The antigen-binding molecule of any one of [33] to [33.6], wherein the antigen-binding molecule is an antibody or an antibody fragment.
[34] A pharmaceutical formulation comprising the antigen-binding molecule of any one of
[33] to [33.7] and a pharmaceutically acceptable carrier.
[35] A method for producing an antigen-binding molecule which has a higher retention property in plasma and/or lower ability of antigen accumulation in plasma than a control antigen-binding molecule, wherein the method comprises the steps of (a) producing an antigen-binding molecule whose antigen-binding activity increases as the concentration of a target tissue-specific compound increases, and (b) measuring the retention property in plasma and/or ability of antigen accumulation in plasma of the antigen-binding molecule produced in (a).
[35.1] The method of [35], which comprises the step of selecting an antigen-binding molecule whose antigen-binding activity in the presence of 1 μM of a target tissue-specific compound is twice or more lower than the antigen-binding activity in the presence of a sufficient amount of the compound.
[35.2] The method of [35] or [35.1], wherein the control antigen-binding molecule is an antigen-binding molecule which does not have antigen-binding activity dependent on the concentration of a target tissue-specific compound.
[36] A method for producing a pharmaceutical formulation, which comprises the step of mixing the antigen-binding molecule of any one of [33] to [33.7] with a pharmaceutically acceptable carrier.
[37] A method for measuring ATP concentration in a solution, which comprises the steps of (i) contacting a split Luc/HEK293 cell expressing P2Y11 with the solution, and (ii) measuring luciferase activity in the cell.
[37.1] The method of [37], which further comprises the step of contacting a solution containing a luciferase substrate with the cell.
[37.2] The method of [37] or [37.1], wherein the solution is intercellular fluid within a tissue in vivo.
[37.3] The method of [37.2], wherein the tissue is a tumor tissue.
[37.4] The method of [37.2] or [37.3], wherein step (i) is the step of transplanting a split Luc/HEK293 cell expressing P2Y11 into the tissue in vivo.

The X axis shows the antibody concentration (μg/mL) and the Y axis shows the relative light unit.

Figure 2:
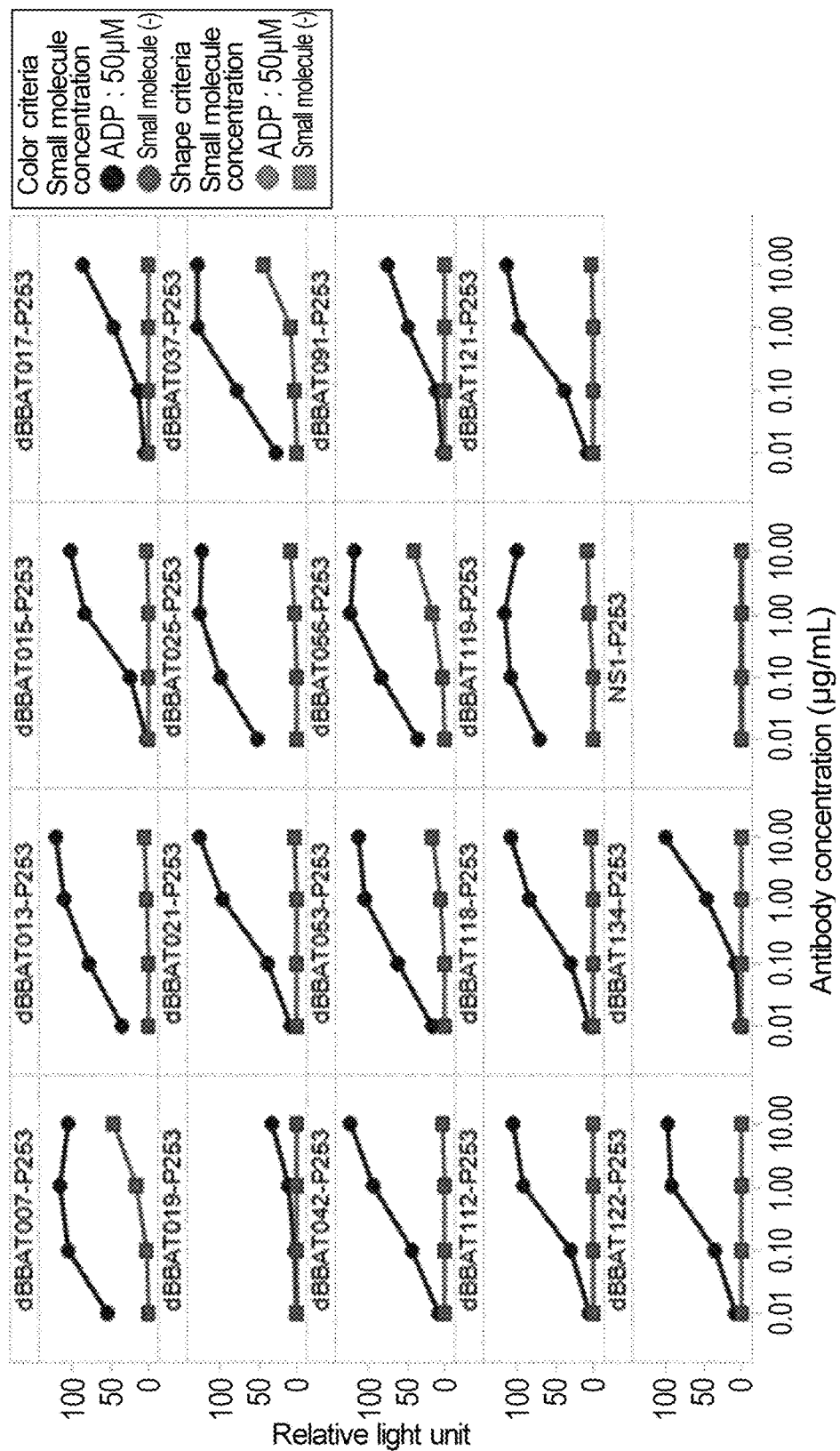

FIG. 2 is a diagram showing the agonist activity of various anti-CD137 antibodies tested using Jurkat cells in the presence or absence of ADP.

The X axis shows the antibody concentration (μg/mL) and the Y axis shows the relative light unit.

Figure 3:
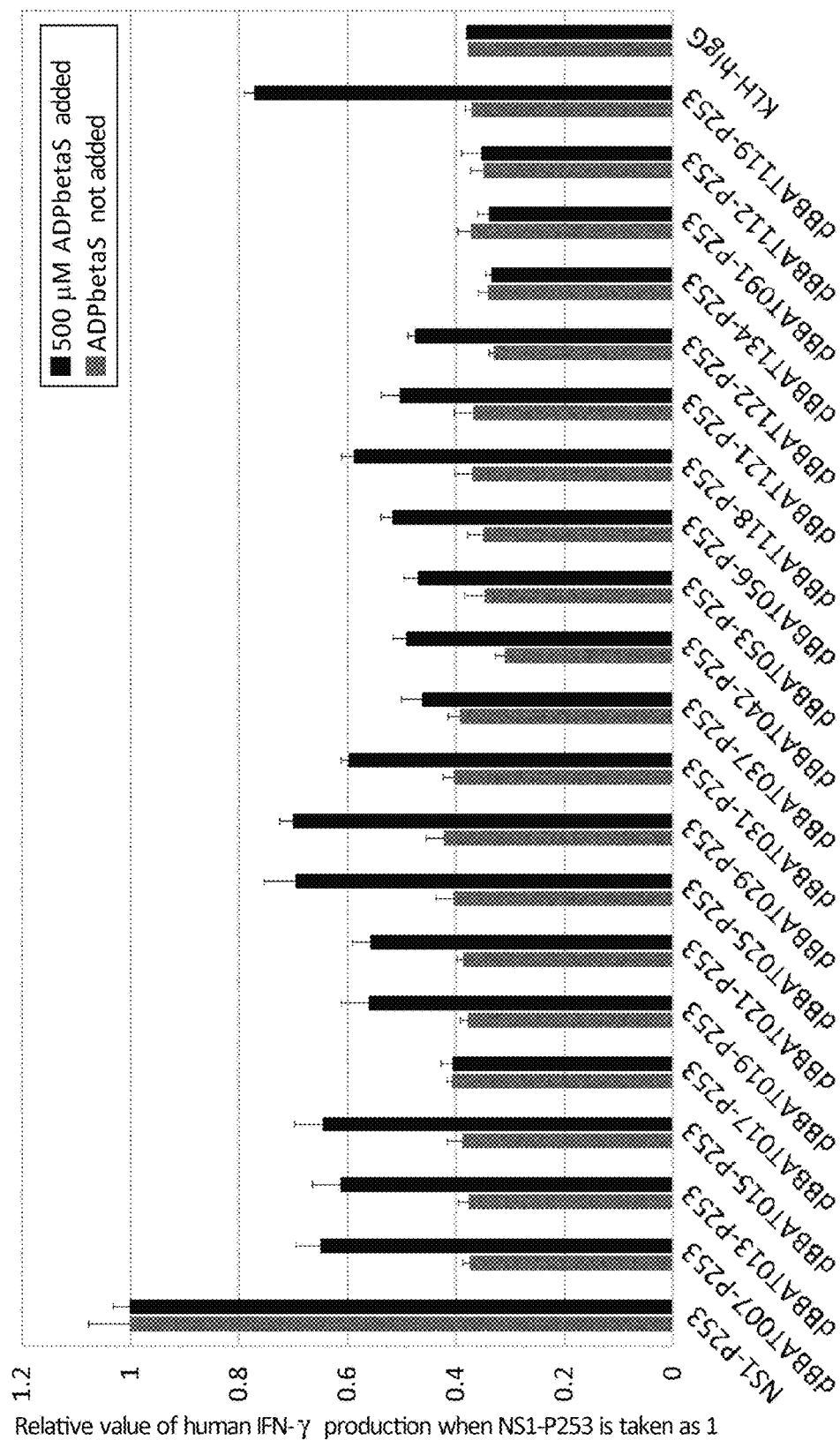

FIG. 3 is a diagram showing the agonist activity of various anti-CD137 antibodies tested using human T cells in the presence or absence of ADPbetaS.

Figure 4:
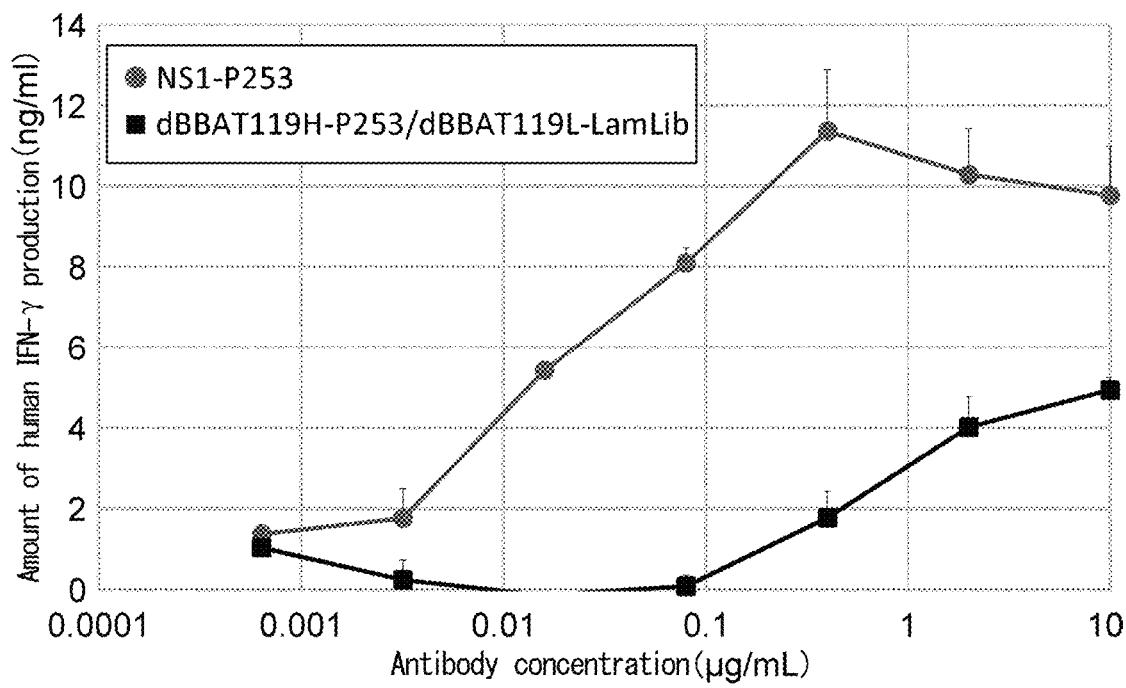

FIG. 4 is a diagram showing the agonist activity of dBBAT119-P253/dBBAT119L-LamLib (small molecule switch anti-CD137 antibody) or NS1-P253 (non-switch anti-CD137 antibody) tested using human T cells in the presence or absence of ADPbetaS.

The X axis shows the antibody concentration μg/mL) and the Y axis shows the amount of IFN-γ production (ng/mL).

Figure 5:
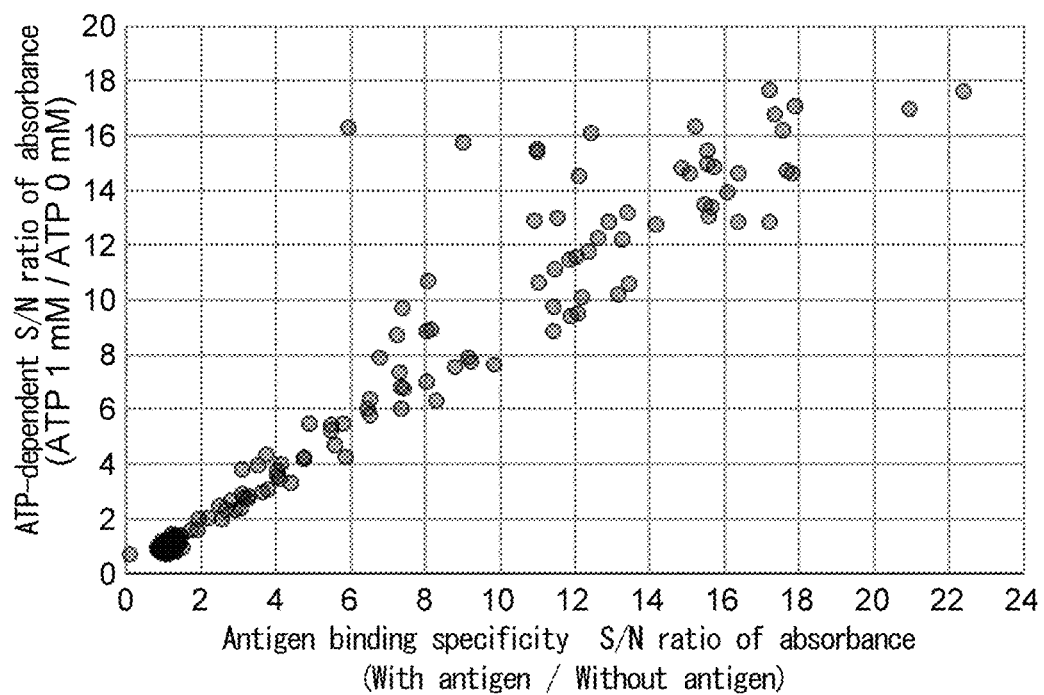

FIG. 5 is a diagram showing the ATP-dependent antigen-binding activity of various anti-CD137 antibodies (switch anti-CD137 antibody with improved binding activity) tested with phage ELISA.

The Y axis shows the S/N ratio of absorbance in the presence/absence of ATP, and the X axis shows the S/N ratio in the presence/absence of the antigen.

Figure 6:
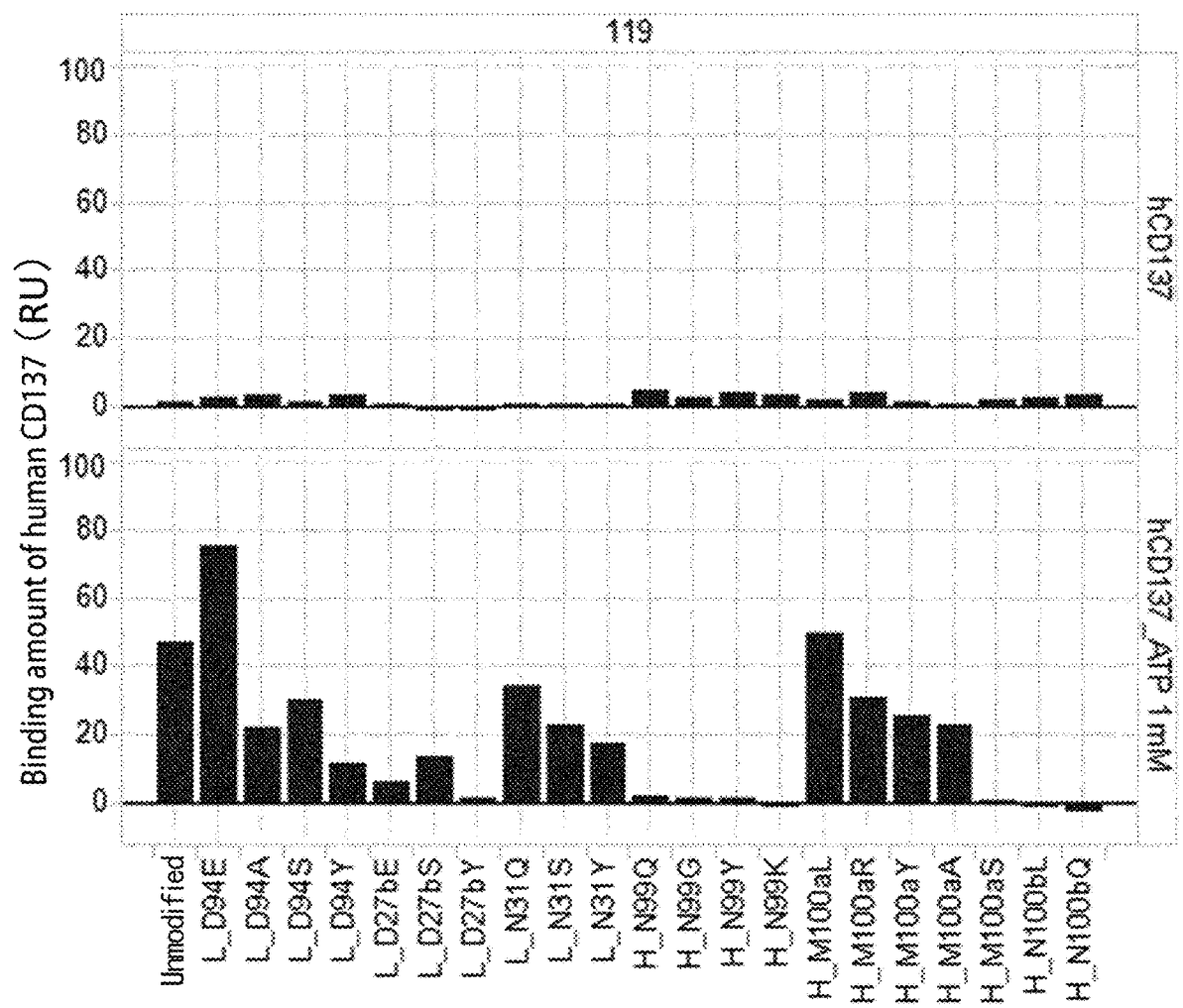

FIG. 6 is a diagram showing the binding activity of various variants of the anti-CD137 antibody (dBBAT119H-P253/dBBAT119L-LamLib) to human CD137 in the presence or absence of ATP.

The upper row shows the binding activity to human CD137 in the absence of ATP and the lower row shows the binding activity to human CD137 in the presence of ATP.

Figure 7:
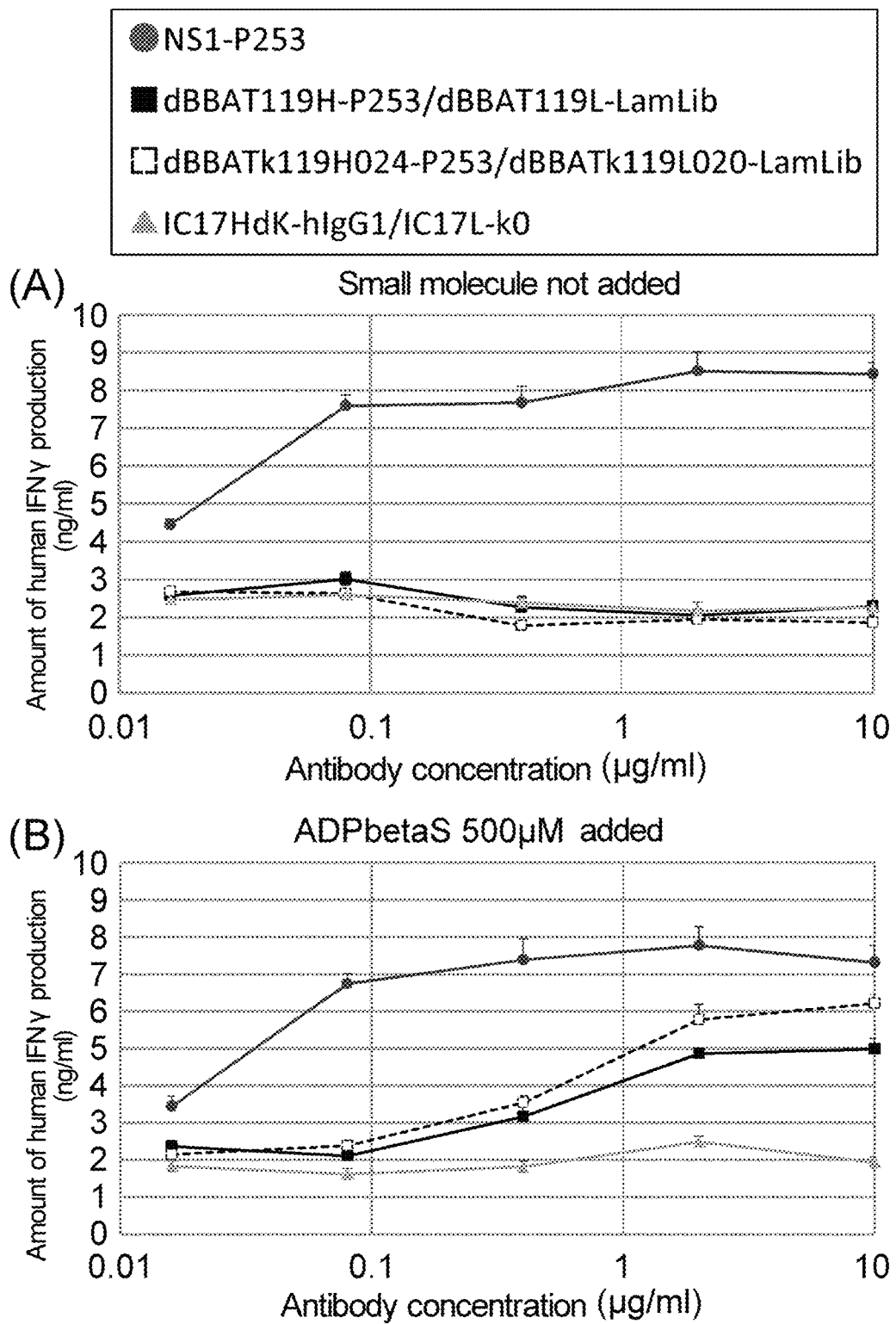

FIG. 7 is a diagram showing the agonist activity of dBBAT119H-P253/dBBAT119L-LamLib, dBBATk119H024-P253/dBBATk119L020-LamLib, IC17HdK-hIgG1/IC17L-k0 (control), or NS1-P253 (non-switch anti-CD137 antibody) tested using human T cells in the presence or absence of ADPbetaS.

Subfigure (A) shows the test results in the absence of ADPbetaS and subfigure (B) shows the test results in the presence of ADPbetaS.

The X axis shows the antibody concentration μg/mL) and the Y axis shows the amount of IFN-γ production (ng/mL).

Figure 8:
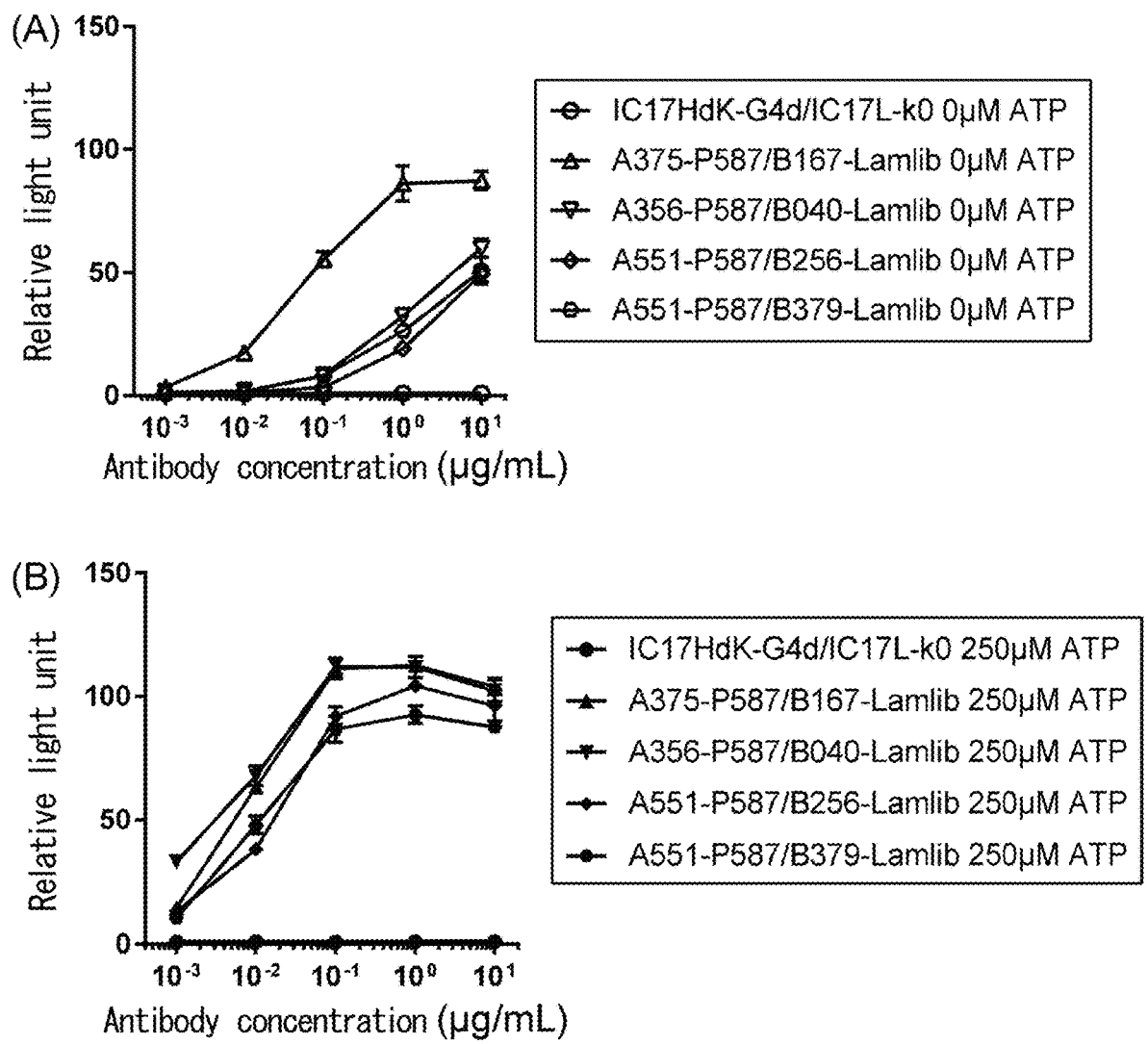

FIG. 8 is a diagram showing the agonist activity of various switch anti-CD137 antibodies tested using 4-1BB Jurkat reporter gene assay in the presence or absence of ATP. Subfigure (A) shows the test results in the absence of ATP and subfigure (B) shows the test results in the presence of ATP.

Figure 9:
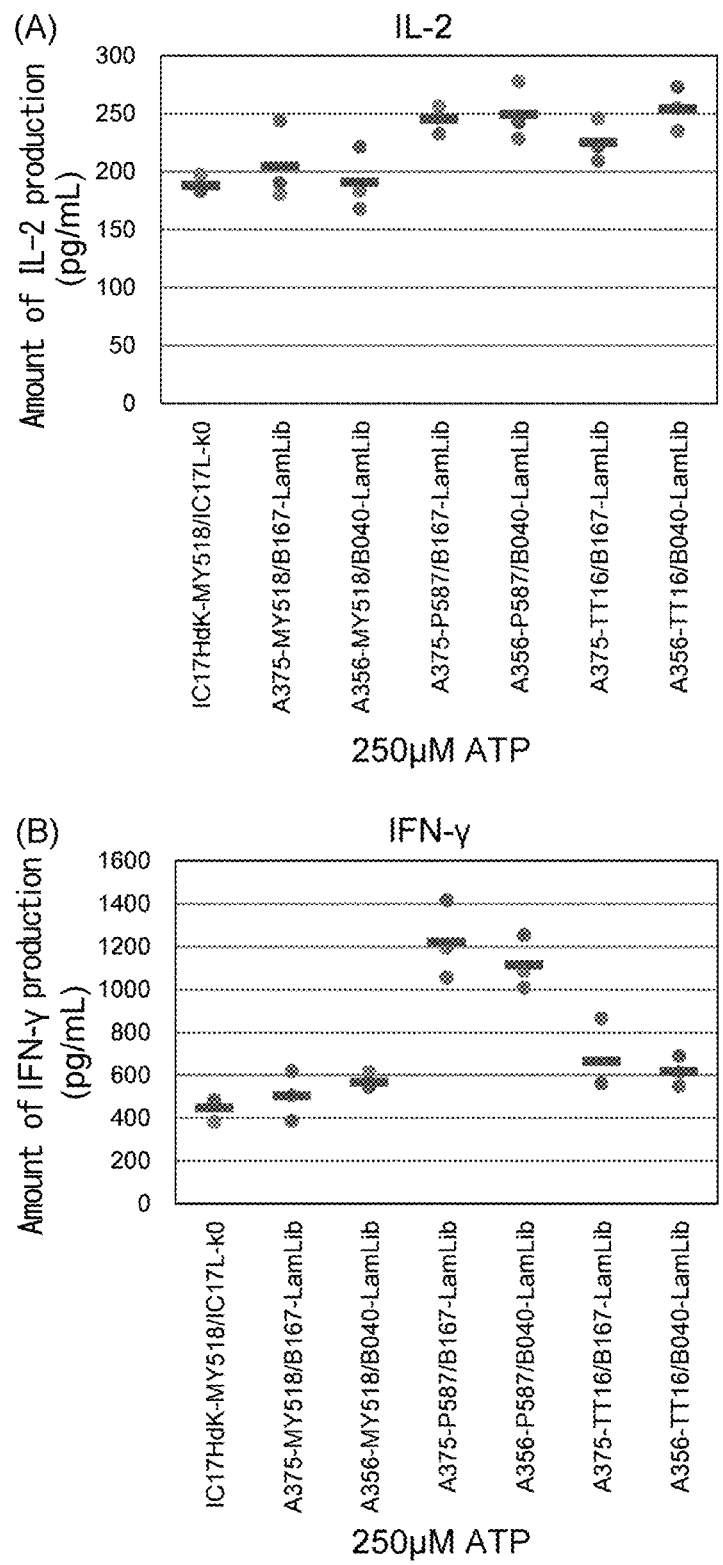

FIG. 9 is a diagram showing the enhancement in agonist activity of various switch anti-CD137 antibodies in the presence of ATP due to increase in the binding activity of heavy chain constant regions to Fcγ receptors, tested using human peripheral blood mononuclear cells. Subfigure (A) shows the agonist activity determined using the amount of IL-2 production as an index, and subfigure (B) shows the agonist activity determined using the amount of IFN-γ production as an index.

Figure 10:
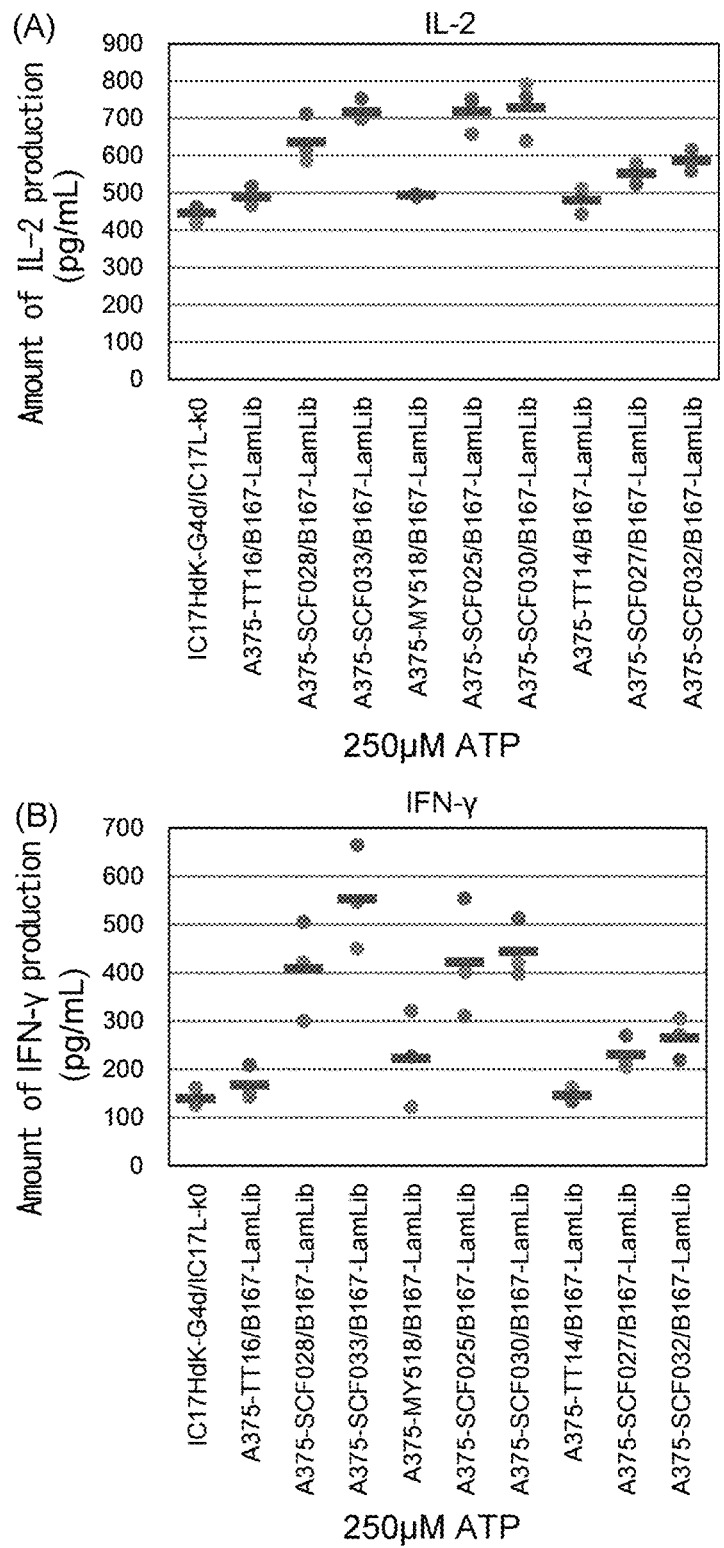

FIG. 10 is a diagram showing the enhancement in agonist activity of various switch anti-CD137 antibodies in the presence of ATP due to increase in the binding activity of heavy chain constant regions to Fcγ receptors or increase in the pI of heavy chain constant regions, tested using human peripheral blood mononuclear cells. Subfigure (A) shows the agonist activity determined using the amount of IL-2 production as an index, and subfigure (B) shows the agonist activity determined using the amount of IFN-γ production as an index.

Figure 11:
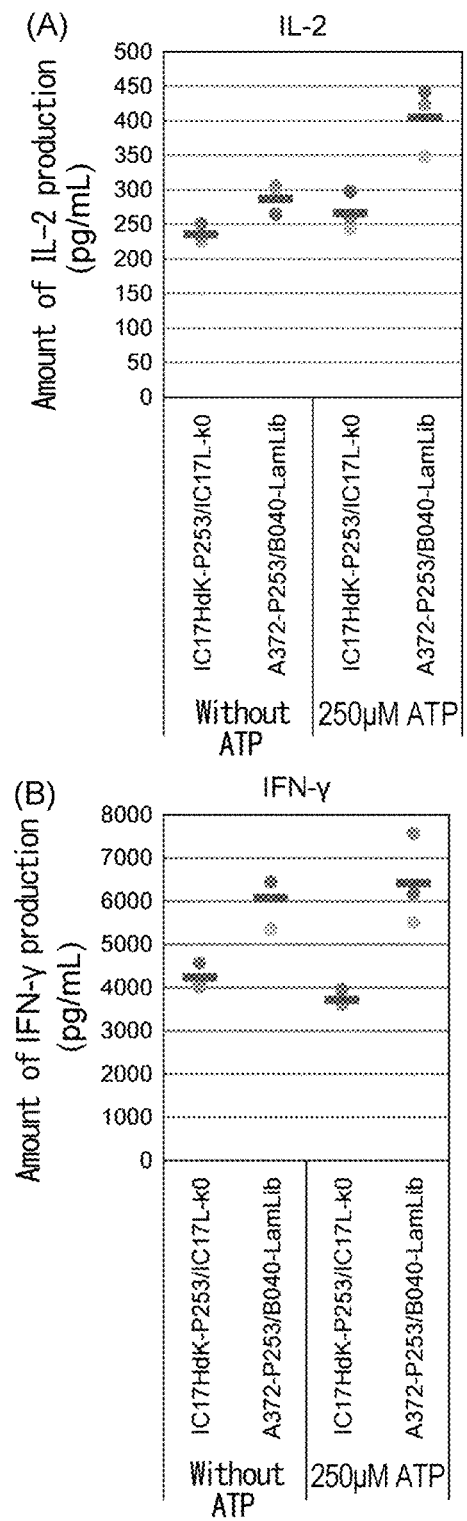

FIG. 11 is a diagram showing the enhancement in agonist activity of various switch anti-CD137 antibodies in the presence or absence of ATP due to increase in the binding activity of heavy chain constant regions to Fcγ receptors, tested using human peripheral blood mononuclear cells. Subfigure (A) shows the agonist activity determined using the amount of IL-2 production as an index, and subfigure (B) shows the agonist activity determined using the amount of IFN-γ production as an index.

Figure 12:
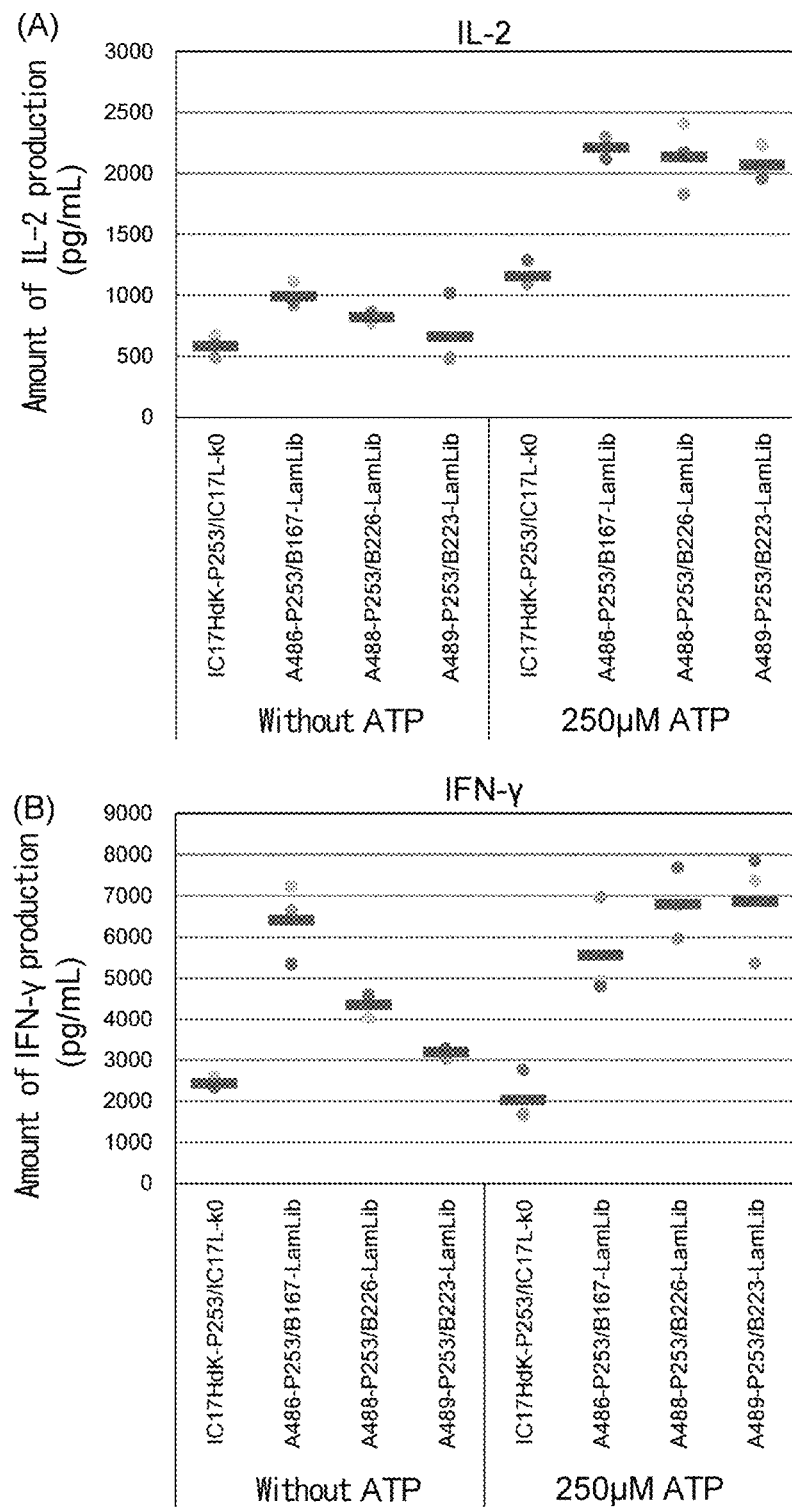

FIG. 12 is a diagram showing the enhancement in agonist activity of various switch anti-CD137 antibodies in the presence or absence of ATP due to increase in the binding activity of heavy chain constant regions to Fcγ receptors, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 13:
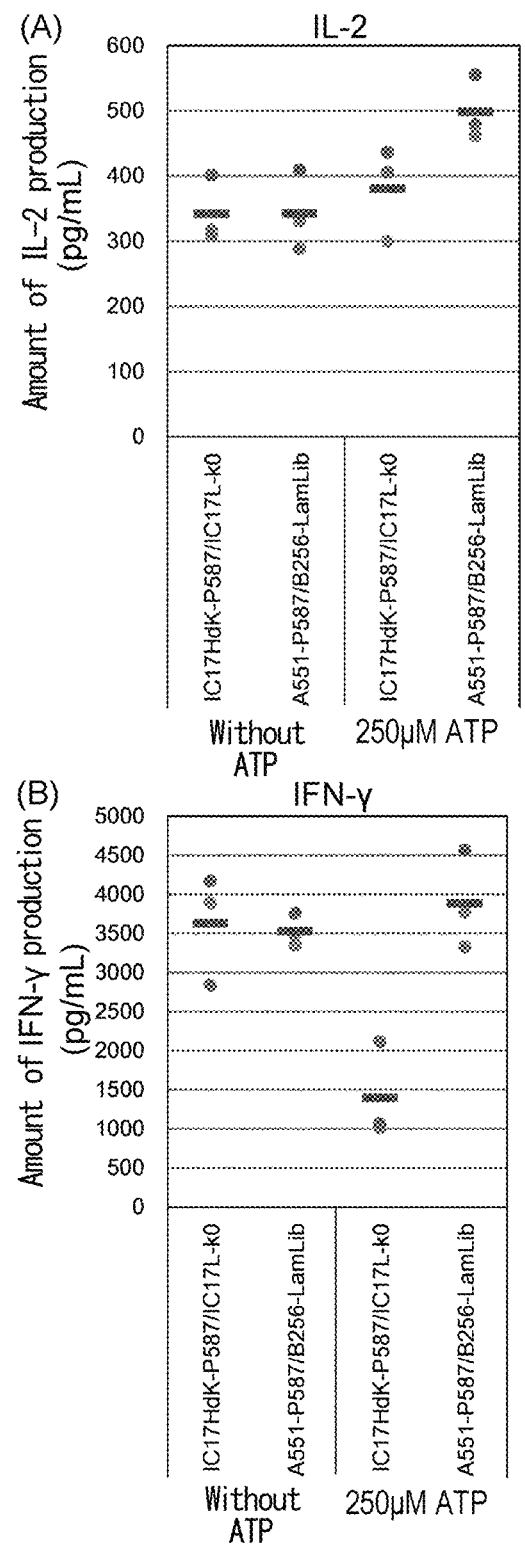

FIG. 13 is a diagram showing the enhancement in agonist activity of various switch anti-CD137 antibodies in the presence or absence of ATP due to increase in the binding activity of heavy chain constant regions to Fcγ receptors, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 14:
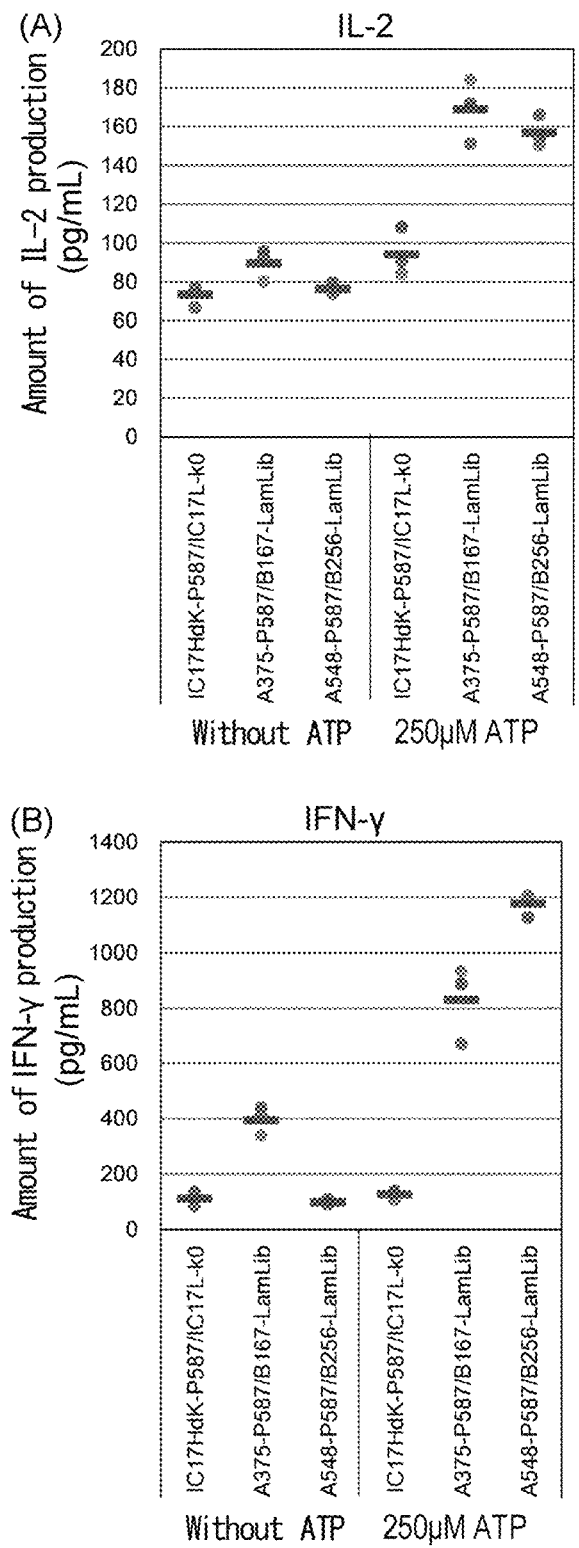

FIG. 14 is a diagram showing the enhancement in agonist activity of various switch anti-CD137 antibodies in the presence or absence of ATP due to increase in the binding activity of heavy chain constant regions to Fcγ receptors, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 15:
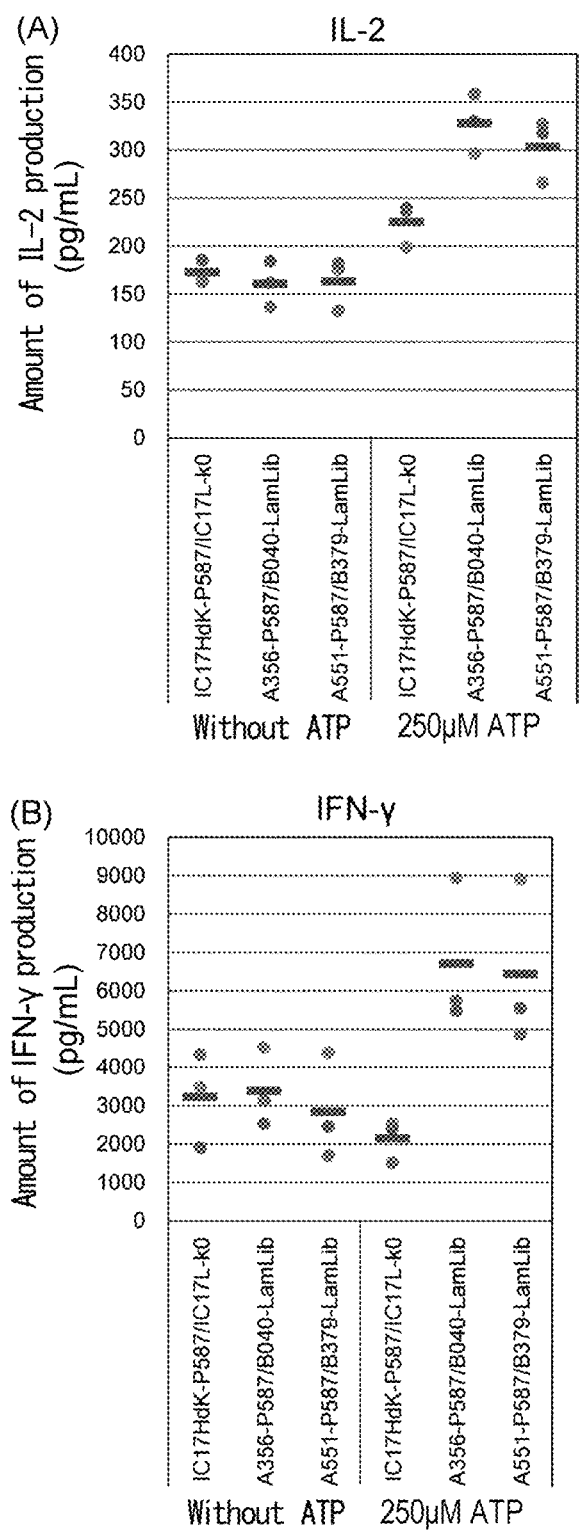

FIG. 15 is a diagram showing the enhancement in agonist activity of various switch anti-CD137 antibodies in the presence or absence of ATP due to increase in the binding activity of heavy chain constant regions to Fcγ receptors, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 16:
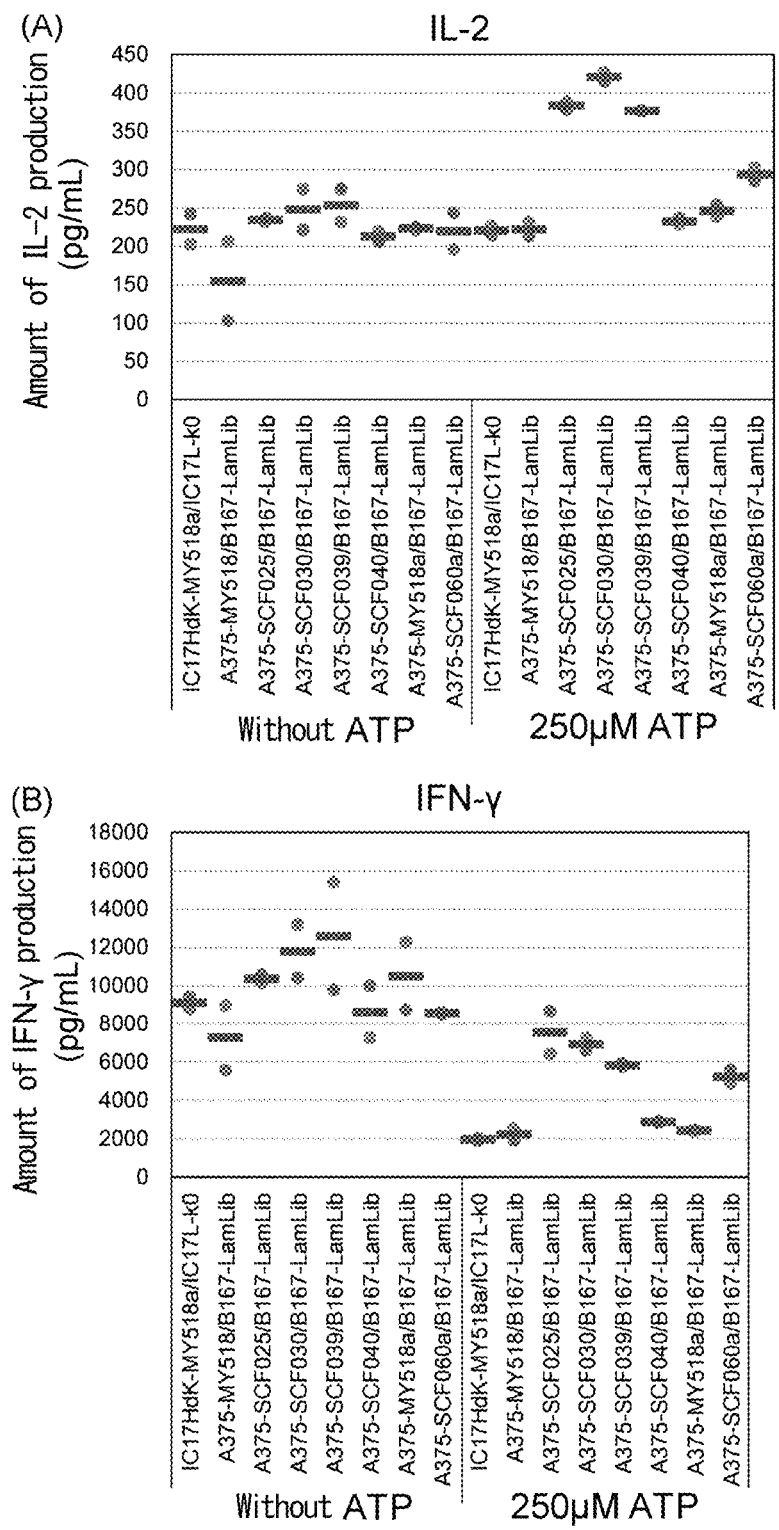

FIG. 16 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 17:
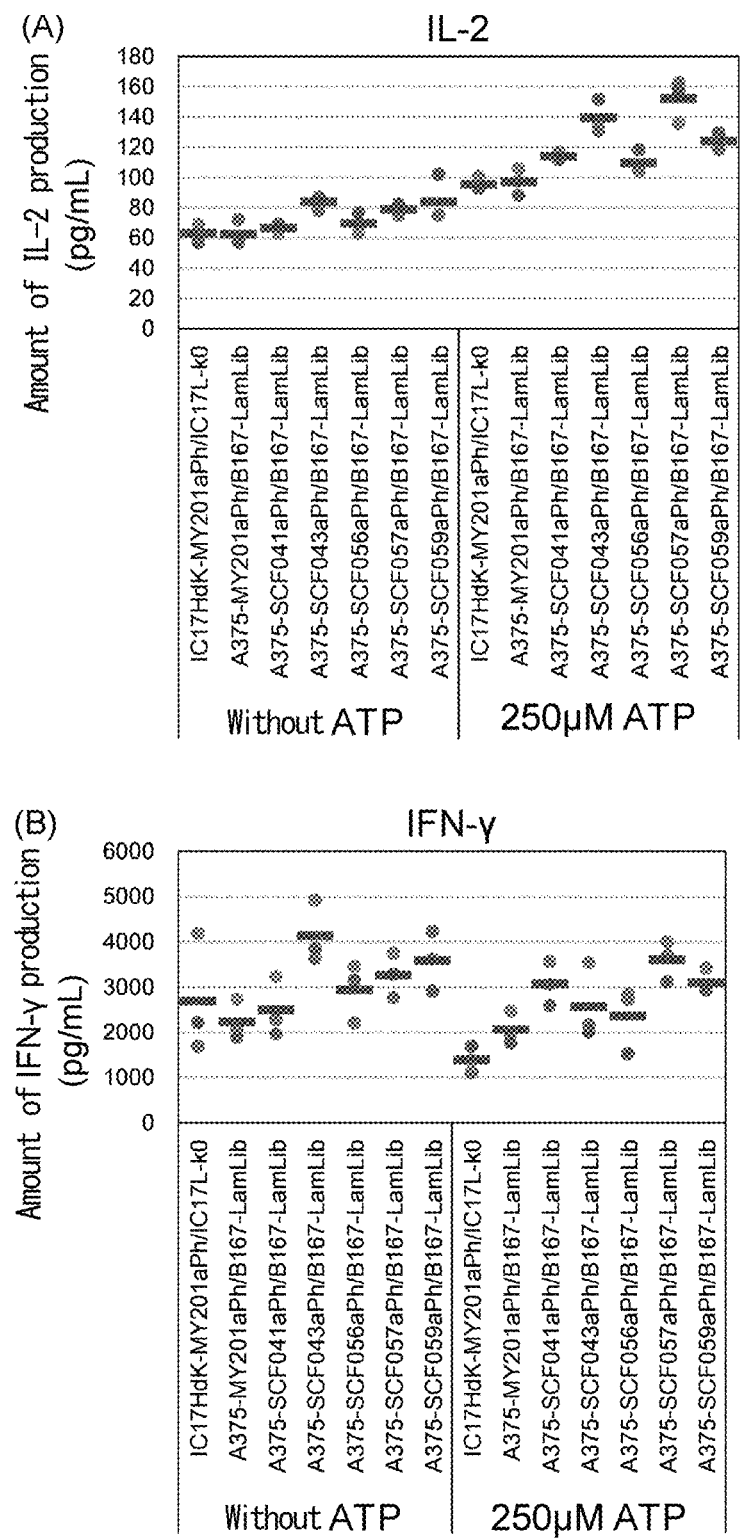

FIG. 17 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 18:
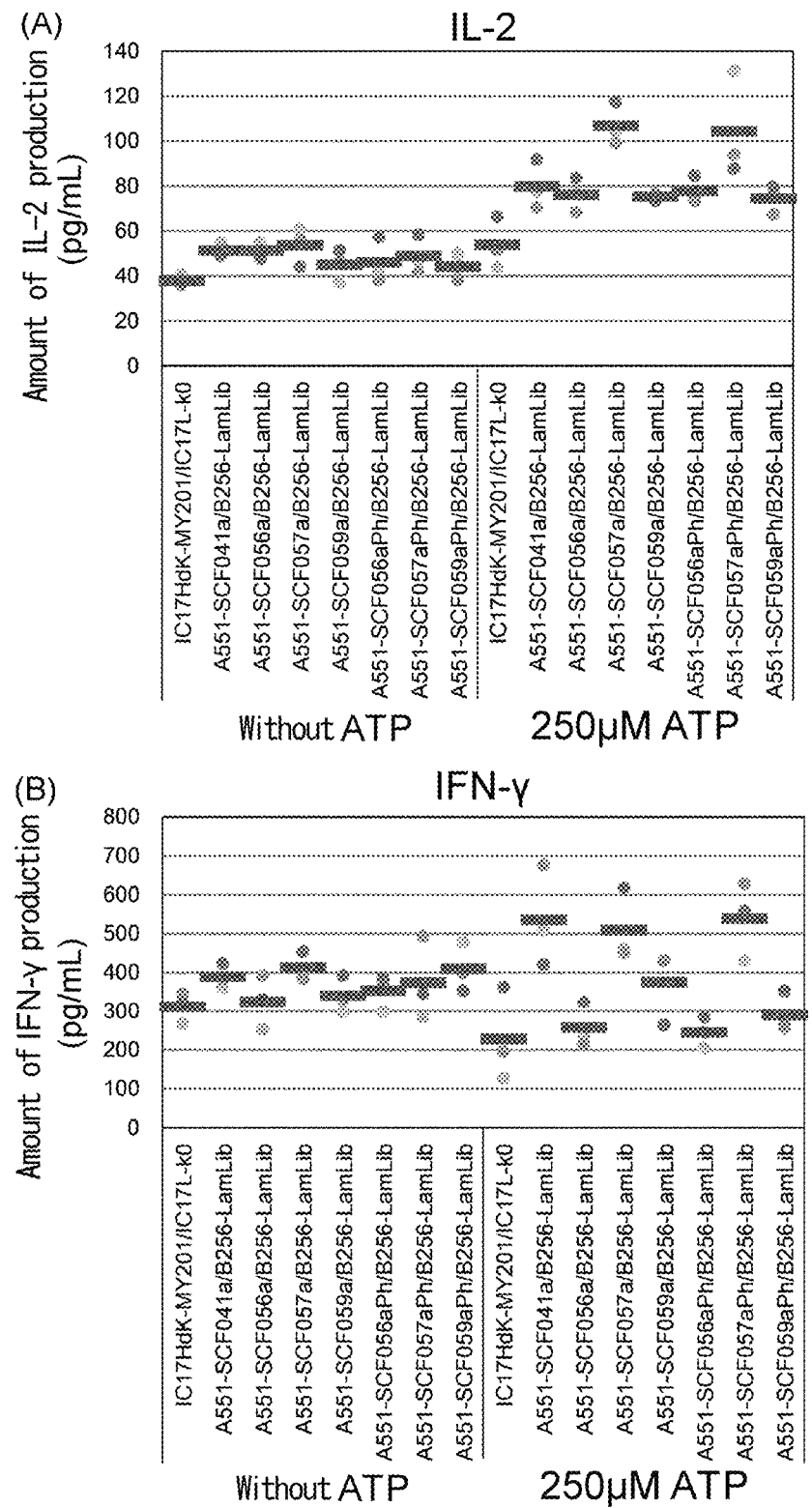

FIG. 18 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 19:
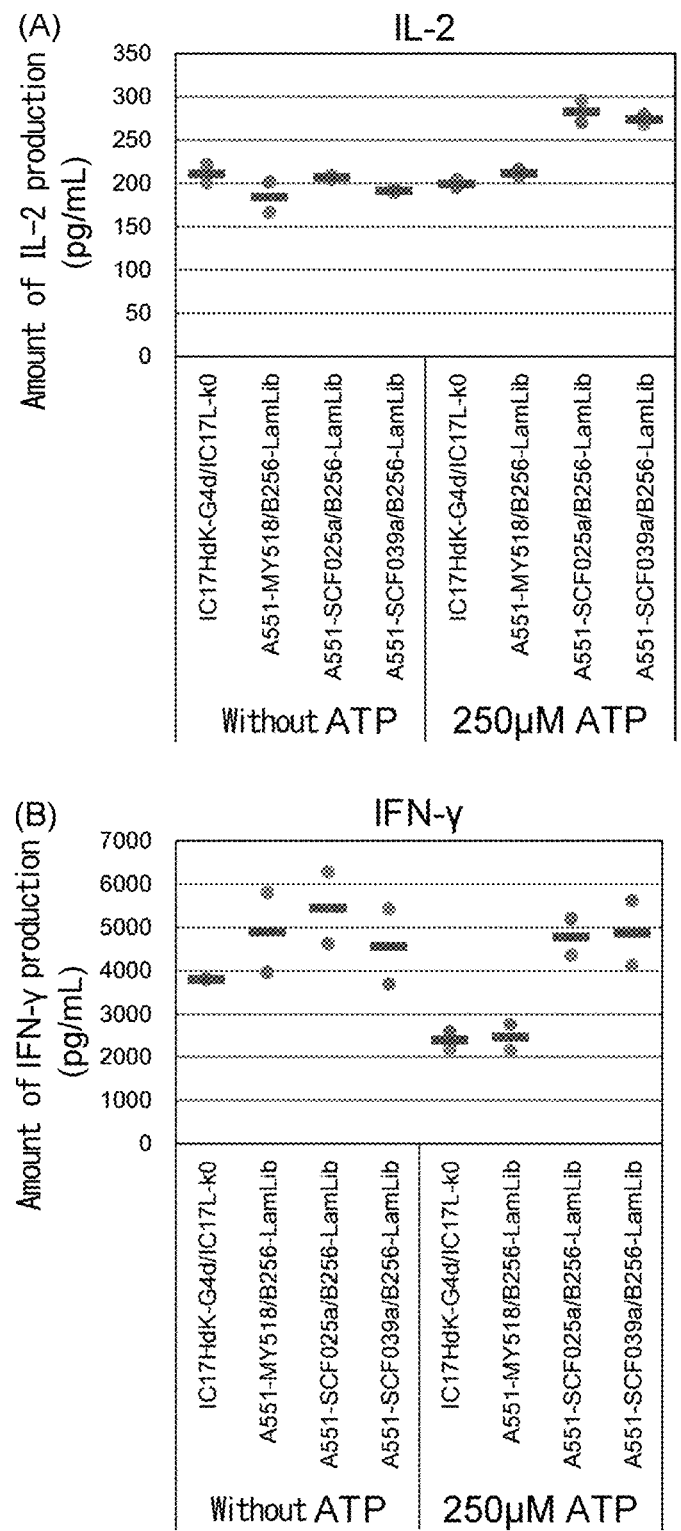

FIG. 19 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 20:
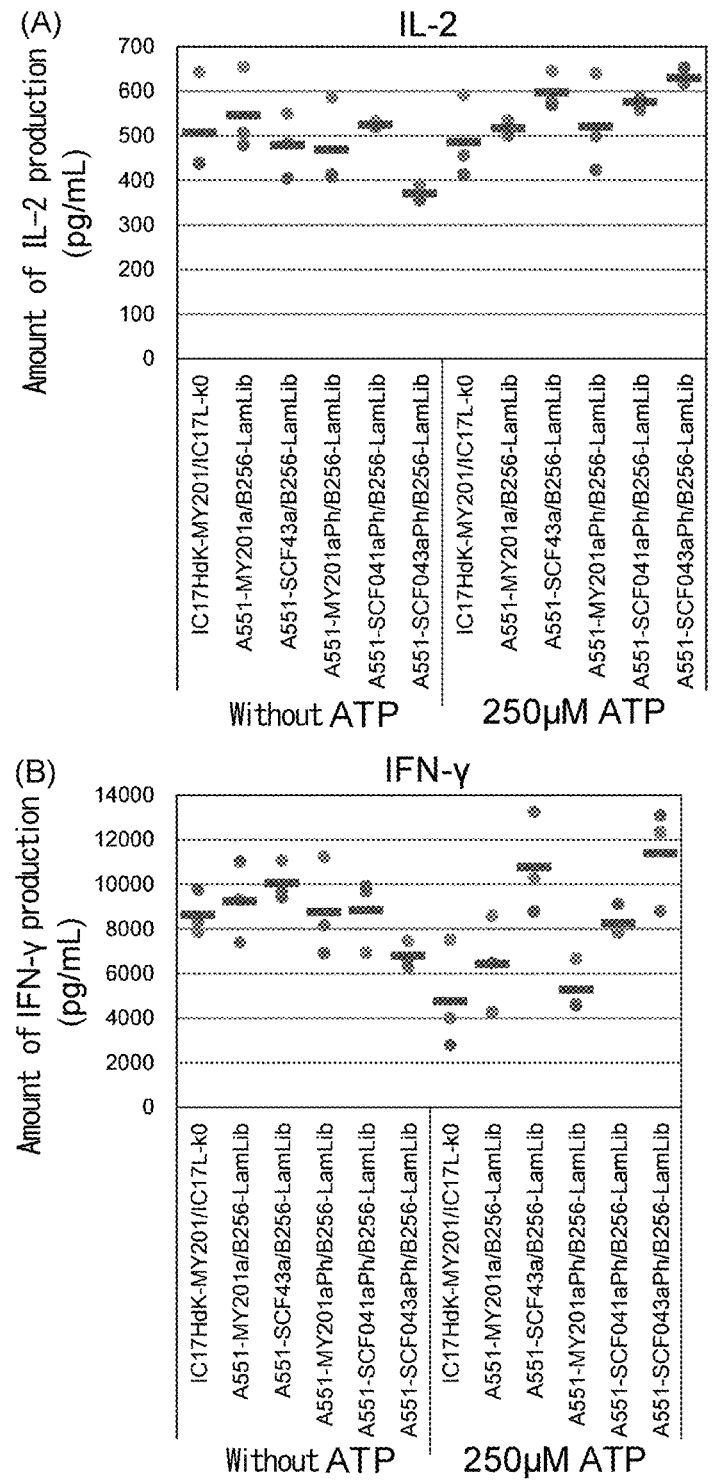

FIG. 20 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 21:
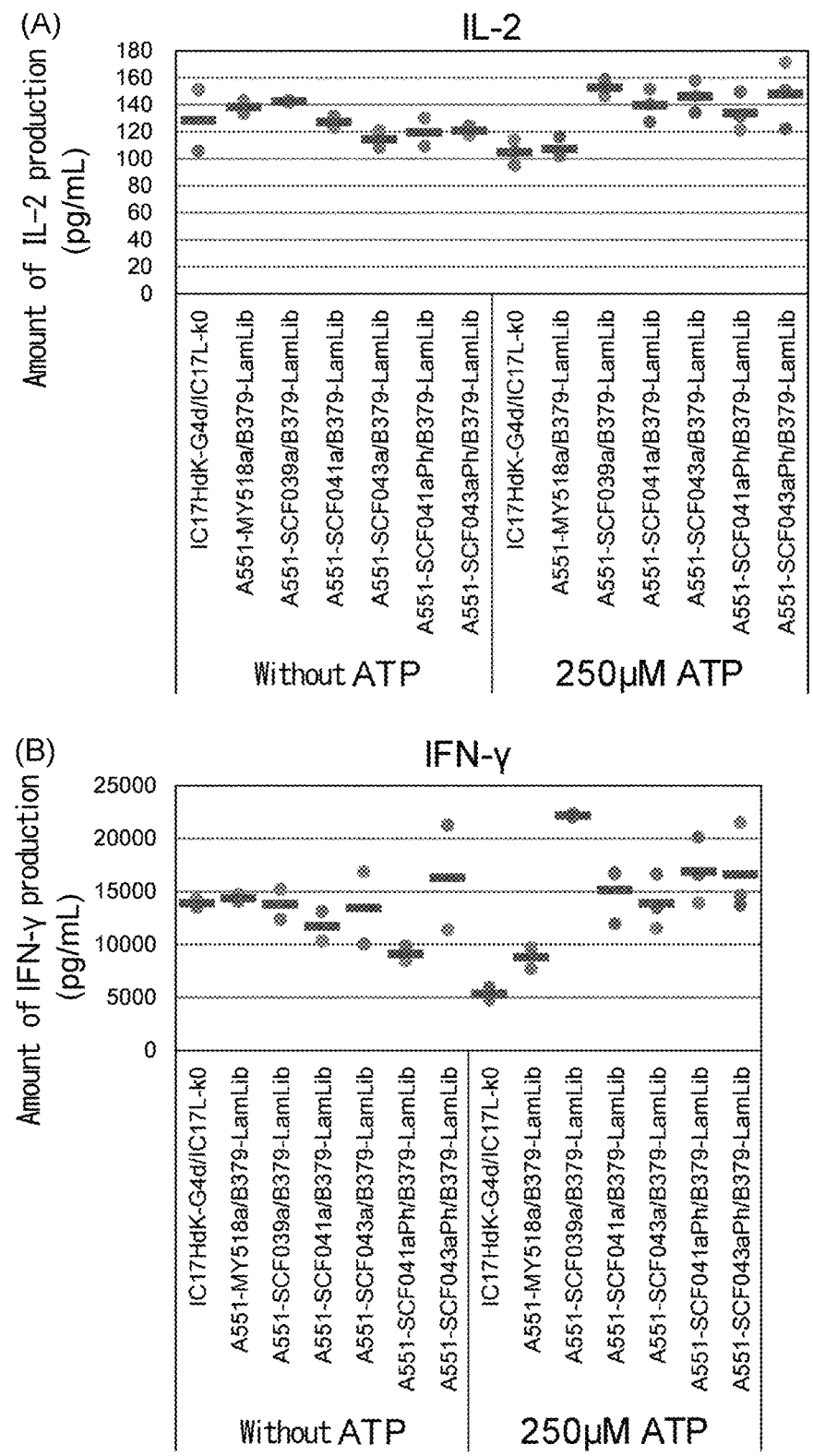

FIG. 21 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 22:
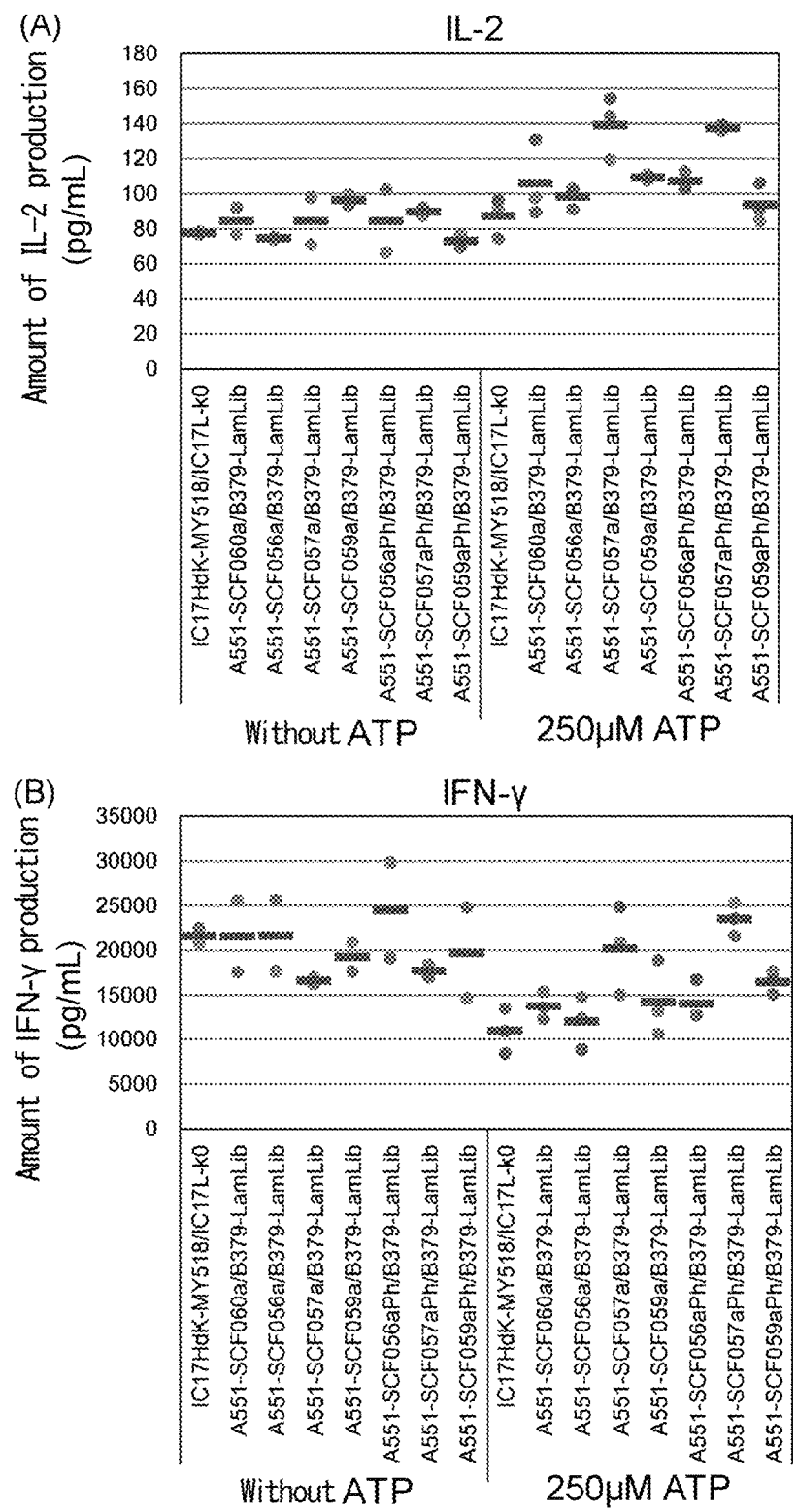

FIG. 22 is a diagram showing the enhancement in agonist activity of various switch anti-CD137 antibodies in the presence or absence of ATP due to increase in the pI of heavy chain constant regions, tested using human peripheral blood mononuclear cells.

Subfigure (A) shows the agonist activity determined using the amount of IL-2 production as an index, and subfigure (B) shows the agonist activity determined using the amount of IFN-γ production as an index.

Figure 23:
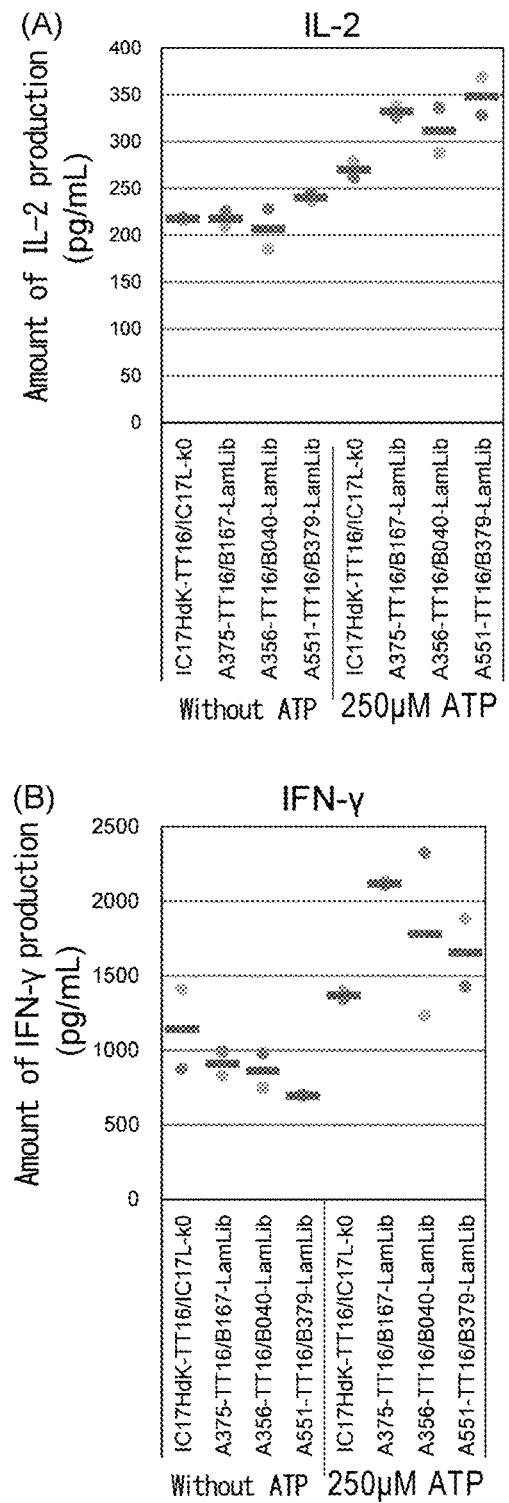

FIG. 23 is a diagram showing the enhancement in agonist activity of various switch anti-CD137 antibodies in the presence or absence of ATP due to increase in the binding activity of heavy chain constant regions to Fcγ receptors, tested using human peripheral blood mononuclear cells. Subfigure (A) shows the agonist activity determined using the amount of IL-2 production as an index, and subfigure (B) shows the agonist activity determined using the amount of IFN-γ production as an index.

Figure 24:
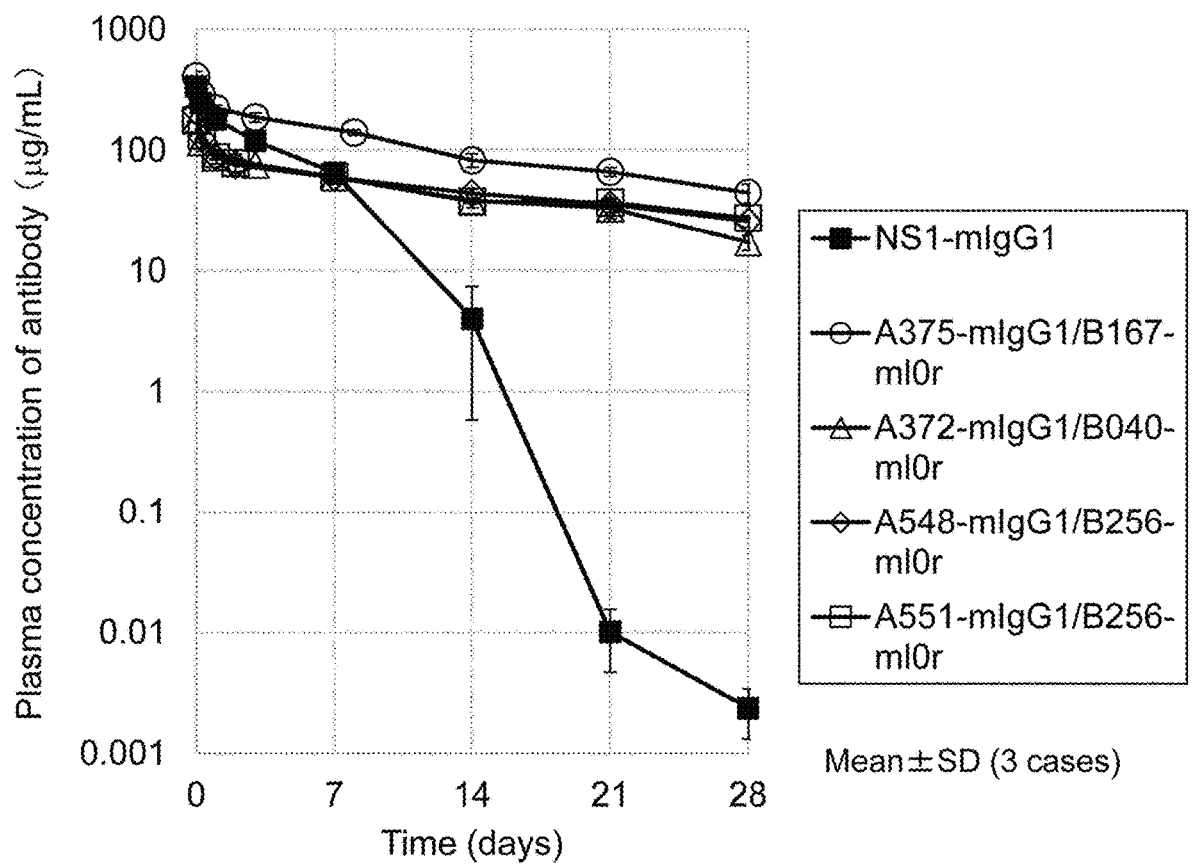

FIG. 24 is a diagram showing the plasma concentration of various switch and non-switch anti-CD137 antibodies tested using human CD137 knock-in mouse.

The Fcs are all of mIgG1.

Figure 25:
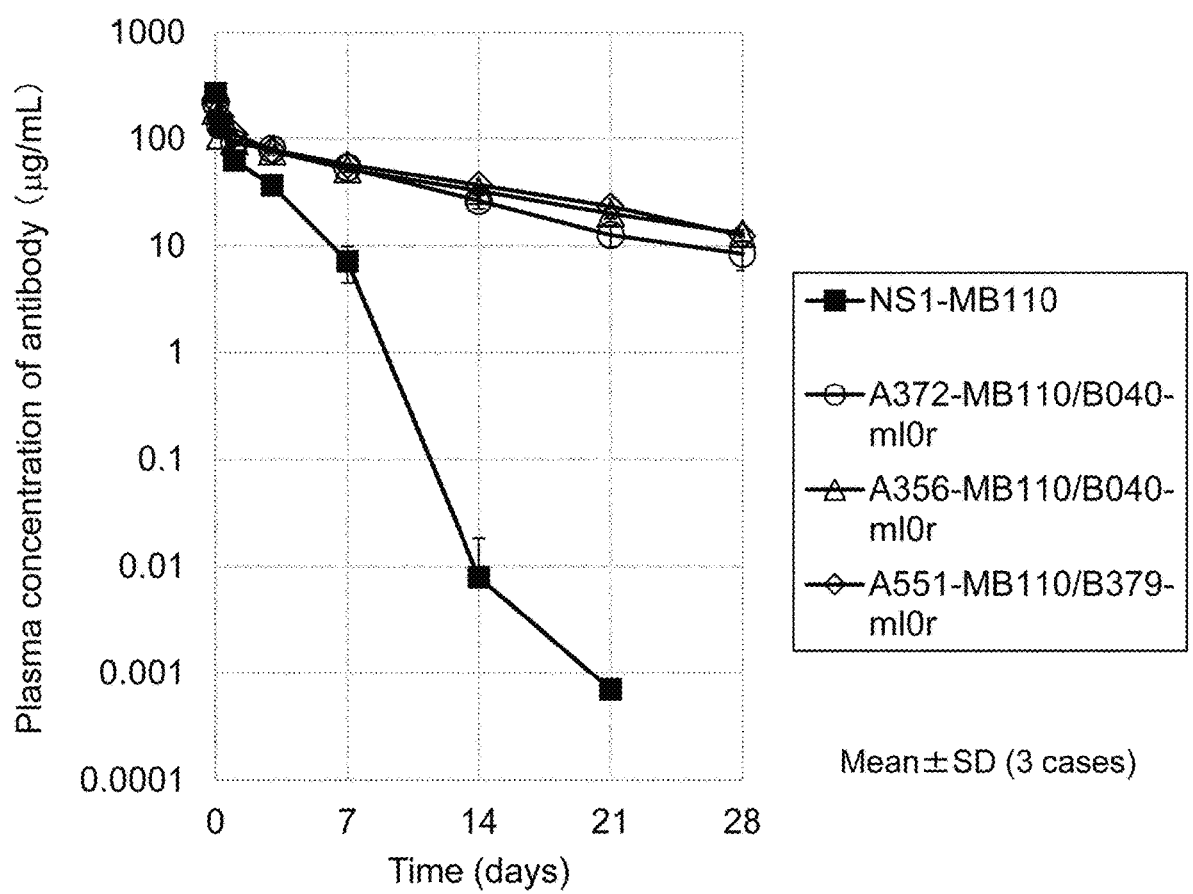

FIG. 25 is a diagram showing the plasma concentration of various switch and non-switch anti-CD137 antibodies tested using human CD137 knock-in mouse.
The Fcs are all of MB110.

Figure 26:
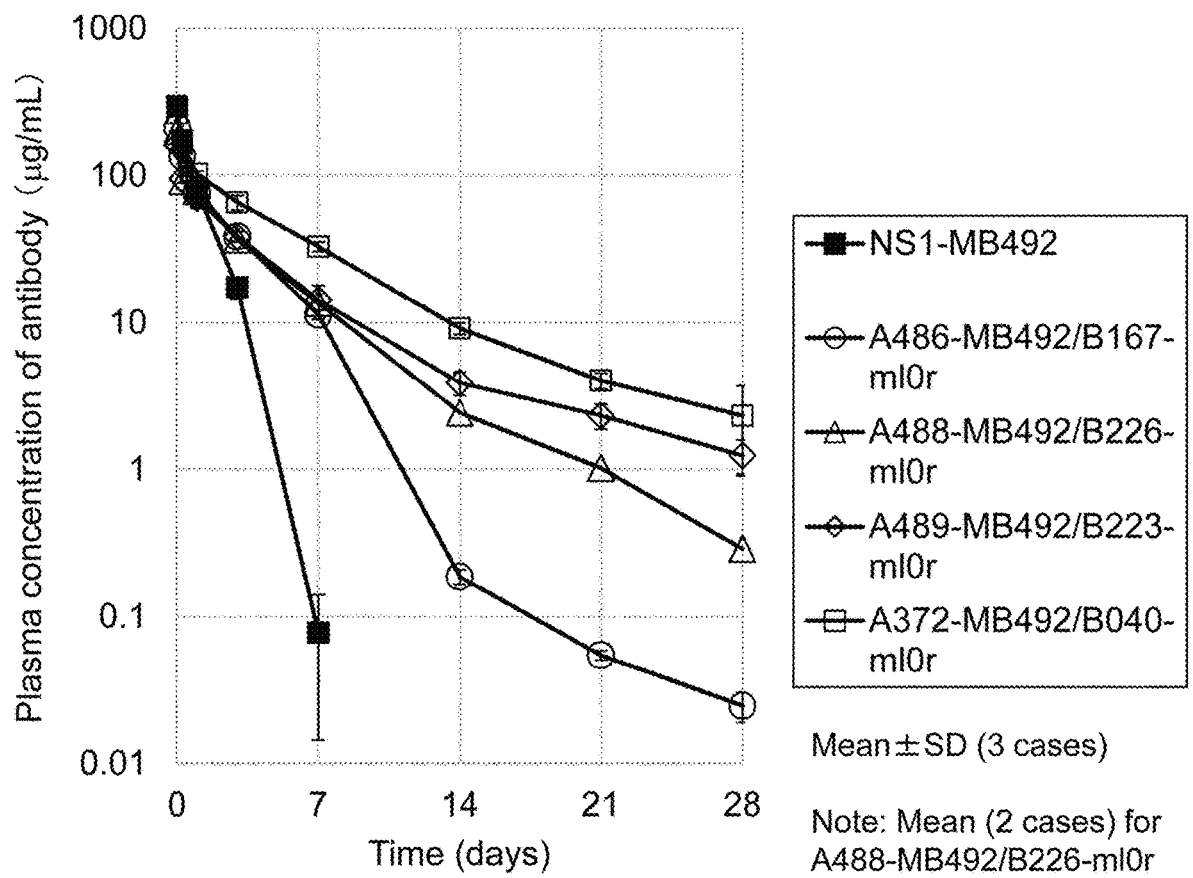

FIG. 26 is a diagram showing the plasma concentration of various switch and non-switch anti-CD137 antibodies tested using human CD137 knock-in mouse. The Fcs are all of MB492.

Figure 27:
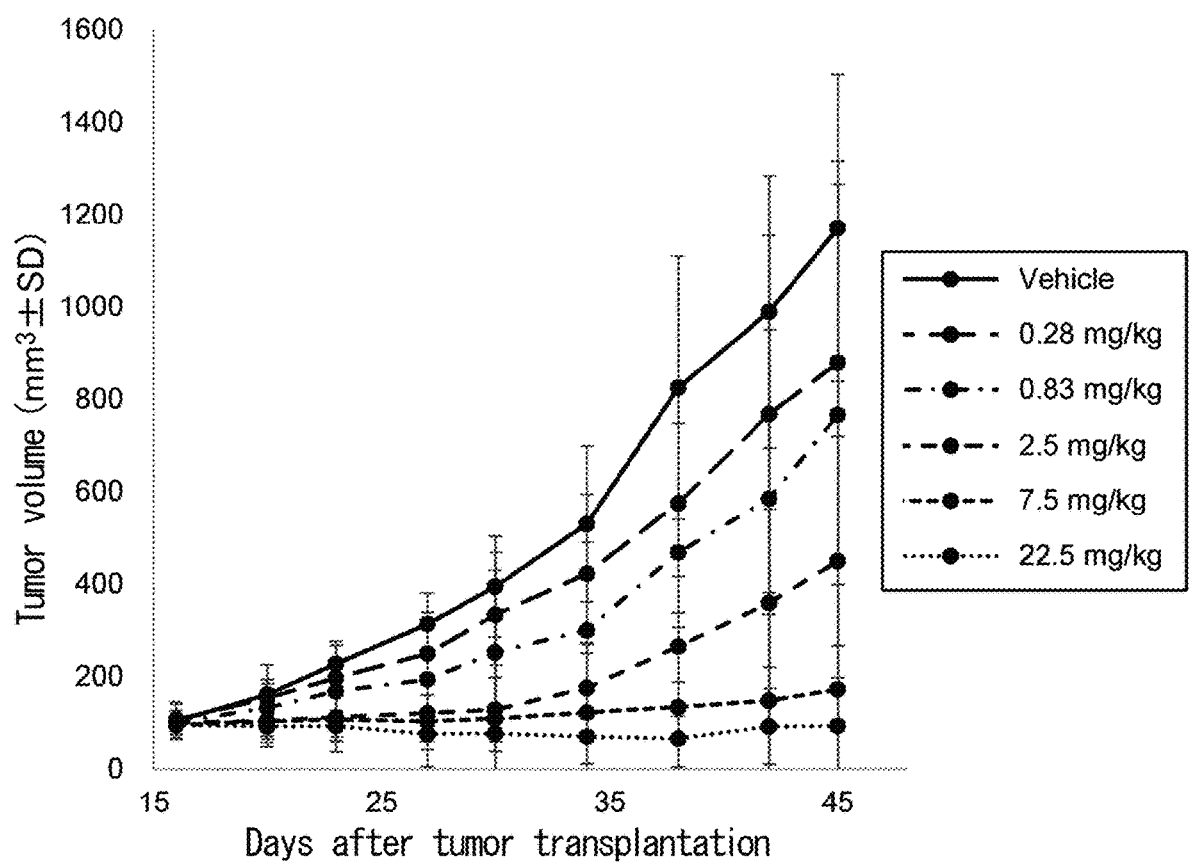

FIG. 27 is a diagram showing the anti-tumor effect of A375-mIgG1/B167-ml0r in a mouse model transplanted with MC38 cells. Each dot shows the mean value of a group (n=5) of tumor volumes.

Figure 28:
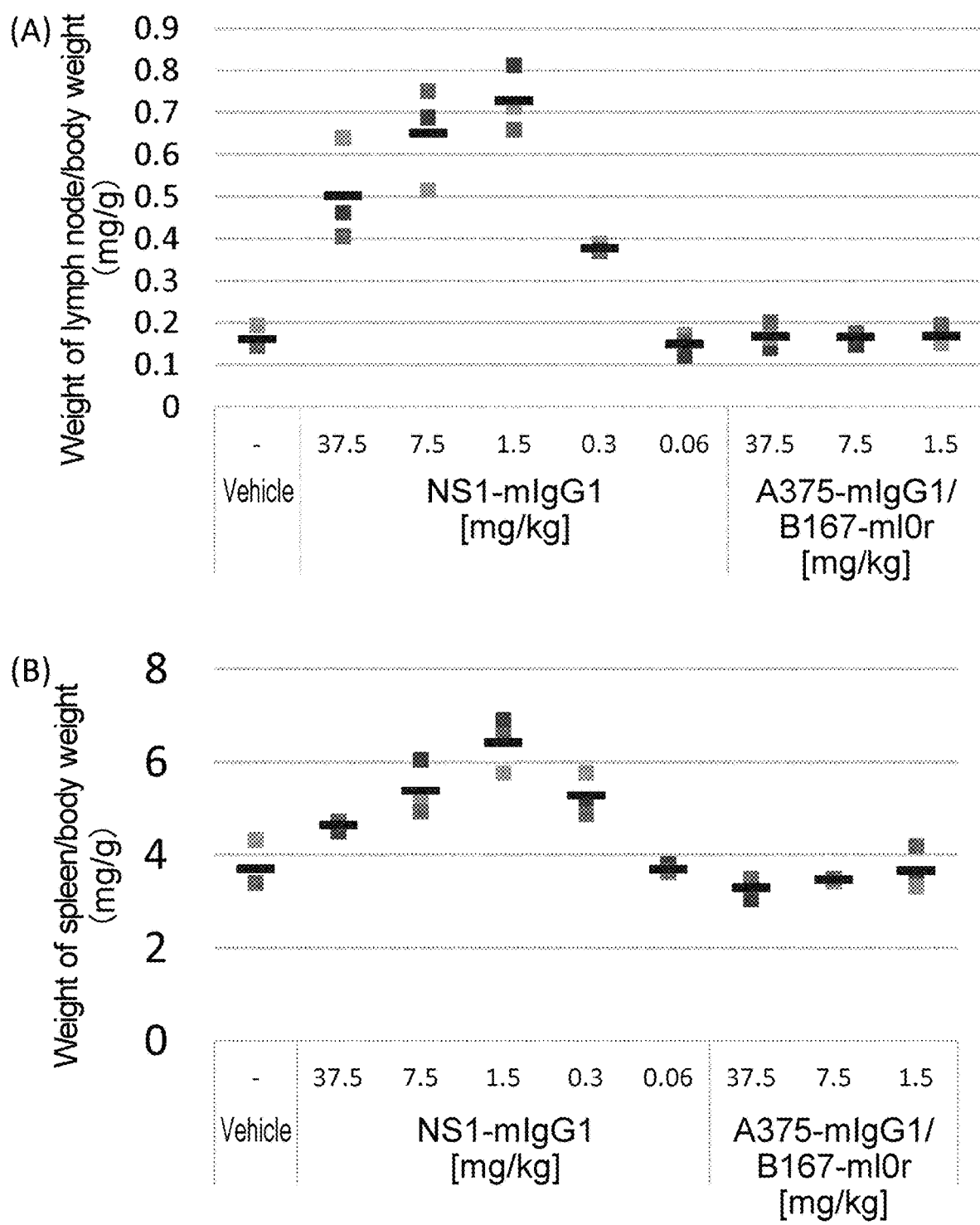

FIG. 28 is a diagram showing the weight of organs in a mouse model transplanted with MC38 cells after administration of antibodies (NO1-mIgG1 or A375-mIgG1/B167-ml0r). Subfigure (A) shows the weight of lymph node and subfigure (B) shows the weight of spleen.

Figure 29:
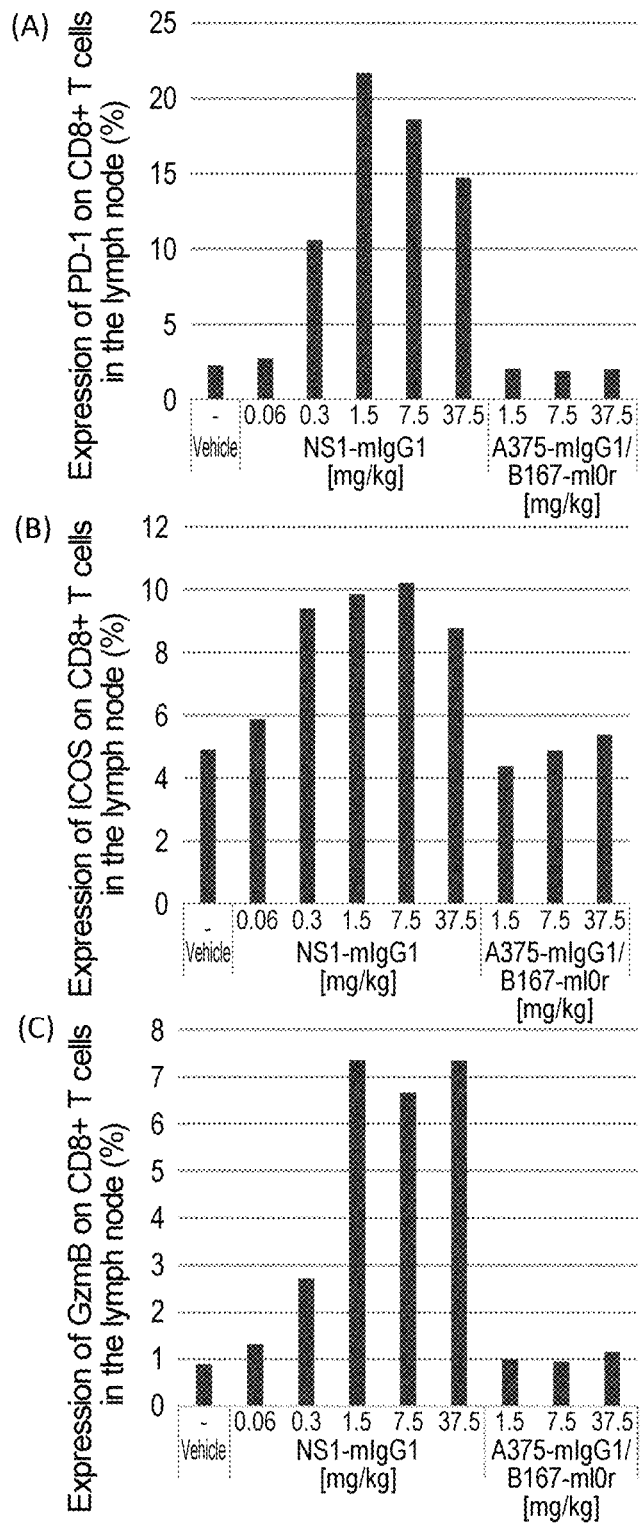

FIG. 29 is a diagram showing the degree of T cell activation in the lymph nodes of a mouse model transplanted with MC38 cells after administration of NO1-mIgG1 or A375-mIgG1/B167-ml0r. Subfigure (A) shows the percentage of PD-1 positive T cells in CD8 positive T cells, subfigure (B) shows the percentage of ICOS positive T cells in CD8 positive T cells, and subfigure (C) shows the percentage of Granzyme B positive T cells in CD8 positive T cells.

Figure 30:
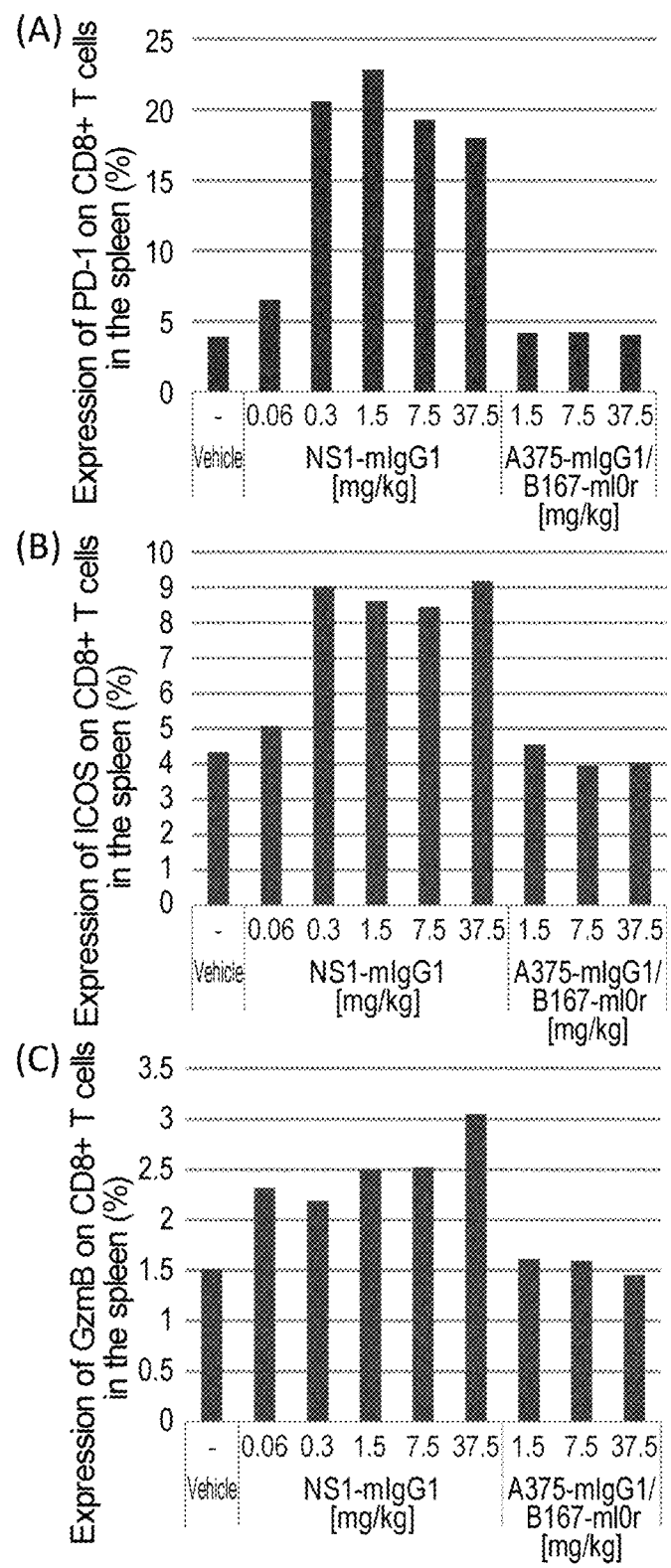

FIG. 30 is a diagram showing the degree of T cell activation in the spleen of a mouse model transplanted with the MC38 cell line after administration of NO1-mIgG1 or A375-mIgG1/B167-ml0r. Subfigure (A) shows the percentage of PD-1 positive T cells in CD8 positive T cells, subfigure (B) shows the percentage of ICOS positive T cells in CD8 positive T cells, and subfigure (C) shows the percentage of Granzyme B positive T cells in CD8 positive T cells.

Figure 31:
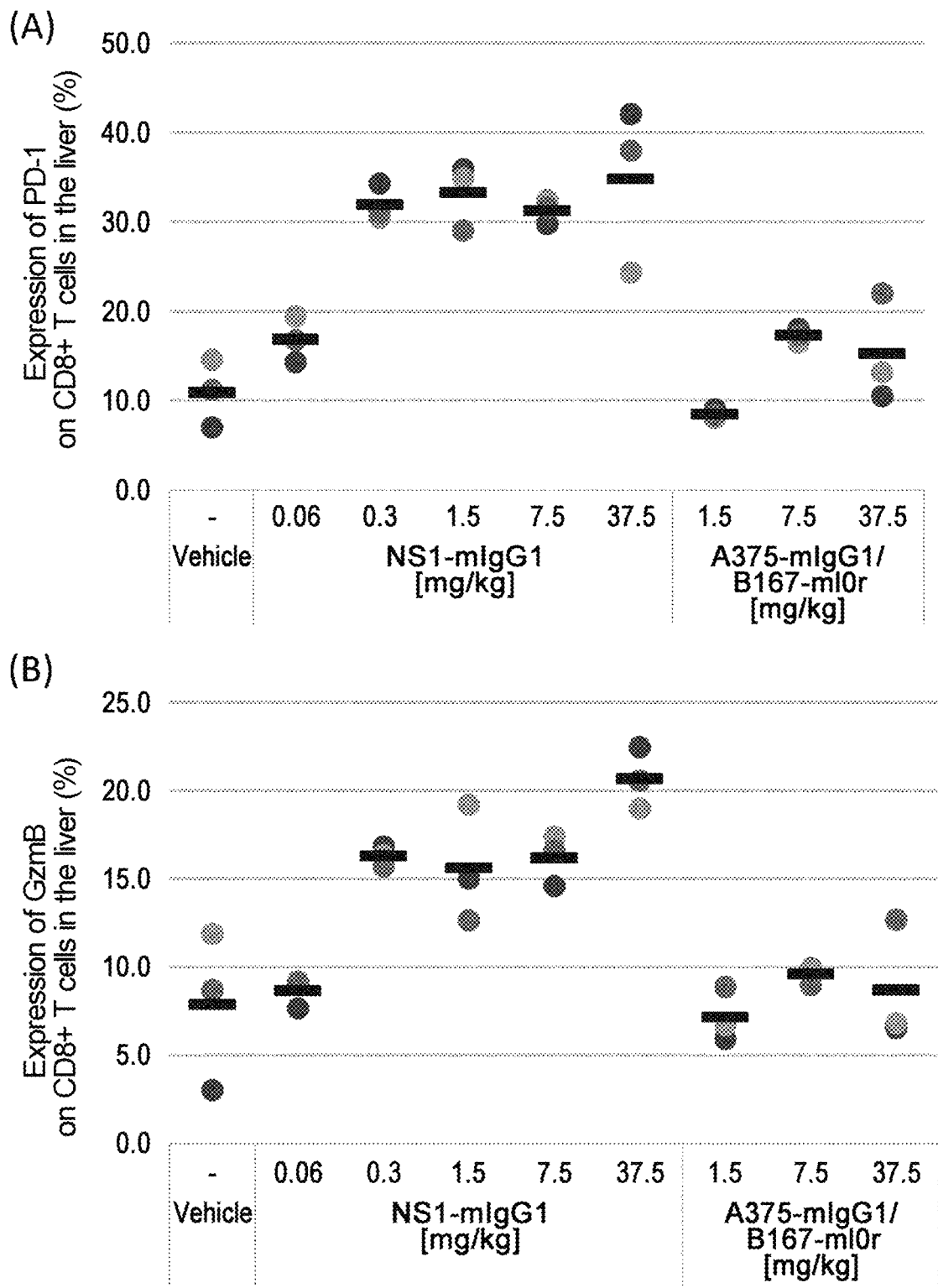

FIG. 31 is a diagram showing the degree of T cell activation in the liver of a mouse model transplanted with the MC38 cell line after administration of NO1-mIgG1 or A375-mIgG1/B167-ml0r.

Subfigure (A) shows the percentage of PD-1 positive T cells in CD8 positive T cells, and subfigure (B) shows the percentage of Granzyme B positive T cells in CD8 positive T cells.

Figure 32:
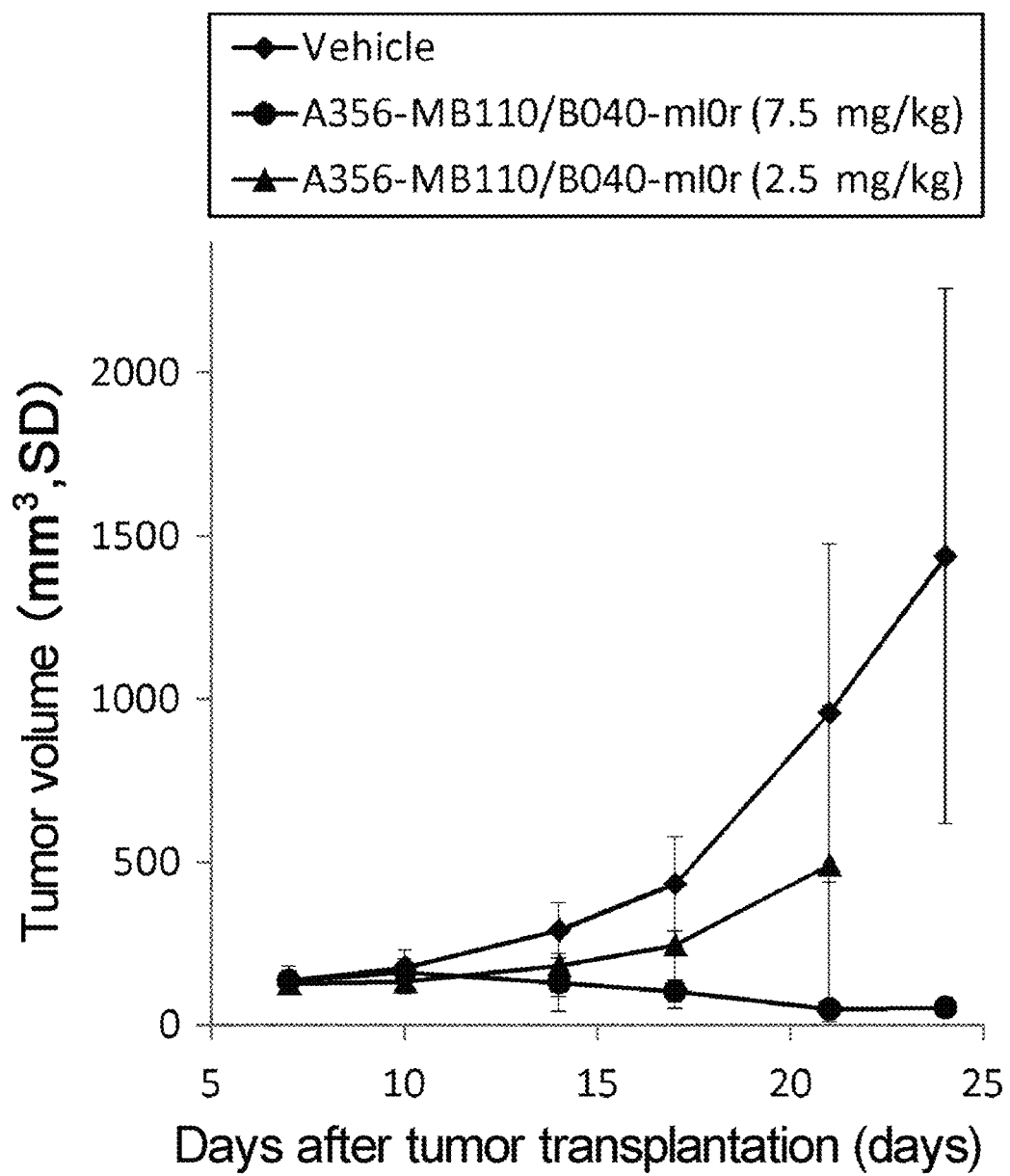

FIG. 32 is a diagram showing the anti-tumor effect of A356-MB110/B040-ml0r in a mouse model transplanted with the MC38 cell line.

Each dot shows the mean value of a group (n=5) of tumor volumes.

Figure 33:
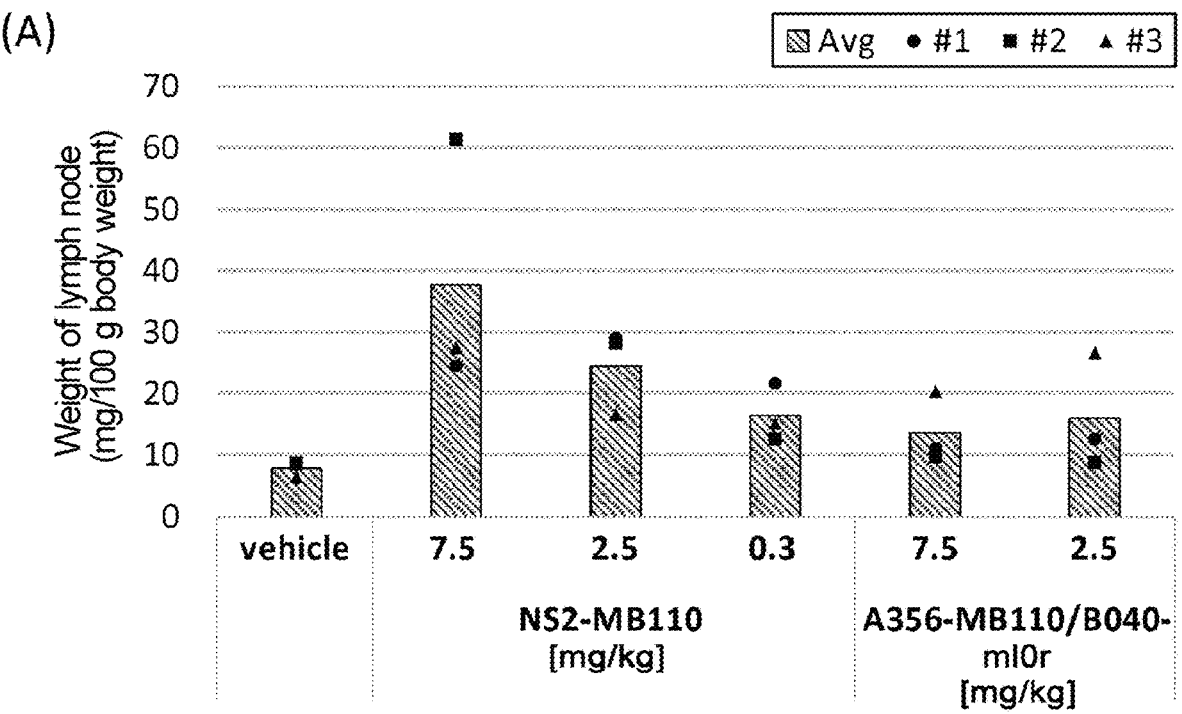
Figure 33:
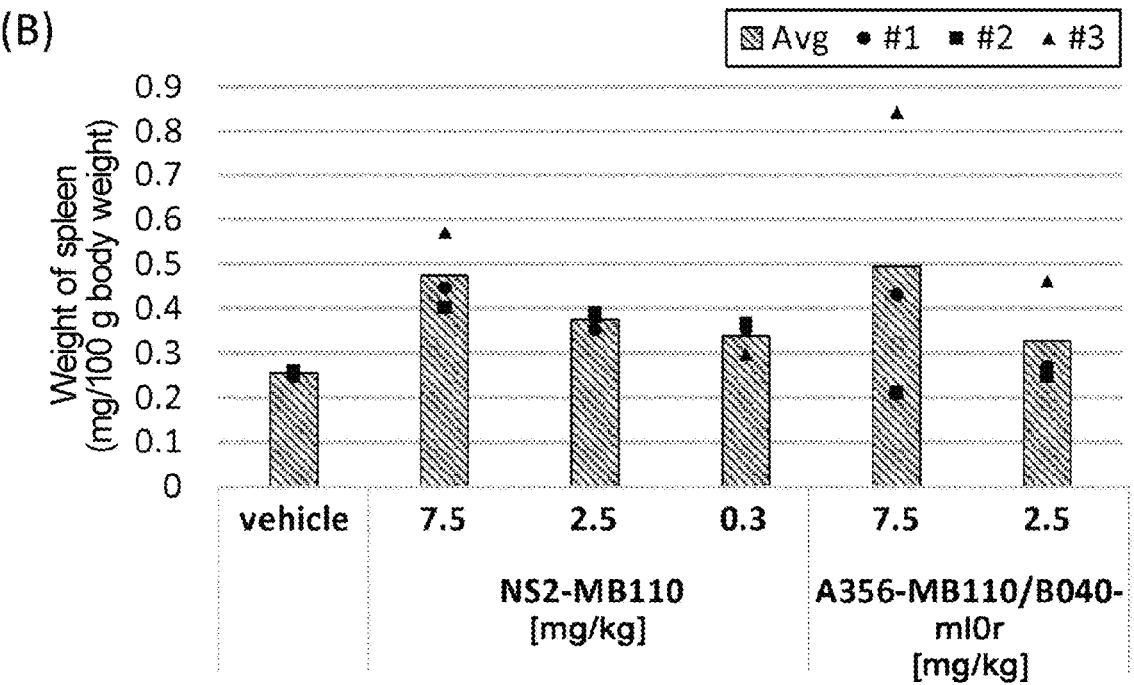

FIG. 33 is a diagram showing the weight of organs in a mouse model transplanted with the MC38 cell line after administration of NS2-MB110 or A356-MB110/B040-ml0r.

Subfigure (A) shows the weight of lymph node and subfigure (B) shows the weight of spleen.

Figure 34:
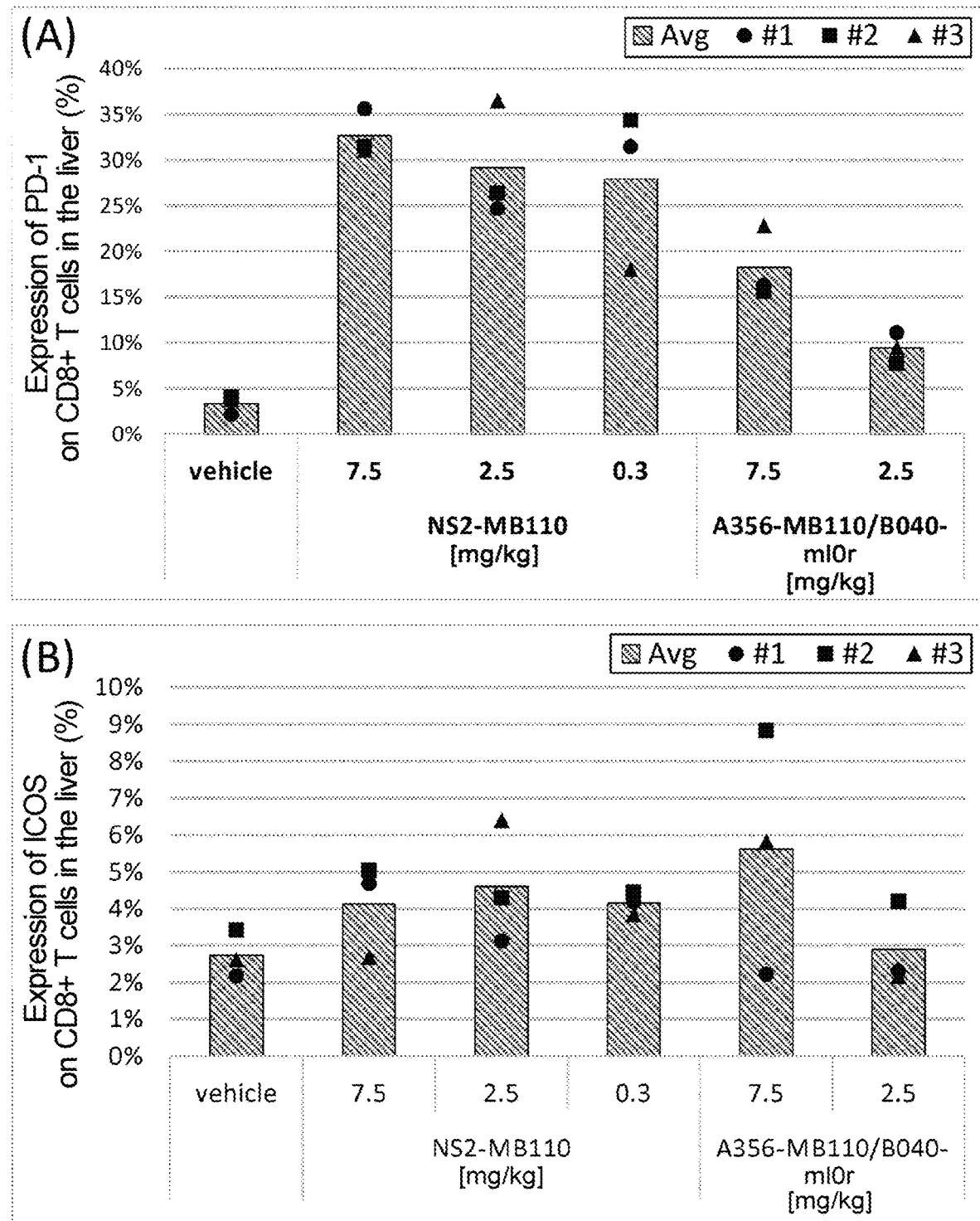

FIG. 34 is a diagram showing the degree of T cell activation in the liver of a mouse model transplanted with the MC38 cell line after administration of NS2-MB110 or A356-MB110/B040-ml0r.

Subfigure (A) shows the percentage of PD-1 positive T cells in CD8 positive T cells, and subfigure (B) shows the percentage of ICOS positive T cells in CD8 positive T cells.

Figure 35:
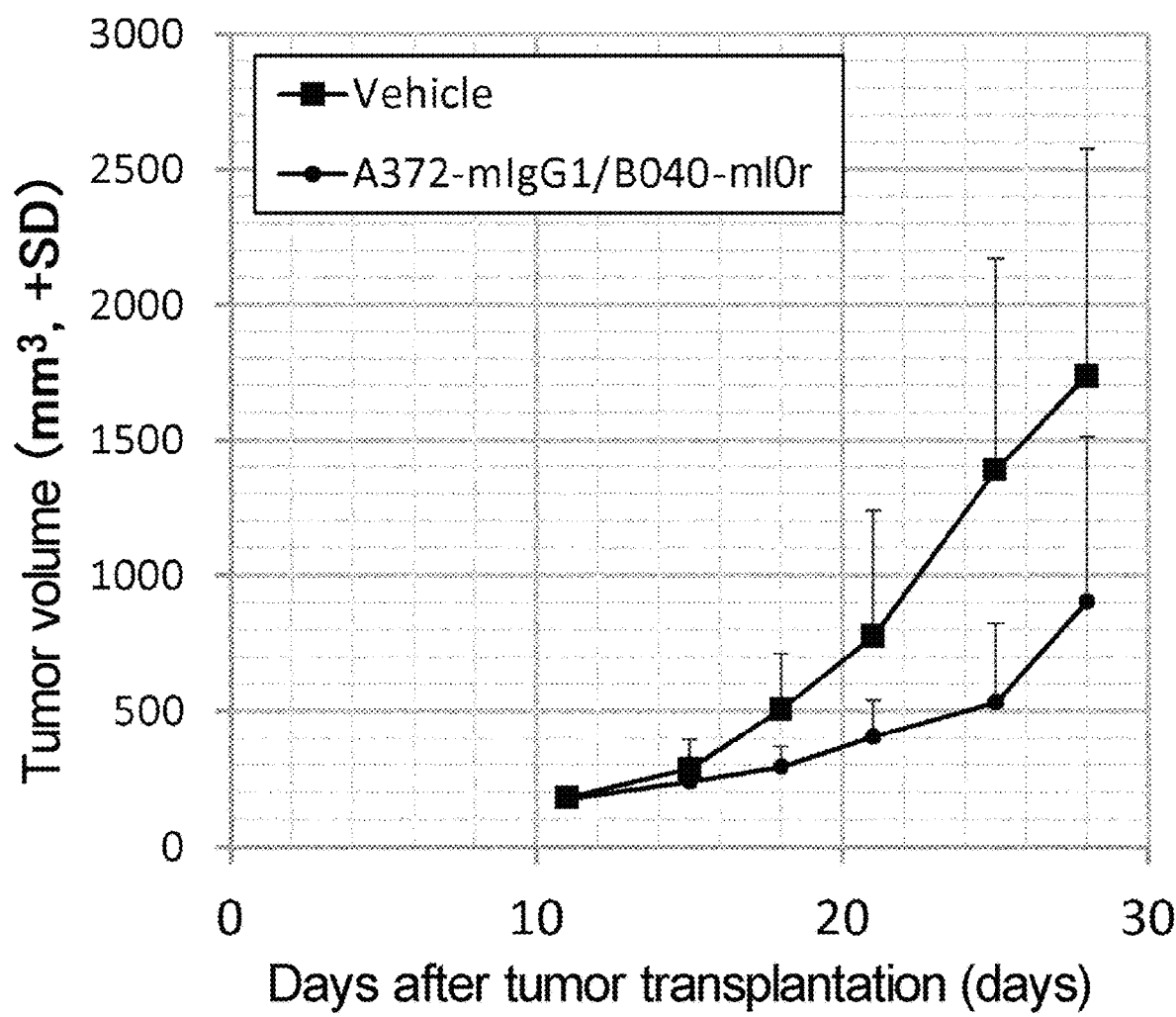

FIG. 35 is a diagram showing the anti-tumor effect of A372-mIgG1/B040-ml0r in a mouse model transplanted with the MC38 cell line.

Each dot shows the mean value of a group (n=5) of tumor volumes.

Figure 36:
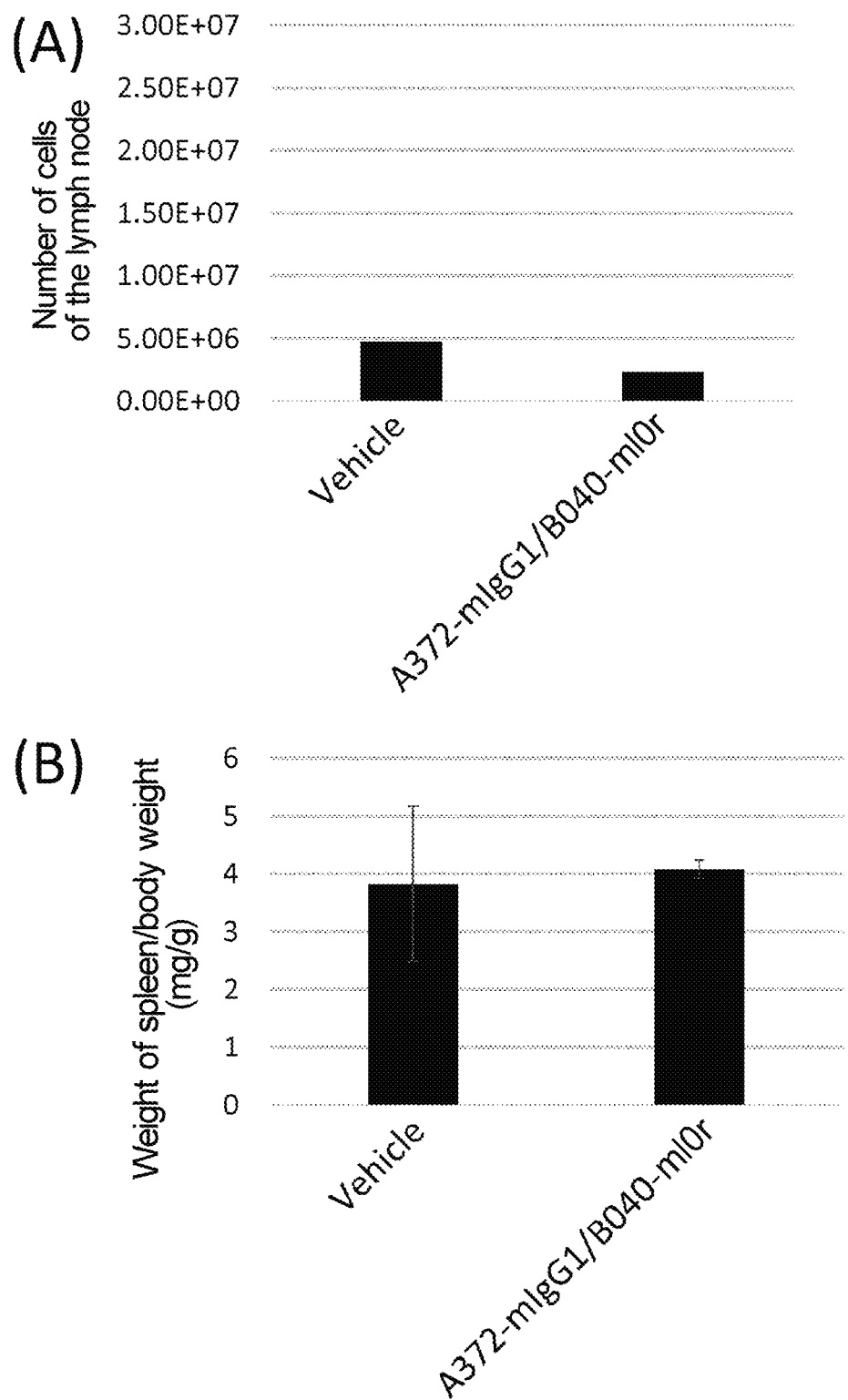

FIG. 36 shows the number of cells of the lymph node (subfigure (A)) and the weight of spleen (subfigure (B)) in a mouse model transplanted with the MC38 cell line after administration of A372-mIgG1/B040-ml0r.

Figure 37:
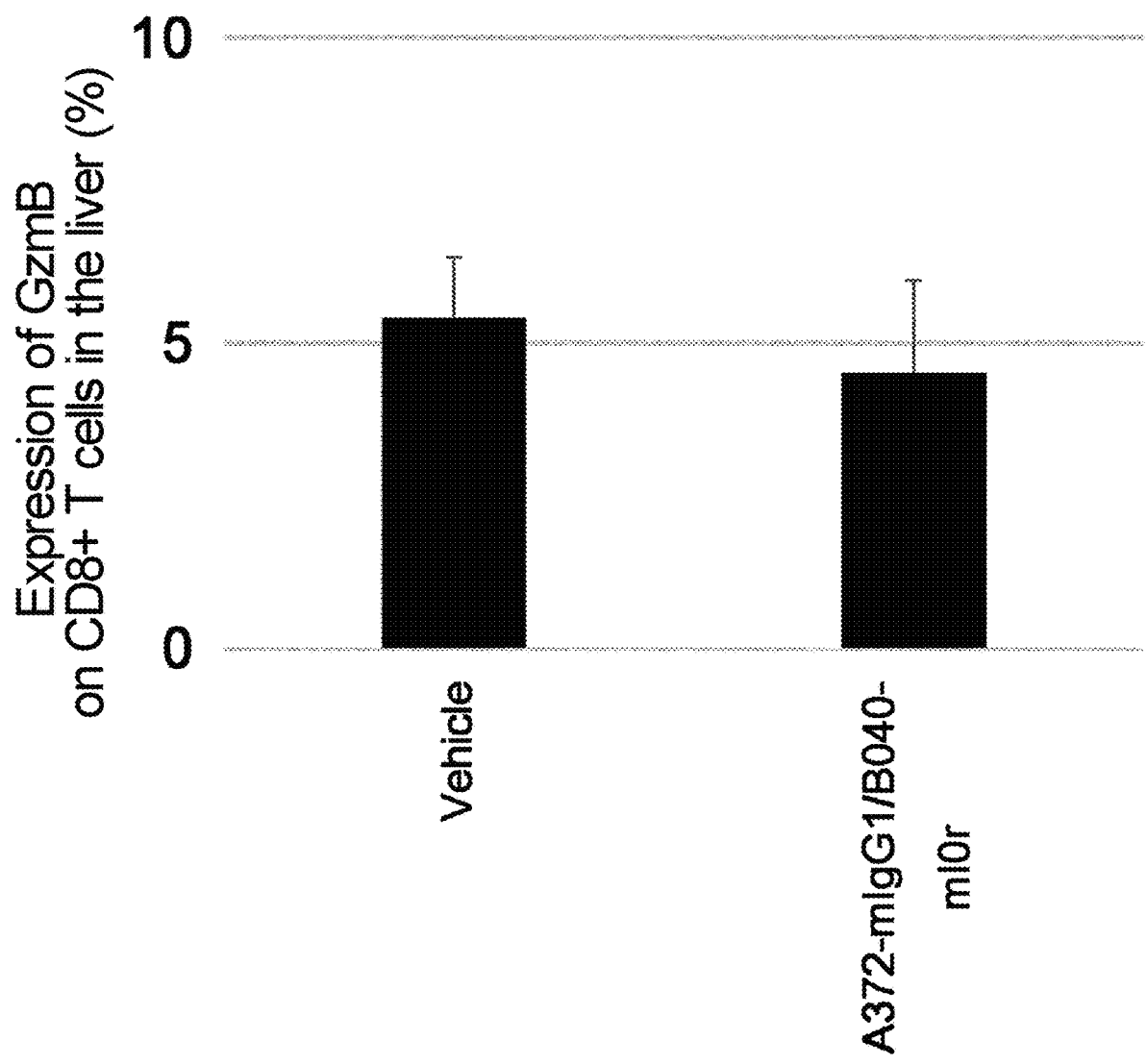

FIG. 37 is a diagram showing the degree of T cell activation in the liver of a mouse model transplanted with the MC38 cell line after administration of A372-mIgG1/B040-ml0r (percentage of Granzyme B positive T cells in CD8 positive T cells).

Figure 38:
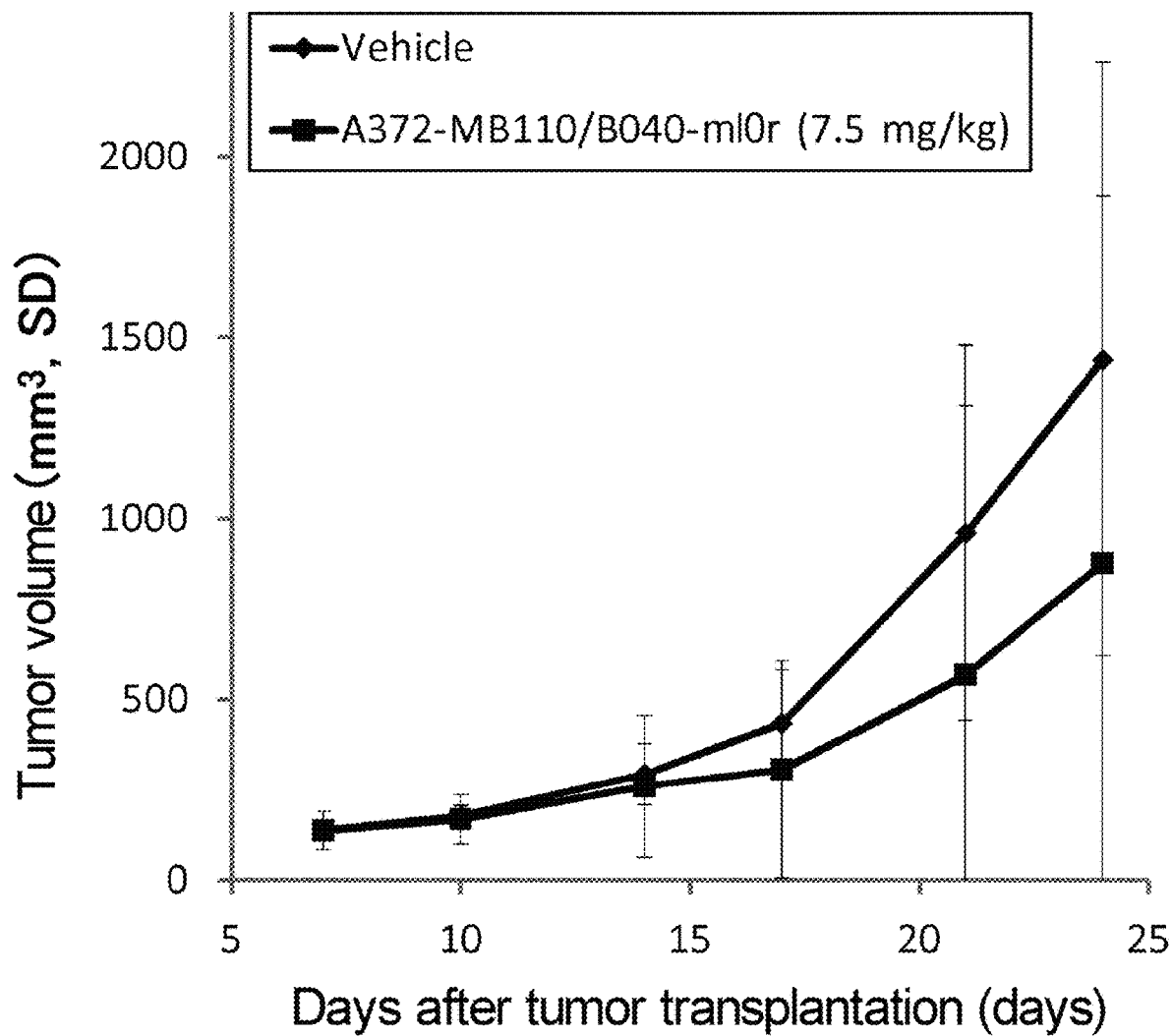

FIG. 38 is a diagram showing the anti-tumor effect of A372-MB110/B040-mI0r in a mouse model transplanted with the MC38 cell line.

Each dot shows the mean value of a group (n=5) of tumor volumes.

Figure 39:
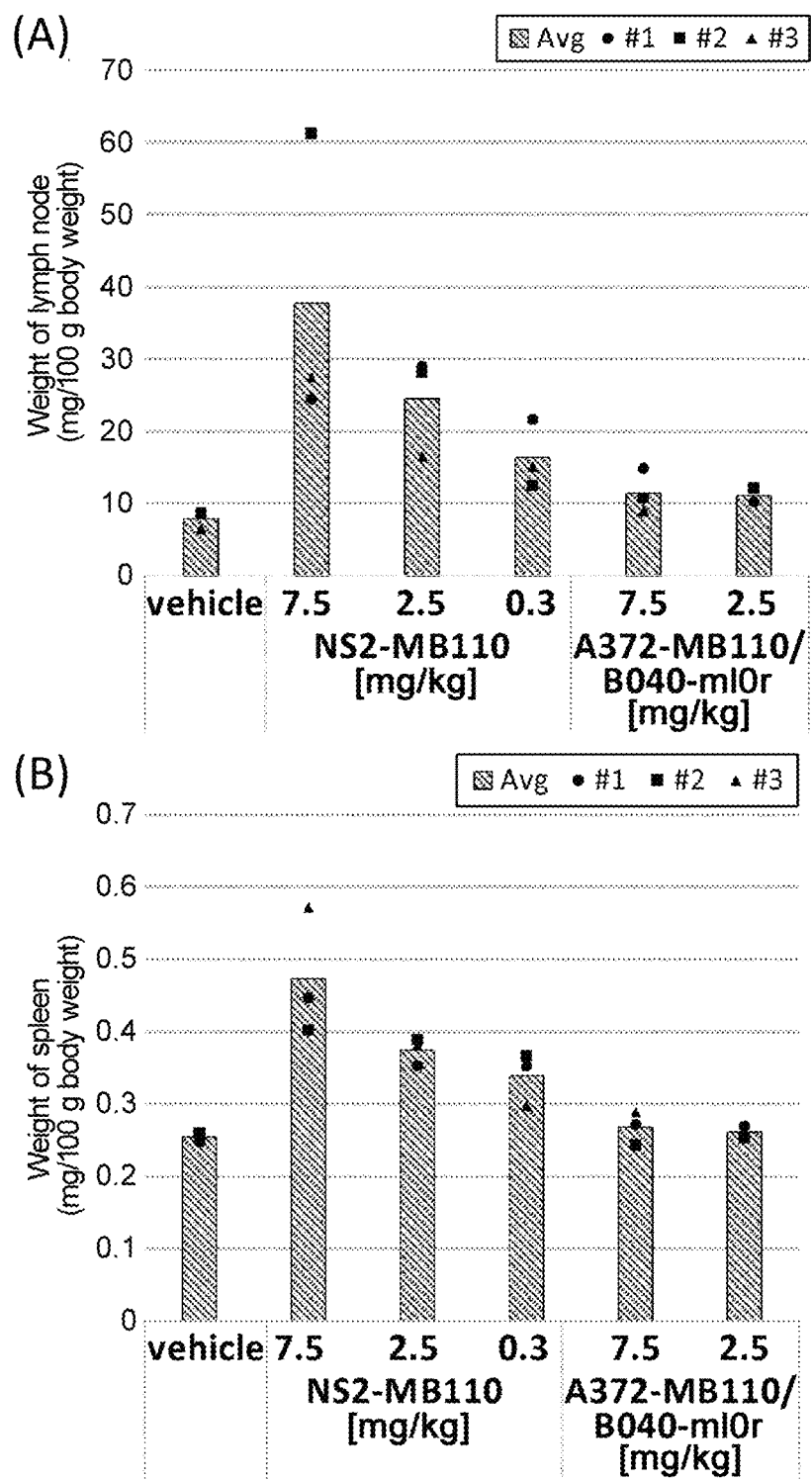

FIG. 39 is a diagram showing the weight of organs in a mouse model transplanted with the MC38 cell line after administration of NS2-MB110 or A372-MB110/B040-mI0r.

Subfigure (A) shows the weight of lymph node and subfigure (B) shows the weight of spleen.

Figure 40:
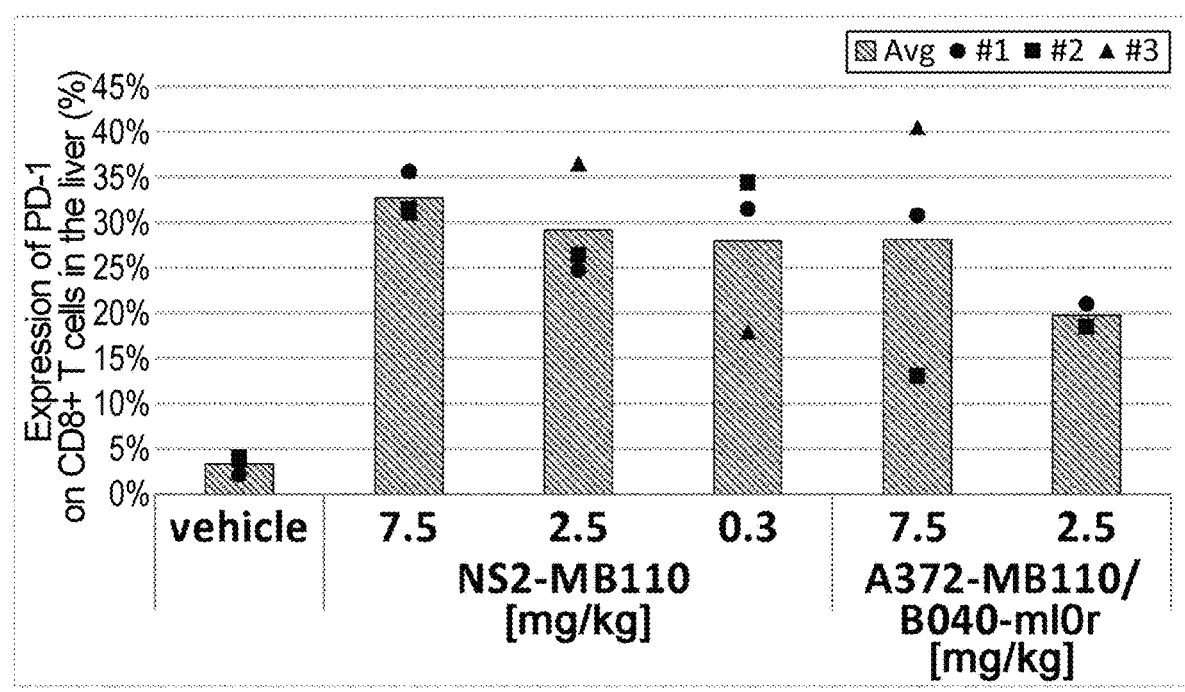

FIG. 40 is a diagram showing the degree of T cell activation in the liver of a mouse model transplanted with the MC38 cell line after administration of NS2-MB110 or A372-MB110/B040-mI0r (percentage of PD-1 positive T cells in CD8 positive T cells).

Figure 41:
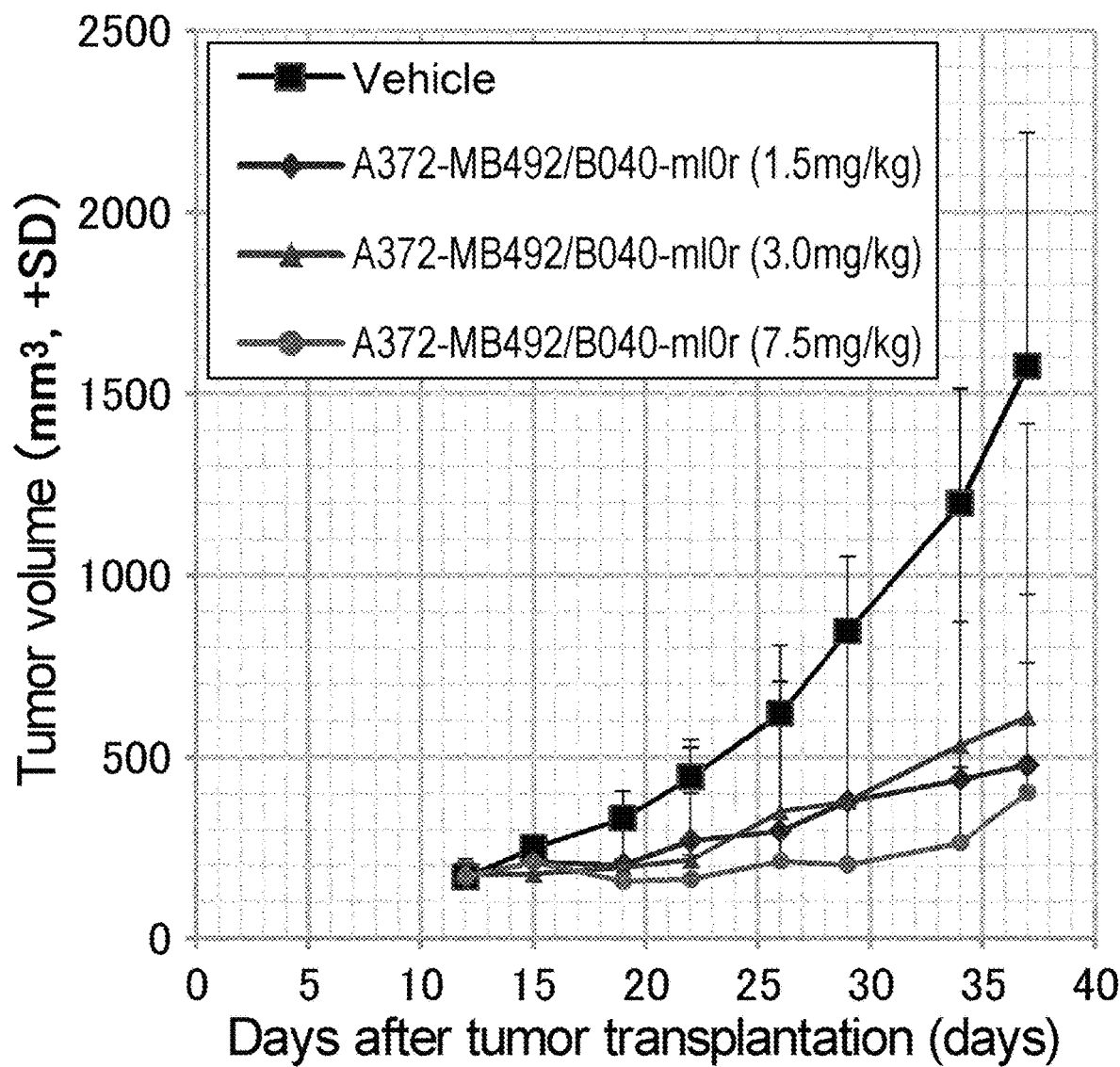

FIG. 41 is a diagram showing the anti-tumor effect of A372-MB492/B040-mI0r in a mouse model transplanted with the MC38 cell line.

Each dot shows the mean value of a group (n=5) of tumor volumes.

Figure 42:
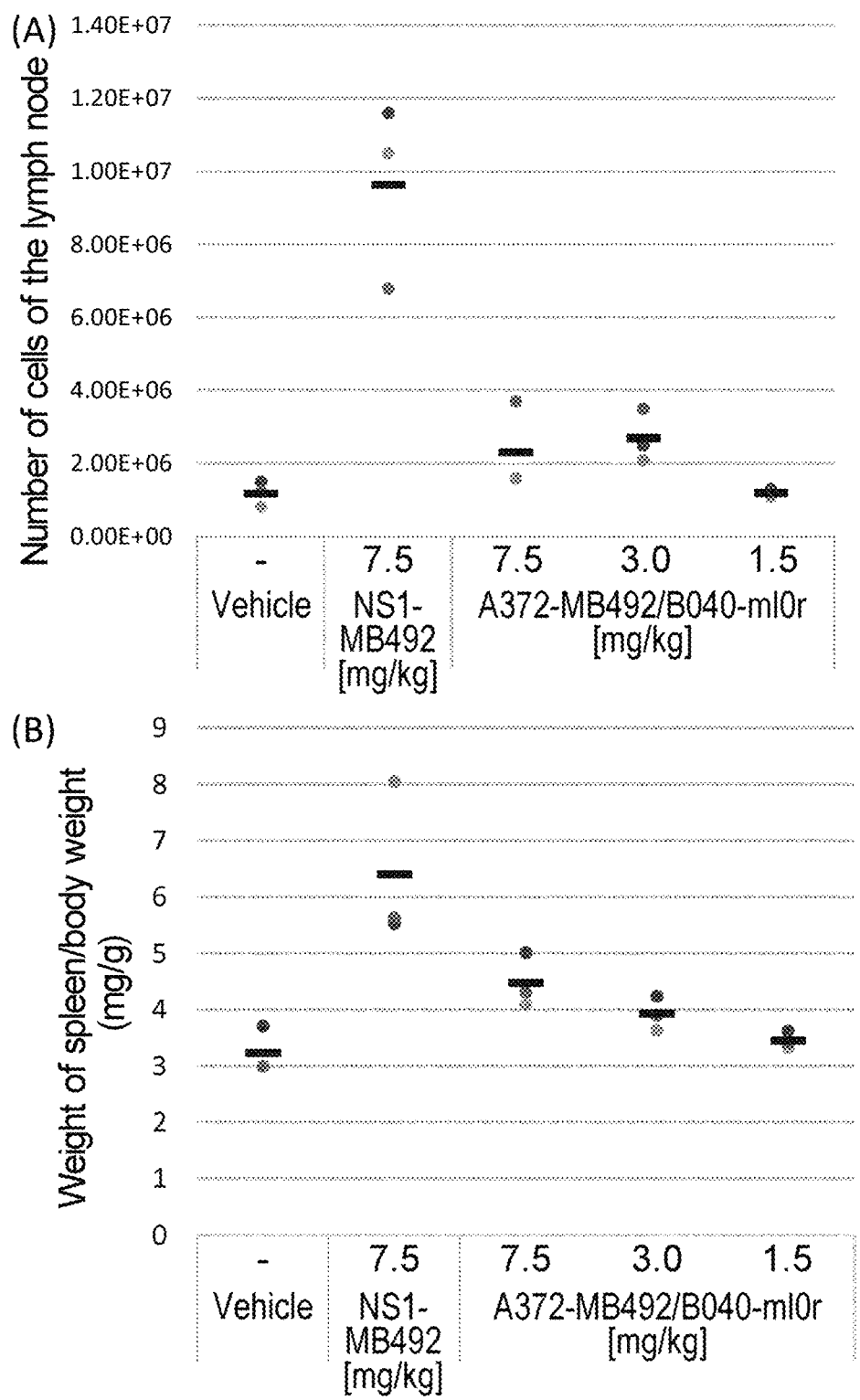

FIG. 42 is a diagram showing the number of cells of the lymph node and the organ weight of spleen in a mouse model transplanted with the MC38 cell line after administration of NS1-MB492 or A372-MB492/B040-mI0r.

Subfigure (A) shows the number of cells of the lymph node and subfigure (B) shows the organ weight of spleen.

Figure 43:
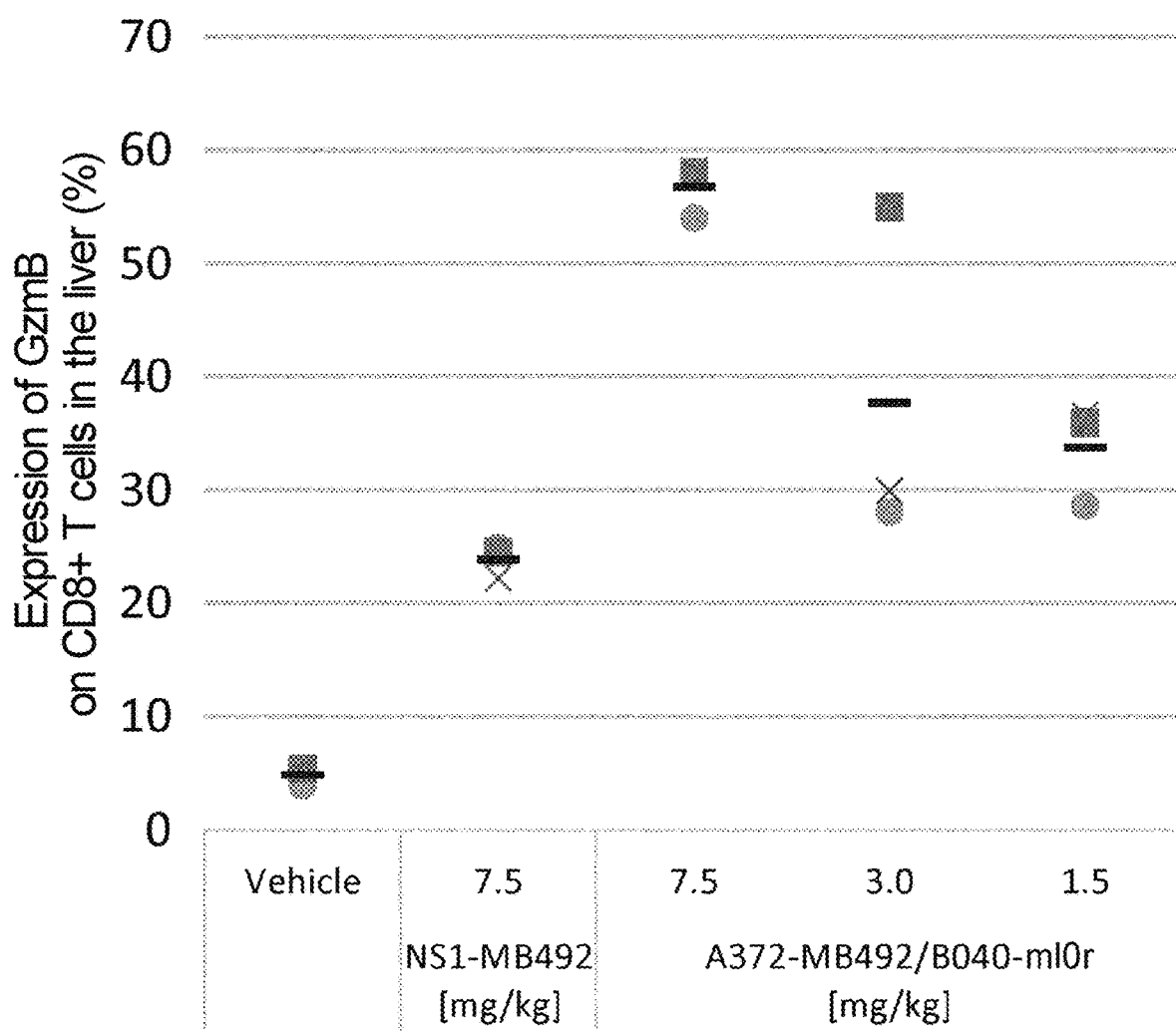

FIG. 43 is a diagram showing the degree of T cell activation in the liver of a mouse model transplanted with the MC38 cell line after administration of NS1-MB492 or A372-MB492/B040-mI0r (percentage of Granzyme B positive T cells in CD8 positive T cells).

Figure 44:
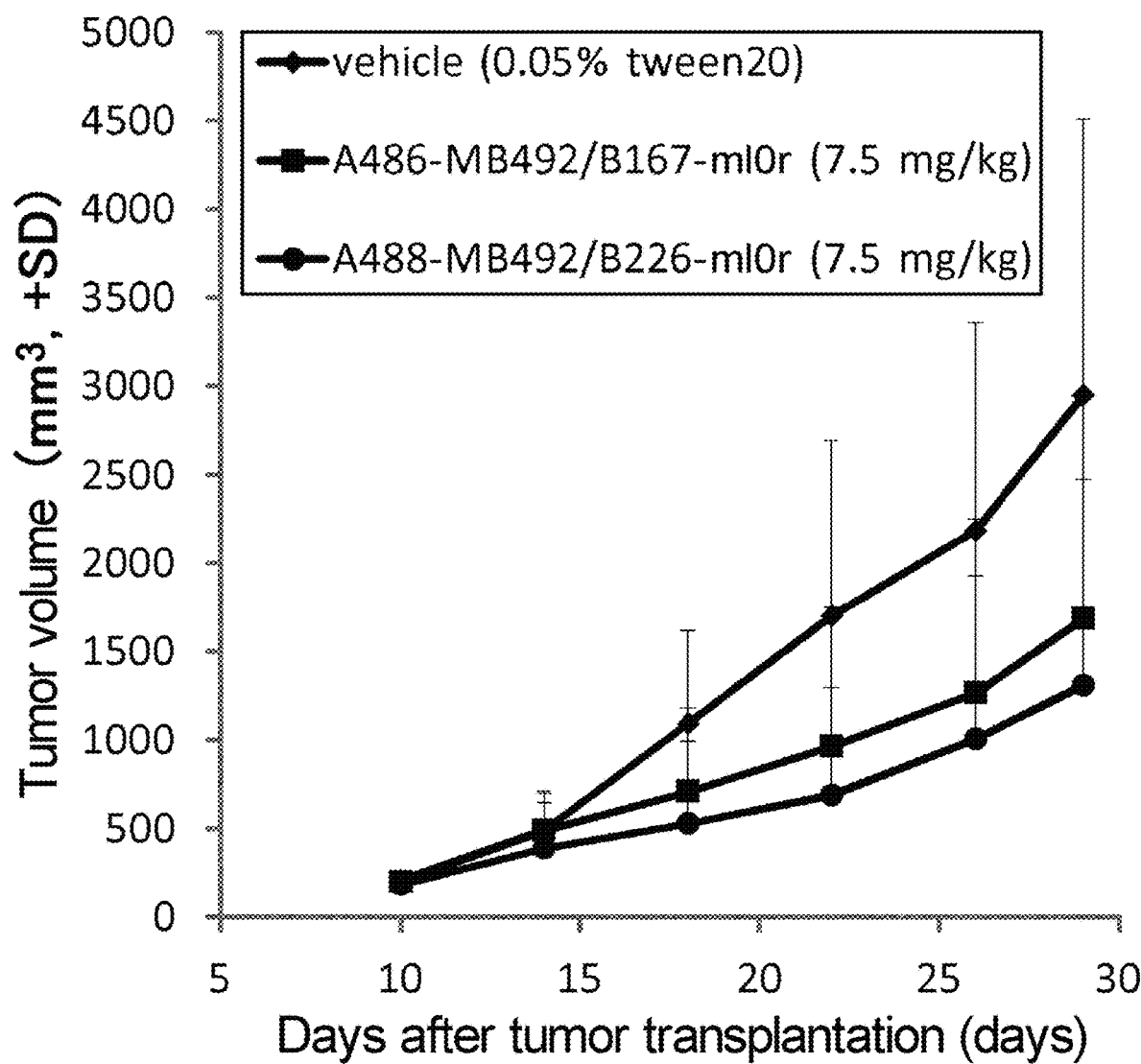

FIG. 44 is a diagram showing the anti-tumor effect of A486-MB492/B167-mI0r or A488-MB492/B226-mI0r in a mouse model transplanted with the MC38 cell line.

Each dot shows the mean value of a group (n=5) of tumor volumes.

Figure 45:
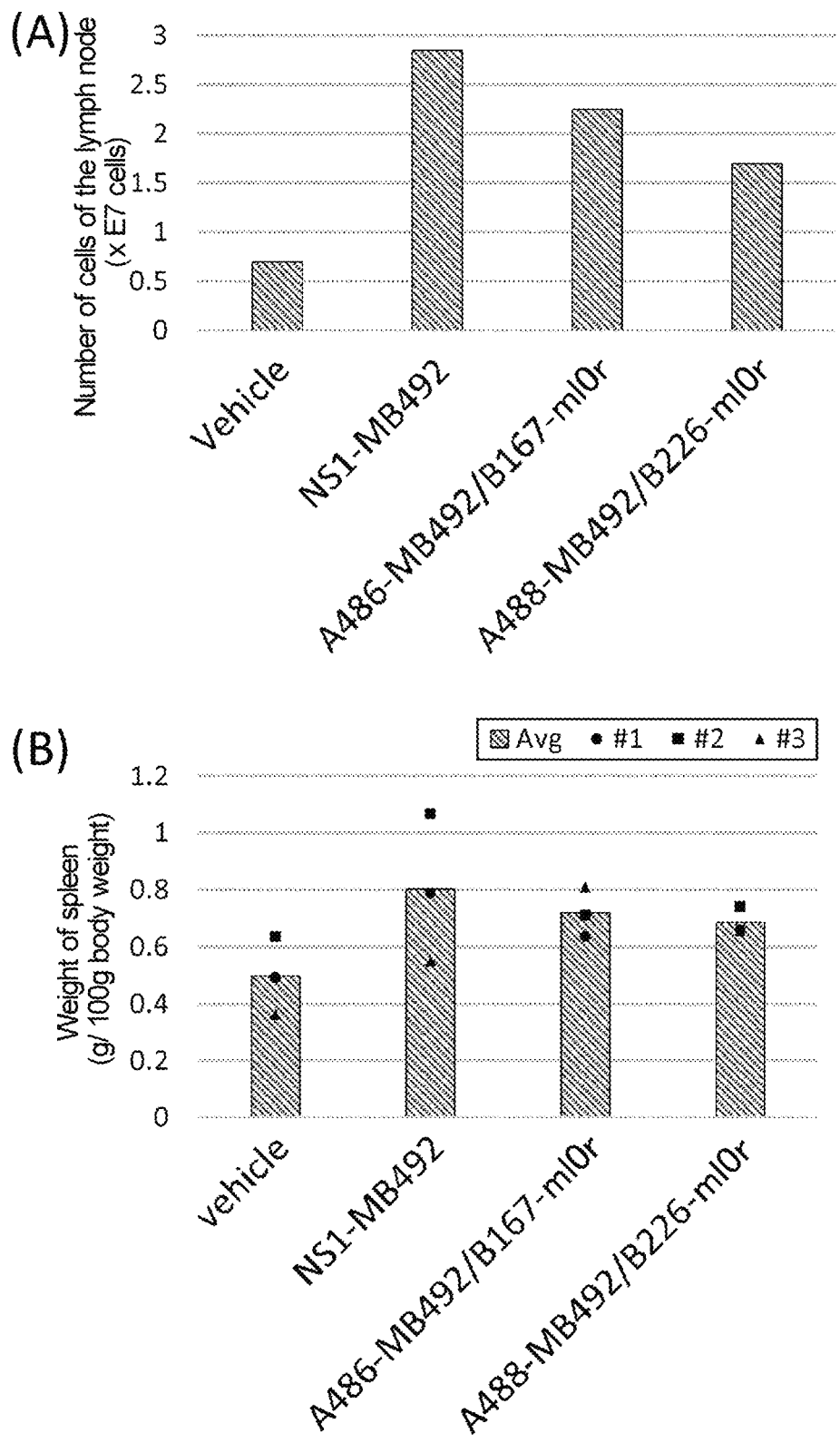

FIG. 45 is a diagram showing the number of cells per lymph node and the weight of spleen in a mouse model transplanted with the MC38 cell line after administration of NS1-MB492, A486-MB492/B167-mI0r, or A488-MB492/B226-mI0r.

Subfigure (A) shows the number of cells per lymph node and subfigure (B) shows the weight of spleen.

Figure 46:
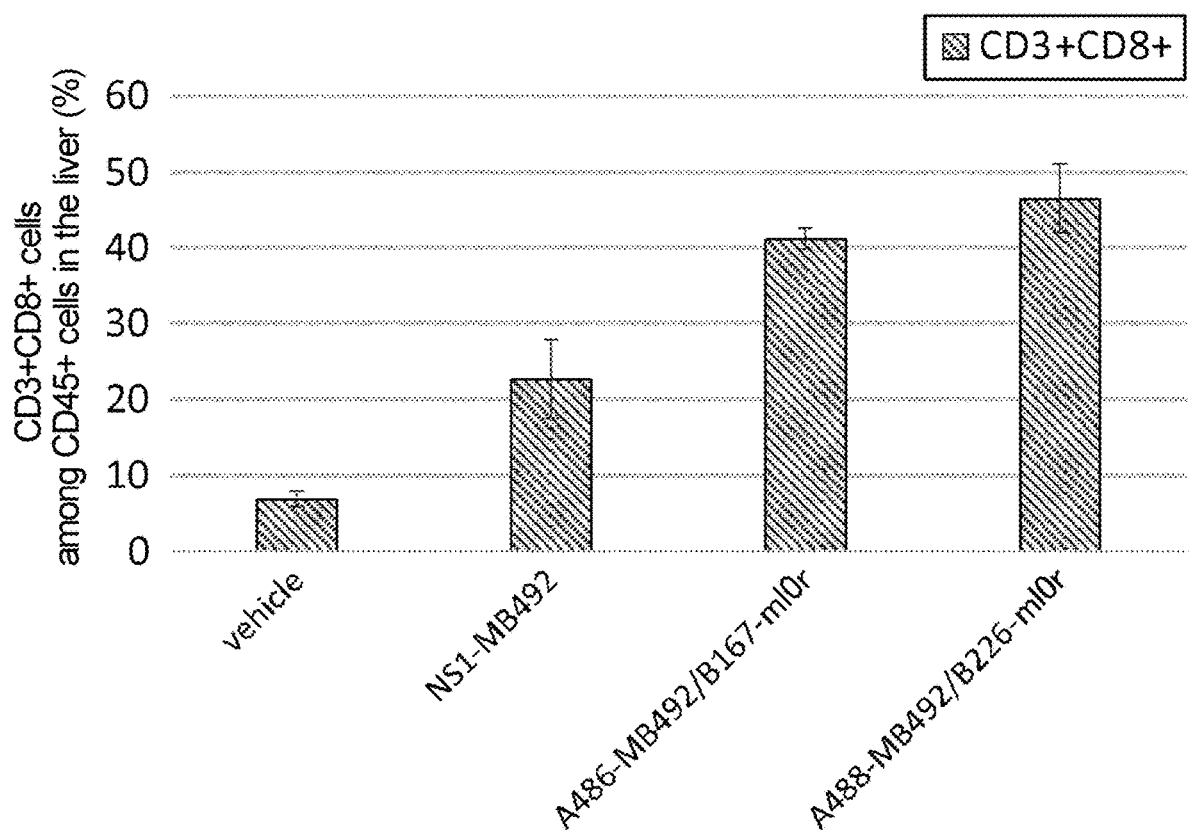

FIG. 46 is a diagram showing the level of infiltration of effector cells in the liver of a mouse model transplanted with the MC38 cell line after administration of NS1-MB492, A486-MB492/B167-mI0r, or A488-MB492/B226-mI0r (percentage of CD3 positive and CD8 positive T cells in CD45 positive T cells).

Figure 47:
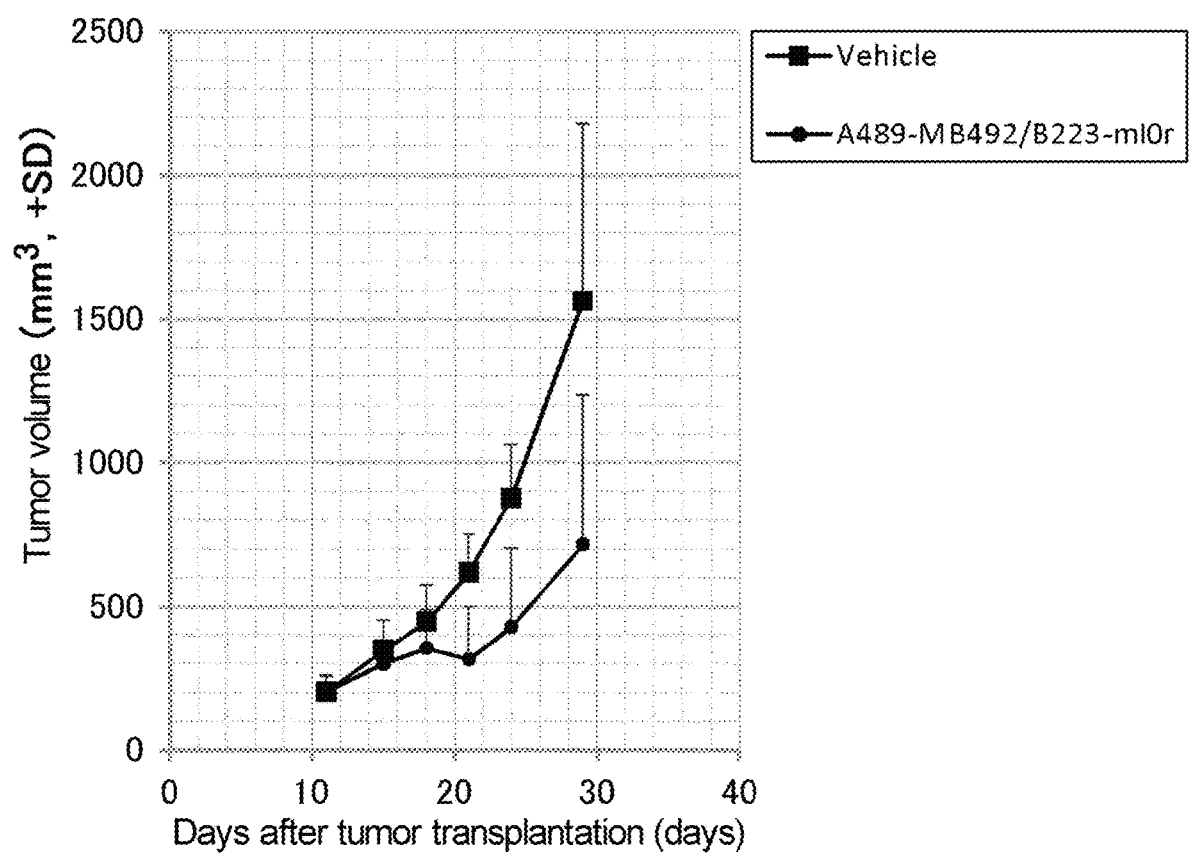

FIG. 47 is a diagram showing the anti-tumor effect of A489-MB492/B223-mI0r in a mouse model transplanted with the MC38 cell line.

Each dot shows the mean value of a group (n=5) of tumor volumes.

Figure 48:
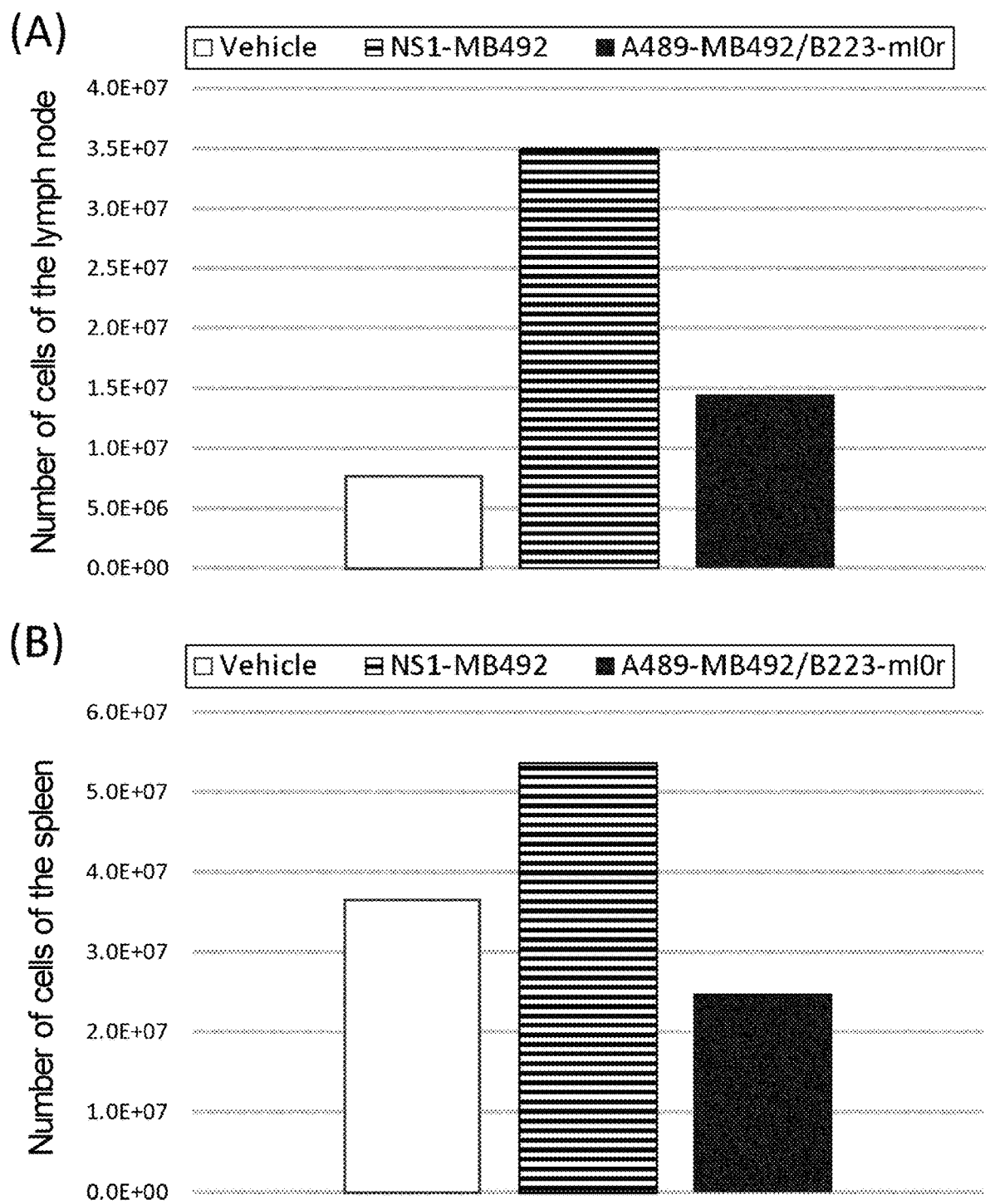

FIG. 48 is a diagram showing the number of cells of the lymph node and the number of cells in a lymphocyte fraction of spleen in a mouse model transplanted with the MC38 cell line after administration of NS1-MB492 or A489-MB492/B223-mI0r.

Subfigure (A) shows the number of cells of the lymph node and subfigure (B) shows the number of cells in a lymphocyte fraction of spleen.

Figure 49:
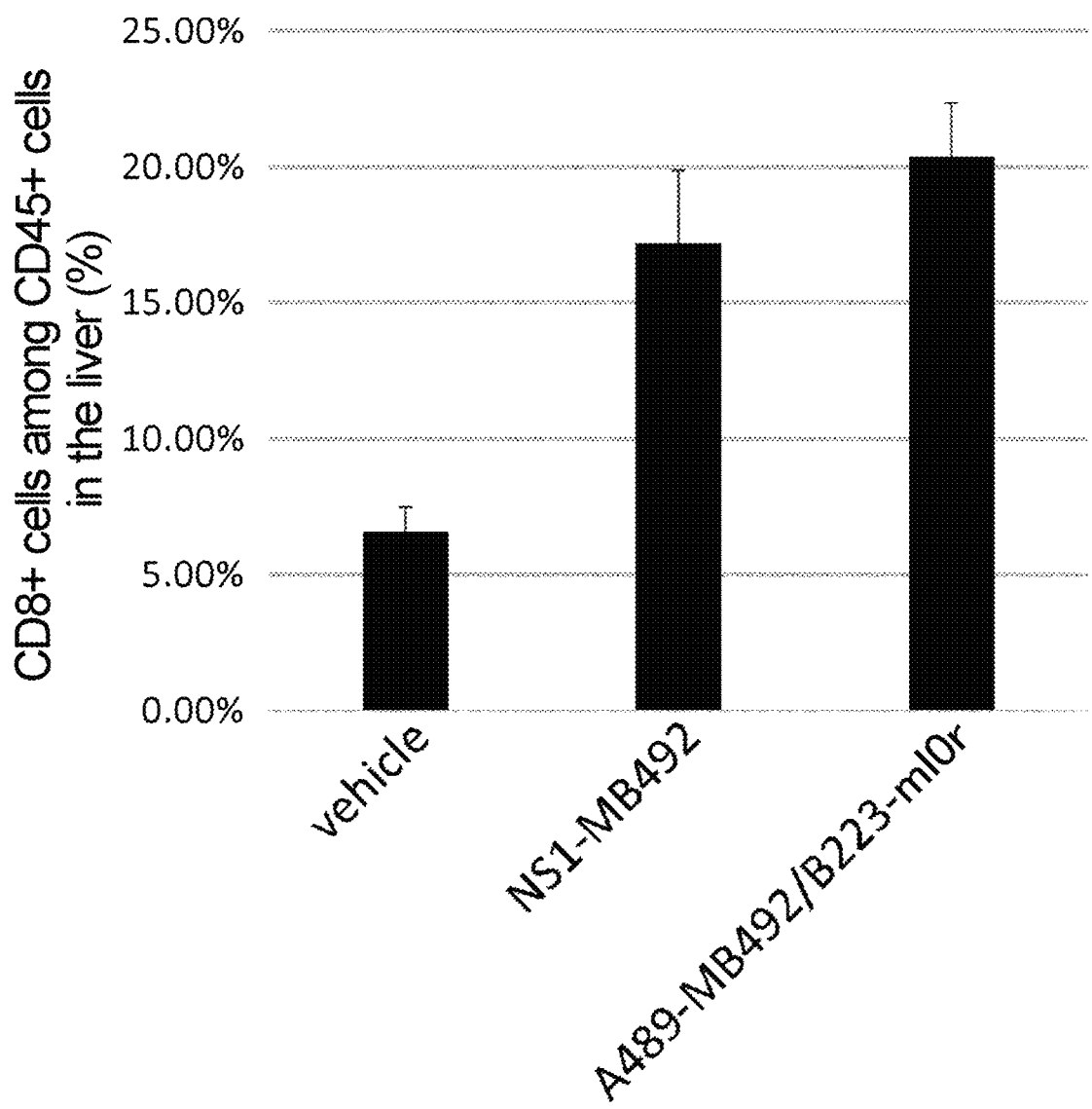

FIG. 49 is a diagram showing the degree of T cell activation in the liver of a mouse model transplanted with the MC38 cell line after administration of NS1-MB492 or A489-MB492/B223-mI0r (percentage of CD8 positive T cells in CD45 positive T cells).

Figure 50:
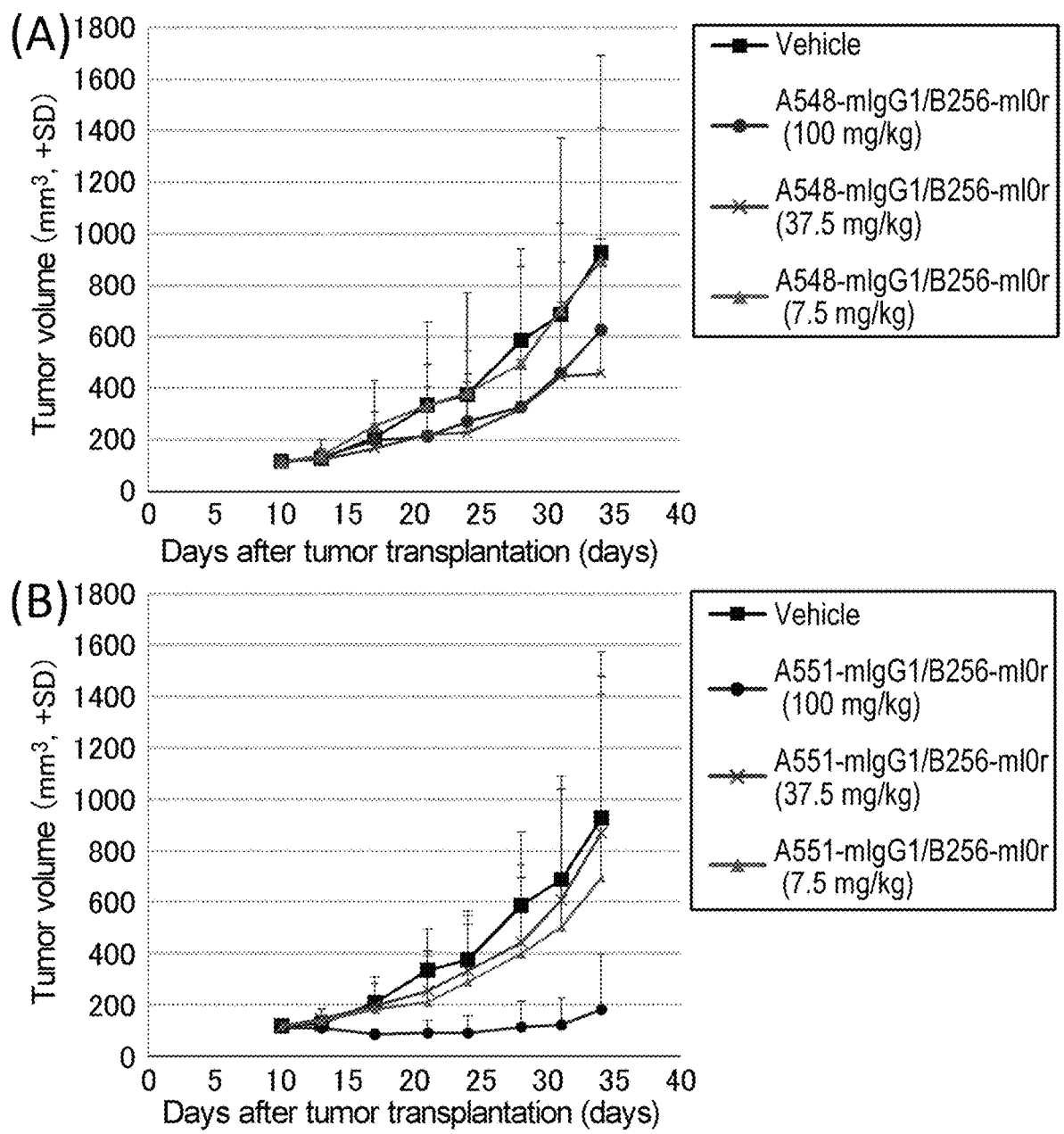

FIG. 50 is a diagram showing the anti-tumor effect of A548-mIgG1/B256-mI0r and A551-mIgG1/B256-mI0r in a mouse model transplanted with the MC38 cell line.

Subfigure (A) shows the anti-tumor effect of A548-mIgG1/B256-mI0r and subfigure (B) shows the anti-tumor effect of A551-mIgG1/B256-mI0r.

Figure 51:
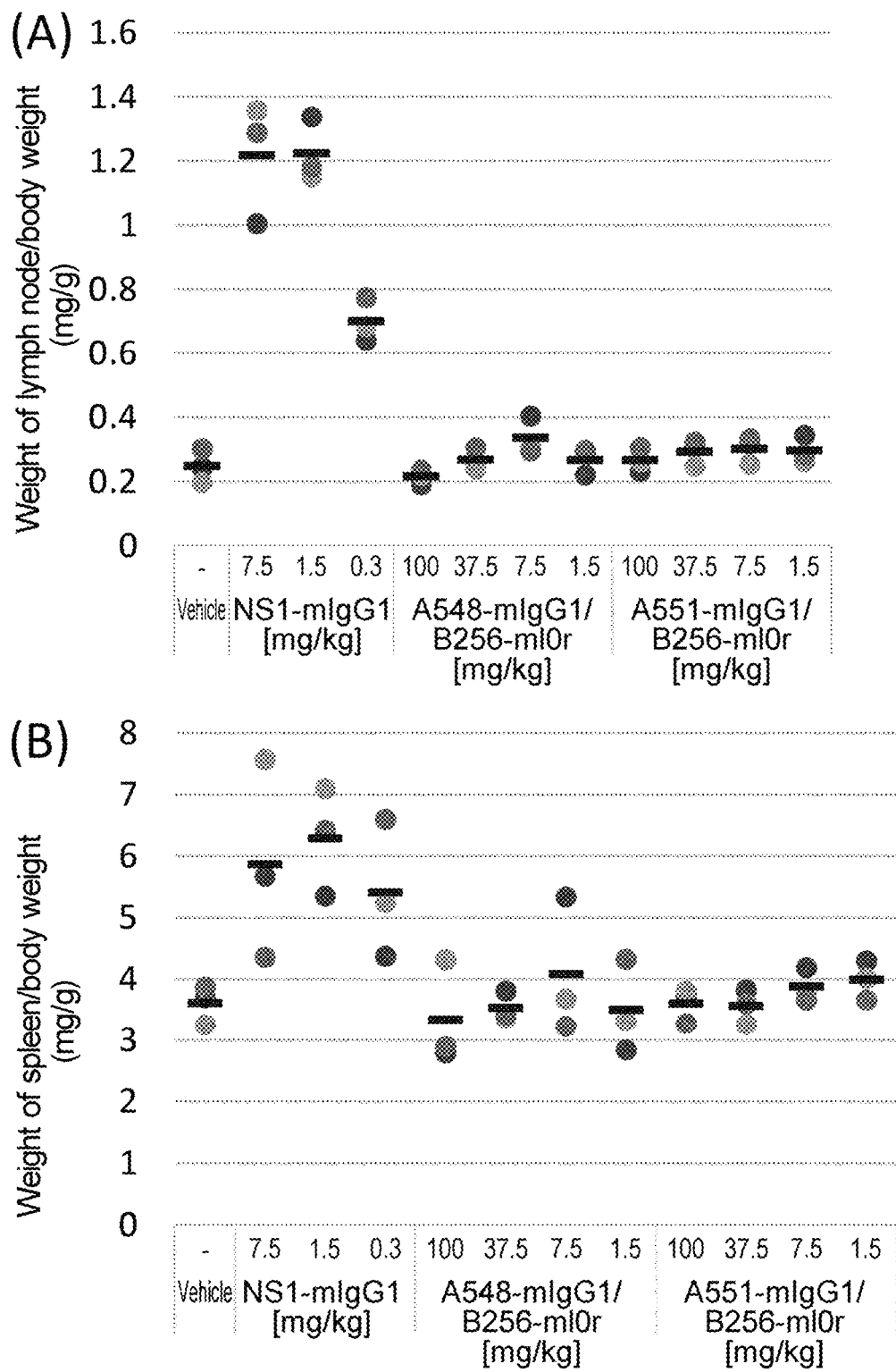

FIG. 51 is a diagram showing the weight of organs in a mouse model transplanted with the MC38 cell line after administration of NS1-mIgG1, A548-mIgG1/B256-mI0r, or A551-mIgG1/B256-mI0r.

Subfigure (A) shows the weight of lymph node and subfigure (B) shows the weight of spleen.

Figure 52:
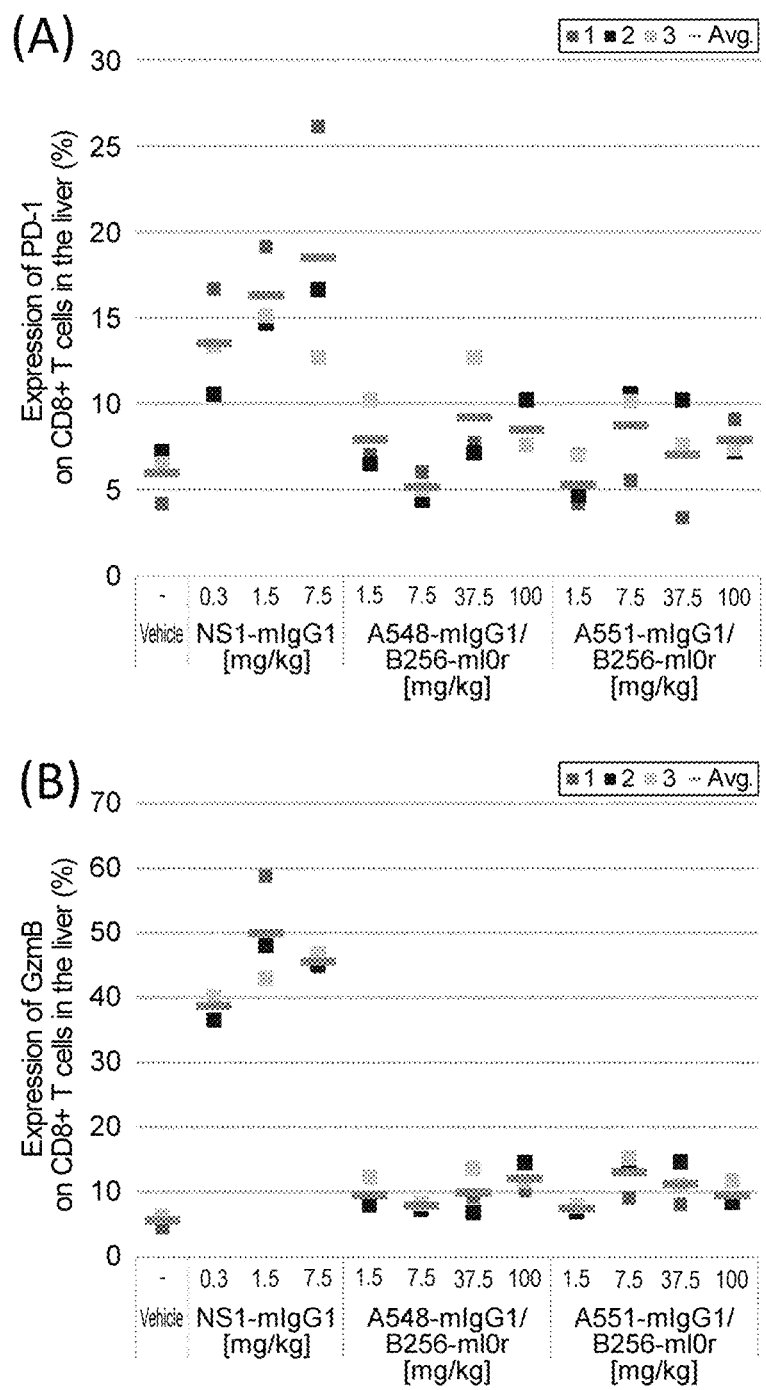

FIG. 52 is a diagram showing the degree of T cell activation in the liver of a mouse model transplanted with the MC38 cell line after administration of NS1-mIgG1, A548-mIgG1/B256-mI0r, or A551-mIgG1/B256-mI0r.

Subfigure (A) shows the percentage of PD-1 positive T cells in CD8 positive T cells, and subfigure (B) shows the percentage of Granzyme B positive T cells in CD8 positive T cells.

Figure 53:
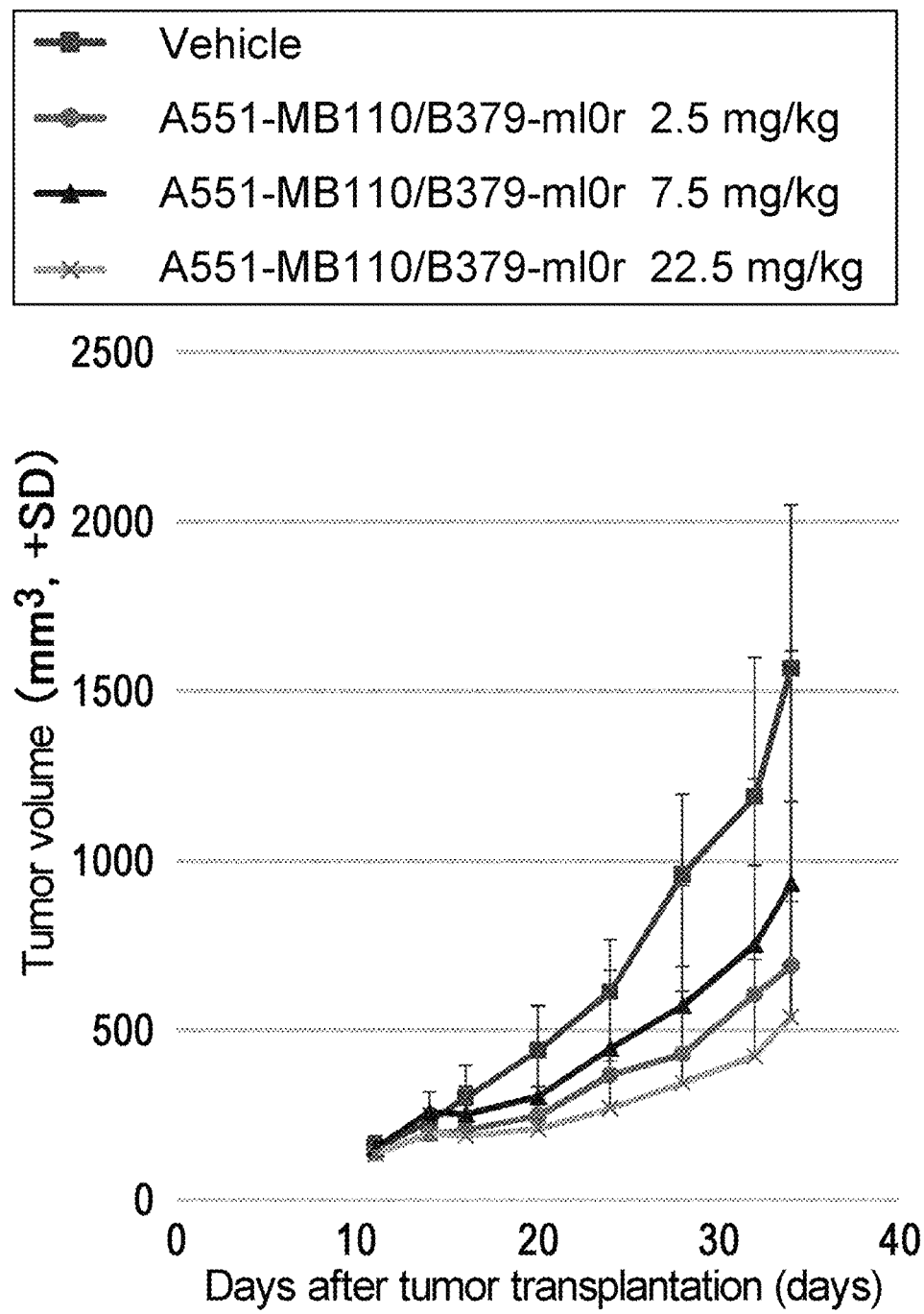

FIG. 53 is a diagram showing the anti-tumor effect of A551-MB110/B379-mI0r in a mouse model transplanted with the MC38 cell line.

Figure 54:
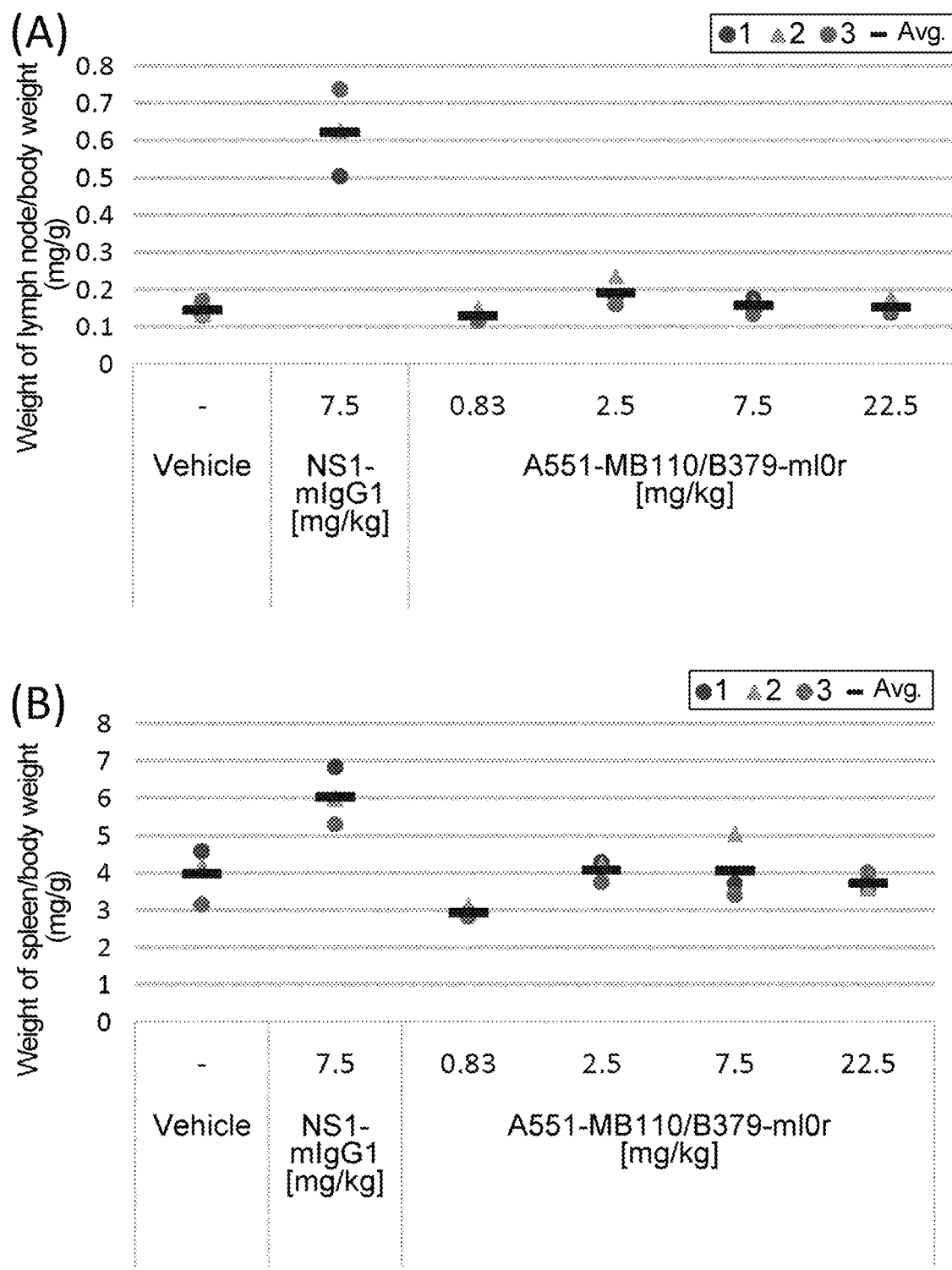

FIG. 54 is a diagram showing the weight of organs in a mouse model transplanted with the MC38 cell line after administration of NS1-mIgG1 or A551-MB110/B379-mI0r.

Subfigure (A) shows the weight of lymph node and subfigure (B) shows the weight of spleen.

Figure 55:
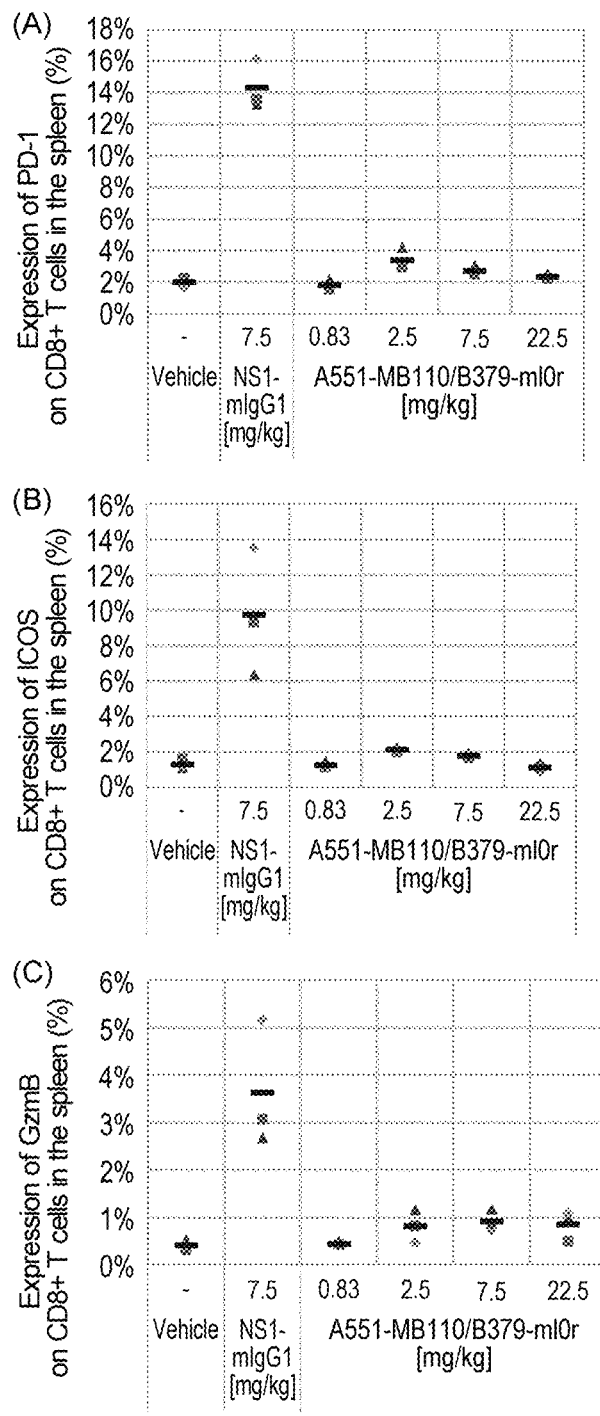

FIG. 55 is a diagram showing the degree of T cell activation in the spleen of a mouse model transplanted with the MC38 cell line after administration of NS1-mIgG1 or A551-MB110/B379-mI0r.

Subfigure (A) shows the percentage of PD-1 positive T cells in CD8 positive T cells, subfigure (B) shows the percentage of ICOS positive T cells in CD8 positive T cells, and subfigure (C) shows the percentage of Granzyme B positive T cells in CD8 positive T cells.

Figure 56:
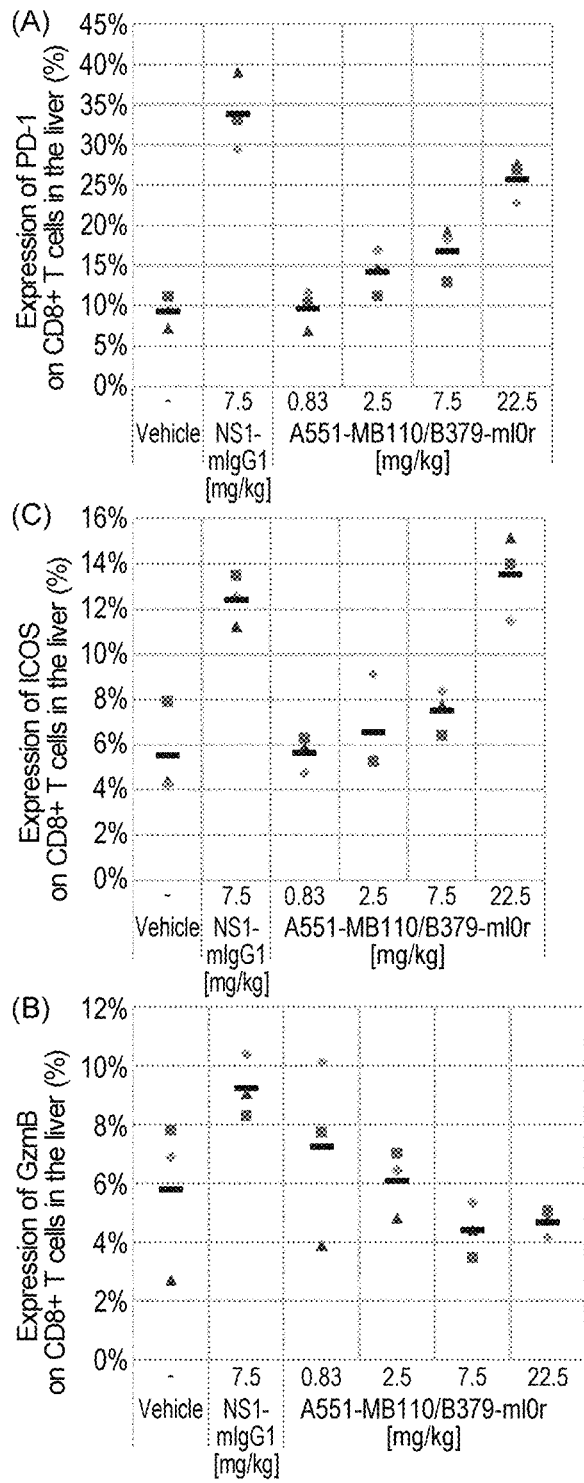

FIG. 56 is a diagram showing the degree of T cell activation in the liver of a mouse model transplanted with the MC38 cell line after administration of NS1-mIgG1 or A551-MB110/B379-mI0r.

Subfigure (A) shows the percentage of PD-1 positive T cells in CD8 positive T cells, subfigure (B) shows the percentage of ICOS positive T cells in CD8 positive T cells, and subfigure (C) shows the percentage of Granzyme B positive T cells in CD8 positive T cells.

Figure 57:
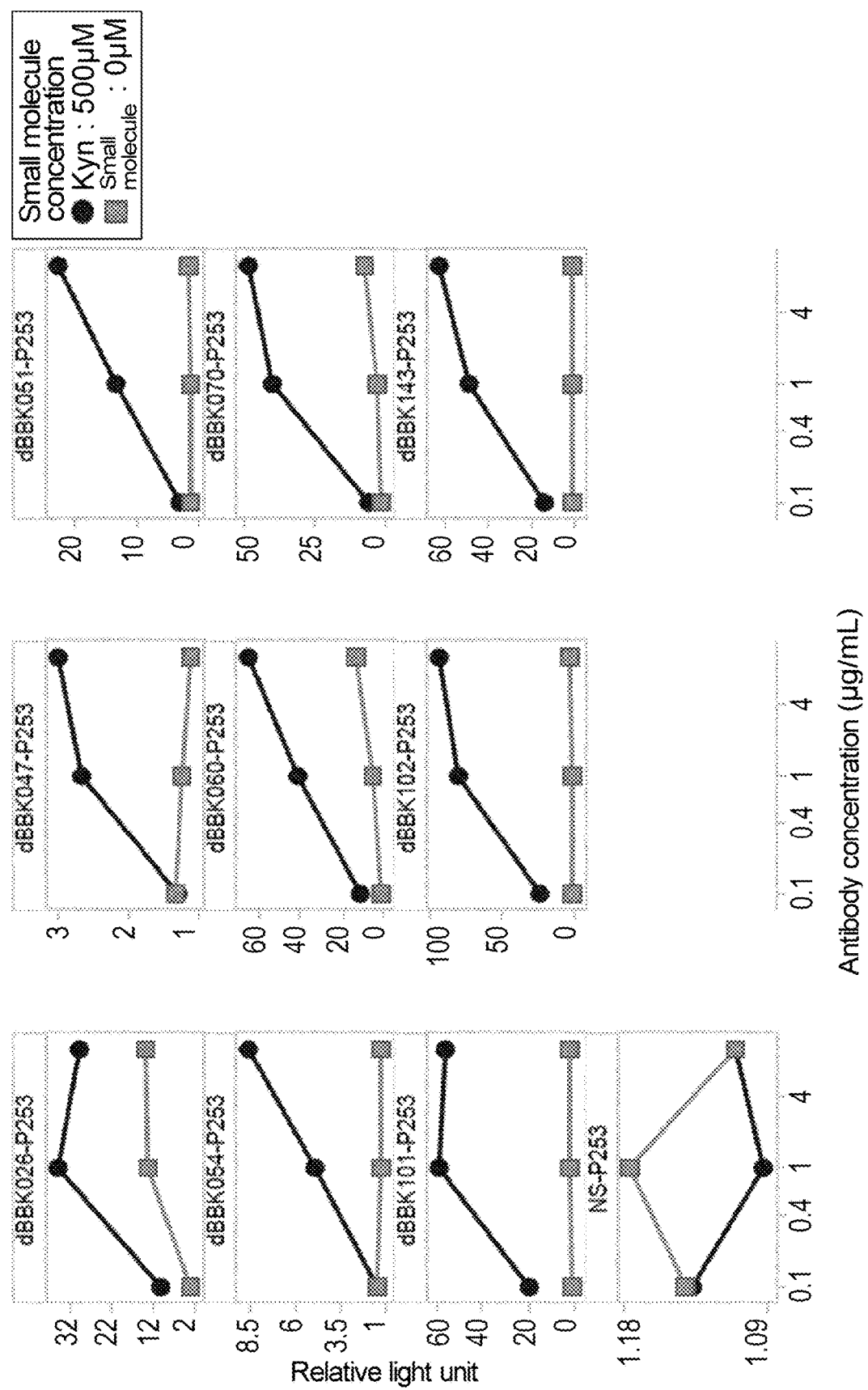

FIG. 57 is a diagram showing the agonist activity of various anti-CD137 antibodies tested using Jurkat cells in the presence or absence of L-kynurenine.

The X axis shows the antibody concentration (μg/mL) and the Y axis shows the relative light unit.

Figure 58:
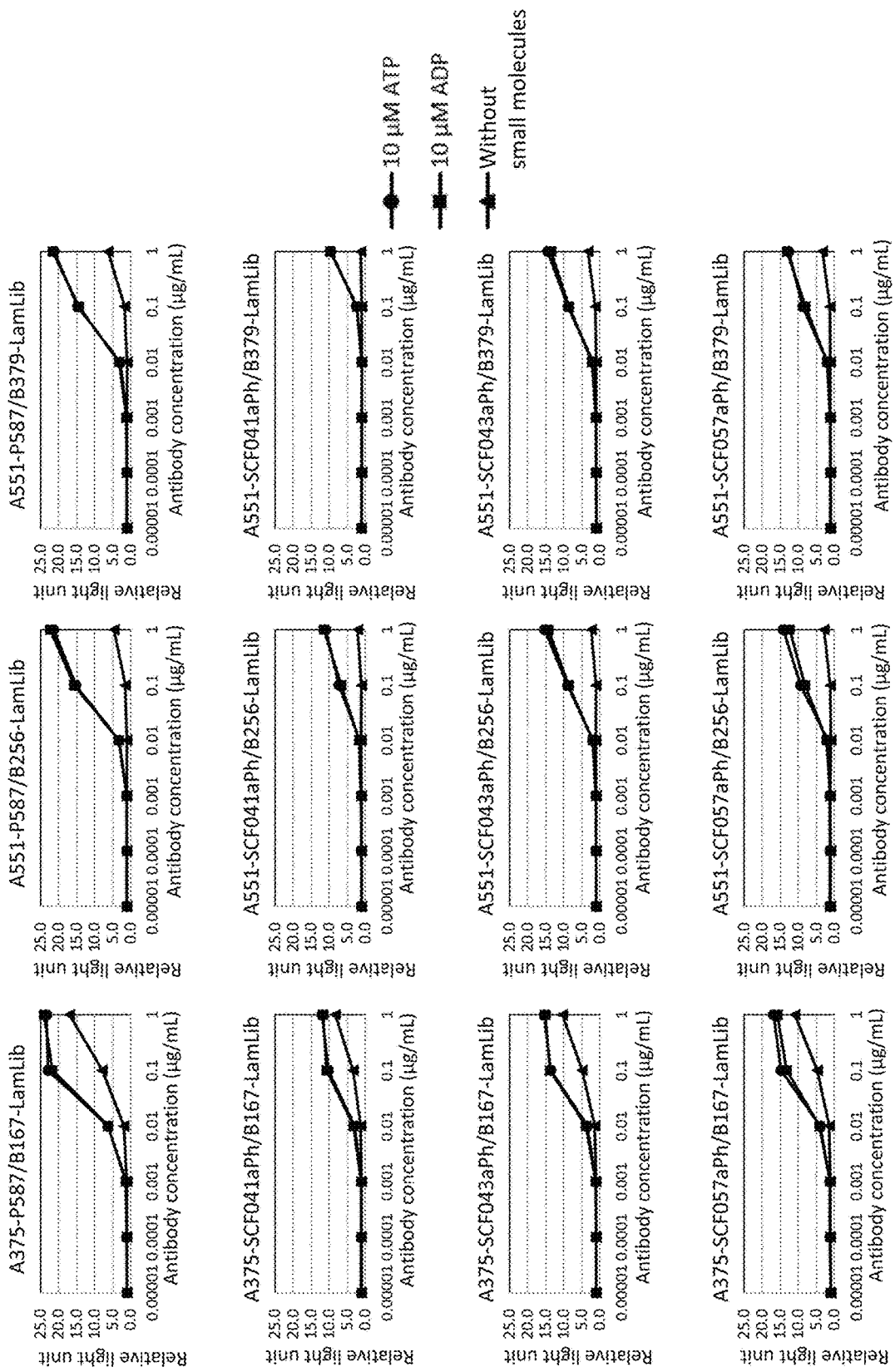

FIG. 58 is a diagram showing the agonist activity of various anti-CD137 antibodies tested using 4-1BB Jurkat cells in the presence or absence of the small molecule compound (ATP or ADP).

The X axis shows the antibody concentration (μg/mL) and the Y axis shows the relative light unit.

Figure 59:
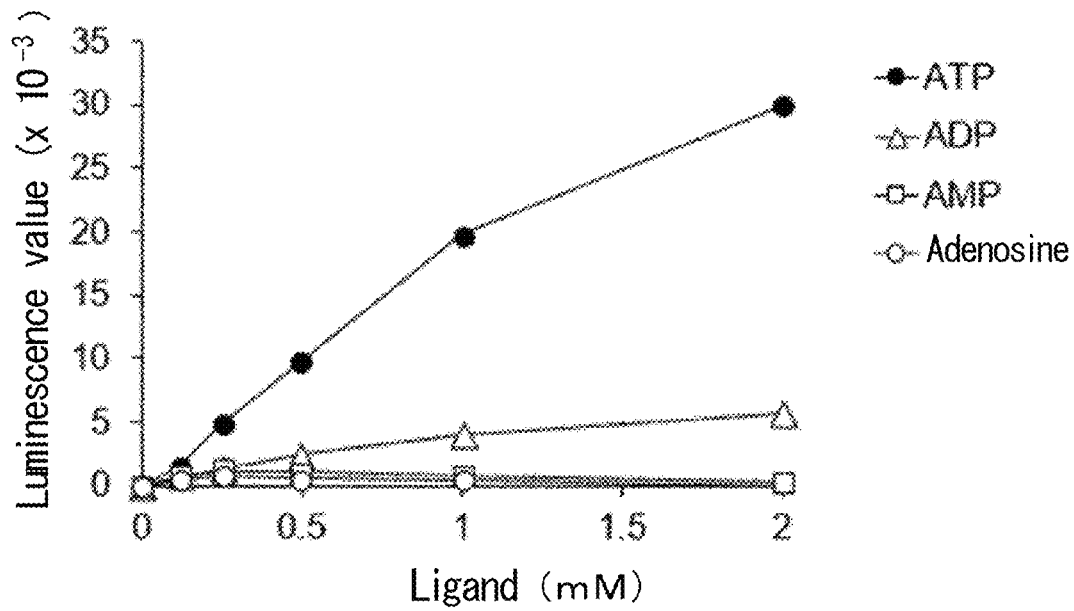

FIG. 59 is a diagram showing the ATP responsiveness (ATP concentration-dependent luciferin luminescence) of P2Y11 split Luc/HEK293 cells produced for determining extracellular ATP levels.

Figure 60:
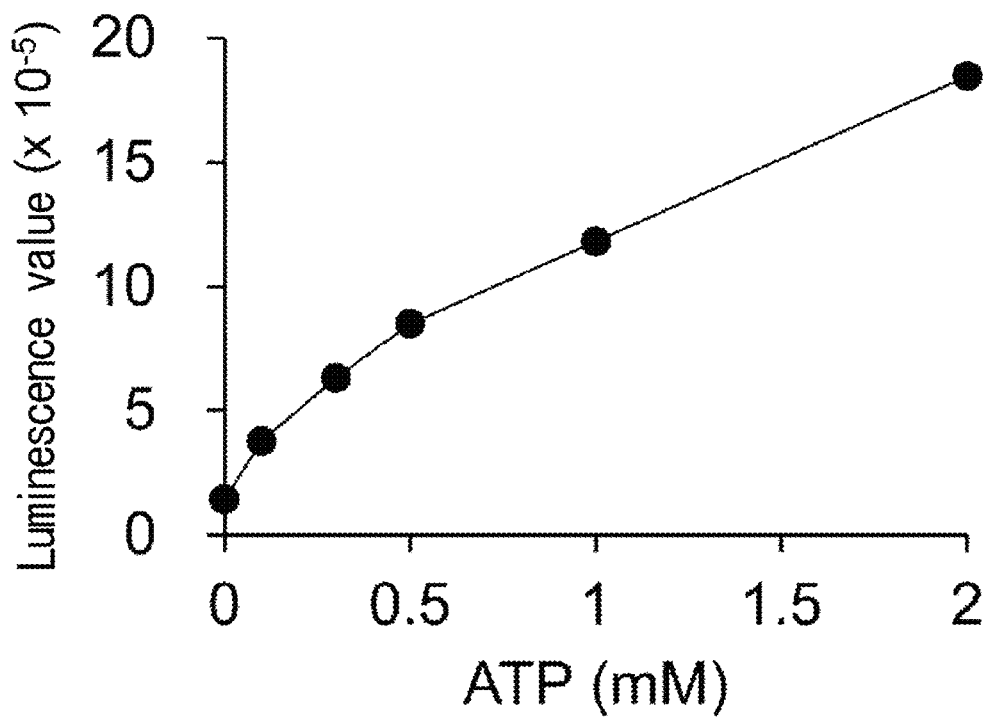

FIG. 60 is a diagram showing the in vivo ATP responsiveness (ATP concentration-dependent luciferin luminescence) of P2Y11 split Luc/HEK293 cells when subcutaneously transplanted to a mouse.

Figure 61:
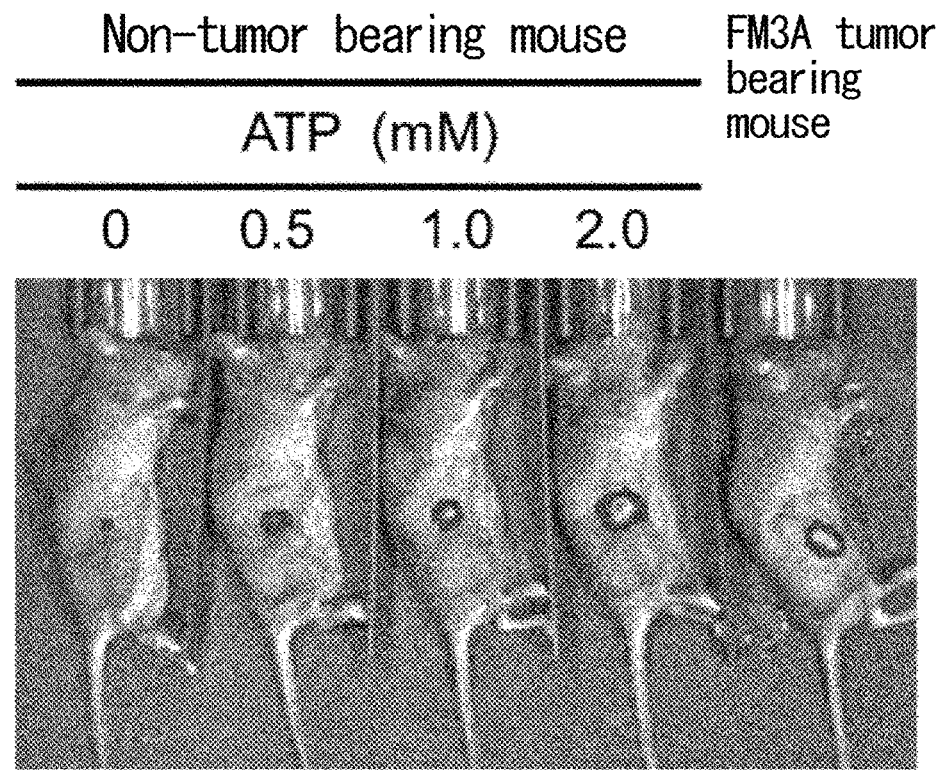

FIG. 61 is a diagram showing the results of luminescence imaging of mice subcutaneously transplanted with P2Y11 split Luc/HEK293 cells and predetermined concentrations of ATP, and of FM3A tumor bearing mouse subcutaneously transplanted with P2Y11 split Luc/HEK293 cells. The marks at the ventral portion of mice indicate the detected luminescence.

Figure 62:
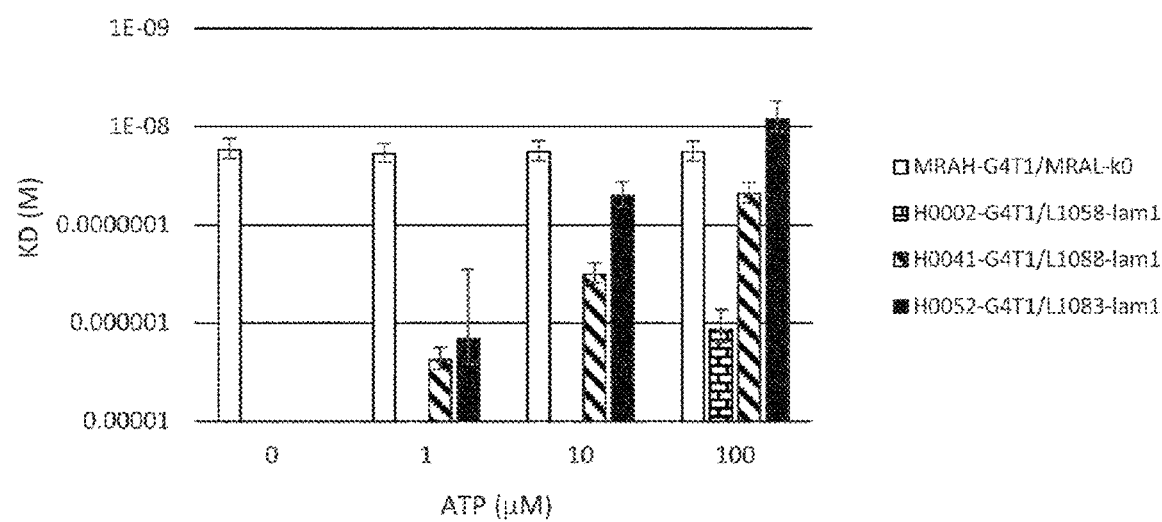

FIG. 62 is a diagram showing the ATP concentration-dependent binding activity (KD value) of anti-hIL6R antibodies MRAH-G4T1/MRAL-k0 (control antibody), and H0002-G4T1/L1058-lam1, H0041-G4T1/L1088-lam1, and H0052-G4T1/L1083-lam1 (all are switch antibodies) against hIL6R.

Figure 63:
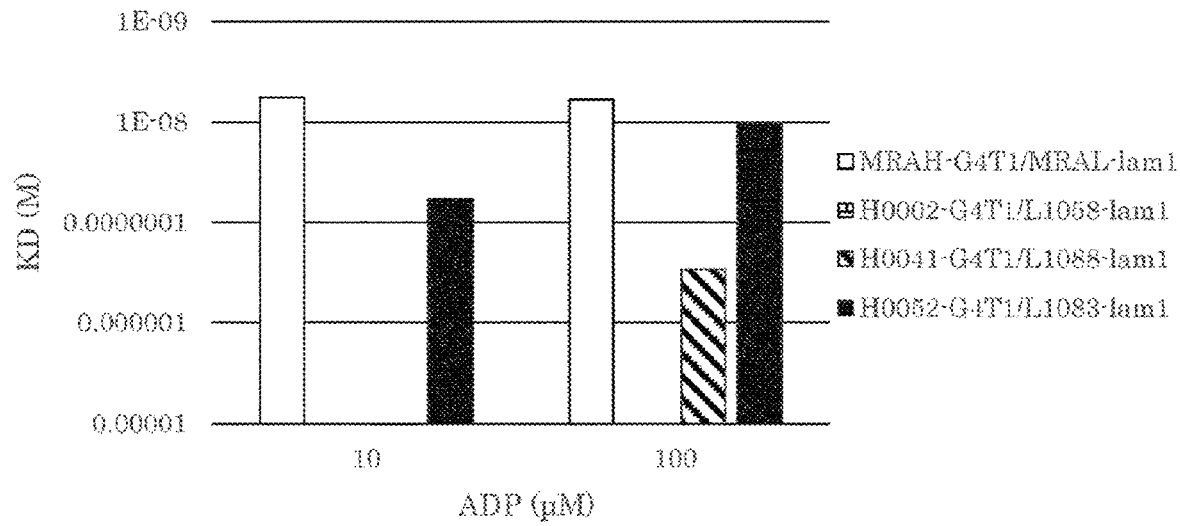

FIG. 63 is a diagram showing the ADP concentration-dependent binding activity (KD value) of anti-hIL6R antibodies MRAH-G4T1/MRAL-k0 (control antibody), and H0002-G4T1/L1058-lam1, H0041-G4T1/L1088-lam1, and H0052-G4T1/L1083-lam1 (all are switch antibodies) against hIL6R.

Figure 64:
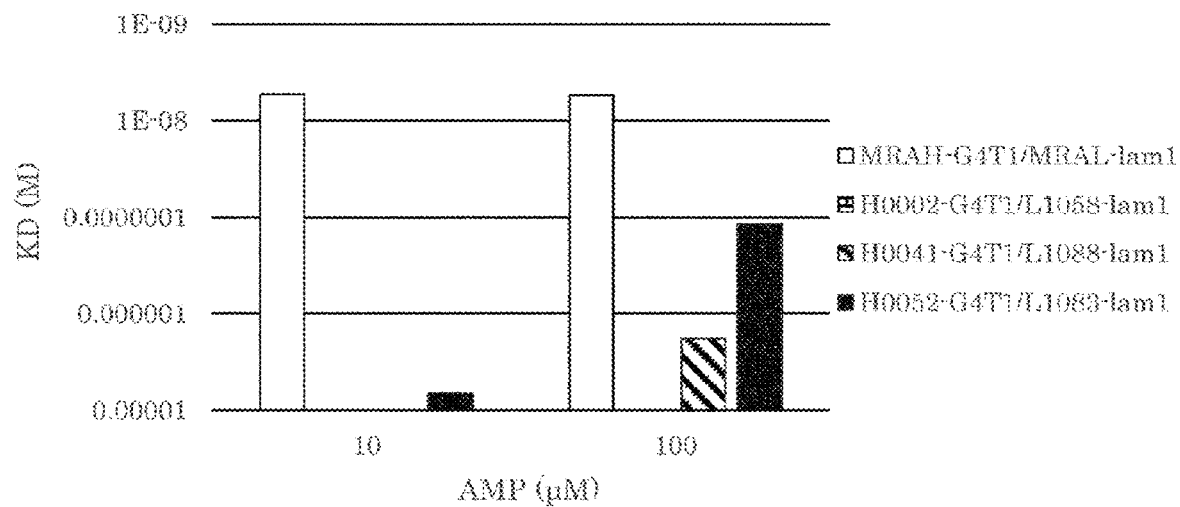

FIG. 64 is a diagram showing the AMP concentration-dependent binding activity (KD value) of anti-hIL6R antibodies MRAH-G4T1/MRAL-k0 (control antibody), and H0002-G4T1/L1058-lam1, H0041-G4T1/L1088-lam1, and H0052-G4T1/L1083-lam1 (all are switch antibodies) against hIL6R.

Figure 65:
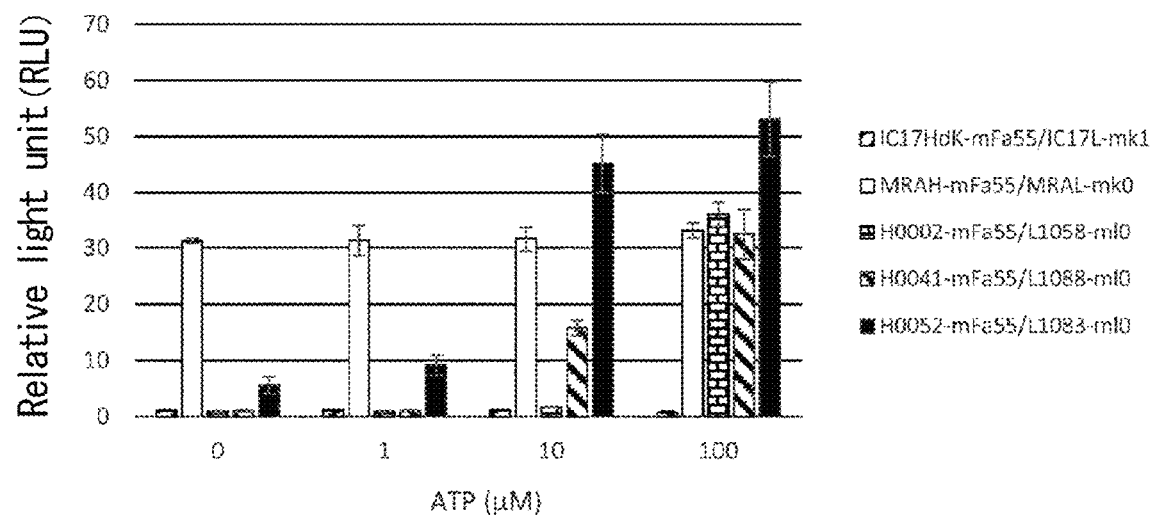

FIG. 65 is a diagram showing the ATP concentration-dependent ADCC activity of anti-hIL6R antibodies MRAH-mFa55/MRAL-mk0 (control antibody), and H0002-mFa55/L1058-ml0, H0041-mFa55/L1088-ml0, and H0052-mFa55/L1083-ml0 (all are switch antibodies).

Figure 66:
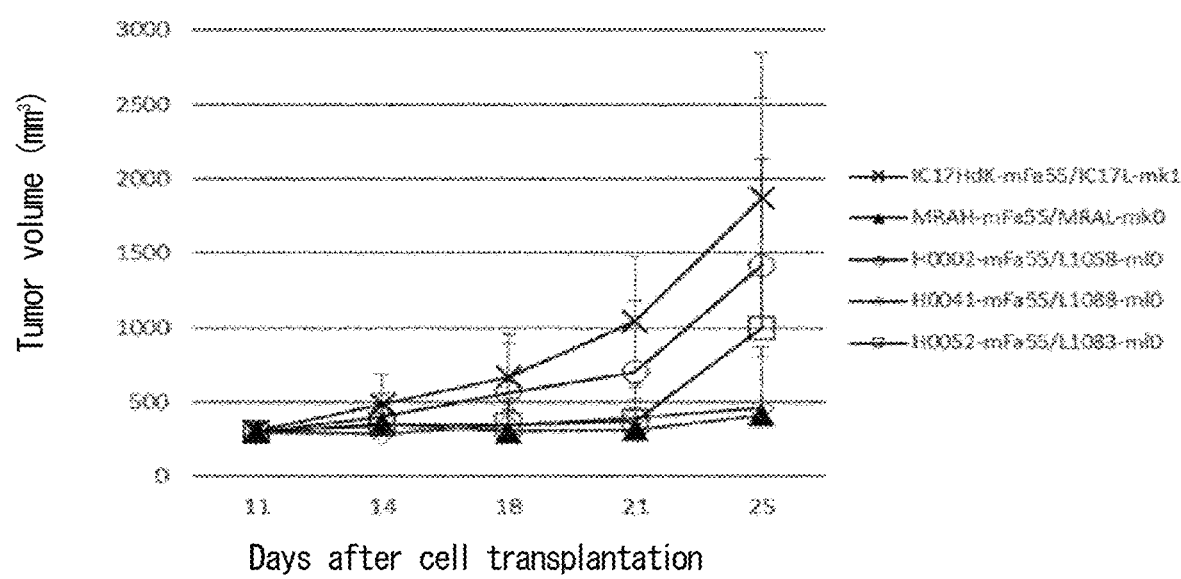

FIG. 66 is a diagram showing the in vivo antitumor activity of anti-hIL6R antibodies MRAH-mFa55/MRAL-mk0 (control antibody), and H0002-mFa55/L1058-ml0, H0041-mFa55/L1088-ml0, and H0052-mFa55/L1083-ml0 (all are switch antibodies). IC17Hdk-mFa55/IC17L-mk1 is the negative control antibody.

Figure 67:
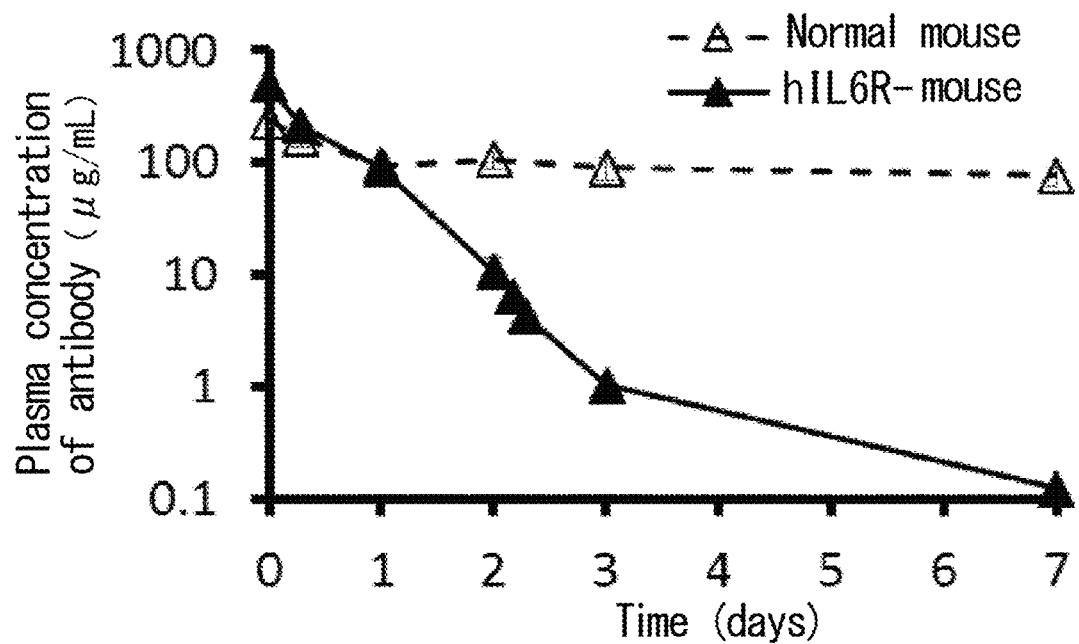

FIG. 67 is a diagram showing the comparison in plasma kinetics of an anti-hIL6R antibody MRAH-mFa55/MRAL-mk0 (control antibody), in normal mice and in hIL6R transgenic mice. The vertical axis of the graph shows the plasma concentration of the antibody.

Figure 68:
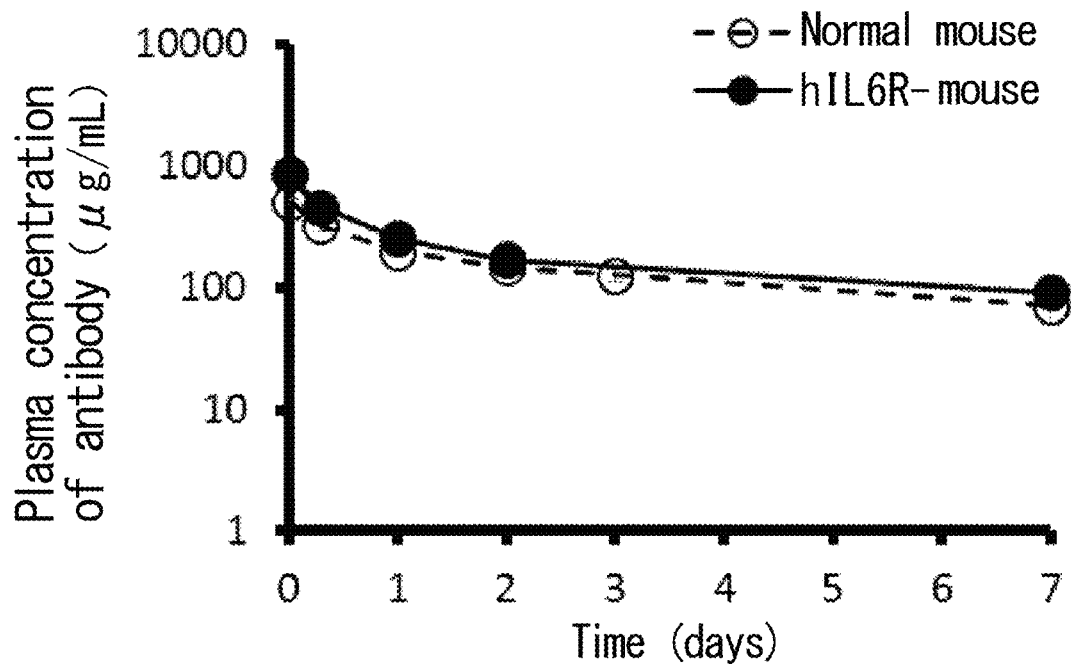

FIG. 68 is a diagram showing the comparison in plasma kinetics of an anti-hIL6R antibody H0002-mFa55/L1058-ml0 (switch antibody), in normal mice and in hIL6R transgenic mice. The vertical axis of the graph shows the plasma concentration of the antibody.

Figure 69:
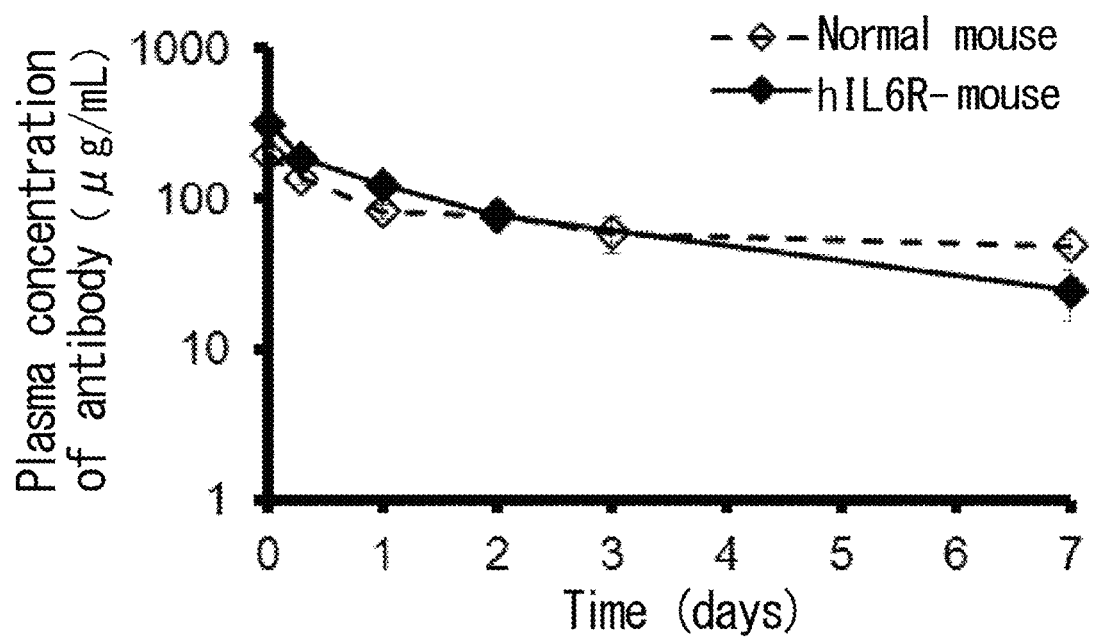

FIG. 69 is a diagram showing the comparison in plasma kinetics of an anti-hIL6R antibody H0041-mFa55/L1088-ml0 (switch antibody), in normal mice and in hIL6R transgenic mice. The vertical axis of the graph shows the plasma concentration of the antibody.

Figure 70:
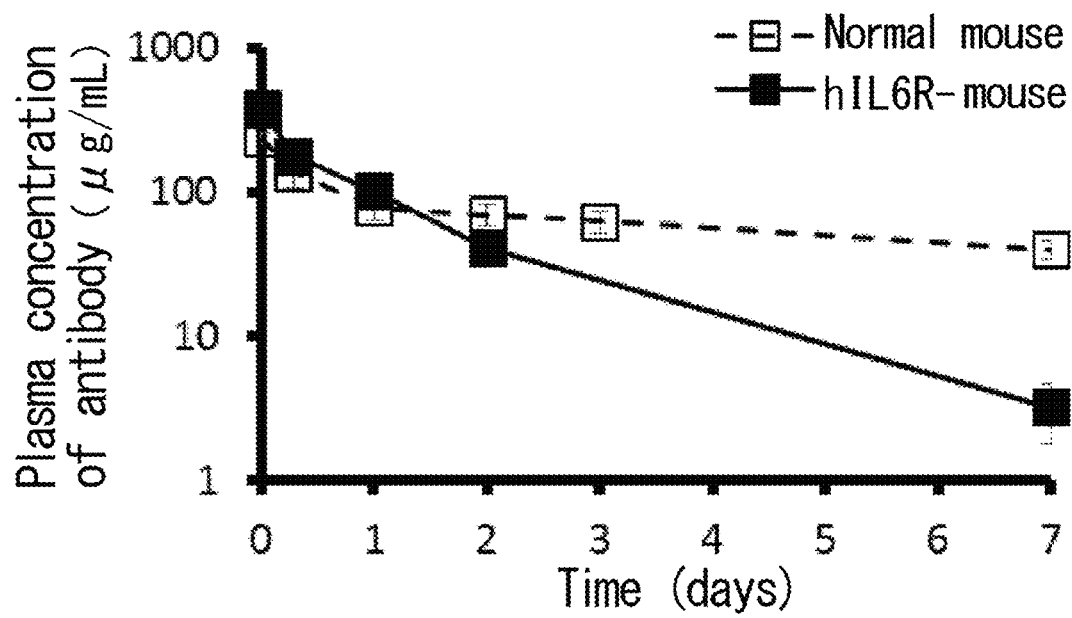

FIG. 70 is a diagram showing the comparison in plasma kinetics of an anti-hIL6R antibody H0052-mFa55/L1083-ml0 (switch antibody), in normal mice and in hIL6R transgenic mice. The vertical axis of the graph shows the plasma concentration of the antibody.

Figure 71:
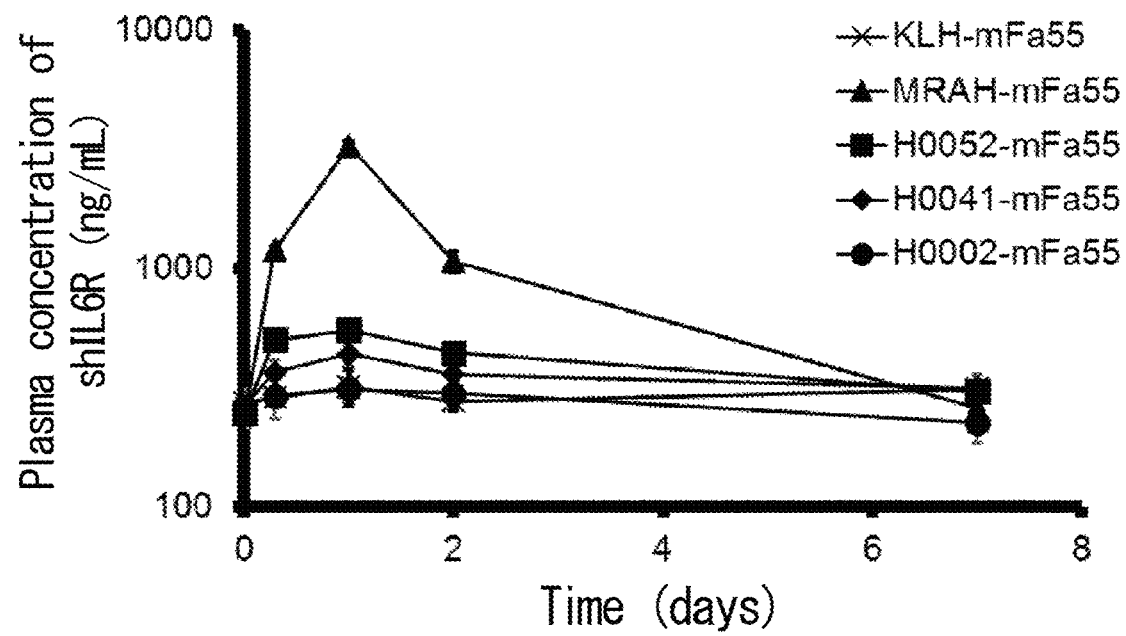

FIG. 71 is a diagram showing the accumulation of antigens in hIL6R transgenic mice after administration of each of an anti-hIL6R non-switch antibody MRAH-mFa55/MRAL-mk0 (control antibody), and anti-hIL6R switch antibodies H0002-mFa55/L1058-ml0, H0041-mFa55/L1088-ml0, and H0052-mFa55/L1083-ml0 (all are switch antibodies). The vertical axis of the graph shows the plasma concentration of soluble hIL6R. IC17Hdk-mFa55/IC17L-mk1 (noted as KLH-mFa55 in the figure) was used as the negative control antibody.

Figure 72:
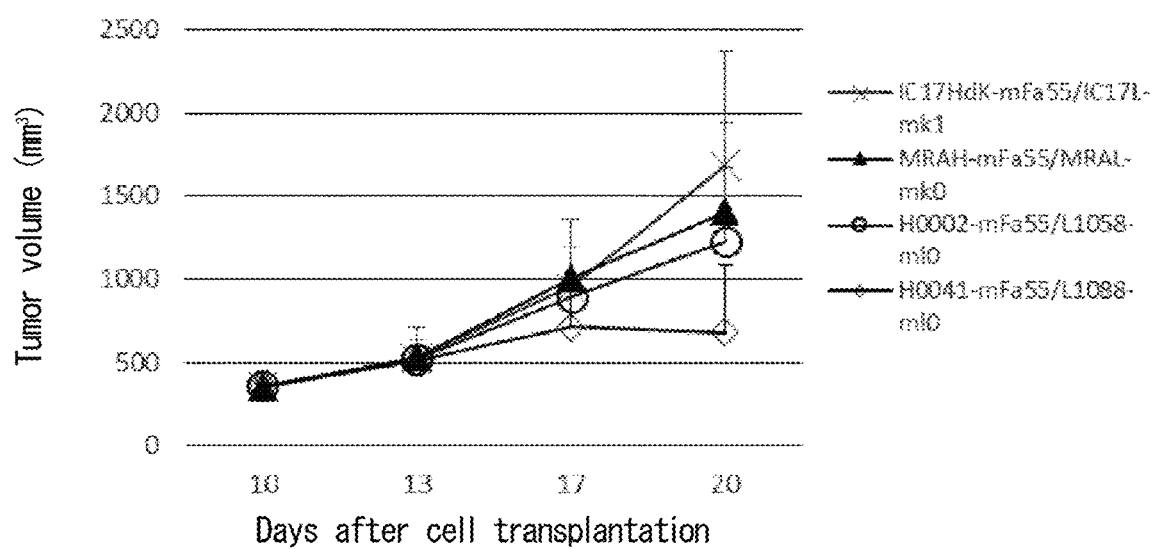

FIG. 72 is a diagram showing the in vivo antitumor activity of an anti-hIL6R non-switch antibody MRAH-mFa55/MRAL-mk0 (control antibody), and anti-hIL6R switch antibodies H0002-mFa55/L1058-ml0 and H0041-mFa55/L1088-ml0 (both are switch antibodies). IC17Hdk-mFa55/IC17L-mk1 is the negative control antibody.

Figure 73:
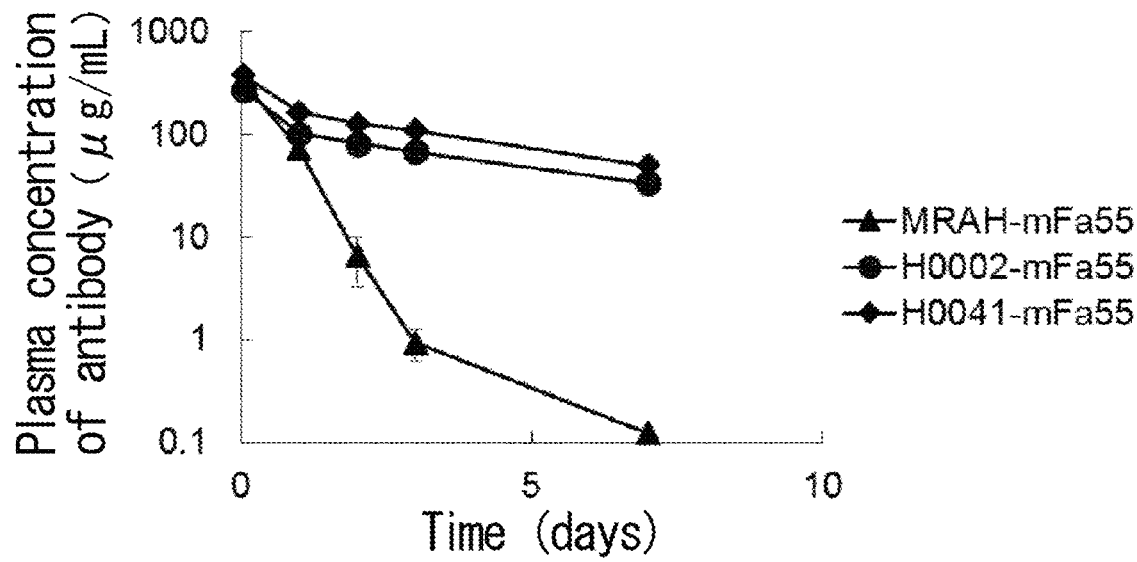

FIG. 73 is a diagram showing the comparison in plasma kinetics of an anti-hIL6R non-switch antibody MRAH-mFa55/MRAL-mk0 (control antibody), and anti-hIL6R switch antibodies H0002-mFa55/L1058-ml0 and H0041-mFa55/L1088-ml0 (both are switch antibodies). The vertical axis of the graph shows the plasma concentration of the antibody.

Figure 74:
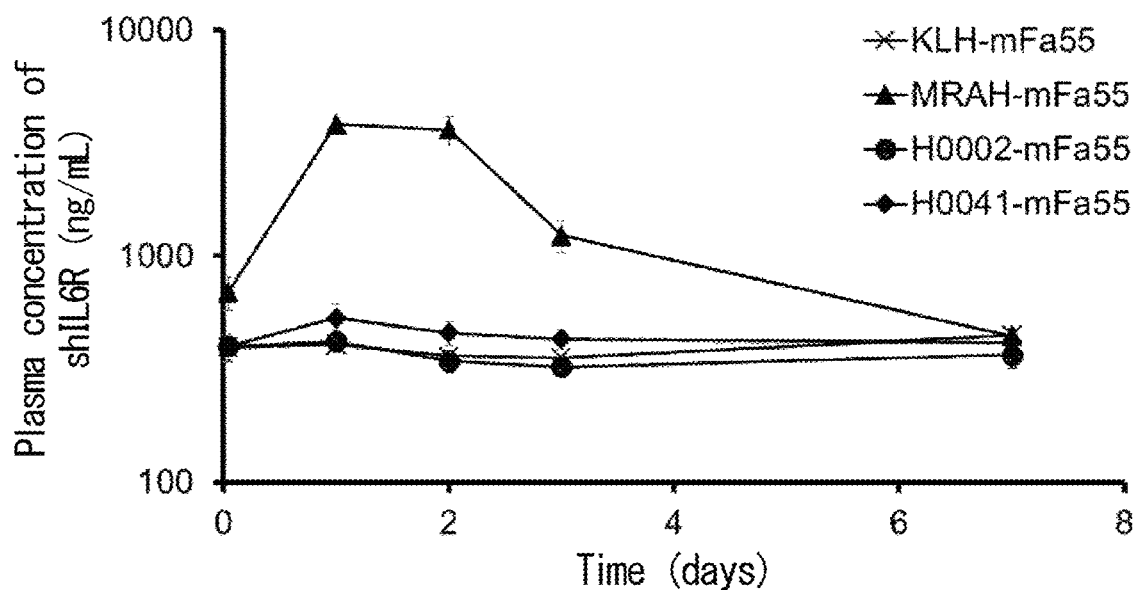

FIG. 74 is a diagram showing the accumulation of antigens after administration of each of an anti-hIL6R non-switch antibody MRAH-mFa55/MRAL-mk0 (control antibody), and anti-hIL6R switch antibodies H0002-mFa55/L1058-ml0 and H0041-mFa55/L1088-ml0 (both are switch antibodies). The vertical axis of the graph shows the plasma concentration of soluble hIL6R. IC17Hdk-mFa55/IC17L-mk1 (noted as KLH-mFa55 in the figure) was used as the negative control antibody.

Figure 75:
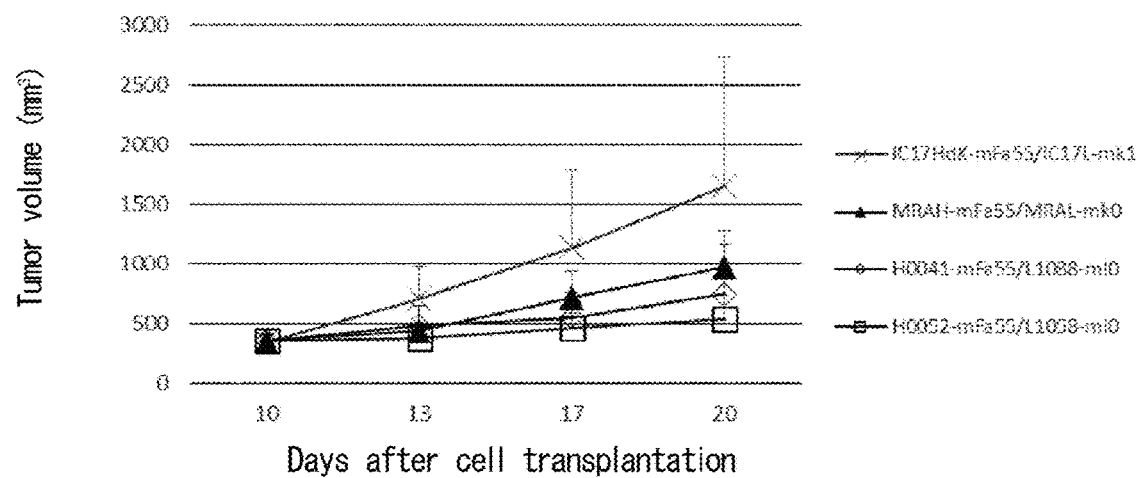

FIG. 75 is a diagram showing the in vivo antitumor activity of an anti-hIL6R non-switch antibody MRAH-mFa55/MRAL-mk0 (control antibody), and anti-hIL6R switch antibodies H0041-mFa55/L1088-ml0 and H0052-mFa55/L1083-ml0 (both are switch antibodies). IC17Hdk-mFa55/IC17L-mk1 is the negative control antibody.

Figure 76:
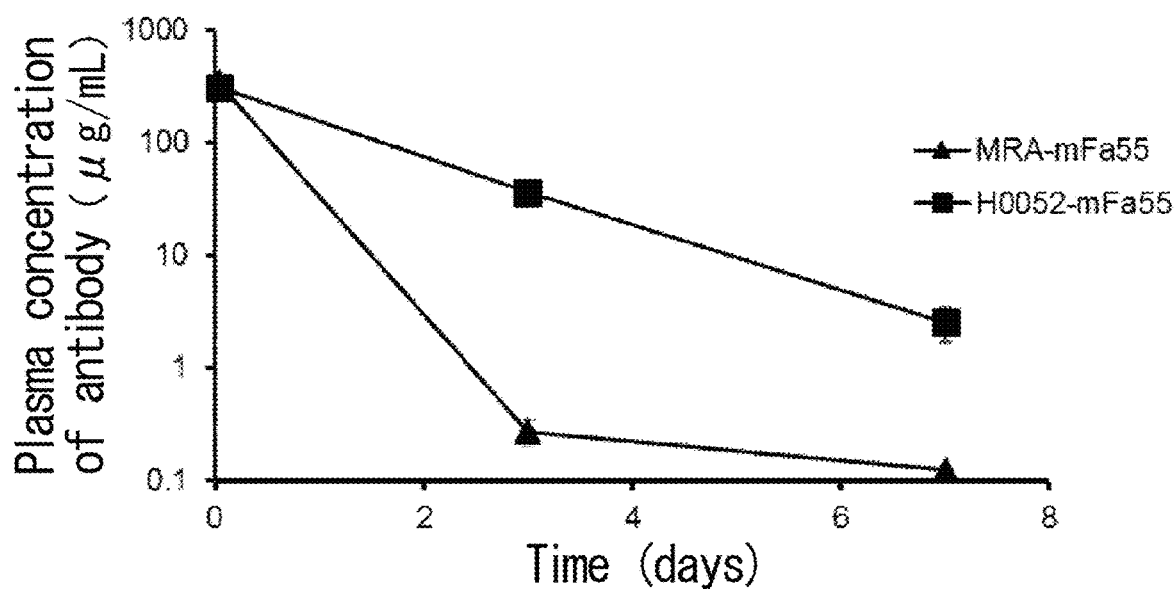

FIG. 76 is a diagram showing the comparison in plasma kinetics of an anti-hIL6R non-switch antibody MRAH-mFa55/MRAL-mk0 (control antibody) and an anti-hIL6R switch antibody H0052-mFa55/L1083-ml0 (switch antibody). The vertical axis of the graph shows the plasma concentration of the antibody.

Figure 77:
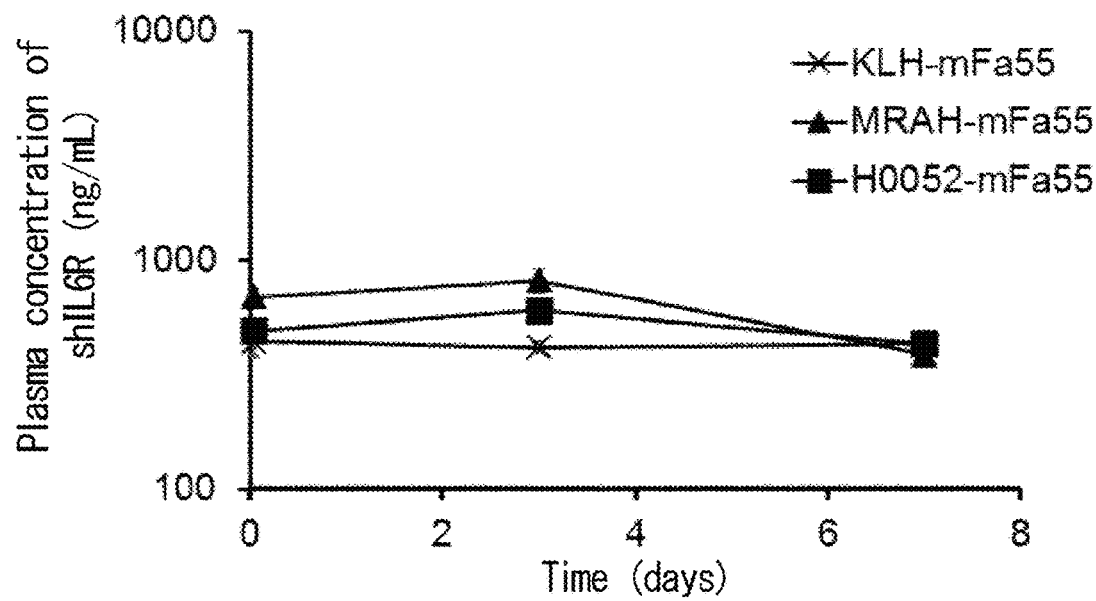

FIG. 77 is a diagram showing the accumulation of antigens after administration of each of an anti-hIL6R non-switch antibody MRAH-mFa55/MRAL-mk0 (control antibody) and an anti-hIL6R switch antibody H0052-mFa55/L1083-ml0 (switch antibody). The vertical axis of the graph shows the plasma concentration of soluble hIL6R. IC17Hdk-mFa55/IC17L-mk1 (noted as KLH-mFa55 in the figure) was used as the negative control antibody.

Figure 78:
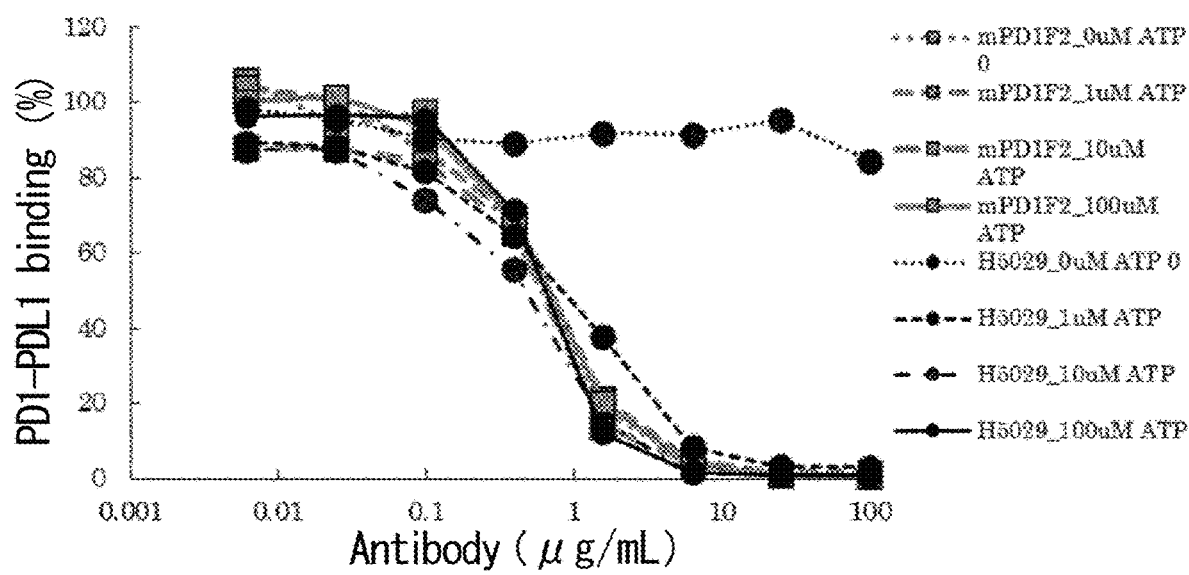

FIG. 78 is a diagram showing the ATP concentration-dependent activity of anti-PD1 antibodies mPD1F2VH-mF18/mPD1F2VL-mk1 (control antibody) and H5029-mFa31/L3021-ml0 (switch antibody) in inhibiting PD-1/PDL-1 binding.

Figure 79:
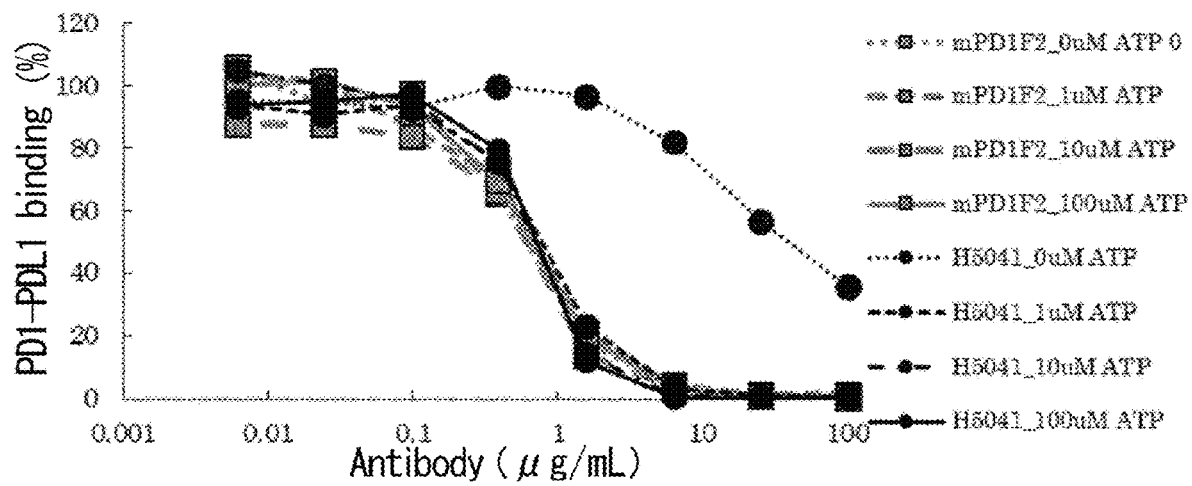

FIG. 79 is a diagram showing the ATP concentration-dependent activity of anti-PD1 antibodies mPD1F2VH-mF18/mPD1F2VL-mk1 (control antibody) and H5041-mFa31/L3021-ml0 (switch antibody) in inhibiting PD-1/PDL-1 binding.

Figure 80:
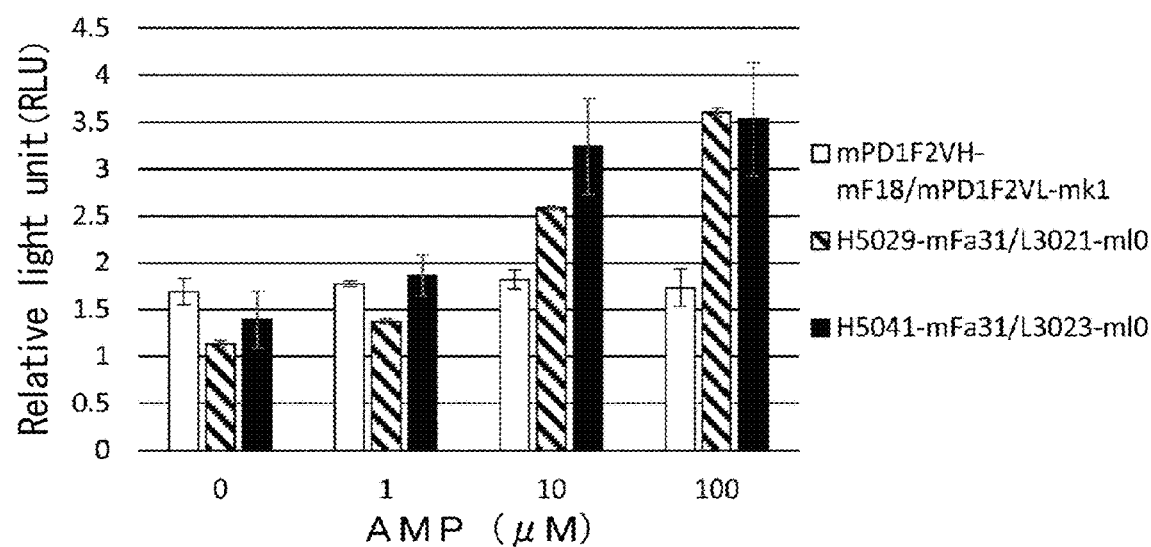

FIG. 80 is a diagram showing the AMP concentration-dependent in vitro neutralizing activity of anti-PD1 antibodies mPD1F2VH-mF18/mPD1F2VL-mk1 (control antibody), and H5029-mFa31/L3021-ml0 and H5041-mFa31/L3021-ml0 (both are switch antibodies).

Figure 81:
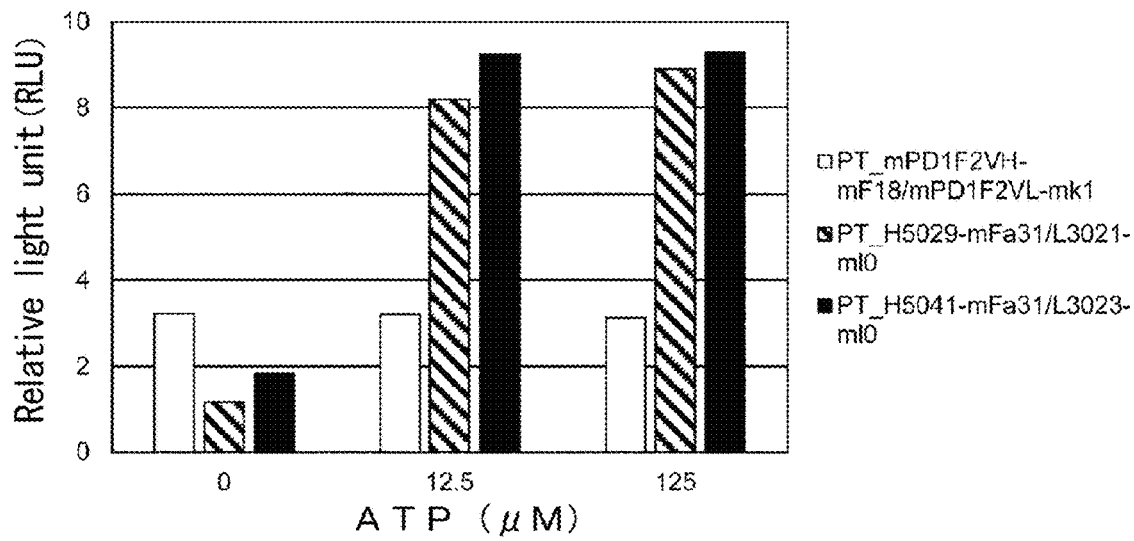

FIG. 81 is a diagram showing the ATP concentration-dependent in vitro neutralizing activity of anti-PD1 antibodies mPD1F2VH-mF18/mPD1F2VL-mk1 (control antibody), and H5029-mFa31/L3021-ml0 and H5041-mFa31/L3021-ml0 (both are switch antibodies).

Figure 82:
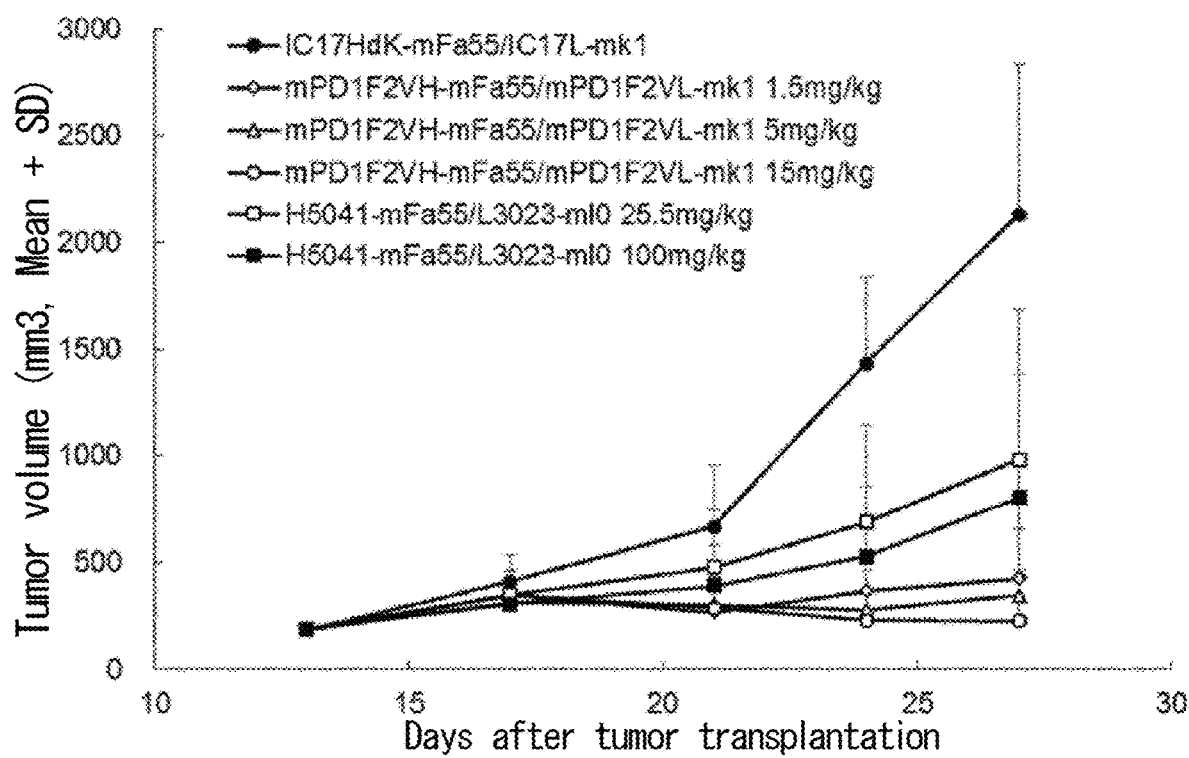

FIG. 82 is a diagram showing the in vivo antitumor activity of anti-PD1 antibodies mPD1F2VH-mFa55/mPD1F2VL-mk1 (control antibody) and H5041-mFa55/L3023-ml0 (switch antibody). IC17Hdk-mFa55/IC17L-mk1 is the negative control antibody.

Figure 83:
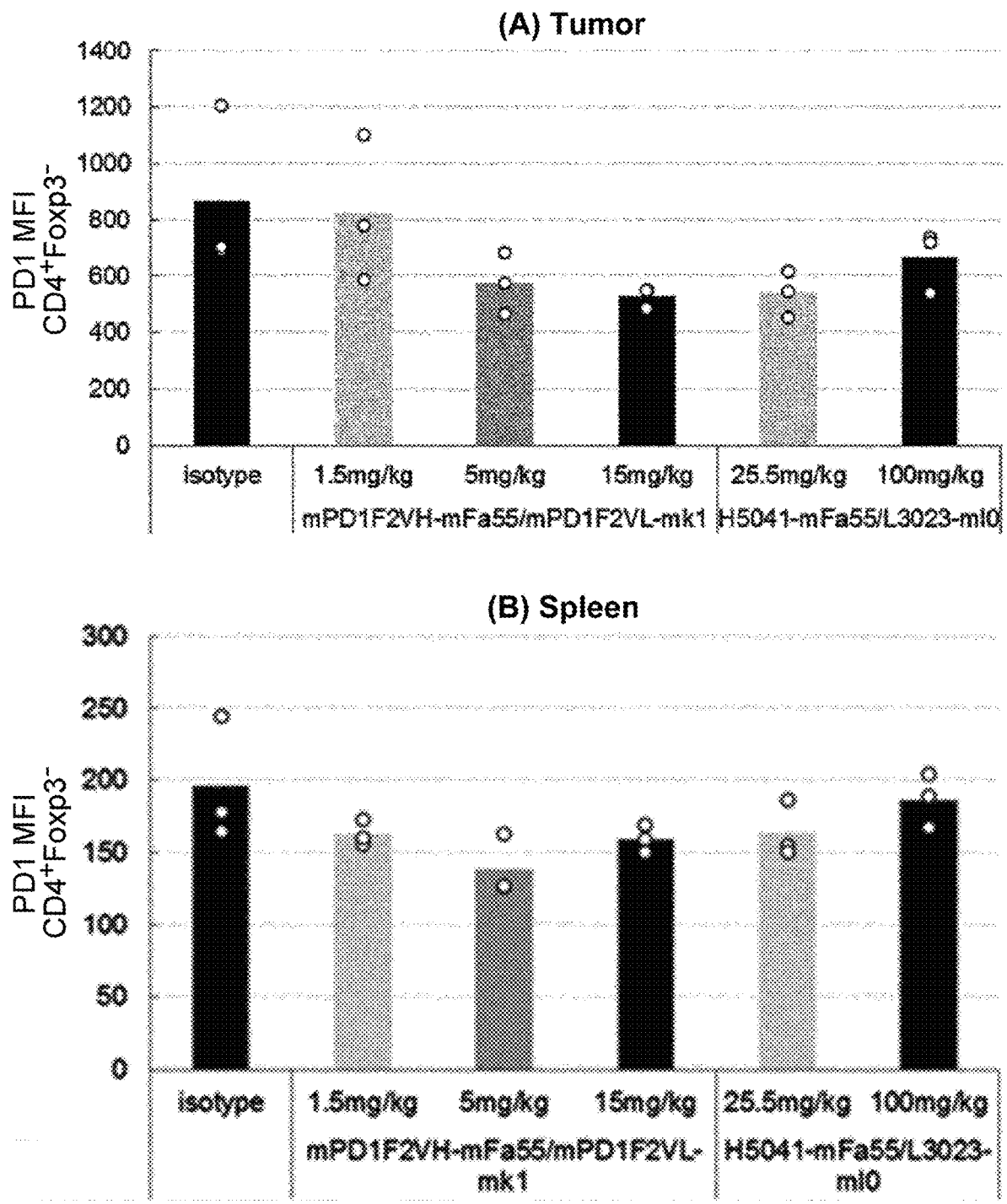

FIG. 83 is a diagram showing the activity of anti-PD1 antibodies mPD1F2VH-mFa55/mPD1F2VL-mk1 (control antibody) and H5041-mFa55/L3023-ml0 (switch antibody)

in eliminating PD-1 expressing cells from (A) the tumor and (B) the spleen. In the figure, "isotype" represents the negative control antibody (IC17Hdk-mFa55/IC17L-mk1).

Figure 84:
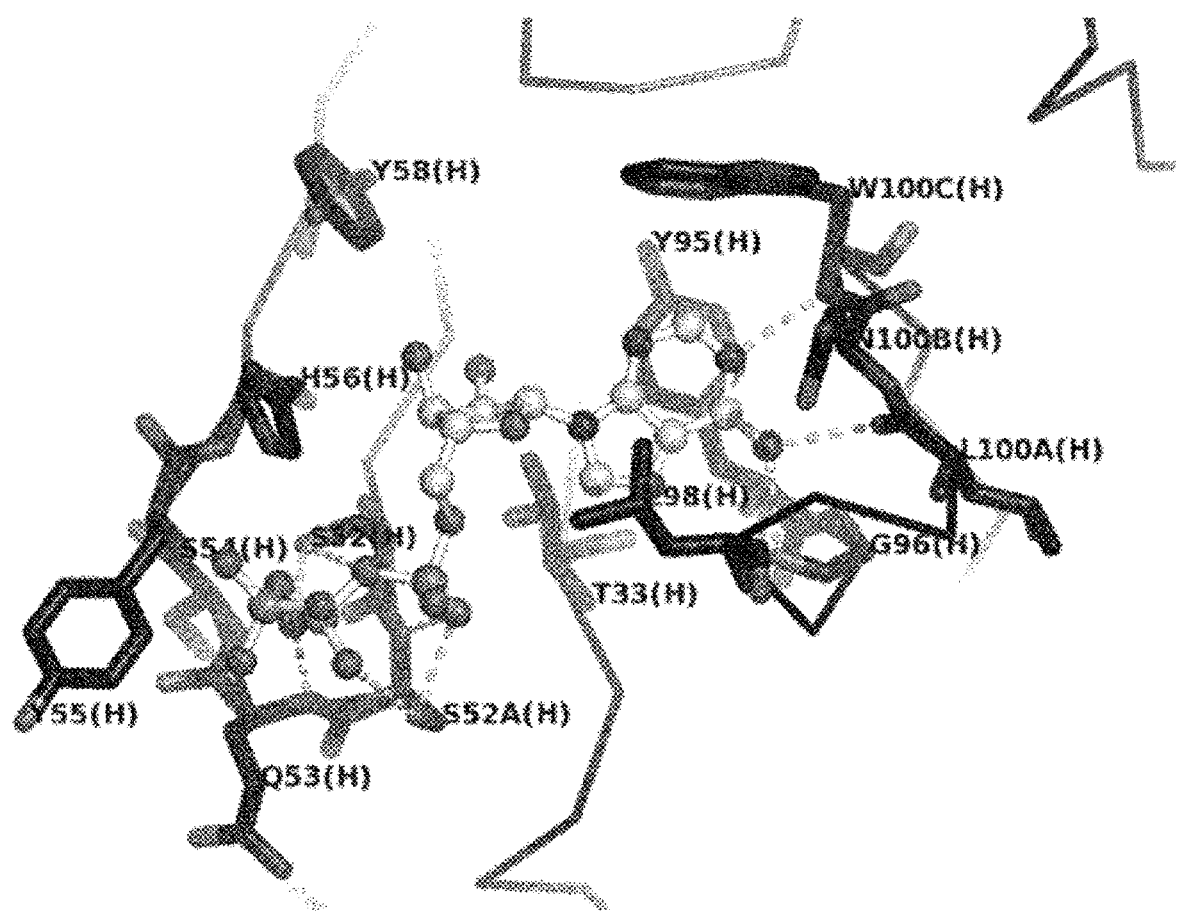

FIG. 84 is a diagram showing the mode of binding between ATP and the anti-hIL6R switch antibody H0041L1088 Fab fragment. In the figure, ATP is shown with the ball-and-stick model and the amino acid residues interacting with ATP are shown with the stick model. The broken lines indicate the hydrogen bonds between the antibody and ATP.

FIG. 85 is a diagram showing the amino acid sequence of the hIL6R extracellular domain (shIL6R) mapped with the epitope of the anti-hIL6R switch antibody H0041L1088. In the figure, the amino acid residues shaded with gray are those (epitope residues) of shIL6R comprising one or more non-hydrogen atoms positioned at a distance of 4.2 Angstrom or less from the ATP or the H0041L1088 Fab in a crystal structure.

Figure 86:
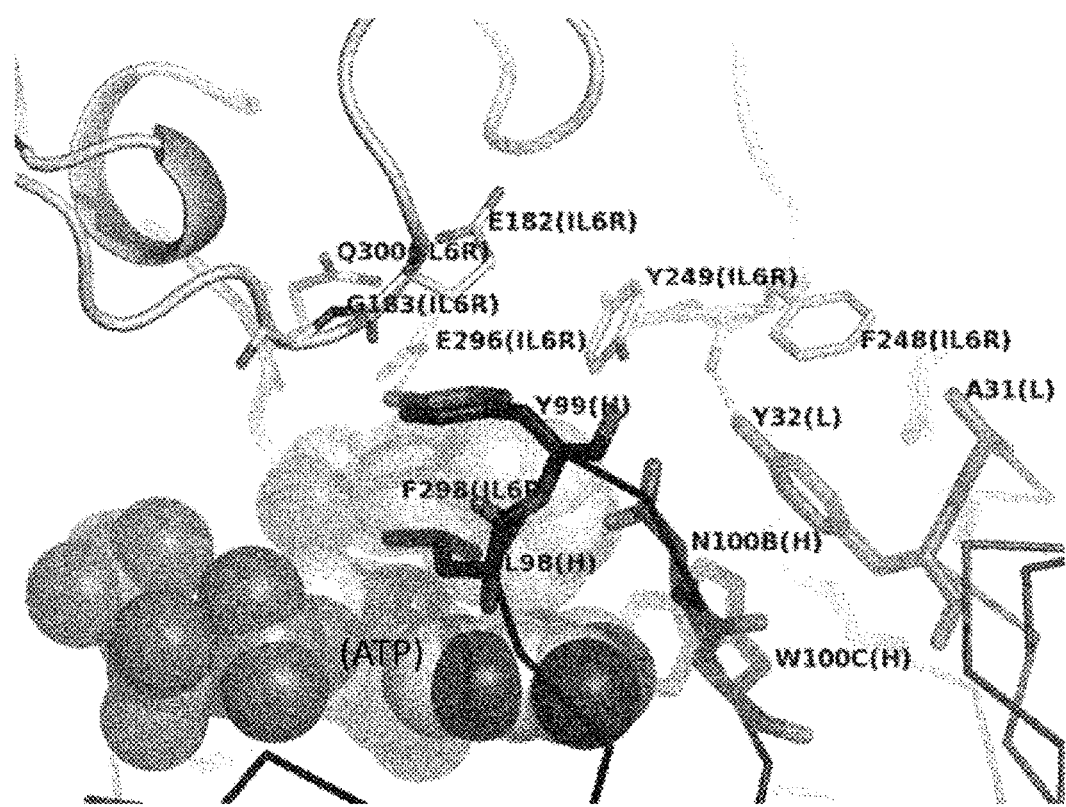

FIG. 86 is a diagram showing the binding details between shIL6R and the ATP-bound H0041L1088 Fab fragment. In the figure, the heavy chain of the antibody is depicted with black, the light chain is depicted with gray, and shIL6R is depicted with white. In the figure, ATP is shown with the ball model, and the epitope residue of shIL6R within 4.2 Angstrom from the antibody or ATP and the paratope residue of the antibody within 4.2 Angstrom from the epitope residue are shown with the stick model. The broken lines indicate the hydrogen bonds between the antibody and shIL6R. To clarify the interaction with ATP, only the F298 of shIL6R is shown with the ball model.

Figure 87:

FIG. 87 is a diagram showing a structure where the structure of FIG. 86 is rotated 180 degrees (viewed from the back).

Figure 88:
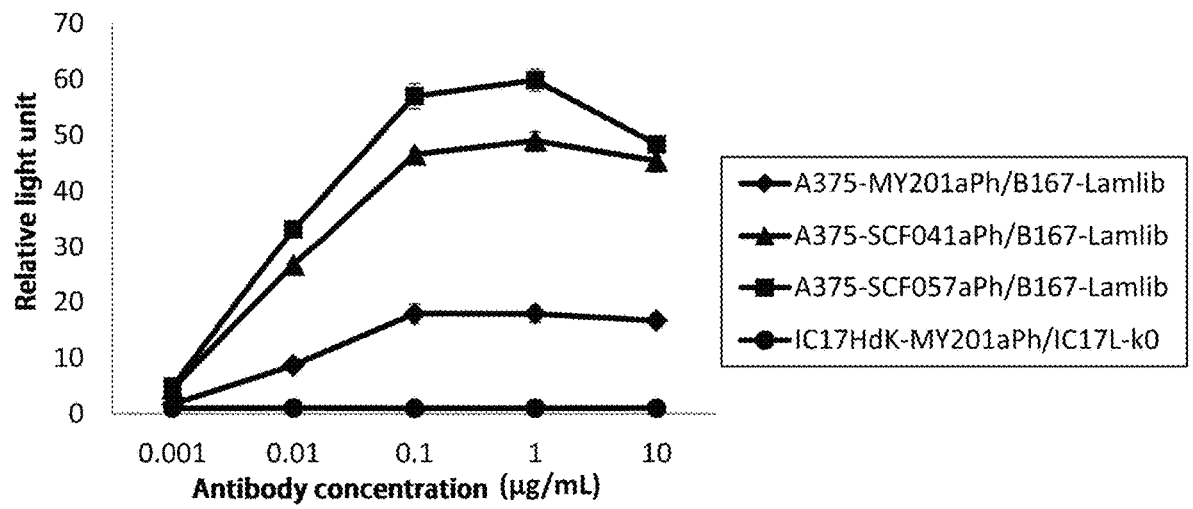

FIG. 88 is a diagram showing the agonist activity of various switch anti-CD137 antibodies tested using 4-1BB Jurkat reporter gene assay in the presence of ATP.

Figure 89:
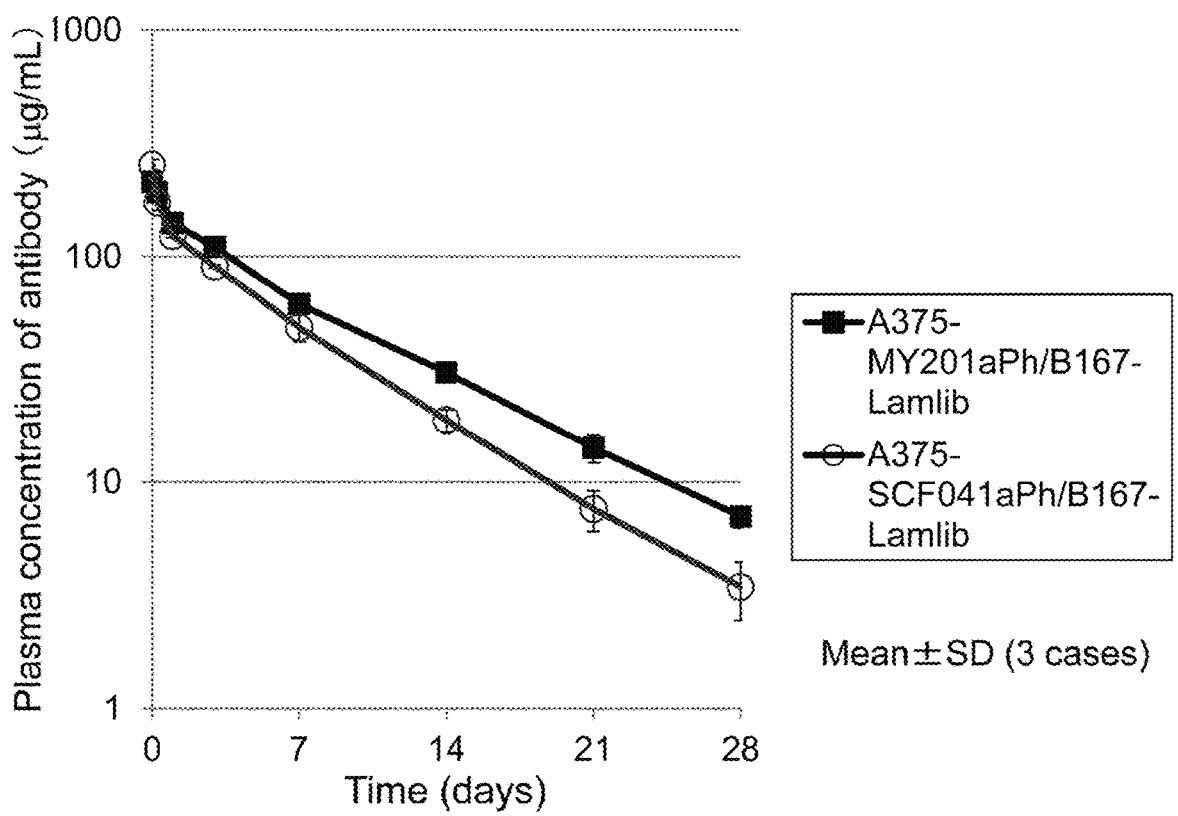

FIG. 89 is a diagram showing the comparison in plasma kinetics of each of the anti-CD137 switch antibodies A375-SCF041aPh/B167-Lamlib and A375-MY201aPh/B167-Lamlib. The vertical axis of the graph shows the plasma concentration of each antibody.

Figure 90:
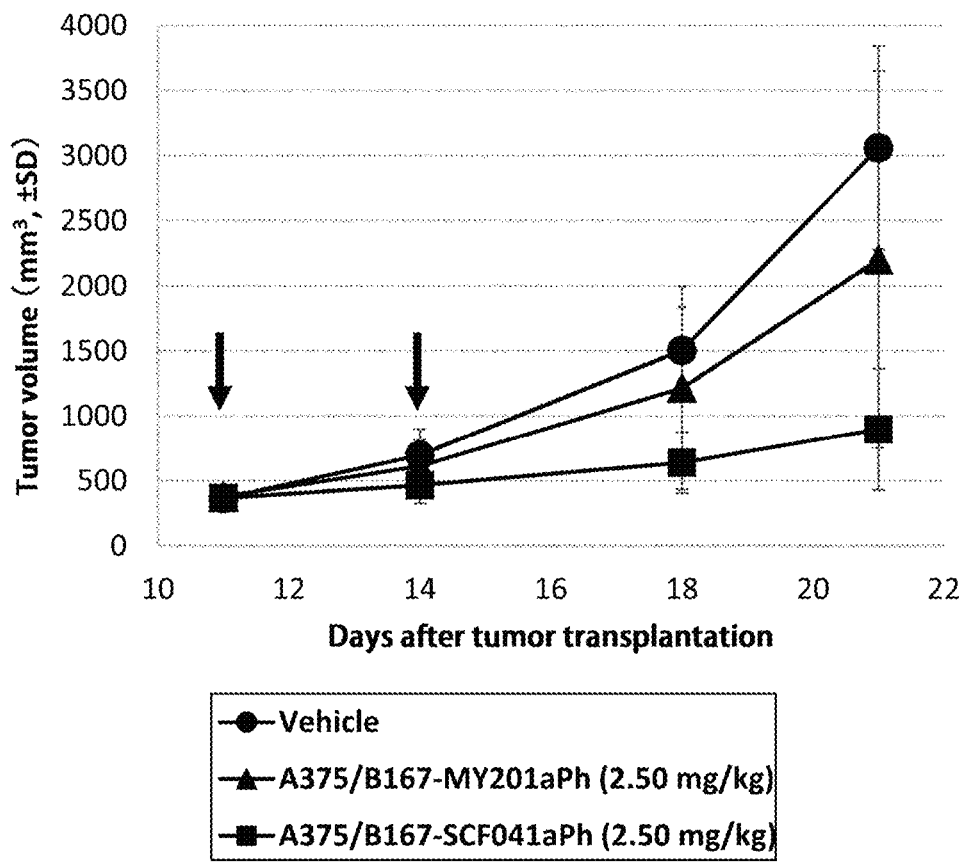

FIG. 90 is a diagram showing the anti-tumor effect of each of A375/B167-SCF041aPh and A375/B167-MY201aPh in a mouse model prepared by transplanting the LLC1/OVA/GPC3 cell line into hCD137KI/mFcγR2bKO/hFcγR2bTg#90 mice.

Each dot shows the mean value of a group (n=5) of tumor volumes.

Figure 91:
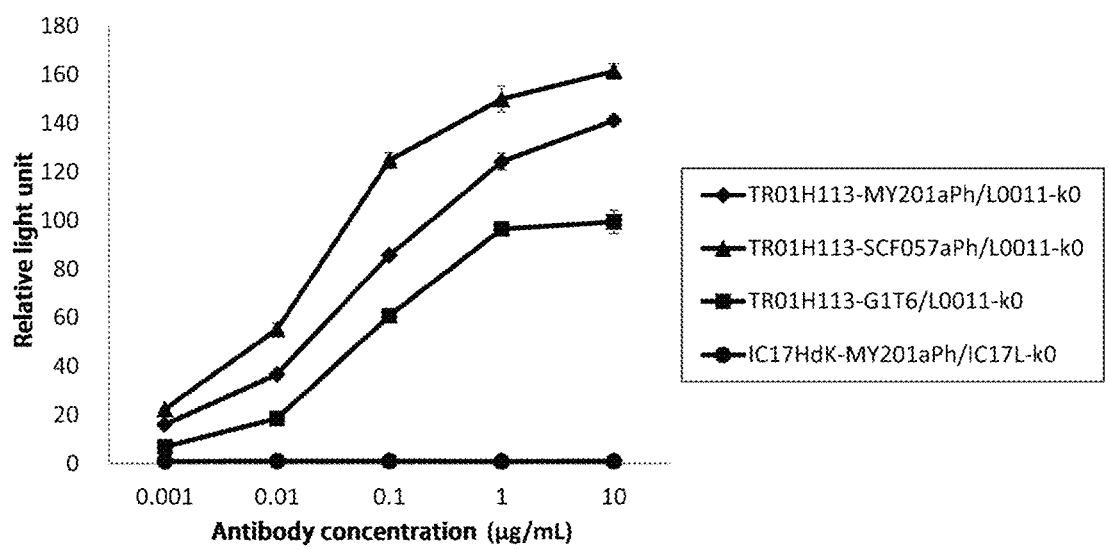

FIG. 91 is a diagram showing the agonist activity of various switch anti-CD3 antibodies tested by a reporter gene assay using T cell activation Bioassay (NFAT) in the presence of ATP.

MODE FOR CARRYING OUT THE INVENTION

I. Definitions

The term "binding activity" refers to the strength of the sum total of noncovalent interactions between one or more binding sites of a molecule (e.g., an antibody) and its binding partner (e.g., an antigen). Herein, "binding activity" is not strictly limited to a 1:1 interaction between members of a binding pair (e.g., antibody and antigen). For example, when the members of a binding pair reflect a monovalent 1:1 interaction, the binding activity is particularly called the intrinsic binding affinity (affinity). When a member of a binding pair is capable of both monovalent binding and multivalent binding, the binding activity is the sum of each binding strength. The binding activity of a molecule X for its partner Y can generally be represented by the dissociation constant (KD) or "binding amount of analyte per unit amount of ligand" (hereinbelow, may be referred to as "binding amount"). Those skilled in the art would understand that, generally, lower value of dissociation constant (KD) means higher binding activity, and higher value of "binding amount of analyte per unit amount of ligand" or "binding amount" means higher binding activity. Binding activity can be measured by common methods known in the art, including those described herein. Specific illustrative and exemplary embodiments for measuring binding activity are described in the following.

A "binding activity-matured" antigen-binding molecule or antibody, or "binding activity-increased (enhanced)" antigen-binding molecule or antibody refers to an antibody with one or more alterations in one or more hypervariable regions (HVRs), compared to a parent antigen-binding molecule or a parent antibody which does not carry such alterations, such alterations resulting in an improvement in the binding activity of the antigen-binding molecule or antibody for antigen.

The terms "anti-CD137 antigen-binding molecule" or "anti-CD137 antibody" and "an antigen-binding molecule that binds to CD137" or "an antibody that binds to CD137" refer to an antigen-binding molecule or antibody that is capable of binding to CD137 with sufficient binding activity such that the antigen-binding molecule or antibody is useful as a diagnostic and/or therapeutic agent in targeting CD137. In certain embodiments, an anti-CD137 antibody binds to an epitope of CD137 that is conserved among CD137 from different species.

The term an anti-CD137 antigen-binding molecule or an anti-CD137 antibody "having CD137 binding activity dependent on a small molecule compound" means an antigen-binding molecule or an antibody that shows higher binding activity to CD137 in the presence of the small molecule compound as compared to binding activity to CD137 in the absence of the small molecule compound. In one embodiment, "the presence of a small molecule compound" refers to the condition where the small molecule compound is present at a concentration of 10 micromolar or more, 50 micromolar or more, 100 micromolar or more, 150 micromolar or more, 200 micromolar or more, or 250 micromolar or more. In one embodiment, the extent of binding activity of an anti-CD137 antigen-binding molecule or antibody to an unrelated, non-CD137 protein in the presence of a small molecule compound is less than about 10% of the binding of the antigen-binding molecule or antibody to CD137 as measured, e.g., by a radioimmunoassay (RIA) or by surface plasmon resonance (SPR). In certain embodiments, in the presence of a low-molecular weight compound, an anti-CD137 antigen-binding molecule or antibody has a dissociation constant (KD) of 1 micromolar or less, 100 nM or less, 10 nM or less, 1 nM or less, 0.1 nM or less, 0.01 nM or less, or 0.001 nM or less (e.g., $10^{-6}$M or less, $10^{-7}$M or less, $10^{-8}$M or less, $10^{-9}$M or less, $10^{-10}$M or less, e.g., from $10^{-6}$M to $10^{-10}$M, from $10^{-7}$M to $10^{-9}$M, e.g., from $10^{-7}$M to $10^{-8}$ M).

Herein, the term "antigen-binding molecule" is used in its broadest sense, and refers to a molecule that specifically binds to an antigenic determinant. In one embodiment, the antigen-binding molecule is an antibody, antibody fragment, or antibody derivative.

An "agonistic antigen-binding molecule" or "agonistic antibody", as used herein, is an antigen-binding molecule or antibody which significantly induces or potentiates a biological activity of the antigen to which it binds (e.g., CD137 and CD3).

Therefore, if the antigen is, for example, CD137, such antigen-binding molecule or antibody having agonistic action is called "CD137 agonistic antigen-binding molecule" or "CD137 agonistic antibody", respectively. In the same manner, if the antigen is, for example, CD3, such antigen-binding molecule or antibody having agonistic action is called "CD3 agonistic antigen-binding molecule" or "CD3 agonistic antibody", respectively.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antigen-binding molecule that binds to the same epitope" or "antibody that binds to the same epitope" as a reference antigen-binding molecule or reference antibody refers to an antibody or antigen-binding molecule that blocks binding of the reference antibody or reference antigen-binding molecule to its antigen in a competition assay by 50% or more, and conversely, the reference antibody blocks binding of the antibody to its antigen in a competition assay by 50% or more. An exemplary competition assay is provided herein. In one embodiment, in the case that the reference antigen-binding molecule or reference antibody shows antigen binding activity in a manner dependent on a low-molecular weight compound, the competitive assay is carried out in the presence of the low-molecular weight compound.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called alpha, delta, epsilon, gamma, and mu, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Cytotoxicity" refers to activity that inhibits or prevents cellular function, and/or causes cell death or destruction. Cytotoxicity may be, for example, antibody-dependent cell-mediated cytotoxicity (ADCC) activity, complement-dependent cytotoxicity (CDC) activity, and cytotoxicity by T cells; and may be cytotoxicity caused by cytotoxic agents (for example, radioisotopes and chemotherapeutic agents) such as immunoconjugates.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) or glycine-lysine (residues 446-447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The term "variant Fc region" herein comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Herein, amino acid alterations or substitutions within an Fc region or a constant region may be represented by the combination of the EU numbering system and amino acids.

For example, 5424N stands for substitution at position 424 in EU numbering from serine (Ser) to asparagine (Asn). EU424N stands for substitution at position 424 in EU numbering from an amino acid (any type) to asparagine (Asn).

The term "Fc region-comprising antibody" herein refers to an antibody that comprises an Fc region. The C-terminal lysine (residue 447 according to the EU numbering system) or C-terminal glycine-lysine (residues 446-447) of the Fc region may be removed, for example, during purification of the antibody or by recombinant engineering of the nucleic acid encoding the antibody. Accordingly, a composition comprising an antibody having an Fc region according to the present disclosure can comprise an antibody with G446-K447, with G446 and without K447, with all G446-K447 removed, or a mixture of three types of antibodies described above.

The terms "full length antibody," "intact antibody," and "whole antibody" are used herein interchangeably to refer to an antibody having a structure substantially similar to a native antibody structure or having heavy chains that contain an Fc region or a variant Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra. Herein, HVR residues or other residues within a variable domain (e.g., FR residues) and amino acid alterations or substitutions at such residues may be represented by the combination of the Kabat numbering system and amino acids. For example, N99 stands for asparagine (Asn) at position 99 in Kabat numbering, and N99A stands for substitution at position 99 in Kabat numbering from asparagine (Asn) to alanine (Ala).

An "immunoconjugate" is an antibody conjugated to one or more heterologous molecule(s), including but not limited to a cytotoxic agent.

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu); chemotherapeutic agents or drugs (e.g., methotrexate, adriamycin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Encoded nucleic acid coding for anti-CD137 antigen-binding molecule" refers to one or more nucleic acid molecules that code for polypeptide(s) constituting the antigen-binding molecule. "Isolated nucleic acid encoding an anti-CD137 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

The term "monoclonal antibody" as used herein refers to an antibody obtained from a population of substantially homogeneous antibodies, i.e., the individual antibodies composing the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR) software, or GENETYX (registered trademark) (Genetyx Co., Ltd.). Those skilled in the art can determine appropriate parameters for aligning sequences, including any algorithms needed to achieve maximal alignment over the full length of the sequences being compared.

The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

An "effective amount" of an agent, e.g., a pharmaceutical formulation, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The term "CD137," as used herein, refers to any native CD137 from any vertebrate source, including mammals such as primates (e.g. humans) and rodents (e.g., mice and rats), unless otherwise indicated. The term encompasses "full-length" unprocessed CD137 as well as any form of CD137 that results from processing in the cell. The term also encompasses naturally occurring variants of CD137, e.g., splice variants or allelic variants.

An amino acid sequence of an exemplary human full-length CD137 is shown in SEQ ID NO: 1 (*NCBI Reference Sequence*: NP_001552.2) and an amino acid sequence of an exemplary human CD137 extracellular region is shown in SEQ ID NO: 2. An amino acid sequence of an exemplary mouse full-length CD137 is shown in SEQ ID NO: 3 (NCBI Reference Sequence: NP_035742.1) and an amino acid sequence of an exemplary mouse CD137 extracellular region is shown in SEQ ID NO: 4. An amino acid sequence of an exemplary monkey full-length CD137 is shown in SEQ ID NO: 5 (NCBI Reference Sequence: ABY47575.1) and an amino acid sequence of an exemplary monkey CD137 extracellular region is shown in SEQ ID NO: 6.

CD137 is a member of tumor necrosis factor (TNF) receptor family. Its alternative names are tumor necrosis factor receptor superfamily member 9 (TNFRSF9), 4-1BB, and ILA. In addition to its expression on activated CD4+ and CD8+ T cells, CD137 is expressed in B cells, dendritic cells, natural killer (NK) and NK-T cells, macrophages, monocytes, neutrophils, CD4+CD25+ regulatory T cells, and vascular endothelial cells. Expression in cancer cells is also reported (Labiano, et al. Oncoimmunology, vol. 24: e1062967 (2015)). The natural CD137 ligand, CD137L, is presented by antigen-presenting cells such as B cells, monocytes/macrophages, and dendritic cells (Watts, et al., Annu. Rev. Immunol., vol. 23: p. 23-68 (2005)). Through its interaction with the ligand, CD137 causes increase of TCR-induced T cell proliferation, cytokine production, functional maturation, suppression of apoptosis, and long-term survival of CD8+ T cells (Nam, et al., Curr. Cancer Drug Targets, vol. 5: p. 357-363 (2005); Watts, et al., Annu. Rev. Immunol., vol. 23: p. 23-68 (2005)).

The terms "carcinoma", "cancer" and "cancerous" refer to or describe the physiological condition in mammals that is typically characterized by unregulated cell growth/proliferation.

The term "tumor" refers to all neoplastic cell growth and proliferation, whether malignant or benign, and all pre-cancerous and cancerous cells and tissues. The terms "carcinoma", "cancer," "cancerous," "cell proliferative disorder," "proliferative disorder" and "tumor" are not mutually exclusive as referred to herein.

The terms "cell proliferative disorder" and "proliferative disorder" refer to disorders that are associated with some degree of abnormal cell proliferation. In one embodiment, the cell proliferative disorder is cancer.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the present disclosure are used to delay development of a disease or to slow the progression of a disease.

II. Compositions and Methods (Anti-CD137 Agonistic Antigen-Binding Molecules)

In one aspect, the present disclosure is based, in part, on anti-CD137 agonistic antigen-binding molecules and uses thereof. In certain embodiments, antibodies that bind to CD137 are provided. The antibodies in the present disclosure can exhibit activating action on immune cells, cytotoxicity, or anti-tumor activity and, therefore, are useful, for example, in diagnosing or treating cancer.

A. Exemplary Anti-CD137 Antigen-Binding Molecules or Antibodies

In one aspect, the present disclosure provides isolated antigen-binding molecules or antibodies that bind to CD137. In certain embodiments, the anti-CD137 antigen-binding molecules or antibodies have CD137 binding activity dependent on a small molecule compound;
    bind to the extracellular region of CD137;
    form a ternary complex together with a low-molecular weight compound and CD137;
    bind to human-derived CD137 and monkey-derived CD137;
    are agonistic for CD137 activity;
    show agonistic activity to CD137 in the presence of a low-molecular weight compound;
    have low agonistic activity to CD137 in the absence of the low-molecular weight compound; and/or
    substantially do not show agonistic activity to CD137 in the absence of the low-molecular weight compound.

Binding Activity of Antigen-Binding Molecules or Antibodies

In certain embodiments, the binding activity of the antigen-binding molecules or antibodies provided herein is, in the presence of a low-molecular weight compound, with dissociation constant (KD) of 1 micromolar or less, 100 nM or less, 10 nM or less, 1 nM or less, 0.1 nM or less, 0.01 nM or less, or 0.001 nM or less (for example, $10^{-6}$ M or less, $10^{-7}$ M or less, $10^{-8}$ M or less, $10^{-9}$ M or less, $10^{-10}$ M or less, for example $10^{-6}$ M to $10^{-10}$ M, $10^{-7}$ M to $10^{-9}$ M, for example $10^{-7}$ M to $10^{-8}$ M).

In one embodiment, binding activity of an antigen-binding molecule or antibody is measured by a radiolabeled antigen binding assay (RIA) and represented by KD. In one embodiment, an RIA is performed with the Fab version of an antibody of interest and its antigen. For example, solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER (registered trademark) multi-well plates (Thermo Scientific) are coated overnight with 5 microgram/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23 degrees C.). In a non-adsorbent plate (Nunc #269620), 100 pM or 26 pM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20 (registered trademark)) in PBS. When the plates have dried, 150 microliter/well of scintillant (MICROSCINT-20 ™; Packard) is added, and the plates are counted on a TOPCOUNT™ gamma counter (Packard) for ten minutes. Concentrations of each Fab that give less than or equal to 20% of maximal binding are chosen for use in competitive binding assays.

In one embodiment, for measuring binding activity of an antibody, ligand-capturing methods, for example, using BIACORE (registered trademark) T200 or BIACORE (registered trademark) 4000 (GE Healthcare, Uppsala, Sweden), which rely upon surface plasmon resonance analysis methods as the measurement principle, are used. BIACORE (registered trademark) Control Software is used for operation of devices. In one embodiment, amine-coupling kit (GE Healthcare, Uppsala, Sweden) is used according to the manufacturer's instructions to let a molecule for ligand capturing, for example, an anti-tag antibody, an anti-IgG antibody, protein A, etc. fixed onto a sensor chip (GE Healthcare, Uppsala, Sweden) coated with carboxymethyl-dextran. The ligand-capturing molecule is diluted with a 10 mM sodium acetate solution at an appropriate pH and is injected at an appropriate flow rate and for an appropriate injection time. Binding activity measurements are measured using a 0.05% polysorbate 20 (in other name Tween (registered trademark)-20)-containing buffer as a measurement buffer, at a flow rate of 10-30 microliter/minute, and at a measurement temperature of preferably at 25 degrees C. or 37 degrees C. For the measurement carried out with an antibody captured by the ligand-capturing molecule as a ligand, an antibody is injected to let a target amount of the antibody captured, and then a serial dilution of an antigen and/or an Fc receptor (analyte) prepared using the measurement buffer is injected. For the measurement carried out with an antigen and/or an Fc receptor captured by the ligand-capturing molecule as a ligand, an antigen and/or an Fc receptor is injected to let a target amount thereof captured, and then a serial dilution of an antibody (analyte) prepared using the measurement buffer is injected.

In one embodiment, the measurement results are analyzed using BIACORE (registered trademark) Evaluation Software. Kinetics parameter calculation is carried out by fitting sensorgrams of association and dissociation at the same time using a 1:1 binding model, and an association rate (kon or ka), a dissociation rate (koff or kd), and an equilibrium dissociation constant (KD) may be calculated. For the case of weak binding activity, in particular, for the cases where dissociation is fast and kinetics parameters are difficult to calculate, the Steady state model may be used to calculate the equilibrium dissociation constant (KD). As additional parameters concerning binding activity, "binding amount of analyte per unit ligand amount" may be calculated by dividing a binding amount of analyte (resonance unit: RU) at a specific concentration by an amount of captured ligand.

Small Molecule Compound-Dependent Binding Activity

In one aspect, the anti-CD137 antigen-binding molecule or antibody has small molecule compound-dependent CD137-binding activity. In one non-limiting embodiment, the anti-CD137 antigen-binding molecule or antibody has a higher binding activity towards CD137 in the presence of a small molecule compound as compared to the binding activity towards CD137 in the absence of the small molecule compound. In a different embodiment, the anti-CD137 antigen-binding molecule or antibody has a higher binding activity towards CD137 in the presence of a high concentration of a small molecule compound compared to the CD137-binding activity in the presence of a low concentration of the small molecule compound. In one preferred embodiment, the binding activity of the anti-CD137 antigen-binding molecule or antibody for CD137 in the presence of a small molecule compound is 2-fold or more, 3-fold or more, 5-fold or more, 10-fold or more, 15-fold or more, 20-fold or more, 25-fold or more, 30-fold or more, 50-fold or more, 100-fold or more, 200-fold or more, 300-fold or more, 500-fold or more $1 \times 10^3$-fold or more, $2 \times 10^3$-fold or more, $3 \times 10^3$-fold or more, $5 \times 10^3$-fold or more, $1 \times 10^4$-fold or more, $2 \times 10^4$-fold or more, $3 \times 10^4$-fold or more, $5 \times 10^4$-fold or more, or $1 \times 10^5$-fold or more, compared to the binding activity in the absence of the small molecule compound. In a different preferred embodiment, the binding activity of the anti-CD137 antigen-binding molecule or antibody for CD137 in the presence of a small molecule compound is higher than 2-fold, higher than 3-fold, higher than 5-fold, higher than 10-fold, higher than 15-fold, higher than 20-fold, higher than 25-fold, higher than 30-fold, higher than 50-fold, higher than 100-fold, higher than 200-folds, higher than 300-fold, higher than 500-fold, higher than $1 \times 10^3$-folds, higher than $2 \times 10^3$-folds, higher than $3 \times 10^3$-fold, higher than $5 \times 10^3$-fold, higher than $1 \times 10^4$-fold, higher than $2 \times 10^4$-fold, higher than $3 \times 10^4$-fold, higher than $5 \times 10^4$-fold, or higher than $1 \times 10^5$-fold, compared to the binding activity in the absence of the small molecule compound.

The concentration of the small molecule compound can be any arbitrary concentration as long as the difference in the binding activity of anti-CD137 antigen-binding molecule or antibody is detected. In one embodiment, the concentration of the small molecule compound "in the presence of a small molecule compound" and/or "in the presence of a high concentration of a small molecule compound" is, for example, 100 nM or more, 500 nM or more, 1 µM or more, 3 µM or more, 5 µM or more, 10 µM or more, 50 µM or more, 100 µM or more, 150 µM or more, 200 µM or more, 250 µM or more, 300 µM or more, 400 µM or more, 500 µM or more, or 1 mM or more. Alternatively, the concentration can be defined to be an amount that is sufficient for the anti-CD137 antigen-binding molecule or antibody to show maximum binding activity. Further, in one embodiment, the concentration of the small molecule compound "in the presence of a low concentration of a small molecule compound" may be, for example, 500 µM or less, 250 µM or less, 200 µM or less, 150 µM or less, 100 µM or less, 50 µM or less, 10 µM or less, 1 µM or less, 500 nM or less, 100 nM or less, 50 nM or less, or 10 nM or 1 nM or less. The case where the concentration of the small molecule compound is zero, or the substantial concentration is zero, can also be selected as an embodiment of the low concentration.

Here, the term "substantial concentration is zero" means, for example, a concentration that is so minute that it cannot be detected by current technology although the small molecule compound is present.

In one embodiment, the binding activity towards CD137 in the presence of a small molecule compound at a concentration of 10 μM, 50 μM, 100 μM, 150 μM, 200 μM or 250 μM is, 2-fold or more, 5-fold or more, 10-fold or more, 15-fold or more, 16-fold or more, 17-fold or more, 18-fold or more, 19-fold or more, or 20-fold or more, compared to the binding activity towards CD137 in the absence of the small molecule compound. In one embodiment, the binding activity of the anti-CD137 antigen-binding molecule or an antibody against CD137 in the presence of a small molecule compound at 10 μM or more is, 2-fold or more, 5-fold or more, 10-fold or more, 15-fold or more, 16-fold or more, 17-fold or more, 18-fold or more, 19-fold or more, or 20-fold or more, compared to the binding activity towards CD137 in the absence of the small molecule compound. In one embodiment, the binding activity of the anti-CD137 antigen-binding molecule or an antibody against CD137 in the presence of a small molecule compound at 100 μM or more is, 2-fold or more, 5-fold or more, 10-fold or more, 15-fold or more, 16-fold or more, 17-fold or more, 18-fold or more, 19-fold or more, or 20-fold or more, compared to the binding activity towards CD137 in the absence of the small molecule compound.

In one embodiment, the binding activity (KD) of the anti-CD137 antigen-binding molecule or antibody towards CD137 in the presence of a small molecule compound at 10 μM or more is, a dissociation constant (KD) of 9×10-7 M or less, 8×10-7 M or less, 7×10-7 M or less, 6×10-7 M or less, 5×10-7 M or less, or 4×10-7 M or less, or preferably, a dissociation constant (KD) of 5×10-7 M or less. In a further embodiment, the binding activity (KD) of the anti-CD137 antigen-binding molecule or antibody towards CD137 in the absence of a small molecule compound is too large to be calculated by Biacore (weak binding activity), or it is a disassociation constant (KD) of 1×10-7 M or more, 5×10-7 M or more, 7×10-7 M or more, 8×10-7 M or more, 9×10-7 M or more, 1×10-6 M or more, 2×10-6 M or more, 3×10-6 M or more, or 4×10-6 M or more, or preferably, is a dissociation constant (KD) of 1×10-6 M or more. In another embodiment, the binding activity (KD) of the anti-CD137 antigen-binding molecule or an antibody towards CD137 in the presence of a small molecule compound at 100 □M or more is, 9×10-7 M or less, 8×10-7 M or less, 7×10-7 M or less, 6×10-7 M or less, 5×10-7 M or less, 4×10-7 M or less, 3×10-7 M or less, 2×10-7 M or less, or 1×10-7 M or less, or preferably, the dissociation constant (KD) is 2×10-7 M or less. In a further embodiment, the binding activity (KD) of the anti-CD137 antigen-binding molecule or an antibody towards CD137 in the absence of the small molecule compound is too large to be calculated by Biacore (weak binding activity), or it is a disassociation constant (KD) of 1×10-7 M or more, 5×10-7 M or more, 7×10-7 M or more, 8×10-7 M or more, 9×10-7 M or more, 1×10-6 M or more, 2×10-6 M or more, 3×10-6 M or more, or 4×10-6 M or more, or preferably, a dissociation constant (KD) of 1×10-6 M or more.

In one embodiment, the binding activity (KD) of the anti-CD137 antigen-binding molecule or antibody towards CD137 in the presence of a small molecule compound at 10 μM or more is a dissociation constant (KD) of 8×10-8 M or less, and the binding activity (KD) towards CD137 in the absence of compound is too large to be calculated by Biacore (weak binding activity). In another embodiment, the binding activity (KD) of the anti-CD137 antigen binding molecule or antibody towards CD137 in the presence of a small molecule compound at 100 □M is a dissociation constant (KD) of 2×10-8 M or less, and the binding activity towards CD137 in the absence of the small molecule compound is too large to be calculated by Biacore (weak binding activity).

In one aspect, the present disclosure provides an anti-CD137 antigen-binding molecule or antibody in which the value of, [binding activity (binding amount) towards CD137 in the presence of a low-molecular compound at 10 μM or more]/[binding activity (binding amount) towards CD137 in the absence of the small molecule compound)] is the same as or greater than the value of a reference anti-CD137 antigen-binding molecule. In a different aspect, the present disclosure provides an anti-CD137 antigen-binding molecule or antibody in which the value of, [binding activity (binding amount) towards CD137 in the presence of a low-molecular compound at 100 μM or more]/[binding activity (binding amount) towards CD137 in the absence of the small molecule compound)] is the same as or greater than the value of a reference anti-CD137 antigen-binding molecule. In any of the above aspects, the reference anti-CD137 antigen-binding molecule can be selected from anti-CD137 antibodies containing HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 contained in A375/B167, A372/B040, A356/B040, A486/B167, A487/B167, A488/B226, A489/B223, A548/B376, A551/B256, A551/B379, A555/B379, A548/B256, or A549/B167 described in Table 17.

In one embodiment, the reference anti-CD137 antigen-binding molecule is an antibody comprising the amino acid sequence of A375/B167, A372/B040, A356/B040, A486/B167, A487/B167, A488/B226, A489/B223, A548/B376, A551/B256, A551/B379, A555/B379, A548/B256, or A549/B167 described in Table 17 as a heavy chain variable region/light chain variable region combination. In a preferred embodiment, the reference antigen-binding molecule is an anti-CD137 antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A375/B167. In a further embodiment, the reference anti-CD137 antigen-binding molecule is an anti-CD137 antibody comprising A375/B167 as a heavy chain variable region/light chain variable region combination. In a different preferable embodiment, the reference antigen-binding molecule is anti-CD137 antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A551/B379. In a further embodiment, the reference anti-CD137 antigen-binding molecule is an anti-CD137 antibody comprising A551/B379 as a heavy chain variable region/light chain variable region combination. In a preferable embodiment, the reference antigen-binding molecule comprises heavy and light chain constant regions of human origin (for example, G1T3 (SEQ ID NO: 138) as the heavy chain constant region, human λ chain Lamlib (SEQ ID NO: 63) as the light chain constant region).

In one aspect, the present disclosure provides an anti-CD137 antigen binding molecule or antibody in which the binding activity (binding amount) towards CD137 in the absence of a small molecule compound is the same as or lower than that of a reference anti-CD137 antigen-binding molecule, and also, the binding activity (binding amount) towards CD137 in the presence of the small molecule compound at 10 μM or more is equal to or more than that of the reference anti-CD137 antigen-binding molecule towards CD137 under the same conditions. In a different aspect, the present disclosure provides an anti-CD137 antigen binding molecule or an antibody in which the binding activity towards CD137 in the absence of a small molecule compound is the same as or lower than that of a reference anti-CD137 antigen-binding molecule, and also, the binding activity (binding amount) towards CD137 in the presence of the small molecule compound at 10 µM or more is equal to or more than the binding activity (binding amount) of the reference anti-CD137 antigen-binding molecule towards CD137 under the same conditions. In any of the above aspects, the reference anti-CD137 antigen binding molecule can be selected from anti-CD137 antibodies containing HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 contained in A375/B167, A372/B040, A356/B040, A486/B167, A487/B167, A488/B226, A489/B223, A548/B376, A551/B256, A551/B379, A555/B379, A548/B256 or A549/B167 described in Table 17.

In one embodiment, the reference anti-CD137 antigen-binding molecule is an anti-CD137 antibody comprising the amino acid sequence of A375/B167, A372/B040, A356/B040, A486/B167, A487/B167, A488/B226, A489/B223, A548/B376, A551/B256, A551/B379, A555/B379, A548/B256, or A549/B167 described in Table 17 as a heavy chain variable region/light chain variable region combination. In a different preferred embodiment, the reference antigen-binding molecule is an anti-CD137 antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A375/B167. In a further embodiment, the reference anti-CD137 antigen-binding molecule is an anti-CD137 antibody comprising A375/B167 as a heavy chain variable region/light chain variable region combination. In a preferable embodiment, the reference antigen-binding molecule is an anti-CD137 antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A551/B379. In a further embodiment, the reference anti-CD137 antigen-binding molecule is an anti-CD137 antibody comprising A551/B379 as a heavy chain variable region/light chain variable region combination. In a preferable embodiment, the reference antigen-binding molecule comprises heavy and light chain constant regions of human origin (for example, G1T3 (SEQ ID NO: 138) as the heavy chain constant region, human λ chain Lamlib (SEQ ID NO: 63) as the light chain constant region).

In one aspect, the present disclosure provides an anti-CD137 antigen-binding molecule or antibody in which the value of, [binding activity (KD) towards CD137 in the presence of a low-molecular compound at 1 µM]/[binding activity (KD) towards CD137 in the presence of the low-molecular compound at 10 µM or more] is the same as or greater than the value of a reference antigen-binding molecule. In a different aspect, the present disclosure provides an anti-CD137 antigen-binding molecule or antibody in which the value of, [binding activity (KD) towards CD137 in the presence of a low-molecular compound at 1 µM]/[binding activity (KD) towards CD137 in the presence of the low-molecular compound at 100 µM or more] is the same as or greater than the value of a reference antigen-binding molecule. In any of the above aspects, the reference antigen-binding molecule can be selected from anti-CD137 antibodies containing HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 contained in A375/B167, A372/B040, A356/B040, A486/B167, A487/B167, A488/B226, A489/B223, A548/B376, A551/B256, A551/B379, A555/B379, A548/B256 or A549/B167 described in Table 17.

In one embodiment, the reference antigen-binding molecule is an antibody comprising the amino acid sequence of A375/B167, A372/B040, A356/B040, A486/B167, A487/B167, A488/B226, A489/B223, A548/B376, A551/B256, A551/B379, A555/B379, A548/B256, or A549/B167 described in Table 17 as a heavy chain variable region/light chain variable region combination. In a preferred embodiment, the reference antigen-binding molecule is an antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A375/B167. In a further embodiment, the reference antigen-binding molecule is an antibody comprising A375/B167 as a heavy chain variable region/light chain variable region combination. In a different embodiment, the reference antigen-binding molecule is an antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A551/B379. In a further embodiment, the reference antigen-binding molecule is an antibody comprising A551/B379 as a heavy chain variable region/light chain variable region combination. In a preferable embodiment, the reference antigen-binding molecule comprises heavy and light chain constant regions of human origin (for example, G1T3 (SEQ ID NO: 138) as the heavy chain constant region, human λ chain Lamlib (SEQ ID NO: 63) as the light chain constant region).

In one embodiment, the binding activity of the anti-CD137 antibody towards CD137, with the presence, absence, high concentration and/or low concentration of a small molecule compound, is measured, for example, by a ligand capture method using BIACORE (registered trademark) T200 with surface plasmon resonance spectroscopy as principle of measurement.

Details of an exemplary method for measuring the binding activity of anti-CD137 antibody towards CD137 are described below. In one embodiment, the binding activity of anti-CD137 antibody towards CD137 is evaluated by BIACORE (registered trademark) T200. In a preferred embodiment, this assay uses 20 mM ACES (pH 7.4), 150 mM NaCl, 2 mM MgCl2, and 0.05% Tween 20 as a running buffer, and is carried out at 37° C. In one embodiment, this measurement is carried out after capturing an antibody as a ligand on the ligand capture molecule. Specifically, a suitable amount (e.g., about 100 RU, 200 RU, 300 RU, 400 RU, or 500 RU) of the antibody is captured by, interacting an antibody solution prepared using the running buffer with a chip prepared firstly by immobilizing Sure Protein A (GE Healthcare) on a Series S Sensor Chip CM3 (GE Healthcare).

In a preferred embodiment, about 100 to 500 RU, preferably about 250 to 400 RU of antibody is captured. Next, the binding activity towards CD137 in the presence and absence of a small molecule compound is evaluated by interacting a CD137 solution prepared using a running buffer added with a small molecule compound to a target concentration (for example, 1 µM, 10 µM, 50 µM or 100 µM), or a CD137 solution prepared using a running buffer that does not contain the small molecule compound. Although the concentration of CD137 in the CD137 solution can be determined appropriately, for example, when hCD137-HisBAP (see Example 1-1) is used as antigen, the measurement is carried out using an antigen concentration of 0 nM, 15.625 nM, 62.5 nM, 250 nM, and 1000 nM, respectively. In one embodiment, the dissociation constant (KD) of anti-CD137 antibody to human CD137 is calculated using Biacore T200 Evaluation Software 2.0. Specifically, the binding rate constant ka (L/mol/s) and the dissociation rate constant kd (1/s) are calculated by global fitting a sensorgram obtained by measurement using the 1:1 Langmuir binding model. The dissociation constant KD (mol/L) is calculated from the values.

Further exemplary assay methods for measuring the binding activity of anti-CD137 antibody to CD137 will be described in detail below. Binding of anti-CD137 antibodies to human CD137 is assessed with Biacore T200. The binding towards human CD137 was measured using 20 mM ACES (pH 7.4), 150 mM NaCl, 2 mM MgCl2, and 0.05% Tween 20 as a running buffer, and this was carried out at 37° C. First, an antibody of about 250 to 400 RU is captured by interacting an antibody solution prepared using the running buffer with a chip where Sure Protein A (GE Healthcare) is immobilized on a Series S Sensor Chip CM3 (GE Healthcare). Next, a human CD137 solution prepared using a running buffer added with ATP in a target concentration (for example, 1 µM, 10 µM, 50 µM or 100 µM), or a human CD137 solution prepared using a running buffer that does not contain ATP, is interacted to evaluate the binding activity towards CD137 in the presence and absence of ATP. hCD137-HisBAP prepared by the method of Example (1-1) is used as human CD137 which is the antigen, and the measurement is carried out at antigen concentrations of 0 nM, 15.625 nM, 62.5 nM, 250 nM, and 1000 nM, respectively. The chip is regenerated using 25 mM NaOH and 10 mM Glycine-HCl (pH 1.5), and measurement is conducted by repeatedly capturing the antibodies. The dissociation constant of each antibody for human CD137 is calculated using Biacore T200 Evaluation Software 2.0. Specifically, the binding rate constant ka (L/mol/s) and the dissociation rate constant kd (1/s) are calculated by global fitting the sensorgram obtained by the measurement using the 1:1 Langmuir binding model. The dissociation constant KD (mol/L) is calculated from the values.

In one embodiment, the binding activity of the anti-CD137 antibody towards CD137 (preferably human CD137) can also be rephrased as "the amount of CD137 binding per unit amount of antibody". Specifically, by using the sensorgrams obtained by the above assay method using BIACORE (registered trademark) T200, the binding amount of CD137 to antibody (RU) is divided by the amount of antibody captured to calculate "the amount of CD137 binding per unit amount of antibody". In one embodiment, the binding activity of the anti-CD137 antibody towards CD137 (preferably human CD137) can also be measured by the method described in Example 5-3 or 6-2.

The terms "small molecule" and "small molecule compound" refer to a naturally-occurring chemical substance other than "biopolymers" present in the living body, or a non-naturally-occurring chemical substance. Preferably, it is a target tissue-specific compound or a non-naturally-occurring compound, but is not limited thereto. In one embodiment, the "small molecule compound" in the present disclosure is a "cancer tissue-specific compound" or a "cancer tissue-specific metabolite". The term in the present disclosure "a compound specific to cancer tissue (cancer tissue-specific compound)" refers to a compound which exists differentially in tumor tissue, compared to non-tumor tissue. As used herein, the term "cancer" is generally used to describe a malignant neoplasm, and may be metastatic or non-metastatic. The term "metabolism" refers to chemical changes that occur within the tissue of an organism, including "assimilation" and "catabolism". Assimilation refers to the biosynthesis or accumulation of molecules, and catabolism refers to the degradation of molecules. A "metabolite" is an intermediate or product resulting from substance metabolism.

The term "target tissue" means any tissue in the living body to which the antigen-binding molecule of the present invention is intended to be delivered. The target tissue may be a histologically distinguishable tissue such as various organs or a pathologically distinguishable tissue such as normal tissues and diseased tissues. In certain embodiments, the target tissue is a tumor tissue. In contrast, "non-target tissue(s)" means tissues in the living body other than the target tissue.

The term "tumor tissue" means a tissue that comprises at least one tumor cell. Generally, a tumor tissue is made of a population of tumor cells constituting the tumor main body (parenchyma) and connective tissues and blood vessels existing in between tumor cells and supporting the tumor (stroma). In some cases, these are clearly distinguishable, but there are cases where these are mixed up. In some cases, there are cells such as immune cells that have infiltrated into the tumor tissue. In contrast, "non-tumor tissue" means a tissue in the living body other than tumor tissue(s). Non-diseased healthy tissues/normal tissues are representatives of such non-tumor tissues.

As a non-limiting embodiment of a cancer tissue-specific compound, or a cancer tissue-specific metabolite as used in the present disclosure, at least one compound selected from the compounds detailed below can be suitably exemplified. The meaning of "at least one compound" includes, in addition to the case where the binding activity against the antigen by the same antigen-binding domains described later depends on one type of cancer tissue-specific compound or cancer tissue-specific metabolite, the case where the binding activity depends on several types of cancer tissue-specific compounds or cancer tissue-specific metabolites.

As used herein, the term "target tissue-specific compound" refers to a compound that is differentially present in target tissue as compared to non-target tissue. In several embodiments, the target tissue-specific compound can be a compound defined by a qualitative target tissue specificity such as being present in target tissue but not in non-target tissues, or being present in non-target tissue but not in target tissue. In a different embodiment, the target tissue-specific compound may be a compound defined by a quantitative target tissue specificity such as being present in target tissue at a concentration which is different (for example, a higher concentration or lower concentration) compared to non-target tissue. In a specific embodiment, the target tissue-specific compound is present in target tissue at a concentration which is, for example, 1.05-fold or more, 1.1-fold or more, 1.15-fold or more, 1.2-fold or more, 1.25-fold or more, 1.3-fold or more, 1.35-fold or more, 1.4-fold or more, 1.45-fold or more, 1.5-fold or more, 1.55-fold or more, 1.6-fold or more, 1.65-fold or more, 1.7-fold or more, 1.75-fold or more, 1.8-fold or more, 1.85-fold or more, 1.9-fold or more, 1.95-fold or more, 2-fold or more, 2.1-fold or more, 2.2-fold or more, 2.3-fold or more, 2.4-fold or more, 2.5-fold or more, 3-fold or more, 5-fold or more, 10-fold or more, 50-fold or more, 100-fold or more, 103-fold or more, 104-fold or more, 105-fold or more, 106-folds or more, or higher compared to non-target tissue. In another embodiment, the target tissue specific compound is present in target tissue at a concentration which is, for example, 1.05-fold or more, 1.1-fold or more, 1.15-fold or more, 1.2-fold or more, 1.25-fold or more, 1.3-fold or more, 1.35-fold or more, 1.4-fold or more, 1.45-fold or more, 1.5-fold or more, 1.55-fold or more, 1.6-fold or more, 1.65-fold or more, 1.7-fold or more, 1.75-fold or more, 1.8-fold or more, 1.85-fold or more, 1.9-fold or more, 1.95-fold or more, 2-fold or more, 2.1-fold or more, 2.2-fold or more, 2.3-fold or more, 2.4-fold or more, 2.5-fold or more, 3-fold or more, 5-fold or more, 10-fold or more, 50-fold or more, 100-fold or more, 103-folds or more, 104-folds or more, 105-folds or more, 106-folds or more, or higher compared to non-target tissue. In a specific embodiment, a target tissue-specific compound, as compared to non-target tissue, is present in a target tissue at a concentration that is statistically significantly higher or lower (i.e., as determined using either one of Welch's t-test or rank sum test of Wilcoxon, the p value is less than 0.05 and/or the q value is less than 0.10). In a specific embodiment, the target tissue-specific compound is a tumor tissue-specific compound.

In a specific embodiment, a tumor tissue-specific compound is a metabolite produced by a metabolism specific to a tumor cell. The metabolite may be a product that is generated by metabolism essential for life activities (primary metabolite), or a product generated by a metabolism not necessarily required for life activities (secondary metabolite). Examples of primary metabolites may include sugars, proteins, lipids, nucleic acids, and the like. Examples of secondary metabolites include antibiotics and dyes. The metabolite may be a biopolymer or a small molecule. In a specific embodiment, the biopolymer is a molecule having a molecular weight of about 5000 or more which consists of one or more types of repeating units, including, for example, polysaccharides, polypeptides, and polynucleotides. In a specific embodiment, small molecules are molecules having a molecular weight of about 500 or less and are chemical substances present within the living body. In a further embodiment, the tumor tissue-specific compound is a small molecule metabolite specifically produced in tumor cells (Eva Gottfried, Katrin Peter and Marina P. Kreutz, From Molecular and Modular Tumor Therapy (2010) 3 (2), 111-132). In a further embodiment, the tumor tissue-specific compound is a metabolite that is produced specifically by a cell infiltrating into tumor tissue (e.g., an immune cell) or a stromal cell (e.g., a cancer associated fibroblast (CAF)) present in a tumor tissue. Examples of immune cells infiltrating into the tumor tissue are dendritic cells, suppressive dendritic cells, regulatory T cells, exhausted T cells, myeloma-derived suppressor cells (MDSCs), and the like. In a further embodiment, a metabolite which is produced by cells present in tumor tissue (e.g., tumor cells, immune cells, stromal cells, etc.), which is released to the outside of the cell when the cells die by apoptosis or necrosis, or the like, can also be included in the tumor tissue-specific compounds of the present disclosure.

To identify a tumor tissue-specific compound, analysis at the transcriptome level (e.g., Dhanasekaran et al. (Nature (2001) 41 2, 822-826), Lapointe et al. (Proc. Natl. Acad. Sci. USA (2004) 101, 811-816), or Perou et al. (Nature (2000) 406, 747-752)), analysis at the proteome level (e.g., Ahram et al. (Mol. Carcinog. (2002) 33, 9-15), and Hood et al. (Mol. Cell. Proteomics (2005) 4, 1741-1753)), and analysis of metabology centering on metabolomic profiling (metabolomics) can be used appropriately. That is, in order to identify a metabolite in a test sample, high performance liquid chromatography (HPLC), nuclear magnetic resonance (NMR) (Brindle et al. (J. Mol. Recognit. (1997) 10, 182-187)), mass spectrometry (GC/MS and LC/MS) (Gates and Sweeley (Clin. Chem. (1978) 24, 1663-1673)), and metabolic profiling that uses ELISA, and such, can be suitably used alone and/or in combination.

In a specific embodiment, the tumor tissue-specific compound is at least one compound selected from the group consisting of: nucleosides having a purine ring structure, amino acids and metabolites thereof, lipids and metabolites thereof, primary metabolites of the carbohydrate metabolism, as well as nicotinamide and its metabolites. In a further embodiment, the tumor tissue-specific compound is at least one compound selected from (1) to (6) below:

(1) nucleosides having a purine structure such as adenosine (ADO), adenosine triphosphate (ATP), adenosine diphosphate (ADP), adenosine monophosphate (AMP), and inosine;

(2) amino acids such as alanine, glutamic acid and aspartic acid;

(3) metabolites of amino acids such as kynurenine, anthranilic acid, 3-hydroxykynurenine, and kynurenic acid;

(4) metabolites of arachidonic acid such as prostaglandin E2;

(5) primary metabolites of the glycolytic pathway or Krebs cycle such as lactic acid, succinic acid, and citric acid; and, (6) metabolites of nicotinamide such as 1-methyl nicotinamide.

(1) Nucleosides Having a Purine Structure Such as Adenosine (ADO), Adenosine Triphosphate (ATP), Adenosine Diphosphate (ADP), Adenosine Monophosphate (AMP), and Inosine It is known that, when tumor cells undergo cell death, a large amount of intracellular ATP leaks out. Therefore, the ATP concentration in tumor tissue is significantly higher than that in normal tissue (PLoS One. (2008) 3, e2599). AMP is metabolized by enzymes on the cell surface such as extracellular-5'-nucleotidase (eco-5'-nucleotidase) (CD73) (Resta and Thompson (Immunol. Rev. (1998) 161, 95-109) and Sadej et al. (Melanoma Res. (2006) 16, 21 3-222)). Adenosine is a purine nucleoside that is constitutively present in the extracellular environment at low concentrations, but a marked increase in the extracellular adenosine concentration has been reported in hypoxic tissues found in solid tumors (Blay and Hoskin (Cancer Res. (1997) 57, 260 2-2605)). CD73 is expressed on the surface of tumors and immune cells (Kobie et al. (J. Immunol. (2006) 17 7, 6780-6786)) and elevated activity has been found in breast cancer (Canbolat et al. (Breast Cancer Res. Treat. (1996) 37, 189-193)), stomach cancer (Durak et al. (Cancer Lett. (1994) 84, 199-202)), pancreatic cancer (Flocke and Mannherz (Biochim. Biophys. Acta (1991) 1076, 273-281)), and glioblastoma (Bardot et al. (Br. J. Cancer (1994) 70, 212-218)). It has been proposed that accumulation of adenosine in tumor tissue is a result of increase in dephosphorylation of AMP by cytoplasmic 5'-nucleotidase (Headrick and Willis (Biochem. J. (1989) 261, 541-550)). Furthermore, regulatory T cells infiltrating into tumor tissue also express ATPase and produce adenosine (Proc. Natl. Acad. Sci. USA (2006) 103 (35), 13132-13137; Curr. Med. Chem. (2011) 18: 5217-5223). The produced adenosine is thought to keep tumor tissues in an immunosuppressive environment via adenosine receptors such as the A2A receptor (Curr. Med. Chem. (2011) 18, 5217-5223). Thus, ATP, ADP, AMP, adenosine, and such that are considered to be accumulated at a high concentration in tumor tissue by metabolism of purine nucleotides are examples of the tumor tissue-specific compounds used in the present disclosure. Additionally, as adenosine undergoes degradation into inosine by adenosine deaminase, inosine is accumulated at a high concentration.

In a specific embodiment, nucleosides having a purine ring structure include adenosine-containing compounds. In specific embodiments, adenosine-containing compounds include, for example, adenosine (ADO), adenosine triphosphate (ATP), adenosine diphosphate (ADP), adenosine monophosphate (AMP), cyclic adenosine monophosphate (cAMP), deoxyadenosine (dADO), deoxyadenosine triphosphate (dATP), deoxyadenosine diphosphate (dADP), deoxyadenosine monophosphate (dAMP), adenosine [γ-thio]triphosphate (ATPγS), and such. In another embodiment, nucleosides having a purine ring structure include inosine which is a metabolite of adenosine.

Furthermore, in a specific embodiment, nucleosides having a purine ring structure include commercially available nucleosides having a purine ring structure such as ADPbetaS (Sigma Inc.) and such.

(2) Amino Acids Such as Alanine, Glutamic Acid and Aspartic Acid

The rate of uptake of glutamine, which acts as a nitrogen carrier in the living body, is increased in tumor cells, and such glutamine incorporation and the resulting conversion to glutamic acid and lactic acid (glutamine degradation (glutaminolysis)) are thought to be features of tumor cells (Mazurek and Eigenbrodt (Anticancer Res. (2003) 23, 1149-1154, and Mazurek et al. (J. cell. Physiol. (1999) 181, 136-146). Glutamine levels in plasma are decreased in cancer patients, while glutamic acid concentration is increased (Droge et al. (Immunobiology (1987) 174, 473-479)), and studies of the metabolism of 13C-labelled glucose in lung cancer tissue showed a correlation among the concentrations of 13C-labeled succinic acid, 13C-labeled alanine, 13C-labeled glutamic acid, and 13C-labeled citrate. For these reasons, alanine, glutamic acid, aspartic acid and such, which are thought to be accumulated in high concentrations in tumor tissue due to, e.g., glutamine degradation, are examples of tumor tissue-specific compounds used in this disclosure.

(3) Metabolites of Amino Acids Such as Kynurenine, Anthranilic Acid, 3-Hydroxykynurenine, and Kynurenic Acid Indoleamine 2,3-dioxygenase (IDO) is a tryptophan-metabolizing enzyme highly expressed in many cancers such as melanoma, colon cancer, kidney cancer and such (Uyttenhove et al. (Nat. Med. (2003) 9, 1269-1274)). IDO catalyzes the conversion of tryptophan to kynurenine. In gliomas which do not express IDO, kynurenine is produced from tryptophan by tryptophan 2,3-dioxygenase (TDO) of the liver (Opitz et al. (Nature (2011) 478 (7368), 197-203)). IDO is also expressed on dendritic cells infiltrating into tumor tissue, and dendritic cells also produce kynurenine (J. Immunol. (2008) 181, 5396-5404). Further, IDO is also expressed in myeloid-derived suppressor cells (MDSC) of tumor tissues, and MDSC also produces kynurenine (Yu et al. (J. Immunol. (2013) 190, 3783-3797)). Kynurenine is converted into anthranilic acid by kynureninase, and to 3-hydroxykynurenine by kynurenine 3-hydroxylase. Both anthranilic acid and 3-hydroxykynurenine are converted to 3-hydroxyanthranilic acid, a precursor of NAD. Kynurenine is converted to kynurenic acid by kynurenine aminotransferase. Due to these reasons, kynurenine and its metabolite, i.e., anthranilic acid, 3-hydroxykynurenine, kynurenic acid and the like are examples of tumor tissue-specific compounds used in the present disclosure, in particular, tumor cell-specific metabolites.

(4) Metabolites of Arachidonic Acid Such as Prostaglandin E2

Prostaglandin E2 (PGE2) promotes the growth of colon cancer cells and suppresses their apoptosis (Sheng et al. (Cancer Res. (1998) 58, 362-366)). Of PGE2 synthetases, it has been mainly found that COX-1 is constitutively expressed in almost all tissues, whereas COX-2 is induced by certain inflammatory cytokines and oncogenes in tumors (Warner and Mitchell (FASEB J. (2004) 18, 790-804)). Overexpression of COX-2 has been reported to be associated with a poor prognosis in breast cancer (Denkert et al. (Clin. Breast Cancer (2004) 4, 428-433)) and rapid disease progression in ovarian cancer (Denker et al. (Mod. Pathol. (2006) 19, 1261-1269)). In addition, regulatory T cells infiltrating into tumor tissue also produce PGE2 (Curr. Med. Chem. (2011) 18, 5217-5223). Due to these reasons, metabolites of arachidonic acid such as PGE2 are examples of tumor tissue-specific compounds, in particular tumor cell-specific metabolites or tumor tissue-infiltrating immune cell-specific metabolites. Besides PGE2, Thromboxane A2 (TXA2) production is enhanced in tumor tissues such as those in colon cancer (J. Lab. Clin. Med. (1993) 122, 518-523).

(5) Primary Metabolites of the Glycolytic Pathway or Krebs Cycle Such as Lactic Acid Succinic Acid and Citric Acid The glycolytic phenotype characterized by upregulation of glycolytic (Embden-Meyerhof pathway) enzymes such as pyruvate kinase, hexokinase, and lactate dehydrogenase (LDH) has been conventionally known as the Warburg effect, a feature of solid tumors. Lactic acid which is the end product of glycolysis, and succinic acid and citric acid produced by the Krebs cycle are known to be accumulated in tumor tissues (Teresa et al. (Mol. Cancer (2009) 8, 41-59)). Due to these reasons, lactic acid, succinic acid, citric acid, and such, which are primary metabolites produced by glycolysis, are examples of tumor tissue-specific compounds, in particular tumor cell-specific metabolites, used in the present disclosure. In addition, it is known that due to cell death, succinate, which is present in a high concentration in cells, leaks out of cells (Nature Immunology, (2008) 9, 1261-1269). This is thought to be the reason for increased succinic acid concentration in tumor tissues where cell death is frequently occurring.

(6) Metabolites of Nicotinamide Such as 1-Methyl Nicotinamide

It is known that nicotinamide N-methyltransferase is highly expressed in a plurality of human tumor tissues. It is also known that 1-methyl-nicotinamide, which is a stable metabolite of nicotinamide produced by this enzyme, is secreted to the outside of tumor cells (Yamada et al. (J. Nutr. Sci. Vitaminol. (2010) 56, 83-86)). Due to this reason, 1-methyl nicotinamide, and such, which are thought to be accumulated in tumor tissue at a high concentration as a result of the metabolism of nicotinamide are examples of tumor tissue-specific compounds used in the present disclosure.

An "antigen-binding molecule" of the present disclosure comprises an "antigen-binding domain." As the "antigen-binding domain", a domain of any structure can be used as long as it binds to the target antigen. In one embodiment, the antigen-binding domains of this disclosure include, for example, variable regions of antibody heavy chains and/or light chains, Avimers containing a module (A domain) of about 35 amino acids contained in various cell membrane proteins in the living body (International Publications WO2004/044011 and WO2005/040229), Adnectins containing the 10Fn3 domain of fibronectin which is a glycoprotein expressed on the cell membrane (International Publication WO2002/032925), Affibodies using as scaffold an IgG binding domain of 58 amino acids of Protein A (WO WO1995/001937), DARPins (Designed Ankyrin Repeat proteins) using an ankyrin repeat (AR) which is a 33-amino-acid repeating sequence as base (International Publication WO2002/020565), Anticalins containing a lipocalin such as neutrophil gelatinase-associated lipocalin (NGAL) as base (International Publication WO2003/029462), variable lymphocyte receptors (VLRs) which are proteins that function in adaptive immune systems of jawless vertebrates such as the Lampetra japonica and Eptatretus, and contain a leucine-rich-repeat module (LRR) module (International Publication WO2008/016854), and such. In a specific embodiment, the antigen binding domain of this disclosure comprises heavy and light chain variable regions of an antibody. In a further embodiment, the antigen-binding domain of the present disclosure includes, for example, scFv (single chain Fv), single chain antibodies, Fv, scFv2 (single chain Fv2), Fab, or F (ab')2.

HVR and Variable Region

In one aspect, the present disclosure provides an anti-CD137 antigen-binding molecule or antibody that comprises at least one, at least two, or all three VH HVR sequences selected from: (a) HVR-H1 comprising the amino acid sequence of SEQ ID NO: 7; (b) HVR-H2 comprising any one of the amino acid sequences selected from SEQ ID NOs: 8, 9, 10, 11, 12, 13, 14, 15, and 16; and (c) HVR-H3 comprising any one of the amino acid sequences selected from SEQ ID NO: 17, 18, 19, or 20. In one embodiment, the anti-CD137 antigen-binding molecule or antibody comprises: (a) HVR-H1 comprising the amino acid sequence of SEQ ID NO: 7; (b) HVR-H2 comprising any one of the amino acid sequences selected from SEQ ID NOs: 8, 9, 10, 11, 12, 13, 14, 15, and 16; and (c) HVR-H3 comprising any one of the amino acid sequences selected from SEQ ID NO: 17, 18, 19, or 20.

In one embodiment, the anti-CD137 antigen-binding molecule is an antibody comprising the amino acid sequence of A375/B167, A372/B040, A356/B040, A486/B167, A487/B167, A488/B226, A489/B223, A548/B376, A551/B256, A551/B379, A555/B379, A548/B256, or A549/B167 described in Table 17 as a heavy chain variable region/light chain variable region combination. In a preferred embodiment, the antigen-binding molecule is an anti-CD137 antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A375/B167. In a further embodiment, the anti-CD137 antigen-binding molecule is an anti-CD137 antibody comprising A375/B167 as a heavy chain variable region/light chain variable region combination. In a different preferable embodiment, the antigen-binding molecule is anti-CD137 antibody comprising HVR-H1, HVR-H2, HVR-H3, HVR-L1, HVR-L2 and HVR-L3 having the same amino acid sequences as HVR-H1, HVR-H2, HVR-H3, HVR-L1, HVR-L2 and HVR-L3 comprised in A551/B379.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 8; and (c) HVR-H3 comprising the amino acid sequence of SEQ ID NO: 17.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 9; and (c) HVR-H3 comprising the amino acid sequence of SEQ ID NO: 17.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 10; and (c) HVR-H3 comprising the amino acid sequence of SEQ ID NO: 17.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 11; and (c) HVR-H3 comprising the amino acid sequence of SEQ ID NO: 18.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 8; and (c) HVR-H3 comprising the amino acid sequence of SEQ ID NO: 18.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 12; and (c) HVR-H3 comprising the amino acid sequence of SEQ ID NO: 18.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 13; and (c) HVR-H3 comprising the amino acid sequence of SEQ ID NO: 18.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 14; and (c) HVR-H3 comprising the amino acid sequence of SEQ ID NO: 19.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 15; and (c) HVR-H3 comprising the amino acid sequence of SEQ ID NO: 20.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 16; and (c) HVR-H3 comprising the amino acid sequence of SEQ ID NO: 20.

In one embodiment, the anti-CD137 antigen-binding molecule or antibody comprises (a) HVR-H1 comprising the amino acid sequence of SEQ ID NO: 7; (b) HVR-H2 comprising the amino acid sequence of SEQ ID NO: 14; and (c) HVR-H3 comprising the amino acid sequence of SEQ ID NO: 17.

In a different aspect, the present disclosure provides an anti-CD137 antigen-binding molecule or antibody that comprises at least one, at least two, or all three VL HVR sequences selected from: (a) HVR-L1 comprising any one of the amino acid sequences selected from SEQ ID NOs: 21, 22, 23, 24, and 25; (b) HVR-L2 comprising the amino acid sequence of SEQ ID NO: 26; and (c) HVR-L3 comprising any one of the amino acid sequences selected from SEQ ID NOs: 27, 28 and 29. In one embodiment, the anti-CD137 antigen-binding molecule or comprises (a) HVR- L1 comprising any one of the amino acid sequences selected from SEQ ID NOs: 21, 22, 23, 24, and 25; (b) HVR-L2 comprising the amino acid sequence of SEQ ID NO: 26; and (c) HVR-L3 comprising any one of the amino acid sequences selected from SEQ ID NOs: 27, 28 and 29.

In one embodiment, the anti-CD137 antigen-binding molecule or antibody comprises (a) HVR-L1 comprising the amino acid sequence of SEQ ID NO: 21; (b) HVR-L2 comprising the amino acid sequence of SEQ ID NO: 26; and (c) HVR-L3 comprising the amino acid sequence of SEQ ID NO: 27.

In one embodiment, the anti-CD137 antigen-binding molecule or antibody comprises (a) HVR-L1 comprising the amino acid sequence of SEQ ID NO: 22; (b) HVR-L2 comprising the amino acid sequence of SEQ ID NO: 26; and (c) HVR-L3 comprising the amino acid sequence of SEQ ID NO: 27.

In one embodiment, the anti-CD137 antigen-binding molecule or antibody comprises (a) HVR-L1 comprising the amino acid sequence of SEQ ID NO: 21; (b) HVR-L2 comprising the amino acid sequence of SEQ ID NO: 26; and (c) HVR-L3 comprising the amino acid sequence of SEQ ID NO: 28.

In one embodiment, the anti-CD137 antigen-binding molecule or antibody comprises (a) HVR-L1 comprising the amino acid sequence of SEQ ID NO: 21; (b) HVR-L2 comprising the amino acid sequence of SEQ ID NO: 26; and (c) HVR-L3 comprising the amino acid sequence of SEQ ID NO: 29.

In one embodiment, the anti-CD137 antigen-binding molecule or antibody comprises (a) HVR-L1 comprising the amino acid sequence of SEQ ID NO: 23; (b) HVR-L2 comprising the amino acid sequence of SEQ ID NO: 26; and (c) HVR-L3 comprising the amino acid sequence of SEQ ID NO: 27.

In one embodiment, the anti-CD137 antigen-binding molecule or antibody comprises (a) HVR-L1 comprising the amino acid sequence of SEQ ID NO: 24; (b) HVR-L2 comprising the amino acid sequence of SEQ ID NO: 26; and (c) HVR-L3 comprising the amino acid sequence of SEQ ID NO: 27.

In one embodiment, the anti-CD137 antigen-binding molecule or antibody comprises (a) HVR-L1 comprising the amino acid sequence of SEQ ID NO: 25; (b) HVR-L2 comprising the amino acid sequence of SEQ ID NO: 26; and (c) HVR-L3 comprising the amino acid sequence of SEQ ID NO: 27.

In another aspect, the anti-CD137 antigen-binding molecule or antibody of this disclosure comprises (a) a VH domain comprising at least one, at least two, or all three VH HVR sequences selected from (i) HVR-H1 comprising the amino acid sequence of SEQ ID NO: 7; (ii) HVR-H2 comprising any one of the amino acid sequences selected from SEQ ID NOs: 8, 9, 10, 11, 12, 13, 14, 15, and 16; and (iii) HVR-H3 comprising any one of the amino acid sequences selected from SEQ ID NOs: 17, 18, 19, or 20; and (b) a VL domain comprising at least one, at least two, or all three VL HVR sequences selected from (i) HVR-L1 comprising any one of the amino acid sequences selected from SEQ ID NOs: 21, 22, 23, 24, and 25; (ii) HVR-L2 comprising the amino acid sequence of SEQ ID NO: 26; and (iii) HVR-L3 comprising any one of the amino acid sequences selected from SEQ ID NOs: 27, 28, and 29.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 17; (d) HVR-L1 comprising the amino acid sequence of SEQ ID NO: 21; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 9; (c) HVR-H3 comprising the amino acid sequence of SEQ ID NO: 17; (d) HVR-L1 comprising the amino acid sequence of SEQ ID NO: 22; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 10; (c) HVR-H3 comprising the amino acid sequence of SEQ ID NO: 17; (d) HVR-L1 comprising the amino acid sequence of SEQ ID NO: 22; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 11; (c) HVR-H3 comprising the amino acid sequence of SEQ ID NO: 18; (d) HVR-L1 comprising the amino acid sequence of SEQ ID NO: 21; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 8; (c) HVR-H3 comprising the amino acid sequence of SEQ ID NO: 18; (d) HVR-L1 comprising the amino acid sequence of SEQ ID NO: 21; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 12; (c) HVR-H3 comprising the amino acid sequence of SEQ ID NO: 18; (d) HVR-L1 comprising the amino acid sequence of SEQ ID NO: 21; (e) HVR-L2 comprising the amino acid sequence of SEQ ID NO: 26; and (f) HVR-L3 comprising the amino acid sequence of SEQ ID NO: 28.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 13; (c) HVR-H3 comprising the amino acid sequence of SEQ ID NO: 18; (d) HVR-L1 comprising the amino acid sequence of SEQ ID NO: 21; (e) HVR-L2 comprising the amino acid sequence of SEQ ID NO: 26; and (f) HVR-L3 comprising the amino acid sequence of SEQ ID NO: 29.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 14; (c) HVR-H3 comprising the amino acid sequence of SEQ ID NO: 19; (d) HVR-L1 comprising the amino acid sequence of SEQ ID NO: 23; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 15; (c) HVR-H3 comprising the amino acid sequence of SEQ ID NO: 20; (d) HVR-L1 comprising the amino acid sequence of SEQ ID NO: 24; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 15; (c) HVR-H3 comprising the amino acid sequence of SEQ ID NO: 20; (d) HVR-L1 comprising the amino acid sequence of SEQ ID NO: 25; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 16; (c) HVR-H3 comprising the amino acid sequence of SEQ ID NO: 20; (d) HVR-L1 comprising the amino acid sequence of SEQ ID NO: 25; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 14; (c) HVR-H3 comprising the amino acid sequence of SEQ ID NO: 19; (d) HVR-L1 comprising the amino acid sequence of SEQ ID NO: 24; (e) HVR-L2 comprising the amino acid sequence of SEQ ID NO: 26; and (f) HVR-L3 comprising the amino acid sequence of SEQ ID NO: 27.

In another aspect, the present disclosure provides an anti-CD137 antigen-binding molecule or antibody comprising (a) HVR-H1 comprising the amino acid sequence of SEQ ID NO: 7; (b) HVR-H2 comprising the amino acid sequence of SEQ ID NO: 14; (c) HVR-H3 comprising the amino acid sequence of SEQ ID NO: 17; (d) HVR-L1 comprising the amino acid sequence of SEQ ID NO: 21; (e) HVR-L2 comprising the amino acid sequence of SEQ ID NO: 26; and (f) HVR-L3 comprising the amino acid sequence of SEQ ID NO: 27.

In a specific embodiment, any one or more amino acids of the above-described anti-CD137 antibody are substituted at the following HVR positions:

In HVR-H2 (SEQ ID NO: 30): positions 5, 6, 7, 10, 13, 14, and/or 17
In HVR-H3 (SEQ ID NO: 31): position 3 and/or 6
In HVR-L1 (SEQ ID NO: 32): positions 4, 5, 9, and/or 11
In HVR-L3 (SEQ ID NO: 33): positions 6, 7, and/or 8.

In a specific embodiment, the substitutions provided by the present specification are conservative substitutions. In a specific embodiment, any one or more substitutions in the following may be performed in any combination:

In HVR-H2 (SEQ ID NO: 8): K5H or S; 56G; T7S; E10Y; D13E; S14Q; V17G or L
In HVR-H3 (SEQ ID NO: 17): A3P, K or I; F6E
In HVR-L1 (SEQ ID NO: 21): R4S; Y5T; Y9F; E11N
In HVR-L3 (SEQ ID NO: 27): E6P; H7A; Q8I

All possible combinations of the above-mentioned substitutions are encompassed in the consensus sequences of SEQ ID NOs: 30, 31, 32 and 33 for HVR-H2, HVR-H3, HVR-L1 and HVR-L3, respectively.

In any of the above embodiments, an anti-CD137 antigen-binding molecule or antibody is humanized. In one embodiment, an anti-CD137 antigen-binding molecule or antibody comprises HVRs as in any of the above embodiments, and further comprises an acceptor human framework, e.g. a human immunoglobulin framework or a human consensus framework. In another embodiment, an anti-CD137 antigen-binding molecule or antibody comprises HVRs as in any of the above embodiments, and further comprises a heavy chain variable region (VH) or a light chain variable region (VL) comprising a framework (FR) sequence. In one embodiment, FR1 in the heavy chain variable region comprises the amino acid sequence of SEQ ID NO: 35, FR2 in the heavy chain variable region comprises the amino acid sequence of SEQ ID NO: 36, FR3 in the heavy chain variable region comprises the amino acid sequence of SEQ ID NO: 37, and FR4 in the heavy chain variable region comprises the amino acid sequence of SEQ ID No: 38. In one embodiment, FR1 in the light chain variable region comprises the amino acid sequence of SEQ ID NO: 39, FR2 in the light chain variable region comprises the amino acid sequence of SEQ ID NO: 40, FR3 in the light chain variable region comprises the amino acid sequence of SEQ ID NO: 41, and FR4 in the light chain variable region comprises the amino acid sequence of SEQ ID NO: 42.

In another aspect, an anti-CD137 antigen-binding molecule or antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 43, 44, 45, 46, 47, 48, 49, 50, 51, 52, or 53. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD137 antigen-binding molecule or antibody comprising that sequence retains the ability to bind to CD137. In certain embodiments, a total of 1 to 10 amino acids have been substituted, inserted and/or deleted in SEQ ID NO: 43, 44, 45, 46, 47, 48, 49, 50, 51, 52, or 53. In certain embodiments, substitutions, insertions, or deletions occur in regions outside the HVRs (i.e., in the FRs). Optionally, the anti-CD137 antibody comprises the VH sequence in SEQ ID NO: 43, 44, 45, 46, 47, 48, 49, 50, 51, 52, or 53, including post-translational modifications of that sequence. In a particular embodiment, the VH comprises one, two or three HVRs selected from: (a) HVR-H1 comprising the amino acid sequence of SEQ ID NO: 7; (b) HVR-H2 comprising any one amino acid sequence selected from SEQ ID NOs: 8, 9, 10, 11, 12, 13, 14, 15, and 16; and (c) HVR-H3 comprising any one amino acid sequence selected from SEQ ID NO: 17, 18, 19, or 20. Post-translational modifications include but are not limited to a modification of glutamine or glutamate in N-terminal of heavy chain or light chain to pyroglutamic acid by pyroglutamylation.

In another aspect, an anti-CD137 antigen-binding molecule or antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 54, 55, 56, 57, 58, 59, or 60. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-CD137 antigen-binding molecule or antibody comprising that sequence retains the ability to bind to CD137. In certain embodiments, a total of 1 to 10 amino acids have been substituted, inserted and/or deleted in SEQ ID NO: 54, 55, 56, 57, 58, 59, or 60. In certain embodiments, the substitutions, insertions, or deletions occur in regions outside the HVRs (i.e., in the FRs). Optionally, the anti-CD137 antigen-binding molecule or antibody comprises the VL sequence in SEQ ID NO: 54, 55, 56, 57, 58, 59, or 60, including post-translational modifications of that sequence. In a particular embodiment, the VL comprises one, two or three HVRs selected from (a) HVR-L1 comprising any one amino acid sequence selected from SEQ ID NOs: 21, 22, 23, 24, and 25; (b) HVR-L2 comprising the amino acid sequence of SEQ ID NO: 26; and (c) HVR-L3 comprising any one amino acid sequence selected from SEQ ID NO: 27, 28, and 29. Post-translational modifications include but are not limited to a modification of glutamine or glutamate in N-terminal of heavy chain or light chain to pyroglutamic acid by pyroglutamylation.

In another aspect, an anti-CD137 antigen-binding molecule or antibody is provided, wherein the antigen-binding molecule or antibody comprises a VH as in any of the embodiments provided above, and a VL as in any of the embodiments provided above.

In one embodiment, the anti-CD137 antigen-binding molecule or antibody comprises the VH and VL sequences in SEQ ID NO: 43 and SEQ ID NO: 54, respectively, including post-translational modifications of those sequences.

In one embodiment, the anti-CD137 antigen-binding molecule or antibody comprises the VH and VL sequences in SEQ ID NO: 44 and SEQ ID NO: 55, respectively, including post-translational modifications of those sequences.

In one embodiment, the anti-CD137 antigen-binding molecule or antibody comprises the VH and VL sequences in SEQ ID NO: 45 and SEQ ID NO: 55, respectively, including post-translational modifications of those sequences.

In one embodiment, the anti-CD137 antigen-binding molecule or antibody comprises the VH and VL sequences in SEQ ID NO: 46 and SEQ ID NO: 54, respectively, including post-translational modifications of those sequences.

In one embodiment, the anti-CD137 antigen-binding molecule or antibody comprises the VH and VL sequences in SEQ ID NO: 47 and SEQ ID NO: 54, respectively, including post-translational modifications of those sequences.

In one embodiment, the anti-CD137 antigen-binding molecule or antibody comprises the VH and VL sequences in SEQ ID NO: 48 and SEQ ID NO: 56, respectively, including post-translational modifications of those sequences.

In one embodiment, the anti-CD137 antigen-binding molecule or antibody comprises the VH and VL sequences in SEQ ID NO: 49 and SEQ ID NO: 57, respectively, including post-translational modifications of those sequences.

In one embodiment, the anti-CD137 antigen-binding molecule or antibody comprises the VH and VL sequences in SEQ ID NO: 50 and SEQ ID NO: 58, respectively, including post-translational modifications of those sequences.

In one embodiment, the anti-CD137 antigen-binding molecule or antibody comprises the VH and VL sequences in SEQ ID NO: 51 and SEQ ID NO: 59, respectively, including post-translational modifications of those sequences.

In one embodiment, the anti-CD137 antigen-binding molecule or antibody comprises the VH and VL sequences in SEQ ID NO: 51 and SEQ ID NO: 60, respectively, including post-translational modifications of those sequences.

In one embodiment, the anti-CD137 antigen-binding molecule or antibody comprises the VH and VL sequences in SEQ ID NO: 52 and SEQ ID NO: 60, respectively, including post-translational modifications of those sequences.

In one embodiment, the anti-CD137 antigen-binding molecule or antibody comprises the VH and VL sequences in SEQ ID NO: 50 and SEQ ID NO: 59, respectively, including post-translational modifications of those sequences.

In one embodiment, the anti-CD137 antigen-binding molecule or antibody comprises the VH and VL sequences in SEQ ID NO: 53 and SEQ ID NO: 54, respectively, including post-translational modifications of those sequences.

The above-mentioned post-translational modifications include but are not limited to a modification of glutamine or glutamate in N-terminal of heavy chain or light chain to pyroglutamic acid by pyroglutamylation.

SEQ ID NOs corresponding to the amino acid sequences of the preferred heavy chain variable region and light chain variable region and their HVR1, 2, and 3 for each anti-CD137 antigen-binding molecule or antibody of the present disclosure are shown in the table below.

TABLE 1

| Heavy chain/light chain variable regions | SEQ ID NO of variable region | | SEQ ID NO of hypervariable region (HVR) | | | | | |
|---|---|---|---|---|---|---|---|---|
| | Heavy chain | Light chain | H1 | H2 | H3 | L1 | L2 | L3 |
| A375/B167 | 43 | 54 | 7 | 8 | 17 | 21 | 26 | 27 |
| A372/B040 | 44 | 55 | 7 | 9 | 17 | 22 | 26 | 27 |
| A356/B040 | 45 | 55 | 7 | 10 | 17 | 22 | 26 | 27 |
| A486/B167 | 46 | 54 | 7 | 11 | 18 | 21 | 26 | 27 |
| A487/B167 | 47 | 54 | 7 | 8 | 18 | 21 | 26 | 27 |
| A488/B226 | 48 | 56 | 7 | 12 | 18 | 21 | 26 | 28 |
| A489/B223 | 49 | 57 | 7 | 13 | 18 | 21 | 26 | 29 |
| A548/B376 | 50 | 58 | 7 | 14 | 19 | 23 | 26 | 27 |
| A551/B256 | 51 | 59 | 7 | 15 | 20 | 24 | 26 | 27 |
| A551/B379 | 51 | 60 | 7 | 15 | 20 | 25 | 26 | 27 |
| A555/B379 | 52 | 60 | 7 | 16 | 20 | 25 | 26 | 27 |
| A548/B256 | 50 | 59 | 7 | 14 | 19 | 24 | 26 | 27 |
| A549/B167 | 53 | 54 | 7 | 14 | 17 | 21 | 26 | 27 |

When an anti-CD137 antigen-binding molecule or antibody provided herein has glutamine as the heavy chain or light chain N terminus amino acid, that amino acid may be substituted by glutamic acid. When an anti-CD137 antibody provided herein has glutamic acid as the heavy chain or light chain N terminus amino acid, that amino acid may be substituted by glutamine.

In a preferred embodiment, the anti-CD137 antigen-binding molecules or antibodies comprising the above-described HVRs, heavy chain variable regions, and/or light chain variable regions all have low-molecular-weight-compound-dependent binding activity toward CD137 as described above.

Constant Regions

In another aspect, the anti-CD137 antigen-binding molecules or antibodies comprise a constant region. The constant region may be a heavy chain constant region (including an Fc region), a light chain constant region, or both. In a further aspect, the anti-CD137 antigen-binding molecules or antibodies comprise an Fc region. In some embodiments, the constant region is the one with the native sequence. Examples of heavy chain constant regions derived from native antibodies include, for example, a heavy chain constant region of human IgG1 (SEQ ID NOs: 61, 62), human IgG2, human IgG3, human IgG4, and such. Examples of light chain constant regions derived from native antibodies include, for example, human kappa chain, human lambda chain (e.g., SEQ ID NO: 63), and such.

A "parent constant region" or "parent Fc region" used herein refers to a constant region or an Fc region prior to introducing amino acid alteration(s) described herein. A "parent antigen-binding molecule" refers to an antigen-binding molecule that comprises the parent constant region or parent Fc region. In some embodiments, the parent Fc region is an Fc region having a native sequence (or an Fc region of a native antibody). Antibodies include, for example, IgA (IgA1, IgA2), IgD, IgE, IgG (IgG1, IgG2, IgG3, IgG4), IgM, etc. Antibodies may be derived from human or monkey (e.g., cynomolgus, rhesus macaque, marmoset, chimpanzee, or baboon). Native antibodies may also include naturally-occurring mutations. A plurality of allotype sequences of IgGs due to genetic polymorphism are described in "Sequences of proteins of immunological interest", NIH Publication No. 91-3242, and any of them may be used in the present disclosure. In one embodiment, the parent Fc region is an Fc region derived from a heavy chain constant region of human IgG1, shown in SEQ ID NO: 61, 62, or 182.

In one aspect, the anti-CD137 antigen-binding molecules or antibodies have an increased isoelectric point (pI), as compared to anti-CD137 antigen-binding molecules or antibodies that comprise a native sequence Fc region or a parent Fc region. In some embodiments, variant Fc regions include at least one amino acid alteration. In further embodiments, the amino acid alteration leads to the elevation of isoelectric point (pI) of the variant Fc region as compared to the parent Fc region. Without being bound by a particular theory, it is believed that the pH of biological fluids (for example, plasma) is in a neutral pH range. In biological fluids, the net positive charge of a pI-increased antigen-binding molecule or antibody is increased due to the increased pI, and as a result the antigen-binding molecule or antibody is more strongly attracted by physicochemical Coulomb interaction to the endothelial cell surface that has a net negative charge compared to an antigen-binding molecule or antibody not having an increased pI. By this, the agonistic antigen-binding molecules (or antibodies), or antigen-bound agonistic antigen-binding molecules (or antibodies) may come closer to the surface of cells which express Fc-gamma receptor, resulting in an increased binding of the antigen-binding molecules or antibodies to Fc-gamma receptor-expressing cells. For those anti-CD137 agonistic antigen-binding molecules or antibodies that show CD137 agonistic activity based on the contribution by binding activity toward Fc-gamma receptor, anti-CD137 agonistic antigen-binding molecules or antibodies having increased binding toward Fc-gamma receptor-expressing cells due to the pI-increasing amino acid alterations can exhibit stronger CD137 agonistic activity as compared to anti-CD137 agonistic antigen-binding molecules or antibodies having no pI-increasing amino acid alterations.

In the present disclosure, pI may be either a theoretical or an experimentally determined pI. The value of pI can be determined, for example, by isoelectric focusing known to those skilled in the art. The value of a theoretical pI can be calculated, for example, using gene and amino acid sequence analysis software (Genetyx, etc.). In calculating, properties of an antibody may be reflected in a calculation formula. For example, (i) generally, Cys conserved within an antibody forms a disulfide bond and does not carry electric charge of the side chain; therefore, such Cys may be excluded from the calculation and only the free-form Cys which does not form a disulfide bond may be included in the calculation. Alternatively, (ii) charge state or isoelectric point of antibodies can change because of post-translational modifications; therefore, a calculation formula may be modified as follows, giving consideration on such post-translational modifications: (a) when the N-terminus of the heavy chain is Q (glutamine), the N-terminal amino group is excluded from the calculation, assuming that pyroglutamylation occurs, (b) when the C-terminus of the heavy chain is K (lysine), K (only one residue) is excluded from the calculation, assuming that truncation occurs; and (c) side chains of all C (cysteine) present at generally conserved positions are excluded from the calculation, assuming that all these C form disulfide bonds within the molecule. In one preferred embodiment, both above-described (i) and (ii) may be reflected in the calculation formula.

In one embodiment, the pI value may be increased, for example, at least by 0.01, 0.03, 0.05, 0.1, 0.2, 0.3, 0.4, 0.5, or more, at least by 0.6, 0.7, 0.8, 0.9, or more, at least by 1.0, 1.1, 1.2, 1.3, 1.4, 1.5, or more, or at least by 1.6, 1.7, 1.8, 1.9, 2.0, 2.1, 2.2, 2.3, 2.4, 2.5, 3.0 or more, as compared to before modification.

In one embodiment, amino acid alterations relating to pI increase and methods for increasing pI of an antigen-binding molecule or antibody are described herein in detail at "III. Compositions and methods (agonistic antigen-binding molecules comprising a variant Fc region with increased isoelectric point (pI))". Those skilled in the art would understand that any amino acid alterations and methods for increasing pI described under "III. Compositions and methods (agonistic antigen-binding molecules comprising a variant Fc region with increased isoelectric point (pI))" can be applied to the anti-CD137 antigen-binding molecules or antibodies.

In one embodiment, the anti-CD137 antigen-binding molecules or antibodies have a variant Fc region with increased pI, and the variant Fc region comprises at least one amino acid alteration of at least one position selected from the group consisting of positions 285, 311, 312, 315, 318, 333, 335, 337, 341, 342, 343, 384, 385, 388, 390, 399, 400, 401, 402, 413, 420, 422, and 431, according to EU numbering. In further embodiments, variant Fc regions with increased pI comprise Arg or Lys at each selected position.

In further embodiments, the anti-CD137 antigen-binding molecules or antibodies have a variant Fc region with increased pI, and the variant Fc region comprises at least one amino acid alteration of at least one position selected from the group consisting of positions 311, 343, and 413, according to EU numbering. In further embodiments, the variant Fc regions with increased pI comprise an amino acid alteration at position 311, 343, or 413 according to EU numbering. In a further embodiment, the variant Fc regions with increased pI comprise Arg or Lys at each selected position.

In another aspect, the present disclosure provides anti-CD137 antigen-binding molecules or antibodies comprising a variant Fc region with increased pI, which comprises amino acid alterations of any one of following (1) to (3): (1) at positions 311 and 343; (2) at positions 311 and 413; and (3) at positions 343 and 413, according to EU numbering. In further embodiments, the variant Fc regions with increased pI comprise Arg or Lys at each selected position.

In one embodiment, the anti-CD137 antigen-binding molecules or antibodies of the present disclosure comprise a variant Fc region which comprises amino acid alteration(s) identified in Table 2 below.

Amino acid alterations for increasing pI of an Fc region

TABLE 2

| Number | Amino acid substitutions (EU numbering) |
|---|---|
| 1 | P343R/D413K |
| 2 | Q311R/P343R |
| 3 | P343R |
| 4 | D413K |
| 5 | Q311R |
| 6 | Q311R/D413K |

In one embodiment, the anti-CD137 antigen-binding molecules or antibodies comprise a variant Fc region prepared by making amino acid alteration(s) to an Fc region having a native sequence. In one embodiment, the variant Fc regions have an increased binding activity towards at least one Fc-gamma receptor selected from the group consisting of Fc-gamma RIa, Fc-gamma RIIa, Fc-gamma RIIb, Fc-gamma RIIIa, and Fc-gamma RIIIb, as compared to an Fc region having a native sequence or a parent Fc region. Preferably, the variant Fc regions have an increased binding activity towards Fc-gamma RIIb, as compared to an Fc region having a native sequence or a parent Fc region. It is reported that an anti-CD137 antibody comprising a variant Fc region with increased binding activity towards Fc-gamma RIIb has increased agonistic activity, as compared to the anti-CD137 antibody comprising an Fc region with a native sequence. In one embodiment, as amino acid alterations to increase binding activity towards Fc-gamma RIIb, amino acid alterations taught in WO2012/115241, WO2014/030728, WO2014/163101, and/or WO2017/104783 may be used, for example. In one preferred embodiment, alterations to increase binding activity towards Fc-gamma RIIb are amino acid alteration(s) of at least one position selected from the group consisting of positions 234, 235, 236, 237, 238, 264, 268, 295, 326, and 330, according to EU numbering.

"Fc gamma receptors" (herein, referred to as Fc gamma receptors, Fc gamma R or FcgR) refers to receptors that may bind to the Fc region of IgG1, IgG2, IgG3, and IgG4 monoclonal antibodies, and practically means any member of the family of proteins encoded by the Fc gamma receptor genes. In humans, this family includes Fc gamma RI (CD64) including isoforms Fc gamma RIa, Fc gamma Rub, and Fc gamma RIc; Fc gamma RII (CD32) including isoforms Fc gamma RIIa (including allotypes H131 (type H) and R131 (type R)), Fc gamma RIIb (including Fc gamma RIIb-1 and Fc gamma RIIb-2), and Fc gamma RIIc; and Fc gamma RIII (CD16) including isoforms Fc gamma RIM (including allotypes V158 and F158), and Fc gamma RIIIb (including allotypes Fc gamma RIIIb-NA1 and Fc gamma RIIIb-NA2), and any human Fc gamma Rs, Fc gamma R isoforms or allotypes yet to be discovered, but is not limited thereto. Fc gamma RIIb1 and Fc gamma RIIb2 have been reported as splicing variants of human Fc gamma RIIb. In addition, a splicing variant named Fc gamma RIIb3 has been reported (J Exp Med, 1989, 170: 1369-1385). In addition to these splicing variants, human Fc gamma RIIb includes AAI46679.1 registered in NCBI and all splicing variants registered in NCBI, which are NP_001002273.1, NP_001002274.1, NP_001002275.1, NP_001177757.1, and NP_003992.3. Furthermore, human Fc gamma RIIb includes every previously-reported genetic polymorphism, as well as Fc gamma RIIb (Arthritis Rheum. 48: 3242-3252 (2003); Kono et al., Hum. Mol. Genet. 14: 2881-2892 (2005); and Kyogoju et al., Arthritis Rheum. 46: 1242-1254 (2002)), and every genetic polymorphism that will be reported in the future.

In Fc gamma RIIa, there are two allotypes, one where the amino acid at position 131 of Fc gamma RIIa is histidine (type H) and the other where the amino acid at position 131 is substituted with arginine (type R) (Warrmerdam, J. Exp. Med. 172: 19-25 (1990)).

The Fc gamma R includes human, mouse, rat, rabbit, and monkey-derived Fc gamma Rs but is not limited thereto, and may be derived from any organism. Mouse Fc gamma Rs include Fc gamma RI (CD64), Fc gamma RH (CD32), Fc gamma RIII (CD16), and Fc gamma RIII-2 (CD16-2), and any mouse Fc gamma Rs, or Fc gamma R isoforms, but are not limited thereto.

In another aspect, the present disclosure provides the anti-CD137 antigen-binding molecules or antibodies comprising a variant Fc region having an increased binding activity towards Fc-gamma RIIb, which comprises amino acid alterations of any one of following (1) to (8): (1) at positions 234, 238, 264, and 330; (2) at positions 234, 238, and 330; (3) at positions 234, 237, 238, and 330; (4) at positions 236, 268, and 330; (5) at positions 235, 236, 268, 295, 326, and 330; according to EU numbering.

In one embodiment, the anti-CD137 antigen-binding molecules or antibodies of the present disclosure comprise a variant Fc region comprising amino acid alterations identified in Table 3 below. In a further embodiment, the anti-CD137 antigen-binding molecules or antibodies of the present disclosure comprises a variant Fc region which further comprises, in addition to the amino acid alteration(s) described in Table 2 (Amino acid alterations involving increasing pI of an Fc region), any one combination of amino acid alterations identified in Table 3 below.

Amino acid alterations for increasing Fc-gamma RIIb binding activity of an Fc region

TABLE 3

| Number | Amino acid substitution (EU numbering) |
|---|---|
| 1 | L234Y/P238D/V264I/A330K |
| 2 | L234Y/P238D/A330K |
| 3 | L234Y/G237D/P238D/A330K |

TABLE 3-continued

| Number | Amino acid substitution (EU numbering) |
|---|---|
| 4 | G236N/H268D/A330K |
| 5 | L235W/G236N/H268D/Q295L/K326T/A330K |

In one embodiment, the present disclosure provides variant Fc regions, including those variant Fc regions that have alteration of at least one amino acid and have binding activity towards Fc-gamma RIIb equivalent to or higher than that of a reference Fc region. In one embodiment, the reference Fc region is an Fc region comprising any one combination of amino acid alterations identified in Table 3 above. In one preferred embodiment, the reference Fc region is an Fc region comprised in a heavy chain constant region TT14 (SEQ ID NO: 149), TT16 (SEQ ID NO: 150), MY201 (SEQ ID NO: 153), or MY518 (SEQ ID NO: 154). In one preferred embodiment, the reference Fc region is an Fc region comprised in a heavy chain constant region MY201 (SEQ ID NO: 153) or MY518 (SEQ ID NO: 154).

In another aspect, the present disclosure provides isolated agonistic antigen-binding molecules or antibodies that comprise a variant Fc region with increased binding activity towards Fc-gamma receptor (preferably, Fc-gamma RIIb) and increased pI. In a certain embodiment, the variant Fc regions described herein comprise at least two amino acid alterations in the parent Fc regions. As described above, an antigen-binding molecule or antibody with an increased pI is more strongly attracted by physicochemical Coulomb interaction to the endothelial cell surface that has a net negative charge compared to an antigen-binding molecule or antibody not having an increased pI. Therefore, for those agonistic antigen-binding molecules or antibodies that show agonistic activity based on the contribution by binding activity toward Fc-gamma receptor (preferably Fc-gamma RIIb), agonistic activity of the antigen-binding molecules or antibodies can be increased by combining amino acid alteration(s) to increase Fc-gamma receptor (preferably Fc-gamma RIIb) and amino acid alteration(s) to increase pI.

In one embodiment, the anti-CD137 antigen-binding molecules or antibodies comprise a variant Fc region that comprises both the amino acid alteration(s) to increase binding activity towards Fc-gamma receptor (e.g., Fc-gamma RIIb) and amino acid alteration(s) to increase isoelectric point (pI), described above. As described above, an antigen-binding molecule or antibody with an increased pI is more strongly attracted by physicochemical Coulomb interaction to the endothelial cell surface that has a net negative charge compared to an antigen-binding molecule or antibody not having an increased pI. Therefore, for those anti-CD137 agonistic antigen-binding molecules or antibodies that show CD137 agonistic activity based on the contribution by binding activity toward Fc-gamma receptor (preferably Fc-gamma RIIb, agonistic activity of the anti-CD137 antigen-binding molecules or antibodies can be increased by combining amino acid alteration(s) to increase Fc-gamma receptor (preferably Fc-gamma RIIb) and amino acid alteration(s) to increase pI.

In one aspect, the present disclosure provides polypeptides comprising a variant Fc region with an increased binding activity towards Fc-gamma RIIb and with an increased pI, which comprises at least three amino acid alterations including (a) at least one amino acid alteration of at least one position selected from the group consisting of positions 234, 235, 236, 237, 238, 264, 268, 295, 326, and 330, according to EU numbering, and (b) at least two amino acid alterations of at least two positions selected from the group consisting of positions 311, 343, and 413, according to EU numbering.

In another aspect, the present disclosure provides polypeptides comprising a variant Fc region with an increased binding activity towards Fc-gamma RIIb and an increased pI, which comprises amino acid alterations of any one of following (1) to (26):

(1) positions 235, 236, 268, 295, 326, 330, 343, and 413;
(2) positions 214, 235, 236, 268, 295, 326, 330, 343, and 413;
(3) positions 234, 238, 250, 264, 307, 330, 343, and 413;
(4) positions 234, 238, 264, 330, 343, and 413;
(5) positions 234, 237, 238, 250, 307, 330, 343, and 413;
(6) positions 234, 237, 238, 330, 343, and 413;
(7) positions 235, 236, 268, 295, 326, 330, 311, and 343;
(8) positions 234, 238, 250, 264, 307, 330, 311, and 343;
(9) positions 234, 238, 264, 330, 311, and 343;
(10) positions 234, 237, 238, 250, 307, 330, 311, and 343;
(11) positions 234, 237, 238, 330, 311, and 343;
(12) positions 235, 236, 268, 295, 326, 330, and 343;
(13) positions 214, 235, 236, 268, 295, 326, 330, and 343;
(14) positions 235, 236, 268, 295, 326, 330, and 413;
(15) positions 214, 236, 268, 330, and 343;
(16) positions 214, 235, 236, 268, 330, and 343;
(17) positions 214, 236, 268, 330, and 413;
(18) positions 214, 236, 268, 330, 343, and 413;
(19) positions 214, 235, 236, 268, 330, 343, and 413;
(20) positions 214, 236, 268, 330, and 311;
(21) positions 214, 235, 236, 268, 330, and 311;
(22) positions 214, 236, 268, 330, 311, and 343;
(23) positions 214, 235, 236, 268, 330, 311, and 343;
(24) positions 214, 236, 268, 330, 311, and 413;
(25) positions 214, 235, 236, 268, 330, 311, and 413;
(26) positions 214, 235, 236, 268, 295, 326, 330, and 311, according to EU numbering.

In one embodiment, the variant Fc regions of the present disclosure comprise any one combination of amino acid alterations identified in Table 4 below.

TABLE 4

| Number | Amino acid substitutions (EU numbering) |
|---|---|
| 1 | L235W/G236N/H268D/Q295L/K326T/A330K/P343R/D413K |
| 2 | K214R/L235W/G236N/H268D/Q295L/K326T/A330K/P343R/D413K |
| 3 | L234Y/P238D/T250V/V264I/T307P/A330K/P343R/D413K |
| 4 | L234Y/P238D/V264I/A330K/P343R/D413K |
| 5 | L234Y/G237D/P238D/T250V/T307P/A330K/P343R/D413K |
| 6 | L234Y/G237D/P238D/A330K/P343R/D413K |
| 7 | L235W/G236N/H268D/Q295L/K326T/A330K/Q311R/P343R |
| 8 | L234Y/P238D/T250V/V264I/T307P/A330K/Q311R/P343R |
| 9 | L234Y/P238D/V264I/A330K/Q311R/P343R |
| 10 | L234Y/G237D/P238D/T250V/T307P/A330K/Q311R/P343R |
| 11 | L234Y/G237D/P238D/A330K/Q311R/P343R |
| 12 | L235W/G236N/H268D/Q295L/K326T/A330K/P343R |
| 13 | K214R/L235W/G236N/H268D/Q295L/K326T/A330K/P343R |
| 14 | L235W/G236N/H268D/Q295L/K326T/A330K/D413K |
| 15 | K214R/G236N/H268D/A330K/P343R |
| 16 | K214R/L235W/G236N/H268D/A330K/P343R |
| 17 | K214R/G236N/H268D/A330K/D413K |
| 18 | K214R/G236N/H268D/A330K/P343R/D413K |
| 19 | K214R/L235W/G236N/H268D/A330K/P343R/D413K |
| 20 | K214R/G236N/H268D/A330K/Q311R |
| 21 | K214R/L235W/G236N/H268D/A330K/Q311R |
| 22 | K214R/G236N/H268D/A330K/Q311R/P343R |
| 23 | K214R/L235W/G236N/H268D/A330K/Q311R/P343R |
| 24 | K214R/G236N/H268D/A330K/Q311R/D413K |
| 25 | K214R/L235W/G236N/H268D/A330K/Q311R/D413K |

TABLE 4-continued

| Number | Amino acid substitutions (EU numbering) |
|---|---|
| 26 | K214R/L235W/G236N/H268D/Q295L/<br>K326T/A330K/Q311R |

In one embodiment, the variant Fc regions comprising any one combination of amino acid alterations described in Table 4 above lacks the amino acid at position 447 according to EU numbering. In a preferred embodiment, the variant Fc regions comprising any one combination of amino acid alterations described in Table 4 above lacks the amino acids at positions 446 and 447 according to EU numbering.

Those skilled in the art would understand that at least one amino acid alteration to increase binding activity towards Fc-gamma R (including Fc-gamma RIIb) as compared to the parent Fc region as described or suggested, for example, in WO2013/047752, WO2013/125667, WO2014/030728, WO2014/163101, or WO2017104783, and at least one amino acid alteration to increase pI as compared to the parent Fc region as described or suggested, for example, in WO2017/104783, WO2017/046994, and any combination of these amino acid alterations may be used, in addition to the alterations provided as illustrations above.

In addition, amino acid alterations performed for other purpose(s) can be combined in a variant Fc region described herein. For example, amino acid substitutions that increase FcRn-binding activity (Hinton et al., J. Immunol. 176(1): 346-356 (2006); Dall'Acqua et al., J. Biol. Chem. 281(33): 23514-23524 (2006); Petkova et al., Intl. Immunol. 18(12): 1759-1769 (2006); Zalevsky et al., Nat. Biotechnol. 28(2): 157-159 (2010); WO 2006/019447; WO 2006/053301; and WO 2009/086320), and amino acid substitutions for improving antibody heterogeneity or stability (WO 2009/041613) may be added. Alternatively, polypeptides with the property of promoting antigen clearance, which are described in WO 2011/122011, WO 2012/132067, WO 2013/046704 or WO 2013/180201, polypeptides with the property of specific binding to a target tissue, which are described in WO 2013/180200, polypeptides with the property for repeated binding to a plurality of antigen molecules, which are described in WO 2009/125825, WO 2012/073992 or WO 2013/047752, can be combined with a variant Fc region described herein. Alternatively, with the objective of conferring binding activity to other antigens, the amino acid alterations disclosed in EP1752471 and EP1772465 may be combined in CH3 of a variant Fc region described herein.

In one embodiment, the anti-CD137 antigen-binding molecules or antibodies of the present disclosure comprise a heavy chain constant region comprising any one amino acid sequence selected from SEQ ID NOs: 64-85. Preferably, the anti-CD137 antigen-binding molecules or antibodies of the present disclosure comprise a heavy chain constant region comprising the amino acid sequence of SEQ ID NO: 75 or 82.

In one preferred embodiment, the anti-CD137 antigen-binding molecules or antibodies comprising the above-described variant Fc region has above-described CD137-binding activity dependent on a small molecule compound.

In one embodiment, the anti-CD137 antigen-binding molecules or antibodies of the present disclosure comprise the following variable region and constant region: a variable region comprising the above-described HVR, heavy chain variable region, and/or light chain variable region; and the above-described variant Fc region. In one preferred embodiment, the anti-CD137 antigen-binding molecules or antibodies of the present disclosure may be any one anti-CD137 antibody selected from the antibodies described in Table 52.

In a further aspect, the present disclosure provides antigen-binding molecules or antibodies binding to the same epitope on CD137 as the anti-CD137 antigen-binding molecules or antibodies provided herein, in the presence of a low-molecular weight compound (e.g., in the presence of 10 micromolar or more, 50 micromolar or more, 100 micromolar or more, 150 micromolar or more, 200 micromolar or more, or 250 micromolar or more of the low-molecular weight compound). For example, in a certain embodiment, those antigen-binding molecules or antibodies are provided that bind to the same epitope with the anti-CD137 antigen-binding molecules or antibodies comprising A375/B167, A372/B040, A356/B040, A486/B167, A487/B167, A488/B226, A489/B223, A548/B376, A551/B256, A551/B379, A555/B379, A548/B256, and/or A549/B167 described in Table 17, as a combination of heavy chain variable region/light chain variable region. In one embodiment, the anti-CD137 antigen-binding molecules or antibodies of the present disclosure having CD137 binding activity that is dependent on antigen-binding activity dependent on a small molecule compound recognize an epitope formed by a complex formed from the antigen (e.g., CD137) and the low-molecular weight compound (e.g., ATP).

In a further aspect, the present disclosure provides antigen-binding molecules or antibodies that compete for the binding to CD137 with the anti-CD137 antigen-binding molecules or antibodies provided herein, in the presence of a low-molecular weight compound (e.g., in the presence of 10 micromolar or more, 50 micromolar or more, 100 micromolar or more, 150 micromolar or more, 200 micromolar or more, or 250 micromolar or more of the low-molecular weight compound). For example, in a certain embodiment, these compete for the site of binding to CD137 with the anti-CD137 antigen-binding molecules or antibodies comprising A375/B167, A372/B040, A356/B040, A486/B167, A487/B167, A488/B226, A489/B223, A548/B376, A551/B256, A551/B379, A555/B379, A548/B256, and/or A549/B167 described in Table 17, as a combination of heavy chain variable region/light chain variable region.

In a further aspect of the present disclosure, an anti-CD137 antigen-binding molecule or antibody according to any of the above embodiments is a monoclonal antibody, including a chimeric, humanized or human antibody. In one embodiment, an anti-CD137 antibody is an antibody fragment, e.g., a Fv, Fab, Fab', scFv, diabody, or F(ab')2 fragment. In another embodiment, the antibody is a full length antibody, e.g., an intact IgG1 antibody or other antibody class or isotype as defined herein.

In a further aspect, an anti-CD137 antigen-binding molecule or antibody according to any of the above embodiments may incorporate any of the features, singly or in combination, as described in Sections 1-7 below:

1. Agonistic Activity of Anti-CD137 Antigen-Binding Molecule or Antibody

In a specific embodiment, the anti-CD137 antigen-binding molecule or antibody in the present disclosure has CD137 agonistic activity. CD137 signaling not only stimulates IFN-γ secretion and proliferation of NK cells (Buechele et al., 2012; Lin et al., 2008; Melero et al., 1998), but also enhances their survival and DC activation indicated by upregulation of co-stimulatory molecules and cytokine secretion (Choi et al., 2009; Futagawa et al., 2002; Wilcox et al., 2002). However, CD137 is best characterized as a co-stimulatory molecule that regulates TCR-induced activation in both CD4+ and CD8+ subsets of T cells. In combination with TCR activation, anti-CD137 agonist antibodies enhance T cell proliferation, stimulate lymphokine secretion, and reduce the sensitivity of T lymphocytes to activation-induced cell death (reviewed in Snel et al., 2011). Of those phenomena, the physiological phenomena observed after CD137 signaling on T cells are mediated by downstream signals activated by CD137 signaling, such as TRAF2, TRAF1, in particular NF-kappaB, JNK, Erk, Akt, survivin, Bcl-XL, and/or Bcl-2 (Ward-Kavanagh et al., Immunity, 44: 1005 (2016)).

In one embodiment, the "anti-CD137 agonistic antigen-binding molecule" or "anti-CD137 agonistic antibody" is an antigen-binding molecule or antibody that, by binding to CD137, transduces the CD137 signal, and significantly induces or enhances IFN-gamma secretion, proliferation, and increased survival of NK cells; DC activation indicated by up-regulation of cytokine secretion and co-stimulatory molecules; TCR induction; T cell proliferation; and/or lymphokine secretion. In a different embodiment, the "anti-CD137 agonistic antigen-binding molecule" or "anti-CD137 agonistic antibody" is an antigen-binding molecule or antibody that transduces the CD137 signal by binding to CD137 on T cells, and significantly induces activation of NF-kappaB of the T cells. Further, the antigen-binding molecule or an antibody "shows CD137 agonistic activity" means that any of the above-mentioned physiological phenomena is observed when the antigen-binding molecule or antibody binds to CD137. The method of measuring CD137 agonistic activity is described in detail in the section of "C. Assays" below.

In a specific embodiment, the anti-CD137 antigen-binding molecule or antibody in the present disclosure has small molecule compound-dependent CD137 agonistic activity. In one non-limiting embodiment, the CD137 agonistic activity of the anti-CD137 antigen binding molecule or antibody against CD137 in the presence of a small molecule compound is higher than the CD137 agonistic activity in the absence of the small molecule compound. In a different embodiment, the CD137 agonistic activity of the anti-CD137 antigen binding molecule or antibody in the presence of a high concentration of a small molecule compound is higher compared to the CD137 agonistic activity in the presence of a low concentration of the small molecule compound. In a further embodiment, the CD137 agonistic activity of the anti-CD137 antigen binding molecule or antibody in the presence of a small molecule compound is 2-fold or more, 3-fold or more, 5-fold or more, 10-fold or more, 20-fold or more, 30-fold or more, 50-fold or more, 100-fold or more, 200-fold or more, 300-fold or more, 500-fold or more, 1×103-fold or more, 2×103-fold or more, 3×103-fold or more, 5×103-fold or more, 1×104-fold or more, 2×104-fold or more, 3×104-fold or more, 5×104-fold or more, or 1×105-fold or more, as compared to the CD137 agonistic activity in the absence of the small molecule compound.

Any suitable concentration may be selected as the concentration of the small molecule compound as long as a difference in the binding activity of the anti-CD137 antigen-binding molecule or antibody is detected. In one embodiment, the anti-CD137 antigen-binding molecule or antibody transduces the CD137 signal by binding to CD137 on the cell surface. Therefore, one skilled in the art would understand that the anti-CD137 antigen-binding molecule or antibody that has small molecule compound-dependent CD137 binding activity has CD137 agonistic activity dependent on the small molecule compound. However, on the other hand, since the methods for measuring binding activity and agonistic activity are different, one skilled in the art would understand that the concentration of a small molecule compound for which a difference in binding activity is detected can be different from the concentration of the small molecule compound for which a difference in agonistic activity is detected (e.g., for an anti-CD137 antigen-binding molecule or antibody whose CD137 binding activity in the presence of a small molecule compound at 10 μM is 2-fold or more compared to the CD137 binding activity in the absence of the small molecule compound, the CD137 agonistic activity (assay value) in the presence of the small molecule compound at 10 μM can be less than 2-fold compared to the CD137 agonistic activity (assay value) in the absence of the small molecule compound). Furthermore, it would be understood by those skilled in the art that the determination of agonistic activity can vary depending on the assay of CD137 agonistic activity (refer to "C. Assays").

In one embodiment, the anti-CD137 antigen-binding molecule or antibody (i) shows agonistic activity towards CD137 in the presence of a small molecule compound at 10 μM, 50 μM, 100 μM, 150 μM, 200 μM, or 250 μM, and (ii) shows substantially no agonistic activity towards CD137 in the absence of the small molecule compound, or has low agonistic activity towards CD137 in the absence of the small molecule compound (compared to the presence of the small molecule compound).

In one embodiment, when the agonistic activity of the anti-CD137 antigen-binding molecule or antibody is evaluated by "a) Agonistic activity assay (PBMC)" explained in detail in "C. Assays", the anti-CD137 antigen-binding molecule or antibody (i) exhibits an agonistic activity towards CD137 in the presence of a small molecule compound at 250 μM, and (ii) has a low agonistic activity towards CD137 in the absence of the small molecule compound (compared to the presence of the small molecule compound). In a further embodiment, the anti-CD137 antigen-binding molecule or antibody (i) shows an agonistic activity towards CD137 in the presence of a small molecule compound at 250 μM, and (ii) shows substantially no agonistic activity towards CD137 in the absence of the small molecule compound.

In one embodiment, when the agonistic activity of the anti-CD137 antigen-binding molecule or antibody is evaluated by "b) Agonistic activity assay (reporter gene assay)" explained in detail in "C. Assays", the anti-CD137 antigen-binding molecule or antibody (i) exhibits agonistic activity towards CD137 in the presence of 10 μM, 50 μM, 100 μM, 150 μM, 200 μM, or 250 μM of a small molecule compound, and (ii) has substantially no agonistic activity towards CD137 or has a lower agonistic activity in the absence of the small molecule compound (as compared to that in the presence of the small molecule compound).

Antibody concentrations in the reporter gene assay may be arbitrarily selected, for example, the final concentration of antibody is 0, 0.001, 0.01, 0.1, 1, or 10 μg/mL. In a preferred embodiment, the final concentration of antibody is 0.1 μg/mL or 1 μg/mL.

In one embodiment, when the final concentration of antibody is 0.1 μg/mL in "b) Agonistic activity assay (reporter gene assay)" explained in detail in "C. Assays", (i) the CD137 agonistic activity (relative light unit) of the anti-CD137 antigen-binding molecule or antibody in the presence 10 μM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound.

In one embodiment, when the final concentration of antibody is 0.1 µg/mL in "b) Agonistic activity assay (reporter gene assay)" explained in detail in "C. Assays", (i) the CD137 agonistic activity (relative light unit) of the anti-CD137 antigen-binding molecule or antibody in the presence 100 µM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound. In one embodiment, when the final concentration of antibody is 0.1 µg/mL in "b) Agonistic activity assay (reporter gene assay)" explained in detail in "C. Assays", (i) the CD137 agonistic activity (relative light unit) of the anti-CD137 antigen-binding molecule or antibody in the presence 250 µM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound. In any of the above embodiments, further, 0.1 µg/mL of an anti-CD137 antigen-binding molecule or antibody exhibits substantially no CD137 agonistic activity in the absence of the small molecule compound.

In one embodiment, when the final concentration of antibody is 1 µg/mL in "b) Agonistic activity assay (reporter gene assay)" explained in detail in "C. Assays", (i) the CD137 agonistic activity (relative light unit) of the anti-CD137 antigen-binding molecule or antibody in the presence 10 µM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound. In one embodiment, when the final concentration of antibody is 0.1 µg/mL in "b) Agonistic activity assay (reporter gene assay)" explained in detail in "Assays" (i) the CD137 agonistic activity (relative light unit) of the anti-CD137 antigen-binding molecule or antibody in the presence 100 µM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound. In one embodiment, when the final concentration of antibody is 0.1 µg/mL in "b) Agonistic activity assay (reporter gene assay)" explained in detail in "C. Assays", (i) the CD137 agonistic activity (relative light unit) of the anti-CD137 antigen-binding molecule or antibody in the presence 250 µM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound. In any of the above embodiments, further, 1 µg/mL of an anti-CD137 antigen-binding molecule or antibody exhibits substantially no CD137 agonistic activity in the absence of the small molecule compound.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson et al. Nat. Med. 9:129-134 (2003). For a review of scFv fragments, see, e.g., Pluckthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005)

and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab (registered trademark) technology; U.S. Pat. No. 7,041,870 describing K-M MOUSE (registered trademark) technology, and U.S. Patent Application Publication No. US 2007/0061900, describing VelociMouse (registered trademark) technology). Human variable regions from intact antibodies generated by such animals may be further modified, e.g., by combining with a different human constant region. Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boemer et al., J. Immunol., 147: 86 (1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the present disclosure may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, NJ, 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, NJ, 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann.

Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

The antigen-binding molecules or antibodies having antigen-binding activity dependent on a low-molecular weight compound of the present disclosure may be selected by conducting screening over a library of antigen-binding molecules. As such library, the above-described combinatorial libraries may be used. The library of antigen-binding molecules may be with unbiased repertoire of antigen-binding molecules (naive library) or may be with biased repertoire of antigen-binding molecules. Examples of the latter type of library include a library of antigen-binding molecules to which binding activity towards a specified compound is conferred in advance. In a certain embodiment, an antigen-binding molecule library is a library of antigen-binding molecules to which amino acid alteration(s) to confer binding activity towards a specified compound is introduced in advance. Examples of such type of library include libraries described, for example, in the International Publication, WO 2015/083764.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for CD137 and the other is for any other antigen. In certain embodiments, bispecific antibodies may bind to two different epitopes of CD137. Bispecific antibodies may also be used to localize cytotoxic agents to cells which express CD137. Bispecific antibodies can be prepared as full length antibodies or antibody fragments.

In one embodiment, the anti-CD137 antigen-binding molecules or antibodies of the present disclosure are bi-specific antibodies, one arm of them having CD137 binding activity dependent on a small molecule compound and another arm of them binding to an antigen different from CD137. The "antigen" different from CD137 is not particularly limited in the structure. In other words, the antigen can be inorganic or organic substances. Exemplary antigens are disclosed in the present specification (e.g., "IV. Compositions and methods (antigen-binding molecules whose binding activity to antigens changes depending on the concentration of a small molecule compound)", "B. Antigen"). In one embodiment, the antigens are preferably antigens expressed in cancer cells, immune cells, stroma cells, or such in cancer tissues or inflammatory tissues.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (scFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting Fab" or "DAF" comprising an antigen binding site that binds to CD137 as well as another, different antigen (see, US 2008/069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 5

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be analyzed to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion of an enzyme (e.g. for ADEPT) or a polypeptide which increases the plasma half-life of the antibody to the N- or C-terminus of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the present disclosure may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about +/−3 amino acids upstream or downstream of position 297, i.e., between positions 294 and 300, due to minor sequence variations in antibodies. Such fucosylation variants may have improved ADCC function.

See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc region variants

In certain embodiments, one or more amino acid modifications may be introduced into the Fc region of an antibody provided herein, thereby generating an Fc region variant (which may be also called "an altered Fc region"). The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the present disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks Fc gamma R binding (hence likely lacking ADCC activity), but retains FcRn binding activity. The primary cells for mediating ADCC, NK cells, express Fc gamma RIII only, whereas monocytes express Fc gamma RI, Fc gamma RII and Fc gamma RIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTITM non-radioactive cytotoxicity assay for flow cytometry (CellTechnology, Inc. Mountain View, CA; and CytoTox 96 (registered trademark) non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103: 2738-2743 (2004)). FcRn binding and in vivo clearance/half life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more amino acid positions 265, 269, 270, 297 and 327, including the so-called "DANA" Fc mutant with substitution of residues 265 and 297 to alanine (U.S. Pat. No. 7,332,581).

Certain antibody variants with increased or decreased binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either increased or decreased) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half lives and increased binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which increase binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

In one embodiment, binding activity towards each human Fc-gamma receptor (Fc-gamma R) of an antibody Fc region (including a variant Fc region (the same applies hereafter)) may be measured by a ligand-capturing method using, for example, BIACORE (registered trademark) T200, which rely upon surface plasmon resonance analysis methods as the measurement principle.

Details of an exemplary method of measuring binding activity of antibody Fc region towards various human Fc-gamma receptors (Fc-gamma Rs) are described below. In one embodiment, binding activity of an antibody Fc region towards Fc-gamma R is evaluated using BIACORE (registered trademark) T200. In a preferred embodiment, this measurement is carried out at 25 degrees C., using a measurement buffer 50 mM phosphate, 150 mM NaCl, 0.05 w/v %-P20, pH 7.4. Specifically, about 1000 RU of an antibody comprising a variant Fc region is first captured onto a sensor chip, with CaptureSelect (trademark) Human Fab-lambda Kinetics Biotin Conjugate (ThermoFisher scientific) immobilized as a ligand-capturing molecule. Human Fc-gamma Rs are diluted with the measurement buffer to 8 nM for Fc-gamma RIa and to 1000 nM for other Fc-gamma Rs, and are allowed to bind to the captured antibody. Binding activity of each antibody towards each Fc-gamma R is assessed by calculating amount of bound Fc-gamma R per unit amount of antibody (RU) using Biacore T200 Evaluation Software 2.0. In one embodiment, binding activity of an antibody Fc region towards various human Fc-gamma receptors (Fc-gamma Rs) may be measured by the method described in Example 7-4.

In one preferred embodiment, the Fc-gamma Rs used for the above-described measurement method may be an extracellular domain of an Fc-gamma R prepared by the method described below. First, synthesis of a gene of an extracellular domain of an Fc-gamma R is carried out by a method known to those skilled in the art. For this synthesis, sequences of each Fc-gamma R is prepared based on information registered at the NCBI.

More specifically, the sequence for Fc-gamma RI is prepared based on the sequence of NCBI accession # NM_000566.3, the sequence for Fc-gamma RIIa is prepared based on the sequence of NCBI accession #

NM_001136219.1, the sequence for Fc-gamma RIIb is prepared based on the sequence of NCBI accession # NM_004001.3, and the sequence for Fc-gamma RIIIa is prepared based on the sequence of NCBI accession # NM_001127593.1, and His-tag is added to the C terminus. Polymorphic sites for Fc-gamma RIIa are prepared with reference to J. Exp. Med., 1990, 172, 19-25, and polymorphic sites for Fc-gamma RIIIa are prepared with reference to J. Clin. Invest., 1997, 100, 1059-1070. Obtained gene fragments are inserted into an expression vector for animal cells to prepare expression vectors. The prepared expression vectors are transiently introduced into FreeStyle293 cells (Invitrogen) derived from human embryonic kidney cancer cells and a protein of interest is allowed to be expressed. Culture supernatant is collected and filtered through 0.22 micro-meter filter, and then purified basically through the hereafter described four steps. As the first step, cation exchange column chromatography (SP Sepharose FF) is carried out; as the second step, affinity column chromatography to His tags (HisTrap HP); as the third step, gel filtration column chromatography (Superdex200); and as the fourth step, aseptic filtration. Note that for Fc-gamma RI, anion-exchange column chromatography using Q sepharose FF is carried out as the first step. Concentration of the purified protein is calculated based on absorptivity coefficient, calculated by measuring absorbance at 280 nm using a spectrophotometer and using PACE or such method for the measured values (Protein Science, 1995, 4, 2411-2423).

In one embodiment, binding activity of an antibody Fc region towards human FcRn may be measured by a ligand-capturing method using, for example, BIACORE (registered trademark) T200, which rely upon surface plasmon resonance analysis methods as the measurement principle.

Details of an exemplary method of measuring binding activity of antibody Fc region towards human FcRn are described below. In one embodiment, binding activity of an antibody Fc region towards human FcRn is evaluated using BIACORE (registered trademark) T200. In a preferred embodiment, this measurement is carried out at 25 degrees C., using a measurement buffer 50 mM phosphate, 150 mM NaCl, 0.05 w/v %-P20, pH 6.0. Specifically, about 400 RU of an antibody comprising an Fc region is first captured onto a sensor chip, onto which CaptureSelect (trademark) Human Fab-lambda Kinetics Biotin Conjugate (ThermoFisher scientific) is immobilized as a ligand-capturing molecule, and then human FcRn diluted using the measurement buffer is allowed to bind thereto. Binding activity of each antibody towards FcRn is assessed by calculating KD (M) using Steady state model in Biacore T200 Evaluation Software 2.0. In one preferred embodiment, the human FcRn protein used in this measurement is prepared according to the method described in Reference Example 2 of WO2010107110. In one embodiment, binding activity of an antibody Fc region towards various human FcRn may be measured by the method described in Example 7-5.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof.

Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-CD137 antigen-binding molecule or antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp2/0 cell). In one embodiment, a method of making an anti-CD137 antigen-binding molecule or antibody is provided, wherein the method comprises culturing a host cell comprising a nucleic acid encoding the antibody, as provided above, under conditions suitable for expression of the anti-CD137 antigen-binding molecule or antibody, and optionally recovering the antibody from the host cell (or host cell culture medium).

For recombinant production of an anti-CD137 antigen-binding molecule or antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, NJ), pp. 255-268 (2003).

C. Assays

Anti-CD137 antigen-binding molecules or antibodies provided herein may be identified, screened for, or characterized for their physical/chemical properties and/or biological activities by various assays known in the art.

1. Binding Assays and Other Assays

In one aspect, an antigen-binding molecule or antibody of the present disclosure is tested for its antigen binding activity, e.g., by known methods such as ELISA, Western blot, etc.

In another aspect, competition assay in the presence of a small molecule compound may be utilized in order to identify an antigen-binding molecule or antibody that competes for the binding to CD137 with the anti-CD137 antigen-binding molecules or antibodies comprising A375/B167, A372/B040, A356/B040, A486/B167, A487/B167, A488/B226, A489/B223, A548/B376, A551/B256, A551/B379, A555/B379, A548/B256, and/or A549/B167 described in Table 17 as a combination of heavy chain variable region/light chain variable region in the presence of a low-molecular weight compound (e.g., in the presence of 10 micromolar or more, 50 micromolar or more, 100 micromolar or more, 150 micromolar or more, 200 micromolar or more, or 250 micromolar or more of the low-molecular weight compound). In certain embodiments, such competing antigen-binding molecules or antibodies bind to the same epitope (e.g., linear epitope or conformational epitope) that is bound by the anti-CD137 antigen-binding molecules or antibodies comprising A375/B167, A372/B040, A356/B040, A486/B167, A487/B167, A488/B226, A489/B223, A548/B376, A551/B256, A551/B379, A555/B379, A548/B256, and/or A549/B167 described in Table 17 as a combination of heavy chain variable region/light chain variable region. Detailed exemplary methods for mapping an epitope to which an antigen-binding molecule or antibody binds are provided in Morris (1996) "Epitope Mapping Protocols," in Methods in Molecular Biology vol. 66 (Humana Press, Totowa, NJ). In one embodiment, the anti-CD137 antigen-binding molecules or antibodies of the present disclosure having CD137 binding activity that is dependent on antigen-binding activity dependent on a small molecule compound recognize an epitope formed by a complex formed from the antigen (e.g., CD137) and the low-molecular weight compound (e.g., ATP).

In an exemplary competition assay using an antibody, immobilized CD137 is incubated in the presence of a low-molecular weight compound (e.g., in the presence of 10 micromolar or more, 50 micromolar or more, 100 micromolar or more, 150 micromolar or more, 200 micromolar or more, or 250 micromolar or more of the low-molecular weight compound) in a solution containing a first labeled antibody binding to CD137 (e.g., the anti-CD137 antibody comprising A375/B167, A372/B040, A356/B040, A486/B167, A487/B167, A488/B226, A489/B223, A548/B376, A551/B256, A551/B379, A555/B379, A548/B256, and/or A549/B167 described in Table 17 as a combination of heavy chain variable region/light chain variable region) and a second unlabeled antibody that is tested for the ability to compete for the binding to CD137 with the first antibody. The second antibody may be present in a hybridoma supernatant. As a control, immobilized CD137 is incubated in a solution comprising the first labeled antibody but not the second unlabeled antibody. After incubation under conditions permissive for binding of the first antibody to [CD137, excess unbound antibody is removed, and the amount of label associated with immobilized CD137 is measured. If the amount of label associated with immobilized CD137 is substantially reduced in the test sample relative to the control sample, then that indicates that the second antibody is competing with the first antibody for binding to CD137. See Harlow and Lane (1988) Antibodies: A Laboratory Manual ch.14 (Cold Spring Harbor Laboratory, Cold Spring Harbor, NY). Those skilled in the art would understand that the assay can be carried out similarly to antigen-binding molecules other than antibodies.

2. Activity assays

In one aspect, assays are provided for identifying biological activity of anti-CD137 antigen-binding molecules or antibodies having the biological activity. Biological activity may include, e.g. CD137 agonist activity; plasma half-life; anti-tumor activity; and low or suppressed systemic reaction in tissues other than tumors. Antigen-binding molecules or antibodies having such biological activity in vivo and/or in vitro are also provided.

In certain embodiments, an antigen-binding molecule (for example, an anti-CD137 antigen-binding molecule) or antibody of the present disclosure is tested for such biological activity.

a) Agonistic activity assay (PBMC)

In one embodiment, the agonistic activity towards CD137 is measured by contacting CD137-expressing cells with an anti-CD137 antigen-binding molecule or antibody in a solution to which a small molecule compound is added or not added. In one embodiment, the agonistic activity towards CD137 in a solution in which the small molecule compound is added, and the agonistic activity towards CD137 in a solution in which the small molecule compound is not added, are respectively evaluated by the amount of cytokine production (e.g., amount of IL-2, IFN-γ, and/or IL-6 production) which is measured within 18 hours, 24 hours, 36 hours, 48 hours, or 72 hours after a CD137-expressing cell and the CD137 antigen-binding molecule or antibody are contacted in the solution. In one embodiment, the solution in which the small molecule compound is added is adjusted such that the concentration of the small molecule compound after adjustment is 10 µM, 50 µM, 100 µM, 150 µM, 200 µM, or 250 µM. In a further embodiment, the CD137-expressing cells to be used are isolated human peripheral blood mononuclear cells (PBMCs), or T cells expanded from the isolated human PBMCs.

In one embodiment, human PBMCs which are isolated from blood collected from healthy individuals by centrifugation at 400×g for 30 minutes at room temperature are used. Preferably, human PBMCs isolated in the following two steps are used. In the first step, Leucosep (Greiner Bio-One) supplemented with Ficoll-Paque PLUS (GE Healthcare) is centrifuged at 1000×g for 1 minute at room temperature, and then blood diluted with PBS is added, and centrifuged at 400×g for 30 minutes at room temperature. In the second step, after the buffy coat is collected from the tube after centrifugation, it is washed with 60 mL of PBS (Wako).

Details of an exemplary method of measuring CD137 agonistic activity using human PBMCs is described below. It is noted that even though the following example uses illustratively ATP as a small molecule compound, this does not exclude other small molecule compounds. In one embodiment, the isolated human PBMCs are diluted to a cell density 5×106/mL with culture medium (5% human serum (SIGMA), 95% AIM-V (Thermo Fischer Scientific)). Then, the isolated human PBMCs are contacted with an anti-human CD3ε antibody and/or an anti-human CD28 antibody, whereby CD137 expression is induced in the human PBMCs. Preferably, 50 µL of 0.04 µg/mL anti-human CD3ε antibody (BD Co., clone SP34) and 20 µg/mL anti-human CD28 antibody (BD, clone: CD28.2) diluted with culture medium is added to the isolated human PBMCs (100 µL at cell density 5×106/mL).

The human PBMC to which anti-human CD3ε antibody and/or anti-human CD28 antibodies were added are then further added with (i) culture medium with or without ATP; and (ii) an anti-CD137 antigen-binding molecule or an antibody. Preferably, 25 µL of the culture medium with or without ATP, is added. Preferably, 25 µL of the anti-CD137 antigen binding molecule or antibody at 40 µg/mL is added. More preferably, the above (i) and (ii) are added about 6 hours after contacting human PBMCs with the anti-human CD3ε antibody and/or the anti-human CD28 antibody. In one embodiment, preferably, the amount of IL-2 production is measured prior to the amount of IFN-γ production. In one embodiment, the amount of IL-2 production is measured within about 24 hours after contacting human PBMCs with the anti-human CD3ε antibody and/or the anti-human CD28 antibody. Preferably, the amount of IL-2 production is measured about 24 hours after contacting human PBMCs with the anti-human CD3ε antibody and/or anti-human CD28 antibody, and about 18 hours after adding the anti-CD137 antigen-binding molecule or antibody.

In another embodiment, the amount of IFN-γ production is measured within about 48 hours after contacting human PBMCs with the anti-human CD3ε antibody and/or anti-human CD28 antibody. Preferably, the amount of IFN-γ production is measured about 48 hours after contacting human PBMCs with the anti-human CD3ε antibody and/or the anti-human CD28 antibody, and about 42 hours after adding the anti-CD137 antigen-binding molecule or antibody. In one embodiment, the amount of IL-2 production and/or the amount of IFN-γ production are/is determined by measuring the amount of IL-2 production and/or the amount of IFN-γ production in the collected culture supernatant. In one embodiment, the human PBMCs added with the anti-human CD3ε antibody and/or anti-human CD28 antibody are left to stand in a 5% CO2 incubator at 37° C. until all measurements are completed.

Details of a further exemplary method of measuring CD137 agonistic activity using human PBMCs are described below. Isolated human PBMCs are diluted to a cell density of 5×106/mL with culture medium (5% human serum (SIGMA), 95% AIM-V (Thermo Fischer Scientific)). Then, the human PBMCs are adjusted to a cell density of 5×106/mL, and 100 µL each of this is seeded into a 96-well multiwell plate (flat bottom, with lid) (Corning). After that, the human PBMCs are subjected to the operation of inducing CD137 expression. For example, CD137 expression in human PBMCs is induced by adding 50 µL, of 0.04 µg/mL anti-human CD3ε antibody (BD Co., clone SP34) and 20 µg/mL anti-human CD28 antibody (BD, clone: CD28.2) diluted with culture medium.

After CD137 expression is induced in human PBMCs, the plate is shaken and left to stand for 6 hours at 37° C. in a 5% CO2 incubator. Then, 25 µL each of 2 mM ATP (SIGMA) diluted with medium or medium only without ATP, and 25 µL of each antibody at 40 µg/mL are added to each well, and the plate is then shaken and left to stand for 18 hours at 37° C. in a 5% CO2 incubator. Then, a part of the culture supernatant is collected, and using this, the amount of IL-2 contained in the culture supernatant is quantified using Human IL-2 DuoSet ELISA kit (R&D systems) or Human IL-2 ELISA Set (BD Biosciences). The plate after the collection of the culture supernatant is again left to stand for 24 hours at 37° C. again in a 5% CO2 incubator. Then, a part of the culture supernatant is collected, and the amount of IFN-γ contained in the culture supernatant is quantified using Human IFN-γ DuoSet ELISA kit (R&D systems) or Human IFN-γ ELISA Development Kit (PeproTech). ELISA is basically performed according to the protocol attached to the kit. For the Human IL-2 DuoSet ELISA kit (R&D systems) and Human IFN-γ DuoSet ELISA kit (R&D systems), color development and color termination are carried out according to the protocol using a substrate solution (R&D systems) containing $H_2O_2$ and tetramethylbenzidine and 1N H2SO4 (Wako). For the Human IL-2 ELISA Set (BD Biosciences), color termination is carried out using 1N H2SO4 (Wako).

For the IFN-γ ELISA Development Kit (PeproTech), color development and color termination are carried out using TMB Chromogen Solution (Thermo Fischer Scientific) and 1N H2SO4 (Wako). Then, the measurement of absorbance is carried out with EnVision (PerkinElmer), and the amounts (pg/mL) of IL-2 and IFN-γ in the culture supernatant are respectively calculated using a calibration curve prepared according to the protocol. In this PBMC assay, the CD137 agonist activity can be expressed as a fold change of the amounts of IL-2 and IFN-γ in the culture supernatant relative to those of a negative control antibody (an antibody that does not bind to CD137). In one embodiment, the CD137 agonistic activity is measured according to the methods described in Examples 5-5-1 and 5-5-2.

In one embodiment, when the agonistic activity towards CD137 is evaluated by the amount of cytokine production (e.g., amount of IL-2, IFN-γ, and/or IL-6 production) in human PBMC assay, an anti-CD137 antigen-binding molecule or antibody can be judged as exhibiting agonistic activity towards CD137 in the presence of a small molecule compound if the amount of cytokine production in the presence of 10 μM, 50 μM, 100 μM, 150 μM, 200 μM, or 250 μM of the small molecule compound when the anti-CD137 antigen-binding molecule or an antibody is added is 1.01-fold or more, 1.02-fold or more, 1.03-fold or more, 1.05-fold or more, 1.06-fold or more, 1.07-fold or more, 1.08-fold or more, 1.09-fold or more, 1.1-fold or more, 1.11-fold or more, 1.12-fold or more, 1.13-fold or more, 1.14-fold or more, or 1.15-fold or more, 1.5-fold or more, 2-fold or more, or 3-fold or more, as compared to the amount of cytokine production when the negative control antibody is added.

In one embodiment, when the agonistic activity towards CD137 is evaluated by the amount of IL-2 production in human PBMC assay, an anti-CD137 antigen-binding molecule or antibody can be judged as exhibiting agonistic activity towards CD137 in the presence of a small molecule compound if the amount of IL-2 production in the presence of 10 μM, 50 μM, 100 μM, 150 μM, 200 μM, or 250 μM of the small molecule compound when the anti-CD137 antigen-binding molecule or an antibody is added is 1.01-fold or more, 1.02-fold or more, 1.03-fold or more, or 1.05-fold or more, and is 1.05-fold or more in a preferred embodiment, as compared to the amount of IL-2 production when a negative control antibody is added. In one embodiment, when the agonistic activity towards CD137 is evaluated by the amount of IFN-γ production in human PBMC assay, an anti-CD137 antigen-binding molecule or an antibody can be judged as exhibiting agonistic activity towards CD137 in the presence of a small molecule compound if the amount of IFN-γ production in the presence of 10 μM, 50 μM, 100 μM, 150 μM, 200 μM, or 250 μM of the small molecule compound when the anti-CD137 antigen-binding molecule or an antibody is added is 1.1-fold or more, 1.11-fold or more, 1.12-fold or more, 1.13-fold or more, 1.14-fold or more, or 1.15-fold or more, and is 1.15 folds or more in a preferred embodiment, as compared to the amount of IFN-γ production when a negative control antibody is added.

In a further embodiment, from among the anti-CD137 antigen-binding molecules or antibodies judged to exhibit agonistic activity towards CD137 in the presence of the small molecule compound in the above-mentioned comparison with the negative control, antibodies to be judged as showing no CD137 agonistic activity or having lower CD137 agonistic activity in the absence of the small molecule compound (compared to that of the presence of the small molecule compound) are further determined. Specifically, when the following (ii) is greater than (i), the anti-CD137 antigen-binding molecule or antibody is judged as showing no CD137 agonist activity or having lower CD137 agonist activity in the absence of the small molecule compound:

(i) The amount of cytokine production in the absence of the small molecule compound when the anti-CD137 antigen-binding molecule or antibody is added]/The amount of cytokine production in the absence of the small molecule compound when the negative control antibody is added]

(ii) The amount of cytokine production in the presence of the small molecule compound when the anti-CD137 antigen-binding molecule or antibody is added]/The amount of cytokine production in the presence of the small molecule compound when the negative control antibody is added]

In a different embodiment, when the CD137 agonistic activities of a first anti-CD137 antigen-binding molecule or antibody and a second anti-CD137 antigen-binding molecule or antibody are compared using the amount of cytokine production (e.g., the amount of IL-2, IFN-γ, and/or IL-6 production) in human PBMC assay, a first anti-CD137 antigen-binding molecule or antibody can be judged as having a higher agonistic activity than a second anti-CD137 antigen-binding molecule or antibody if (i) the amount of cytokine production when the first anti-CD137 antigen-binding molecule or antibody is added in the presence of 10 μM, 50 μM, 100 μM, 150 μM, 200 μM, or 250 μM of a small molecule compound is 1.01-fold or more, 1.02-fold or more, 1.03-fold or more, 1.04-fold or more, 1.05-fold or more, 1.06-fold or more, 1.07-fold or more, 1.08-fold or more, 1.09-fold or more, 1.1-fold or more, 1.11-fold or more, 1.12-fold or more, 1.13-fold or more, 1.14-fold or more, or 1.15-fold or more, 1.5-fold or more, 2-fold or more, or 3-fold or more, as compared to (ii) the amount of cytokine production when the second anti-CD137 antigen-binding molecule or antibody is added under the same conditions.

In one embodiment, when the agonistic activity towards CD137 is evaluated by the amount of IL-2 production in human PBMC assay, a first anti-CD137 antigen-binding molecule or antibody can be judged as having a higher agonistic activity than a second anti-CD137 antigen-binding molecule or antibody if (i) the amount of cytokine production when the first anti-CD137 antigen-binding molecule or antibody is added in the presence of 10 μM, 50 μM, 100 μM, 150 μM, 200 μM, or 250 μM of a small molecule compound is 1.01-fold or more, 1.02-fold or more, 1.03-fold or more, or 1.04-fold or more, or is 1.04-fold or more in a preferable embodiment, as compared to (ii) the amount of IL-2 production when the second anti-CD137 antigen-binding molecule or antibody is added under the same conditions.

In one embodiment, when the agonistic activity towards CD137 is evaluated by the amount of IFN-γ production in human PBMC assay, a first anti-CD137 antigen-binding molecule or antibody can be judged as having a higher agonistic activity than a second anti-CD137 antigen-binding molecule or antibody if (i) the amount of cytokine production when the first anti-CD137 antigen-binding molecule or antibody is added in the presence of 10 µM, 50 µM, 100 µM, 150 µM, 200 µM, or 250 µM of a small molecule compound is 1.05-fold or more, 1.06-fold or more, 1.07-fold or more, 1.08-fold or more, 1.09-fold or more, or 1.1-fold or more, or is 1.1-fold or more in a preferable embodiment, as compared to (ii) when the second anti-CD137 antigen-binding molecule or antibody is added under the same conditions. In one embodiment, the first anti-CD137 antigen-binding molecule or antibody is an antigen-binding molecule or an antibody comprising the parent Fc region, and the second anti-CD137 antigen-binding molecule is an antigen-binding molecule or antibody comprising a variant Fc region.

In one embodiment, the method described in Examples 5-5-1 and 5-5-2 may be used to measure CD137 agonistic activity using human PBMCs, and the method described in Example 2-6 may be used to measure CD137 agonistic activity using T cells expanded from the isolated human PBMCs.

In one embodiment, agonistic activity towards CD137 may be measured by contacting CD8-positive or CD4-positive T cells isolated from human PBMCs with an anti-CD137 antigen-binding molecule or antibody, in a solution to which a small molecule compound is added or not added. At this time, FcγRIIb-expressing cells may be further added to the solution. Alternatively, agonistic activity towards CD137 may be measured by contacting B cells (which may be isolated from human PBMCs, or a known B cell line may be used) with an anti-CD137 antigen-binding molecule or antibody. In one embodiment, the agonistic activity towards CD137 may be evaluated by the amount of cytokine production (for example, amounts of IL-2, IFN-γ and/or the amount of IL-6 production) that is measured after contacting, in a solution, CD8-positive T cells, CD4-positive T cells, or B cells with an anti-CD137 antigen-binding molecule or antibody.

In one embodiment, agonistic activity assays using human peripheral blood mononuclear cells (PBMCs) are isolated from blood collected from healthy individuals. Thus, in any of the above embodiments, it would be understood by those skilled in the art that the assay results using the assays may differ by each blood sample donor. Considering this point, antibodies whose CD137 agonistic activity is not exhibited for a part or a majority of human PBMCs isolated from multiple donors may not be judged to exhibit CD137 agonistic activity, even though the criteria for agonistic activity are met in another part of human PBMCs. Furthermore, when an assay according to the above-described method is performed on human PBMCs isolated from a plurality of donors and criteria for CD137 agonistic activity are met in a majority of the donors, it may be judged that CD137 agonistic activity is exhibited. Alternatively, when an assay according to the above-described method is performed on human PBMCs isolated from a plurality of donors, the average or median of the assay values (e.g., amounts of IL-2, IFN-γ, and/or IL-6 production) may be used to determine the presence or absence of CD137 agonistic activity. In one embodiment, when the assay is performed according to the above method on human PBMCs isolated from a plurality of donors, the number of donors is, for example, 2 or more, 3 or more, 4 or more, 5 or more, 10 or more, 15 or more, or 20 or more.

b) Agonistic Activity Assay (Reporter Gene Assay)

In one embodiment, the agonistic activity towards CD137 is evaluated by a reporter gene assay in a solution in which a small molecule compound is added, or not added. In one embodiment, the agonistic activity towards CD137 in a solution in which the small molecule compound is added, and the agonistic activity towards CD137 in a solution in which the small molecule compound is not added, are respectively evaluated by a luciferase luminescence signal measured after contacting T cells expressing the NF-kappaB-luciferase reporter construct and CD137 with an anti-CD137 antigen-binding molecule, and left to stand a certain time, in the respective solution. In one embodiment, the solution in which the small molecule compound is added is adjusted such that the small molecule compound concentration after adjustment is 10 µM, 50 µM, 100 µM, 150 µM, 200 µM, or 250 µM. T cells expressing the NF-kappaB-luciferase reporter construct and CD137 are preferably, GloResponse™ NF-kappaB-Luc2/4-1BB Jurkat cell line (Promega, CS196004).

Details of an exemplary method of measuring CD137 agonistic activity using a reporter gene assay are described below. In the following examples, ATP is used as an example of the small molecule compound, but other small molecule compounds are not excluded. In one embodiment, first, FcγRIIB-expressing cells are adjusted to a concentration of 5×104/mL with medium (CHO culture medium (90% Ham's F12, 10% FBS)), and left to stand overnight at 37° C. in a 5% CO2 incubator. In one embodiment, as FcgRIIB-expressing cells, not only cells forced to express FcgRIIB, but also cell lines that endogenously express FcgRIIB, such as B cell lines, B cells isolated from a living body, or the like can be used. In a preferred embodiment, the FcγRIIB-expressing cells are FcγRIIB CHO-K1 cells (Promega). Next, after the medium is removed by aspiration, GloResponse™ NF-kappaB-Luc2/4-1BB Jurkat cell line (hereinafter, "4-1BB Jurkat") adjusted to 2×106/mL with different medium (99% RPMI, 1% FBS) is added. In a preferred embodiment, per 200 µL of FcγRIIB-expressing cells adjusted with medium, 25 µL of GloResponse™ NF-kappaB-Luc2/4-1BB Jurkat cell line cells adjusted with medium is added. Subsequently, 25 µL each of anti-CD137 antigen-binding molecule diluted with the above-mentioned medium (99% RPMI, 1% FBS) to become a desired concentration (e.g., final concentration of 0, 0.001, 0.01, 0.1, 1, 10 µg/mL) is added, and further, 25 µL of the ATP solution diluted with the above-mentioned medium (99% RPMI, 1% FBS) to become a desired concentration (e.g., final concentration is 0, 10, 50, 100, 150, 200, 250 µM) is added. In one embodiment, the luciferase luminescence signal is measured after standing for 2 hours or less, 4 hours or less, 6 hours or less, 24 hours or less, following the addition of the anti-CD137 antigen-binding molecule to 4-1BB Jurkat. In a preferred embodiment, 4-1BB Jurkat is left to stand at 37° C. for 6 hours in a 5% CO2 incubator. After standing, 75 µL of Bio-Glo reagent is added, and the luminescence is measured with a plate reader. In one preferred embodiment, the Bio-Glo reagent is Bio-Glo Luciferase Assay System (buffer and substrate). In one embodiment, in order to keep the temperature during the reaction constant, the 4-1BB Jurkat may be left to stand at room temperature for 5 minutes, 10 minutes, 15 minutes, or 20 minutes after being removed from the incubator. In a preferable embodiment, the 4-1BB Jurkat is left to stand at room temperature for 15 minutes after being removed from the incubator. In one embodiment, the luminescence value of 4-1BB Jurkat added with an anti-CD137 antigen-binding molecule is divided by the luminescence value of 4-1BB Jurkat not added with the anti-CD137 antigen-binding molecule, and this value is taken as fold induction (relative light unit) and used as index for evaluating the CD137 agonistic activity of each antigen-binding molecule.

A further exemplary method of measuring CD137 agonistic activity using a reporter gene assay is described below. 200 µL, each of FcγRIIB CHO-K1 cells (Promega) adjusted to a concentration of $5\times10^4$/mL with medium is added to each well of a 96-well plate, and left to stand overnight at 37° C. in a 5% CO2 incubator. As culture medium, CHO culture medium (90% Ham's F12, 10% FBS) is used. Then, after the medium is completely removed by aspiration, 25 µL, of GloResponse™ NFBK-Luc2/4-1BB Jurkat cell line adjusted to $2\times10^6$/mL with assay medium (99% RPMI, 1% FBS) is added to each well. Subsequently, 25 µM each of each antigen solution diluted with assay medium to a final concentration of 0, 0.001, 0.01, 0.1, 1, or 10 µg/mL is added, and finally, 25 µL, of ATP solution diluted with assay medium to 0 or 250 µM is added. After the plate is left to stand for 6 hours at 37° C. in a 5% CO2 incubator, it is left to stand at room temperature for 15 minutes, and 75 µL, of Bio-Glo reagent is added to each well. As Bio-Glo reagent, for example, Bio-Glo Luciferase Assay System (buffer and substrate) may be used. Thereafter, the luminescence of each well is measured with a plate reader. The value obtained by dividing the luminescence value of each well by the luminescence value of the well which is not added with any antibody is defined as fold induction. In the reporter gene assay, the CD137 agonistic activity may be evaluated by fold change (relative light unit) of the luminescence of wells added with each antibody against the luminescence amount of wells which are not added with any antibody.

A further exemplary method of measuring CD137 agonistic activity using a reporter gene assay is described below. To each well of a 384-well plate, 10 µL of FcγRIIB CHO-K1 Cells (Promega) adjusted to a concentration of $2\times10^6$/mL with assay medium (99% RPMI, 1% FBS) is added. Subsequently, 10 µL of an antibody solution containing ADP, or an antibody solution containing ATP, or an antibody solution not containing ATP or ADP, is added to each well. 10 µL of GloResponse™ NF-κB-Luc2/4-1BB Jurkat cell line adjusted to $2\times10^6$/mL with the assay medium (99% RPMI, 1% FBS) is then added to each well. The final concentration of ADP is 50 µM and the final concentration of ATP is 50 µM. After the plate is left to stand at 37° C. for 6 hours in a 5% CO2 incubator, it is left to stand at room temperature for 15 minutes, and 30 µL of Bio-Glo reagent is added to each well. As Bio-Glo reagent, Bio-Glo Luciferase Assay System (buffer and substrate) was used. Thereafter, the luminescence of each well is measured with a plate reader. The CD137 agonistic activity may be evaluated by the relative light unit (also called luminescence fold or fold change) of the luminescence of wells added with each antibody against the luminescence of wells which are not added with any antibody.

A further exemplary method of measuring CD137 agonistic activity using a reporter gene assay is described below. To each well of a 384-well plate, 10 µL of FcγRIIB CHO-K1 Cells (Promega) adjusted to a concentration of $4\times10^5$/mL with assay medium (99% RPMI, 1% FBS) is added. Subsequently, 10 µL of an antibody solution containing ADP, or an antibody solution containing ATP, or an antibody solution not containing ATP or ADP, is added to each well. 10 µL of GloResponse™ NF-κB-Luc2/4-1BB Jurkat cell line adjusted to $2\times10^6$/mL with the assay medium (99% RPMI, 1% FBS) is then added to each well. The final concentration of ADP is 10 µM and the final concentration of ATP is 10 µM. After the plate is left to stand at 37° C. for 6 hours in a 5% CO2 incubator, it is left to stand at room temperature for 15 minutes, and 30 µL of Bio-Glo reagent is added to each well. As Bio-Glo reagent, Bio-Glo Luciferase Assay System (buffer and substrate) was used. Thereafter, the luminescence of each well is measured with a plate reader. The CD137 agonistic activity may be evaluated by the relative light unit (also called luminescence fold or fold change) of the luminescence of wells added with each antibody against the luminescence of wells which are not added with any antibody.

In one embodiment, when the agonistic activity towards CD137 is measured using a reporter gene assay, an anti-CD137 antigen-binding molecule or antibody can be judged as exhibiting an agonistic activity towards CD137 in the presence of a small molecule compound if (i) the agonistic activity towards CD137 (relative light unit) in the presence of 10 µM, 50 µM, 100 µM, 150 µM, 200 µM, or 250 µM of the small molecule compound is 1.1-fold or more, 1.2-fold or more, 1.3-fold or more, 1.5-fold or more, 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to (ii) the CD137 agonistic activity (relative light unit) in the absence of the small molecule compound. In one embodiment, the final concentration of the antibody in (i) and (ii) above is 0, 0.001, 0.01, 0.1, 1, or 10 µg/mL, and in a preferred embodiment, it is 0.1 µg/mL or 1 µg/mL.

In a further embodiment, when the anti-CD137 antigen-binding molecule or antibody is added at a specific concentration (for example, at a final concentration of 0.001, 0.01, 0.1, 1, or 10 µg/mL, or 0.1 µg/mL or 1 µg/mL in a preferred embodiment), the anti-CD137 antigen-binding molecule or antibody is judged as exhibiting substantially no CD137 agonistic activity in the absence of a small molecule compound if the fold induction (relative light unit) in the absence of the small molecule compound is 10 or less, 9 or less, 8 or less, or 5 or less in a preferred embodiment, and substantially 1 in a more preferred embodiment. In one embodiment, "fold induction (relative light unit) in the absence of a small molecule compound is substantially 1" means cases when the fold induction (relative light unit) in the absence of a small molecule compound is less than 2-fold, less than 1.9-fold, less than 1.8-fold, less than 1.7-fold, less than 1.6-fold, less than 1.5-fold, less than 1.4-fold, less than 1.3-fold, less than 1.2-fold, or less than 1.1-fold.

c) Plasma Concentration

In one embodiment, the blood kinetics of an anti-CD137 antigen-binding molecule or antibody of the present disclosure are measured and/or compared using human CD137 knock-in mice. Human CD137 knock-in mouse is prepared, for example, by replacing the mouse CD137 gene with the human CD137 gene by introducing a human CD137 gene replacement vector into mouse embryonic stem cells (ES cells). In one embodiment, a CD137 antigen-binding molecule or antibody of the present disclosure is administered through a single intravenous administration into human CD137 knock-in mice, and blood is collected multiple times over time from immediately after administration to around 5 days, 10 days, 15 days, 20 days, 25 days, or 30 days after administration. In a preferred embodiment, the CD137 antigen-binding molecule or antibody of the present disclosure is administered through a single intravenous administration into human CD137 knock-in mice, and blood is collected multiple times over time from 5 minutes to 28 days after administration. Plasma is rapidly separated from the collected blood, and antibody concentration in plasma is measured by electrochemiluminescence (ECL). In one embodiment, the antibody concentration in plasma can be measured by the method described in Example 6-3-2.

In the measurement of plasma half-life using human CD137 knock-in mouse, if an anti-CD137 antigen-binding molecule or antibody disappears from plasma slower than a reference molecule, the anti-CD137 antigen-binding molecule or antibody is judged as having more improved blood kinetics than the reference molecule. In addition, if an anti-CD137 antigen-binding molecule or antibody having binding activity dependent on a small molecule compound (switch molecule or switch antibody) disappears from plasma slower than an anti-CD137 antigen-binding molecule or antibody not having binding activity dependent on a small molecule compound (non-switch molecule or non-switch antibody), it can be judged that the switch molecule (or switch antibody) does not bind to CD137 expressed in a non-tumor tissue compared to the non-switch molecule (non-switch antibody).

d) Anti-Tumor Activity

In one aspect, an anti-CD137 antigen-binding molecule or antibody thereof is tested for its ability to inhibit cell growth or proliferation in vivo. In certain embodiments, an anti-CD137 antigen-binding molecule or antibody thereof is tested for its ability to inhibit tumor growth in vivo. In vivo model systems, such as allograft models or xenograft models, can be used for such testing. In an exemplary xenograft system, human tumor cells are introduced into a suitably immunocompromised non-human animal, e.g., an athymic "nude" mouse. An antibody of the present disclosure is administered to the animal. The ability of the antibody to inhibit or decrease tumor growth is measured. In certain embodiments of the above xenograft system, the human tumor cells are tumor cells from a human patient. Such xenograft models are commercially available from Oncotest GmbH (Frieberg, Germany). In certain embodiments, the human tumor cells are introduced into a suitably immunocompromised non-human animal by subcutaneous injection or by transplantation into a suitable site, such as a mammary fat pad.

In one embodiment, anti-tumor activity of the anti-CD137 antigen-binding molecules or antibodies of the present disclosure may be measured and/or compared using a syngeneic tumor cell graft model based on the above-described human CD137 knocked-in mice. Cancer cell line to use in the test may be suitably selected, but preferably is mouse colon cancer cell line MC38 cell line. In one embodiment, MC38 cell line is transplanted under the skin in the abdominal area of a mouse, and a model is regarded established when tumor volume reaches about 50-300 mm3. Following the establishment of the model, MC38 cell transplanted mice are grouped and then receive administration of each anti-CD137 antigen-binding molecule or antibody. In one embodiment, tumor volume measurement is carried out at a frequency of once to twice a week, in order to evaluate anti-tumor activity. Tumor volume is calculated using the following equation: tumor volume=(major axis× minor axis× minor axis)/2. In one embodiment, the anti-tumor activity of the anti-CD137 antigen-binding molecules or antibodies may be tested and evaluated following the method described in Example 6-4.

In one embodiment, the anti-CD137 antigen-binding molecules or antibodies are recognized as exhibiting anti-tumor activity when the tumor volume in the anti-CD137 antigen-binding molecule or antibody-administered group is smaller than that in the Vehicle group, or the increase in tumor volume in the anti-CD137 antigen-binding molecule or antibody-administered group is smaller than that in the Vehicle group.

e) Systemic Reaction

In one embodiment, the systemic reaction to the anti-CD137 antigen-binding molecules or antibodies of the present disclosure is measured and/or compared using a syngeneic tumor cell graft model based on the above-described human CD137 knocked-in mice. Organs to measure the systemic reaction may be suitably selected, but preferably are liver, spleen, and/or lymph nodes. In one embodiment, the systemic reaction is evaluated by extirpating liver, spleen, and/or lymph nodes from human CD137 knocked-in mice at a suitable time following the administration of the anti-CD137 antigen-binding molecules or antibodies. When the organ to extirpate is spleen and/or lymph nodes, the organ is weighed and/or cells in the lymphocyte fraction are counted. In the counting, preferably, lymphocyte fraction after hemolysis is used for spleen and lymphocyte fraction obtained by homogenization is used for lymph nodes. When the organ to extirpate is liver, cells in the lymphocyte fraction obtained with Liver dissociation kit, mouse (Milteny Biotec) are counted. Furthermore, T cell analysis using flowcytometry (FCM) may be carried out on lymphocyte fraction from each organ (liver, spleen, and/or lymph nodes). In the FCM analysis, Grazyme B expression or PD-1 expression or ICOS expression in CD8-alpha positive T cells or a ratio of CD8-alpha positive T cells to CD45 positive cells is used, for example. In one embodiment, systemic reaction to the anti-CD137 antigen-binding molecules or antibodies may be tested and evaluated following the method described in Example 6-4.

In one embodiment, the anti-CD137 antigen-binding molecules or antibodies are recognized as causing suppressed systemic reaction and/or suppressed activation of immune cells in non-tumor tissues (e.g., liver, spleen, and/or lymph nodes) as compared to a reference molecule, when the anti-CD137 antigen-binding molecule or antibody-administered group shows a lower value in the evaluation of the above-described various indicators than that for the group receiving administration of the same amount of the reference molecule. Furthermore, when the group receiving the administration of the anti-CD137 antigen-binding molecule or antibody having binding activity dependent on a small molecule compound (switch molecule or switch antibody) shows a lower value in the evaluation of the above-described various indicators than that for the group receiving administration of the same amount of an anti-CD137 antigen-binding molecule or antibody that does not have binding activity dependent on a small molecule compound (non-switch molecule or non-switch antibody), the switch molecule (or switch antibody) is recognized as causing suppressed systemic reaction and/or suppressed activation of immune cells in non-tumor tissues (e.g., liver, spleen, and/or lymph nodes) as compared to the non-switch molecule (or non-switch antibody).

It would be appreciated that any of the above-described measurement methods can be carried out using the immunoconjugates of the present disclosure in place of or in addition to the anti-CD137 antigen-binding molecules or antibodies.

D. Immunoconjugates

The present disclosure also provides immunoconjugates comprising an anti-CD137 antigen-binding molecule or antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., Cancer Res. 53:3336-3342 (1993); and Lode et al., Cancer Res. 58:2925-2928 (1998)); an anthracycline such as daunomycin or doxorubicin (see Kratz et al., Current Med. Chem. 13:477-523 (2006); Jeffrey et al., Bioorganic & Med. Chem. Letters 16:358-362 (2006); Torgov et al., Bioconj. Chem. 16:717-721 (2005); Nagy et al., Proc. Natl. Acad. Sci. USA 97:829-834 (2000); Dubowchik et al., Bioorg. & Med. Chem. Letters 12:1529-1532 (2002); King et al., J. Med. Chem. 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include 211At, 131I, 125I, 90Y, 186Re, 188Re, 153Sm, 212Bi, 32P, 212Pb and radioactive isotopes of Lu. When the radioconjugate is used for detection, it may comprise a radioactive atom for scintigraphic studies, for example Tc-99m or 123I, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

n antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCI), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionuclide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

E. Methods and Compositions for Diagnostics and Detection

In certain embodiments, any of the anti-CD137 antigen-binding molecules or antibodies provided herein is useful for detecting the presence of CD137 antigen-binding molecule or in a biological sample. The term "detecting" as used herein encompasses quantitative or qualitative detection. In certain embodiments, a biological sample comprises a cell or tissue.

In one embodiment, an anti-CD137 antigen-binding molecule or antibody for use in a method of diagnosis or detection is provided. In a further aspect, a method of detecting the presence of CD137 in a biological sample is provided. In certain embodiments, the method comprises contacting the biological sample with an anti-CD137 antigen-binding molecule or antibody as described herein under conditions permissive for binding of the anti-CD137 antigen-binding molecule or antibody to CD137, and detecting whether a complex is formed between the anti-CD137 antigen-binding molecule or antibody and CD137. Such method may be an in vitro or in vivo method. In one embodiment, an anti-CD137 antigen-binding molecule or antibody is used to select subjects eligible for therapy with an anti-CD137 antigen-binding molecule or antibody, e.g. where CD137 is a biomarker for selection of patients.

Exemplary disorders that may be diagnosed using an antibody of the present disclosure include cancer.

In certain embodiments, labeled anti-CD137 antigen-binding molecules or antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes 32P, 14C, 125I, 3H, and 131I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, those coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-CD137 antigen-binding molecule or antibody as described herein are prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); small molecule (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX (registered trademark), Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

Active ingredients may be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Therapeutic Compositions

Any of the anti-CD137 antigen-binding molecules or antibodies provided herein may be used in therapeutic methods.

In one aspect, in the present disclosure, anti-CD137 antigen-binding molecules or antibodies for use as a medicament are provided. In the present disclosure, examples of the medicament specifically include those for inducing anti-tumor action, for example, inhibition of neovascularization in tumors, inhibition of tumor cell proliferation, depletion of tumor-promoting B cells, etc., via activation of cells resulting from the binding of the anti-CD137 antigen-binding molecules or antibodies to CD137 expressed on immune cells such as T cells. In further aspects, in the present disclosure, anti-CD137 antigen-binding molecules or antibodies for use in treating tumor are provided. In certain embodiments, anti-CD137 antigen-binding molecules or antibodies for use in a method of treatment are provided. In certain embodiments, the present disclosure provides anti-CD137 antigen-binding molecules or antibodies for use in a method of treating an individual having tumor comprising administering to the individual an effective amount of an anti-CD137 antigen-binding molecule or antibody. In further embodiments, in the present disclosure, examples of tumor include solid tumor into which B cells, dendritic cells, natural killer cells, macrophages, CD8-positive T cells, and/or regulatory T cells (Treg cells) have infiltrated.

In further aspects, the present disclosure provides anti-CD137 antigen-binding molecules or antibodies for use in a method of activating immune cells in an individual, the method comprising administering to the individual an effective amount of an anti-CD137 antigen-binding molecule or antibody to activate immune cells such as B cells, dendritic cells, natural killer cells, macrophages, and/or CD8-positive T cells (more specifically, these immune cells having infiltrated into a tumor tissue).

In further aspects, the present disclosure provides anti-CD137 antigen-binding molecules or antibodies for use in a method of damaging cells (e.g., tumor cells) in an individual, the method comprising administering to the individual an effective amount of an anti-CD137 antigen-binding molecule or antibody. In certain embodiments, examples of the tumor include solid tumor into which B cells, dendritic cells, natural killer cells, macrophages, CD8-positive T cells, and/or regulatory T cells (Treg cells) have infiltrated. An "individual" according to any of the above embodiments is preferably a human.

In further aspects, the present disclosure provides use of anti-CD137 antigen-binding molecules or antibodies in the manufacture or preparation of a medicament. In one embodiment, the medicament is for treating tumor (depending on context, it may be more appropriate to call this as "cancer" (the same applies hereafter)). In further embodiments, the medicament is for use in a method of treating tumor (or cancer depending on context), the method comprising administering to an individual having the tumor (or cancer depending on context) an effective amount of the medicament. In further embodiments, the medicament is for inducing anti-tumor action, for example, inhibition of neovascularization in tumors, inhibition of tumor cell proliferation, depletion of tumor-promoting B cells, etc., via activation of cells resulting from the binding of an anti-CD137 antigen-binding molecule or antibody to CD137 expressed on immune cells such as T cells. In further embodiments, the medicament is for use in a method for, for example, inhibiting neovascularization in tumors, inhibiting tumor cell proliferation, depleting tumor-promoting B cells, etc., via activation of cells resulting from the binding of an anti-CD137 antigen-binding molecule or antibody to CD137 expressed on immune cells such as T cells in an individual, the method comprising administering to the individual an effective amount of the medicament therefor. An "individual" according to any of the above embodiments may be a human.

In further aspects, the present disclosure provides methods for treating tumor. In one embodiment, the methods comprise administering to an individual having such tumor an effective amount of an anti-CD137 antigen-binding molecule or antibody. In further embodiments, in the present disclosure, examples of the tumor include solid tumor into which B cells, dendritic cells, natural killer cells, macrophages, CD8-positive T cells, and/or regulatory T cells (Treg cells) have infiltrated.

In further aspects, the present disclosure provides methods for activating an immune cell in an individual. In one embodiment, the method comprises administering to the individual an effective amount of an anti-CD137 antigen-binding molecule or antibody. In further embodiments, in the present disclosure, the immune cell includes immune cells such as B cells, dendritic cells, natural killer cells, macrophages, and/or CD8-positive T cells (more specifically, these immune cells having infiltrated into a tumor tissue).

In further aspects, the present disclosure provides methods for damaging cells (specifically, tumor cells) in an individual. In one embodiment, the methods include those methods that comprise administering to an individual an effective amount of an anti-CD137 antigen-binding molecule or antibody. In certain embodiments, examples of the tumor include solid tumor into which B cells, dendritic cells, natural killer cells, macrophages, CD8-positive T cells, and/or regulatory T cells (Treg cells) have infiltrated. An "individual" according to any of the above embodiments may be a human.

In further aspects, in the present disclosure, pharmaceutical preparations comprising an anti-CD137 antigen-binding molecule or antibody to be used for the above-described methods of treatment, uses in treating, and medicaments may comprise an effective amount of the anti-CD137 antigen-binding molecule or antibody which has lower level of immunological activation in a non-tumor tissue, compared to an anti-CD137 antigen-binding molecule that does not have CD137 binding activity dependent on a small molecule compound.

In one embodiment, the non-tumor tissues include lymph nodes, spleen, and/or liver.

In further embodiments, the pharmaceutical preparations comprising an anti-CD137 antigen-binding molecule or antibody to be used for the above-described methods of treatment, uses in treating, and medicaments may comprise an effective amount of the anti-CD137 antigen-binding molecule or antibody which substantially does not bind to CD137 expressed in a non-tumor tissue.

In further embodiments, the pharmaceutical preparations comprising an anti-CD137 antigen-binding molecule or antibody to be used for the above-described methods of treatment, uses in treating, and medicaments may comprise an effective amount of the anti-CD137 antigen-binding molecule or antibody which has prolonged blood half-life as compared to an anti-CD137 antigen-binding molecule that does not have CD137 binding activity dependent on a small molecule compound.

In further embodiments, the pharmaceutical preparations comprising an anti-CD137 antigen-binding molecule or antibody to be used for the above-described methods of treatment, uses in treating, and medicaments may comprise an effective amount of the anti-CD137 antigen-binding molecule or antibody which has low level of side effects as compared to an anti-CD137 antigen-binding molecule that does not have CD137 binding activity dependent on a small molecule compound.

In further embodiments, the side effects include elevated AST, elevated ALT, fever, nausea, acute hepatitis, liver damage, splenomegaly, enteritis, skin suppurative inflammation, neutropenia, lymphopenia, thrombopenia, expression of transaminase, and/or hyperbilirubinemia.

In one embodiment, the anti-CD137 antigen-binding molecules of the present disclosure have low side effects, and thus the dosage can be increased without concerns about side effects, and as a result, they can exhibit stronger drug efficacy (cytotoxic activity or antitumor activity).

In a further aspect, the present disclosure provides pharmaceutical formulations comprising any of the anti-CD137 antigen-binding molecules or antibodies provided herein, e.g., for use in any of the above therapeutic methods. In one embodiment, a pharmaceutical formulation comprises any of the anti-CD137 antigen-binding molecules or antibodies provided herein and a pharmaceutically acceptable carrier.

An antigen-binding molecule or antibody of the present disclosure can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the present disclosure would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the present disclosure will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 microgram/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 microgram/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. The progress of this therapy is easily monitored by conventional techniques and assays.

It is understood that any of the above formulations or therapeutic methods may be carried out using an immunoconjugate of the present disclosure place of or in addition to an anti-CD137 antigen-binding molecule or antibody.

H. Articles of Manufacture

In another aspect of the present disclosure, an article of manufacture containing materials useful for the treatment, prevention and/or diagnosis of the disorders described above is provided. The article of manufacture comprises a container and a label on or a package insert associated with the container. Suitable containers include, for example, bottles, vials, syringes, IV solution bags, etc. The containers may be formed from a variety of materials such as glass or plastic. The container holds a composition which is by itself and may have a sterile access port (for example the container may be an intravenous solution bag or a vial having a stopper pierceable by a hypodermic injection needle). At least one active ingredient in the composition is an antibody of the present disclosure. The label or package insert indicates that the composition is used for treating the condition of choice. The article of manufacture in this embodiment of the present disclosure may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The term "package insert" is used to refer to instructions customarily included in commercial packages of therapeutic products, that contain information about the indications, usage, dosage, administration, combination therapy, contraindications and/or warnings concerning the use of such therapeutic products.

It is understood that any of the above articles of manufacture may include an immunoconjugate of the present disclosure in place of or in addition to an anti-CD137 antigen-binding molecule or antibody.

III. Compositions and Methods (Agonistic Antigen-Binding Molecules and Cytotoxic Antigen-Binding Molecules Comprising a Variant Fc Region with Increased Isoelectric Point (pI))

In one aspect, the present disclosure provides agonistic antigen-binding molecules or antibodies comprising a variant Fc region with increased isoelectric point (pI) and methods of using the same. In some embodiments, polypeptides comprising a pI-increased variant Fc region comprise at least one amino acid alteration to the parent Fc region. In further embodiments, each such amino acid alteration causes isoelectric point (pI) of the variant Fc region elevated in comparison to the parent Fc region. Without being bound by a particular theory, it is believed that the pH of biological fluids (for example, plasma) is in a neutral pH range. In biological fluids, the net positive charge of a pI-increased antigen-binding molecule or antibody is increased due to the increased pI, and as a result the antigen-binding molecule or antibody is more strongly attracted by physicochemical Coulomb interaction to the endothelial cell surface that has a net negative charge compared to an antigen-binding molecule or antibody not having an increased pI. By this, the agonistic antigen-binding molecules (or antibodies), or antigen-bound agonistic antigen-binding molecules (or antibodies) can come closer to the surface of cells which express Fc-gamma receptor, resulting in an increased binding of the antigen-binding molecules or antibodies to Fc-gamma receptor-expressing cells. For those agonistic antigen-binding molecules or antibodies that show agonistic activity based on the contribution by binding activity toward Fc-gamma receptor, agonistic antigen-binding molecules or antibodies having increased binding toward Fc-gamma receptor-expressing cells due to the pI-increasing amino acid alterations can exhibit stronger agonistic activity as compared to agonistic antigen-binding molecules or antibodies having no pI-increasing amino acid alterations. In one embodiment, the agonistic antigen-binding molecules are anti-CD137 antigen-binding molecules or anti-CD3 antigen-binding molecules. In a further embodiment, the agonistic antigen-binding molecules are anti-CD137 antibodies or anti-CD3 antibodies.

In a different aspect, the present disclosure provides cytotoxic antigen-binding molecules or antibodies comprising a variant Fc region with increased isoelectric point (pI) and methods of using the same. In biological fluids, the net positive charge of a pI-increased antigen-binding molecule or antibody is increased due to the increased pI, and as a result the antigen-binding molecule or antibody is more strongly attracted by physicochemical Coulomb interaction to the endothelial cell surface that has a net negative charge compared to an antigen-binding molecule or antibody not having an increased pI. By this, the cytotoxic antigen-binding molecules (or antibodies), or antigen-bound cytotoxic antigen-binding molecules (or antibodies) can come closer to the surface of cells which express Fc-gamma receptor, resulting in an increased binding of the antigen-binding molecules or antibodies to Fc-gamma receptor-expressing cells. For those cytotoxic antigen-binding molecules or antibodies that show cytotoxic activity based on the contribution by binding activity toward Fc-gamma receptor, cytotoxic antigen-binding molecules or antibodies having increased binding toward Fc-gamma receptor-expressing cells due to the pI-increasing amino acid alterations can exhibit stronger agonistic activity as compared to cytotoxic antigen-binding molecules or antibodies having no pI-increasing amino acid alterations.

In one embodiment, the cytotoxicity possessed by cytotoxic antigen-binding molecules includes, for example, antibody-dependent cellular cytotoxicity (ADCC) and antibody-dependent cellular phagocytosis (ADCP) which are caused by effector cells.

In the present disclosure, pI may be either a theoretical or an experimentally determined pI. The value of pI can be determined, for example, by isoelectric focusing known to those skilled in the art. The value of a theoretical pI can be calculated, for example, using gene and amino acid sequence analysis software (Genetyx, etc.). In calculating, properties of an antibody may be reflected in a calculation formula. For example, (i) generally, Cys conserved within an antibody forms a disulfide bond and does not carry electric charge of the side chain; therefore, such Cys may be excluded from the calculation and only the free-form Cys which does not form a disulfide bond may be included in the calculation. Alternatively, (ii) charge state, or isoelectric point of antibodies can be changed because of the post-translational modifications; therefore, a calculation formula may be modified as follows, giving consideration on such post-translational modifications: (a) when the N-terminus of the heavy chain is Q (glutamine), the N-terminal amino group is excluded from the calculation, assuming that pyro-glutamylation occurs, (b) when the C-terminus of the heavy chain is K (lysine), K (only one residue) is excluded from the calculation, assuming that truncation occurs; and (c) side chains of all C (cysteine) present at generally conserved positions are excluded from the calculation, assuming that all these C form disulfide bonds within the molecule. In one preferred embodiment, both the above-described (i) and (ii) may be reflected in the calculation formula.

In one embodiment, the pI value may be increased, for example, at least by 0.01, 0.03, 0.05, 0.1, 0.2, 0.3, 0.4, 0.5, or more, at least by 0.6, 0.7, 0.8, 0.9, or more, at least by 1.0, 1.1, 1.2, 1.3, 1.4, 1.5, or more, or at least by 1.6, 1.7, 1.8, 1.9, 2.0, 2.1, 2.2, 2.3, 2.4, 2.5, 3.0 or more, as compared to before modification.

In certain embodiments, the amino acid for increased pI can be exposed on the surface of the variant Fc region. In the present disclosure, an amino acid that can be exposed on the surface generally refers to an amino acid residue located on the surface of a polypeptide constituting a variant Fc region. An amino acid residue located on the surface of a polypeptide refers to an amino acid residue whose side chain can be in contact with solvent molecules (which in general are mostly water molecules). However, the side chain does not necessarily have to be wholly in contact with solvent molecules, and when even a portion of the side chain is in contact with the solvent molecules, the amino acid is defined as an "amino acid residue located on the surface". The amino acid residues located on the surface of a polypeptide also include amino acid residues located close to the surface and thereby can have an electric charge influence from another amino acid residue whose side chain, even partly, is in contact with the solvent molecules. Those skilled in the art can prepare a homology model of a polypeptide for example, using commercially available softwares. Alternatively, it is possible to use methods known to those skilled in the art, such as X-ray crystallography. The amino acid residues that can be exposed on the surface are determined, for example, using coordinates from a three-dimensional model using a computer program such as InsightII program (Accelrys). Surface-exposable sites may be determined using algorithms known in the technical field (for example, Lee and Richards (J. Mol. Biol. 55:379-400 (1971)); Connolly (J. Appl. Cryst. 16:548-558 (1983)). Surface-exposable sites can be determined using software suitable for protein modeling and three-dimensional structure information. Software available for such purposes includes, for example, the SYBYL Biopolymer Module software (Tripos Associates). When an algorithm requires a user input size parameter, the "size" of a probe which is used in the calculation may be set to about 1.4 Angstrom (A) or less in radius. Furthermore, methods for determining surface-exposable regions using software for personal computers have been described by Pacios (Comput. Chem. 18(4):377-386 (1994); J. Mol. Model. 1:46-53 (1995)). Based on such information as described above, appropriate amino acid residues located on the surface of a polypeptide that constitutes a variant Fc region can be selected.

Methods for increasing pI by introducing a single amino acid-substitution into an antibody constant region are not particularly limited and, for example, can be carried out based on the methods described in WO 2014/145159. As amino acid substitutions to introduce into a constant region, it is preferable to introduce amino acid substitution(s) for reducing the number of amino acids having negative charge (e.g., aspartic acid or glutamic acid) while increasing amino acids having positive charge (e.g., arginine or lysine), as in the case of the variable region.

Although not particularly limited, as sites to introduce the amino acid substitutions within a constant region, such sites at which amino acid side chains may be exposed on the antibody molecule surface are preferred. Preferred examples include methods of introducing a plurality of amino acid substitutions in combination into such sites that may be exposed on the antibody molecule surface. Alternatively, it is preferred that the plurality of amino acid substitutions to introduce are at the sites proximal to each other in the three-dimensional structure. The multiple amino acid substitutions to be introduced are preferably substitutions to positively charged amino acids that may in some cases lead to the state where multiple positive charges are carried at proximal sites in the three-dimensional structure, although they are not particularly limited thereto. The definition of "proximal sites in the three-dimensional structure" herein is not particularly limited, but for example, it may mean a state where single amino acid substitution or multiple amino acid substitutions are introduced in 45 Angstroms or less, in 40 Angstroms or less, in 30 Angstroms or less, in 20 Angstroms or less, preferably in 15 Angstroms or less, or more preferably 10 Angstroms or less from each other. Whether the amino acid substitutions of interest are at sites exposed on the antibody molecule surface, or whether the multiple sites of amino acid substitutions are proximally positioned can be determined by known methods such as X-ray crystallography.

In one embodiment, the pI-increased variant Fc regions comprise at least one amino acid alteration of at least one position selected from the group consisting of positions 285, 311, 312, 315, 318, 333, 335, 337, 341, 342, 343, 384, 385, 388, 390, 399, 400, 401, 402, 413, 420, 422, and 431, according to EU numbering. In further embodiments, the pI-increased variant Fc regions comprise Arg or Lys at each selected position.

In further embodiments, the pI-increased variant Fc regions comprise at least one amino acid alteration of at least one position selected from the group consisting of positions 311, 343, and 413, according to EU numbering. In further embodiments, the pI-increased variant Fc regions comprise an amino acid alteration at positions 311, 343, or 413, according to EU numbering. In further embodiments, the pI-increased variant Fc regions comprise Arg or Lys at each selected position.

In another aspect, the present disclosure provides polypeptides comprising a pI-increased variant Fc region, which comprises amino acid alterations of any one of following (1) to (3): (1) at positions 311 and 343; (2) at positions 311 and 413; and (3) at positions 343 and 413, according to EU numbering. In further embodiments, the pI-increased variant Fc regions comprise Arg or Lys at each selected position.

A method for increasing the pI of a protein is, for example, to reduce the number of amino acids with a negatively charged side chain (for example, aspartic acid and glutamic acid) and/or to increase the number of amino acids with a positively charged side chain (for example, arginine, lysine and histidine) at a neutral pH condition. Amino acids with a negatively charged side chain have a negative charge represented as −1 at a pH condition that is sufficiently higher than their side chain pKa, which is a theory well known to those skilled in the art. For example, the theoretical pKa for the side chain of aspartic acid is 3.9, and the side chain has a negative charge represented as −1 at a neutral pH condition (for example, in a solution of pH7.0). Conversely, amino acids with a positively charged side chain have a positive charge represented as +1 at a pH condition that is sufficiently lower than their side chain pKa. For example, the theoretical pKa for the side chain of arginine is 12.5, and the side chain has a positive charge represented as +1 at a neutral pH condition (for example, in a solution of pH7.0). Meanwhile, amino acids whose side chain has no charge at a neutral pH condition (for example, in a solution of pH7.0) are known to include 15 types of natural amino acids, i.e., alanine, cysteine, phenylalanine, glycine, isoleucine, leucine, methionine, asparagine, proline, glutamine, serine, threonine, valine, tryptophan, and tyrosine. As a matter of course, it is understood that amino acids for increasing the pI may be unnatural amino acids.

From the above, a method for increasing the pI of a protein at a neutral pH condition (for example, in a solution of pH7.0) can confer a charge alteration of +1 to a protein of interest, for example, by substituting amino acids with non-charged side chains for aspartic acid or glutamic acid (whose side chain has a negative charge of −1) in the amino acid sequence of the protein. Furthermore, a charge alteration of +1 can be conferred to the protein, for example, by substituting arginine or lysine (whose side chain has a positive charge of +1) for amino acids whose side chain has no charge. Moreover, a charge alteration of +2 can be conferred at a time to the protein by substituting arginine or lysine (whose side chain has a positive charge of +1) for aspartic acid or glutamic acid (whose side chain has a negative charge of −1). Alternatively, to increase the pI of a protein, amino acids with a side chain having no charge and/or preferably amino acids having a positively charged side chain can be added or inserted into the amino acid sequence of the protein, or amino acids with a side chain having no charge and/or preferably amino acids with a negatively charged side chain present in the amino acid sequence of the protein can be deleted. It is understood that, for example, the N-terminal and C-terminal amino acid residues of a protein have a main chain-derived charge (NH3+ of the amino group at the N-terminus and COO— of the carbonyl group at the C-terminus) in addition to their side chain-derived charges. Thus, the pI of a protein can also be increased by performing to the main chain-derived functional groups some addition, deletion, substitution, or insertion.

The substitution of an amino acid to increase the pI includes, for example, substitution of an amino acid whose side chain has no charge for an amino acid having a negatively charged side chain, substitution of an amino acid having a positively charged side chain for an amino acid whose side chain has no charge, and substitution of an amino acid having a positively charged side chain for an amino acid having a negatively charged side chain in the amino acid sequence of a parent Fc region, which are performed alone or in appropriate combinations.

The insertion or addition of an amino acid to increase the pI includes, for example, insertion or addition of an amino acid whose side chain has no charge, and/or insertion or addition of an amino acid having a positively charged side chain in the amino acid sequence of a parent Fc region, which are performed alone or in appropriate combinations.

The deletion of an amino acid to increase the pI includes, for example, deletion of an amino acid whose side chain has no charge, and/or deletion of an amino acid having a negatively charged side chain in the amino acid sequence of a parent Fc region, which are performed alone or in appropriate combinations.

In one embodiment, natural amino acids used for increasing pI can be classified as follows: (a) an amino acid with a negatively charged side chain can be Glu (E) or Asp (D); (b) an amino acid whose side chain has no charge can be Ala (A), Asn (N), Cys (C), Gln (Q), Gly (G), His (H), Ile (I), Leu (L), Met (M), Phe (F), Pro (P), Ser (S), Thr (T), Trp (W), Tyr (Y), or Val (V); and (c) an amino acid with a positively charged side chain can be His (H), Lys (K), or Arg (R). In one embodiment, the amino acid insertion or substitution after modification is Lys (K) or Arg (R).

In another aspect, the invention provides isolated agonistic antigen-binding molecules or antibodies comprising variant Fc regions with increased Fc gamma receptor-binding activity (preferably, Fc gamma RIIb-binding activity) and increased pI. In certain embodiments, a variant Fc region described herein comprises at least two amino acid alterations in a parent Fc region. As described above, an antigen-binding molecule or antibody having increased pI is more strongly attracted by physicochemical Coulomb interaction to the endothelial cell surface that has a net negative charge compared to an antigen-binding molecule or antibody not having an increased pI. Therefore, for agonistic antigen-binding molecules or antibodies that show agonistic activity based on the contribution by binding activity toward Fc-gamma receptor (preferably Fc-gamma RIIb), it is possible to increase the agonistic activity of the antigen-binding molecules or antibodies by combining amino acid alteration (s) to increase Fc-gamma receptor (preferably Fc-gamma RIIb) and amino acid alteration(s) to increase pI. To the term "Fc-gamma receptor", explanation described under "II. Compositions and methods (anti-CD137 agonistic antigen-binding molecules)" similarly apply.

In one embodiment, in one aspect, the present disclosure provides polypeptides comprising variant Fc regions with increased FcγRIIb-binding activity and increased pI comprising at least three amino acid alterations comprising: (a) at least one amino acid alteration of at least one position selected from the group consisting of: 231, 232, 233, 234, 235, 236, 237, 238, 239, 264, 266, 267, 268, 271, 295, 298, 325, 326, 327, 328, 330, 331, 332, 334, and 396, according to EU numbering, and (b) at least two amino acid alterations of at least two positions selected from the group consisting of: 285, 311, 312, 315, 318, 333, 335, 337, 341, 342, 343, 384, 385, 388, 390, 399, 400, 401, 402, 413, 420, 422, and 431, according to EU numbering.

In one aspect, the present disclosure provides a polypeptide comprising a variant Fc region that results in increased FcγRIIb-binding activity and increased pI, which polypeptide comprises at least 3 amino acid alterations comprising (a) at least one amino acid alteration at at least one position selected from the group consisting of positions 234, 235, 236, 237, 238, 264, 268, 295, 326, and 330 represented by EU numbering, and (b) at least 2 amino acid mutations at at least 2 positions selected from the group consisting of positions 311, 343, and 413 represented by EU numbering.

In another aspect, the present disclosure provides a polypeptide comprising a variant Fc region that results in increased FcγRIIb-binding activity and increased pI, comprising at least one amino acid alteration from any one of (1) to (26) below (represented by EU numbering):
(1) positions 235, 236, 268, 295, 326, 330, 343, and 413;
(2) positions 214, 235, 236, 268, 295, 326, 330, 343, and 413;
(3) positions 234, 238, 250, 264, 307, 330, 343, and 413;
(4) positions 234, 238, 264, 330, 343, and 413;
(5) positions 234, 237, 238, 250, 307, 330, 343, and 413;
(6) positions 234, 237, 238, 330, 343, and 413;
(7) positions 235, 236, 268, 295, 326, 330, 311, and 343;
(8) positions 234, 238, 250, 264, 307, 330, 311, and 343;
(9) positions 234, 238, 264, 330, 311, and 343;
(10) positions 234, 237, 238, 250, 307, 330, 311, and 343;
(11) positions 234, 237, 238, 330, 311, and 343;
(12) positions 235, 236, 268, 295, 326, 330, and 343;
(13) positions 214, 235, 236, 268, 295, 326, 330, and 343;
(14) positions 235, 236, 268, 295, 326, 330, and 413;
(15) positions 214, 236, 268, 330, and 343;
(16) positions 214, 235, 236, 268, 330, and 343;
(17) positions 214, 236, 268, 330, and 413;
(18) positions 214, 236, 268, 330, 343, and 413;
(19) positions 214, 235, 236, 268, 330, 343 and 413;
(20) positions 214, 236, 268, 330, and 311;
(21) position 214, 235, 236, 268, 330, and 311;
(22) positions 214, 236, 268, 330, 311, and 343;
(23) positions 214, 235, 236, 268, 330, 311, and 343;
(24) positions 214, 236, 268, 330, 311, and 413;
(25) positions 214, 235, 236, 268, 330, 311, and 413; and
(26) positions 214, 235, 236, 268, 295, 326, 330, and 311.

In one embodiment, the variant Fc region of the present disclosure includes the amino acid alterations set forth in Table 6 below.

Amino acid alterations that increase the pI of the Fc region

TABLE 6

| No | Amino acid substitution (EU numbering) |
|---|---|
| 1 | P343R/D413K |
| 2 | Q311R/P343R |
| 3 | P343R |
| 4 | D413K |
| 5 | Q311R |
| 6 | Q311R/D413K |

In one embodiment, in addition to the amino acid alterations described in Table 6 (amino acid alterations that increase the pI of Fc), the variant Fc region of the present disclosure includes amino acid alterations described in Table 7 below.

Amino acid alterations that increase FcγRIIb-binding activity of the Fc region

TABLE 7

| No | Amino acid substitution (EU numbering) |
|---|---|
| 1 | L234Y/P238D/V264I/A330K |
| 2 | L234Y/P238D/A330K |
| 3 | L234Y/G237D/P238D/A330K |
| 4 | G236N/H268D/A330K |
| 5 | L235W/G236N/H268D/Q295L/K326T/A330K |

In one embodiment, the variant Fc region of the present disclosure includes the amino acid alterations described in Table 8 below. In a preferred embodiment, the variant Fc region of the present disclosure includes the amino acid deletion at position 447 according to EU numbering, in addition to the amino acid alterations described in Table 8 below. In a further preferred embodiment, the variant Fc region of the present disclosure includes the amino acid deletions at positions 446 and 447 according to EU numbering, in addition to the amino acid alterations described in Table 8 below.

TABLE 8

| No | Amino acid substitution (EU numbering) |
|---|---|
| 1 | L235W/G236N/H268D/Q295L/K326T/A330K/P343R/D413K |
| 2 | K214R/L235W/G236N/H268D/Q295L/K326T/A330K/P343R/D413K |
| 3 | L234Y/P238D/T250V/V264I/T307P/A330K/P343R/D413K |
| 4 | L234Y/P238D/V264I/A330K/P343R/D413K |
| 5 | L234Y/G237D/P238D/T250V/T307P/A330K/P343R/D413K |
| 6 | L234Y/G237D/P238D/A330K/P343R/D413K |
| 7 | L235W/G236N/H268D/Q295L/K326T/A330K/Q311R/P343R |
| 8 | L234Y/P238D/T250V/V264I/T307P/A330K/Q311R/P343R |
| 9 | L234Y/P238D/V264I/A330K/Q311R/P343R |
| 10 | L234Y/G237D/P238D/T250V/T307P/A330K/Q311R/P343R |
| 11 | L234Y/G237D/P238D/A330K/Q311R/P343R |
| 12 | L235W/G236N/H268D/Q295L/K326T/A330K/P343R |
| 13 | K214R/L235W/G236N/H268D/Q295L/K326T/A330K/P343R |
| 14 | L235W/G236N/H268D/Q295L/K326T/A330K/D413K |
| 15 | K214R/G236N/H268D/A330K/P343R |
| 16 | K214R/L235W/G236N/H268D/A330K/P343R |
| 17 | K214R/G236N/H268D/A330K/D413K |
| 18 | K214R/G236N/H268D/A330K/P343R/D413K |
| 19 | K214R/L235W/G236N/H268D/A330K/P343R/D413K |
| 20 | K214R/G236N/H268D/A330K/Q311R |
| 21 | K214R/L235W/G236N/H268D/A330K/Q311R |
| 22 | K214R/G236N/H268D/A330K/Q311R/P343R |
| 23 | K214R/L235W/G236N/H268D/A330K/Q311R/P343R |
| 24 | K214R/G236N/H268D/A330K/Q311R/D413K |
| 25 | K214R/L235W/G236N/H268D/A330K/Q311R/D413K |
| 26 | K214R/L235W/G236N/H268D/Q295L/K326T/A330K/Q311R |

Besides the alterations exemplified above, those skilled in the art would understand that at least one amino acid alteration that increases binding activity towards FcγR including FcγRIIb as compared to a parent Fc region, for example, as described or suggested in WO 2013/047752, WO 2013/125667, WO 2014/030728, WO 2014/163101, or WO 2017104783, and at least one amino acid alteration that increases pI as compared to a parent Fc region, for example, as described or suggested in WO 2017/104783 or WO 2017/046994, and combinations of those amino acid alterations, can be used.

In one embodiment, the agonistic antigen-binding molecule or antibody comprises both a variant Fc region and an antigen-binding domain. In a further embodiment, the antigen is a membrane antigen. In a further embodiment, the antigen is a receptor expressed on the cell surface. In some embodiments, the parent Fc region is derived from human IgG1. In a further embodiment, the polypeptide is an antibody. In a further embodiment, the polypeptide is an Fc fusion protein.

In one aspect, the present disclosure provides a method for producing an agonistic antigen-binding molecule that comprises the above-detailed variant Fc region (a variant Fc region with increased isoelectric point (pI)).

In one embodiment, the method of the present disclosure has the features of: introducing into a parent Fc region at least one amino acid alteration (as described above) that leads to an increased isoelectric point (pI) as compared to that of the parent agonist antigen-binding molecule comprising the parent Fc region; and identifying and isolating an agonistic antigen-binding molecule wherein the agonistic activity of the agonistic antigen-binding molecule including a variant Fc region obtained as a result of the above introduction is increased compared to that of the parent agonistic antigen-binding molecule.

In one embodiment, the method of the present disclosure has the features of obtaining an expression vector comprising a suitable promoter operably linked to a gene encoding the above-mentioned agonistic antigen-binding molecule identified and isolated as above, introducing the vector into a host cell, culturing the host cell to produce the agonistic antigen-binding molecule, and recovering the above-mentioned agonistic antigen-binding molecule from the host cell culture.

In one embodiment, the method of the present disclosure can produce an agonistic antigen-binding molecule whose agonistic activity towards an antigen in the presence of 10 µM, 50 µM, 100 µM, 150 µM, 200 µM, or 250 µM of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to the agonistic activity towards the antigen in the absence of the small molecule compound.

In one embodiment, by the method of the present disclosure, one can produce an agonistic antigen-binding molecule whose agonistic activity towards an antigen in the presence of 10 µM or more of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to the agonistic activity towards the antigen in the absence of the small molecule compound.

In one embodiment, the method of the present disclosure can produce an agonistic antigen-binding molecule whose agonistic activity towards an antigen in the presence of 50 µM or more of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to the agonistic activity towards the antigen in the absence of the small molecule compound.

In one embodiment, the method of the present disclosure can produce an agonistic antigen-binding molecule whose agonistic activity towards an antigen in the presence of 250 µM or more of a small molecule compound is 2-fold or more, 3-fold or more, 5-fold or more, 10-fold or more, 20-fold or more, 30-fold or more, 50-fold or more, 60-fold or more, 70-fold or more, 80-fold or more, or 90-fold or more higher, as compared to the agonistic activity towards the antigen in the absence of the small molecule compound.

In one embodiment, in such a method, the agonistic activity of an agonistic antigen-binding molecule towards an antigen can be evaluated by the amount of IL-2 and/or IFN-γ produced by antigen-expressing cells.

In one embodiment, in such a method, the agonistic activity of an agonistic antigen-binding molecule towards an antigen can be evaluated by the amount of IL-2 and/or IFN-γ produced by isolated human peripheral blood mononuclear cells (PBMCs) or human peripheral blood mononuclear cell (PBMC)-derived T cells.

In one embodiment, in such a method, the agonistic activity of an agonistic antigen-binding molecule towards an antigen can be evaluated by a reporter gene assay.

IV. Compositions and Methods (Antigen-Binding Molecules Whose Binding Activity to Antigens Changes Depending on the Concentration of a Small Molecule Compound)

A. Antigen-Binding Molecules Whose Binding Activity to Antigens Changes Depending on the Concentration of a Low-Molecular Weight Compound In one aspect, the present invention provides antigen-binding molecules whose antigen-binding activity changes depending on the concentration of a small molecule compound. The molecules may also be referred to as small molecule compound-dependent antigen-binding molecules (having antigen-binding activity dependent on the concentration of a small molecule compound). In some aspect, the antigen-binding molecules are antibodies. In some embodiments, the antigen-binding molecules of the present invention have antigen-binding activity which increases as the concentration of the small molecule compound becomes higher. In some embodiments, the antigen-binding molecules of the present invention have antigen-binding activity which decreases as the concentration of the small molecule compound becomes higher. In one embodiment, when the binding activity of an antigen-binding molecule in the presence of a small molecule compound is compared with the binding activity of the antigen-binding molecule in the absence of the small molecule compound, either one value is higher than the other value. In another embodiment, when the binding activity of an antigen-binding molecule in the presence of high concentration of a small molecule compound is compared with the binding activity of the antigen-binding molecule in the presence of low concentration of the small molecule compound, either one value is higher than the other value. In certain embodiments, the small molecule compound in the present invention is a target tissue-specific compound. In further embodiments, the small molecule compound in the present invention is a tumor tissue-specific compound.

In another aspect, the present invention provides antigen-binding molecules having high retention property in plasma. In further aspect, the antigen-binding molecules have antigen-binding activity which increases as concentration of a small molecule compound becomes higher. In certain embodiments, the small molecule compound is a target tissue-specific compound. In further embodiments, the antigen-binding molecules have higher antigen-binding activity in a target tissue as compared to the antigen-binding activity in a non-target tissue. In some aspect, the antigen-binding molecules are antibodies. Without being bound by a particular theory, the above-described change in plasma kinetics may be understood in the following manner. When an antigen-binding molecule's antigen binding activity is high depending on the concentration of a target tissue-specific compound, antigen binding activity of that antigen-binding molecule in tissues other than the target tissue would be lower. As a result, antigen-dependent elimination (clearance) of that antigen-binding molecule in tissues other than the target tissue would also become lower. Lower antigen-dependent elimination (clearance) in most tissues in the living body (i.e. tissues other than the target tissue) leads in total to higher retention property in plasma of the antigen-binding molecule. Determination on whether an antigen-binding molecule in the present invention has high retention property in plasma can be made by comparison relative to a control antigen-binding molecule. In some embodiments, those antigen-binding molecules that have increased antigen-binding activity when the concentration of a target tissue-specific compound becomes higher have higher retention property in plasma as compared to a control antigen-binding molecule. In one embodiment, the control antigen-binding molecule does not have antigen binding activity dependent on the concentration of a small molecule compound. In certain embodiments, an antigen-binding molecule that does not have antigen binding activity dependent on the concentration of a small molecule compound means an antigen-binding molecule for which difference in antigen binding activity in the presence of the small molecule compound and in the absence of the small molecule compound is, for example, 2-fold or smaller, 1.8-fold or smaller, 1.5-fold or smaller, 1.3-fold or smaller, 1.2-fold or smaller, or 1.1-fold or smaller. From the point of view of making comparison, it is preferable that antigen binding activity of the antigen-binding molecules of the present invention and control antigen-binding molecules in the presence of sufficient amount of small molecule compound are substantially the same to each other.

Here, the magnitude of antigen-dependent elimination of an antigen-binding molecule detected in vivo is considered to change according to quantitative balance of antigens and antigen-binding molecules present in the plasma. Generally, it is considered that the more antigens are present/the less antigen-binding molecules are present in the plasma, the more detectable the antigen-dependent elimination of the antigen-binding molecule becomes. Conversely, it is considered that the less antigens are present/the more antigen-binding molecules are present in the plasma, the less detectable the antigen-dependent elimination of the antigen-binding molecule becomes. The antigen-binding molecules of the present invention need not to show high retention property in plasma under every condition, but it is enough that the antigen-binding molecules show high retention property in plasma under suitable condition where sufficient antigen-dependent elimination is detected. If the amount of an antigen in plasma is too small, retention property in plasma may be evaluated after increasing the antigen amount by any artificial means.

In another aspect, the present invention provides antigen-binding molecules having low ability of antigen accumulation in plasma. In further aspect, the antigen-binding molecules have antigen-binding activity which increases as concentration of a small molecule compound becomes higher. In certain embodiments, the small molecule compound is a target tissue-specific compound. In further embodiments, the antigen-binding molecules have higher antigen-binding activity in a target tissue as compared to the antigen-binding activity in a non-target tissue. In some aspect, the antigen-binding molecules are antibodies. Without being bound by a particular theory, the above-described change in plasma kinetics may be understood in the following manner. When an antigen-binding molecule's antigen binding activity is high depending on the concentration of a target tissue-specific compound, antigen binding activity of that antigen-binding molecule in tissues other than the target tissue would be lower. As a result, that antigen-binding molecule would have lower ability of forming antigen-antibody complex in tissues other than the target tissue. Generally, it is known that when an antigen is bound by an antigen-binding molecule such as antibody, clearance of the antigen becomes lower and plasma antigen concentration increases (antigen accumulates). Lower ability of forming antigen-antibody complex in most tissues in the living body (i.e. tissues other than the target tissue) leads in total to lower antigen accumulation (in other words, antigen-binding molecule's lower ability of antigen accumulation). Determination on whether an antigen-binding molecule in the present invention has low ability of antigen accumulation in plasma can be made by comparison relative to a control antigen-binding molecule. In some embodiments, those antigen-binding molecules that have increased antigen-binding activity when the concentration of a target tissue-specific compound becomes higher have lower ability of antigen accumulation in plasma as compared to a control antigen-binding molecule. In one embodiment, the control antigen-binding molecule does not have antigen binding activity dependent on the concentration of a small molecule compound. In certain embodiments, an antigen-binding molecule that does not have antigen binding activity dependent on the concentration of a small molecule compound means an antigen-binding molecule for which difference in antigen binding activity in the presence of the small molecule compound and in the absence of the small molecule compound is, for example, 2-fold or smaller, 1.8-fold or smaller, 1.5-fold or smaller, 1.3-fold or smaller, 1.2-fold or smaller, or 1.1-fold or smaller. From the point of view of making comparison, it is preferable that antigen binding activity of the antigen-binding molecules of the present invention and control antigen-binding molecules in the presence of sufficient amount of compound are substantially the same to each other.

Here, the amount of an antigen-antibody complex formed in vivo is considered to depend on the amount of an antigen and an antigen-binding molecule present in the plasma. Generally, it is considered that the more antigens/antibodies are present in the plasma, the more antigen-antibody complexes are formed. Conversely, it is considered that the less antigens/antibodies are present in the plasma, the less antigen-antibody complexes are formed. The antigen-binding molecules of the present invention need not to show low ability of antigen accumulation in plasma under every condition, but it is enough that the antigen-binding molecules show low ability of antigen accumulation in plasma under suitable condition where sufficient amount of antigen-antibody complex is formed. If the amount of an antigen in plasma is too small, ability of antigen accumulation in plasma may be evaluated after increasing the antigen amount by any artificial means.

In some embodiments, difference in antigen-binding activity dependent on the concentration of a small molecule compound of the antigen-binding molecules of the present invention is, for example, twice or more, three times or more, five times or more, 10 times or more, 20 times or more, 30 times or more, 50 times or more, 100 times or more, 200 times or more, 300 times or more, 500 times or more, 1×103 times or more, 2×103 times or more, 3×103 times or more, 5×103 times or more, 1×104 times or more, 2×104 times or more, 3×104 times or more, 5×104 times or more, or 1×105 times or more.

In some embodiments, binding activity of antigen-binding molecules may be expressed by a KD (dissociation constant) value. In further embodiments, when the KD value for an antigen-binding molecule in the presence of a small molecule compound and the KD value of the antigen-binding molecule in the absence of the small molecule compound are compared, either one value is smaller than the other value. Alternatively, in another embodiment, when the KD value of an antigen-binding molecule in the presence of high concentration of a small molecule compound is compared with the KD value of the antigen-binding molecule in the presence of low concentration of the small molecule compound, either one value is smaller than the other value. In further embodiments, difference in KD values of the antigen-binding molecules is, for example, twice or more, three times or more, five times or more, 10 times or more, 20 times or more, 30 times or more, 50 times or more, 100 times or more, 200 times or more, 300 times or more, 500 times or more, 1×103 times or more, 2×103 times or more, 3×103 times or more, 5×103 times or more, 1×104 times or more, 2×104 times or more, 3×104 times or more, 5×104 times or more, or 1×105 times or more. The KD value of the smaller one may be, for example, $9\times10^{-7}$ M or less, $8\times10^{-7}$ M or less, $7\times10^{-7}$ M or less, $6\times10^{-7}$ M or less, $5\times10^{-7}$ M or less, $4\times10^{-7}$ M or less, $3\times10^{-7}$ M or less, $2\times10^{-7}$ M or less, $1\times10^{-7}$ M or less, $9\times10^{-8}$ M or less, $8\times10^{-8}$ M or less, $7\times10^{-8}$ M or less, $6\times10^{-8}$ M or less, $5\times10^{-8}$ M or less, $4\times10^{-8}$ M or less, $3\times10^{-8}$ M or less, $2\times10^{-8}$ M or less, $1\times10^{-8}$ M or less, $9\times10^{-9}$ M or less, $8\times10^{-9}$ M or less, $7\times10^{-9}$ M or less, $6\times10^{-9}$ M or less, $5\times10^{-9}$ M or less, $4\times10^{-9}$ M or less, $3\times10^{-9}$ M or less, $2\times10^{-9}$ M or less, $1\times10^{-9}$ M or less, $9\times10^{-10}$ M or less, $8\times10^{-10}$ M or less, $7\times10^{-10}$ M or less, $6\times10^{-10}$ M or less, $5\times10^{-10}$ M or less, $4\times10^{-10}$ M or less, $3\times10^{-10}$ M or less, $2\times10^{-10}$ M or less, $1\times10^{-10}$ M or less. The KD value of the larger one may be, for example, $1\times10^{-8}$ M or more, $2\times10^{-8}$ M or more, $3\times10^{-8}$ M or more, $4\times10^{-8}$ M or more, $5\times10^{-8}$ M or more, $6\times10^{-8}$ M or more, $7\times10^{-8}$ M or more, $8\times10^{-8}$ M or more, $9\times10^{-8}$ M or more, $1\times10^{-7}$ M or more, $2\times10^{-7}$ M or more, $3\times10^{-7}$ M or more, $4\times10^{-7}$ M or more, $5\times10^{-7}$ M or more, $6\times10^{-7}$ M or more, $7\times10^{-7}$ M or more, $8\times10^{-7}$ M or more, $9\times10^{-7}$ M or more, $1\times10^{-6}$ M or more, $2\times10^{-6}$ M or more, $3\times10^{-6}$ M or more, $4\times10^{-6}$ M or more, $5\times10^{-6}$ M or more, $6\times10^{-6}$ M or more, $7\times10^{-6}$ M or more, $8\times10^{-6}$ M or more, $9\times10^{-6}$ M or more.

In another embodiment, binding activity of antigen-binding molecules may be expressed by a kd (dissociation rate constant) value, in place of the KD value.

In another embodiment, binding activity of antigen-binding molecules may be expressed by amount of an antigen that has bound to an antigen-binding molecule. For example, in surface plasmon resonance assays, binding amount of an antigen-binding molecule immobilized on a sensor chip and binding amount of an antigen which has further bound thereto are each measured as resonance unit (RU). Antigen binding activity may be expressed using binding amount of the antigen obtained therefrom as an indicator, or may alternatively be expressed using the value obtained by dividing the amount of bound antigen by the amount of bound antigen-binding molecule (i.e., amount of bound antigen per unit amount of antigen-binding molecule) as an indicator. Specific methods for measuring and calculating the binding amount will be described below in the Examples. In some embodiments, when an amount of bound antigen in the presence of a small molecule compound is compared with an amount of bound antigen in the absence of the small molecule compound, either one value is larger than the other value. In another embodiment, when an amount of bound antigen in the presence of high concentration of a small molecule compound is compared with an amount of bound antigen in the presence of low concentration of the small molecule compound, either one value is larger than the other value. In further embodiments, difference in binding amount of an antigen is, for example, twice or more, three times or more, five times or more, 10 times or more, 20 times or more, 30 times or more, 50 times or more, 100 times or more, 200 times or more, 300 times or more, 500 times or more, $1\times10^3$ times or more, $2\times10^3$ times or more, $3\times10^3$ times or more, $5\times10^3$ times or more, $1\times10^4$ times or more, $2\times10^4$ times or more, $3\times10^4$ times or more, $5\times10^4$ times or more, or $1\times10^5$ times or more. The binding amount of an antigen of the larger value may be, for example, 0.01 or more, 0.02 or more, 0.03 or more, 0.04 or more, 0.05 or more, 0.06 or more, 0.07 or more, 0.08 or more, 0.09 or more, 0.1 or more, 0.2 or more, 0.3 or more, 0.4 or more, 0.5 or more, 0.6 or more, 0.7 or more, 0.8 or more, 0.9 or more, 1 or more. The binding amount of an antigen of the smaller value may be, for example, 0.5 or less, 0.4 or less, 0.3 or less, 0.2 or less, 0.1 or less, 0.09 or less, 0.08 or less, 0.07 or less, 0.06 or less, 0.05 or less, 0.04 or less, 0.03 or less, 0.02 or less, 0.01 or less, 0.009 or less, 0.008 or less, 0.007 or less, 0.006 or less, 0.005 or less, 0.004 or less, 0.003 or less, 0.002 or less, 0.001 or less.

In some embodiments, the KD values, kd values, or values of binding amount expressed herein are measured or calculated by carrying out surface plasmon resonance assay at 25 degrees C. or 37 degrees C. (for example, see the Examples herein).

Concentration of a small molecule compound may be freely selected, as long as difference in binding activity for an antigen-binding molecule can be detected. In certain embodiments, high concentration includes, for example, 1 nM or higher concentration, 3 nM or higher concentration, 10 nM or higher concentration, 30 nM or higher concentration, 100 nM or higher concentration, 300 nM or higher concentration, 1 micromolar or higher concentration, 3 micromolar or higher concentration, 10 micromolar or higher concentration, 30 micromolar or higher concentration, 100 micromolar or higher concentration, 300 micromolar or higher concentration, 1 mM or higher concentration, 3 mM or higher concentration, 10 mM or higher concentration, 30 mM or higher concentration, 100 mM or higher concentration, 300 mM or higher concentration, 1 M or higher concentration. Alternatively, high concentration herein may be such concentration securing sufficient amount to allow each antigen-binding molecule to show maximum binding activity. In one embodiment, 1 micromolar, 10 micromolar, 100 micromolar, 1 mM, or sufficient amount to allow each antigen-binding molecule to show maximum binding activity may be selected as high concentration herein. In certain embodiments, low concentration includes, for example, 1 mM or lower concentration, 300 micromolar or lower concentration, 100 micromolar or lower concentration, 30 micromolar or lower concentration, 10 micromolar or lower concentration, 3 micromolar or lower concentration, 1 micromolar or lower concentration, 300 nM or lower concentration, 100 nM or lower concentration, 30 nM or lower concentration, 10 nM or lower concentration, 3 nM or lower concentration, 1 nM or lower concentration, 300 pM or lower concentration, 100 pM or lower concentration, 30 pM or lower concentration, 10 pM or lower concentration, 3 pM or lower concentration, 1 pM or lower concentration, etc. Alternatively, low concentration herein may be such concentration at which each antigen-binding molecule shows minimum binding activity. The case of substantially "zero" concentration (i.e., absence of the small molecule compound) may be selected as one embodiment of low concentration. In one embodiment, 1 mM, 100 micromolar, 10 micromolar, 1 micromolar, a concentration at which each antigen-binding molecule shows minimum binding activity, or the absence of the small molecule compound may be selected as low concentration herein. In another embodiment, as the ratio of high concentration to low concentration, for example, the values of 3 times or more, 10 times or more, 30 times or more, 100 times or more, 300 times or more, $1\times10^3$ times or more, $3\times10^3$ times or more, $1\times10^4$ times or more, $3\times10^4$ times or more, $1\times10^5$ times or more, $3\times10^5$ times or more, $1\times10^6$ times or more, $3\times10^6$ times or more, $1\times10^7$ times or more, $3\times10^7$ times or more, $1\times10^8$ times or more, $3\times10^8$ times or more, $1\times10^9$ times or more, $3\times10^9$ times or more, $1\times10^{10}$ times or more, $3\times10^{10}$ times or more, $1\times10^{11}$ times or more, $3\times10^{11}$ times or more, $1\times10^{12}$ times or more may be selected.

In another embodiment, antigen-binding molecules of the present invention show cytotoxicity against cells expressing their antigens. When a target cell expresses the antigen on its surface and the antigen-binding molecule of the present invention binds thereto, the cell may be damaged. Damage to cells may be such damages caused by effector cells, e.g. antibody-dependent cellular cytotoxicity (ADCC) and antibody-dependent cellular phagocytosis (ADCP), and may be such damages caused by complement, e.g. complement-dependent cytotoxicity (CDC). Alternatively, damage may be such damages caused by a cytotoxic agent (e.g., radioisotopes or chemotherapeutic agents) as in immunoconjugates. Cytotoxicity herein may include actions to induce cell death, actions to suppress cell proliferation, actions to damage cell functions, etc. In the presence of sufficient amount of the antigen-binding molecule of the present invention, damage may be caused to, for example, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more of the cells expressing the antigen. Measurement for such cytotoxic activity may be carried out as comparison to the measurement in the absence of the antigen-binding molecule of the present invention or in the presence of a negative control antigen-binding molecule. Exemplary cytotoxicity assays are provided herein.

In another embodiment, the antigen-binding molecules of the present invention show neutralizing activity to their antigens. Neutralizing activity means an activity to neutralize (or inhibit, block) a biological activity associated with the antigens. In one embodiment, the biological activity is brought about by the binding between a ligand and a receptor. In certain embodiments, the antigen-binding molecules of the present invention inhibit such binding between a ligand and a receptor. In the presence of sufficient amount of the antigen-binding molecule of the present invention, biological activity may be inhibited, for example, by 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, or 95% or more. Measurement for such inhibitory activity may be carried out as comparison to the measurement in the absence of the antigen-binding molecule of the present invention or in the presence of a negative control antigen-binding molecule. Specific methods for measuring neutralizing activity are provided herein.

In another embodiment, the antigen-binding molecules of the present invention comprise an Fc region. In further embodiments, the antigen-binding molecules of the present invention comprise a constant region. Constant region may be a heavy chain constant region (comprising an Fc region), a light chain constant region, or both. In some embodiments, Fc region is the one with the native sequence. Examples of heavy chain constant region derived from native sequence antibodies include, for example, heavy chain constant regions of human IgG1 (SEQ ID NO: 219), human IgG2 (SEQ ID NO: 220), human IgG3 (SEQ ID NO: 221), human IgG4 (SEQ ID NO: 222), etc. Other examples of heavy chain constant region include heavy chain constant regions such as SEQ ID NO: 215, SEQ ID NO: 217. Examples of light chain constant region derived from native sequence antibodies include, for example, light chain constant regions of human kappa-chain (SEQ ID NO: 186, SEQ ID NO: 199, SEQ ID NO: 218), human lambda-chain (SEQ ID NO: 189, SEQ ID NO: 216), etc.

In another embodiment, Fc region may be a variant Fc region prepared by introducing amino acid alteration(s) to a native sequence Fc region. In certain embodiments, a variant Fc region has enhanced binding activity to at least one Fc gamma receptor selected from the group consisting of Fc gamma RIa, Fc gamma RIIa, Fc gamma R11b, and Fc gamma RIIIa, as compared to the native sequence Fc region.

In further embodiments, the antigen-binding molecules of the present invention are antibodies. In certain embodiments, the antibodies are monoclonal antibodies, including chimeric antibodies, humanized antibodies, or human antibodies. In one embodiment, the antibodies are antibody fragments, for example, Fv, Fab, Fab', scFv, diabodies, or F(ab')2 fragments, etc. In another embodiment, the antibodies are full length antibodies, for example, intact IgG1 antibodies, intact IgG4 antibodies, or other antibody class or isotype as defined herein.

In another embodiment, the antigen-binding molecules of the present invention form a ternary complex together with a small molecule compound and an antigen. In certain embodiments, the antigen-binding molecules are antibodies. In one embodiment, the antigen-binding molecules of the present invention bind to a small molecule compound via the heavy chain CDR1, CDR2, CDR3. In one embodiment, the antigen-binding molecules of the present invention have a binding motif towards the small molecule compound. The binding motif to the small molecule compound is made, for example, from at least one amino acid present at position 33, position 52, position 52a, position 53, position 55, position 56, position 58, position 95, position 96, position 98, position 100a, position 100b, position 100c, according to Kabat numbering. In further embodiments, the antigen-binding molecules of the present invention bind to the small molecule compound via at least one amino acid selected from the group consisting of position 33, position 52, position 52a, position 53, position 55, position 56, position 58, position 95, position 96, position 98, position 100a, position 100b, position 100c, according to Kabat numbering. An antigen may further bind to a complex formed from the binding between the antigen-binding molecule of the present invention and a small molecule compound. Furthermore, the small molecule compound may be present at the interface of the interaction between the antigen-binding molecule and the antigen and may bind to both of them. Formation of a ternary complex by an antigen-binding molecule of the present invention together with a small molecule compound and an antigen can be confirmed, for example, by crystallography as described below or such techniques. In certain embodiments, the small molecule compound is an adenosine-containing compound.

In one embodiment, the small molecule compound of the present disclosure is a "target tissue-specific compound". In further embodiments, the "target tissue-specific compound" is a tumor tissue-specific compound. Exemplary target tissue-specific compounds and tumor tissue-specific compounds are disclosed herein (e.g., "II. Compositions and methods (anti-CD137 agonistic antigen-binding molecules)", "A. Exemplary anti-CD137 antigen-binding molecules or antibodies", "[Small molecule compound-dependent binding activity]").

B. Antigen

Herein, "antigens" are not particularly limited in their structure, as long as they comprise epitopes to which antigen-binding molecules of the present invention bind. Antigens can be inorganic or organic substances. In some embodiments, examples of antigens include: 17-IA, 4-1BB, 4Dc, 6-keto-PGF1a, 8-iso-PGF2a, 8-oxo-dG, A1 adenosine receptor, A33, ACE, ACE-2, activin, activin A, activin AB, activin B, activin C, activin RIA, activin RIA ALK-2, activin RIB ALK-4, activin RIIA, activin RIIB, ADAM, ADAM10, ADAM12, ADAM15, ADAM17/TACE, ADAMS, ADAMS, ADAMTS, ADAMTS4, ADAMTS5, addressin, aFGF, ALCAM, ALK, ALK-1, ALK-7, alpha-1-antitrypsin, alpha-V/beta-1 antagonist, ANG, Ang, APAF-1, APE, APJ, APP, APRIL, AR, ARC, ART, artemin, anti-Id, ASPARTIC, atrial natriuretic peptide, av/b3 integrin, Axl, b2M, B7-1, B7-2, B7-H, B-lymphocyte stimulating factor (BlyS), BACE, BACE-1, Bad, BAFF, BAFF-R, Bag-1, BAK, Bax, BCA-1, BCAM, Bcl, BCMA, BDNF, b-ECGF, bFGF, BID, Bik, BIM, BLC, BL-CAM, BLK, BMP, BMP-2 BMP-2a, BMP-3 Osteogenin, BMP-4 BMP-2b, BMP-5, BMP-6 Vgr-1, BMP-7 (OP-1), BMP-8 (BMP-8a, OP-2), BMPR, BMPR-IA (ALK-3), BMPR-IB (ALK-6), BRK-2, RPK-1, BMPR-II (BRK-3), BMP, b-NGF, BOK, bombesin, bone-derived neurotrophic factor, BPDE, BPDE-DNA, BTC, complement factor 3 (C3), C3a, C4, C5, C5a, C10, CA125, CAD-8, calcitonin, cAMP, carcinoembryonic antigen (CEA), cancer associated antigen, cathepsin A, cathepsin B, cathepsin C/DPPI, cathepsin D, cathepsin E, cathepsin H, cathepsin L, cathepsin O, cathepsin S, cathepsin V, cathepsin X/Z/P, CBL, CCI, CCK2, CCL, CCL1, CCL11, CCL12, CCL13, CCL14, CCL15, CCL16, CCL17, CCL18, CCL19, CCL2, CCL20, CCL21, CCL22, CCL23, CCL24, CCL25, CCL26, CCL27, CCL28, CCL3, CCL4, CCL5, CCL6, CCL7, CCL8, CCL9/10, CCR, CCR1, CCR10, CCR10, CCR2, CCR3, CCR4, CCR5, CCR6, CCR7, CCR8, CCR9, CD1, CD2, CD3, CD3E, CD4, CD5, CD6, CD7, CD8, CD10, CD11a, CD11b, CD11c, CD13, CD14, CD15, CD16, CD18, CD19, CD20, CD21, CD22, CD23, CD25, CD27L, CD28, CD29, CD30, CD30L, CD32, CD33 (p67 protein), CD34, CD38, CD40, CD40L, CD44, CD45, CD46, CD49a, CD52, CD54, CD55, CD56, CD61, CD64, CD66e, CD74, CD80 (B7-1), CD89, CD95, CD123, CD137, CD138, CD140a, CD146, CD147, CD148, CD152, CD164, CEACAMS, CFTR, cGMP, CINC, Botulinum toxin, Clostridium perfringens toxin, CKb8-1, CLC, CMV, CMV UL, CNTF, CNTN-1, COX, C-Ret, CRG-2, CT-1, CTACK, CTGF, CTLA-4, PD1, PDL1, LAG3, TIM3, galectin-9, CX3CL1, CX3CR1, CXCL, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCR, CXCR1, CXCR2, CXCR3, CXCR4, CXCR5, CXCR6, cytokeratin tumor associated antigen, DAN, DCC, DcR3, DC-SIGN, complement regulatory factor (Decay accelerating factor), des (1-3)-IGF-I (brain IGF-1), Dhh, digoxin, DNAM-1, Dnase, Dpp, DPPIV/CD26, Dtk, ECAD, EDA, EDA-A1, EDA-A2, EDAR, EGF, EGFR (ErbB-1), EMA, EMMPRIN, ENA, endothelin receptor, enkephalinase, eNOS, Eot, eotaxin 1, EpCAM, ephrin B2/EphB4, EPO, ERCC, E-selectin, ET-1, factor IIa, factor VII, factor VIIIc, factor IX, fibroblast activation protein (FAP), Fas, FcR1, FEN-1, ferritin, FGF, FGF-19, FGF-2, FGF-3, FGF-8, FGFR, FGFR-3, fibrin, FL, FLIP, Flt-3, Flt-4, follicle stimulating hormone, fractalkine, FZD1, FZD2, FZD3, FZD4, FZD5, FZD6, FZD7, FZD8, FZD9, FZD10, G250, Gas6, GCP-2, GCSF, GD2, GD3, GDF, GDF-1, GDF-3 (Vgr-2), GDF-5 (BMP-14, CDMP-1), GDF-6 (BMP-13, CDMP-2), GDF-7 (BMP-12, CDMP-3), GDF-8 (myostatin), GDF-9, GDF-15 (MIC-1), GDNF, GDNF, GFAP, GFRa-1, GFR-alpha1, GFR-alpha2, GFR-alpha3, GITR, glucagon, Glut4, glycoprotein IIb/IIIa (GPIIb/IIIa), GM-CSF, gp130, gp72, GRO, growth hormone releasing hormone, hapten (NP-cap or NIP-cap), HB-EGF, HCC, HCMV gB envelope glycoprotein, HCMV gH envelope glycoprotein, HCMV UL, hematopoietic growth factor (HGF), Hep B gp120, heparanase, Her2, Her2/neu (ErbB-2), Her3 (ErbB-3), Her4 (ErbB-4), herpes simplex virus (HSV) gB glycoprotein, HSV gD glycoprotein, HGFA, high molecular weight melanoma-associated antigen (HMW-MAA), HIV gp120, HIV IIIB gp 120 V3 loop, HLA, HLA-DR, HM1.24, HMFG PEM, HRG, Hrk, human cardiac myosin, human cytomegalovirus (HCMV), human growth hormone (HGH), HVEM, I-309, IAP, ICAM, ICAM-1, ICAM-3, ICE, ICOS, IFNg, Ig, IgA receptor, IgE, IGF, IGF binding protein, IGF-1R, IGFBP, IGF-I, IGF-II, IL, IL-1, IL-1R, IL-2, IL-2R, IL-4, IL-4R, IL-5, IL-5R, IL-6, IL-6R, IL-8, IL-9, IL-10, IL-12, IL-13, IL-15, IL-18, IL-18R, IL-21, IL-23, IL-27, interferon (INF)-alpha, INF-beta, INF-gamma, inhibin, iNOS, insulin A chain, insulin B chain, insulin-like growth factor1, integrin alpha2, integrin alpha3, integrin alpha4, integrin alpha4/beta1, integrin alpha4/beta7, integrin alpha5 (alpha V), integrin alpha5/beta1, integrin alpha5/beta3, integrin alpha6, integrin beta1, integrin beta2, interferon gamma, IP-10, I-TAC, JE, kallikrein 2, kallikrein 5, kallikrein 6, kallikrein 11, kallikrein 12, kallikrein 14, kallikrein 15, kallikrein L1, kallikrein L2, kallikrein L3, kallikrein L4, KC, KDR, keratinocyte growth factor (KGF), laminin 5, LAMP, LAP, LAP (TGF-1), latent TGF-1, latent TGF-1 bp1, LBP, LDGF, LECT2, lefty, Lewis-Y antigen, Lewis-Y associated antigen, LFA-1, LFA-3, Lfo, LIF, LIGHT, lipoprotein, LIX, LKN, Lptn, L-selectin, LT-a, LT-b, LTB4, LTBP-1, lung surface, luteinizing hormone, lymphotoxin beta receptor, Mac-1, MAdCAM, MAG, MAP2, MARC, MCAM, MCAM, MCK-2, MCP, M-CSF, MDC, Mer, METALLOPROTEASES, MGDF receptor, MGMT, MHC (HLA-DR), MIF, MIG, MIP, MIP-1-alpha, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, MPIF, Mpo, MSK, MSP, mucin (Muc1), MUC18, Mullerian-inhibiting substance, Mug, MuSK, NAIP, NAP, NCAD, N-C adherin, NCA 90, NCAM, NCAM, neprilysin, neurotrophin-3, -4, or -6, neurturin, nerve growth factor (NGF), NGFR, NGF-beta, nNOS, NO, NOS, Npn, NRG-3, NT, NTN, OB, OGG1, OPG, OPN, OSM, OX40L, OX40R, p150, p95, PADPr, parathyroid hormone, PARC, PARP, PBR, PBSF, PCAD, P-cadherin, PCNA, PDGF, PDGF, PDK-1, PECAM, PEM, PF4, PGE, PGF, PGI2, PGJ2, PIN, PLA2, placental alkaline phosphatase (PLAP), P1GF, PLP, PP14, proinsulin, prorelaxin, protein C, PS, PSA, PSCA, prostate-specific membrane antigen (PSMA), PTEN, PTHrp, Ptk, PTN, R51, RANK, RANKL, RANTES, RANTES, relaxin A chain, relaxin B chain, renin, respiratory syncytial virus (RSV) F, RSV Fgp, Ret, Rheumatoid factor, RLIP76, RPA2, RSK, 5100, SCF/KL, SDF-1, SERINE, serum albumin, sFRP-3, Shh, SIGIRR, SK-1, SLAM, SLPI, SMAC, SMDF, SMOH, SOD, SPARC, Stat, STEAP, STEAP-II, TACE, TACI, TAG-72 (tumor-associated glycoprotein-72), TARC, TCA-3, T-cell receptor (for example, T-cell receptor alpha/beta), TdT, TECK, TEM1, TEM5, TEM7, TEM8, TERT, testis PLAP-like alkaline phosphatase, TfR, TGF, TGF-alpha, TGF-beta, TGF-beta Pan Specific, TGF-betaRI (ALK-5), TGF-betaRII, TGF-betaRIIb, TGF-betaRIII, TGF-beta1, TGF-beta2, TGF-beta3, TGF-beta4, TGF-beta5, thrombin, thymus Ck-1, thyroid-stimulating hormone, Tie, TIMP, TIQ, tissue factor, TMEFF2, Tmpo, TMPRSS2, TNF, TNF-alpha, TNF-alphabeta, TNF-beta2, TNFc, TNF-RI, TNF-RII, TNFRSF10A (TRAIL R1 Apo-2, DR4), TNFRSF10B (TRAIL R2 DR5, KILLER, TRICK-2A, TRICK-B), TNFRSF10C (TRAIL R3 DcR1, LIT, TRID), TNFRSF10D (TRAIL R4 DcR2, TRUNDD), TNFRSF11A (RANK ODF R, TRANCE R), TNFRSF11B (OPG OCIF, TR1), TNFRSF12 (TWEAK R FN14), TNFRSF13B (TACI), TNFRSF13C (BAFF R), TNFRSF14 (HVEM ATAR, HveA, LIGHT R, TR2), TNFRSF16 (NGFR p75NTR), TNFRSF17 (BCMA), TNFRSF18 (GITR AITR), TNFRSF19 (TROY TAJ, TRADE), TNFRSF19L (RELT), TNFRSF1A (TNF RI CD120a, p55-60), TNFRSF1B (TNF RII CD120b, p75-80), TNFRSF26 (TNFRH3), TNFRSF3 (LTbR TNF RIII, TNFC R), TNFRSF4 (OX40 ACT35, TXGP1 R), TNFRSF5 (CD40 p50), TNFRSF6 (Fas Apo-1, APT1, CD95), TNFRSF6B (DcR3 M68, TR6), TNFRSF7 (CD27), TNFRSF8 (CD30), TNFRSF9 (4-1BB CD137, ILA), TNFRSF21 (DR6), TNFRSF22 (DcTRAIL R2 TNFRH2), TNFRST23 (DcTRAIL R1 TNFRH1), TNFRSF25 (DR3 Apo-3, LARD, TR-3, TRAMP, WSL-1), TNFSF10 (TRAIL Apo-2 ligand, TL2), TNFSF11 (TRANCE/RANK ligand ODF, OPG ligand), TNFSF12 (TWEAK Apo-3 ligand, DR3 ligand), TNFSF13 (APRIL TALL2), TNFSF13B (BAFF BLYS, TALL1, THANK, TNFSF20), TNFSF14 (LIGHT HVEM ligand, LTg), TNFSF15 (TL1A/VEGI), TNFSF18 (GITR ligand AITR ligand, TL6), TNFSF1A (TNF-α Conectin, DIF, TNFSF2), TNFSF1B (TNF-b LTa, TNFSF1), TNFSF3 (LTb TNFC, p33), TNFSF4 (OX40 ligand gp34, TXGP1), TNFSFS (CD40 ligand CD154, gp39, HIGM1, IMD3, TRAP), TNFSF6 (Fas ligand Apo-1 ligand, APT1 ligand), TNFSF7 (CD27 ligand CD70), TNFSF8 (CD30 ligand CD153), TNFSF9 (4-1BB ligand CD137 ligand), TP-1, t-PA, Tpo, TRAIL, TRAIL R, TRAIL-R1, TRAIL-R2, TRANCE, transferrin receptor, TRF, Trk, TROP-2, TLR1 (Toll-like receptor 1), TLR2, TLR3, TLR4, TLRS, TLR6, TLR7, TLR8, TLR9, TLR10, TSG, TSLP, tumor associated antigen CA125, tumor associated antigen expressing Lewis-Y associated carbohydrates, TWEAK, TXB2, Ung, uPAR, uPAR-1, urokinase, VCAM, VCAM-1, VECAD, VE-Cadherin, VE-cadherin-2, VEFGR-1 (flt-1), VEGF, VEGFR, VEGFR-3 (flt-4), VEGI, VIM, virus antigen, VLA, VLA-1, VLA-4, VNR integrin, von Willebrand factor, WIF-1, WNT1, WNT2, WNT2B/13, WNT3, WNT3A, WNT4, WNTSA, WNTSB, WNT6, WNT7A, WNT7B, WNT8A, WNT8B, WNT9A, WNT9A, WNT9B, WNT10A, WNT10B, WNT11, WNT16, XCL1, XCL2, XCR1, XCR1, XEDAR, XIAP, XPD, HMGB1, IgA, A beta, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, high molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, and SIP. In some embodiments, examples of antigens include receptors for hormone and growth factors. In certain embodiments, antigens are those that are expressed in or secreted from cells present in tumor tissues (e.g., tumor cells, immune cells, stromal cells, or such).

C. Activities, Compositions, and Methods

In one embodiment, cytotoxic activity in the present invention includes, for example, antibody-dependent cell-mediated cytotoxicity (ADCC) activity, antibody-dependent cellular phagocytosis (ADCP), complement-dependent cytotoxicity (CDC) activity, and cytotoxic activity by T cells. CDC activity refers to cytotoxic activity by the complement system. On the other hand, ADCC activity refers to the activity of damaging target cells via effector cells, which occurs when antigen-binding molecules bind to antigens present on the cell surface of target cells and effector cells further bind to the antigen-binding molecules. Whether an antigen-binding molecule of interest has an ADCC activity or whether it has a CDC activity can be measured using known methods (for example, Current Protocols in Immunology, Chapter 7. Immunologic studies in humans, Editor, Coligan et al., (1993)).

In one embodiment, "neutralizing activity" in the present invention refers to an activity of an antigen-binding molecule to inhibit a biological activity through its binding to a molecule involved in that biological activity. In some embodiments, the biological activity is brought about by the binding between a ligand and a receptor. In certain embodiments, an antigen-binding molecule binds to a ligand or receptor, thereby inhibits the binding between the ligand and the receptor. When the antigen-binding molecule is an antibody, the antigen-binding molecule having such a neutralizing activity is called a neutralizing antibody. The neutralizing activity of a test substance may be measured by comparing the biological activities in the presence of a ligand between conditions when the test substance is present or absent.

In one aspect, the present invention provides methods for producing an antigen-binding molecule whose antigen-binding activity changes depending on the concentration of a compound. When the compound is a target tissue-specific compound, the present invention provides methods for producing an antigen-binding molecule that exerts its action specifically in the target tissue. In certain embodiments, the target tissue is a tumor tissue. When the compound is a tumor tissue-specific compound, the present invention provides methods for producing an antigen-binding molecule for use in treating a tumor. In some aspect, these methods for producing comprise a step of selecting an antigen-binding molecule whose antigen-binding activity in the presence of the compound is different from its antigen-binding activity in the absence of the compound. In some aspect, these methods for producing comprise a step of selecting an antigen-binding molecule whose antigen-binding activity in the presence of high concentration of the compound is different from its antigen-binding activity in the presence of low concentration of the compound. In some embodiments, these methods for producing comprise the steps of (a) obtaining an antigen-binding activity of an antigen-binding molecule in the presence of a compound, (b) obtaining an antigen-binding activity of the antigen-binding molecule in the absence of the compound, and (c) selecting an antigen-binding molecule whose antigen-binding activity in the presence of the compound is different from its antigen-binding activity in the absence of the compound. In some embodiments, these methods for producing comprise the steps of (a) obtaining an antigen-binding activity of an antigen-binding molecule in the presence of high concentration of a compound, (b) obtaining an antigen-binding activity of the antigen-binding molecule in the presence of low concentration of the compound, and (c) selecting an antigen-binding molecule whose antigen-binding activity in the presence of high concentration of the compound is different from its antigen-binding activity in the presence of low concentration of the compound.

In further aspect, the present invention provides methods for producing an antigen-binding molecule whose antigen-binding activity increases as the concentration of a compound becomes higher. Alternatively, in another aspect, the present invention provides methods for producing an antigen-binding molecule whose antigen-binding activity decreases as the concentration of a compound becomes higher. The methods for producing comprise a step of selecting an antigen-binding molecule whose antigen-binding activity in the presence of the compound is higher than its antigen-binding activity in the absence of the compound. In another embodiment, the methods for producing comprise a step of selecting an antigen-binding molecule whose antigen-binding activity in the absence of the compound is lower than its antigen-binding activity in the presence of the compound. In another aspect, the methods for producing comprise a step of selecting an antigen-binding molecule whose antigen-binding activity in the absence of the compound is higher than its antigen-binding activity in the presence of the compound. In another embodiment, the methods for producing comprise a step of selecting an antigen-binding molecule whose antigen-binding activity in the presence of the compound is lower than its antigen-binding activity in the absence of the compound. In further aspect, the methods for producing comprise a step of selecting an antigen-binding molecule whose antigen-binding activity in the presence of high concentration of the compound is higher than its antigen-binding activity in the presence of low concentration of the compound. In another embodiment, the methods for producing comprise a step of selecting an antigen-binding molecule whose antigen-binding activity in the presence of low concentration of the compound is lower than its antigen-binding activity in the presence of high concentration of the compound. In another aspect, the methods for producing comprise a step of selecting an antigen-binding molecule whose antigen-binding activity in the presence of low concentration of the compound is higher than its antigen-binding activity in the presence of high concentration of the compound. In another embodiment, the methods for producing comprise a step of selecting an antigen-binding molecule whose antigen-binding activity in the presence of high concentration of the compound is lower than its antigen-binding activity in the presence of low concentration of the compound.

In another aspect, the present invention provides methods for producing an antigen-binding molecule having high retention property in plasma. In some embodiments, the methods for producing comprise a step of producing an antigen-binding molecule whose antigen-binding activity increases as the concentration of a compound becomes higher. In further embodiments, the methods for producing comprise the steps of (a) producing an antigen-binding molecule whose antigen-binding activity increases as the concentration of a compound becomes higher; and (b) measuring retention property in plasma of the antigen-binding molecule produced in (a). In certain embodiments, the compound is a target tissue-specific compound. In further embodiments, the compound is a tumor tissue-specific compound. Determination on whether an antigen-binding molecule in the present invention has high retention property in plasma can be made by comparison relative to a control antigen-binding molecule. In some embodiments, those antigen-binding molecules whose antigen-binding activity increases as the concentration of a target tissue-specific compound becomes higher have higher retention property in plasma as compared to a control antigen-binding molecule. In one embodiment, the control antigen-binding molecule does not have antigen binding activity dependent on the concentration of a compound. In certain embodiments, an antigen-binding molecule that does not have antigen binding activity dependent on the concentration of a compound means an antigen-binding molecule for which difference in antigen binding activity in the presence of the compound and in the absence of the compound is, for example, 2-fold or smaller, 1.8-fold or smaller, 1.5-fold or smaller, 1.3-fold or smaller, 1.2-fold or smaller, or 1.1-fold or smaller. From the point of view of making comparison, it is preferable that antigen binding activity of the antigen-binding molecules of the present invention and control antigen-binding molecules in the presence of sufficient amount of compound are substantially the same to each other.

In another aspect, the present invention provides methods for producing an antigen-binding molecule having low ability of antigen accumulation in plasma. In some embodiments, the methods for producing comprise a step of producing an antigen-binding molecule whose antigen-binding activity increases as the concentration of a compound becomes higher. In further embodiments, the methods for producing comprise the steps of (a) producing an antigen-binding molecule whose antigen-binding activity increases as the concentration of a compound becomes higher; and (b) measuring ability of antigen accumulation in plasma for the antigen-binding molecule produced in (a). In certain embodiments, the compound is a target tissue-specific compound. In further embodiments, the compound is a tumor tissue-specific compound. Determination on whether an antigen-binding molecule in the present invention has low ability of antigen accumulation in plasma can be made by comparison relative to a control antigen-binding molecule. In some embodiments, those antigen-binding molecules whose antigen-binding activity increases as the concentration of a target tissue-specific compound becomes higher have lower ability of antigen accumulation in plasma as compared to a control antigen-binding molecule. In one embodiment, the control antigen-binding molecule does not have antigen binding activity dependent on the concentration of a compound. In certain embodiments, an antigen-binding molecule that does not have antigen binding activity dependent on the concentration of a compound means an antigen-binding molecule for which difference in antigen binding activity in the presence of the compound and in the absence of the compound is, for example, 2-fold or smaller, 1.8-fold or smaller, 1.5-fold or smaller, 1.3-fold or smaller, 1.2-fold or smaller, or 1.1-fold or smaller. From the point of view of making comparison, it is preferable that antigen binding activity of the antigen-binding molecules of the present invention and control antigen-binding molecules in the presence of sufficient amount of compound are substantially the same to each other.

In some embodiments, for the antigen-binding molecules produced by the methods of the present invention, the difference in antigen-binding activity dependent on the concentration of a compound is, for example, twice or more, three times or more, five times or more, 10 times or more, 20 times or more, 30 times or more, 50 times or more, 100 times or more, 200 times or more, 300 times or more, 500 times or more, $1 \times 10^3$ times or more, $2 \times 10^3$ times or more, $3 \times 10^3$ times or more, $5 \times 10^3$ times or more, $1 \times 10^4$ times or more, $2 \times 10^4$ times or more, $3 \times 10^4$ times or more, $5 \times 10^4$ times or more, or $1 \times 10^5$ times or more. In some embodiments, antigen-binding activity may be expressed by a KD (dissociation constant) value or by a kd (dissociation rate constant) value. Alternatively, it may be expressed by using an amount of an antigen that has bound to an antigen-binding molecule as described above. Alternatively, in another embodiment, antigen-binding molecule's cytotoxic activity or neutralizing activity may be used as an alternative indicator to the antigen-binding activity.

In certain embodiments, the higher one of antigen-binding activities include, for example, the KD value of $9 \times 10^{-7}$ M or less, $8 \times 10^{-7}$ M or less, $7 \times 10^{-7}$ M or less, $6 \times 10^{-7}$ M or less, $5 \times 10^{-7}$ M or less, $4 \times 10^{-7}$ M or less, $3 \times 10^{-7}$ M or less, $2 \times 10^{-7}$ M or less, $1 \times 10^{-7}$ M or less, $9 \times 10^{-8}$ M or less, $8 \times 10^{-8}$ M or less, $7 \times 10^{-8}$ M or less, $6 \times 10^{-8}$ M or less, $5 \times 10^{-8}$ M or less, $4 \times 10^{-8}$ M or less, $3 \times 10^{-8}$ M or less, $2 \times 10^{-8}$ M or less, $1 \times 10^{-8}$ M or less, $9 \times 10^{-9}$ M or less, $8 \times 10^{-9}$ M or less, $7 \times 10^{-9}$ M or less, $6 \times 10^{-9}$ M or less, $5 \times 10^{-9}$ M or less, $4 \times 10^{-9}$ M or less, $3 \times 10^{-9}$ M or less, $2 \times 10^{-9}$ M or less, $1 \times 10^{-9}$ M or less, or, for example, the amount of bound antigen of 0.01 or more, 0.02 or more, 0.03 or more, 0.04 or more, 0.05 or more, 0.06 or more, 0.07 or more, 0.08 or more, 0.09 or more, 0.1 or more, 0.2 or more, 0.3 or more, 0.4 or more, 0.5 or more, 0.6 or more, 0.7 or more, 0.8 or more, 0.9 or more, 1 or more.

In certain embodiments, the lower one of antigen-binding activities include, for example, the KD value of $1 \times 10^{-8}$ M or more, $2 \times 10^{-8}$ M or more, $3 \times 10^{-8}$ M or more, $4 \times 10^{-8}$ M or more, $5 \times 10^{-8}$ M or more, $6 \times 10^{-8}$ M or more, $7 \times 10^{-8}$ M or more, $8 \times 10^{-8}$ M or more, $9 \times 10^{-8}$ M or more, $1 \times 10^{-7}$ M or more, $2 \times 10^{-7}$ M or more, $3 \times 10^{-7}$ M or more, $4 \times 10^{-7}$ M or more, $5 \times 10^{-7}$ M or more, $6 \times 10^{-7}$ M or more, $7 \times 10^{-7}$ M or more, $8 \times 10^{-7}$ M or more, $9 \times 10^{-7}$ M or more, $1 \times 10^{-6}$ M or more, $2 \times 10^{-6}$ M or more, $3 \times 10^{-6}$ M or more, $4 \times 10^{-6}$ M or more, $5 \times 10^{-6}$ M or more, $6 \times 10^{-6}$ M or more, $7 \times 10^{-6}$ M or more, $8 \times 10^{-6}$ M or more, $9 \times 10^{-6}$ M or more, or, for example, the amount of bound antigen of 0.5 or less, 0.4 or less, 0.3 or less, 0.2 or less, 0.1 or less, 0.09 or less, 0.08 or less, 0.07 or less, 0.06 or less, 0.05 or less, 0.04 or less, 0.03 or less, 0.02 or less, 0.01 or less, 0.009 or less, 0.008 or less, 0.007 or less, 0.006 or less, 0.005 or less, 0.004 or less, 0.003 or less, 0.002 or less, 0.001 or less.

Concentration of a compound may be freely selected, as long as difference in binding activity for an antigen-binding molecule can be detected. Examples of concentration (high concentration and low concentration) are provided herein. In certain embodiments, examples of high concentration include, for example, 1 micromolar or higher concentration, 3 micromolar or higher concentration, 10 micromolar or higher concentration, 30 micromolar or higher concentration, 100 micromolar or higher concentration, 300 micromolar or higher concentration, 1 mM or higher concentration. Alternatively, high concentration herein may be such concentration securing sufficient amount to allow each antigen-binding molecule to show maximum binding activity. In certain embodiments, examples of low concentration include, for example, 1 mM or lower concentration, 300 micromolar or lower concentration, 100 micromolar or lower concentration, 30 micromolar or lower concentration, 10 micromolar or lower concentration, 3 micromolar or lower concentration, 1 micromolar or lower concentration. Alternatively, low concentration herein may be such concentration at which each antigen-binding molecule shows minimum binding activity. The case of substantially "zero" concentration (i.e., absence of the compound) may be one embodiment of low concentration.

In further aspect, these methods for producing comprise a step of selecting an antigen-binding molecule whose antigen-binding activity in the presence of the compound is different from its antigen-binding activity in the absence of the compound, from a library of antigen-binding molecules. The library of antigen-binding molecules may be with unbiased repertoire of antigen-binding molecules (naive library) or may be with biased repertoire of antigen-binding molecules. Examples of the latter type of library include a library of antigen-binding molecules to which binding activity to a specified compound is conferred in advance. In certain embodiments, an antigen-binding molecule library is a library of antigen-binding molecules to which amino acid alteration(s) to confer binding activity to a specified compound is introduced in advance. Examples of such type of library include libraries described, for example, in the International Publication, WO 2015/083764.

In certain embodiments, the methods for production further comprise the steps of (d) obtaining a nucleic acid that encodes the antigen-binding molecule selected in (c), (e) introducing the nucleic acid of (d) into a host cell, and (f) culturing the host cell of (e) so that the antigen-binding molecule is expressed. The nucleic acid of (d) may be one or more nucleic acid(s) and may be included in one or more vector(s) (e.g., an expression vector). In certain embodiments, the methods for production further comprise the step of (g) recovering the antigen-binding molecule from cell culture of (f).

The antigen-binding molecules produced by the methods for production of the present invention are also included in the present invention.

In further aspect, the present invention provides pharmaceutical preparations comprising an antigen-binding molecule provided herein. In one embodiment, the above-mentioned pharmaceutical preparations further comprise a pharmaceutically acceptable carrier. In further embodiments, the present invention provides pharmaceutical preparations for use in the treatment of a tumor.

In further aspect, the present invention provides methods for producing a pharmaceutical preparation, comprising mixing an antigen-binding molecule provided herein with a pharmaceutically acceptable carrier. In further embodiments, the present invention provides methods for producing a pharmaceutical preparation for use in the treatment of a tumor.

In one embodiment, an antigen-binding molecule provided herein, when administered to a living body, shows stronger antigen-binding activity in a tumor tissue than in a non-tumor tissue. Such difference in response needs not to be observed for every dose of the antigen-binding molecule, and it is enough that the difference is observed for a specified range of doses. In another embodiment, targeted cells (cells expressing the antigen) are more strongly damaged in a tumor tissue than in a non-tumor tissue. In another embodiment, targeted cells are damaged at a lower dose in a tumor tissue than in a non-tumor tissue. Alternatively, in another embodiment, therapeutic effect is observed at a lower dose than the dose at which side effect is observed. The therapeutic effect herein is development of an anti-tumor effect (for example, regression of a tumor, induction of cell death to tumor cells, or inhibition of proliferation of tumor cells, etc.) and a side effect is occurrence of an adverse event in normal tissues (for example, damage to normal tissues).

In one embodiment, the degree of efficacy as medicament brought by the antigen-binding molecule provided herein differs depending on whether the antigen-binding molecule has antigen binding activity dependent on the concentration of a compound (i.e., changing according to the concentration of the compound). In some embodiments, the antigen-binding molecules of the present invention are an antigen-binding molecule whose antigen-binding activity increases as the concentration of the compound becomes higher. In some embodiments, a control antigen-binding molecule is an antigen-binding molecule that does not have antigen binding activity dependent on the concentration of a compound. In certain embodiments, the compound is a tumor tissue-specific compound. In certain embodiments, an antigen-binding molecule that does not have antigen binding activity dependent on the concentration of a compound means an antigen-binding molecule for which difference in antigen binding activity in the presence of the compound and in the absence of the compound is, for example, 2-fold or smaller, 1.8-fold or smaller, 1.5-fold or smaller, 1.3-fold or smaller, 1.2-fold or smaller, or 1.1-fold or smaller. It is preferable that antigen binding activity of the antigen-binding molecules of the present invention and control antigen-binding molecules in the presence of sufficient amount of a compound are substantially the same to each other.

In one embodiment, for an antigen-binding molecule of the present invention and a control antigen-binding molecule, effects as medicament caused thereby are different. In certain embodiment, effects as medicament are different in a tissue where the concentration of a compound is low. Examples of a tissue with low concentration of the compound include non-tumor tissues such as normal tissues. An antigen-binding molecule may be provided as a pharmaceutical preparation comprising the antigen-binding molecule. In some embodiments, in a tissue with low concentration of the compound, the antigen-binding molecule of the present invention has lower activity of damaging a targeted cell (a cell expressing the antigen) as compared to the control antigen-binding molecule. In some embodiments, in a tissue with low concentration of the compound, the antigen-binding molecule of the present invention require a higher dose to damage a cell as compared to the control antigen-binding molecule. In some embodiments, in a tissue with low concentration of the compound, the antigen-binding molecule of the present invention shows lower level of a side effect as compared to the control antigen-binding molecule. In some embodiments, in a tissue with low concentration of the compound, a dose at which a side effect is observed is higher for the antigen-binding molecule of the present invention as compared to the control antigen-binding molecule. These differences in response need not to be observed for every tissue (e.g., all tissues showing low concentration of the compound), and it is enough that the differences are observed for some tissues. In certain embodiments, a side effect is an adverse event in normal tissues (for example, damage to normal tissues).

In one embodiment, for an antigen-binding molecule of the present invention and a control antigen-binding molecule, effects as medicament caused thereby are substantially the same. In certain embodiments, the effects as medicament are substantially the same in a tissue where the concentration of a compound is high. Examples of a tissue with high concentration of the compound include a tumor tissue. An antigen-binding molecule may be provided as a pharmaceutical preparation comprising the antigen-binding molecule. In some embodiments, in a tissue with high concentration of the compound, an activity of damaging a targeted cell (a cell expressing the antigen) is substantially the same for the antigen-binding molecule of the present invention and the control antigen-binding molecule. In some embodiments, in a tissue with high concentration of the compound, a dose required to damage a cell is substantially the same for the antigen-binding molecule of the present invention and the control antigen-binding molecule. In some embodiments, in a tissue with high concentration of the compound, a level of therapeutic effect is substantially the same for the antigen-binding molecule of the present invention and the control antigen-binding molecule. In some embodiments, in a tissue with high concentration of the compound, a dose at which therapeutic effect is observed is substantially the same for the antigen-binding molecule of the present invention and the control antigen-binding molecule. In certain embodiments, the therapeutic effect is an anti-tumor effect (for example, regression of a tumor, induction of cell death to tumor cells, or inhibition of proliferation of tumor cells, etc.).

In further aspect, an antigen-binding molecule for use as a medicament is provided. In further aspect, an antigen-binding molecule for use in the treatment of a tumor is provided. In further aspect, use of an antigen-binding molecule in the manufacture of a medicament is provided. In further aspect, use of an antigen-binding molecule for treating a tumor is provided. In further aspect, a method of treating a tumor comprising administering an effective amount of an antigen-binding molecule to an individual having the tumor is provided. The "individual" in any of the above-described embodiments is preferably a human.

<Methods for Measuring ATP Concentration>

In another aspect, the present invention provides methods for measuring ATP concentration in a solution. In some embodiments, the above-mentioned methods comprise the steps of (a) contacting a split Luc/HEK293 cell expressing P2Y receptor with the solution, and (b) measuring luciferase activity in the cell. P2Y receptor is a cell surface receptor, and a seven-transmembrane, G protein-coupled receptor (GPCR), whose endogenous ligand is extracellular purine nucleotides (ATP, ADP), pyrimidine nucleotides (UTP, UDP), sugar nucleotides, and such. In further embodiments, the P2Y receptor is P2Y1 (Accession No. U42029), P2Y2 (Accession No. U07225), P2Y4 (Accession No. X91852), P2Y6 (Accession No. X97058), P2Y11 (Accession No. AF030335), P2Y12 (Accession No. AJ320495), P2Y13 (Accession No. AF295368), or P2Y14 (Accession No. D13626). In certain embodiments, the P2Y receptor is P2Y11 (Accession No. AF030335). The split Luc/HEK293 cell is recombinant cells prepared using the split luciferase technology owned by ProbeX (Misawa et al., Anal. Chem. (2010) 82, 2552-2560), and expresses the following two proteins: (i) a fusion protein in which the C-terminal fragment out of the two fragments of a luciferase molecule split into two is attached to the C-terminus of the P2Y receptor, and (ii) a fusion protein in which the N-terminal fragment out of the two fragments of a luciferase molecule split into two is attached to the N-terminus of beta-arrestin (Accession No. NM_004313).

When ATP is added to the split Luc/HEK293 cells expressing the P2Y receptor, interaction between the P2Y receptor and beta-arrestin occurs in the proximity of the cell membrane, and as a result split luciferase fragments associate to reconstitute an active luciferase molecule within the cell. The activity of luciferase can be measured using a substrate of luciferase such as, for example, luciferin. In some embodiments, the above-described methods further comprise the step of contacting the cell with a solution containing a luciferase substrate. The solution containing a luciferase substrate may be allowed to contact with the cell before the step of (a) or after the step of (a).

In some embodiments, the solution for which ATP concentration is measured may be an in vitro solution or a body fluid in an in vivo tissue. In further embodiments, the body fluid may be selected from the group consisting of blood, lymph fluid, tissue fluid (inter-tissue fluid, intercellular fluid, interstitial fluid), body cavity fluid (serous cavity fluid, pleural fluid, ascites fluid, pericardial fluid), cerebrospinal fluid (spinal fluid), joint fluid (synovial fluid), and aqueous humor (hydatoid). In certain embodiments, the body fluid is intercellular fluid. In another embodiment, the tissue may be a healthy tissue/normal tissue, and may be a diseased tissue (e.g., a tumor tissue). In one embodiment, when the above-described methods measure the ATP concentration in the body fluid within an in vivo tissue, the step of (i) may be a step of transplanting the split Luc/HEK293 cell expressing the P2Y receptor into the in vivo tissue.

In some embodiments, luciferase activity can be measured by detecting the light emitted when luciferase reacts with its substrate such as luciferin. In the case that the solution is an in vitro solution, such luminescence may be measured using a device for detecting luminescence such as a plate reader. In the case that the solution is a body fluid in an in vivo tissue, the luminescence may be measured using an in vivo luminescence imaging device and such. Quantification based on the measurements can be carried out by methods known in the art, for example, by measuring solutions containing a known concentration of ATP and preparing a calibration curve showing the correlation between ATP concentration and luminescence intensity.

V. Screening Methods (1) A Method of Screening for an Antigen-Binding Domain or Antigen-Binding Molecule which has Antigen-Binding Activity Dependent on a Molecular Compound, Utilizing Multivalent Antigens In one aspect, the present disclosure provides a method of highly efficiently and highly accurately screening for, identifying, and obtaining an antigen-binding domain or antigen-binding molecule which has antigen-binding activity dependent on a molecular compound, using a fusion molecule obtained by fusing two or more molecules (two or more units) of an antigen to one molecule (one unit) of a fusion partner molecule.

In one aspect, in the method of the present disclosure, the method of screening for an antigen-binding domain or antigen-binding molecule which has antigen-binding activity dependent on a molecular compound, comprises:
  (a) contacting, in the presence of a small molecule compound, an antigen-binding domain or antigen-binding molecule or a library of antigen-binding domains or antigen-binding molecules with a fusion molecule in which two or more units of the antigen are fused to one unit of a fusion partner,
  (b) placing the antigen-binding domain or antigen-binding molecule bound to the antigen within the fusion molecule in step (a) in the absence of, or presence of a low concentration of, the compounds, and
  (c) isolating an antigen-binding domain or antigen-binding molecule dissociated in step (b).

In one embodiment, in the method of the present disclosure, the fusion partner molecule to which two or more molecules (two or more units) of the antigen are fused is a dimer Fc region.

In one embodiment, in the method of the present disclosure, the Fc region comprises a first Fc subunit and a second Fc subunit, and one antigen is fused to each of the first and second Fc subunits.

In one embodiment, in the method of the present disclosure, one of the antigens is fused to the N-terminus of each of the first and second Fc subunits.

In one embodiment, in the method of the present disclosure, the library of antigen-binding domains or antigen-binding molecules is a phage library.

In one embodiment, in the method of the present disclosure, the phages included in the phage library are phages presenting on their surface two or more antigen-binding domains or antigen-binding molecules.

In one embodiment, in the method of the present disclosure, the phages included in the phage library are phages having a defect in the helper phage-derived pIII gene.

In one embodiment, in the method of the present disclosure, the antigen may be any antigen as described above, and examples may include various types of "antigens" described in "IV. Compositions and methods (antigen-binding molecules whose binding activity to antigens changes depending on the concentration of a small molecule compound)", "B. Antigen". In one embodiment, as the antigen, membrane-type antigens (e.g. costimulatory molecules such as CD137, CTLA4, CD40, OX40, RANK, GITR, and ICOS) can be preferably given.

In one embodiment, in the method of the present disclosure, the fusion between the Fc region (Fc subunit) and the antigen can be produced by a conventional method using genetic recombination technology as described above.

In one embodiment, in the method of the present disclosure, as the small molecule compound, the various compounds as described above (e.g., tumor tissue-specific compounds such as nucleosides having a purine ring structure such as adenosine (ADO), adenosine triphosphate (ATP), adenosine diphosphate (ADP), adenosine monophosphate (AMP), inosine, and further, commercially available ADP-betaS (manufactured by Sigma); amino acids such as alanine, glutamic acid, and aspartic acid; metabolites of amino acids such as kynurenine, anthranilic acid, 3-hydroxykynurenine, and kynurenic acid; metabolites of arachidonic acid such as prostaglandin E2; primary metabolites of the glycolytic pathway or the Krebs cycle such as lactic acid, succinic acid, and citric acid; and nicotinamide metabolites such as 1-methyl nicotinamide) can be given.

In one embodiment, in the method of the present disclosure, contact of an antigen (e.g., a fusion molecule of an Fc region and an antigen) with a phage library of antigen-binding domains or antigen-binding molecules, isolation of an antigen-binding domain or antigen-binding molecule bound to the antigen, assay of the isolated antigen-binding domain or antigen-binding molecule in the presence or absence of a small molecule compound can be done according to the above-described method and the method described below in the Examples, referring to well-known methods in the technical field of the present invention.

In one embodiment, the method of the present disclosure can include the method described in Example 2.

(2) A Method of Screening for an Antigen-Binding Domain or Antigen-Binding Molecule which has Antigen-Binding Activity Dependent on Two or More Different Small Molecule Compounds In one aspect, the present disclosure provides a method of screening for an antigen-binding domain or antigen-binding molecule which has antigen binding activity dependent on two or more different small molecule compounds.

In one embodiment, the method of the present disclosure comprises:
  (a) contacting an antigen-binding domain or an antigen-binding molecule or a library of antigen-binding domains or antigen-binding molecules with an antigen in the presence of a first small molecule compound,
  (b) placing an antigen-binding domain or antigen-binding molecule bound to the antigen in step (a) in the absence of, or the presence of a low concentration of, the first compound,
  (c) isolating an antigen-binding domain or antigen-binding molecule dissociated in step (b), (d) contacting an antigen-binding domain or antigen-binding molecule isolated in step (c) with the antigen in the presence of a second small molecule compound, (e) placing an antigen-binding domain or an antigen-binding molecule bound to the antigen in step (d) in the absence of, or the presence of a low concentration of, the second compound, and, (f) isolating an antigen-binding domain or an antigen-binding molecule disassociated in step (e), wherein the method does not comprise, between steps (c) and (d), amplifying a gene encoding the antigen-binding domain or antigen-binding molecule isolated in step (c).

In one embodiment, in the method of the present disclosure, the library of antigen-binding domains or antigen-binding molecules is a phage library.

In one embodiment, in the method of the present disclosure, the antigen may be any antigen as described above, preferably a membrane-type antigen (e.g., costimulatory molecules such as CD137, CTLA4, CD40, OX40, RANK, GITR, and ICOS).

In one embodiment, in the method of the present disclosure, as the small molecule compounds, the various compounds as described above (e.g., tumor tissue-specific compounds such as nucleosides having a purine ring structure such as adenosine (ADO), adenosine triphosphate (ATP), adenosine diphosphate (ADP), adenosine monophosphate (AMP), and inosine; amino acids such as alanine, glutamic acid, and aspartic acid;

metabolites of amino acids such as kynurenine, anthranilic acid, 3-hydroxykynurenine, and kynurenic acid; metabolites of arachidonic acid such as prostaglandin E2; primary metabolites of the glycolytic pathway or the Krebs cycle such as lactic acid, succinic acid, and citric acid; and nicotinamide metabolites such as 1-methyl nicotinamide) can be given. In one embodiment, in the method of the present disclosure, the first small molecule compound and the second small molecule compound can be any two types of different compounds selected from the above-mentioned various small molecule compounds.

In one embodiment, in the method of the present disclosure, contact of an antigen with a phage library of antigen-binding domains or antigen-binding molecules, isolation of an antigen-binding domain or antigen-binding molecule bound to the antigen, assay of the isolated antigen-binding domain or antigen-binding molecule in the presence or absence of a first small molecule compound, and assay in the presence or absence of a second small molecule compound can be done according to the above-described method and the method described below in the Examples, referring to well-known methods in the technical field of the present invention.

In one embodiment, as the method of the present disclosure, the method described in Example 9 can be given.

(3) A Method of Screening for an Antigen-Binding Domain or Antigen-Binding Molecule which has Antigen-Binding Activity Dependent on a Small Molecule Compound, Using a Naive Library In one aspect, the present disclosure provides a method of screening for an antigen-binding domain or antigen-binding molecule which has antigen-binding activity dependent on a small molecule compound, using a naive library comprising a plurality of phages presenting antigen-binding domains or antigen-binding molecules (e.g., Fab domains) of different human antibody sequences generated from human lymphocytes (e.g., human PBMCs) that have not received antigen stimulation.

In one embodiment, the method of the present disclosure comprises:

(a) contacting a naive library of antigen-binding domains or antigen-binding molecules with an antigen in the presence of a small molecule compound, (b) placing an antigen-binding domain or antigen-binding molecule bound to the antigen in step (a) in the absence of, or presence of a low concentration of, the compound, and (c) isolating an antigen-binding domain or antigen-binding molecule dissociated in step (b).

In one embodiment, in the method of the present disclosure, the naive library is a phage library comprising phages presenting on their surface two or more antigen-binding domains or antigen-binding molecules.

In one embodiment, in the method of the present disclosure, the naive library is a library comprising phages having a defect in the helper phage-derived pIII gene.

In one embodiment, in the method of the present disclosure, the naive library is a library comprising phages prepared by increasing the expression of the antigen-binding domain or antigen-binding molecule with a small molecule additive that increases the level of expression from a promoter regulating the expression of the antigen-binding domain or antigen-binding molecule.

In one embodiment, in the method of the present disclosure, the small molecule additive is isopropyl-β-thiogalactopyranoside (IPTG) or arabinose.

In one embodiment, in the method of the present disclosure, the antigen may be any antigen as described above, preferably a membrane-type antigen (e.g., a costimulatory molecule such as CD137, CTLA4, CD40, OX40, RANK, GITR, or ICOS).

In one embodiment, in the method of the present disclosure, as the small molecule compound, the various compounds as described above (e.g., tumor tissue-specific compounds such as nucleosides having a purine ring structure such as adenosine (ADO), adenosine triphosphate (ATP), adenosine diphosphate (ADP), adenosine monophosphate (AMP), and inosine; amino acids such as alanine, glutamic acid, and aspartic acid; metabolites of amino acids such as kynurenine, anthranilic acid, 3-hydroxykynurenine, and kynurenic acid, metabolites of arachidonic acid such as prostaglandin E2; primary metabolites of the glycolytic pathway or the Krebs cycle such as lactic acid, succinic acid, and citric acid; and nicotinamide metabolites such as 1-methyl nicotinamide) can be given.

In one embodiment, in the method of the present disclosure, contact of an antigen with a phage library of antigen-binding domains or antigen-binding molecules, isolation of an antigen-binding domain or antigen-binding molecule bound to the antigen, assay of the isolated antigen-binding domain or antigen-binding molecule in the presence or absence of a small molecule compound can be done according to the above-described method and the method described below in the Examples, referring to well-known methods in the technical field of the present invention.

In one embodiment, as the method of the present disclosure, the method described in Example 10 can be given.

EXAMPLES

The following are examples of methods and compositions of the present disclosure. In view of the general description above, it is understood that various other embodiments may be implemented.

Example 1: Antigen Preparation (1-1) Preparation of the Human CD137 Extracellular Region The human CD137 extracellular domain (also called hCD137) was prepared with methods known to those skilled in the art. Specifically, downstream of a gene fragment encoding an extracellular region of human CD137, a gene fragment encoding a histidine tag and a gene fragment encoding a specific sequence to which biotin is added (AviTag sequence, SEQ ID NO: 86) are linked. The gene fragment encoding a protein in which the extracellular region of human CD137, the histidine tag and Avitag are linked (human CD137 or hCD137-HisBAP, SEQ ID NO: 87), was incorporated into an animal cell expression vector. The constructed plasmid vector was transfected into FreeStyle293 cells (Invitrogen) using 293-fectin (Invitrogen). At this time, a plasmid vector comprising an EBNA1-expressing gene (SEQ ID NO: 88) was transfected at the same time. Cells transfected with the genes according to the aforementioned procedure were cultured at 37° C., 8% $CO_2$; and the protein of interest (human CD137 extracellular region) was secreted into the culture supernatant. This cell culture medium was filtered through a 0.22 μm filter to obtain a culture supernatant. The culture supernatant was applied to the HisTrap-HP (GE Healthcare) and the human CD137 extracellular region was bound to the column.

The human CD137 extracellular region was eluted using a solution of 20 mM sodium phosphate, 500 mM sodium chloride, and 500 mM imidazole, pH 7.5. Aggregates were then removed by gel-filtration chromatography using Superdex 200 26/600 (GE healthcare) to yield a purified human CD137 extracellular region. The concentration of human CD137 was calculated using the method of Pace et al. based on the amino acid sequence excluding the signal sequence inferred from SEQ ID NO: 87 (SEQ ID NO: 183) (Pace, C. N., et al. Protein Science 1995; 4; 2411-2423).

(1-2) Preparation of the Human CD137 Extracellular Domain (hCD137(FXa Digested))

The human CD137 extracellular domain (also called hCD137(FXa digested)) was prepared in a method known to those skilled in the art. Specifically, a gene fragment encoding the Factor Xa cleavable sequence and a gene fragment encoding the constant region of an antibody were joined downstream of a gene fragment encoding the extracellular region of human CD137. A gene fragment encoding a protein in which the extracellular region of human CD137, the FactorXa cleavable sequence and the antibody constant region are linked (hCD137-F-Fc, SEQ ID NO: 89) was incorporated into an animal expression vector. The constructed plasmid vector was transfected into FreeStyle293 cells (Invitrogen) using 293-fectin (Invitrogen). At this time, a plasmid vector containing the EBNA1-encoding gene (SEQ ID NO: 88) was transfected at the same time. Cells transfected with genes according to the aforementioned procedures were cultured at 37° C., 8% $CO_2$; and hCD137-F-Fc was secreted into the culture supernatant. The cell culture medium was filtered through a 0.22 μm filter, and the culture supernatant was collected.

Culture supernatants were applied to a column packed with Protein A (MabSelect SuRe, GE Healthcare). hCD137-F-Fc was bound to the column and eluted with 50 mM acetic acid solution. After the eluate was neutralized with 1 M Tris-HCl, pH 8.0, the solvent of hCD137-F-Fc was replaced with 20 mM Tris, 100 mM sodium chloride, 2 mM calcium chloride, pH 8.0. Next, Factor Xa Protease (NEW ENGLAND BioLabs, Cat#. P8010L) was added and hCD137-F-Fc was digested. A protease inhibitor (DNS-GGACK, Calbiochem, Cat#251700) was then added to stop the reaction. 5 M sodium chloride was added to the protease reaction solution, and the total volume of the prepared solution was applied to HiTrap Benzamidine (GE Healthcare, Cat#17-5143-01). The column-filtered solution was further applied to a Protein A column (MabSelect SuRe, GE Healthcare), and pass fractions were collected. The pass fractions were removed of aggregates by gel-filtration chromatography using Superdex 200 Increase, 10/30 (GE Healthcare, Cat#28990944), yielding a purified human CD137 extracellular region.

(1-3) Preparation of Biotinylated Fc-Fused Human CD137

Biotinylated Fc-fused human CD137 (also referred to as "biotinylated hCD137-Fc" or "bio-hCD137-Fc", or hCD137-Fc-Bio) was prepared by methods known to those skilled in the art. Specifically, a gene fragment encoding the constant region of an antibody and a gene fragment encoding a specific sequence to which biotin is added (AviTag sequence, SEQ ID NO: 86) were joined downstream of a gene fragment encoding the extracellular region of human CD137. A gene fragment encoding a protein (Fc-fused human CD137, SEQ ID NO: 90) in which the human CD137 extracellular region, the antibody constant region, and Avitag have been linked was incorporated into an animal expression vector. The constructed plasmid vector was transfected into FreeStyle293 cells (Invitrogen) using 293-fectin (Invitrogen). At this time, a gene expressing EBNA1 (SEQ ID NO: 88) and a gene expressing biotin ligase (BirA, SEQ ID NO: 91) were simultaneously transfected, and biotin was added for the purpose of biotinylating Fc-fused human CD137. Cells transfected with the genes according to the aforementioned procedures were cultured at 37° C., 8% $CO_2$; and the protein of interest (biotinylated Fc-fused human CD137) was secreted into the culture supernatant. This cell culture was filtered through a 0.22 μm filter to obtain the culture supernatant.

The culture supernatant was applied to a column packed with Protein A (MabSelect SuRe, GE Healthcare), and biotinylated Fc-fused human CD137 was bound to the column. Biotinylated Fc-fused human CD137 was eluted using a 50 mM acetic acid solution. Aggregates were then removed by gel-filtration chromatography with Superdex 200, 26/600 (GE Healthcare), and purified biotinylated Fc-fused human CD137 was obtained.

(1-4) Preparation of Fc-Fused Human CD137

Fc-fused human CD137 (also referred to as hCD137-Fc) was prepared by methods known to those skilled in the art. Specifically, a gene fragment encoding the constant region of an antibody and a gene fragment encoding a specific sequence to which biotin is added (AviTag sequence, SEQ ID NO: 86) were joined downstream of a gene fragment encoding the extracellular region of human CD137. Gene fragments encoding a protein (Fc-fused human CD137, SEQ ID NO: 90) in which the extracellular region of human CD137, the antibody constant region, and Avitag have been linked was incorporated into an animal expression vector. The constructed plasmid vector was transfected into FreeStyle293F cells (Invitrogen) using 293-fectin (Invitrogen). At this time, a gene expressing a gene expressing EBNA1 (SEQ ID NO: 88) was simultaneously transfected. Cells transfected with the genes according to the aforementioned procedures were cultured at 37° C., 8% $CO_2$, and the protein of interest (Fc-fused human CD137) was secreted into the culture supernatant. This cell culture was filtered through a 0.22 μm filter to obtain the culture supernatant.

The culture supernatant was applied to a column packed with Protein A (MabSelect SuRe, GE Healthcare), and Fc-fused human CD137 was bound to the column. Fc-fused human CD137 was eluted using a 50 mM acetic acid solution. Next, aggregates were removed by gel-filtration chromatography with Superdex 200, 26/600 (GE Healthcare), and purified Fc-fused human CD137 was obtained.

(1-5) Preparation of Biotinylated Fc-Fused Monkey CD137

Biotinylated Fc-fused monkey CD137 (also referred to as "cyCD137-Fc-BAP") was prepared by methods known to those skilled in the art. Specifically, a gene fragment encoding the constant region of an antibody and a gene fragment encoding a specific sequence to which biotin is added (AviTag sequence, SEQ ID NO: 86) were joined downstream of a gene fragment encoding the extracellular region of monkey CD137. A gene fragment encoding a protein in which the monkey CD137 extracellular region, the antibody constant region, and Avitag are linked (Fc-fused monkey CD137, SEQ ID NO: 92) was incorporated into an animal expression vector.

The constructed plasmid vector was transfected into FreeStyle293 cells (Invitrogen) using 293-fectin (Invitrogen). At this time, a gene expressing EBNA1 (SEQ ID NO: 88) and a gene expressing biotin ligase (BirA, SEQ ID NO: 91) were simultaneously transfected; and biotin was added for the purpose of labeling Fc-fused monkey CD137 with biotin. Cells transfected with the genes according to the aforementioned procedures were cultured at 37° C., 8% $CO_2$; and the protein of interest (biotinylated Fc-fused monkey CD137) was secreted into the culture supernatant. This cell culture was filtered through a 0.22 μm filter to obtain the culture supernatant.

The culture supernatant was applied to a column packed with Protein A (MabSelect SuRe, GE Healthcare), and biotinylated Fc-fused monkey CD137 was bound to the column. Biotinylated Fc-fused monkey CD137 was eluted using a 50 mM acetic acid solution. Aggregates were then removed by gel-filtration chromatography using Superdex 200 increase 10/300 (GE Healthcare), and purified biotinylated Fc-fused monkey CD137 was obtained.

Example 2: Obtaining ATP-Dependent CD137 Antibodies (2-1) Obtaining Antibodies with a Small Molecule-Dependent Antigen-Binding Activity (Small-Molecule Switch Antibodies) from a Rationally Designed Library Utilizing ATP (1)

(2-1-1) Panning

Antibodies that exhibit binding activity towards antigens in the presence of adenosine triphosphate (adenosine 5'-triphosphate; ATP) were obtained from a rationally designed antibody phage display library constructed in a prior patent, WO2015/083764. Note that antibodies with a small molecule-dependent antigen (e.g., CD137) binding activity may be referred to as "switch antibodies" or "small-molecule switch antibodies", and antibodies with an ATP-dependent antigen (e.g., CD137) binding activity may be referred to as "switch antibodies" or "ATP switch antibodies". For acquisition, phages presenting antibodies that display binding activity in the presence of ATP towards the antigen captured on the beads were harvested. Subsequently, phages were collected from eluates eluted from the beads in the absence of ATP.

Phages were produced in a general method from *E. coli* carrying the constructed phage display phagemid. Specifically, *E. coli* carrying the constructed phagemid vector was infected with M13KO7ΔpIII (designated as "hyperphage") (PROGEN Biotechnik), and phages were harvested from supernatants cultured overnight at 30° C. A phage library solution was obtained by diluting with Tris-Buffered Saline (TBS) a population of phages precipitated by adding 2.5 M NaCl/10% PEG to the *E. coli* culture in which phage production was performed. BSA was then added to the phage library solution at a final concentration of 4%. Panning was performed using an antigen immobilized on magnetic beads. For magnetic beads, Sera-Mag NeutrAvidin beads (Thermo Fisher Scientific) or Dynabeads M-280 StreptAvidin (Life Technologies) were used. As antigen, biotinylated adenosine triphosphate (adenosine 5'-triphosphate; ATP) purchased from Jena Bioscience, or hCD137-Fc-Bio (SEQ ID NO: 90) or bio-hCD137 (SEQ ID NO: 89) which has been biotinylated from hCD137(FXa digested) using No weight Premeasured NHS-PEO4-Biotin (PIERCE) made in Examples 1-2 and 1-3 was used.

Panning was performed to efficiently obtain small molecule that can play a switch role in cancer tissues dependent switch antibodies. Specifically, panning to enrich antibodies that bind to an antigen in the presence of ATP which is a small molecule, and do not bind to the antigen in the absence of ATP was performed with reference to the methods shown in the prior patent WO2015/083764. In Round 1, for all of biotinylated hCD137 (bio-hCD137), hCD137-Fc-Bio and biotinylated ATP (bio-ATP), panning was performed using a method in which solid-phase immobilization of biotinylated antigens on magnetic beads (termed "bead solid-phase method") precedes addition of a prepared phage library solution. For Bio-ATP, panning to enrich antibodies that can bind to an antigen (Bio-ATP) in the absence of ATP as a small-molecule compound was performed with reference to the methods described in the prior patent WO2015/083764 above. For hCD137-Fc-Bio, 4 nmol of an unbiotinylated human IgG1 Fc region was added to remove antibodies that bind to the Fc region. The harvested phage was added to the *E. coli* strain ER2738 to infect the phage with *E. coli*, then the harvested *E. coli* was infected with the hyperphage, and the phage was harvested from the supernatant cultured overnight at 30° C.

From Round 2 on, panning was performed only on biotinylated hCD137 (bio-hCD137) and hCD137-Fc-Bio to enrich antibodies that bind to the antigen in the presence of ATP and not to the antigen in the absence of ATP in the bead solid-phase method, by referring to the method shown in the prior patent WO2015/083764. For hCD137-Fc-Bio in both cases, 4 nmol of an unbiotinylated human IgG1 Fc region was added to remove antibodies that bind to the Fc region. Similar panning was repeated until Round 5 to enrich the antibody sequences of interest.

(2-1-2) Binding Activity Assessment in the Presence and Absence of ATP by Phage ELISA From single colonies of *E. coli* obtained by the methods described above, the phage-containing culture supernatant was harvested using a conventional method (Methods Mol. Biol. (2002) 178, 133-145). NucleoFast 96 (MACHEREY-NAGEL) was used to ultrafilter the harvested culture supernatant. Flow-through was removed by centrifuging (4,500 g, 45 min) NucleoFast 96 to which 100 μL of culture supernatant has been applied in each well. NucleoFast 96 was washed again by centrifugation (4,500 g for 30 min) by adding 100 μL of $H_2O$ to each well. Finally, 100 μL of TBS was added, and the phage solution contained in the supernatants in the wells of NucleoFast 96, which were left to stand at room temperature for 5 minutes, was recovered.

Purified phages with added TBS or ATP/TBS were subject to ELISA by the following procedure. 384-well Streptavidin-coated Microplates (Greiner) were coated overnight with 10 μL TBS containing the biotinylated antigens (bio-hCD137, hCD137-Fc-Bio, and bio-Fc) produced in Example 1. After biotinylated antigens that did not bind to the plate were removed by washing each well of the plate with Tris-Buffered Saline with Tween 20 (TBST), the wells were blocked with 80 μL of 2% Skim Milk-TBS for 1 hour or more. 2% Skim Milk-TBS was removed by TBST washes, after which the antibody-presenting phages were allowed to bind to the biotinylated antigen present in each well in the absence and presence of ATP, by leaving the plates with the prepared purified phages added to each well for 1 hour at room temperature. To each well washed with TBST or ATP/TBST, HRP-conjugated anti-M13 antibodies (GE Healthcare 27-9421-01) diluted with TBS or ATP/TBS were added, and the plate was incubated for one hour. After washing with TBST or ATP/TBST, color development of the solution in each well to which the TMB single solution (ZYMED) was added was stopped by the addition of sulfuric acid, and then color development was measured by absorbance at 450 nm.

As a result, several antibodies with altered binding activity to bio-hCD137 or hCD137-Fc-Bio in the presence and absence of ATP were identified.

The results of phage ELISA using clones after Round 4 and 5 panning are shown in Table 9.

Here, clones with an absorbance of 0.2 or more in the presence of ATP and an S/N ratio of absorbance higher than 2 in the presence/absence of the antigen were determined as positive clones. Furthermore, among the positive clones, clones with an absorbance S/N higher than 2 in the presence/absence of ATP were judged to be clones with ATP-dependent antigen-binding activity (switch clones).

TABLE 9

|  | Antigen used in panning | | | |
| --- | --- | --- | --- | --- |
|  | Biotinylated hCD137 | | hCD137-Fc-Bio | |
| Round | 4 | 5 | 4 | 5 |
| Number of clones subjected to ELISA | 384 | 384 | 384 | 384 |
| Number of positive clones (absorbance in ATP + ≥0.2; antigen +/− ratio > 2.0) | 31 | 4 | 125 | 169 |
| Number of switch clones (ATP +/− ratio > 2) | 12 | 2 | 118 | 164 |

(2-1-3) Sequence Analysis of Switch Antibodies Whose Antigen-Binding Activity is Altered by the Presence/Absence of ATP The nucleotide sequences of genes amplified using specific primers pBAD-F, Glseq-R from clones with ATP-dependent antigen-binding activity (switch clones) based on the phage ELISA results were analyzed. As a result of the analysis, the nucleotide sequences of clones judged to bind to human CD137 in the presence of ATP and not to human CD137 in the absence of ATP were obtained.

(2-2) Obtaining Antibodies that Bind to Antigens in the Presence of a Small Molecule from a Rationally Designed Library Utilizing ATP (2)

(2-2-1) Panning

Antibodies that exhibit binding activity to antigens in the presence of ATP were obtained from a rationally designed antibody phage display library constructed in the prior patent WO2015/083764. For acquisition, phages presenting antibodies which show binding activity to antigens in the presence of ATP were recovered, followed by phage recovery from the eluate eluted from the beads in the absence of ATP.

Phages were produced in a general method from E. coli carrying the constructed phage display phagemid. Specifically, E. coli carrying the constructed phagemid vector was infected with M13KO7TC (WO2015046554A1) or M13KO7ΔpIII (hyperphage) (PROGEN Biotechnik), and phages were recovered from supernatants cultured overnight at 30° C. A phage library solution was obtained by diluting with TBS a population of phages precipitated by adding 2.5 M NaCl/10% PEG to an E. coli culture in which phage production was performed. BSA was then added to the phage library solution at a final concentration of 4%.

Panning was performed using antigens immobilized on magnetic beads. NeutrAvidin-coated beads (Sera-Mag SpeedBeads NeutrAvidin-coated), NeutrAvidin beads (TAMAGAWA SEIKI) or Dynabeads MyOne StreptAvidin T1 (Thermo Fisher Scientific) were used as magnetic beads. As antigen, hCD137-Fc-Bio or bio-hCD137 produced in Example 1 was used.

Panning was performed to efficiently obtain small molecule switch antibodies which are dependent on the small molecule that can play a switch role in cancer tissues. Specifically, panning to enrich antibodies that bind to antigens in the presence of adenosine triphosphate (adenosine 5'-triphosphate; ATP) which is a small molecule, and which do not bind antigens in the absence of ATP was performed with reference to the methods described in the prior patent WO2015/083764. For bio-hCD137, the method which adds the prepared phage library solution after solid-phase immobilization of biotinylated antigens onto magnetic beads in advance (referred to as the "bead solid-phase method") and the method which adds magnetic beads after mixing the prepared phage library solution with biotinylated antigens in advance (referred to as the "liquid-phase method") were performed. For hCD137-Fc-Bio, 4 nmol of an unbiotinylated human IgG1 Fc region was added to remove antibodies that bind to the Fc region, and panning was performed only in the liquid-phase method. The collected phages were added to the E. coli strain ER2738 and allowed to infect the E. coli, then the collected E. coli was infected with M13KO7TC (WO2015046554A1) or M13KO7ΔpIII (hyperphage) (PROGEN Biotechnik), and after culturing overnight at 30° C. phages were collected from the supernatant. Similar panning was repeated until Round 5.

(2-2-2) Binding Activity Assessment in the Presence and Absence of ATP by Phage ELISA From single colonies of E. coli obtained after each Round by the methods described above, phage-containing culture supernatants were harvested using a conventional method (Methods Mol. Biol. (2002) 178, 133-145). NucleoFast 96 (MACHEREY-NAGEL) was used to ultrafilter the harvested culture supernatants. Flow-through was removed by centrifuging (4,500 g, 45 min) the NucleoFast 96 in which 100 μL of culture supernatant was applied to each well. The NucleoFast 96, in which 100 μL of $H_2O$ was added to each well, was washed again by centrifugation (4,500 g for 30 min). Finally, 100 μL of TBS was added, and the phage solution contained in the supernatants of the NucleoFast 96 wells, which were left to stand at room temperature for 5 minutes, was recovered.

Purified phages with added TBS or ATP/TBS were subject to ELISA by the procedures below. StreptaWell 96 microtiter plates (Roche) were immobilized overnight with 100 μL of TBS containing the biotinylated antigens (hCD137-Fc-Bio or bio-hCD137) produced in Example 1. After removal of the biotinylated antigen that did not bind to the plates by washing each well of the plates with TBST, the wells were blocked with 250 μL of 2% SkimMilk-TBS for 1 hour or more. The 2% SkimMilk-TBS was removed, and then antibody-presenting phages were bound to the biotinylated antigen present in each well in the absence and presence of ATP by leaving the plates with the prepared purified phages added to each well at 37° C. for 1 hour. To each well washed with TBST or ATP/TBST, HRP-conjugated anti-M13 antibodies (GE Healthcare 27-9421-01) diluted in TBS or ATP/TBS were added, and the plate was incubated for one hour. After TBST or ATP/TBST washes, color development of the solution in each well to which the TMB single solution (ZYMED) was added was stopped by the addition of sulfuric acid, and then color development was measured by absorbance at 450 nm.

As a result, several antibodies with altered binding activity towards bio-hCD137 or hCD137-Fc-Bio in the presence and absence of ATP were identified.

As an example, the results of phage ELISA using clones after Round 5 panning are shown in Table 10.

Here, clones with an absorbance of 0.2 or greater in the presence of ATP and an S/N ratio of absorbance greater than 2 in the presence/absence of the antigen were determined as positive clones. In addition, among the positive clones, those with an S/N ratio of absorbance higher than 2 in the presence/absence of ATP were determined as clones with ATP-dependent antigen-binding activity (switch clones).

TABLE 10

| | Antigen used in panning | | | |
|---|---|---|---|---|
| | hCD137-Fc-Bio | hCD137-Fc-Bio | Biotinylated hCD137 | Biotinylated hCD137 |
| Panning method | Liquid-phase | Liquid-phase | Liquid-phase | Bead solid-phase |
| Helper phage used in panning | M13KO7 ΔpIII | M13KO7ΔpIII and M13KO7TC | M13KO7ΔpIII | M13KO7ΔpIII |
| Number of clones subjected to ELISA | 384 | 96 | 96 | 96 |
| Number of positive clones (absorbance in ATP + ≥0.2; antigen +/− ratio > 2) | 383 | 79 | 41 | 29 |
| Number of switch clones (ATP +/− ratio > 2 ) | 375 | 77 | 40 | 29 |

(2-2-3) Sequence Analysis of Switch Antibodies Whose Antigen-Binding Activity is Altered by the Presence/Absence of ATP The nucleotide sequences of genes amplified from clones with ATP-dependent antigen-binding activity (switch clones) based on the phage ELISA results were analyzed using specific primers pBAD-F, Glseq-R. As a result of the analysis, the nucleotide sequences of clones judged to bind to human CD137 in the presence of ATP and not to human CD137 in the absence of ATP were obtained.

(2-3) Selection of Switch Antibodies

Seventeen samples were selected from the clones judged to have ATP-dependent antigen binding activity obtained as a result of the analyses in Examples 2-1-3 and 2-2-3, and the clone names were re-assigned as described in Table 11.

TABLE 11

| | Phage name | Clone name of antibody variable region |
|---|---|---|
| 1 | dBBATk14-4_003 | dBBAT007 |
| 2 | dBBATk14-4_089 | dBBAT013 |
| 3 | dBBATk17-4_002 | dBBAT015 |
| 4 | dBBATk17-4_009 | dBBAT017 |
| 5 | dBBATk17-4_075 | dBBAT019 |
| 6 | dBBATk05-5_052 | dBBAT021 |
| 7 | dBBATk05-5_076 | dBBAT025 |
| 8 | dBBATk12-5_038 | dBBAT029 |
| 9 | dBBATk12-5_048 | dBBAT031 |
| 10 | dBBATk14-5_012 | dBBAT037 |
| 11 | dBBATk14-5_053 | dBBAT042 |
| 12 | dBBAHk14SF-3_016 | dBBAT053 |
| 13 | dBBAHk14SF-3_032 | dBBAT056 |
| 14 | dBBAHk14FF-4_028 | dBBAT091 |
| 15 | dBBAHk14FS-5_074 | dBBAT112 |
| 16 | dBBAHk14MS-5_034 | dBBAT118 |
| 17 | dBBAHk14MS-5_093 | dBBAT119 |

(2-4) Expression and Purification of Switch Antibodies Whose Antigen-Binding Activity is Altered by the Presence/Absence of ATP Genes encoding the variable regions of the antibodies described in Table 11, which were obtained from a rationally designed phage library, were inserted into human IgG1/Lambda plasmids for expression in animals. Antibodies were expressed using the methods below. The prepared plasmids were introduced by the lipofection method into the human fetal kidney cell-derived line FreeStyle 293-F (Invitrogen), which was suspended in the FreeStyle 293 Expression Medium (Invitrogen) at a cell density of $1.33 \times 10^6$ cells/mL, of which 3 mL was seeded in each well of 6-well plates. Antibodies were purified using rProtein A Sepharose™ Fast Flow (Amersham Biosciences) from culture supernatants cultured for four days in a $CO_2$ incubator (37° C., 8% $CO_2$, 90 rpm) in a method known to those skilled in the art. Spectrophotometers were used to measure the absorbance at 280 nm of the purified antibody solutions. From the measured values obtained, the concentrations of the purified antibodies were calculated using the extinction coefficients calculated by the PACE method (Protein Science (1995) 4, 2411-2423).

(2-5) Assessment of the Anti-CD137 Antibodies Identified by the Phage Display Method (2-5-1) Expression and Purification of Switch Antibodies which Bind to Antigens Depending on the Presence or Absence of ATP and its Metabolites Genes encoding the variable regions of antibodies obtained from a human rationally designed phage library were inserted into animal expression plasmids having a heavy chain constant region fused with a gene encoding Gly and Lys downstream of a modified human IgG1 (P253) (SEQ ID NO: 93) and a light-chain constant region, Lambda chain Lamlib (SEQ ID NO: 63). Clone names and sequence numbers were listed in Table 12.

Evaluated Clones

TABLE 12

| | Clone name | SEQ ID NO of heavy chain (full length) | SEQ ID NO of light chain (full length) |
|---|---|---|---|
| 1 | dBBAT007-P253 | 94 | 113 |
| 2 | dBBAT013-P253 | 95 | 114 |
| 3 | dBBAT015-P253 | 96 | 115 |
| 4 | dBBAT017-P253 | 97 | 116 |
| 5 | dBBAT019-P253 | 98 | 117 |
| 6 | dBBAT025-P253 | 99 | 118 |
| 7 | dBBAT029-P253 | 100 | 119 |
| 8 | dBBAT031-P253 | 100 | 119 |
| 9 | dBBAT037-P253 | 101 | 120 |
| 10 | dBBAT042-P253 | 102 | 121 |
| 11 | dBBAT053-P253 | 103 | 122 |
| 12 | dBBAT056-P253 | 104 | 123 |
| 13 | dBBAT021-P253 | 105 | 124 |
| 14 | dBBAT091-P253 | 106 | 125 |
| 15 | dBBAT112-P253 | 107 | 126 |
| 16 | dBBAT118-P253 | 108 | 127 |
| 17 | dBBAT119-P253 | 109 | 128 |
| 18 | dBBAT121-P253 | 110 | 129 |
| 19 | dBBAT122-P253 | 111 | 130 |
| 20 | dBBAT134-P253 | 112 | 131 |

Antibodies were expressed and purified using methods known to those skilled in the art. Spectrophotometers were used to measure the absorbance at 280 nm of the purified antibody solutions. From the measured values obtained, the concentrations of the purified antibodies were calculated using the extinction coefficients calculated by the PACE method (Protein Science (1995) 4, 2411-2423).

(2-5-2) Assessment of the Effects of ATP, ADP, and AMP on Human CD137 Binding by Surface Plasmon Resonance Biacore T200 (GE Healthcare) was used to analyze the interaction of antigen-antibody reaction between the anti-CD137 antibodies and hCD137 (FXa digest). The anti-CD137 antibodies were captured on Sensor chip CM3 (GE Healthcare) to which Protein G (CALBIOCHEM) was immobilized in appropriate amounts by an amine-coupling method, and hCD137 (FXa digest) prepared in Example 1-2 was allowed to interact. For the running buffer, 20 mM ACES, 150 mM NaCl, 2 mM $MgCl_2$, 0.05% Tween20 (pH 7.4) was used, and 10 mM Glycine-HCl (pH 1.5) was used as the regeneration solution.

After capturing of the anti-CD137 antibodies suspended in TBS, 500 nM hCD137 (FXa digest) was injected into each flow cell at a flow rate of 10 μL/min for three minutes. This three-minute period served as the binding phase for hCD137 (FXa digest), and after the binding phase ended, the two-minute period of switching to the running buffer served as the dissociation phase for hCD137 (FXa digest). After completion of the dissociation phase, the regenerative solution was injected at a flow rate of 30 μl/min for 30 seconds. The above was the cycle for measuring the binding activity of anti-CD137 antibodies. The binding amount of hCD137 (FXa digest) that interacted with the anti-CD137 antibody in the binding phase was adjusted by the amount of antibody captured. Biacore T200 Evaluation Software Version 2.0 was used to display the binding amount (RU) per capture ligand 1RU, and values of the antibody capture amount (amount of antibody captured) and antigen-binding amount were obtained. The binding amount of antigen is shown in Table 13. Since the binding amount of antigen reflects the binding activity, it can be said that dependence on a small molecule is recognized when the value in the presence of the small molecule (ATP, ADP or AMP) is higher than the value without the small molecule. In particular, the larger the difference is, the higher the dependence is on a small molecule.

TABLE 13

| | Small molecule species, concentration condition | | | | | | |
|---|---|---|---|---|---|---|---|
| Clone name | 1 mM ATP | 100 μM ATP | 100 μM ADP | 10 μM ADP | 1 mM AMP | 100 μM AMP | Without small molecule |
| dBBAT007-P253 | 49.2 | 29.5 | 89.0 | 70.0 | 28.5 | 16.5 | 3.6 |
| dBBAT013-P253 | 26.2 | 8.1 | 77.3 | 48.5 | 13.8 | 6.6 | 2.7 |
| dBBAT015-P253 | 8.3 | 3.1 | 41.8 | 17.9 | 11.9 | 5.5 | 1.5 |
| dBBAT017-P253 | 9.8 | 5.0 | 39.7 | 18.8 | 6.8 | 4.8 | 4.4 |
| dBBAT019-P253 | 3.8 | 3.0 | 25.7 | 7.4 | 11.1 | 4.6 | 3.7 |
| dBBAT021-P253 | 9.2 | 2.4 | 56.6 | 19.6 | 5.7 | 3.0 | 2.9 |
| dBBAT025-P253 | 28.5 | 10.0 | 89.1 | 55.7 | 16.4 | 6.1 | 4.4 |
| dBBAT029-P253 | 10.9 | 6.9 | 53.3 | 38.5 | 17.4 | 11.4 | 3.7 |
| dBBAT031-P253 | 8.4 | 5.0 | 47.8 | 33.3 | 14.8 | 8.3 | 2.8 |
| dBBAT037-P253 | 27.5 | 15.9 | 72.1 | 62.9 | 21.7 | 13.8 | 3.8 |
| dBBAT042-P253 | 11.7 | 4.3 | 58.7 | 19.1 | 7.8 | 4.7 | 2.9 |
| dBBAT053-P253 | 15.0 | 8.4 | 46.9 | 40.4 | 9.6 | 6.9 | 1.9 |
| dBBAT056-P253 | 20.3 | 13.4 | 59.4 | 50.7 | 12.8 | 9.7 | 3.7 |
| dBBAT118-P253 | 27.7 | 14.1 | 76.9 | 62.9 | 14.9 | 8.7 | 3.3 |
| dBBAT121-P253 | 11.5 | 4.8 | 42.3 | 24.7 | 6.1 | 2.6 | 1.9 |
| dBBAT122-P253 | 11.5 | 4.7 | 55.5 | 19.2 | 5.7 | 4.1 | 3.3 |
| dBBAT134-P253 | 5.2 | 4.4 | 29.3 | 16.2 | 3.7 | 4.5 | 3.0 |
| dBBAT091-P253 | 6.2 | 3.0 | 33.0 | 20.0 | 2.9 | 3.3 | 1.5 |
| dBBAT112-P253 | 12.6 | 6.3 | 43.0 | 27.4 | 6.5 | 4.8 | 3.7 |
| dBBAT119-P253 | 45.7 | 12.9 | 112.5 | 67.2 | 58.6 | 26.9 | 3.3 |

(2-5-3) Assessment of Binding Activity to a Monkey CD137 Antigen

The obtained antibodies were evaluated for binding to monkey CD137 by ELISA. The cyCD137-Fc-BAP prepared in Example 1 was immobilized on Streptawell microtiter plates. After the unbound antigen was removed from the plates by washing each well of the plates with the wash buffer, the wells were blocked with 150 μL of a blocking buffer (TBS with 2% BSA) for 1 hour or more. The blocking buffer was removed from each well, and 100 μL of the purified antibodies diluted in TBS with a final concentration of 1 mM ADP, or TBS with a final concentration 1 mM ADP was added to each well. The plate to which the antibody was added was shaken at 600 rpm for 1 hour. The AP-conjugated anti-human lambda antibodies (BETHYL) diluted in TBS with a final concentration of 1 mM ADP were added to each well after washing with a wash buffer (TBS with 0.1% Tween20) containing a final concentration of 1 mM ADP. After incubation for one hour and washing with a wash buffer containing a final concentration of 1 mM ATP, Blue-Phos phosphate substrate (KPL) was added. Color development was measured by absorbance at 600 nm. The increase rate in absorbance at an antibody concentration of 0 μg/mL is shown in Table 14. Samples with a concentration-dependent increase in the absorbance ratio can be said to be bound to monkey CD137.
Absorbance Ratio concentration of ATP was 50 μM. Plates were left to stand for six hours at 37° C. in a 5% $CO_2$ incubator followed by 15 minutes at room temperature, and 30 μL of the Bio-Glo reagent was added to each well. The Bio-Glo Luciferase Assay System (Buffer and Substrate) was used for the Bio-Glo reagent. Subsequently, the luminescence of each well was measured with a plate reader. The value of the luminescence of each well divided by the value of the luminescence of the well without antibody added was the luminescence fold and served as an indicator for evaluating the activity of each antibody.

Figure 1:
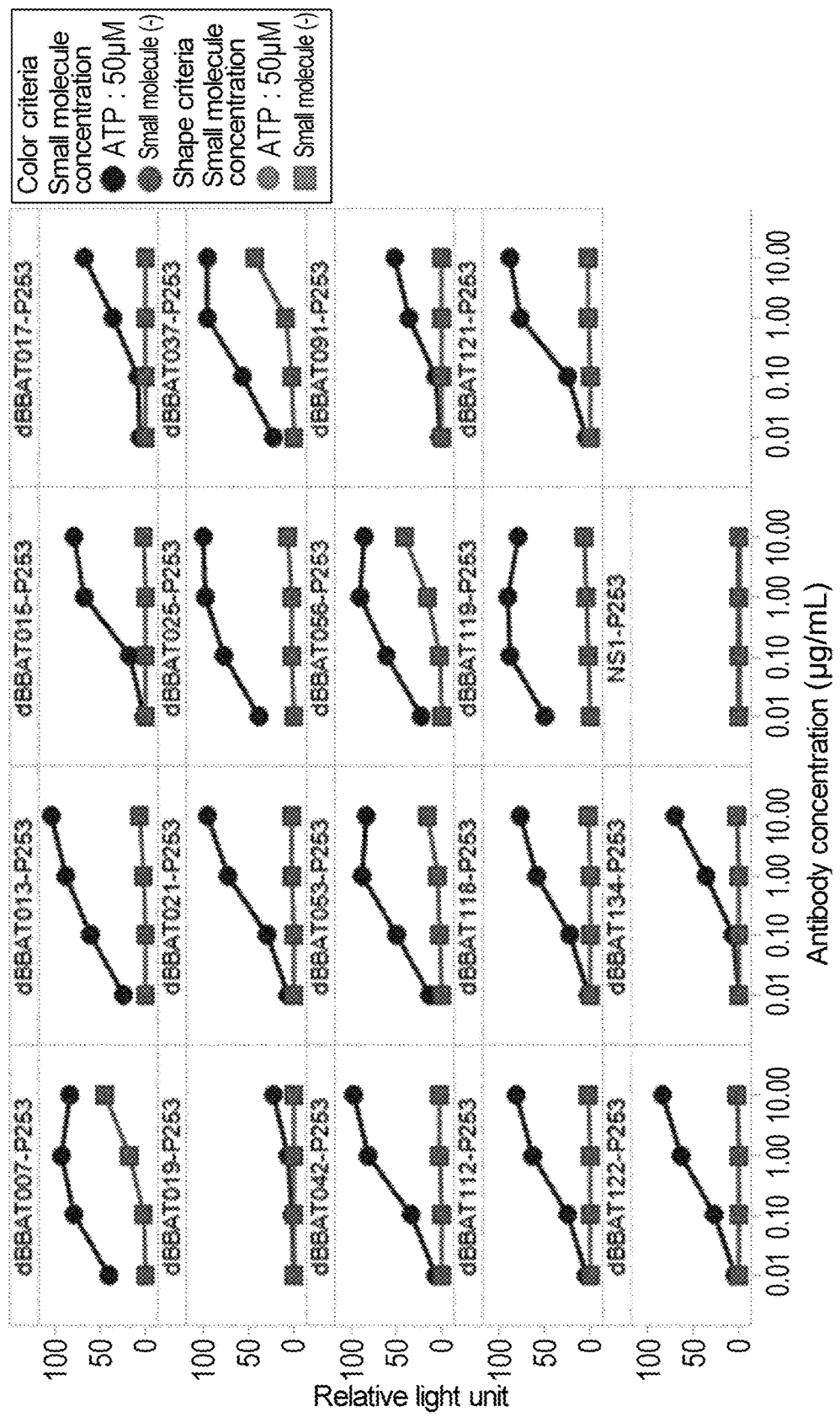
FIG. 1 is a diagram showing the agonist activity of various anti-CD137 antibodies tested using Jurkat cells in the presence or absence of ATP.

The results obtained are shown in FIGS. 1 and 2. From FIGS. 1 and 2, it was confirmed that all antibodies except NS1-P253, which is a non-switch antibody, exhibited human CD137 agonist activity in an ATP- and ADP-dependent manner.

TABLE 14

| Monkey CD137 | | dBBAT007 | dBBAT013 | dBBAT015 | dBBAT017 | dBBAT019 | dBBAT021 |
|---|---|---|---|---|---|---|---|
| Antibody concentration [μg/mL] | 10 | 30.5 | 43.2 | 42.9 | 25.6 | 40.5 | 40.5 |
| | 2.5 | 30.2 | 42.4 | 32.4 | 8.7 | 40.3 | 14.0 |
| | 0.625 | 29.2 | 33.3 | 14.4 | 3.1 | 39.1 | 4.6 |
| | 0.156 | 22.0 | 15.3 | 3.6 | 1.4 | 23.7 | 1.7 |
| | 0.039 | 0.7 | 4.2 | 1.5 | 1.2 | 8.2 | 1.2 |
| | 0.010 | 3.8 | 1.5 | 1.1 | 1.2 | 2.5 | 0.9 |
| | 0 | 1.0 | 1.0 | 1.0 | 1.0 | 1.0 | 1.0 |

| Monkey CD137 | | dBBAT025 | dBBAT029 | dBBAT037 | dBBAT042 |
|---|---|---|---|---|---|
| Antibody concentration [μg/mL] | 10 | 72.0 | 50.3 | 32.5 | 41.8 |
| | 2.5 | 67.6 | 42.7 | 12.7 | 40.0 |
| | 0.625 | 49.7 | 26.7 | 4.6 | 31.3 |
| | 0.156 | 20.7 | 9.7 | 1.9 | 12.2 |
| | 0.039 | 4.5 | 2.0 | 1.3 | 2.9 |
| | 0.010 | 1.6 | 1.1 | 1.1 | 1.3 |
| | 0 | 1.0 | 1.0 | 1.0 | 1.0 |

| | | dBBAT053 | dBBAT056 | dBBAT091 | dBBAT112 | dBBAT118 |
|---|---|---|---|---|---|---|
| Antibody concentration [μg/mL] | 10 | 17.9 | 23.1 | 15.1 | 19.8 | 35.4 |
| | 2.5 | 6.9 | 10.7 | 5.5 | 8.1 | 30.6 |
| | 0.625 | 2.3 | 3.6 | 1.7 | 2.8 | 18.1 |
| | 0.156 | 1.0 | 1.3 | 0.7 | 1.0 | 7.1 |
| | 0.039 | 0.7 | 0.8 | 0.5 | 0.6 | 1.8 |
| | 0.010 | 0.8 | 1.2 | 0.6 | 0.6 | 1.0 |
| | 0 | 1.0 | 1.0 | 1.0 | 1.0 | 1.0 |

| | | dBBAT119 | dBBAT121 | dBBAT122 | dBBAT134 |
|---|---|---|---|---|---|
| Antibody concentration [μg/mL] | 10 | 55.3 | 26.0 | 31.9 | 33.9 |
| | 2.5 | 56.6 | 16.4 | 16.7 | 16.8 |
| | 0.625 | 57.2 | 5.9 | 5.7 | 5.8 |
| | 0.156 | 47.7 | 1.3 | 1.9 | 2.2 |
| | 0.039 | 26.6 | 0.6 | 1.0 | 1.2 |
| | 0.010 | 10.2 | 0.6 | 0.9 | 1.0 |
| | 0 | 1.0 | 1.0 | 1.0 | 1.0 |

(2-5-4) Assessment of CD137 Agonist Activity Using Jurkat Cells.

The GloResponse™ NF-kappa B-Luc2/4-1BB Jurkat cell line (Promega) was used for measuring the in vitro antibody activity. To each well of 384-well plates, 100_, of FcγRIIB CHO-K1 cells (Promega) prepared at a concentration of $2\times10^6$/mL with an assay medium (99% RPMI, 1% FBS) was added. Subsequently, 10 μL of an antibody solution containing ADP, an antibody solution containing ATP, or an antibody solution containing no ATP or ADP was added to each well. Then, 10 μL of the GloResponse™ NF-κB-Luc2/4-1BB Jurkat cell line prepared to $2\times10^6$/mL with an assay medium (99% RPMI, 1% FBS) was added to each well. The final concentration of ADP was 50 μM; and the final (2-6) Assessment of In Vitro CD137 Agonist Activity of Switch Antibodies Acquired from Panning Using Human T Cells (2-6-1) Expansion of Human T Cell Cultures Human peripheral blood mononuclear cells isolated from blood samples of healthy volunteers were used. 50 mL of blood was mixed with 0.5 mL of heparin and further diluted with 50 mL of PBS. Human peripheral blood mononuclear cells were isolated in the two steps below. In the first step, Leucosep (greiner bio-one) added with Ficoll-Paque PLUS (GE Healthcare) was centrifuged at 1000×g for one minute at room temperature, followed by addition of PBS-diluted blood, and centrifugation at room temperature was performed at 400×g for 30 minutes. In the second step, the buffy coat was collected from the tubes after centrifugation and then washed with 60 ml of PBS (Wako). Then, a T cell activation/expansion kit/human (MACS Miltenyi biotec) was used to expand cultures of the T cells.

(2-6-2) Assessment of CD137 Agonist Activity In Vitro Using Human T Cells $2 \times 10^4$ human peripheral blood mononuclear cell-derived T cells and $2 \times 10^4$ REC-1 cells were suspended in 100 µL of RPMI1640 medium containing 30 U/mL human IL-2 (SIGMA), 10 ng/mL PMA (SIGMA), 0.5 µg/mL Ionomycin, 500 µM ADPbetaS (Sigma), and 10% FBS (Sigma), and seeded in 96-well multiple-well flat-bottom plates (Corning) with the control antibody IC17HdK-hIgG1/IC17L-k0, NS1-P253 which is an antibody with ATP-independent human CD137-binding activity (referred to as "non-switch antibody" or "non-switch CD137 antibody" throughout the Examples), or any of the clones described in Table 12. NS1-P253, IC17HdK-hIgG1/IC17L-k0 and the clones described in Table 12 were evaluated at 10 µg/mL. IFN-γ production in the ADPbetaS-minus medium was also evaluated. The plates were shaken and then left at 37° C. for 72 hours in a 5% CO$_2$ incubator. Subsequently, the culture supernatants were harvested and the amount of IFN-γ contained in the culture supernatants was quantified using the Human IFN-γ ELISA Development Kit (PeproTech). ELISA was performed according to the instructions of the kit manufacturer (PeproTech). Absorbance measurements were made with EnVision (PerkinElmer).

The results are shown in FIG. 3.

It was confirmed that dBBAT007-P253, dBBAT013-P253, dBBAT015-P253, dBBAT019-P253, dBBAT021-P253, dBBAT025-P253, dBBAT031-P253, dBBAT042-P253, dBBAT056-P253, dBBAT118-P253, dBBAT121-P253, dBBAT122-P253, and dBBAT119-P253 exhibit the human CD137 agonist activity in an ADPbetaS-dependent manner. ADPbetaS is an analogue of ADP that is less susceptible to hydrolysis than ADP. This indicates a possibility that these human CD137 switch antibodies exhibit human CD137 agonist activity in a manner dependent on a small molecule such as ATP, ADP or AMP.

(2-6-3) Assessment of CD137 Agonist Activity In Vitro Using Human T Cells (2)

$2 \times 10^4$ human peripheral blood mononuclear cell-derived T cells and $2 \times 10^4$ REC-1 cells were suspended in 100 µL of RPMI1640 medium containing 30 U/mL human IL-2 (SIGMA), 10 ng/mL PMA (SIGMA), 0.5 µg/mL Ionomycin, 500 µM ADPbetaS (Sigma), and 10% FBS (Sigma), and seeded in 96-well multiple-well flat-bottom plates (Corning), with either NS1-P253 (non-switch antibody) or dBBAT119-P253. NS1-P253 and dBBAT119-P253 were evaluated at 10, 2, 0.4, 0.08, 0.016, 0.0032, and 0.00064 µg/mL. The plates were shaken and then left at 37° C. for 72 hours in a 5% CO$_2$ incubator. Subsequently, the culture supernatants were harvested and the amount of IFN-γ contained in the culture supernatants was quantified using the Human IFN-γ ELISA Development Kit (PeproTech). ELISA was performed according to the instructions of the kit manufacturer (PeproTech). Absorbance measurements were conducted with EnVision (PerkinElmer).

The results are shown in FIG. 4.

It was confirmed that dBBAT119-P253 exhibits human CD137 agonist activity in the presence of ADM. This indicates a possibility that dBBAT119-P253 exhibits human CD137 agonist activity in a manner dependent on a small molecule such as ATP, ADP or AMP.

Example 3: Enhancement of Binding Activity of Antibodies that Bind Antigens in the Presence of Small Molecules Using Rationally Designed Light-Chain and Heavy-Chain Libraries (3-1) Construction of a Library for Enhancing Binding Activity Using a Rationally Designed Light Chain Library For the antibody library containing a large number of antibodies harvested in Example 2-2-1 with ATP-dependent antigen binding activity, enhancement of binding activity was performed by re-librarization of the antibody light chains.

The light-chain and heavy-chain regions of a rationally designed antibody phage display library constructed in the prior patent WO2015/083764 were used to construct an antibody light chain library and an antibody heavy chain library for enhancing binding activity. They were introduced into the above light chain library or the light-chain or heavy-chain regions of the phagemid vector library harvested in Example 2-2-1, and introduced into the *E. coli* strain ER2738 by electroporation.

(3-2) Enhancement of Binding Activity of Antibodies with ATP-Dependent Antigen-Binding Activity Using a Rationally Designed Library Phages were produced in a general method from *E. coli* carrying the constructed phage display phagemid. Specifically, *E. coli* carrying the constructed phagemid vector was infected with M13KO7TC (WO2015/046554) or M13KO7ΔpIII (hyperphage) (PROGEN Biotechnik), and phages were harvested from supernatants cultured overnight at 30° C. A phage library solution was obtained by diluting with TBS a population of phages precipitated by adding 2.5 M NaCl/10% PEG to the *E. coli* culture in which phage production was performed. BSA was then added to the phage library solution at a final concentration of 4%. Panning was performed using the antigen immobilized on magnetic beads. NeutrAvidin coated beads (Sera-Mag SpeedBeads NeutrAvidin-coated), NeutrAvidin beads (TAMAGAWA SEIKI) or Dynabeads MyOne StreptAvidin T1 (Thermo Fisher Scientific) were used as magnetic beads. As antigen, biotinylated hCD137-Fc was used.

Panning was performed to efficiently obtain small molecule switch antibodies which are dependent on the small molecule that can play a switch role in cancer tissues. Specifically, panning to enrich antibodies that bind to antigens in the presence of adenosine triphosphate (adenosine 5'-triphosphate; ATP) which is a small molecule, and which do not bind antigens in the absence of ATP was performed with reference to the methods described in the prior patent WO2015/083764.

(3-3) Assessment of Binding Activity in the Presence and Absence of ATP by Phage ELISA From single colonies of *E. coli* obtained after each round by the methods described above, phage-containing culture supernatants were harvested using a conventional method (Methods Mol. Biol. (2002) 178, 133-145). Binding activity to human CD137 in the presence and absence of ATP was then confirmed by phage ELISA with the methods described in Example 2-2-2.

The results are shown in FIG. 5.

A number of clones were obtained that were judged to be clones having ATP-dependent antigen binding activity, with an S/N ratio of absorbance greater than 2 in the presence/absence of the antigen and an S/N ratio of absorbance greater than 2 in the presence/absence of ATP (switch clones).

Example 4: Production of Modified CD137 Antibodies and Assessment of their Activities (4-1) Increase of Binding Activity Due to Alteration of dBBAT119H-P253/dBBAT119L-LamLib Variants of the heavy chain variable region, dBBAT119H, and the light-chain variable region, dBBAT119L, of the anti-CD137 antibody (clonal name: dBBAT119H-P253/dBBAT119L-LamLib) obtained in Example 2-4, were produced by methods known to those skilled in the art, such as PCR. For the heavy-chain variable region, variants were made in which D10 (referring to aspartic acid (Asp) at position 10 (Kabat numbering)) and G17 (referring to glycine (Gly) at position 17 (Kabat numbering)) of dBBAT119H were replaced with glycine (Gly) and serine (Ser), respectively, to produce dBBAT119H010; and N99 (referring to asparagine (Asn) at position 99 (Kabat numbering)), M100a (referring to methionine (Met) at position 100a (Kabat numbering)), and N100b (referring to asparagine (Asn) at position 100b (Kabat numbering)) of dBBAT119H010 were replaced with other amino acids. For the light-chain variable region, variants were created in which F87 (referring to phenylalanine (Phe) at position 87 (Kabat numbering)) of dBBAT119L was replaced with tyrosine (Tyr) to produce dBBAT119L010; and D27b (referring to aspartate (Asp) at position 27b (Kabat numbering)), N31 (referring to asparagine (Asn) at position 31 (Kabat numbering)), and D94 (referring to aspartate (Asp) at position 94 (Kabat numbering)) of dBBAT119L010 were replaced with other amino acids.

For variants of the heavy-chain variable region, binding activity to human CD137 was measured by BiacoreT200 (GE Healthcare), a surface plasmon resonance analyzer. Antibodies were captured by interacting purified variants with the Protein G (CALBIOCHEM)-immobilized Series S Sensor Chip CM3 (GE Healthcare). An ATP-supplemented human CD137 (FXa digested) solution or a human CD137 (FXa digested) solution without ATP was then interacted in the presence of ATP and in the absence of ATP to assess the binding activity of the variants towards human CD137 (FXa digested). Measurements were taken at 25° C. using 20 mM ACES, 150 mM NaCl, 0.05% Tween20, and 2 mM $MgCl_2$, pH 7.4 as running buffer. The results of measurements showed that the L100a variant (the variant in which methionine (Met) at position 100a (Kabat numbering) was replaced with leucine (Leu)) had enhanced binding activity to human CD137 only in the presence of ATP (FIG. 6). The heavy-chain variable region of the L100a variant is dBBATk119H024 (SEQ ID NO: 132). The binding amount of human CD137 was adjusted by the capture amount (1000 RU) of each variant.

For variants of the light-chain variable region, the binding activity to human CD137 (FXa digested) was determined by BiacoreT200 under similar conditions as described above. The results of measurements showed that the E94 variant (a variant in which aspartate (Asp) at position 94 (Kabat numbering) was replaced by glutamate (Glu)) had enhanced binding activity to human CD137 only in the presence of ATP (FIG. 6). The light-chain variable region of the E94 variant is dBBATk119L020 (SEQ ID NO: 133).

Such variants combining these heavy-chain and light-chain variants are abbreviated as dBBATk119H024-P253/dBBATk119L020-LamLib (heavy-chain variable region SEQ ID NO: 132; light-chain variable region SEQ ID NO: 133; heavy-chain constant region SEQ ID NO: 93; and light-chain constant region SEQ ID NO: 63).

The antibodies in the present specification are designated according to the following rule: (heavy chain variable region)–(heavy chain constant region)/(light chain variable region)–(light chain constant region).

For example, by the antibody name of dBBAT119H-P253/dBBAT119L-LamLib, it means that the heavy chain variable region of the antibody is dBBAT119H, the heavy chain constant region is P253, the light chain variable region is dBBAT119L, and the light chain constant region is LamLib.

(4-2) Assessment of CD137 Agonist Activity of Modified Anti-Human CD137 Antibodies In Vitro Using Human T Cells (4-2-1) Expansion of Human T Cell Cultures Human T cells were expanded and cultured as described in Example 2-6-1.

(4-2-2) Assessment of CD137 Agonist Activity In Vitro Using Human T Cells

The methods described in Example 2-6-2 evaluated IFN-γ production in the presence of NS1-P253 (non-switch antibody), dBBAT119H-P253/dBBAT119L-LamLib, dBBATk119H024-P253/dBBATk119L020-LamLib, or the control antibody, IC17HdK-hIgG1/IC17L-k0 at 10, 2, 0.4, 0.08, and 0.016 μg/ml, respectively. IFN-γ production in the ADPbetaS-minus medium was also evaluated.

The both results are shown in FIG. 7.

The modified dBBATk119H024-P253/dBBATk119L020-LamLib exhibited a stronger ADPbetaS-dependent agonist activity than dBBAT119H-P253/dBBAT119L-LamLib. This indicates a possibility that dBBATk119H024-P253/dBBATk119L020-LamLib exhibits stronger ATP-, ADP-, and AMP-dependent human CD137 agonist activities than dBBAT119H-P253/dBBAT119L-LamLib.

Example 5: Further Modifications of the CD137 Antibodies (5-1) Search for Modifications that Increase the Binding Activity by Introducing Comprehensive Modifications To produce superior anti-CD137 antibodies, amino acid modifications were introduced comprehensively into the heavy chain variable region, dBBATk119H024, and the light chain variable region, dBBATk119L020, of the anti-CD137 antibodies produced in Examples 4-1. By methods known to those skilled in the art, such as PCR, variants were each made in which each of all the amino acid residues constituting the CDRs of dBBATk119H024 and dBBATk119L020 were replaced by all 18 amino acids except cysteine. Measurements of the approximately 1200 variants produced to bind human CD137 were performed using Biacore4000. Antibodies were captured by interacting culture supernatants of the variants with the Protein G (CALBIOCHEM)-immobilized Series S Sensor Chip CM3 (GE Healthcare). A small molecule (ATP)-supplemented human CD137 solution or a human CD137 solution without addition of the small molecule was then interacted in the presence of the small molecule or in the absence of the small molecule to assess the binding activity of the antibodies towards human CD137. Measurements were taken at 25° C. using $CaCl_2$)-supplemended running buffer of 20 mM ACES, 150 mM NaCl, 0.02% Tween20, and 2 mM $MgCl_2$, pH 7.4.

(5-2) Increase of ATP Binding

The antibody heavy-chain gene A002-P253 (SEQ ID NO: 134) was created by combining the modifications found in Example 5-1 that increase the binding activity to human CD137 in the presence of the small molecule, in the dBBATk119H024-P253 gene having dBBATk119H024

(SEQ ID NO: 132) as the heavy-chain variable region, and P253 (SEQ ID NO: 93) as the heavy-chain constant region which was generated by introducing S267E/L328F modification into and deleting C-terminal Gly and Lys from human IgG1. The antibody light-chain gene B040-Lamlib (SEQ ID NO: 135) was also created by combining the modifications found in Example 5-1 that increased the binding activity to human CD137 in the presence of the small molecule, in the antibody light chain dBBATk119L020-Lamlib having dBBATk119L020 (SEQ ID NO: 133) as the light-chain variable region and human λ chain Lamlib (SEQ ID NO: 63) as the light-chain constant region. These genes were combined to express and purify antibodies by methods known to those skilled in the art to produce the anti-CD137 antibody of interest, A002-P253/B040-Lamlib. The heavy-chain variable region of A002-P253/B040-Lamlib is A002 (SEQ ID NO: 136), the light-chain variable region is B040 (SEQ ID NO: 137), the heavy-chain constant region is P253 (SEQ ID NO: 93), and the light-chain constant region is human λ chain Lamlib (SEQ ID NO: 63).

For the heavy-chain variable region of A002-P253/B040-Lamlib produced in this section, various variants were made in which the 53rd, 54th or 55th amino acids in Kabat numbering were replaced by other amino acids with the purpose of increasing ATP-binding activity. Table 15 shows amino acid modifications (Kabat numbering) from A002 in the heavy-chain variable regions of the generated antibodies.

TABLE 15

| Heavy-chain variable region | Amino acid alteration from A002 (Kabat numbering) |
| --- | --- |
| A002 | — |
| A146 | S54A/N55S |
| A159 | R53S/N55S |
| A160 | R53T/N55S |
| A161 | R53Q/N55S |
| A162 | R53K/N55S |
| A163 | R53H/N55S |
| A164 | R53S/N55T |
| A165 | R53T/N55T |
| A166 | R53Q/N55T |
| A167 | R53K/N55T |
| A168 | R53H/N55T |
| A169 | R53S/N55H |
| A170 | R53T/N55H |
| A171 | R53Q/N55H |

The binding activities of the produced variants towards ATP and human CD137 were evaluated by Biacore T200.

Measurement of the ATP-binding activity was performed at 37° C. using 20 mM ACES (pH 7.4), 150 mM NaCl, 2 mM MgCl$_2$, and 0.05% Tween20 as running buffer. At first, antibodies were captured by interacting antibody solutions prepared in running buffer with the Sure Protein A (GE Healthcare)-immobilized Series S Sensor Chip CM3 (GE Healthcare). Binding activity of the antibodies was then assessed by interaction with an ATP solution prepared in running buffer. The chip was regenerated using 25 mM NaOH and 10 mM Glycine-HCl (pH 1.5), and measurements were performed by repeatedly capturing antibodies. The binding amount of ATP for each antibody was calculated by adjusting the binding amount of ATP when injected at the concentration of 100 nM by the amount of antibody captured on the chip surface as the amount of ATP per unit amount of antibody. Measurement of the binding activity towards human CD137 was performed at 37° C. using 20 mM ACES (pH 7.4), 150 mM NaCl, 2 mM MgCl$_2$, and 0.05% Tween20 as running buffer. At first, antibodies were captured by interacting antibody solutions prepared in running buffer with the Sure Protein A (GE Healthcare)-immobilized Series S Sensor Chip CM3 (GE Healthcare). Then, the binding activity to human CD137 was assessed by interaction with a human CD137 solution supplemented with 100 μM ATP as the small molecule. For the human CD137 antigen, hCD137-HisBAP prepared in Example (1-1) was used, and measurements were performed at the antigen concentration of 0, 15.625, 62.5, 250 or 1000 nM. The chip was regenerated using 25 mM NaOH and 10 mM Glycine-HCl (pH 1.5), and measurements were performed by repeatedly capturing antibodies. Dissociation constant (KD) of the respective antibodies for human CD137 was calculated using Biacore T200 Evaluation Software 2.0. Specifically, the association rate constant ka (L/mol/s) and the dissociation rate constant kd (1/s) were calculated by global fitting of the sensorgrams obtained by measurement with the 1:1 Langmuir binding model, and the dissociation constant KD (mol/L) was calculated from these values.

Table 16 shows the results of these measurements.

Analysis to binding to ATP and human CD137

TABLE 16

| Antibody name | Binding to ATP | Parameter for binding to human CD137 (ATP = 100 μM) | | |
| --- | --- | --- | --- | --- |
| | | ka | kd | KD |
| A002-P253/B040-Lamlib | −0.0001 | 3.94E+04 | 2.89E−03 | 7.35E−08 |
| A146-P253/B040-Lamlib | −0.0001 | 7.80E+04 | 2.32E−02 | 2.97E−07 |
| A159-P253/B040-Lamlib | 0.0013 | 8.21E+04 | 3.83E−02 | 4.66E−07 |
| A160-P253/B040-Lamlib | −0.0001 | 9.59E+03 | 2.46E−02 | 2.56E−06 |
| A161-P253/B040-Lamlib | 0.0010 | 1.87E+04 | 2.35E−02 | 1.25E−06 |
| A162-P253/B040-Lamlib | 0.0002 | 1.47E+05 | 3.17E−02 | 2.16E−07 |
| A163-P253/B040-Lamlib | 0.0016 | 5.60E+04 | 1.36E−02 | 2.43E−07 |
| A164-P253/B040-Lamlib | 0.0017 | 9.81E+04 | 4.38E−02 | 4.46E−07 |
| A165-P253/B040-Lamlib | 0.0002 | 1.14E+04 | 1.96E−02 | 1.72E−06 |
| A166-P253/B040-Lamlib | 0.0011 | 1.21E+04 | 1.92E−02 | 1.59E−06 |
| A167-P253/B040-Lamlib | 0.0001 | 8.45E+04 | 3.96E−02 | 4.69E−07 |
| A168-P253/B040-Lamlib | 0.0017 | 7.01E+04 | 1.81E−02 | 2.58E−07 |
| A169-P253/B040-Lamlib | 0.0011 | 1.15E+04 | 5.88E−03 | 5.11E−07 |
| A170-P253/B040-Lamlib | 0.0000 | 5.13E+03 | 5.36E−03 | 1.04E−06 |
| A171-P253/B040-Lamlib | 0.0012 | 4.93E+03 | 5.24E−03 | 1.06E−06 |

As shown in Table 16, variants in which the 53rd, 54th or 55th amino acids (Kabat numbering) of the heavy-chain variable region were replaced by other amino acids had increased ATP-binding activity compared to the A002-P253/B040-Lamlib antibody before modification, except for A146-P253/B040-Lamlib and A160-P253/B040-Lamlib. Comparison of the association rate constant ka (L/mol/s) also shows that the association rate constant for human CD137 was increased for A146-P253/B040-Lamlib, A159-P253/B040-Lamlib, A162-P253/B040-Lamlib, A163-P253/B040-Lamlib, A164-P253/B040-Lamlib, A167-P253/B040-Lamlib and A168-P253/B040-Lamlib among the antibodies evaluated above.

(5-3) Increase of the Binding Activity by Introduction of Comprehensive Modifications To generate better anti-CD137 antibodies, modifications found in Example 5-1 that increase the human CD137-binding activity in the presence of a small molecule and that decrease binding to human CD137 under conditions where the small molecule is absent, and modifications found in Example 5-2 that increase ATP-binding activity and increase the association rate constant for human CD137 were combined to generate anti-human CD137 antibodies that exhibit a better profile. Antibody heavy-chain genes were generated that combine the modifications found in Examples 5-1 and 5-2 in the antibody heavy-chain gene A002-G1T3 having A002 (SEQ ID NO: 136) as the heavy-chain variable region, and G1T3 (SEQ ID NO: 138) as the heavy-chain constant region, which was generated by introducing K214R/Q419E modification into and deleting C-terminal Gly and Lys from human IgG1. An antibody light-chain genes were generated by combining the modifications found in Example 5-1 in the antibody light chain B040-Lamlib having B040 (SEQ ID NO: 137) as the light-chain variable region and human λ chain Lamlib as the light-chain constant region.

As subject of comparison, the antibody heavy-chain gene 20H4.9-P253 having the heavy-chain variable region 20H4.9 (SEQ ID NO: 139) of the existing anti-CD137 antibody described in U.S. Pat. No. 8,137,667 and P253 (SEQ ID NO: 93) as the heavy-chain constant region; and an antibody light-chain gene that combines the light-chain variable region 20H4.9LC (SEQ ID NO: 140) with human κ chain k0 (SEQ ID NO: 141) as the light-chain constant region were generated. As another subject of comparison, the antibody heavy-chain gene MOR-7480.1H-P253 having the heavy-chain variable region MOR-7480.1H (SEQ ID NO: 142) which constitutes the existing anti-CD137 antibody MOR-7480.1 described in U.S. Pat. No. 8,337,850, and P253 (SEQ ID NO: 93) as the heavy-chain constant region; and the antibody light chain MOR-7480.1L-lam combining the light chain variable region MOR-7480.1L (SEQ ID NO: 143) with human λ chain lam (SEQ ID NO: 63) as the light-chain constant region, were produced (note: both human λ chain Lamlib and lam have the same amino acid sequence (SEQ ID NO: 63)).

These genes were combined to express and purify antibodies using methods known to those skilled in the art to produce the anti-CD137 antibodies of interest. Table 17 is a list of sequence numbers of the heavy-chain variable region, light-chain variable region, heavy-chain constant region, light-chain constant region, and hypervariable region (Hyper Variable Region; also referred to as HVR or CDR) of the antibodies generated.

Amino acid sequences of the heavy chains and light chains, and their hypervariable regions (indicated by sequence ID numbers)

Binding of the generated variants to ATP and to human CD137 was evaluated in Biacore T200. Measurements of human CD137 binding were performed at 37° C. using 20 mM ACES (pH 7.4), 150 mM NaCl, 2 mM $MgCl_2$, and 0.05% Tween20 as running buffer. At first, 250-400 RU of antibodies were captured by interacting the antibody solutions prepared in running buffer with the Sure Protein A (GE Healthcare)-immobilized Series S Sensor Chip CM3 (GE Healthcare). The human CD137-binding activity in the presence of ATP or in the absence of ATP was then assessed by interacting with a human CD137 solution prepared in running buffer supplemented with a desired concentration of ATP, or a human CD137 solution prepared in running buffer without ATP. For the human CD137 antigen, hCD137-HisBAP prepared in Example (1-1) was used, and the KD value measurements were performed at an antigen concentration of 0, 15.625, 62.5, 250, and 1000 nM. For evaluation of the binding amount, measurements were performed at an antigen concentration of 0 and 1000 nM. The chip was regenerated using 25 mM NaOH and 10 mM Glycine-HCl (pH 1.5), and measurements were performed by repeatedly capturing antibodies. Dissociation constant of the respective antibodies for human CD137 was calculated using Biacore T200 Evaluation Software 2.0. Specifically, the association rate constant ka (L/mol/s) and the dissociation rate constant kd (1/s) were calculated by global fitting of the sensorgrams obtained by measurement with the 1:1 Langmuir binding model, and the dissociation constant KD (mol/L) was calculated from these values.

Table 18 shows the results of these measurements. Binding Analysis of the Modified Antibodies to Human CD137

TABLE 17

| Antibody name | Variable region | | Constant region | | Hypervariable region (HVR) | | | | | |
|---|---|---|---|---|---|---|---|---|---|---|
| | Heavy chain | Light chain | Heavy chain | Light chain | H1 | H2 | H3 | L1 | L2 | L3 |
| A375-G1T3/B167-Lamlib | 43 | 54 | 138 | 63 | 7 | 8 | 17 | 21 | 26 | 27 |
| A372-G1T3/B040-Lamlib | 44 | 55 | 138 | 63 | 7 | 9 | 17 | 22 | 26 | 27 |
| A356-G1T3/B040-Lamlib | 45 | 55 | 138 | 63 | 7 | 10 | 17 | 22 | 26 | 27 |
| A486-G1T3/B167-Lamlib | 46 | 54 | 138 | 63 | 7 | 11 | 18 | 21 | 26 | 27 |
| A487-G1T3/B167-Lamlib | 47 | 54 | 138 | 63 | 7 | 8 | 18 | 21 | 26 | 27 |
| A488-G1T3/B226-Lamlib | 48 | 56 | 138 | 63 | 7 | 12 | 18 | 21 | 26 | 28 |
| A489-G1T3/B223-Lamlib | 49 | 57 | 138 | 63 | 7 | 13 | 18 | 21 | 26 | 29 |
| A548-G1T3/B376-Lamlib | 50 | 58 | 138 | 63 | 7 | 14 | 19 | 23 | 26 | 27 |
| A551-G1T3/B256-Lamlib | 51 | 59 | 138 | 63 | 7 | 15 | 20 | 24 | 26 | 27 |
| A551-G1T3/B379-Lamlib | 51 | 60 | 138 | 63 | 7 | 15 | 20 | 25 | 26 | 27 |
| A555-G1T3/B379-Lamlib | 52 | 60 | 138 | 63 | 7 | 16 | 20 | 25 | 26 | 27 |
| A548-G1T3/B256-Lamlib | 50 | 59 | 138 | 63 | 7 | 14 | 19 | 24 | 26 | 27 |
| A549-G1T3/B167-Lamlib | 53 | 54 | 138 | 63 | 7 | 14 | 17 | 21 | 26 | 27 |

TABLE 18

| Antibody name | Binding to human CD137 | | | | | | $K_D$ (M) for human CD137 | |
|---|---|---|---|---|---|---|---|---|
| | Without ATP | ATP = 1 μm | ATP = 10 μm | ATP = 100 μm | ADP = 10 μm | AMP = 10 μm | Without ATP | ATP = 1 μm |
| 20H4.9-P253/20H4.9LC-k0 | 0.280 | 0.283 | 0.283 | 0.283 | 0.287 | 0.287 | 2.68E−08 | 2.17E−08 |
| MOR-7480.1H-P253/MOR-7480.1L-Iam | 0.260 | 0.261 | 0.261 | 0.261 | 0.266 | 0.266 | 8.22E−08 | 8.40E−08 |
| A375-G1T3/B167-Lamlib | 0.053 | 0.179 | 0.255 | 0.275 | 0.280 | 0.276 | N.A. | 4.43E−07 |
| A372-G1T3/B040-Lamlib | 0.017 | 0.135 | 0.242 | 0.269 | 0.284 | 0.245 | N.A. | 1.14E−06 |
| A356-G1T3/B040-Lamlib | 0.008 | 0.083 | 0.211 | 0.262 | 0.278 | 0.255 | N.A. | N.A. |
| A486-G1T3/B167-Lamlib | 0.128 | 0.260 | 0.282 | 0.292 | 0.294 | 0.289 | 1.04E−06* | 7.30E−08 |
| A487-G1T3/B167-Lamlib | 0.110 | 0.229 | 0.270 | 0.282 | 0.283 | 0.279 | 1.43E−06* | 1.63E−07 |
| A488-G1T3/B226-Lamlib | 0.042 | 0.135 | 0.232 | 0.268 | 0.281 | 0.261 | N.A. | 4.24E−07 |
| A489-G1T3/B223-Lamlib | 0.004 | 0.095 | 0.214 | 0.257 | 0.276 | 0.261 | N.A. | 4.42E−06 |
| A548-G1T3/B376-Lamlib | 0.012 | 0.149 | 0.245 | 0.270 | 0.270 | 0.262 | N.A. | 6.75E−07 |
| A551-G1T3/B256-Lamlib | 0.006 | 0.133 | 0.254 | 0.285 | 0.285 | 0.275 | N.A. | 1.23E−06 |
| A551-G1T3/B379-Lamlib | 0.014 | 0.173 | 0.271 | 0.290 | 0.291 | 0.283 | N.A. | 5.59E−07 |
| A555-G1T3/B379-Lamlib | 0.017 | 0.180 | 0.267 | 0.282 | 0.282 | 0.274 | N.A. | 4.77E−07 |
| A548-G1T3/B256-Lamlib | 0.009 | 0.156 | 0.257 | 0.284 | 0.287 | 0.276 | N.A. | 9.31E−07 |
| A549-G1T3/B167-Lamlib | 0.048 | 0.209 | 0.261 | 0.277 | 0.279 | 0.272 | N.A. | 2.04E−07 |

| Antibody name | $K_D$ (M) for human CD137 | | | |
|---|---|---|---|---|
| | ATP = 10 μm | ATP = 100 μm | ADP = 10 μm | AMP = 10 μm |
| 20H4.9-P253/20H4.9LC-k0 | 2.03E−08 | 2.04E−08 | 1.90E−08 | 2.17E−08 |
| MOR-7480.1H-P253/MOR-7480.1L-Iam | 7.50E−08 | 6.31E−08 | 7.30E−08 | 8.46E−08 |
| A375-G1T3/B167-Lamlib | 6.17E−08 | 1.35E−08 | 5.43E−09 | 8.91E−09 |
| A372-G1T3/B040-Lamlib | 1.58E−07 | 5.25E−08 | 9.36E−09 | 1.47E−07 |
| A356-G1T3/B040-Lamlib | 4.90E−07 | 1.19E−07 | 3.31E−08 | 1.34E−07 |
| A486-G1T3/B167-Lamlib | 1.08E−08 | 3.22E−09 | 2.48E−09 | 4.33E−09 |
| A487-G1T3/B167-Lamlib | 2.70E−08 | 7.33E−09 | 3.01E−09 | 3.86E−09 |
| A488-G1T3/B226-Lamlib | 1.33E−07 | 5.77E−08 | 1.60E−08 | 6.80E−08 |
| A489-G1T3/B223-Lamlib | 3.45E−07 | 1.59E−07 | 5.45E−08 | 1.05E−07 |
| A548-G1T3/B376-Lamlib | 7.69E−08 | 1.53E−08 | 1.55E−08 | 3.71E−08 |
| A551-G1T3/B256-Lamlib | 1.44E−07 | 2.91E−08 | 2.81E−08 | 6.12E−08 |
| A551-G1T3/B379-Lamlib | 7.17E−08 | 1.58E−08 | 1.51E−08 | 3.25E−08 |
| A555-G1T3/B379-Lamlib | 5.84E−08 | 1.35E−08 | 1.31E−08 | 2.75E−08 |
| A548-G1T3/B256-Lamlib | 1.08E−07 | 2.63E−08 | 2.14E−08 | 4.61E−08 |
| A549-G1T3/B167-Lamlib | 2.83E−08 | 6.12E−09 | 5.53E−09 | 1.35E−08 |

N.A.: It is too weak to determine a KD value.
*The KD value was determined with a steady state model.

The values of "Binding to human CD137" in Table 18 above indicate the binding amount of human CD137 per unit amount of antibody when human CD137 was allowed to interact at 1000 nM under each ATP concentration condition described above, and "KD (M) for human CD137" indicates the dissociation constant for human CD137 under each ATP concentration condition. The KD values marked with * in the table were calculated with a steady state model. The binding amount of all the generated variants in the presence of 10 μM ATP was more than that under the condition where ATP was present at 1 μM, and even more in the presence of 100 μM, suggesting that they bind to human CD137 in an ATP concentration-dependent manner. On the other hand, the subjects of comparison, 20H4.9-P253/20H4.9LC-k0 and MOR-7480.1 H-P253/MOR-7480.1L-lam, did not show binding to human CD137 in an ATP concentration-dependent manner.

(5-4) Assessment of the In Vitro ATP-Dependent CD137 Agonist Activity of the Modified Anti-Human CD137 Antibodies Using the 4-1BB Jurkat Reporter Gene Assay The GloResponse™ NF-κ B-Luc2/4-1BB Jurkat cell line (Promega, CS196004) was used for measurement of the in vitro activity of the generated variants. To each well of 96-well plates, 200 μL each of FcγRIIB CHO-K1 Cells (Promega) prepared at the concentration of 5×10⁴/mL with the medium was added and left to stand overnight at 37° C. in a 5% CO₂ incubator. A CHO culture medium (90% Ham's F12, 10% FBS) was used for the culture medium. Then, after all the medium was aspirated away, 25 μL of the GloResponse™ NF-κB-Luc2/4-1BB Jurkat cell line prepared to 2×10⁶/mL with an assay medium (99% RPMI, 1% FBS) was added to each well. Subsequently, 25 μL of each antibody solution diluted with the assay medium was added so that the final concentration was 0, 0.001, 0.01, 0.1, 1, and 10 μg/mL; and finally 25 μL of an ATP solution diluted with the assay medium was added so that the final concentration became 0 and 250 μM. The plates were left to stand for 6 hours at 37° C. in a 5% CO₂ incubator and 15 minutes at room temperature; and 75 μL of the Bio-Glo reagent was added to each well. The Bio-Glo Luciferase Assay System (Buffer and Substrate) was used for the Bio-Glo reagent. Subsequently, the luminescence of each well was measured with a plate reader. The value of the luminescence of each well divided by the value of the luminescence of the well without antibody addition was the Relative Light Unit (fold induction) and served as an indicator for evaluating the CD137 agonist activity of each antibody.

The results are shown in FIG. 8.

(5-5) Assessment of In Vitro ATP-Dependent CD137 Agonist Activity of Modified Anti-Human CD137 Antibodies Using Human Peripheral Blood Mononuclear Cells (5-5-1) Isolation of Human Peripheral Blood Mononuclear Cells Human peripheral blood mononuclear cells (PBMC) were isolated from blood samples of healthy volunteers in the Applicant's company isolated as described in Example 2-6-1. Subsequently, the cells were diluted in a medium (5% human serum (SIGMA), 95% AIM-V (Thermo Fischer Scientific) at a cell density of $5 \times 10^6$/mL.

(5-5-2) Assessment of CD137 Agonist Activity Using Human Peripheral Blood Mononuclear Cells Human peripheral blood mononuclear cells were adjusted to a cell density $5 \times 10^6$/mL and seeded into 96-well multiple-well flat-bottom plates (Corning) at 100 μL each. Subsequently, 50 μL of 0.04 μg/mL anti-human CD3ε antibody (BD, clone SP34) and 20 μg/mL anti-human CD28 antibody (BD, clone: CD28. 2) diluted in a medium were added. The plates were shaken and then left to stand in a 5% $CO_2$ incubator at 37° C. for 6 hours. Each well was then supplemented with 25 μL of 2 mM ATP (SIGMA)-medium or an ATP-free medium and 25 μL of each antibody at 40 μg/mL, and the plates were shaken before being left in a 5% $CO_2$ incubator at 37° C. for 18 hours. Subsequently, part of the culture supernatant was harvested, and the culture supernatant was used to quantify the IL-2 content in the culture supernatant using the Human IL-2 DuoSet ELISA kit (R&D systems) or the Human IL-2 ELISA Set (BD Biosciences). After harvesting the culture supernatant, the plates were left again in a 5% $CO_2$ incubator at 37° C. for 24 hours. Subsequently, part of the culture supernatant was harvested, and the amount of IFN-γ contained in the culture supernatant was quantified using the Human IFN-γ DuoSet ELISA kit (R&D systems) or the Human IFN-γ ELISA Development Kit (PeproTech). ELISA was performed basically according to the attached protocol of the kit. For the Human IL-2 DuoSet ELISA kit (R&D systems) and the Human IFN-γ DuoSet ELISA kit (R&D systems), color development and termination of the color development were performed according to protocols using a substrate solution (R&D systems) containing $H_2O_2$ and tetramethylbenzidine, and 1N $H_2SO_4$ (Wako). For the Human IL-2 ELISA Set (BD Biosciences), color development was terminated using 1 N $H_2SO_4$ (Wako). For the IFN-γ ELISA Development Kit (PeproTech), the TMB Chromogen Solution (Thermo Fischer Scientific) and 1N $H_2SO_4$ (Wako) were used for color development and termination of the color development. Absorbance measurements were then made with EnVision (PerkinElmer).

The results are detailed in Example 5-5-3 and later.

(5-5-3) Evaluation of the Enhancement of Agonist Activity of the Heavy Chain Constant Region by Increasing Fcγ Receptor-Binding Activity By in vitro assessment using human peripheral blood monocytes as described in Examples 5-5-1 and 5-5-2, the effect of using P587, MY518, TT14, and TT16 which variously increased the FcγRIIb-binding activity of the heavy chain constant region on CD137 agonist activity was evaluated.

The antibodies evaluated are as shown in Table 19.

Production of the antibodies recited in Table 19 is described in Example 7-1. Compared to the amounts of IL-2 and IFN-γ in the culture supernatant when a negative control antibody (IC17HdK-MY518/IC17L-k0, IC17HdK-G4d/IC17L-k0) was added in the presence of 250 μM ATP, when the addition of an antibody increased the amount of IL-2 in the culture supernatant by 1.05 fold or more and the amount of IFN-γ by 1.15 fold or more, it was judged that the antibody demonstrates CD137 agonist activity. Measurement of the agonist activity using human peripheral blood mononuclear cells (PBMC) may differ from donor to donor of the blood sample. In view of this point, it was determined that antibodies that did not show CD137 agonist activity for some or more than half of the human PBMC isolated from multiple donors can be judged not to show CD137 agonist activity, even if they met the standards for agonist activity for the other portion of human PBMC.

Antibodies which are judged to exhibit CD137 agonist activity in the presence of 250 μM ATP are shown in Table 19. This indicates that the CD137 agonist activity was enhanced by combining TT16 with P587 which increases the FcγRIIb-binding activity of the heavy chain constant region (FIGS. 9 and 10). It is thought that the agonistic activity was enhanced by increasing the binding activity towards FcγRIIb-expressing cells, which are cross-linking scaffolds required for the antibody to exhibit agonistic activity towards CD137-expressing cells (see Protein Eng Des Sel. 2013 October; 26(10): 589-598. Published online 2013 Jun. 5. doi:10.1093/protein).

TABLE 19

| Name of antibody evaluated | Name of antibody judged to have activity in the presence of ATP |
| --- | --- |
| A375-MY518/B167-LamLib | A375-P587/B167-LamLib |
| A356-MY518/B040-LamLib | A356-P587/B040-LamLib |
| A375-P587/B167-LamLib | A375-TT16/B167-LamLib |
| A356-P587/B040-LamLib | A356-TT16/B040-LamLib |
| A375-TT16/B167-LamLib | |
| A356-TT16/B040-LamLib | |
| A375-TT14/B167-LamLib | |

(5-5-4) Assessment of ATP-Dependent CD137 Agonist Activity of Variable Regions

The ATP-dependent CD137 agonist activity of each variable region by combining the heavy chain constant regions P587 and P253 with various variable regions was evaluated by in vitro assessment using human peripheral blood monocytes as described in Examples 5-5-1 and 5-5-2.

The antibodies evaluated are as shown in Table 20. Production of the antibodies recited in Table 20 is described in Example 7-1. Compared to the amounts of IL-2 and IFN-γ in the culture supernatant when a negative control antibody (IC17HdK-P253/IC17L-k0, IC17HdK-P587/IC17L-k0) was added in the presence of 250 μM ATP, when the addition of an antibody increased the amount of IL-2 in the culture supernatant by 1.05 fold or more and the amount of IFN-γ by 1.15 fold or more, it was judged that the antibody demonstrates CD137 agonist activity. Measurement of the agonist activity using human peripheral blood mononuclear cells (PBMC) may differ from donor to donor of the blood sample. In view of this point, it was determined that antibodies that did not show CD137 agonist activity for some or more than half of the human PBMC isolated from multiple donors can be judged not to show CD137 agonist activity, even if they met the standards for agonist activity for the other portion of human PBMC. The antibodies judged to exhibit CD137 agonist activity in the presence of 250 μM ATP are as shown in Table 20 (FIG. 11, FIG. 12, FIG. 13, FIG. 14 and FIG. 15).

In addition, among the antibodies judged to show CD137 agonist activity in the presence of 250 μM ATP, antibodies whose fold change relative to the group added with a negative control antibody (IC17HdK-P253/IC17L-k0, IC17HdK-P587/IC17L-k0) with respect to both the amounts of IL-2 and IFN-γ in the culture supernatant under the ATP-free condition was smaller than the fold change relative to the negative control under conditions in the presence of 250 μM ATP were judged to have a lower CD137 agonist activity under the ATP-free condition. The antibodies that showed CD137 agonist activity in the presence of 250 μM ATP and were judged to have lower CD137 agonist activity in the absence of ATP are as shown in Table 20 (FIG. 11, FIG. 12, FIG. 13, FIG. 14 and FIG. 15). These antibodies were judged to exhibit ATP-dependent CD137 agonist activity.

From the above, it was confirmed that for the variable regions, the combinations of the heavy chain variable region/light chain variable region of (A375/B167), (A356/B040), (A372/B040), (A486/B167), (A488/B226), (A489/B223), (A551/B256), (A548/B256), and (A551/B379) exhibit CD137 agonist activity in an ATP-dependent manner.

fold or more in the culture supernatant relative to the group added with antibodies containing a heavy chain constant region that does not contain these amino acid modifications, A375-TT16/B167-LamLib, A375-MY518/B167-LamLib, and A375-TT14/B167-LamLib, it was judged that the CD137 agonist activity was enhanced. Compared to antibodies comprising a heavy-chain constant region without the pI-increasing amino acid modifications, antibodies comprising a heavy-chain constant region into which the amino acid modifications shown to have enhanced CD137 agonist activity in the presence of 250 μM ATP are shown in Table 22 (FIG. 10).

This indicates that independent of the degree of increase in the FcγRIIb-binding activity of the heavy-chain constant

TABLE 20

| Name of antibody evaluated | Name of antibody judged to have activity in the presence of ATP | Name of antibody judged to have lower activity in the absence of ATP |
| --- | --- | --- |
| A372-P253/B040-LamLib | A372-P253/B040-LamLib | A372-P253/B040-LamLib |
| A486-P253/B167-LamLib | A486-P253/B167-LamLib | A486-P253/B167-LamLib |
| A488-P253/B226-LamLib | A488-P253/B226-LamLib | A488-P253/B226-LamLib |
| A489-P253/B223-LamLib | A489-P253/B223-LamLib | A489-P253/B223-LamLib |
| A551-P587/B256-LamLib | A551-P587/B256-LamLib | A551-P587/B256-LamLib |
| A375-P587/B167-LamLib | A375-P587/B167-LamLib | A375-P587/B167-LamLib |
| A548-P587/B256-LamLib | A548-P587/B256-LamLib | A548-P587/B256-LamLib |
| A356-P587/B040-LamLib | A356-P587/B040-LamLib | A356-P587/B040-LamLib |
| A551-P587/B379-LamLib | A551-P587/B379-LamLib | A551-P587/B379-LamLib |

(5-5-5) Assessment of the Potentiating Effect on CD137 Agonist Activity of Combining Alterations that Increase the pI of the Heavy-Chain Constant Region with the Heavy-Chain Constant Region with Increased Fcγ Receptor-Binding Activity The effect on CD137 agonist activity of introducing various amino acid modifications that increase the pI of the heavy-chain constant region into the heavy-chain constant region with variously increased FcγRIIb-binding activity was assessed by in vitro evaluation using human peripheral blood monocytes described in Examples 5-5-1 and 5-5-2. The amino acid alterations that increase pI were introduced into the heavy chain constant regions TT16, MY518, and TT14, and thereby heavy-chain constant regions TT16+P343R/D413K (SCF028), TT16+Q311R/P343R (SCF033), MY518+P343R/D413K (SCF025), MY518+Q311R/P343R (SCF030), TT14+P343R/D413K (SCF027), and TT14+Q311R/P343R (SCF032) were generated.

The names of the evaluated antibodies into which the amino acid alterations that increase pI have been introduced, and the names of the corresponding antibodies before the amino acid alterations that increase the pI were introduced are as shown in Table 21. Production of the antibodies recited in Table 21 is described in Example 7-2.

Regarding assessment of the enhancement of agonist activity by introducing pI-increasing amino acid modifications, when addition of an antibody increased the amount of IL-2 by 1.04 fold or more and the amount of IFN-γ by 1.1 region, introduction of the modifications that increase the pI of the heavy-chain constant region enhances the CD137 agonist activity of the anti-human CD137 antibody. It was suggested that: combining modifications that increase the pI of the heavy-chain constant region with modifications that increase the FcγRIIb binding of the heavy chain constant region into a heavy-chain constant region enhanced the interaction with the negatively charged FcγRIIb-expressing cell surface; and immune complexes of antibodies or antigen-bound antibodies approached the FcγRIIb-expressing cell surface more closely; and this further increased the binding to FcγRIIb-expressing cells which are cross-linking scaffolds required for antibodies to exhibit agonistic activity towards CD137-expressing cells; and thus the agonistic activity was further enhanced.

TABLE 21

| Name of evaluated heavy-chain constant region into which amino acid alterations that increase pI have been introduced | Name of corresponding heavy-chain constant region before introduction of amino acid alterations that increase pI | Introduced pI alterations |
| --- | --- | --- |
| A375-SCF028/B167-LamLib | A375-TT16/B167-LamLib | P343R/D413K |
| A375-SCF033/B167-LamLib | A375-TT16/B167-LamLib | Q311R/P343R |
| A375-SCF025/B167-LamLib | A375-MY518/B167-LamLib | P343R/D413K |
| A375-SCF030/B167-LamLib | A375-MY518/B167-LamLib | Q311R/P343R |
| A375-SCF027/B167-LamLib | A375-TT14/B167-LamLib | P343R/D413K |
| A375-SCF032/B167-LamLib | A375-TT14/B167-LamLib | Q311R/P343R |

TABLE 22

| Name of antibody judged to exhibit enhanced agonistic activity |
| --- |
| A375-SCF028/B167-LamLib |
| A375-SCF033/B167-LamLib |
| A375-SCF025/B167-LamLib |
| A375-SCF030/B167-LamLib |

TABLE 22-continued

Name of antibody judged to exhibit enhanced agonistic activity

A375-SCF027/B167-LamLib
A375-SCF032/B167-LamLib (5-5-6) Evaluation of the Effect on Agonist Activity by Introducing Modifications that Increase the pI of the Heavy-Chain Constant Region The effect on CD137 agonist activity of introducing various amino acid modifications that increase the pI of the heavy-chain constant regions MY201aPh and MY518 was assessed by in vitro evaluation using human peripheral blood monocytes described in Examples 5-5-1 and 5-5-2. The heavy-chain constant regions MY518, MY518a and MY201aPh were introduced with amino acid modifications that increase pI; and MY518+P343R/D413K (SCF025), MY518+Q311R/P343R(SCF030), MY518+P343R (SCF039), MY518+D413K (SCF040), MY518a+Q311R (SCF060a), MY201aPh+P343R(SCF041aPh), MY201aPh+P343R/D413K (SCF043aPh), MY201aPh+Q311R (SCF056aPh), MY201aPh+Q311R/P343Rb(SCF057aPh), and MY201aPh+Q311R/D413K (SCF059aPh) were thereby generated. The names of the evaluated antibodies into which the amino acid alterations that increase pI have been introduced, and the names of the antibodies before the amino acid alterations that increase the corresponding pI were introduced are shown in Table 23. Production of the antibodies recited in Table 23 is described in Example 7-2.

Regarding assessment of the enhancement of agonist activity by introducing pI-increasing amino acid modifications, when addition of an antibody increased the amount of IL-2 by 1.04 fold or more and the amount of IFN-γ by 1.1 fold or more in the culture supernatant relative to the group added with antibodies comprising a heavy chain constant region that does not contain these amino acid modifications, A375-MY518a/B167-LamLib and A375-MY201aPh/B167-LamLib, it was judged that the CD137 agonist activity was enhanced. Compared to antibodies comprising a heavy-chain constant region without the pI-increasing amino acid modifications, antibodies comprising a heavy-chain constant region into which the amino acid alterations shown to have enhanced CD137 agonist activity in the presence of 250 μM ATP are shown in Table 24 (FIGS. 16 and 17).

TABLE 23

| Name of evaluated heavy-chain constant region into which amino acid alterations that increase pI have been introduced | Name of corresponding heavy-chain constant region before introduction of amino acid alterations that increase pI | Introduced pI alterations |
| --- | --- | --- |
| A375-SCF025/B167-LamLib | A375-MY518/B167-LamLib | P343R/D413K |
| A375-SCF030/B167-LamLib | A375-MY518/B167-LamLib | Q311R/P343R |
| A375-SCF039/B167-LamLib | A375-MY518/B167-LamLib | P343R |
| A375-SCF040/B167-LamLib | A375-MY518/B167-LamLib | D413K |
| A375-SCF060a/B167-LamLib | A375-MY518a/B167-LamLib | Q311R |
| A375-SCF041aPh/B167-LamLib | A375-MY201aPh/B167-LamLib | P343R |
| A375-SCF043aPh/B167-LamLib | A375-MY201aPh/B167-LamLib | P343R/D413K |
| A375-SCF056aPh/B167-LamLib | A375-MY201aPh/B167-LamLib | Q311R |
| A376-SCF057aPh/B167-LamLib | A375-MY201aPh/B167-LamLib | Q311R/P343R |
| A375-SCF059aPh/B167-LamLib | A375-MY201aPh/B167-LamLib | Q311R/D413K |

TABLE 24

Name of antibody judged to exhibit enhanced agonistic activity

A375-SCF025/B167-LamLib
A375-SCF030/B167-LamLib

TABLE 24-continued

Name of antibody judged to exhibit enhanced agonistic activity

A375-SCF039/B167-LamLib
A375-SCF040/B167-LamLib
A375-SCF060a/B167-LamLib
A375-SCF041aPh/B167-LamLib
A375-SCF043aPh/B167-LamLib
A375-SCF056aPh/B167-LamLib
A375-SCF057aPh/B167-LamLib
A375-SCF059aPh/B167-LamLib (5-5-7) Assessment of ATP-Dependent CD137 Agonist Activity of Anti-Human CD137 Antibodies which Combine the Generated Variable Regions and Constant Regions The ATP-dependent CD137 agonist activity of anti-human CD137 antibodies made by combining the above-described variable regions with the pI-increasing heavy chain constant regions was assessed by in vitro evaluation using human peripheral blood monocytes described in Examples 5-5-1 and 5-5-2. The evaluated antibodies are shown in Table 25.

Compared to the amounts of IL-2 and IFN-γ in the culture supernatant when a negative control antibody (IC17HdK-MY518a/IC17L-k0, IC17HdK-MY201aPh/IC17L-k0, IC17HdK-MY201/IC17L-k0, IC17HdK-G4d/IC17L-k0, IC17HdK-MY518/IC17L-k0, or IC17HdK-TT16/IC17L-k0) was added in the presence of 250 μM ATP, when the addition of an antibody increased the amount of IL-2 in the culture supernatant by 1.05 fold or more and the amount of IFN-γ by 1.15 fold or more, it was judged that the antibody demonstrates CD137 agonist activity. Measurement of the agonist activity using human peripheral blood mononuclear cells (PBMC) may differ from donor to donor of the blood sample. In view of this point, it was determined that antibodies that did not show CD137 agonist activity for some or more than half of the human PBMC isolated from multiple donors can be judged not to show CD137 agonist activity, even if they met the standards for agonist activity for the other portion of human PBMC. The antibodies judged to exhibit CD137 agonist activity in the presence of 250 μM ATP are shown in Table 25 (FIG. 16, FIG. 17, FIG. 18, FIG. 19, FIG. 20, FIG. 21, FIG. 22, and FIG. 23).

In addition, among the antibodies judged to show CD137 agonist activity in the presence of 250 μM ATP, antibodies whose fold change relative to the group added with a negative control antibody (IC17HdK-MY518a/IC17L-k0, IC17HdK-MY201aPh/IC17L-k0, IC17HdK-MY201/IC17L-k0, IC17HdK-G4d/IC17L-k0, IC17HdK-MY518/IC17L-k0, or IC17HdK-TT16/IC17L-k0) with respect to both the amounts of IL-2 and IFN-γ in the culture supernatant under the ATP-free condition was smaller than the fold change relative to the negative control under conditions in the presence of 250 μM ATP, were judged to have a lower CD137 agonist activity under the ATP-free condition. The antibodies judged to have a lower CD137 agonist activity in the absence of ATP are shown in Table 25 (FIG. 16, FIG. 17, FIG. 18, FIG. 19, FIG. 20, FIG. 21, FIG. 22, and FIG. 23). These antibodies were shown to exhibit ATP-dependent CD137 agonist activity.

7480.1 L-ml0r abbreviation: NS2-MB492), and anti-human CD137 switch antibodies (A375-mIgG1/B167-ml0r, A372-mIgG1/B040-ml0r, A372-MB110/B040-ml0r, A372-MB492/B040-ml0r, A356-MB110/B040-ml0r, A486-MB492/B167-ml0r, A488-MB492/B226-ml0r, A489-MB492/B223-ml0r, A551-mIgG1/B256-ml0r, A551-MB110/B379-ml0r, and A548-mIgG1/B256-ml0r) were produced.

TABLE 25

| Name of antibody evaluated | Name of antibody judged to have activity in the presence of ATP | Name of antibody judged to have lower activity in the absence of ATP |
|---|---|---|
| A375-MY518/B167-LamLib | A375-SCF025/B167-LamLib | A375-SCF025/B167-LamLib |
| A375-SCF025/B167-LamLib | A375-SCF030/B167-LamLib | A375-SCF030/B167-LamLib |
| A375-SCF030/B167-LamLib | A375-SCF039/B167-LamLib | A375-SCF039/B167-LamLib |
| A375-SCF039/B167-LamLib | A375-SCF040/B167-LamLib | A375-SCF040/B167-LamLib |
| A375-SCF040/B167-LamLib | A375-MY518a/B167-LamLib | A375-MY518a/B167-LamLib |
| A375-MY518a/B167-LamLib | A375-SCF060a/B167-LamLib | A375-SCF060a/B167-LamLib |
| A375-SCF060a/B167-LamLib | A375-SCF041aPh/B167-LamLib | A375-SCF041aPh/B167-LamLib |
| A375-MY201aPh/B167-LamLib | A375-SCF043aPh/B167-LamLib | A375-SCF043aPh/B167-LamLib |
| A375-SCF041aPh/B167-LamLib | A375-SCF056aPh/B167-LamLib | A375-SCF056aPh/B167-LamLib |
| A375-SCF043aPh/B167-LamLib | A375-SCF057aPh/B167-LamLib | A375-SCF057aPh/B167-LamLib |
| A375-SCF056aPh/B167-LamLib | A375-SCF059aPh/B167-LamLib | A551-SCF041a/B256-LamLib |
| A375-SCF057aPh/B167-LamLib | A551-SCF041a/B256-LamLib | A551-SCF057a/B256-LamLib |
| A375-SCF059aPh/B167-LamLib | A551-SCF057a/B256-LamLib | A551-SCF059a/B256-LamLib |
| A551-SCF041a/B256-LamLib | A551-SCF059a/B256-LamLib | A551-SCF057aPh/B256-LamLib |
| A551-SCF056a/B256-LamLib | A551-SCF057aPh/B256-LamLib | A551-SCF025a/B256-LamLib |
| A551-SCF057a/B256-LamLib | A551-SCF059aPh/B256-LamLib | A551-SCF039a/B256-LamLib |
| A551-SCF059a/B256-LamLib | A551-SCF025a/B256-LamLib | A551-SCF043a/B256-LamLib |
| A551-SCF056aPh/B256-LamLib | A551-SCF039a/B256-LamLib | A551-SCF041aPh/B256-LamLib |
| A551-SCF057aPh/B256-LamLib | A551-MY201a/B256-LamLib | A551-SCF043aPh/B256-LamLib |
| A551-SCF059aPh/B256-LamLib | A551-SCF043a/B256-LamLib | A551-SCF039a/B379-LamLib |
| A551-MY518/B256-LamLib | A551-SCF041aPh/B256-LamLib | A551-SCF041a/B379-LamLib |
| A551-SCF025a/B256-LamLib | A551-SCF043aPh/B256-LamLib | A551-SCF043a/B379-LamLib |
| A551-SCF039a/B256-LamLib | A551-SCF039a/B379-LamLib | A551-SCF041aPh/B379-LamLib |
| A551-MY201a/B256-LamLib | A551-SCF041a/B379-LamLib | A551-SCF043aPh/B379-LamLib |
| A551-SCF043a/B256-LamLib | A551-SCF043a/B379-LamLib | A551-SCF060a/B379-LamLib |
| A551-MY201aPh/B256-LamLib | A551-SCF041aPh/B379-LamLib | A551-SCF057a/B379-LamLib |
| A551-SCF041aPh/B256-LamLib | A551-SCF043aPh/B379-LamLib | A551-SCF059a/B379-LamLib |
| A551-SCF043aPh/B256-LamLib | A551-SCF060a/B379-LamLib | A551-SCF056aPh/B379-LamLib |
| A551-MY518a/B379-LamLib | A551-SCF057a/B379-LamLib | A551-SCF057aPh/B379-LamLib |
| A551-SCF039a/B379-LamLib | A551-SCF059a/B379-LamLib | A551-SCF059aPh/B379-LamLib |
| A551-SCF041a/B379-LamLib | A551-SCF056aPh/B379-LamLib | A375-TT16/B167-LamLib |
| A551-SCF043a/B379-LamLib | A551-SCF057aPh/B379-LamLib | A356-TT16/B040-LamLib |
| A551-SCF041aPh/B379-LamLib | A551-SCF059aPh/B379-LamLib | A551-TT16/B379-LamLib |
| A551-SCF043aPh/B379-LamLib | A375-TT16/B167-LamLib | |
| A551-SCF060a/B379-LamLib | A356-TT16/B040-LamLib | |
| A551-SCF056a/B379-LamLib | A551-TT16/B379-LamLib | |
| A551-SCF057a/B379-LamLib | | |
| A551-SCF059a/B379-LamLib | | |
| A551-SCF056aPh/B379-LamLib | | |
| A551-SCF057aPh/B379-LamLib | | |
| A551-SCF059aPh/B379-LamLib | | |
| A375-TT16/B167-LamLib | | |
| A356-TT16/B040-LamLib | | |
| A551-TT16/B379-LamLib | | |

Example 6: Human CD137 Knock-in Mouse Administration Test of Anti-Human CD137 Switch Antibodies (6-1) Generation of Antibodies for Human CD137 Knock-in Mouse Administration Study Anti-human CD137 switch and non-switch antibodies having a mouse constant region were generated for the human CD137 knock-in mouse administration study. Specifically, anti-human CD137 non-switch antibodies (20H4.9-mIgG1/20H4.9LC-mk0 abbreviation: NS1-mIgG1, 20H4.9-MB110/20H4.9LC-mk0 abbreviation: NS1-MB110, 20H4.9-MB492/20H4.9LC-mk0 abbreviation: NS1-MB492, MOR-7480.1 H-MB110/MOR-7480.1 L-ml0r abbreviation: NS2-MB110, MOR-7480.1 H-MB492/MOR- For the heavy chains of the NS1-mIgG1, NS1-MB110 and NS1-MB492 antibodies, genes of the antibody heavy chains were generated by combining the heavy-chain variable region 20H4.9 (SEQ ID NO: 139) with any of:
(i) mIgG1, heavy-chain constant region of murine IgG1 (SEQ ID NO: 144),
(ii) MB110 as described in WO2014030750 (SEQ ID NO: 145), and
(iii) MB492 as described in WO2014030750 (SEQ ID NO: 146), as the heavy-chain constant region. That is, the genes of 20H4.9-mIgG1, 20H4.9-MB110, and 20H4.9-MB492 were generated.

For the light chain of the NS1-mIgG1, NS1-MB110, and NS1-MB492 antibodies, the antibody light chain gene 20H4.9LC-mk0 was generated by combining the light-chain variable region 20H4.9LC (SEQ ID NO: 140) with the murine κ chain mk0 (SEQ ID NO: 147) as the light-chain constant region. By combining these heavy-chain and light-chain genes, each antibody was expressed and purified by methods known to those skilled in the art.

For the heavy chains of the NS2-MB110 and NS2-MB492 antibodies, genes of the antibody heavy chains were generated by combining the heavy-chain variable region MOR-7480.1 H (SEQ ID NO: 142) with either:
(i) MB110 (SEQ ID NO: 145), or
(ii) MB492 (SEQ ID NO: 146),
as heavy-chain constant region. That is, the MOR-7480.1H-MB110 and MOR-7480.1H-MB492 genes were generated.

For the light chains of the NS2-MB110 and NS2-MB492 antibodies, the antibody light chain gene MOR-7480.1L-ml0r was generated by combining the light-chain variable region MOR-7480.1L (SEQ ID NO: 143) with the murine λ chain ml0r (SEQ ID NO: 148) as the light-chain constant region. By combining these heavy-chain and light-chain genes, each antibody was expressed and purified by methods known to those skilled in the art.

For anti-CD137 switch antibodies, genes of the antibody heavy chains and antibody light chains in Tables 26 and 27 below were generated; and each antibody was expressed and purified by combining these genes by methods known to those skilled in the art.

Antibody heavy chains of anti-CD137 switch antibodies having a murine constant region

TABLE 26

| Full-length heavy chain | A375-mIgG1 | Variable region A375 (SEQ ID NO: 43) Constant region mIgG1 (SEQ ID NO: 144) |
| Full-length heavy chain | A372-mIgG1 | Variable region A372 (SEQ ID NO: 44) Constant region mIgG1 (SEQ ID NO: 144) |
| Full-length heavy chain | A372-MB110 | Variable region A372 (SEQ ID NO: 44) Constant region MB110 (SEQ ID NO: 145) |
| Full-length heavy chain | A372-MB492 | Variable region A372 (SEQ ID NO: 44) Constant region MB492 (SEQ ID NO: 146) |
| Full-length heavy chain | A356-MB110 | Variable region A356 (SEQ ID NO: 45) Constant region MB110 (SEQ ID NO: 145) |
| Full-length heavy chain | A486-MB492 | Variable region A486 (SEQ ID NO: 46) Constant region MB492 (SEQ ID NO: 146) |
| Full-length heavy chain | A488-MB492 | Variable region A488 (SEQ ID NO: 48) Constant region MB492 (SEQ ID NO: 146) |
| Full-length heavy chain | A489-MB492 | Variable region A489 (SEQ ID NO: 49) Constant region MB492 (SEQ ID NO: 146) |
| Full-length heavy chain | A548-mIgG1 | Variable region A548 (SEQ ID NO: 50) Constant region mIgG1 (SEQ ID NO: 144) |
| Full-length heavy chain | A551-mIgG1 | Variable region A551 (SEQ ID NO: 51) Constant region mIgG1 (SEQ ID NO: 144) |
| Full-length heavy chain | A551-MB110 | Variable region A551 (SEQ ID NO: 51) Constant region MB110 (SEQ ID NO: 145) |

Antibody light chains of anti-CD137 switch antibodies having a murine constant region

TABLE 27

| Full-length light chain | B040-ml0r | Variable region B040 (SEQ ID NO: 55) Constant region ml0r (SEQ ID NO: 148) |
| Full-length light chain | B167-ml0r | Variable region B167 (SEQ ID NO: 54) Constant region ml0r (SEQ ID NO: 148) |
| Full-length light chain | B226-ml0r | Variable region B226 (SEQ ID NO: 56) Constant region ml0r (SEQ ID NO: 148) |
| Full-length light chain | B223-ml0r | Variable region B223 (SEQ ID NO: 57) Constant region ml0r (SEQ ID NO: 148) |
| Full-length light chain | B256-ml0r | Variable region B256 (SEQ ID NO: 59) Constant region ml0r (SEQ ID NO: 148) |
| Full-length light chain | B379-ml0r | Variable region B379 (SEQ ID NO: 60) Constant region ml0r (SEQ ID NO: 148) |

(6-2) Assessment of the Human CD137-Binding Activity of Antibodies Prepared for the Human CD137 Knock-in Mouse Administration Study The binding activity of the anti-human CD137 non-switch antibody and the anti-CD137 switch antibody produced in Example 6-1 towards human CD137 was evaluated. Measurements of human CD137 binding were taken at 37° C. using 20 mM ACES (pH 7.4), 150 mM NaCl, 2 mM $MgCl_2$, and 0.05% Tween20 as running buffer. At first, antibodies were captured by interacting antibody solutions prepared in running buffer with the rabbit anti-mouse IgG (Thermo Scientific)-immobilized Series S Sensor Chip CM5 (GE Healthcare). The human CD137-binding activity in the presence of ATP and in the absence of ATP was then assessed by interacting with a human CD137 solution prepared in running buffer supplemented with a desired concentration of ATP, or a human CD137 solution prepared in running buffer without ATP. For the human CD137 antigen, hCD137 (FXa digested) prepared in Example (1-2) was used, and measurements were performed at an antigen concentration of 0, 15.625, 62.5, 250, and 1000 nM. The chip was regenerated using 25 mM NaOH and 10 mM Glycine-HCl (pH 1.5), and measurements were performed by repeatedly capturing antibodies. Dissociation constant (KD) of the respective antibodies for human CD137 was calculated using Biacore T200 Evaluation Software 2.0. Specifically, the association rate constant ka (L/mol/s) and the dissociation rate constant kd (1/s) were calculated by global fitting of the sensorgrams obtained by measurement with the 1:1 *Langmuir* binding model, and the dissociation constant KD (mol/L) was calculated from these values.

Table 28 shows the results of these measurements.

Analysis of human CD137 binding of anti-CD137 antibodies having a murine constant region

TABLE 28

| | $K_D$ (M) for human CD137 | | | |
|---|---|---|---|---|
| Antibody name | Without ATP | ATP = 1 μM | ATP = 10 μM | ATP = 100 μM |
| NS1-mIgG1 | 6.17E−08 | 5.62E−08 | 5.44E−08 | 5.36E−08 |
| NS1-MB110 | 6.10E−08 | 5.65E−08 | 5.39E−08 | 5.19E−08 |
| NS1-MB492 | 6.16E−08 | 5.49E−08 | 5.35E−08 | 5.04E−08 |
| NS2-MB110 | 1.88E−07 | 1.44E−07 | 1.02E−07 | 1.04E−07 |
| NS2-MB492 | 2.16E−07 | 1.70E−07 | 1.12E−07 | 1.12E−07 |
| A375-mIgG1/ B167-ml0r | N.A. | 3.43E−07 | 1.14E−07 | 2.92E−08 |
| A372-mIgG1/ B040-ml0r | N.A. | 4.78E−07 | 2.59E−07 | 1.08E−07 |
| A372-MB110/ B040-ml0r | N.A. | 6.11E−07 | 2.64E−07 | 1.12E−07 |
| A372-MB492/ B040-ml0r | N.A. | 7.82E−07 | 2.51E−07 | 1.04E−07 |
| A356-MB110/ B040-ml0r | N.A. | 1.01E−06 | 4.10E−07 | 1.68E−07 |
| A486-MB492/ B167-ml0r | N.A. | 1.31E−07 | 2.70E−08 | 7.67E−09 |
| A488-MB492/ B226-ml0r | N.A. | N.D. | 1.36E−07 | 8.25E−08 |
| A489-MB492/ B223-ml0r | N.A. | 1.62E−06 | 3.58E−07 | 1.54E−07 |
| A551-mIgG1/ B256-ml0r | N.A. | 7.55E−07 | 2.31E−07 | 6.22E−08 |
| A551-MB110/ B379-ml0r | N.A. | 5.12E−07 | 1.43E−07 | 3.51E−08 |
| A548-mIgG1/ B256-ml0r | N.A. | 8.61E−07 | 2.19E−07 | 5.58E−08 |

N.A.: It is too weak to determine a KD value.
N.D.: Not determined.

Both the anti-human CD137 non-switch antibody and the anti-human CD137 switch antibody generated above, which comprise a murine constant region, were confirmed to bind to human CD137. All anti-human CD137 switch antibodies were also shown to bind to human CD137 in an ATP concentration-dependent manner. On the other hand, for the non-switch antibodies, no such ATP concentration-dependent binding to human CD137 was observed, and the binding was almost the same at any ATP concentration.

(6-3) Plasma Kinetic Assessment of Modified Antibodies in Human CD137 Knock-in Mouse (6-3-1) Generation of Human CD137 Knock-in Mouse By introducing a human CD137 gene substitution vector into mouse embryonic stem cells (ES cells), a human CD137 knock-in mouse was generated in which the mouse CD137 gene was replaced by a human CD137 gene. This mouse is described as an hCD137 KI mouse.

(6-3-2) Measurement of Anti-Human CD137 Antibody Concentration in Plasma in the hCD137KI Mouse Model Following generation of the hCD137KI mouse in Example 6-3-1, the respective antibodies were administered intravenously at a single dose to the hCD137KI mouse as shown in Table 29. In Table 29, NS1-mIgG1, NS1-MB110 and NS1-MB492 are all non-switch antibodies, and the other is a switch antibody. Blood was collected multiple times over time from 5 minutes to 28 days after administration. The obtained blood was centrifuged to separate plasma. Plasma was stored in a freezer set below −20° C. until measurement.

Group details for the plasma kinetic evaluation study

TABLE 29

| Group | Number of animals | Pharmaceutical agent | Dose [mg/kg] |
|---|---|---|---|
| 1 | 3 | NS1-mIgG1 | 7.5 single administration |
| 2 | 3 | NS1-MB110 | 7.5 single administration |
| 3 | 3 | NS1-MB492 | 7.5 single administration |
| 4 | 3 | A375-mIgG1/B167-ml0r | 7.5 single administration |
| 5 | 3 | A356-MB110/B040-ml0r | 7.5 single administration |
| 6 | 3 | A372-mIgG1/B040-ml0r | 7.5 single administration |
| 7 | 3 | A372-MB110/B040-ml0r | 7.5 single administration |
| 8 | 3 | A372-MB492/B040-ml0r | 7.5 single administration |
| 9 | 3 | A486-MB492/B167-ml0r | 7.5 single administration |
| 10 | 3 | A488-MB492/B226-ml0r | 7.5 single administration |
| 11 | 3 | A489-MB492/B223-ml0r | 7.5 single administration |
| 12 | 3 | A548-mIgG1/B256-ml0r | 7.5 single administration |
| 13 | 3 | A551-mIgG1/B256-ml0r | 7.5 single administration |
| 14 | 3 | A551-MB110/B379-ml0r | 7.5 single administration |

The concentration of each switch antibody in plasma was measured by the electrochemiluminescence (ECL) method. Specifically, hCD137 (Sino Biological Inc.) was diluted in PBS (−) and added to MULTI-ARRAY 96-well Plate (Meso Scale Diagnostics, LLC). hCD137 was added to the plate and shaken at room temperature for one hour, and hCD137 was immobilized to the plate. Next, for blocking, a PBS solution containing 1% BSA and 0.05% Tween 20 was added, and shaken at room temperature for one hour. Calibration curves for individual switch antibodies were prepared at plasma concentrations of 64, 32, 16, 8, 4, 2, and 1 ng/mL. After addition of a PBS solution containing 3 mM ADP, 1% BSA, and 0.05% Tween 20 to the hCD137-immobilized plate, two-fold volume of plasma samples diluted in a PBS solution containing 1% BSA and 0.05% Tween20, as well as calibration curve samples were added thereto. After the plate was shaken at room temperature for one hour, a biotinylated anti-mouse IgG antibody (Jackson ImmunoResearch Laboratories, Inc.) was added. In addition, after the plate was shaken at room temperature for one hour, SULFO-TAG Labeled Streptavidin (Meso Scale Diagnostics, LLCs) was added. In addition, after the plate was shaken at room temperature for one hour, Read buffer T (Meso Scale Diagnostics, LLCs) diluted two-fold with a PBS solution containing 2 mM ADP, 1% BSA, and 0.05% Tween 20 was added. Measurement of antibody concentrations in the hCD137KI mouse plasma was performed by detection using SULFO-TAG on SECTOR Imager (Meso Scale Diagnostics, LLC). Calculation of individual antibody concentrations in the mouse plasma was performed using SOFTmax PRO (Molecular Devices).

The concentration of non-switch antibodies in plasma was measured by the electrochemiluminescence (ECL) method. Specifically, hCD137 (Sino Biological Inc.) was diluted in PBS(−) and added to a MULTI-ARRAY 96-well Plate (Meso Scale Diagnostics, LLC). hCD137 was added to the plate and shaken at room temperature for one hour, and hCD137 was immobilized to the plate. Next, for blocking, a PBS solution containing 1% BSA and 0.05% Tween 20 was added, and shaken at room temperature for one hour. Calibration curves for individual non-switch antibodies were prepared at plasma concentrations of 32, 16, 8, 4, 2, 1, and 0.5 ng/mL. Plasma samples diluted in a PBS solution containing 1% BSA, 0.05% Tween20 as well as calibration curve samples were added to the hCD137 immobilized plate. After the plate was shaken at room temperature for one hour, a biotinylated anti-mouse IgG antibody (Jackson ImmunoResearch Laboratories, Inc.) was added. In addition, after the plate was shaken at room temperature for one hour, SULFO-TAG Labeled Streptavidin (Meso Scale Diagnostics, LLCs) was added. In addition, after the plate was shaken at room temperature for one hour, Read buffer T (Meso Scale Diagnostics, LLCs) diluted two-fold was added. Measurement of antibody concentrations in the hCD137KI mouse plasma was performed similarly to that for the switch antibody described above.

The results are shown in FIGS. 24, 25, and 26.

FIG. 24 shows a time course of the mean plasma concentrations in the hCD137 KI mouse of antibodies having mIgG1 as Fc (NS1-mIgG1 as a non-switch antibody, and A375-mIgG1/B167-ml0r, A372-mIgG1/B040-ml0r, A548-mIgG1/B256-ml0r or A551-mIgG1/B256-ml0r as a switch antibody) among the antibodies shown in Table 29. FIG. 25 shows a time course of the mean plasma concentrations in the hCD137 KI mouse of antibodies having MB110 as Fc (NS1-MB110 as a non-switch antibody, and A356-MB110/B040-ml0r, A372-MB110/B040-ml0r, and A551-MB110/B379-ml0r as switch antibodies). FIG. 26 shows a time course of the mean plasma concentrations in the CD137 KI mouse of antibodies having MB492 as Fc (NS1-MB492 as a non-switch antibody, and A372-MB492/B040-ml0r, A486-MB492/B167-ml0r, A488-MB492/B226-ml0r, or A489-MB492/B223-ml0r as a switch antibody). In FIG. 26, as for A488-MB492/B226-ml0r, a sharp decline in the plasma-concentration time course suspected to be caused by ADA was confirmed in one subject, and the average value was taken from two subjects.

In the hCD137 KI mouse, with any Fc, the switch antibody showed a slower elimination from plasma than the non-switch antibody. This is thought to be because compared to the switch antibody, the non-switch antibody bound to CD137 expressed in the body and eliminated from the plasma faster. Further, it was suggested that the extracellular ATP concentration in a normal tissue was sufficiently low to the extent that the switch antibodies used in this study did not bind to human CD137. These results suggest that the binding to an antigen expressed systemically can be reduced by using the switch antibodies, and thus an antibody with enhanced blood kinetics can be prepared.

(6-4) Movement of Drug Efficacy and Systemic Response Markers of Anti-CD137 Antibodies by a Syngeneic Tumor-Cell Transplantation Model Using the hCD137KI Mouse (6-4-1) Generation of Cell Lines and a Syngeneic Tumor Transplantation Mouse Model, as Well as Method of Evaluating Anti-Tumor Effect and Systemic Response Cells of the murine colorectal cancer cell line MC38 licensed from the National Cancer Institute and the hCD137 KI mouse described in Example 6-3-1 were used for various studies. The model was formed when the tumor volume reached approximately 50-300 mm$^3$ by implanting the MC38 cell line subcutaneously in the abdomen of mice. After establishment of the model, mice transplanted with MC38 cell line were grouped and then various anti-CD137 antibodies were administered.

For evaluation of the anti-tumor effect, measurement of the tumor volume was performed at a frequency of 1-2 times per week. The tumor volume was calculated according to the formula below:

Tumor volume (mm3)=the length (mm)×the width (mm)×the width (mm)/2

By removing the liver and spleens or lymph nodes at the appropriate time after antibody administration, systemic responses were assessed by organ weight, cell count of lymphocyte fractions, or T cell analysis using flow cytometry (FCM). In the assessment of these indicators, the subject switch antibody was assessed to have suppressed systemic responses and/or T cell activation in non-tumor tissues (e.g., lymph nodes, spleens, and liver) when the indicator of systemic response was low compared to the same amount of non-switch antibody (control anti-human CD137 antibody with no ATP-dependent human CD137 binding activity).

The antibodies produced in Example 6-1 (production of antibodies for the human CD137 knock-in mouse administration test) were used in various tests.

(6-4-2) Collection of Various Organs from the MC38 Cell-Line Transplanted Mouse and Preparation of Lymphocyte Fractions Weight measurement of the collected spleens and lymph nodes, and cell counting of the lymphocyte fractions were performed. Lymphocyte fractions obtained using the Liver dissociation kit, mouse (Milteny Biotec) were also used for assessment of liver activation. The lymphocyte fractions after red blood cell lysis were used for evaluation of activation in the spleens, and the lymphocyte fractions obtained by grinding were used for evaluation of activation in the lymph nodes.

(6-4-3) FCM Analysis Using Lymphocyte Fractions from Various Organs

For assessment of activation markers by FCM, the Granzyme B or PD-1 expression or ICOS expression on CD8α-positive T cells or the percentage of CD8α-positive T cells in CD45 positive cells were used. For this reason, a fluorescently labeled anti-Granzyme B antibody, an anti-PD-1 antibody, an anti-ICOS antibody, an anti-CD8a antibody and an anti-CD45 antibody were used in FCM analysis. Measurements were made with BD LSRFortessa™ X-20 (BD Biosciences).

(6-4-4) Drug Efficacy (Anti-Tumor Effect) Studies on the A375-mIgG1/B167-ml0r Antibody Following establishment of the MC38 transplantation mouse model in Example 6-4-1, Vehicle and A375-mIgG1/B167-ml0r were administered at the doses shown in Table 30. Antibody administration was performed twice via the tail vein route on the day of grouping and four days after grouping. For Vehicle, PBS containing 0.05% Tween-20 was used.

Group details for the A375-mIgG1/B167-ml0r efficacy study

TABLE 30

| Group | Number of animals | Pharmaceutical agent | Dose [mg/kg] | Day of administration |
|---|---|---|---|---|
| 1 | 5 | Vehicle | — | On the day of grouping and four days after grouping |
| 2 | 5 | A375-mIgG1/B167-ml0r | 22.5 | On the day of grouping and four days after grouping |
| 3 | 5 | A375-mIgG1/B167-ml0r | 7.5 | On the day of grouping and four days after grouping |
| 4 | 5 | A375-mIgG1/B167-ml0r | 2.5 | On the day of grouping and four days after grouping |
| 5 | 5 | A375-mIgG1/B167-ml0r | 0.83 | On the day of grouping and four days after grouping |
| 6 | 5 | A375-mIgG1/B167-ml0r | 0.28 | On the day of grouping and four days after grouping |

The anti-tumor effect in each group was assessed by the tumor volume calculated as described in Example 6-4-1. As a result, the dose-dependent anti-tumor effect of the A375-mIgG1/B167-ml0r antibody was confirmed (FIG. 27).

(6-4-5) Antibody Administration and Sampling as Well as FCM Analysis for the Assessment of Systemic Effects of A375-mIgG1/B167-ml0r Following establishment of the MC38 transplantation mouse model in Example 6-4-1, Vehicle, NS1-mIgG1 (non-switch antibody) and A375-mIgG1/B167-ml0r were administered as shown in Table 31. Antibody administration was performed twice via the tail vein route on the day of grouping and three days after grouping. For Vehicle, PBS containing 0.05% Tween-20 was used.

Five days after the initial administration, the liver, lymph nodes, and spleens were collected as shown in Example 6-4-2 (collection of various organs from the MC38 cell line-transplanted mouse and preparation of lymphocyte fractions). Further, for the spleens and lymph nodes, the organs from three mice were pooled, and FCM analysis was performed as shown in Example 6-4-3 (FCM analysis using lymphocyte fractions from various organs).

Group details for assessment of systemic responses with the A375-mIgG1/B167-ml0r antibody

TABLE 31

| Group | Number of animals | Pharmaceutical agent | Dose [mg/kg] | Day of administration | Day of sampling |
|---|---|---|---|---|---|
| 1 | 3 | Vehicle | — | On the day of grouping and three days after grouping | Five days after grouping |
| 2 | 3 | NS1-mIgG1 | 0.06 | On the day of grouping and three days after grouping | Five days after grouping |
| 3 | 3 | NS1-mIgG1 | 0.3 | On the day of grouping and three days after grouping | Five days after grouping |
| 4 | 3 | NS1-mIgG1 | 1.5 | On the day of grouping and three days after grouping | Five days after grouping |

TABLE 31-continued

| Group | Number of animals | Pharmaceutical agent | Dose [mg/kg] | Day of administration | Day of sampling |
|---|---|---|---|---|---|
| 5 | 3 | NS1-mIgG1 | 7.5 | On the day of grouping and three days after grouping | Five days after grouping |
| 6 | 3 | NS1-mIgG1 | 37.5 | On the day of grouping and three days after grouping | Five days after grouping |
| 7 | 3 | A375-mIgG1/ B167-ml0r | 1.5 | On the day of grouping and three days after grouping | Five days after grouping |
| 8 | 3 | A375-mIgG1/ B167-ml0r | 7.5 | On the day of grouping and three days after grouping | Five days after grouping |
| 9 | 3 | A375-mIgG1/ B167-ml0r | 37.5 | On the day of grouping and three days after grouping | Five days after grouping |

The systemic effects by the administered antibodies were evaluated. As a result of evaluating the organ weight of the lymph nodes and spleens, an increase in the organ weight was observed when NS1-mIgG1 was administered at 0.3 mg/kg, and more intense organ hypertrophy was observed at 1.5 mg/kg and 7.5 mg/kg. On the other hand, organ enlargement was not observed at any dose of 1.5 mg/kg, 7.5 mg/kg, or 37.5 mg/kg when A375-mIgG1/B167-ml0r was administered (FIG. 28).

In addition, as a result of assessing T cell activation by FCM evaluation, an increase in the expression of all the markers PD-1, ICOS and Granzyme B was observed at 0.3 mg/kg after NS1-mIgG1 administration. On the other hand, when A375-mIgG1/B167-ml0r was administered, there was a remarkable inhibition of expression of all the markers PD-1, ICOS and Granzyme B at the doses of 1.5 mg/kg, 7.5 mg/kg, and 37.5 mg/kg (FIG. 29 and FIG. 30). Since the A375-mIgG1/B167-ml0r results showed that organ weight was correlated with T cell activation markers in the lymph nodes and spleens, organ weight was used mainly as an indicator of lymph node- and spleen-derived immune cell activation in the subsequent evaluations of antibodies.

As a result of evaluating the activation of T cells in the liver, an increase in the expressions of PD-1 and Granzyme B was observed when NS1-mIgG1 was administered at 0.3 mg/kg. On the other hand, when A375-mIgG1/B167-ml0r was administered, the expressions were suppressed at all doses of 1.5 mg/kg, 7.5 mg/kg, and 37.5 mg/kg (FIG. 31).

Thus, the switch antibody inhibited the activation of T cells in the lymph nodes, spleens, and liver compared with the same amount of non-switch antibody.

(6-4-6) Drug Efficacy (Anti-Tumor Effect) Study on the A356-MB110/B040-ml0r Antibody Following establishment of the MC38 transplantation mouse model in Example 6-4-1, Vehicle and A356-MB110/B040-ml0r were administered at the doses shown in Table 32. Antibody administration was performed twice via the tail vein route on the day of grouping and three days after grouping. For Vehicle, PBS containing 0.05% Tween-20 was used.

Group details for the A356-MB110/B040-ml0r efficacy study

TABLE 32

| Group | Number of animals | Pharmaceutical agent | Dose [mg/kg] | Day of administration |
|---|---|---|---|---|
| 1 | 5 | Vehicle | — | On the day of grouping and three days after grouping |
| 2 | 5 | A356-MB110/ B040-ml0r | 7.5 | On the day of grouping and three days after grouping |
| 3 | 5 | A356-MB110/ B040-ml0r | 2.5 | On the day of grouping and three days after grouping |

The anti-tumor effect in each group was assessed by tumor volume calculated as described in Example 6-4-1. The results confirmed the dose-dependent anti-tumor effect of A356-MB110/B040-ml0r (FIG. 32).

(6-4-7) Antibody Administration and Sampling as Well as FCM-Analysis for the Assessment of Systemic Effects of A356-MB110/B040-ml0r Following establishment of the MC38 transplantation mouse model in Example 6-4-1, Vehicle, NS2-MB110 (non-switch antibody) and A356-MB110/B040-ml0r were administered as shown in Table 33. Antibody administration was performed twice via the tail vein route on the day of grouping and three days after grouping. For Vehicle, PBS containing 0.05% Tween-20 was used.

Seven days after the first administration, the liver, lymph nodes, and spleens were collected in the manner shown in Example 6-4-2 (collection of various organs from mice transplanted with the MC38 cell line and preparation of lymphocyte fractions). For the spleens and lymph nodes, only organ weight measurement was performed.

Group details for the assessment of systemic responses with the A356-MB110/B040-ml0r antibody

TABLE 33

| Group | Number of animals | Pharmaceutical agent | Dose [mg/kg] | Day of administration | Day of sampling |
|---|---|---|---|---|---|
| 1 | 3 | Vehicle | — | On the day of grouping and three days after grouping | Seven days after grouping |
| 2 | 3 | NS2-MB110 | 7.5 | On the day of grouping and three days after grouping | Seven days after grouping |
| 3 | 3 | NS2-MB110 | 2.5 | On the day of grouping and three days after grouping | Seven days after grouping |
| 4 | 3 | NS2-MB110 | 0.3 | On the day of grouping and three days after grouping | Seven days after grouping |
| 5 | 3 | A356-MB110/ B040-ml0r | 7.5 | On the day of grouping and three days after grouping | Seven days after grouping |
| 6 | 3 | A356-MB110/ B040-ml0r | 2.5 | On the day of grouping and three days after grouping | Seven days after grouping |

Systemic effects of the administered antibodies were evaluated. The result of evaluating the organ weight of the lymph nodes and spleens when NS2-MB110 and A356-MB110/B040-ml0r were administered showed that hypertrophy was observed also when NS2-MB110 was administered at 2.5 mg/kg. On the other hand, at the time of A356-MB110/B040-ml0r administration, lymphadenopathy was suppressed even at 7.5 mg/kg, and splenomegaly was suppressed at 2.5 mg/kg (FIG. 33).

In addition, the result of evaluating T cell activation in the liver showed that an increase in the PD-1 expression in CD8α-positive cells was also observed when NS2-MB110 was administered at 0.3 mg/kg. In the meantime, when A356-MB110/B040-ml0r was administered, the PD-1 expression was suppressed at 7.5 mg/kg, and remarkably suppressed at 2.5 mg/kg. A slight increase in the ICOS expression in CD8α-positive cells was also observed upon administration of the NS2-MB110 antibody at 0.3 mg/kg. On the other hand, it was observed that the expression of Vehicle was suppressed at 2.5 mg/kg when A356-MB110/B040-ml0r was administered (FIG. 34).

Thus, the switch antibody inhibited the activation of T cells in the lymph nodes, spleens, and liver compared with the non-switch antibody.

(6-4-8) Drug Efficacy (Anti-Tumor Effect) Study on the A372-mIgG1/B040-ml0r Antibody Following establishment of the MC38 transplantation mouse model in Example 6-4-1, Vehicle and A372-mIgG1/B040-ml0r were administered at the doses shown in Table 34. Antibody administration was performed four times via the tail vein route on the day of grouping, and 4 days, 7 days, and 10 days after grouping. For Vehicle, PBS containing 0.05% Tween-20 was used.

Group details for the A372-mIgG1/B040-ml0r efficacy study

TABLE 34

| Group | Number of animals | Pharmaceutical agent | Dose [mg/kg] | Day of administration |
|---|---|---|---|---|
| 1 | 5 | Vehicle | — | On the day of grouping, and four, seven, and ten days after grouping |
| 2 | 5 | A372-mIgG1/B040-ml0r | 7.5 | On the day of grouping, and four, seven, and ten days after grouping |

The anti-tumor effect in each group was assessed by tumor volume calculated as described in Example 6-4-1. As a result, an anti-tumor effect of the A372-mIgG1/B040-ml0r antibody was observed at 7.5 mg/kg administration (FIG. 35).

(6-4-9) Antibody Administration and Sampling as Well as FCM Analysis for the Assessment of Systemic Effects of A372-mIgG1/B040-ml0r Following establishment of the MC38 transplantation mouse model in Example 6-4-1, Vehicle and A372-mIgG1/B040-ml0r were administered as shown in Table 35. Antibody administration was performed three times via the tail vein route on the day of grouping, and 3 days and 6 days after grouping. For Vehicle, PBS containing 0.05% Tween-20 was used.

Seven days after the initial administration, the liver, lymph nodes, and spleens were collected in the manner shown in Example 6-4-2 (collection of various organs from mice transplanted with the MC38 cell line and preparation of lymphocyte fractions). For the spleens, only measurement of the organ weight was conducted; and for the lymph nodes, only cell counting of the lymphocyte fractions obtained from lymphocytes pooled from three mice was done.

Group details for the assessment of systemic responses with the A372-mIgG1/B040-ml0r antibody

TABLE 35

| Group | Number of animals | Pharmaceutical agent | Dose [mg/kg] | Day of administration | Day of sampling |
|---|---|---|---|---|---|
| 1 | 3 | Vehicle | — | On the day of grouping, and three and six days after grouping | Seven days after grouping |
| 2 | 3 | A372-mIgG1/B040-ml0r | 7.5 | On the day of grouping, and three and six days after grouping | Seven days after grouping |

Systemic effects of the administered antibodies were evaluated. As a result of measuring the number of cells in the lymph nodes and evaluating the organ weight in the spleens, it was confirmed that there was no increase in the number of cells in the lymph nodes and an increase in the weight of the spleens at the time of A372-mIgG1/B040-ml0r administration, and that the organ weight was equivalent to that in the Vehicle group (FIG. 36).

As a result of evaluating T cell activation in the liver, the granzyme B expression levels were similar to those in the Vehicle group when A372-mIgG1/B040-ml0r was administered (FIG. 37).

Thus, it was confirmed that the switch antibody inhibited the activation of T cells in the lymph nodes, spleens, and liver.

(6-4-10) Drug Efficacy (Anti-Tumor Effect) Study on the A372-MB110/B040-ml0r Antibody Following establishment of the MC38 transplantation mouse model in Example 6-4-1, Vehicle and A372-MB110/B040-ml0r were administered at the doses shown in Table 36. Antibody administration was performed twice via the tail vein route on the day of grouping and four days after grouping. For Vehicle, PBS containing 0.05% Tween-20 was used.

Group details for the A372-MB110/B040-ml0r efficacy study

TABLE 36

| Group | Number of animals | Pharmaceutical agent | Dose [mg/kg] | Day of administration |
|---|---|---|---|---|
| 1 | 5 | Vehicle | — | On the day of grouping and three days after grouping |
| 2 | 5 | A372-MB110/B040-ml0r | 7.5 | On the day of grouping and three days after grouping |

The anti-tumor effect in each group was assessed by tumor volume calculated as described in Example 6-4-1. As a result, the anti-tumor effect of A372-MB110/B040-ml0r was confirmed (FIG. 38).

(6-4-11) Antibody Administration and Sampling as Well as FCM Analysis for Assessment of the Systemic Effects of A372-MB110/B040-ml0r Following establishment of the MC38 transplantation mouse model in Example 6-4-1, Vehicle, NS2-MB110 (non-switch antibody) and A372-MB110/B040-ml0r were administered as shown in Table 37. Antibody administration was performed twice via the tail vein route on the day of grouping and 3 days after grouping. For Vehicle, PBS containing 0.05% Tween-20 was used.

Seven days after the initial administration, the liver, lymph nodes, and spleens were collected as shown in Example 6-4-2 (collection of various organs from mice transplanted with the MC38 cell line and preparation of lymphocyte fractions). For the spleens and lymph nodes, only organ weight measurement was performed.

Group details for the assessment of systemic responses with the A372-MB110/B040-ml0r antibody

TABLE 37

| Group | Number of animals | Pharmaceutical agent | Dose [mg/kg] | Day of administration | Day of sampling |
|---|---|---|---|---|---|
| 1 | 3 | Vehicle | — | On the day of grouping and three days after grouping | Seven days after grouping |
| 2 | 3 | N52-MB110 | 7.5 | On the day of grouping and three days after grouping | Seven days after grouping |
| 3 | 3 | N52-MB110 | 2.5 | On the day of grouping and three days after grouping | Seven days after grouping |
| 4 | 3 | N52-MB110 | 0.3 | On the day of grouping and three days after grouping | Seven days after grouping |
| 5 | 3 | A372-MB110/B040-ml0r | 7.5 | On the day of grouping and three days after grouping | Seven days after grouping |
| 6 | 3 | A372-MB110/B040-ml0r | 2.5 | On the day of grouping and three days after grouping | Seven days after grouping |

Systemic effects of the administered antibodies were evaluated. As a result of evaluating the organ weight of the lymph nodes and spleens, increases in the organ weight were observed when NS2-MB110 was administered at 2.5 mg/kg and 7.5 mg/kg. On the other hand, inhibition of organomegaly was observed at both doses of 2.5 mg/kg and 7.5 mg/kg when A372-MB110/B040-ml0r was administered (FIG. 39).

As a result of evaluating the activation of T cells in the liver, an increase in the expression of PD-1 was observed when NS2-MB110 was administered. This was also seen when A372-MB110/B040-ml0r was administered (FIG. 40).

In conclusion, the switch antibody inhibited the activation of T cells in the lymph nodes and spleens compared with the non-switch antibody.

(6-4-12) Drug Efficacy (Anti-Tumor Effect) Study on the A372-MB492/B040-ml0r Antibody Following establishment of the MC38 transplantation mouse model in Example 6-4-1, Vehicle and A372-MB492/B040-ml0r were administered at the doses shown in Table 38. Antibody administration was performed twice via the tail vein route on the day of grouping and three days after grouping. For Vehicle, PBS containing 0.05% Tween-20 was used.

Group details for the A372-MB492/B040-ml0r efficacy study

TABLE 38

| Group | Number of animals | Pharmaceutical agent | Dose [mg/kg] | Day of administration |
|---|---|---|---|---|
| 1 | 5 | Vehicle | — | On the day of grouping and three days after grouping |
| 2 | 5 | A372-MB492/B040-ml0r | 1.5 | On the day of grouping and three days after grouping |
| 3 | 5 | A372-MB492/B040-ml0r | 3.0 | On the day of grouping and three days after grouping |
| 4 | 5 | A372-MB492/B040-ml0r | 7.5 | On the day of grouping and three days after grouping |

The anti-tumor effect in each group was assessed by tumor volume calculated as described in Example 6-4-1. As a result, an anti-tumor effect of the A372-MB492/B040-ml0r antibody was observed at all doses (FIG. 41).

(6-4-13) Antibody Administration and Sampling as Well as FCM Analysis for Assessment of the Systemic Effects of the A372-MB492/B040-ml0r Antibody Following establishment of the MC38 transplantation mouse model in Example 6-4-1, Vehicle, NS1-MB492 (non-switch antibody) and A372-MB492/B040-ml0r were administered as shown in Table 39. Antibody administration was performed twice via the tail vein route on the day of grouping and 3 days after grouping. For Vehicle, PBS containing 0.05% Tween-20 was used.

Eight days after the initial administration, the liver, lymph nodes, and spleens were collected in the manner shown in Example 6-4-2 (collection of various organs from mice transplanted with the MC38 cell line and preparation of lymphocyte fractions). For the spleens, only measurement of the organ weight was conducted; and for the lymph nodes, only cell counting of the prepared lymphocyte fractions was performed.

Group details for the assessment of systemic responses of the A372-MB492/B040-ml0r antibody

TABLE 39

| Group | Number of animals | Pharmaceutical agent | Dose [mg/kg] | Day of administration | Day of sampling |
|---|---|---|---|---|---|
| 1 | 3 | Vehicle | — | On the day of grouping and three days after grouping | Eight days after grouping |
| 2 | 3 | NS1-MB492 | 7.5 | On the day of grouping and three days after grouping | Eight days after grouping |
| 3 | 3 | A372-MB492/B040-ml0r | 1.5 | On the day of grouping and three days after grouping | Eight days after grouping |
| 4 | 3 | A372-MB492/B040-ml0r | 3.0 | On the day of grouping and three days after grouping | Eight days after grouping |
| 5 | 3 | A372-MB492/B040-ml0r | 7.5 | On the day of grouping and three days after grouping | Eight days after grouping |

Systemic effects by the administered antibodies were evaluated. Increase in the organ weight from the organ weight of the spleens when NS1-MB492 was administered, and increase in the lymphocyte fractions from cell count measurement when NS1-MB492 was administered were observed. On the other hand, when A372-MB492/B040- ml0r was administered at the dose of 1.5 mg/kg, 3.0 mg/kg, and 7.5 mg/kg, inhibition of organomegaly was observed compared with NS1-MB492 (FIG. 42).

As a result of evaluating the activation of T cells in the liver, an increase in the expression of Granzyme B was observed when NS1-MB492 and A372-MB492/B040-ml0r were administered compared with Vehicle (FIG. 43).

In conclusion, the switch antibody inhibited the activation of T cells in the lymph nodes and spleens compared with the non-switch antibody.

(6-4-14) Drug Efficacy (Anti-Tumor Effect) Study on the A486-MB492/B167-ml0r and A488-MB492/B226-ml0r Antibodies Following establishment of the MC38 transplantation mouse model in Example 6-4-1, Vehicle, A486-MB492/B167-ml0r and A488-MB492/B226-ml0r were administered at the doses shown in Table 40. Grouping was performed 10 days after cell transplantation, and antibody administration was performed via the tail vein route 11, 15, 18, and 22 days after cell transplantation for a total of four times. For Vehicle, PBS containing 0.05% Tween-20 was used.

Group details for the drug efficacy study on the A486-MB492/B167-ml0r and A488-MB492/B226-ml0r antibodies

TABLE 40

| Group | Number of animals | Pharmaceutical agent | Dose [mg/kg] | Day of administration |
|---|---|---|---|---|
| 1 | 5 | Vehicle | — | 11, 15, 18, and 22 days after transplantation |
| 2 | 5 | A486-MB492/B167-ml0r | 7.5 | 11 15 18 and 22 days after transplantation |
| 3 | 5 | A488-MB492/B226-ml0r | 7.5 | 11 15 18 and 22 days after transplantation |

The anti-tumor effect in each group was assessed by tumor volume calculated as described in Example 6-4-1. The results confirmed anti-tumor effects of A486-MB492/B167-ml0r and A488-MB492/B226-ml0r (FIG. 44).

(6-4-15) Antibody Administration and Sampling as Well as FCM Analysis for Assessment of the Systemic Effects of A486-MB492/B167-ml0r and A488-MB492/B226-ml0r Following establishment of the MC38 transplantation mouse model in Example 6-4-1, Vehicle, NS1-MB492 (non-switch antibody), A486-MB492/B167-ml0r and A488-MB492/B226-ml0r were administered as shown in Table 41. Grouping was performed 10 days after cell transplantation, and antibody administration was performed via the tail vein route 11, 15, 18, and 22 days after cell transplantation for a total of four times. For Vehicle, PBS containing 0.05% Tween-20 was used.

The liver, lymph nodes, and spleens were collected 13 days after the initial administration in the manner as shown in Example 6-4-2 (collection of various organs from mice transplanted with the MC38 cell line and preparation of lymphocyte fractions). For the spleens, only measurement of the organ weight was conducted; and for the lymph nodes, only cell counting of the lymphocyte fractions was performed.

Group details for the assessment of systemic responses with the A486-MB492/B167-ml0r and A488-MB492/B226-ml0r antibodies

TABLE 41

| Group | Number of animals | Pharmaceutical agent | Dose [mg/kg] | Day of administration | Day of sampling |
|---|---|---|---|---|---|
| 1 | 3 | Vehicle | — | 11, 15, 18, and 22 days after transplantation | 24 days after transplantation (13 days after initial administration) |
| 2 | 3 | NS1-MB492 | 7.5 | 11, 15, 18, and 22 days after transplantation | 24 days after transplantation (13 days after initial administration) |
| 3 | 3 | A486-MB492/B167-ml0r | 7.5 | 11, 15, 18, and 22 days after transplantation | 24 days after transplantation (13 days after initial administration) |
| 4 | 3 | A488-MB492/B226-ml0r | 7.5 | 11, 15, 18, and 22 days after transplantation | 24 days after transplantation (13 days after initial administration) |

As a result of cell count measurement of the lymphocyte fractions for the lymph nodes and measurement of spleen weight, increases in the lymphocyte cell count and spleen weight were observed when NS1-MB492 was administered. On the other hand, it was observed that increases in the lymphocyte count and spleen weight were suppressed when A486-MB492/B167-ml0r and A488-MB492/B226-ml0r were administered compared with those when NS1-MB492 was administered (FIG. 45).

As a result of evaluating the activation of T cells in the liver, an increase in the percentage of CD8α-positive cells was observed when NS1-MB492, A486-MB492/B167-ml0r and A488-MB492/B226-ml0r were administered, as compared with Vehicle (FIG. 46).

From the above, it was confirmed that compared with the non-switch antibody, the switch antibody inhibited the activation of T cells in the lymph nodes and spleens.

(6-4-16) Drug Efficacy (Anti-Tumor Effect) Study on the A489-MB492/B223-ml0r Antibody Following establishment of the MC38 transplantation mouse model in Example 6-4-1, Vehicle and A489-MB492/B223-ml0r were administered at the doses shown in Table 42. Antibody administration was performed four times via the tail vein route on the following day of grouping and four, seven, and ten days after grouping. For Vehicle, PBS containing 0.05% Tween-20 was used.

Group details for the drug efficacy study on A489-MB492/B223-ml0r

TABLE 42

| Group | Number of animals | Pharmaceutical agent | Dose [mg/kg] | Day of administration |
|---|---|---|---|---|
| 1 | 5 | Vehicle | — | On the following day of grouping, and four, seven, and ten days after grouping |
| 2 | 5 | A489-MB492/B223-ml0r | 7.5 | On the following day of grouping, and four, seven, and ten days after grouping |

The anti-tumor effect in each group was assessed by tumor volume calculated as described in Example 6-4-1. As a result, an anti-tumor effect was confirmed at 7.5 mg/kg administration (FIG. 47).

(6-4-17) Antibody Administration and Sampling as Well as FCM Analysis for the Assessment of Systemic Effects of the A489-MB492/B223-ml0r Antibody Following establishment of the MC38 transplantation mouse model in Example 6-4-1, Vehicle, NS1-MB492 (non-switch antibody) and A489-MB492/B223-ml0r were administered as shown in Table 43. Antibody administration was performed via the tail vein route on the day of grouping, and 3 days and 6 days after grouping for a total of three times. For Vehicle, PBS containing 0.05% Tween-20 was used.

Seven days after the initial administration, the liver, lymph nodes, and spleens were collected in the manner as shown in Example 6-4-2 (collection of various organs from mice transplanted with the MC38 cell line and preparation of lymphocyte fractions). For the spleens and lymph nodes, only cell count measurement of the prepared lymphocyte fractions was performed.

Group details for the assessment of systemic responses of the A489-MB492/B223-ml0r antibody

TABLE 43

| Group | Number of animals | Pharmaceutical agent | Dose [mg/kg] | Day of administration | Day of sampling |
|---|---|---|---|---|---|
| 1 | 3 | Vehicle | — | On the day of grouping, and three and six days after grouping | Seven days after grouping |
| 2 | 3 | NS1-MB492 | 7.5 | On the day of grouping, and three and six days after grouping | Seven days after grouping |
| 3 | 3 | A489-MB492/B223-ml0r | 7.5 | On the day of grouping, and three and six days after grouping | Seven days after grouping |

As a result of cell count measurement of the lymphocyte fractions for the lymph nodes and spleens, increases in the cell count were observed when NS1-MB492 was administered. On the other hand, suppression of increase in the lymphocyte count was observed when A489-MB492/B223-ml0r was administered compared with that when NS1-MB492 was administered (FIG. 48).

As a result of evaluating the activation of T cells in the liver, an increase in the percentage of CD8α-positive cells was observed when NS1-MB492 and A489-MB492/B223-ml0r were administered, as compared with Vehicle (FIG. 49).

From the above, it was confirmed that compared with the non-switch antibody, the switch antibody inhibited the activation of T cells in the lymph nodes and spleens.

(6-4-18) Drug Efficacy (Anti-Tumor Effect) Study on the A548-mIgG1/B256-ml0r and A551-mIgG1/B256-ml0r Antibodies Following establishment of the MC38 transplantation mouse model in Example 6-4-1, Vehicle, A548-mIgG1/B256-ml0r and A551-mIgG1/B256-ml0r were administered at the doses shown in Table 44. Antibody administration was performed twice via the tail vein route on the day of grouping and three days after grouping. For Vehicle, PBS containing 0.05% Tween-20 was used.

Group details for the drug efficacy study on the A548-mIgG1/B256-ml0r and A551-mIgG1/B256-ml0r antibodies

TABLE 44

| Group | Number of animals | Pharmaceutical agent | Dose [mg/kg] | Day of administration |
|---|---|---|---|---|
| 1 | 5 | Vehicle | — | On the day of grouping and three days after grouping |
| 2 | 5 | A548-mIgG1/B256-ml0r | 7.5 | On the day of grouping and three days after grouping |
| 3 | 5 | A548-mIgG1/B256-ml0r | 37.5 | On the day of grouping and three days after grouping |
| 4 | 4 | A548-mIgG1/B256-ml0r | 100 | On the day of grouping and three days after grouping |
| 5 | 5 | A551-mIgG1/B256-ml0r | 7.5 | On the day of grouping and three days after grouping |
| 6 | 5 | A551-mIgG1/B256-ml0r | 37.5 | On the day of grouping and three days after grouping |
| 7 | 4 | A551-mIgG1/B256-ml0r | 100 | On the day of grouping and three days after grouping |

The anti-tumor effect in each group was assessed by tumor volume calculated as described in Example 6-4-1. The results showed an anti-tumor effect by administration of A548-mIgG1/B256-ml0r at 37.5 mg/kg and 100 mg/kg. A551-mIgG1/B256-ml0r also showed a significant anti-tumor effect at 100 mg/kg (FIG. 50).

(6-4-19) Antibody Administration and Sampling as Well as FCM Analysis for the Assessment of Systemic Effects of the A548-mIgG1/B256—and A551-mIgG1/B256-Antibodies Following establishment of the MC38 transplantation mouse model in Example 6-4-1, Vehicle, NS1-mIgG1 (non-switch antibody), A548-mIgG1/B256-ml0r and A551-mIgG1/B256-ml0r were administered as shown in Table 45. Antibody administration was performed twice via the tail vein route on the day of grouping and 3 days after grouping. For Vehicle, PBS containing 0.05% Tween-20 was used.

Five days after the initial administration, the liver, lymph nodes, and spleens were collected in the manner as shown in Example 6-4-2 (collection of various organs from mice transplanted with the MC38 cell line and preparation of lymphocyte fractions). For the spleens and lymph nodes, only organ weight measurement was performed.

Group details for assessment of systemic responses with the A548-mIgG1/B256-ml0r and A551-mIgG1/B256-ml0r antibodies

TABLE 45

| Group | Number of animals | Pharmaceutical agent | Dose [mg/kg] | Day of administration | Day of sampling |
|---|---|---|---|---|---|
| 1 | 3 | Vehicle | — | On the day of grouping and three days after grouping | Five days after grouping |
| 2 | 3 | NS1-mIgG1 | 0.3 | On the day of grouping and three days after grouping | Five days after grouping |
| 3 | 3 | NS1-mIgG1 | 1.5 | On the day of grouping and three days after grouping | Five days after grouping |
| 4 | 3 | NS1-mIgG1 | 7.5 | On the day of grouping and three days after grouping | Five days after grouping |
| 5 | 3 | A548-mIgG1/B256-ml0r | 1.5 | On the day of grouping and three days after grouping | Five days after grouping |
| 6 | 3 | A548-mIgG1/B256-ml0r | 7.5 | On the day of grouping and three days after grouping | Five days after grouping |
| 7 | 3 | A548-mIgG1/B256-ml0r | 37.5 | On the day of grouping and three days after grouping | Five days after grouping |
| 8 | 3 | A548-mIgG1/B256-ml0r | 100 | On the day of grouping and three days after grouping | Five days after grouping |
| 9 | 3 | A551-mIgG1/B256-ml0r | 1.5 | On the day of grouping and three days after grouping | Five days after grouping |
| 10 | 3 | A551-mIgG1/B256-ml0r | 7.5 | On the day of grouping and three days after grouping | Five days after grouping |
| 11 | 3 | A551-mIgG1/B256-ml0r | 37.5 | On the day of grouping and three days after grouping | Five days after grouping |
| 12 | 3 | A551-mIgG1/B256-ml0r | 100 | On the day of grouping and three days after grouping | Five days after grouping |

As a result of evaluating the organ weight of the lymph nodes and spleens, increases in the organ weight were observed when NS1-mIgG1 was administered at 0.3 mg/kg, 1.5 mg/kg, and 7.5 mg/kg. On the other hand, organ hypertrophy was not observed when A548-mIgG1/B256-ml0r or A551-mIgG1/B256-ml0r was administered at any dose of 1.5 mg/kg, 7.5 mg/kg, 37.5 mg/kg, and 100 mg/kg (FIG. 51).

As a result of evaluating the activation of T cells in the liver, increases in the expressions of both Granzyme B and PD-1 were observed when NS1-mIgG1 was administered at 0.3 mg/kg. On the other hand, the expressions were suppressed when A548-mIgG1/B256-ml0r and A551-mIgG1/B256-ml0r were administered at any dose of 1.5 mg/kg, 7.5 mg/kg, 37.5 mg/kg, and 100 mg/kg (FIG. 52).

Thus, compared with the non-switch antibody, the switch antibody inhibited the activation of T cells in the lymph nodes, spleens, and liver.

(6-4-20) Drug Efficacy (Anti-Tumor Effect) Study on the A551-MB110/B379-ml0r Antibody Following establishment of the MC38 transplantation mouse model in Example 6-4-1, Vehicle and A551-MB110/B379-ml0r were administered at the doses shown in Table 46.

Antibody administration was performed twice via the tail vein route on the day of grouping and three days after grouping. For Vehicle, PBS containing 0.05% Tween-20 was used.

Group details for the drug efficacy study of the A551-MB110/B379-ml0r antibody

TABLE 46

| Group | Number of animals | Pharmaceutical agent | Dose [mg/kg] | Day of administration |
|---|---|---|---|---|
| 1 | 6 | Vehicle | — | On the day of grouping and three days after grouping |
| 2 | 5 | A551-MB110/B379-ml0r | 2.5 | On the day of grouping and three days after grouping |
| 3 | 6 | A551-MB110/B379-ml0r | 7.5 | On the day of grouping and three days after grouping |
| 4 | 6 | A551-MB110/B379-ml0r | 22.5 | On the day of grouping and three days after grouping |

The anti-tumor effect in each group was assessed by tumor volume calculated as described in Example 6-4-1. As a result, an anti-tumor effect was confirmed at any dosages (FIG. 53).

(6-4-21) Antibody Administration and Sampling as Well as FCM Analysis for the Assessment of Systemic Effects Following establishment of the MC38 transplantation mouse model in Example 6-4-1, Vehicle, NS1-mIgG1 (non-switch antibody) and A551-MB110/B379-ml0r were administered as shown in Table 47. Antibody administration was performed twice via the tail vein route on the day of grouping and 3 days after grouping. For Vehicle, PBS containing 0.05% Tween-20 was used.

The liver, lymph nodes, and spleens were collected 5 days after the initial administration in the manner as shown in Example 6-4-2 (collection of various organs from the MC38 cell line transplanted mice and preparation of lymphocyte fractions), and FCM analysis was performed in the manner as shown in Example 6-4-3 (FCM analysis using lymphocyte fractions of various organs).

Group details for the assessment of systemic responses with the A551-MB110/B379-ml0r antibody

TABLE 47

| Group | Number of animals | Pharmaceutical agent | Dose [mg/kg] | Day of administration | Day of sampling |
|---|---|---|---|---|---|
| 1 | 3 | Vehicle | — | On the day of grouping and three days after grouping | Five days after grouping |
| 2 | 3 | NS1-mIgG1 | 7.5 | On the day of grouping and three days after grouping | Five days after grouping |
| 3 | 3 | A551-MB110/B379-ml0r | 0.83 | On the day of grouping and three days after grouping | Five days after grouping |
| 4 | 3 | A551-MB110/B379-ml0r | 2.5 | On the day of grouping and three days after grouping | Five days after grouping |
| 5 | 3 | A551-MB110/B379-ml0r | 7.5 | On the day of grouping and three days after grouping | Five days after grouping |
| 6 | 3 | A551-MB110/B379-ml0r | 22.5 | On the day of grouping and three days after grouping | Five days after grouping |

As a result of evaluating the organ weight of the lymph nodes and spleens, an increase in the organ weight was observed when NS1-mIgG1 was administered at 7.5 mg/kg. On the other hand, no organ enlargement was observed when A551-MB110/B379-ml0r was administered at any dose of 0.83 mg/kg, 2.5 mg/kg, 7.5 mg/kg and 22.5 mg/kg (FIG. 54). In addition, in the assessment of T cell activation in the spleens by FCM evaluation, the increase in activation markers (PD-1, ICOS, Granzyme B) observed upon NS1-mIgG1 administration was not confirmed when A551-MB110/B379-ml0r was administered at any dose (FIG. 55).

In the assessment of T cell activation in the liver, increases in the expressions of both PD-1 and ICOS were observed when NS1-mIgG1 was administered at 7.5 mg/kg. On the other hand, suppression of the expression to the Vehicle level when A551-MB110/B379-ml0r was administered at 0.83 mg/kg and 2.5 mg/kg, and the expressions were suppressed even more than that of NS1-mIgG1 when it was administered at 7.5 mg/kg (FIG. 56).

Thus, compared with the non-switch antibody, the switch antibody inhibited the activation of T cells in the lymph nodes, spleens, and liver.

Example 7: Generation of Modified Fc Capable of Enhancing Agonist Activity (7-1) Generation of variants with increased FcγR-binding activity Heavy chain constant region TT14 (SEQ ID NO: 149) which increases the FcγRIIb-binding activity as described in WO2017104783 (heavy chain constant region containing T250V/T307P as amino acid modifications and L234Y/P238D/V264I/A330K as amino acid modifications to increase FcγRIIb-binding activity in the Fc region comprising SEQ ID NO: 182 (modified positions are both in EU numbering)), TT16 (SEQ ID NO: 150) comprising the G237D amino acid mutation introduced into heavy chain constant region TT11 which increases FcγRIIb-binding activity as described in WO2017104783 (heavy chain constant region containing amino acid modification of T250V/T307P and L234Y/P238D/A330K as modifications to increase FcγRIIb-binding activity in the Fc region comprising SEQ ID NO: 182 (modified positions are both in EU numbering)), heavy chain constant region P587 (SEQ ID NO: 151) which increases FcγRIIb-binding activity as described in WO2014163101; and P253 (SEQ ID NO: 93) which was pre-existing FcγRIIb increased binding heavy chain constant region, were combined with the heavy chain variable region of the switch antibody (A375; A372; A356; A486; A488; A489; A548; and A551) or the heavy chain variable region of the negative control antibody (IC17HdK (SEQ ID NO: 152)). This created genes with combination of each constant region and heavy chain variable region as follows.

TABLE 48

| Full-length heavy chain | Heavy-chain variable region (SEQ ID NO) | Heavy-chain constant region (SEQ ID NO) |
| --- | --- | --- |
| A375-TT14 | A375 (SEQ ID NO: 43) | TT14 (SEQ ID NO: 149) |
| A375-TT16 | A375 (SEQ ID NO: 43) | TT16 (SEQ ID NO: 150) |
| A375-P587 | A375 (SEQ ID NO: 43) | P587 (SEQ ID NO: 151) |
| A372-P253 | A372 (SEQ ID NO: 44) | P253 (SEQ ID NO: 93) |
| A356-TT16 | A356 (SEQ ID NO: 45) | TT16 (SEQ ID NO: 150) |
| A356-P587 | A356 (SEQ ID NO: 45) | P587 (SEQ ID NO: 151) |
| A486-P253 | A486 (SEQ ID NO: 46) | P253 (SEQ ID NO: 93) |
| A488-P253 | A488 (SEQ ID NO: 48) | P253 (SEQ ID NO: 93) |
| A489-P253 | A489 (SEQ ID NO: 49) | P253 (SEQ ID NO: 93) |
| A548-P587 | A548 (SEQ ID NO: 50) | P587 (SEQ ID NO: 151) |
| A551-TT16 | A551 (SEQ ID NO: 51) | TT16 (SEQ ID NO: 150) |
| A551-P587 | A551 (SEQ ID NO: 51) | P587 (SEQ ID NO: 151) |
| IC17HdK-TT16 | IC17HdK (SEQ ID NO: 152) | TT16 (SEQ ID NO: 150) |
| IC17HdK-P587 | IC17HdK (SEQ ID NO: 152) | P587 (SEQ ID NO: 151) |
| IC17HdK-P253 | IC17HdK (SEQ ID NO: 152) | P253 (SEQ ID NO: 93) |

The heavy chain variable region of a switch antibody (A375, A356, and A551) or the heavy chain variable region of a negative control antibody (IC17HdK (SEQ ID NO: 152)) was combined with the heavy chain constant region MY201 (SEQ ID NO: 153) (a heavy chain constant region containing G236N/H268D/A330K as amino acid modifications that increase the activity to bind FcγRIIb in the Fc region comprising the amino acid sequence of SEQ ID NO: 182 (the modification positions are all in EU numbering)) or MY518 (SEQ ID NO: 154) (a heavy chain constant region containing L235W/G236N/H268D/Q295L/K326T/A330K as amino acid modifications that increase the activity to bind FcγRIIb in the Fc region comprising the amino acid sequence of SEQ ID NO: 182 (the modification positions are all in EU numbering), which are described in WO 2017104783 and have increased binding activity to FcγR, the heavy chain constant region MY201a (SEQ ID NO: 155) or MY518a (SEQ ID NO: 156) in which the K214R modification has been introduced into MY201 or MY518, or the heavy chain constant region MY201aPh (SEQ ID NO: 157) in which the L235W modification has been introduced into MY201a. This created genes with combinations of each constant region and heavy chain variable region as follows.

TABLE 49

| Full-length heavy chain | Heavy-chain variable region (SEQ ID NO) | Heavy-chain constant region (SEQ ID NO) |
| --- | --- | --- |
| A375-MY201aPh | A375 (SEQ ID NO: 43) | MY201aPh (SEQ ID NO: 157) |
| A375-MY518 | A375 (SEQ ID NO: 43) | MY518 (SEQ ID NO: 154) |
| A375-MY518a | A375 (SEQ ID NO: 43) | MY518a (SEQ ID NO: 156) |

TABLE 49-continued

| Full-length heavy chain | Heavy-chain variable region (SEQ ID NO) | Heavy-chain constant region (SEQ ID NO) |
|---|---|---|
| A356-MY518 | A356 (SEQ ID NO: 45) | MY518 (SEQ ID NO: 154) |
| A551-MY201a | A551 (SEQ ID NO: 51) | MY201aSEQ ID NO: 155) |
| A551-MY201aPh | A551 (SEQ ID NO: 51) | MY201aPh (SEQ ID NO: 157) |
| A551-MY518 | A551 (SEQ ID NO: 51) | MY518 (SEQ ID NO: 154) |
| A551-MY518a | A551 (SEQ ID NO: 51) | MY518a (SEQ ID NO: 156) |
| IC17HdK-MY201 | IC17HdK (SEQ ID NO: 152) | MY201 (SEQ ID NO: 153) |
| IC17HdK-MY201aPh | IC17HdK (SEQ ID NO: 152) | MY201aPh (SEQ ID NO: 157) |
| IC17HdK-MY518 | IC17HdK (SEQ ID NO: 152) | MY518 (SEQ ID NO: 154) |
| IC17HdK-MY518a | IC17HdK (SEQ ID NO: 152) | MY518a (SEQ ID NO: 156) |

As shown in Table 50, the antibodies of interest were expressed and purified using methods known to those skilled in the art, by combining the above antibody heavy chain genes with the antibody light chain gene of a switch antibody (B040-Lamlib, B167-Lamlib, B226-Lamlib, B223-Lamlib, B256-Lamlib, and B379-Lamlib made in Examples 5-2 and 5-3) or the antibody light chain gene of the negative control antibody (IC17L-k0, generated by combining the light chain variable region IC17L (SEQ ID NO: 158) with human x chain k0 (SEQ ID NO: 141) as the light chain constant region).

Variants with increased FcγR-binding activity

TABLE 50

| Variable region (heavy chain/light chain) | Heavy-chain constant region | Light-chain constant region | Antibody name |
|---|---|---|---|
| A375/B167 | MY201aPh | Lamlib | A375-MY201aPh/B167-Lamlib |
| | MY518 | Lamlib | A375-MY518/B167-Lamlib |
| | MY518a | Lamlib | A375-MY518a/B167-Lamlib |
| | P587 | Lamlib | A375-P587/B167-Lamlib |
| | TT14 | Lamlib | A375-TT14/B167-Lamlib |
| | TT16 | Lamlib | A375-TT16/B167-Lamlib |
| A372/B040 | P253 | Lamlib | A372-P253/B040-Lamlib |
| A356/B040 | MY518 | Lamlib | A356-MY518/B040-Lamlib |
| | P587 | Lamlib | A356-P587/B040-Lamlib |
| | TT16 | Lamlib | A356-TT16/B040-Lamlib |
| A486/B167 | P253 | Lamlib | A486-P253/B167-Lamlib |
| A488/B226 | P253 | Lamlib | A488-P253/B226-Lamlib |
| A489/B223 | P253 | Lamlib | A489-P253/B223-Lamlib |
| A548/B256 | P587 | Lamlib | A548-P587/B256-Lamlib |
| A551/B256 | MY201a | Lamlib | A551-MY201a/B256-Lamlib |
| | MY201aPh | Lamlib | A551-MY201 aPh/B256-Lamlib |
| | MY518 | Lamlib | A551-MY518/B256-Lamlib |
| | P587 | Lamlib | A551-P587/B256-Lamlib |
| A551/B379 | MY518a | Lamlib | A551-MY518a/B379-Lamlib |
| | P587 | Lamlib | A551-P587/B379-Lamlib |
| | TT16 | Lamlib | A551-TT16/B379-Lamlib |
| IC17HdK/IC17L | MY201 | k0 | IC17HdK-MY201/IC17L-k0 |
| | MY201aPh | k0 | IC17HdK-MY201aPh/IC17L-k0 |
| | MY518 | k0 | IC17HdK-MY518/IC17L-k0 |
| | MY518a | k0 | IC17HdK-MY518a/IC17L-k0 |
| | P253 | k0 | IC17HdK-P253/IC17L-k0 |
| | P587 | k0 | IC17HdK-P587/IC17L-k0 |
| | TT16 | k0 | IC17HdK-TT16/IC17L-k0 |

(7-2) Generation of Variants with Increased pI by Amino Acid Modification of the Constant Region A heavy chain constant region was generated by combining a heavy chain constant region with increased FcγR-binding activity made in Example 7-1 with Q311R, P343R and D413K, which are amino acid mutations that increase pI without greatly altering the FcγR-binding activity as described in WO2017046994.

Specifically, genes of the heavy chain constant region with amino acid mutations introduced into each of the antibody heavy chain constant region genes were generated as shown below.

Introduction of P343R/D413K into MY518 (SEQ ID NO: 154): SCF025 (SEQ ID NO: 64)
Introduction of P343R/D413K into MY518a (SEQ ID NO: 156): SCF025a (SEQ ID NO: 65)
Introduction of P343R/D413K into TT14 (SEQ ID NO: 149): SCF027 (SEQ ID NO: 66)
Introduction of P343R/D413K into TT16 (SEQ ID NO: 150): SCF028 (SEQ ID NO: 67)
Introduction of Q311R/P343R into MY518 (SEQ ID NO: 154): SCF030 (SEQ ID NO: 68)
Introduction of Q311R/P343R into TT14 (SEQ ID NO: 149): SCF032 (SEQ ID NO: 69)
Introduction of Q311R/P343R into TT16 (SEQ ID NO: 150): SCF033 (SEQ ID NO: 70)
Introduction of P343R into MY518 (SEQ ID NO: 154): SCF039 (SEQ ID NO: 71)
Introduction of P343R into MY518a (SEQ ID NO: 156): SCF039a (SEQ ID NO: 72)

Introduction of D413K into MY518 (SEQ ID NO: 154): SCF040 (SEQ ID NO: 73)
Introduction of P343R into MY201a (SEQ ID NO: 155): SCF041a (SEQ ID NO: 74)
Introduction of P343R into MY201aPh (SEQ ID NO: 157): SCF041aPh (SEQ ID NO: 75)
Introduction of D413K into MY201a (SEQ ID NO: 155): SCF042a (SEQ ID NO: 76)
Introduction of P343R/D413K into MY201a (SEQ ID NO: 155): SCF043a (SEQ ID NO: 77)
Introduction of P343R/D413K into MY201aPh (SEQ ID NO: 157): SCF043aPh (SEQ ID NO: 78)
Introduction of Q311R into MY201a (SEQ ID NO: 155): SCF056a (SEQ ID NO: 79)
Introduction of Q311R into MY201aPh (SEQ ID NO: 157): SCF056aPh (SEQ ID NO: 80)
Introduction of Q311R/P343R into MY201a (SEQ ID NO: 155): SCF057a (SEQ ID NO: 81)
Introduction of Q311R/P343R into MY201aPh (SEQ ID NO: 157): SCF057aPh (SEQ ID NO: 82)
Introduction of Q311R/D413K into MY201a (SEQ ID NO: 155): SCF059a (SEQ ID NO: 83)
Introduction of Q311R/D413K into MY201aPh (SEQ ID NO: 157): SCF059aPh (SEQ ID NO: 84)
Introduction of Q311R into MY518a (SEQ ID NO: 156): SCF060a (SEQ ID NO: 85)

Antibody heavy chain genes were produced as shown in Table 51 below by combining a heavy chain constant region gene produced here with a gene of the heavy chain variable region A375 (SEQ ID NO: 43), or A551 (SEQ ID NO: 51).

TABLE 51

| Full-length heavy chain | Heavy-chain variable region (SEQ ID NO) | Heavy-chain constant region (SEQ ID NO) |
| --- | --- | --- |
| A375-SCF025 | A375 (SEQ ID NO: 43) | SCF025 (SEQ ID NO: 64) |
| A375-SCF027 | A375 (SEQ ID NO: 43) | SCF027 (SEQ ID NO: 66) |
| A375-SCF028 | A375 (SEQ ID NO: 43) | SCF028 (SEQ ID NO: 67) |
| A375-SCF030 | A375 (SEQ ID NO: 43) | SCF030 (SEQ ID NO: 68) |
| A375-SCF032 | A375 (SEQ ID NO: 43) | SCF032 (SEQ ID NO: 69) |
| A375-SCF033 | A375 (SEQ ID NO: 43) | SCF033 (SEQ ID NO: 70) |
| A375-SCF039 | A375 (SEQ ID NO: 43) | SCF039 (SEQ ID NO: 71) |
| A375-SCF040 | A375 (SEQ ID NO: 43) | SCF040 (SEQ ID NO: 73) |
| A375-SCF041aPh | A375 (SEQ ID NO: 43) | SCF041aPh (SEQ ID NO: 75) |
| A375-SCF043aPh | A375 (SEQ ID NO: 43) | SCF043aPh (SEQ ID NO: 78) |
| A375-SCF056aPh | A375 (SEQ ID NO: 43) | SCF056aPh (SEQ ID NO: 80) |
| A375-SCF057aPh | A375 (SEQ ID NO: 43) | SCF057aPh (SEQ ID NO: 82) |
| A375-SCF059aPh | A375 (SEQ ID NO: 43) | SCF059aPh (SEQ ID NO: 84) |
| A375-SCF060a | A375 (SEQ ID NO: 43) | SCF060a (SEQ ID NO: 85) |
| A551-SCF025a | A551 (SEQ ID NO: 51) | SCF025a (SEQ ID NO: 65) |
| A551-SCF039a | A551 (SEQ ID NO: 51) | SCF039a (SEQ ID NO: 72) |
| A551-SCF041a | A551 (SEQ ID NO: 51) | SCF041a (SEQ ID NO: 74) |
| A551-SCF041aPh | A551 (SEQ ID NO: 51) | SCF041aPh (SEQ ID NO: 75) |
| A551-SCF043a | A551 (SEQ ID NO: 51) | SCF043a (SEQ ID NO: 77) |
| A551-SCF043aPh | A551 (SEQ ID NO: 51) | SCF043aPh (SEQ ID NO: 78) |
| A551-SCF056a | A551 (SEQ ID NO: 51) | SCF056a (SEQ ID NO: 79) |
| A551-SCF056aPh | A551 (SEQ ID NO: 51) | SCF056aPh (SEQ ID NO: 80) |
| A551-SCF057a | A551 (SEQ ID NO: 51) | SCF057a (SEQ ID NO: 81) |
| A551-SCF057aPh | A551 (SEQ ID NO: 51) | SCF057aPh (SEQ ID NO: 82) |
| A551-SCF059a | A551 (SEQ ID NO: 51) | SCF059a (SEQ ID NO: 83) |
| A551-SCF059aPh | A551 (SEQ ID NO: 51) | SCF059aPh (SEQ ID NO: 84) |
| A551-SCF060a | A551 (SEQ ID NO: 51) | SCF060a (SEQ ID NO: 85) |

In addition, by combining these antibody heavy chain genes with the B167-Lamlib, the B256-Lamlib, and the B379-Lamlib genes produced in Example 5-3 as antibody light chain genes, the desired antibody was expressed and purified as shown in Table 52 by methods known to those skilled in the art.

TABLE 52

| Variable region (heavy chain/light chain) | Heavy-chain constant region | Light-chain constant region | Antibody name |
| --- | --- | --- | --- |
| A375/B167 (A375 SEQ ID NO: 43) (B167 SEQ ID NO: 54) | SCF025 (SEQ ID NO: 64) | Lamlib (SEQ ID NO: 63) | A375-SCF025/B167-LamLib |
| | SCF027 (SEQ ID NO: 66) | Lamlib (SEQ ID NO: 63) | A375-SCF027/B167-LamLab |
| | SCF028 (SEQ ID NO: 67) | Lamlib (SEQ ID NO: 63) | A375-SCF028/B167-LamLib |
| | SCF030 (SEQ ID NO: 68) | Lamlib (SEQ ID NO: 63) | A375-SCF030/B167-LamLib |
| | SCF032 (SEQ ID NO: 69) | Lamlib (SEQ ID NO: 63) | A375-SCF032/B167-LamLib |
| | SCF033 (SEQ ID NO: 70) | Lamlib (SEQ ID NO: 63) | A375-SCF033/B167-LamLib |
| | SCF039 (SEQ ID NO: 71) | Lamlib (SEQ ID NO: 63) | A375-SCF039/B167-LamLib |
| | SCF040 (SEQ ID NO: 73) | Lamlib (SEQ ID NO: 63) | A375-SCF040/B167-LamLib |
| | SCF041aPh (SEQ ID NO: 75) | Lamlib (SEQ ID NO: 63) | A375-SCF041aPh/B167-LamLib |
| | SCF043aPh (SEQ ID NO: 78) | Lamlib (SEQ ID NO: 63) | A375-SCF043aPh/B167-LamLib |
| | SCF056aPh (SEQ ID NO: 80) | Lamlib (SEQ ID NO: 63) | A375-SCF056aPh/B167-LamLib |
| | SCF057aPh (SEQ ID NO: 82) | Lamlib (SEQ ID NO: 63) | A375-SCF057aPh/B167-LamLib |
| | SCF059aPh (SEQ ID NO: 84) | Lamlib (SEQ ID NO: 63) | A375-SCF059aPh/B167-LamLib |

TABLE 52-continued

| Variable region (heavy chain/light chain) | Heavy-chain constant region | Light-chain constant region | Antibody name |
|---|---|---|---|
| | SCF060a (SEQ ID NO: 85) | Lamlib (SEQ ID NO: 63) | A375-SCF060a/B167-LamLib |
| A551/B256 | SCF025a (SEQ ID NO: 65) | Lamlib (SEQ ID NO: 63) | A551-SCF025a/B256-LamLib |
| (A551 | SCF039a (SEQ ID NO: 72) | Lamlib (SEQ ID NO: 63) | A551-SCF039a/B256-LamLib |
| SEQ ID NO: 51) | SCF041a (SEQ ID NO: 74) | Lamlib (SEQ ID NO: 63) | A551-SCF041a/B256-LamLib |
| (B256 | SCF041aPh (SEQ ID NO: 75) | Lamlib (SEQ ID NO: 63) | A551-SCF041aPh/B256-LamLib |
| SEQ ID NO: 59) | SCF043a (SEQ ID NO: 77) | Lamlib (SEQ ID NO: 63) | A551-SCF043a/B256-LamLib |
| | SCF043aPh (SEQ ID NO: 78) | Lamlib (SEQ ID NO: 63) | A551-SCF043aPh/B256-LamLib |
| | SCF056a (SEQ ID NO: 79) | Lamlib (SEQ ID NO: 63) | A551-SCF056a/B256-LamLib |
| | SCF056aPh (SEQ ID NO: 80) | Lamlib (SEQ ID NO: 63) | A551-SCF056aPh/B256-LamLib |
| | SCF057a (SEQ ID NO: 81) | Lamlib (SEQ ID NO: 63) | A551-SCF057a/B256-LamLib |
| | SCF057aPh (SEQ ID NO: 82) | Lamlib (SEQ ID NO: 63) | A551-SCF057aPh/B256-LamLib |
| | SCF059a (SEQ ID NO: 83) | Lamlib (SEQ ID NO: 63) | A551-SCF059a/B256-LamLib |
| | SCF059aPh (SEQ ID NO: 84) | Lamlib (SEQ ID NO: 63) | A551-SCF059aPh/B256-LamLib |
| A551/B379 | SCF039a (SEQ ID NO: 72) | Lamlib (SEQ ID NO: 63) | A551-SCF039a/B379-LamLib |
| (A551 | SCF041a (SEQ ID NO: 74) | Lamlib (SEQ ID NO: 63) | A551-SCF041a/B379-LamLib |
| SEQ ID NO: 51) | SCF041aPh (SEQ ID NO: 75) | Lamlib (SEQ ID NO: 63) | A551-SCF041aPh/B379-LamLib |
| (B379 | SCF043a (SEQ ID NO: 77) | Lamlib (SEQ ID NO: 63) | A551-SCF043a/B379-LamLib |
| SEQ ID NO : 60) | SCF043aPh (SEQ ID NO: 78) | Lamlib (SEQ ID NO: 63) | A551-SCF043aPh/B379-LamLib |
| | SCF056a (SEQ ID NO: 79) | Lamlib (SEQ ID NO: 63) | A551-SCF056a/B379-LamLib |
| | SCF056aPh (SEQ ID NO: 80) | Lamlib (SEQ ID NO: 63) | A551-SCF056aPh/B379-LamLib |
| | SCF057a (SEQ ID NO: 81) | Lamlib (SEQ ID NO: 63) | A551-SCF057a/B379-LamLib |
| | SCF057aPh (SEQ ID NO: 82) | Lamlib (SEQ ID NO: 63) | A551-SCF057aPh/B379-LamLib |
| | SCF059a (SEQ ID NO: 83) | Lamlib (SEQ ID NO: 63) | A551-SCF059a/B379-LamLib |
| | SCF059aPh (SEQ ID NO: 84) | Lamlib (SEQ ID NO: 63) | A551-SCF059aPh/B379-LamLib |
| | SCF060a (SEQ ID NO: 85) | Lamlib (SEQ ID NO: 63) | A551-SCF060a/B379-LamLib |

(7-3) Generation of Control Antibodies for Comparison of Agonist Activity

Antibodies (IC17HdK-MY201/IC17L-k0; IC17HdK-MY201aPh/IC17L-k0; IC 17HdK-MY518/IC17L-k0; IC 17HdK-MY518a/IC17L-k0; IC17HdK-P253/IC17L-k0; IC17HdK-P587/IC17L-k0; IC17HdK-TT16/IC17L-k0) with the heavy chain variable region IC17HdK (SEQ ID NO: 152) produced in Example 7-1 as a control antibody for comparison of agonist activity were produced. In addition, the antibody of interest (IC17HdK-G4d/IC17L-k0) was expressed and purified by methods known in the art by combining the gene of the antibody light chain IC17L-k0 (SEQ ID NO: 158, variable region; SEQ ID NO: 141, constant region) with the gene of the antibody heavy chain gene IC17HdK-G4d which was produced by combining the gene of the heavy chain variable region IC17HdK (SEQ ID NO: 152) with the G4d gene (SEQ ID NO: 159) from which Gly and Lys of the C-terminus of the heavy chain constant region of human IgG4 had been removed. These control antibodies were used in Example 5.

(7-4) Evaluation of Human Fcγ Receptor Binding of Variants with Increased pI by Amino Acid Modification of the Constant Region Biacore T200 (GE Healthcare) was used to evaluate the binding activity to the respective human Fcγ receptor (hereafter referred to as FcγR). Measurement was performed at 25° C. using 50 mM phosphate, 150 mM NaCl, 0.05 w/v %-P20, pH 7.4 as buffer. About 1000 RU of antibody was captured using a sensor chip immobilized with CaptureSelect™ Human Fab-lambda Kinetics Biotin Conjugate (Thermo Fisher Scientific) as a molecule for ligand capturing. Human FcγR was diluted to 8 nM for FcγRIa and 1000 nM for other FcγR in the measurement buffer, and it was interacted to the captured antibody. The binding activity of each antibody to FcγR was assessed by calculating the binding amount of FcγR (RU) per unit amount of antibody using Biacore T200 Evaluation Software 2.0.

The extracellular domain of FcγR was prepared by the methods below. First, gene synthesis of the extracellular domain of FcγR was carried out by a method known to those skilled in the art. At that time, the FcγR sequences were prepared based on the NCBI-registered data. Specifically, the FcγRI sequence was generated based on NCBI Accession No. NM_000566.3, the FcγRIIa sequence on NCBI Accession No. NM_001136219.1, the FcγRIIb sequence on NCBI Accession No. NM_004001.3, and the FcγRIIIa sequence on NCBI Accession No. NM_001127593.1; and a His tag was added to their C termini. The polymorphic site of FcγRIIa was produced by referring to J. Exp. Med., 1990, 172, 19-25; and the polymorphic site of FcγRIIIa was produced with reference to J. Clin. Invest., 1997, 100, 1059-1070. The resulting gene fragments were inserted into an animal cell expression vector to produce expression vectors. The produced expression vectors were transiently introduced into human embryonic kidney cell-derived FreeStyle293 cells (Invitrogen), and the proteins of interest were expressed. The culture supernatants were collected and then passed through a 0.22 μm filter, and they were purified in principle by the four steps below.

The first step was performed by cation-exchange column chromatography (SP Sepharose FF), the second step by affinity column chromatography (HisTrap HP) for His tag, the third step by gel-filtration column chromatography (Superdex200), and the fourth step by sterile filtration. However, for FcγR1, anion-exchange column chromatography with Q Sepharose FF was performed in the first step. Concentrations of the purified proteins were calculated by measuring the absorbance at 280 nm using a spectrophotometer and the absorbance coefficients calculated from the obtained values by the methods of PACE et al. (Protein Science, 1995, 4, 2411-2423).

Table 53 shows the binding amount per unit amount of antibody, as well as the amount relative to the binding amount of A375-G1T3/B167-Lamlib. All the antibodies in Table 53 showed greater binding amount for human FcγRIIb per unit amount of antibody than that of A375-G1T3/B167-Lamlib, and the relative value was 2.85-14.26 when the binding amount of A375-G1T3/B167-Lamlib to human FcγRIIb was set to 1.0. The amount of human FcγRIIb binding per unit amount of antibody and the relative values of binding amount were similar in the presence or absence of amino acid modifications for increasing pI of the constant region. Also, the binding amount of antibodies containing the L235W modification to hFcgRIa was reduced compared to that of A375-TT14/B167-Lamlib.

Binding activity of each human FcγR

TABLE 53

| | Amount of binding per 1RU of antibody (RU) | | | | | | Relative value of binding amount |
|---|---|---|---|---|---|---|---|
| Abbreviated name | hFcgRIa | hFcgRIIaH | hFcgRIIaR | hFcgRIIb | hFcgRIIIaF | hFcgRIIIaV | hFcgRIa |
| A375-G1T3/B167-Lamlib | 0.0813 | 0.0567 | 0.0463 | 0.0110 | 0.0213 | 0.0700 | 1.00 |
| A375-MY201A/B167-Lamlib | 0.0396 | 0.0534 | 0.0338 | 0.0401 | 0.0007 | 0.0024 | 0.49 |
| A375-MY201aPh/B167-Lamlib | 0.0040 | 0.0328 | 0.0335 | 0.0313 | 0.0007 | 0.0011 | 0.05 |
| A375-MY518/B167-Lamlib | 0.0020 | 0.0466 | 0.0460 | 0.0482 | 0.0009 | 0.0015 | 0.02 |
| A375-MY518a/B167-Lamlib | 0.0033 | 0.0479 | 0.0470 | 0.0489 | 0.0006 | 0.0009 | 0.04 |
| A375-TT11/B167-Lamlib | 0.0075 | 0.0020 | 0.0041 | 0.0477 | −0.0009 | −0.0010 | 0.09 |
| A375-TT14/B167-Lamlib | 0.0045 | 0.0042 | 0.0067 | 0.0805 | 0.0000 | 0.0003 | 0.05 |
| A375-TT16/B167-Lamlib | 0.0034 | 0.0126 | 0.0359 | 0.1090 | 0.0001 | −0.0002 | 0.04 |
| A375-P587/B167-Lamlib | 0.0962 | 0.0029 | 0.0371 | 0.1427 | 0.0001 | 0.0001 | 1.18 |
| A375-P253/B167-Lamlib | 0.0937 | 0.0497 | 0.1678 | 0.1563 | 0.0056 | 0.0019 | 1.15 |
| A375-SCF025/B167-Lamlib | 0.0022 | 0.0514 | 0.0519 | 0.0512 | 0.0012 | 0.0014 | 0.03 |
| A375-SCF025a/B167-Lamlib | 0.0021 | 0.0514 | 0.0518 | 0.0511 | 0.0009 | 0.0016 | 0.03 |
| A375-SCF027/B167-Lamlib | 0.0044 | 0.0031 | 0.0058 | 0.0766 | −0.0005 | −0.0006 | 0.05 |
| A375-SCF028/B167-Lamlib | 0.0027 | 0.0101 | 0.0299 | 0.0995 | −0.0009 | −0.0010 | 0.03 |
| A375-SCF030/B167-Lamlib | 0.0020 | 0.0533 | 0.0532 | 0.0532 | 0.0017 | 0.0020 | 0.02 |
| A375-SCF032/B167-Lamlib | 0.0049 | 0.0030 | −0.0004 | 0.0782 | −0.0007 | −0.0007 | 0.06 |
| A375-SCF033/B167-Lamlib | 0.0033 | 0.0103 | 0.0255 | 0.0979 | 0.0000 | 0.0002 | 0.04 |
| A375-SCF039/B167-Lamlib | 0.0018 | 0.0535 | 0.0542 | 0.0531 | 0.0008 | 0.0013 | 0.02 |
| A375-SCF039a/B167-Lamlib | 0.0018 | 0.0542 | 0.0554 | 0.0540 | 0.0012 | 0.0013 | 0.02 |
| A375-SCF040/B167-Lamlib | 0.0016 | 0.0454 | 0.0446 | 0.0465 | 0.0010 | 0.0013 | 0.02 |
| A375-SCF041a/B167-Lamlib | 0.0446 | 0.0571 | 0.0376 | 0.0433 | 0.0009 | 0.0022 | 0.55 |
| A375-SCF042a/B167-Lamlib | 0.0396 | 0.0522 | 0.0327 | 0.0393 | 0.0003 | 0.0014 | 0.49 |
| A375-SCF043a/B167-Lamlib | 0.0429 | 0.0552 | 0.0361 | 0.0419 | 0.0011 | 0.0025 | 0.53 |
| A375-SCF056a/B167-Lamlib | 0.0395 | 0.0529 | 0.0331 | 0.0399 | 0.0011 | 0.0023 | 0.49 |
| A375-SCF057a/B167-Lamlib | 0.0405 | 0.0525 | 0.0367 | 0.0412 | 0.0013 | 0.0025 | 0.50 |
| A375-SCF059a/B167-Lamlib | 0.0380 | 0.0502 | 0.0319 | 0.0358 | 0.0010 | 0.0021 | 0.47 |
| A375-SCF060a/B167-Lamlib | 0.0021 | 0.0463 | 0.0459 | 0.0472 | 0.0011 | 0.0008 | 0.03 |
| A375-SCF041aPh/B167-Lamlib | 0.0013 | 0.0371 | 0.0371 | 0.0350 | 0.0007 | 0.0005 | 0.02 |
| A375-SCF043aPh/B167-Lamlib | 0.0011 | 0.0349 | 0.0349 | 0.0339 | 0.0001 | 0.0001 | 0.01 |
| A375-SCF056aPh/B167-Lamlib | 0.0019 | 0.0314 | 0.0299 | 0.0292 | 0.0010 | 0.0010 | 0.02 |
| A375-SCF057aPh/B167-Lamlib | 0.0021 | 0.0365 | 0.0364 | 0.0345 | −0.0003 | 0.0005 | 0.03 |
| A375-SCF059aPh/B167-Lamlib | 0.0089 | 0.0332 | 0.0319 | 0.0291 | 0.0003 | 0.0028 | 0.11 |

| | Relative value of binding amount | | | | |
|---|---|---|---|---|---|
| Abbreviated name | hFcgRIIaH | hFcgRIIaR | hFcgRIIb | hFcgRIIIaF | hFcgRIIIaV |
| A375-G1T3/B167-Lamlib | 1.00 | 1.00 | 1.00 | 1.00 | 1.00 |
| A375-MY201A/B167-Lamlib | 0.94 | 0.73 | 3.66 | 0.04 | 0.03 |
| A375-MY201aPh/B167-Lamlib | 0.58 | 0.72 | 2.85 | 0.03 | 0.02 |
| A375-MY518/B167-Lamlib | 0.82 | 0.99 | 4.40 | 0.04 | 0.02 |
| A375-MY518a/B167-Lamlib | 0.84 | 1.01 | 4.46 | 0.03 | 0.01 |
| A375-TT11/B167-Lamlib | 0.03 | 0.09 | 4.35 | −0.04 | −0.01 |
| A375-TT14/B167-Lamlib | 0.07 | 0.14 | 7.34 | 0.00 | 0.00 |
| A375-TT16/B167-Lamlib | 0.22 | 0.77 | 9.94 | 0.00 | 0.00 |
| A375-P587/B167-Lamlib | 0.05 | 0.80 | 13.02 | 0.00 | 0.00 |
| A375-P253/B167-Lamlib | 0.88 | 3.62 | 14.26 | 0.26 | 0.03 |
| A375-SCF025/B167-Lamlib | 0.91 | 1.12 | 4.67 | 0.06 | 0.02 |
| A375-SCF025a/B167-Lamlib | 0.91 | 1.12 | 4.67 | 0.04 | 0.02 |
| A375-SCF027/B167-Lamlib | 0.06 | 0.12 | 6.99 | −0.02 | −0.01 |
| A375-SCF028/B167-Lamlib | 0.18 | 0.64 | 9.08 | −0.04 | −0.01 |
| A375-SCF030/B167-Lamlib | 0.94 | 1.15 | 4.85 | 0.08 | 0.03 |
| A375-SCF032/B167-Lamlib | 0.05 | −0.01 | 7.14 | −0.03 | −0.01 |
| A375-SCF033/B167-Lamlib | 0.18 | 0.55 | 8.94 | 0.00 | 0.00 |
| A375-SCF039/B167-Lamlib | 0.94 | 1.17 | 4.85 | 0.04 | 0.02 |
| A375-SCF039a/B167-Lamlib | 0.96 | 1.20 | 4.93 | 0.06 | 0.02 |
| A375-SCF040/B167-Lamlib | 0.80 | 0.96 | 4.24 | 0.05 | 0.02 |
| A375-SCF041a/B167-Lamlib | 1.01 | 0.81 | 3.95 | 0.04 | 0.03 |
| A375-SCF042a/B167-Lamlib | 0.92 | 0.71 | 3.59 | 0.01 | 0.02 |
| A375-SCF043a/B167-Lamlib | 0.97 | 0.78 | 3.82 | 0.05 | 0.04 |
| A375-SCF056a/B167-Lamlib | 0.93 | 0.71 | 3.64 | 0.05 | 0.03 |
| A375-SCF057a/B167-Lamlib | 0.93 | 0.79 | 3.76 | 0.06 | 0.04 |
| A375-SCF059a/B167-Lamlib | 0.88 | 0.69 | 3.27 | 0.05 | 0.03 |
| A375-SCF060a/B167-Lamlib | 0.82 | 0.99 | 4.31 | 0.05 | 0.01 |
| A375-SCF041aPh/B167-Lamlib | 0.65 | 0.80 | 3.20 | 0.03 | 0.01 |
| A375-SCF043aPh/B167-Lamlib | 0.62 | 0.75 | 3.10 | 0.00 | 0.00 |

TABLE 53-continued

| | | | | | |
|---|---|---|---|---|---|
| A375-SCF056aPh/B167-Lamlib | 0.55 | 0.64 | 2.67 | 0.05 | 0.01 |
| A375-SCF057aPh/B167-Lamlib | 0.64 | 0.79 | 3.15 | −0.02 | 0.01 |
| A375-SCF059aPh/B167-Lamlib | 0.59 | 0.69 | 2.66 | 0.01 | 0.04 |

(7-5) Assessment of Human FcRn Binding of Variants with Increased pI by Amino Acid Modification of the Constant Region Biacore T200 (GE Healthcare) was used to assess the binding activity to human FcRn. Measurement was performed at 25° C. using 50 mM phosphate, 150 mM NaCl, 0.05 w/v %-P20, pH 6.0 as buffer. Human FcRn proteins used for this determination were prepared by the procedure described in WO2010107110. About 400 RU of antibody was captured using a sensor chip immobilized with CaptureSelect™ Human Fab-lambda Kinetics Biotin Conjugate (Thermo Fisher Scientific) as a molecule for ligand capturing, followed by the binding of human FcRn diluted in measuring buffer. The activity of the respective antibodies to bind FcRn was assessed by calculating KD (mol/L) by the steady-state model using Biacore T200 Evaluation Software 2.0. The KD values were similar in the presence or absence of amino acid modifications for increasing pI of the constant region. Table 54 shows the KD (mol/L) of the respective antibodies for human FcRn.

TABLE 54

| Abbreviated name | $K_D$ (mol/L) |
|---|---|
| A375-G1T3/B167-Lamlib | 1.27E−06 |
| A375-MY201a/B167-Lamlib | 1.19E−06 |
| A375-MY201aPh/B167-Lamlib | 1.18E−06 |
| A375-MY518/B167-Lamlib | 1.27E−06 |
| A375-MY518a/B167-Lamlib | 1.32E−06 |
| A375-TT11/B167-Lamlib | 1.56E−06 |
| A375-TT14/B167-Lamlib | 1.77E−06 |
| A375-TT16/B167-Lamlib | 1.51E−06 |
| A375-P587/B167-Lamlib | 1.70E−06 |
| A375-P253/B167-Lamlib | 1.42E−06 |
| A375-SCF025/B167-Lamlib | 1.10E−06 |
| A375-SCF025a/B167-Lamlib | 1.13E−06 |
| A375-SCF027/B167-Lamlib | 1.33E−06 |
| A375-SCF028/B167-Lamlib | 1.27E−06 |
| A375-SCF030/B167-Lamlib | 8.63E−07 |
| A375-SCF032/B167-Lamlib | 9.66E−07 |
| A375-SCF033/B167-Lamlib | 8.74E−07 |
| A375-SCF039/B167-Lamlib | 1.09E−06 |
| A375-SCF039a/B167-Lamlib | 1.11E−06 |
| A375-SCF040/B167-Lamlib | 1.46E−06 |
| A375-SCF041a/B167-Lamlib | 1.10E−06 |
| A375-SCF042a/B167-Lamlib | 1.49E−06 |
| A375-SCF043a/B167-Lamlib | 1.18E−06 |
| A375-SCF056a/B167-Lamlib | 9.56E−07 |
| A375-SCF057a/B167-Lamlib | 9.28E−07 |
| A375-SCF059a/B167-Lamlib | 1.03E−06 |
| A375-SCF060a/B167-Lamlib | 1.01E−06 |
| A375-SCF041aPh/B167-Lamlib | 1.13E−06 |
| A375-SCF043aPh/B167-Lamlib | 1.21E−06 |
| A375-SCF056aPh/B167-Lamlib | 1.00E−06 |
| A375-SCF057aPh/B167-Lamlib | 9.09E−07 |
| A375-SCF059aPh/B167-Lamlib | 1.05E−06 |

Example 8: Obtaining Kynurenine (Kyn)-Dependent CD137 Antibodies (8-1) Obtaining Antibodies with Kynurenine-Dependent Human CD137-Binding Activity from a Rationally Designed Antibody Library Antibodies showing binding activity to human CD137 in the presence of kynurenine and no binding activity in the absence of kynurenine were obtained from a rationally designed antibody phage display library (kynurenine library) for obtaining kynurenine switch antibodies utilizing panning against kynurenine, which was constructed as described in International Publication WO2015/083764. For acquisition, biotinylated antigens bound by phages in the presence of kynurenine were captured by the beads, and phages presenting antibodies which show binding activity towards the antigens in the presence of kynurenine were recovered. Phages were then collected from eluates eluted from the beads.

Phages were produced in a general manner from E. coli carrying the constructed phage display phagemid. Specifically, E. coli carrying the constructed phagemid vector was infected with M13KO7ΔpIII (designated as "hyperphage") (PROGEN Biotechnik), and phages were recovered from supernatants cultured overnight at 30° C. A phage library solution was obtained by diluting a population of phages precipitated by adding 2.5 M NaCl/10% PEG to the E. coli culture in which phage production was performed with Tris Buffered Saline (TBS). BSA was then added to the phage library solution at a final concentration of 4%. Panning was performed using the antigen immobilized on magnetic beads. Sera-Mag SpeedBeads NeutrAvidin-coated (Thermo Fisher Scientific), FG beads NeutrAvidin (Tamakawa Seminator), or Dynabeads MyOne Streptavidin T1 (Life Technologies) were used as magnetic beads. As antigen, biotinylated hCD137-Fc (hCD137-Fc-Bio) prepared as described in Example 1-3 (preparation of biotinylated Fc-fused human CD137) was used.

Panning was performed to efficiently obtain small molecule switch antibodies which are dependent on the small molecule that can play a switch role in cancer tissues. Specifically, panning to enrich antibodies that bind to antigens in the presence of kynurenine which is a small molecule, and which do not bind antigens in the absence of kynurenine was performed with reference to the methods described in prior patent WO2015/083764. In Round 1, panning was performed on hCD137-Fc-Bio or biotinylated kynurenines (bio-Kyn) (Compound 028 (represented by [Formula 28]), 029 (represented by [Formula 29]), and 036 (represented by [Formula 36]) as described in WO2015/083764). Panning for hCD137-Fc-Bio was performed by adding the phage solution to the antigen, followed by recovery of the phage bound to the antigen with magnetic beads; and panning for bio-Kyn was performed in a manner that adds the prepared phage library solution after first immobilizing the biotinylated antigen on magnetic beads. For Bio-Kyn, panning to enrich antibodies that are capable of antigen-binding in the absence of kynurenine as a small molecule was performed with reference to the methods described in the above patent WO2015/083764. For hCD137-Fc-Bio, 4 nmol of an unbiotinylated human IgG1 Fc region was added to remove antibodies that bind to the Fc region. The recovered phages were added to the E. coli strain ER2738 to infect the phages to E. coli, then the recovered E. coli was infected with the hyperphages, and the phages were recovered from the supernatants cultured overnight at 30° C.

After Round 2, panning to enrich antibodies that bind to antigens in the presence of kynurenine and do not bind to antigens in the absence of kynurenine was performed on hCD137-Fc-Bio with reference to the methods shown in the prior patent WO2015/083764. In both cases, 4 nmol of an unbiotinylated human IgG1 Fc region was added to remove antibodies that bind to the Fc region for hCD137-Fc-Bio. Similar panning was repeated until Round 5 to enrich the antibody sequences of interest.

(8-2) Obtaining Antibodies that Bind hCD137 in the Presence of Kynurenine from an Antibody Library (8-2-1) Preparation of hCD137p12-FX-Fc-Bio hCD137p12-FX-Fc-Bio was prepared in a manner known to those skilled in the art. Specifically, a gene fragment encoding the Factor Xa cleavable sequence and a gene fragment encoding the antibody constant region were joined downstream of a gene fragment encoding the human CD137 extracellular domain region. A gene fragment encoding a protein (hCD137p12-FX-Fc-Bio, SEQ ID NO: 160) in which the extracellular portion of human CD137, the FactorXa cleavable sequence and the antibody constant region are linked, was incorporated into an animal expression vector. The constructed plasmid vector was introduced into FreeStyle293 cells (Invitrogen) using 293-fectin (Invitrogen). At this time, a plasmid vector comprising genes expressing BirA and EBNA1 (SEQ ID NO: 88) was introduced at the same time. Biotin was added to the culture. Cells transduced with genes according to the aforementioned procedures were cultured at 37° C., 8% $CO_2$, and hCD137p12-FX-Fc-Bio was secreted into the culture supernatant. This culture supernatant was collected. Protein A was used to purify hCD137p12-FX-Fc-Bio from the culture supernatant.

With the use of a rationally designed library, it was thought that by panning antibodies exhibiting antigen-binding activity only in the presence of a small molecule, it was possible to obtain small-molecule switch antibodies exhibiting antigen-binding activity in the presence of the small molecule. That is, from the kynurenine library constructed in the manner described in International Publication WO2015/083764, phages presenting antibodies that display binding activity in the presence of kynurenine towards hCD137 captured in the beads were recovered. In the present method of acquisition, biotinylated hCD137-Fc (hCD137-Fc-Bio) prepared as described in Example 1-3 (preparation of biotin-labeled Fc-fused human CD137) or hCD137p12-FX-Fc-Bio was used as an antigen.

The E. coli carrying a phage-display phagemid vector constructed as described in International Publication WO2015/083764 was infected with M13KO7ΔpIII (hyperphage)

(PROGEN Biotechnik), and phages were recovered from supernatants after culturing overnight at 30° C. An antibody-multivalent-display phage library solution was prepared by diluting with TBS a population of phages precipitated by adding 2.5 M NaCl/10% PEG to the E. coli culture in which phage production was performed. BSA was then added to the phage library solution at a final concentration of 4%. Panning with the antigen immobilized on magnetic beads was performed. FG beads NeutrAvidin (Tamakawa Seminator) or Dynabeads MyOne Streptavidin T1 (Life Technologies) were used as magnetic beads.

In Round 1 of panning, enrichment of phages that are capable of binding to the antigen in the presence of kynurenine was carried out. Specifically, the phage library was contacted with the antigen and kynurenine for one hour at room temperature by adding to 0.8 mL of the prepared phage library solution, a final concentration of 500 μM kynurenine and 4 nmol of unbiotinylated human IgG1 Fc region (hFC) with 125 pmol of the biotin-labeled antigen. BSA-blocked magnetic beads (FG beads NeutrAvidin) were added, and antigen-phage complexes were allowed to bind magnetic beads for 15 minutes at room temperature. The beads were washed twice with 0.5 mL kynurenine/TBST and once with kynurenine/TBS. Subsequently, 0.5 mL of 1 mg/mL trypsin solution was added to the mixture. After the mixture was suspended at room temperature for 15 minutes, the phage solution was recovered from beads that were immediately separated using a magnetic stand. The recovered phages were added to 20 ml of the E. coli strain ER2738 in the log growth phase (OD600 0.4-0.7). The E. coli were infected with the phages by culturing E. coli at 37° C. for one hour with gentle stirring. The infected E. coli were seeded in plates at 225 mm×225 mm. Antibody-monovalent-presenting phage libraries were then prepared by infecting cultures of disseminated E. coli with M13KO7TC (WO2015046554A1) (helper phage) (Takara) and harvesting phages from supernatants cultured overnight at 30° C.

For Round 2 panning, the phage library was contacted with the antigen and kynurenine for one hour at room temperature by adding to 0.8 mL of the prepared phage library solution, a final concentration of 500 μM kynurenine and 4 nmol of biotin-unlabeled human IgG1 Fc region along with 40 pmol of the biotin-labeled antigen. BSA-blocked magnetic beads (Dynabeads MyOne Streptavidin T1) were added, and antigen-phage complexes were allowed to bind magnetic beads for 15 minutes at room temperature. The beads were washed twice with 0.5 mL kynurenine/TBST and once with kynurenine/TBS. Subsequently, 0.5 mL of 1 mg/mL trypsin solution was added to the mixture. After the mixture was suspended at room temperature for 15 minutes, the phage solution was recovered from beads that were immediately separated using a magnetic stand. Subsequently, the antibody monovalent-display phage library solution was prepared in the same manner as Round 1 above.

For Round 3 panning, the phage library was contacted with the antigen and kynurenine for one hour at room temperature by adding 0.8 mL of the prepared phage library solution, a final concentration of 500 μM kynurenine and 4 nmol biotin-unlabeled human IgG1 Fc region along with 10 pmol of the biotin-labeled antigen. BSA-blocked magnetic beads (FG beads NeutrAvidin) were added, and antigen-phage complexes were allowed to bind magnetic beads for 15 minutes at room temperature. The beads were washed three times with 0.5 mL of kynurenine/TBST and twice with kynurenine/TBS. Subsequently, 0.5 mL of 1 mg/mL trypsin solution was added to the mixture. After the mixture was suspended at room temperature for 15 minutes, the phage solution was recovered from beads that were immediately separated using a magnetic stand. Subsequently, the antibody monovalent-display phage library solution was prepared in the same manner as Round 1 above. For Round 4 panning, panning was performed under similar conditions of Round 3 panning. However, Dynabeads MyOne Streptavidin T1 was used as the magnetic bead.

(8-3) Obtaining Antibodies that Bind to Human CD137 in the Presence of Kynurenine from Antibody Libraries Utilizing SS-Biotinylated Antigens and Negative Selection Methods (8-3-1) Preparation of hCD137p12-FX-Fc hCD137p12-FX-Fc was Prepared in a Manner Known to Those Skilled in the Art.

Specifically, a gene fragment encoding the Factor Xa cleavage sequence and a gene fragment encoding the antibody constant region were joined downstream of the gene fragment encoding the human CD137 extracellular domain region. A gene fragment encoding a protein in which the extracellular portion of the human CD137, the FactorXa cleavage sequence and the antibody constant region are linked (hCD137p12-FX-Fc, SEQ ID NO: 160) was incorporated into an animal expression vector. The constructed plasmid vector was introduced into FreeStyle293 cells (Invitrogen) using 293-fectin (Invitrogen). At this time, a plasmid vector comprising genes expressing EBNA1 (SEQ ID NO: 88) was introduced at the same time. Cells transduced with genes according to the aforementioned procedures were cultured at 37° C., 8% $CO_2$, and hCD137p12-FX-Fc-Bio was secreted into the culture supernatant. Protein A was used to purify hCD137p12-FX-Fc-Bio from this cell culture supernatant.

(8-3-2) Obtaining Antibodies that Bind Human CD137 in the Presence of Kynurenine from an Antibody Library by Use of SS-Biotinylated Antigens and a Negative Selection Method When obtaining small-molecule switch antibodies that exhibit antigen-binding activity in the presence of a small molecule, it was thought that after antibody display phages that bound to antigen with magnetic beads are captured using an antigen biotinylated (SS-biotinylated) via a linker with a disulfide bond (SS bond), only the antigen-bound antibody display phages could be eluted from the beads by using dithiothreitol (DTT) or such to cleave SS bonds under reducing conditions. A kynurenine library constructed as described in International Publication WO2015/083764 was screened for antibodies that show binding activity to antigens in the presence of kynurenine. For screening, the antibody phage display library was first contacted with biotin-labeled antigen-magnetic beads in the absence of kynurenine, and phages displaying antibodies that have antigen-binding activity even in the absence of kynurenine were removed. Subsequent screening for antibodies with antigen-binding activity was performed only in the presence of kynurenine by conducting panning similarly under the conditions in presence of kynurenine. In this method, a biotin-labeled antigen (SS-biotinylated antigen) was used as the antigen according to the attached protocols using hCD137-Fc prepared as described in Example 1-4, or hCD137p12-FX-Fc prepared in (8-3-1) and the EZ-Link Sulfo-NHS-SS-Biotinylation kit (Thermo Fisher Scientific). Note that hCD137-Fc-Bio prepared by the methods of Example 1-3 or hCD137p12-FX-Fc-Bio prepared in (8-2-1) were used for negative selection.

The *E. coli* carrying a phage display phagemid vector constructed as described in International Publication WO2015/083764 were infected with M13KO7ΔpIII (hyperphage) (PROGEN Biotechnik), and phages were recovered from supernatants after culturing overnight at 30° C. Antibody multivalent display phage libraries were prepared by diluting with TBS a population of phages precipitated by adding 2.5 M NaCl/10% PEG to the *E. coli* culture in which phage production was performed. BSA was then added to the phage library solution at a final concentration of 4%. Panning with the antigen immobilized on magnetic beads was performed. Sera-Mag SpeedBeads NeutrAvidin-coated (Thermo Fisher Scientific), FG beads NeutrAvidin (Tamakawa Seminator), or Dynabeads MyOne Streptavidin T1 (Life Technologies) were used as magnetic beads.

In Round 1 of panning, enrichment of phages that are capable of binding to the antigen in the presence of kynurenine was carried out using a negative selection method.

Specifically, 800 pmol of hCD137-Fc-Bio or hCD137p12-FX-Fc-Bio was added to Sera-Mag Speed-Beads NeutrAvidin-coated blocked with skim milk that has been pre-incubated with Streptavidin (Roche) and allowed to bind for 15 minutes at room temperature. The beads were washed three times with TBST, and 0.8 mL of BSA-blocked phage library solution was added and allowed to bind for one hour at room temperature. By separating the beads using a magnetic stand, antigens and phages that did not bind to the beads were collected.

Then, 225 pmol of SS-biotinylated hCD137-Fc or 450 pmol of SS-biotinylated hCD137p12-FX-Fc-Bio was added to FG beads NeutrAvidin blocked with skim milk that has been incubated with Streptavidin (Roche), and allowed to bind for 15 minutes at room temperature. The beads were washed three times with TBST, and a final concentration of 0.2 mM kynurenine and 4 nmol of hFc were added along with the recovered phages; and the phage library was contacted with the antigen as well as kynurenine for one hour at room temperature. The beads were washed twice with 0.5 mL kynurenine/TBST (0.2 mM kynurenine, 0.1% Tween20, TBS, pH 7.4), and once with kynurenine/TBS (0.2 mM kynurenine, TBS, pH 7.4). Subsequently, 500 μL of a TBS solution containing a final concentration of 25 mM DTT was added and after five minutes of stirring at room temperature, phages were recovered from the separated beads using a magnetic stand. Trypsin was then added to the mixtures to a final concentration of 1 mg/mL. The mixture was stirred at room temperature for 15 minutes before phages were recovered from the separated beads using a magnetic stand. The recovered phages were added to 20 ml of the *E. coli* strain ER2738 in the log growth phase (OD600 0.4-0.7). The *E. coli* were infected with phages by culturing *E. coli* at 37° C. for one hour with gentle stirring. The infected *E. coli* were seeded in plates at 225 mm×225 mm. An antibody multivalent-display phage library was then prepared by infecting cultures of the disseminated *E. coli* with hyperphages, and recovering phages from supernatants cultured overnight at 30° C.

For Round 2 panning, 400 pmol of hCD137-Fc-Bio or hCD137p12-FX-Fc-Bio was added to Sera-Mag Speed-Beads NeutrAvidin-coated blocked with skim milk pre-incubated with Streptavidin (Roche), and allowed to bind for 15 minutes at room temperature. To beads washed three times with TBST, 0.4 mL of the BSA-blocked phage library solution was added and allowed to bind for one hour at room temperature. By separating the beads using a magnetic stand, antigen and phages that did not bind to the beads were recovered. The recovered phages were again incubated with Sera-Mag SpeedBeads NeutrAvidin-coated that has been incubated with 400 pmol of hCD137-Fc-Bio or hCD137p12-FX-Fc-Bio in a similar procedure, and then antigens and phages that did not bind to the beads were collected using a magnetic stand.

56. 3 pmol of SS-biotinylated hCD137-Fc or 113 pmol of SS-biotinylated hCD137p12-FX-Fc was added to FG beads NeutrAvidin blocked with skim milk that has been pre-incubated with Streptavidin (Roche) and allowed to bind for 15 minutes at room temperature. The beads were washed three times with TBST, and a final concentration of 0.2 mM kynurenine and 4 nmol of unbiotinylated human IgG1 Fc region were added along with the recovered phages; and the phage library was contacted with the antigen as well as kynurenine for one hour at room temperature. The beads were washed three times with 0.5 mL kynurenine/TBST (0.2 mM kynurenine, 0.1% Tween20, TBS, pH 7.4), and twice with kynurenine/TBS (0.2 mM kynurenine, TBS, pH 7.4). Subsequently, 5000_, of a TBS solution containing a final concentration of 25 mM DTT was added and after 5 minutes of stirring at room temperature, phages were recovered from the separated beads using a magnetic stand. Subsequently, an antibody multivalent-display phage library solution was prepared in the same manner as Round 1 above.

For Round 3 panning, 200 pmol of hCD137-Fc-Bio or hCD137p12-FX-Fc-Bio was added to Sera-Mag Speed-Beads NeutrAvidin-coated blocked with skim milk that has been pre-incubated with Streptavidin (Roche), and allowed to bind at room temperature for 15 minutes. The beads were washed three times with TBST, and 0.2 mL of a BSA-blocked phage library solution was added and allowed to bind for one hour at room temperature. By separating the beads using a magnetic stand, antigens and phages that did not bind to the beads were recovered. The recovered phages were again incubated with Sera-Mag SpeedBeads NeutrAvidin-coated that has been incubated with 200 pmol of hCD137-Fc-Bio or hCD137p12-FX-Fc-Bio in a similar procedure, and then antigens and phages that did not bind to the beads were recovered using a magnetic stand.

12. 5 pmol of SS-biotinylated hCD137-Fc or 25 pmol of SS biotinylated hCD137p12-FX-Fc was added to FG beads NeutrAvidin blocked with skim milk that has been incubated with Streptavidin (Roche), and allowed to bind at room temperature for 15 minutes. The beads were washed three times with TBST, and a final concentration of 0.2 mM kynurenine and 4 nmol of unbiotinylated human IgG1 Fc region were added along with the recovered phages; and the phage library was contacted with the antigen as well as kynurenine for one hour at room temperature.

The beads were washed five times with 0.5 mL kynurenine/TBST (0.2 mM kynurenine, 0.1% Tween20, TBS, pH 7.4), and five times with kynurenine/TBS (0.2 mM kynurenine, TBS, pH 7.4). Subsequently, 500 µL of a TBS solution containing a final concentration of 25 mM DTT was added, and after 5 minutes of stirring at room temperature, phages were recovered from the separated beads using a magnetic stand. Subsequently, an antibody multivalent-display phage library solution was prepared in the same manner as Round 1 above. For Round 4 panning, panning was performed under similar conditions of Round 3 panning. However, Dynabeads MyOne Streptavidin T1 was used instead of FG beads NeutrAvidin for magnetic beads. For Round 5 panning, panning was performed under similar conditions of Round 3 panning.

(8-4) Assessment of Kynurenine-Dependent Anti-CD137 Antibodies Identified by Phage Display (8-4-1) Expression and Purification of Switch Antibodies which Change their Binding to Antigens by the Presence/Absence of Kynurenine Genes encoding the variable regions of antibodies obtained from the kynurenine libraries described herein were inserted into animal expression plasmids having human IgG1 or modified human IgG1 (P253) and kappa chains. The clone names and sequence numbers are listed in Table 55.

Evaluated Clones

TABLE 55

| Clone name | SEQ ID NO of heavy chain (full length) | SEQ ID NO of light chain (full length) | Example |
| --- | --- | --- | --- |
| dBBK026-P253 | 161 | 169 | 8-1 |
| dBBK051-P253 | 162 | 170 | 8-1 |
| dBBK054-P253 | 163 | 171 | 8-1 |
| dBBK060-P253 | 164 | 172 | 8-1 |
| dBBK070-P253 | 165 | 173 | 8-1 |
| dBBK101-P253 | 166 | 174 | 8-2 |

TABLE 55-continued

| Clone name | SEQ ID NO of heavy chain (full length) | SEQ ID NO of light chain (full length) | Example |
| --- | --- | --- | --- |
| dBBK102-P253 | 167 | 175 | 8-2 |
| dBBK143-P253 | 168 | 176 | 8-2 |

Antibodies were expressed and purified using methods known to those skilled in the art. Spectrophotometers were used to measure the absorbance of the purified antibody solution at 280 nm. From the measured values obtained, concentrations of the purified antibodies were calculated using the extinction coefficients calculated by the PACE method (Protein Science (1995) 4, 2411-2423).

(8-4-2) Assessing the Impact of Kynurenine on Human CD137 Binding by Surface Plasmon Resonance Biacore T200 (GE Healthcare) was used to analyze the interaction of the antigen-antibody response between the anti-CD137 antibody and hCD137-His-BAP (SEQ ID NO: 87). Sensor chip CM3 (GE Healthcare) immobilized with appropriate amounts of Sure protein A by the amine-coupling method was captured with the anti-CD137 antibody to interact with hCD137-His-BAP prepared in Example 1-1. TBS was used as the running buffer, and 10 mM Glycine-HCl (pH 1.5) and 25 mM NaOH were used as the regeneration solution.

After capture of the anti-CD137 antibody suspended in TBS, 500 nM hCD137-His-BAP was injected into each flow cell at a flow rate of 10 µL/min for 3 minutes. This 3-minute period was the binding phase for hCD137-His-BAP, and after the binding phase was terminated, the 5-minute period of switching to running buffer was the dissociation phase for hCD137-His-BAP. After completion of the dissociation phase, the regenerative solution was injected at a flow rate of 30 µl/min for 10 seconds. The above was the cycle for measuring the binding activity of anti-CD137 antibodies. The binding amount of hCD137-His-BAP that interacted with the anti-CD137 antibody in the binding phase was analyzed by Biacore T200 Evaluation Software Version 2.0 is shown in Table 56.

Table showing the amount of antigen binding in the presence of kynurenine.

TABLE 56

| Clone name | Without small molecule | 500 µM Kynurenine |
| --- | --- | --- |
| dBBK026-P253 | 18.2 | 60 |
| dBBK047-P253 | −2 | 10.4 |
| dBBK051-P253 | −2.3 | 30 |
| dBBK054-P253 | −2.2 | 3.6 |
| dBBK060-P253 | 2.8 | 38.5 |
| dBBK070-P253 | −1.4 | 2.6 |
| dBBK101-P253 | −3.6 | 21.2 |
| dBBK102-P253 | −2.5 | 9.9 |
| dBBK143-P253 | −1.9 | 44.3 |

(8-4-3) Assessment of Binding Activity of the Obtained Antibodies Towards Partial CD137 Sequences (8-4-3-1) Preparation of Antigens with Partial Sequences of CD137

Antigens with CD137 partial sequences were prepared by methods known to those skilled in the art. Specifically, a gene fragment encoding the antibody constant region was linked downstream of a gene fragment encoding a portion of the human CD137 extracellular region. A gene fragment encoding a protein (Table 57) in which a portion of the human CD137 extracellular domain and an antibody constant region are linked was incorporated into an animal expression vector. The constructed plasmid vector was introduced into Expi293 cells (Invitrogen) using Expi-Fectamine293 (Invitrogen), and the protein of interest was secreted into culture supernatant. Protein A was used from the culture supernatant to purify the protein of interest.

Antigens with CD137 partial sequences

TABLE 57

| Name of antigen having a partial sequence of CD137 | SEQ ID NO |
|---|---|
| hCD137.1-F-G1d | 177 |
| hCD137.1.2-F.G1d | 178 |
| hCD137.2.4-F.G1d | 179 |
| hCD137.2.3-F.G1d | 180 |
| hCD137.3.4-F.G1d | 181 |

(8-4-3-2) Confirmation of Binding

Whether the obtained antibodies bind to antigens having a partial sequence of CD137 was assessed by ELISA. First, various antigens prepared in Example 1 or Example 8-4-3-1 were immobilized on Maxisorp 384 microtiter plates. After the unbound antigens were removed from the plates by washing each well of the plates with the Wash Buffer, the wells were blocked with 50 μL of Blocking Buffer (Block-Ace-containing TBS) for one hour or more. To wells from which the Blocking Buffer was removed, each well was supplemented with 10 μL of the purified antibodies prepared at 10 μg/mL in TBS with a final concentration of 500 μM L-kynurenine or TBS with a final concentration of 500 μM kynurenine, and it was left at rest for one hour. AP-conjugated anti-human Kappa antibodies (BIOSOURCE) diluted in TBS with a final concentration of 500 μM kynurenine were added to each well after washing with the Wash Buffer containing a final concentration of 500 μM kynurenine (TBS with 0.1% Tween20). After one hour of incubation, the BluePhos phosphate substrate (KPL) was added after washing with Wash Buffer containing 500 μM kynurenine. Color development of the solution in each well was measured by absorbance at 620 nm after the color development reaction of the solution in each well was stopped by adding the BluePhos Stop Solution. The ratio of absorbance by setting the value of the well with an antibody concentration of 0 μg/mL to 1 is shown. By judging on the binding with an absorbance ratio of greater than or equal to 2, it is suggested that the evaluated clones include antibodies that exhibit different binding properties.

CHO-K1 Cells prepared at a concentration of 2×10⁶/mL with an assay medium (99% RPMI, 1% FBS) was added. Antibody solutions with kynurenine or without kynurenine were added to each well at 10 pt. Then, 10 μL of the GloResponse™ NF-κB-Luc2/4-1BB Jurkat cell line prepared to 2×10⁶/mL with the assay medium (99% RPMI, 1% FBS) was added to each well. The final concentration of kynurenine was 500 μM. Plates were left to stand for six hours at 37° C. in a 5% $CO_2$ incubator, followed by 15 minutes at room temperature, and 30 μL of the Bio-Glo reagent was added to each well. The Bio-Glo Luciferase Assay System (Buffer and Substrate) was used for the Bio-Glo reagent. Subsequently, the luminescence of each well was measured with a plate reader. The value of luminescence of each well divided by the value of luminescence of the well without antibody added was the luminescence fold and served as an indicator for evaluating the activity of each antibody.

The results obtained are shown in FIG. 57.

The luminescence fold was higher when the L-kynurenine concentration was 500 μM than when it was 0 μM, indicating that the agonist activity was changed by the concentration or presence of kynurenine.

Example 9: Obtaining ATP- and AMP-Dependent CD137-Binding Antibodies by Double Round Selection (9-1) Obtaining Antibodies that Bind to Antigens in the Presence of ATP and AMP, Respectively, from a Rationally Designed Library Using a Double Round Selection Method Antibodies that exhibit binding activity to an antigen in the presence of a specific small molecule have been obtained, but the acquisition of antibodies that exhibit binding activity to an antigen in the presence of a plurality of different small molecules has never been reported. One way to solve this issue is to consider alternating panning, which changes the small molecule used for each round of panning, e.g., ATP and AMP. However, in this case, there is a problem that selection pressure is applied for the respective small molecule at each round, and thus the selection pressure cannot be equally applied for both small molecules at the same time. To solve this issue, a double round selection method was implemented. The double round selection method is a procedure in which two panning cycles are performed on a single antigen in a single panning round (J Mol Biol. 1992 Aug. 5; 226(3):889-96.). Here, for example, in the case of the phage display method, one round refers to

TABLE 58

| Clone name | hCD137. 1-F.G1d | hCD137.1. 2-F.G1d | hCD137.2. 4-F.G1d | hCD137.2. 3-F.G1d | hCD137.3. 4-F.G1d | hCD137-Fc | cyCD137-Fc-BAP |
|---|---|---|---|---|---|---|---|
| dBBK026-P253 | 1.0 | 1.2 | 1.2 | 1.1 | 4.2 | 5.7 | 8.3 |
| dBBK047-P253 | 1.2 | 1.2 | 2.1 | 4.0 | 4.8 | 2.4 | 1.2 |
| dBBK051-P253 | 1.2 | 1.2 | 1.2 | 1.2 | 3.3 | 3.7 | 5.9 |
| dBBK054-P253 | 3.3 | 10.1 | 1.3 | 1.1 | 1.3 | 8.6 | 1.1 |
| dBBK060-P253 | 1.2 | 1.4 | 1.4 | 1.2 | 1.2 | 4.9 | 1.0 |
| dBBK070-P253 | 1.8 | 2.0 | 1.3 | 1.1 | 1.2 | 9.2 | 3.1 |
| dBBK101-P253 | 1.3 | 1.2 | 1.1 | 1.0 | 1.1 | 3.7 | 5.3 |
| dBBK102-P253 | 1.2 | 1.2 | 1.1 | 1.1 | 1.1 | 2.8 | 4.3 |

(8-5) In Vitro Activity Assessment of the Obtained Antibodies

The GloResponse™ NF-κB-Luc2/4-1BB Jurkat cell line (Promega) was used for measuring the in vitro antibody activity. To each well of 384-well plates, 10 μL of FcγRIIB the step of recovering phages from E. coli to re-infecting the E. coli with the phages after panning; and in the case of the ribosome display method, one round refers to the step from in vitro transcription to gene amplification by PCR. Although double round selection for one type of antigen has been reported, there is no report of application in acquiring small molecule-dependent antibodies, and naturally there is no report of application in acquiring antibodies that show dependency on multiple distinct small molecules. By modifying the double round selection method and applying selective pressure on both ATP and AMP in one round, the inventors believe that it is possible to obtain antibodies that exhibit antigen-binding activity in an ATP- and AMP-dependent manner more efficiently.

Antibodies exhibiting antigen-binding activity in the presence of ATP and AMP were obtained from a rationally designed antibody phage display library constructed in prior patent WO2015/083764. The panning conditions are shown in Table 59. Conditions 1 and 2 were applied to the conventional panning condition and the above alternating panning condition; while Condition 3 was applied to the above double round selection method. Here, the double round selection was performed in Round 2 and Round 3. Biotinylated hCD137-Fc was used as the antigen.

In Table 59, ATP indicates panning using ATP, AMP indicates panning using AMP, and Double indicates panning using double round selection.

TABLE 59

| Condition | Round 1 | Round 2 | Round 3 |
|---|---|---|---|
| 1 | ATP | ATP | ATP |
| 2 | ATP | AMP | ATP |
| 3 | ATP | Double | Double |

Phages were produced in a general manner from *E. coli* carrying the constructed phage display phagemid. Specifically, *E. coli* carrying the constructed phagemid vector was infected with M13KO7TC (WO2015046554A1) or M13KO7ΔpIII (hyperphage) (PROGEN Biotechnik), and phages were recovered from supernatants cultured overnight at 30° C. Antibody phage display libraries were prepared by diluting with TBS, a population of phages precipitated by adding 2.5M NaCl/10% PEG to the *E. coli* culture in which phage production was performed.

BSA was then added to the phage library solution at a final concentration of 4%. Panning was performed using the antigen immobilized on magnetic beads. As magnetic beads, NeutrAvidin beads (TAMAGAWA SEIKO or Dynabeads MyOne StreptAvidin T1 (Thermo Fisher Scientific) were used.

The prepared phage library solution was supplemented with biotinylated hCD137-Fc and ATP at a final concentration of 1 mM and reacted at room temperature for 60 minutes. Blocked magnetic beads were added to the reaction solution of phage and antigen, and they were reacted at room temperature for 15 minutes. The beads were washed twice or three times with TBS/0.1% Tween20 buffer containing 1 mM ATP, and once or twice with TBS containing 1 mM ATP. The beads to which TBS was subsequently added were suspended at room temperature, and the phage solution was recovered from the beads separated using a magnetic stand. After two repetitions of this procedure, the eluted phage solution was mixed. A final concentration of 1 mg/mL trypsin was added to the recovered phage solution. The recovered phages were added to 20 mL of the *E. coli* strain ER2738 in the log growth phase (OD600 0.4-0.7). The *E. coli* were infected with the phages by culturing the *E. coli* for one hour at 37° C. with stirring. The *E. coli* were seeded in plates at 225 mm×225 mm. The *E. coli* were infected with M13KO7TC (WO2015046554A1) or M13KO7ΔpIII (referred as hyperphage) (PROGEN Biotechnik), and cultured overnight at 30° C.; and phages were recovered from supernatants. Under Condition 1, this procedure was repeated three times. Under Condition 2, after the above-mentioned procedure was performed once, ATP was changed to AMP and the above-mentioned procedure was performed again (Round 2), and afterwards the above-mentioned procedure was performed again with ATP (Round 3).

On the other hand, under Condition 3, after the above procedure was performed once, double round selection was performed in Round 2 and Round 3. Specifically, the prepared phage library solution was first supplemented with biotinylated hCD137-Fc and a final concentration of 1 mM AMP, and they were reacted at room temperature for 60 minutes. Blocked magnetic beads were added to the reaction solution of phage and antigen, and they were reacted at room temperature for 15 minutes. The beads were washed twice or three times with TBS/0.1% Tween20 buffer containing 1 mM AMP, and once or twice with TBS containing 1 mM AMP. The beads to which TBS was subsequently added were suspended at room temperature, and the phage solution was recovered from the beads separated using a magnetic stand. After two repetitions of this procedure, the eluted phage solution was mixed. Furthermore, the recovered phage library solution was then added with biotinylated hCD137-Fc and a final concentration of 1 mM ATP, and they were reacted at room temperature for 60 minutes. Blocked magnetic beads were added to the reaction solution of phage and antigen, and they were reacted at room temperature for 15 minutes. The beads were washed twice or three times with TBS/0.1% Tween20 buffer containing 1 mM ATP, and once or twice with TBS containing 1 mM ATP. The beads to which TBS was subsequently added were suspended at room temperature, and the phage solution was recovered from the beads separated using a magnetic stand. After two repetitions of this procedure, the eluted phage solution was mixed. A final concentration of 1 mg/mL trypsin was added to the recovered phage solution. The recovered phages were added to 20 mL of the *E. coli* strain ER2738 in the log growth phase (OD600 0.4-0.7). The *E. coli* were infected with the phages by culturing the *E. coli* for one hour at 37° C. with stirring. The *E. coli* were seeded in plates at 225 mm×225 mm. The *E. coli* were infected with M13KO7TC (WO2015046554A1) or M13KO7ΔpIII (referred as hyperphage) (PROGEN Biotechnik), and cultured overnight at 30° C.; and phages were recovered from supernatants.

(9-2) Assessment of Binding Activity in the Presence and Absence of ATP or AMP by Phage ELISA From single colonies of *E. coli* obtained by the methods described above, phage-containing culture supernatants were harvested using a conventional method (Methods Mol. Biol. (2002) 178, 133-145). NucleoFast 96 (MACHEREY-NAGEL) was used to ultrafilter the harvested culture supernatant. Flow-through was removed by centrifuging (4,500 g, 45 min) the NucleoFast 96 in which 100 µL of culture supernatant was applied to each well. The NucleoFast 96, in which 100 µL of H$_2$O was added to each well, was washed again by centrifugation (4,500 g, 30 min). Finally, 100 µL of TBS was added, and the phage solution contained in the supernatants of the NucleoFast 96 wells, which were left to stand at room temperature for 5 minutes, was recovered.

TBS, 1 mM AMP/TBS or 1 mM ATP/TBS was added to the purified phages which were then subject to ELISA with the procedure below. 384 Well Microplates Streptavidin-coated (greiner, 781990) was coated overnight with 100 µL of TBS containing biotinylated hCD137-Fc prepared in Example 1. After the unbound antigens were removed from the plates by washing each well of the plates with TBST, the wells were blocked with 250 μL of 0.4% Block Ace, 1% BSA, 0.02% Tween, 0.05% ProClin 300-TBS for one hour or more. The antibody-presenting phages were then allowed to bind to the antigen present in each well in the absence and presence of ATP or AMP by keeping the plates with the prepared purified phages added in each well at 37° C. for one hour. Each well was washed with TBST, 1 mM ATP/TBST or 1 mM AMP/TBST, and supplemented with an HRP-conjugated anti-M13 antibody (Amersham Pharmacia Biotech) diluted in TBS, 1 mM AMP/TBS or 1 mM ATP/TBS and incubated for one hour. After washing with TBST, 1 mM ATP/TBST or 1 mM AMP/TBST, color development of the solution in each well to which the TMB single solution (ZYMED) was added was stopped by the addition of sulfuric acid, and then the color development was measured by absorbance at 450 nm.

The results of phage ELISA are shown in Table 60.

Here, clones with an S/N ratio of absorbance higher than 2 in the presence of ATP (the ratio of absorbance in the presence of antigen to that in the absence of antigen) were judged as positive for binding, and those with an absorbance ratio of 3 or higher in the presence/absence of ATP or AMP were judged as clones with antigen-binding activity dependent on ATP or AMP (switch clones). As a result, for hCD137-Fc, most of the clones obtained from Condition 1 showed binding in the presence of ATP but failed to show binding in the presence of AMP. Among the clones that showed binding in the presence of ATP and no binding in the absence of ATP obtained from Condition 2, there were multiple antibodies that showed binding even in the presence of AMP, but the percentage was 50% or less. On the other hand, under Condition 3, where double round selection was performed, 65% or more of clones showing binding in the presence of ATP and no binding in the absence of ATP were able to show binding even in the presence of AMP.

For the resulting clones, the amplified heavy chain genes were sequenced using specific primers, pBAD-F, G1seq-R.

As a result, under Condition 3 in which double round selection was performed, the obtained antibody heavy chain sequences showing human CD137 binding dependent on both ATP and AMP were 3 times more than Condition 1 which was performed with only ATP, and about 1.5 times more than Condition 2 which used ATP and AMP alternately. This indicates that double round selection is a more valuable approach in obtaining antibodies that exhibit antigen-binding activity dependent on a plurality of distinct small molecules.

Example 10: Obtaining ATP-Dependent Anti-Mouse CTLA4-Binding Antibodies from a Naive Library (10-1) Obtaining Antibodies that Bind to Murine CTLA4 in the Presence of Small Molecules from a Naive Human Antibody Library by Bead Panning A human antibody phage display library consisting of a plurality of phages presenting Fab domains of different human antibody sequences was constructed according to methods known to those skilled in the art using poly(A) RNA made from human PBMC, commercially available human poly(A) RNA or such as template.

From the constructed naive human antibody phage display library, antibodies showing binding activity to the murine CTLA4 extracellular domain (mCTLA4) in the presence of small molecules were screened. That is, phages presenting antibodies that exhibit binding activity to the mCTLA4 captured by the beads in the presence of small molecules were collected. Phages were recovered from the phage eluates eluted from the beads in the absence of small molecules. Biotinylated mCTLA4 (mCTLA4-His-Biotin) was used as the antigen in this method. mCTLA4-His-Biotin was obtained from biotinylation (PIERCE Cat. No. 21329) of mCTLA4-His (Sino Biologics Inc. 50503-MO8H, Accession No. NP_033973.2) by the amine-coupling method, which was made by fusing a His tag to the extracellular domain of mCTLA4.

Phages produced from E. coli carrying the constructed phage display phagemids were purified by general methods. A phage library solution was subsequently dialyzed with TBS and obtained. Panning with the antigen immobilized on magnetic beads was performed. As magnetic beads, NeutrAvidin coated beads (Sera-Mag SpeedBeads NeutrAvidin-coated) or Streptavidin coated beads (Dynabeads M-280 Streptavidin) were used.

In order to efficiently obtain small molecule switch antibodies which are dependent on the small molecule that can play a switch role in cancer tissues, panning to enrich antibodies that bind to antigens in the presence of adenosine triphosphate (adenosine 5'-triphosphate; ATP) and ATP metabolites, and which do not bind antigens in the absence of ATP was performed with reference to the methods described in the prior patent WO2013/180200.

Specifically, the prepared phage library solution was supplemented with biotinylated mCTLA4 and ATP and ATP metabolites at a final concentration of 1 mM, and reacted at room temperature for 60 minutes. Blocked magnetic beads were added to the reaction solution of phage and antigen, and they were reacted at room temperature for 15 minutes.

TABLE 60

|  | Condition 1 | Condition 2 | Condition 3 |
|---|---|---|---|
| Number of clones subjected to ELISA | 96 | 96 | 96 |
| Number of positive clones (S/N ratio > 2, ATP) | 69 | 88 | 91 |
| Number of ATP switch clones (ATP +/− ratio >= 3) | 65 | 84 | 82 |
| Number of ATP, AMP switch clones (ATP +/− ratio >= 3 and AMP +/− ratio >= 3) | 13 | 40 | 54 |
| Proportion of ATP, AMP switch clones | 20.0% | 47.6% | 65.9% |
| Number of ATP, AMP switch clone sequences (ATP +/− ratio >= 3 and AMP +/− ratio >= 3) | 13 | 25 | 38 |

The beads were washed twice or three times with TBS/0.1% Tween20 buffer containing 1 mM ATP, and once or twice with TBS containing 1 mM ATP. The beads to which TBS was subsequently added were suspended at room temperature, and the phage solution was recovered from the beads separated using a magnetic stand. Subsequently, the beads were added with a final concentration of 1 mg/mL trypsin in Round 1 and with TBS in Round 2 and onward, and they were suspended at room temperature; and phage solutions were recovered from the beads separated using a magnetic stand. If TBS was used, this procedure was repeated twice, following by mixing of the eluted phage solution and addition of a final concentration of 1 mg/mL trypsin to the recovered phage solution. The recovered phages were added to 10 mL of E. coli strain ER2738 in the log growth phase (0D600 0.4-0.7). The E. coli were infected with the phages by culturing the E. coli for one hour at 37° C. with stirring. The E. coli were seeded in plates at 225 mm×225 mm. The E. coli were infected with M13KO7TC (WO2015046554A1) or M13KO7ΔpIII (referred as hyperphage) (PROGEN Biotechnik), and cultured overnight at 30° C.; and phages were recovered from supernatants. During culturing, the condition of adding 100 µM IPTG and the condition of not adding IPTG were used to induce expression of the Fab genes from the lac promoter. This procedure was repeated four times.

(10-2) Assessment of Binding Activity in the Presence and Absence of Small Molecules by Phage ELISA From single colonies of E. coli obtained in Example 10-1, the phage-containing culture supernatants were harvested using a conventional method (Methods Mol. Biol. (2002) 178, 133-145). NucleoFast 96 (MACHEREY-NAGEL) was used to ultrafilter the harvested culture supernatants. 100 µL of each culture supernatant was applied to each well of NucleoFast 96 and centrifugation at 4,500 g for 45 min was performed to remove flow-through. 100 µL of $H_2O$ was added and washing by centrifugation (4,500 g, 30 min) was carried out again. Finally, 100 µL of TBS was added, left to stand at room temperature for 5 minutes, and the phage solution contained in the supernatants was recovered.

TBS was added to the purified phages which were then subject to ELISA with the procedure below. StreptaWell 96 microtiter plates (Roche) were coated overnight with 100 µL of TBS containing mCTLA4-His-Biotin. After the unbound mCTLA4-His-Biotin was removed from the plates by washing each well of the plates with TBST, the wells were blocked with 250 µL of 2% skim milk-TBS for more than one hour. The antibody-presenting phages were then allowed to bind mCTLA4-His-Biotin present in each well in the absence and presence of ATP by removing 2% skim milk-TBS, followed by keeping the plates with the prepared purified phages added in each well at room temperature for one hour. Each well was washed with TBST or ATP/TBST, and supplemented with an HRP-conjugated anti-M13 antibody (Amersham Pharmacia Biotech) diluted in TBS or ATP/TBS and incubated for one hour. After washing with TBST or ATP/TBST, color development of the solution in each well to which the TMB single solution (ZYMED) was added was stopped by the addition of sulfuric acid, and then the color development was measured by absorbance at 450 nm. As a result, several antibodies that bind to mCTLA4 only in the presence of ATP were confirmed.

The results of phage ELISA are shown in Table 61.

Here, clones with an absorbance higher than 0.2 in the presence of ATP were judged as positive, and those with an absorbance ratio higher than 2 in the presence/absence of ATP were judged as clones with ATP-dependent antigen-binding activity (switch clones).

TABLE 61

| Helper phage used in panning | M13KO7TC | M13KO7TC | M13KO7ΔpIII |
|---|---|---|---|
| IPTG concentration when culturing for panning | 0 µM | 100 µM | 0 µM |
| Number of clones subjected to ELISA | 96 | 96 | 96 |
| Number of positive clones (absorbance > 0.2) | 20 | 41 | 62 |
| Number of switch clones (SM +/− ratio > 2) | 0 | 12 | 16 |

The above-mentioned invention has been described in detail with examples and illustrations for the purposes of assisting a clear understanding, and the description and illustrations herein should not be construed as limiting the scope of the invention.

All disclosures of patents and scientific literatures cited herein throughout are explicitly incorporated by reference.

Example 11: Assessment of the In Vitro ATP- and ADP-Dependent CD137 Agonist Activity of the Modified Anti-Human CD137 Antibodies Using the 4-1BB Jurkat Reporter Gene Assay The GloResponse™ NF-κB Luc2/4-1BB Jurkat cell line (Promega, CS196004) was used for measurement of the in vitro activity of the variants generated in Example 7-2 (Table 52). To each well of 384-well plates, 10 µL each of FcγRIIB CHO-K1 Cells (Promega) prepared at the concentration of $4\times10^5$/mL with an assay medium (99% RPMI, 1% FBS) was added. Subsequently, 10 µL of an antibody solution containing ADP, or an antibody solution containing ATP, or an antibody solution without ATP or ADP was added each well. Then, 10 µL of the GloResponse™ NF-κB-Luc2/4-1BB Jurkat cell line prepared to $2\times10^6$/mL with the assay medium (99% RPMI, 1% FBS) was added to each well. The final concentration of ADP was 10 µM, and the final concentration of ATP was 10 µM. The plates were left to stand for 6 hours at 37° C. in a 5% CO2 incubator and 15 minutes at room temperature; and 30 µL of the Bio-Glo reagent was added to each well. The Bio-Glo Luciferase Assay System (Buffer and Substrate) was used for the Bio-Glo reagent. Subsequently, the amount of luminescence of each well was measured with a plate reader.

The value of the luminescence of each well divided by the value of the luminescence of the well without antibody addition was defined as "relative light unit" (fold induction), and it served as an indicator for evaluating the CD137 agonist activity of each antibody.

The results are shown in FIG. 58. From FIG. 58, it was confirmed that A375-P587/B167-LamLib, A551-P587/B256-LamLib, A551-P587/B379-LamLib, A375-SCF041aPh/B167-LamLib, A551-SCF041aPh/B256-LamLib, A551-SCF041aPh/B379-LamLib, A375-SCF043aPh/B167-LamLib, A551-SCF043aPh/B256-LamLib, A551-SCF043aPh/B379-LamLib, A375-SCF057aPh/B167-LamLib, A551-SCF057aPh/B256-LamLib, and A551-SCF057aPh/B379-LamLib show human CD137 agonist activity in a ATP- and ADP-dependent manner.

Example 12: Measurement of the Extracellular ATP Level in Tumor Sites

The ATP-switch antibody binds to the target molecule in the presence of ATP and exhibits drug efficacy. Assessment of the extracellular ATP level in tumor tissue sites was performed using P2Y11 split Luc/HEK293 cells. The cells were produced with ProbeX using the company's split-luciferase technology. The cells express the luciferase C-terminal protein bound to purinergic receptor P2Y11 (Accession No. AF030335) with ATP as ligand, and the luciferase N-terminal protein bound to β-arrestin-2 isoform 1 (Accession No. NM_004313). The active luciferase is generated by association of the two luciferase fragments that are separately present in the cells by ATP stimulation, and luminescence using luciferin as a substrate can be obtained.

(12-1) ATP Responsiveness of P2Y11 Split Luc/HEK293 Cells

P2Y11 split Luc/HEK293 cells were cultured and maintained in Dulbecco's modified Eagle's medium (Dulbecco's Modified Eagle's Medium-high glucose: D5796/Sigma-Aldrich) containing 10% fetal bovine serum, 0.8 mg/mL G418 (Geneticin™), and 0.05 mg/mL phleomycin D1 (Zeocin™) for passage. P2Y11 split Luc/HEK293 cells were plated in 96 well microplate (µCLEAR™, WHITE, CELLSTAR™/ Greiner Bio-One) at 30000 cells/well, cultured overnight, and then the culture solution was removed from each well and replaced with 0.18 mL of culture solution containing 0.5 mg/mL luciferin (VivoGlo™ Luciferin, In Vivo Grade/ Promega). To achieve final concentrations of 0, 0.125, 0.25, 0.5, 1.0, and 2.0 mM, 0.02 mL of an adenosine, AMP, ADP, or ATP solution was added, and luminescence values were measured on the plate reader EnVision (Perkin Elmer) after 30 minutes of incubation in a $CO_2$ incubator (37° C., 5% $CO_2$).

The results are shown in FIG. 59. P2Y11 split Luc/ HEK293 cells increased their luminescence in an ATP-specific manner dependent on the ligand concentration.

(12-2) Evaluation of the Extracellular ATP Concentration in Tumor Tissue Sites

The P2Y11 split Luc/HEK293 cells were detached from the culture flasks by Cell Dissociation Buffer, enzyme-free, and PBS (Thermo Fisher Scientific), washed with HBSS, and then made into an HBSS cell suspension, which was used for measuring the in vivo extracellular ATP level.

(12-2-1) Creation of an In Vivo ATP Calibration Curve 0.2 mL of a cell suspension containing a fixed concentration of ATP, 1 mg/mL luciferin (VivoGlo, Promega), and $1.0×10^7$ cells/mL of P2Y11 split Luc/HEK293 cells was transplanted subcutaneously into the ventral region of C3H/ HeN mice, and 20 minutes later, luminescence imaging measurements were performed under isoflurane anesthesia with an in vivo imaging device, IVIS spectrum CT. The acquired imaging images were analyzed by the Living Image Software, and an ATP calibration curve under the in vivo measurement condition was prepared from the calculated luminescence values and the concentrations of the added ATP.

FIG. 60 shows the results. P2Y11 split Luc/HEK293 cells exhibited ATP concentration-dependent luminescence even under the in vivo conditions when transplanted subcutaneously into the C3H/HeN mice, which could be made into a calibration curve for evaluating ATP levels in vivo.

(12-2-2) Evaluation of the Extracellular ATP Level in Tumor Tissue Sites 0.2 mL of a cell suspension containing 1 mg/mL luciferin (VivoGlo, Promega) and $1.0×10^7$ cells/mL of P2Y11 split Luc/HEK293 cells was transplanted subcutaneously into the tumor site of FM3A tumor-bearing mice (tumor volume 200-300 $mm^3$) and luminescence imaging measurements were performed 20 minutes later under isoflurane anesthesia by the in vivo imaging device, IVIS spectrum CT. The acquired imaging images were analyzed by the Living Image Software, the ATP level was calculated from the luminescence value of the tumor site using the in vivo ATP calibration curve, and this was set as the level of extracellular ATP at the tumor site.

The results of luminescence imaging measurement are shown in FIG. 61 and the extracellular ATP levels at the tumor site, calculated from the calibration curve of ATP, are shown in Table 62. The luminescence level at the tumor tissue site (FM3A tumor-bearing mouse) was higher than that at the background (normal site), and the extracellular ATP level at the tumor tissue site in the FM3A transplantation model was calculated to be an average of 1.31 mM on the prepared in vivo ATP calibration curve.

TABLE 62

| FM3A tumor bearing mouse | 1 | 2 | 3 | Mean ± SD |
|---|---|---|---|---|
| Extracellular ATP (mM) | 0.81 | 1.26 | 1.86 | 1.31 ± 0.53 |

Example 13: ATP-Dependent Antitumor Activity of Anti-hIL6R Antibodies Having ATP-Dependent Binding Properties (13-1) Preparation of Anti-hIL6R Antibodies Having ATP-Dependent Binding Properties By referring to the methods described in WO2015/083764 and WO2013/180200, the acquired antibodies were optimized to generate anti-human interleukin 6 receptor (hIL6R) antibodies having ATP-dependent binding properties. Heavy chains and light chains were combined as shown in Table 63 to express and purify anti-hIL6R antibodies in a manner known to those skilled in the art.

Combinations of heavy chains and light chains of antibodies

TABLE 63

| Antibody name | VH | CH | VL | CL |
|---|---|---|---|---|
| MRAH-G4T1/ MRAL-k0 | MRAH SEQ ID NO: 190 | G4T1 SEQ ID NO: 198 | MRAL SEQ ID NO: 191 | k0 SEQ ID NO: 199 |
| H0002-G4T1/ L1058-lam1 | H0002 SEQ ID NO: 192 | | L1058 SEQ ID NO: 193 | lam1 SEQ ID NO: 189 |
| H0041-G4T1/ L1088-lam1 | H0041 SEQ ID NO: 194 | | L1088 SEQ ID NO: 195 | |
| H0052-G4T1/ L1083-lam1 | H0052 SEQ ID NO: 196 | | L1083 SEQ ID NO: 197 | | hIL6R (SEQ ID NO: 200) was genetically synthesized as an antigen and inserted into a plasmid for animal expression, and then it was introduced into CHO cells, and thus, a stable expression line (hIL6R-CHO) which constitutively expresses the antigen was cloned. The antigenic protein was expressed and purified using the methods below. The hIL6R-CHO line was suspended at an appropriate cell density, seeded and cultured in flasks, and the antigen was purified from the culture supernatant in a manner known to those skilled in the art. Spectrophotometers were used to measure the absorbance at 280 nm of the purified antigen solution. Concentrations of the purified antigen were calculated from the obtained measurement values using absorption coefficients calculated by the PACE method (Protein Science (1995) 4, 2411-2423).

(13-2) Calculation of ATP Concentration-Dependent KD Values of Anti-hIL6R Antibodies Affinity analysis for hIL6R in the presence of each ATP concentration of 0, 1, 10, and 100 μM was performed on Biacore T200 using the antibodies described in Table 63. Measurements were performed at a flow rate of 10 μL/min, interaction time of 1 min, dissociation time of 1 min, and single cycle kinetics at 37° C. For the buffer, 20 mM ACES, 150 mM NaCl, 2 mM MgCl$_2$, and 0.05% Tween20, pH 7.4 containing different concentrations (0, 1, 10, and 100 μM) of ATP was used. The accessory Biacore Evaluation Software of Biacore T200 was used for analysis, and the 1:1 Langmuir binding model was used for the fitting model. The results of the analysis are shown in Table 64 and FIG. 62.

Calculation of ATP concentration-dependent KD values (M) of anti-hIL6R antibodies

TABLE 64

| Antibody name | | ATP concentration (μM) | | | |
|---|---|---|---|---|---|
| | | 0 | 1 | 10 | 100 |
| MRAH-G4T1/ | Mean | 1.70E−08 | 1.88E−08 | 1.79E−08 | 1.80E−08 |
| MRAL-k0 | SD | 3.81E−09 | 4.07E−09 | 4.08E−09 | 4.00E−09 |
| H0002-G4T1/ | Mean | N.A.* | N.A.* | N.A.* | 1.16E−06 |
| L1058-lam1 | SD | N.A.* | N.A.* | N.A.* | 4.23E−07 |
| H0041-G4T1/ | Mean | N.A.* | 2.38E−06 | 3.20E−07 | 4.83E−08 |
| L1088-lam1 | SD | N.A.* | 6.00E−07 | 7.45E−08 | 1.16E−08 |
| H0052-G4T1/ | Mean | N.A.* | 1.45E−06 | 5.05E−08 | 8.31E−09 |
| L1083-lam1 | SD | N.A.* | 1.17E−06 | 1.41E−08 | 2.84E−09 |

*Samples with the comment "Kinetic constants cannot be uniquely determined" in the Biacore analysis were regarded as Rejected, and the results are shown as "N.A."

The results showed that the KD for hIL6R of MRAH-G4T1/MRAL-k0 was not affected by ATP concentration in the assay, but the KD for hIL6R of H0002-G4T1/L1058-lam1, H0041-G4T1/L1088-lam1, and H0052-G4T1/L1083-lam1 became smaller with a higher concentration of ATP in the assay. That is, the higher the ATP concentration in the assay was, the stronger the binding activity became. The results confirmed that H0002-G4T1/L1058-lam1, H0041-G4T1/L1088-lam1, and H0052-G4T1/L1083-lam1 have ATP-dependent hIL6R-binding activity.

Hereinafter, an antibody whose antigen-binding activity does not depend on the ATP concentration, such as MRAH-G4T1/MRAL-k0, may be referred to as a non-switch antibody, and an antibody whose antigen-binding activity depends on the ATP concentration, such as H0002-G4T1/L1058-lam1, H0041-G4T1/L1088-lam1, and H0052-G4T1/L1083-lam1, may be referred to as a switch antibody.

(13-3) Calculation of ADP- and AMP-Concentration-Dependent KD Values of Anti-hIL6R Antibodies The antibodies described in Table 63 were then used to perform hIL6R affinity analysis in the presence of 10 and 100 μM of ADP or AMP instead of ATP by using Biacore T200 according to the conditions described above. The analysis results of the measurement using ADP are shown in Table 65 and FIG. 63, and the analysis results of the measurement using AMP are shown in Table 66 and FIG. 64. Antibodies with a response of 10 RU or less at the time of measurement were considered unanalyzable and are designated as N.D.

Calculation of ADP concentration-dependent KD values (M) of anti-hIL6R antibodies

TABLE 65

| | ADP concentration (μM) | |
|---|---|---|
| Antibody name | 10 | 100 |
| MRAH-G4T1/MRAL-lam1 | 5.64E−09 | 5.96E−09 |
| H0002-G4T1/L1058-lam1 | N.D. | N.D. |
| H0041-G4T1/L1088-lam1 | 1.03E−05 | 2.96E−07 |
| H0052-G4T1/L1083-lam1 | 5.81E−08 | 1.01E−08 |

Calculation of AMP concentration-dependent KD values (M) of anti-hIL6R antibodies

TABLE 66

| | AMP concentration (μM) | |
|---|---|---|
| Antibody name | 10 | 100 |
| MRAH-G4T1/MRAL-lam1 | 5.33E−09 | 5.46E−09 |
| H0002-G4T1/L1058-lam1 | N.D. | N.D. |
| H0041-G4T1/L1088-lam1 | N.D. | 1.81E−06 |
| H0052-G4T1/L1083-lam1 | 6.64E−06 | 1.18E−07 |

The results showed that the KD for hIL6R of MRAH-G4T1/MRAL-k0 was not affected by ADP and AMP concentrations in the assay, but similar to the case of ATP, higher ADP or AMP concentrations in the assay were accompanied by smaller KD for hIL6R of H0002-G4T1/L1058-lam1, H0041-G4T1/L1088-lam1, and H0052-G4T1/L1083-lam1, i.e., stronger binding activity. The results confirmed that H0002-G4T1/L1058-lam1, H0041-G4T1/L1088-lam1, and H0052-G4T1/L1083-lam1 have ADP- or AMP-dependent binding activities towards hIL6R.

(13-4) Assessment of ATP Concentration-Dependent ADCC Activity of Anti-hIL6R Antibodies Antibodies were prepared in a manner known to those skilled in the art as in Table 67 by changing the heavy-chain constant regions of the above-noted antibodies to mFa55 (SEQ ID NO: 184), in which ADCC activity is enhanced by adding the FcγRIV binding-enhancing modifications to mIgG2a, and by changing the light-chain constant region from human to mouse. In addition, KLH-mFa55 (IC17Hdk-mFa55/IC17L-mk1) was prepared as a negative control.

Combinations of heavy chains and light chains of antibodies

TABLE 67

| Antibody name | VH | CH | VL | CL |
|---|---|---|---|---|
| IC17HdK-mFa55/ IC17L-mk1 | IC17HdK SEQ ID NO: 187 | mFa55 SEQ ID NO: 184 | IC17L SEQ ID NO: 188 | mk1 SEQ ID NO: 185 |
| MRAH-mFa55/ MRAL-mk0 | MRAH SEQ ID NO: 190 | | MRAL SEQ ID NO: 191 | mk0 SEQ ID NO: 211 |
| H0002-mFa55/ L1058-ml0 | H0002 SEQ ID NO: 192 | | L1058 SEQ ID NO: 193 | ml0 SEQ ID NO: 212 |
| H0041-mFa55/ L1088-ml0 | H0041 SEQ ID NO: 194 | | L1088 SEQ ID NO: 195 | |
| H0052-mFa55/ L1083-ml0 | H0052 SEQ ID NO: 196 | | L1083 SEQ ID NO: 197 | |

These antibodies were used to evaluate ADCC against Hepa1-6 (hIL6R-Hepa1-6), a murine hepatoma line that expresses full-length hIL6R (SEQ ID NO: 213) as prepared by methods known to those skilled in the art, according to the methods below.

The mFcγRIV ADCC Reporter Bioassay, Core Kit (Promega) was used for the measurements below. To each well of the 96-well plate, 100 μL of hIL6R-Hepa1-6 prepared in a medium at a concentration of 2×105/mL was added, and the plate was left to stand at 37° C. for 21 hours. For the culture medium, 90% DMEM, 10% FBS, 600 μg Geneticin, and 500 μg Zeocin were used. After the plate was centrifuged for five minutes at 200×g, 4° C., the supernatant of each well was aspirated. A solution of the antibodies described in Table 67 diluted in assay buffer to a final concentration of 0.2 μg/mL, an ATP solution diluted in assay buffer to a final concentration of 0, 1, 10, and 100 μM, and 25 μL of a solution prepared by adding 0.69 mL of the kit accessory effector cell to 3.82 mL of assay buffer were mixed to a total of 75 μL, and the mixtures were added to each well and left to stand at 37° C. for six hours. For the assay buffer, 1.5 mL of the kit accessory low IgG serum was added to 36 mL of RPMI 1640 and used. The plate was then left to stand at room temperature for 15 minutes, and 75 μL of the Bio-Glo reagent was added to each well. The Bio-glo Luciferase Assay System (Buffer and Substrate) was used for the Bio-Glo reagent. Luminescence of each well was then measured with a plate reader. The value of luminescence in each well divided by the value of luminescence in the well without antibody addition was the fold of induction, and it served as an indicator for evaluating the ADCC of each antibody.

The results obtained are shown in FIG. 65. In the figure, fold of induction was denoted as the relative light unit (RLU).

The results showed that the ADCC of MRAH-mFa55/MRAL-mk0, a non-switch antibody, towards hIL6R-expressing cells was not affected by ATP concentration in the assay, but the ADCC of switch antibodies H0002-mFa55/L1058-ml0, H0041-mFa55/L1088-ml0, and H0052-mFa55/L1083-ml0 became stronger with higher ATP concentration in the assay. The results confirmed that H0002-mFa55/L1058-ml0, H0041-mFa55/L1088-ml0, and H0052-mFa55/L1083-ml0 have ATP-dependent cytotoxic activity towards hIL6R.

(13-5) Assessment of the In Vivo Antitumor Activity of Anti-hIL6R Antibodies

As the ADCC of each antibody was confirmed, a test was conducted to evaluate the in vivo antitumor activity of these antibodies using a tumor-bearing murine model of C57BL/6 mice with hIL6R-Hepa1-6 according to the methods below.

An anti-asialo GM1 antibody (Wako Pure Chemical Industries) was dissolved in 1 mL of distilled water (Otsuka Pharmaceutical Factory) and then diluted with 4 mL of PBS. The anti-asialo GM1 antibody prepared this way was administered intraperitoneally to 100 C57BL/6 mice at a dose of 0.1 mL per mouse. One day later, a mixed solution was prepared in which the same volume of Matrigel Matrix (Corning) was added to a cell suspension of hIL6R-Hepa1-6 suspended to 1×108/mL in Hanks' Balanced Salt solution (Sigma). The mixed solution was injected subcutaneously into 100 C57BL/6 mice at a dose of 0.2 ml per mouse, and the cells were implanted. The tumor diameter of the mice was measured by calipers, and the tumor volume was defined as (major axis)×(minor axis)×(minor axis)× (1/2). Measurement of the tumor diameter was performed by an individual unaware of the contents of the drug solution administered to each mouse. The tumor diameters and body weights of 100 of the above C57BL/6 mice were measured on the 11th day after cell transplantation. Based on this value, randomization of the mice was performed, and the mice were divided into a total of five groups: four groups of 10 animals each and one group of 8 animals; and each group received a solution of the antibodies shown in Table 67 via tail vein. Here, the group of 8 animals received H0002-mFa55/L1058-ml0. The dosage (mL) of the antibody solution administered was (0.01 (mL/g))×(body weight (g) of each mouse). The tumor diameters and body weights of C57BL/6 mice grouped above were measured in the same manner on the 14th, 18th, 21st, and 25th day after transplantation. On the 18th day after transplantation, solutions of the antibodies shown in Table 67 were administered to the corresponding group via tail vein at the dosage defined by the same calculation formula described above based on the measured body weight data. The mean tumor volume in each antibody treatment group on each day of measurement was calculated, and it served as an index for evaluating the in vivo antitumor activity of each antibody.

The results obtained are shown in FIG. 66.

Among the switch antibodies for which ATP-dependent ADCC was confirmed, H0041-mFa55/L1088-ml0 and H0052-mFa55/L1083-ml0 were confirmed to exhibit antitumor activity towards hIL6R-expressing cells to the same extent as MRAH-mFa55/MRAL-mk0, which is a non-switch antibody, from the above results. The results suggested that extracellular ATP in the vicinity of tumors was present at a concentration level that H0041-mFa55/L1088-ml0 and H0052-mFa55/L1083-ml0 functioned similarly to MRAH-mFa55/MRAL-mk0.

Example 14: Assessment of Systemic Effects of Anti-hIL6R Antibodies Having ATP-Dependent Binding Properties To evaluate the effects of anti-hIL6R antibodies having ATP-dependent binding properties in normal tissues, normal mice (C57BL/6) and transgenic mice systemically overexpressing hIL6R (hIL6R-tgm) (Proc Natl Acad Sci U.S.A. 1995 May 23; 92(11):4862-4866) were used to evaluate the plasma kinetics of the antibodies. For this assessment, the antibodies described in Table 67 were administered to normal mice (C57BL/6) and hIL6R-tgm, and their plasma kinetics were compared. In hIL6R-tgm, it has been reported that ordinary antibodies that bind to hIL6R disappear through membrane-type hIL6R as a result of binding to systemically expressed membrane-type hIL6R (Nature Biotechnology volume 28, pages 1203-1207 (2010)).

2 mg/mL of MRAH-mFa55/MRAL-mk0, H0002-mFa55/L1058-ml0, H0041-mFa55/L1088-ml0, or H0052-mFa55/L1083-ml0 was administered intravenously to normal mice and hIL6R-tgm at a single dose of 10 mL/kg. In normal mice, blood was collected 5 minutes, 7, 24, 48, 72, and 168 hours after administration in all groups of MRAH-mFa55/MRAL-mk0 group, H0002-mFa55/L1058-ml0 group, H0041-mFa55/L1088-ml0 group, and H0052-mFa55/L1083-ml0 group. For hIL6R-tgm, blood was collected 5 minutes, 7, 24, 48, 52, 55, 72, and 168 hours after administration in the MRAH-mFa55/MRAL-mk0 group, and 5 minutes, 7, 24, 48, 72, and 168 hours after administration in the H0002-mFa55/L1058-ml0 group, H0041-mFa55/L1088-ml0 group, and H0052-mFa55/L1083-ml0 group. The obtained blood was rapidly centrifuged at 4° C., 12,000 rpm, 10 minutes; and plasma was separated. Plasma was stored in a freezer set to −20° C. or lower until measurement.

Concentration of each antibody in the plasma was measured by the electrochemiluminescence (ECL) method. The hIL6R solution was added to MULTI-ARRAY PR Plate (Meso Scale Diagnostics, LLCs), left to stand at 37° C. for one hour, and hIL6R was immobilized to the plate. For the calibration curve, MRAH-mFa55/MRAL-mk0, H0041-mFa55/L1088-ml0, and H0052-mFa55/L1083-ml0 were prepared at plasma concentrations of 8, 4, 2, 1, 0.5, 0.25, and 0.125 ∞g/mL; and H0002-mFa55/L1058-ml0 was prepared at plasma concentrations of 64, 32, 16, 8, 4, 2, and 1 μg/mL. After addition of 1 M Tris-HCl solution, pH 8.0 containing 0.05% Tween20 and 1% BSA to the hIL6R-immobilized plate, plasma samples diluted 250 fold in 0.3 M acetic acid solution, as well as calibration curve samples were added quickly, and an ATP solution was further added and mixed. After the plate was left to stand for one hour at room temperature, a biotin-labeled anti-mouse IgG antibody (Southern Biotechnology Associates, Inc) was added and left to stand at room temperature for one hour. Subsequently, Streptavidin SULFO-TAG Labeled (Meso Scale Diagnostics, LLC) was added, left to stand at room temperature for one hour, followed by addition of Read buffer T (Meso Scale Diagnostics, LLC), and reaction was measured with an electrochemical luminescence device, SECTOR Imager 6000 (Meso Scale Diagnostics, LLC). SOFTmax PRO (Molecular Devices) was used to calculate the concentration of each antibody in mouse plasma.

The soluble antigen concentration in plasma was measured by ECL. Murine plasma samples diluted 50 fold were mixed with a SULFO-TAG (Meso Scale Diagnostics, LLC)-labeled anti-human IL6R antibody (R&D Systems), a biotin-labeled anti-human IL6R antibody (R&D Systems), and excessive anti-human IL6R antibody tocilizumab (in-house manufactured product), and the mixture was incubated overnight at 37° C. After the mixture was added to the blocked Streptavidin-coated standard 96-well plate (Meso Scale Diagnostics, LLC), followed by addition of Read buffer, reaction was measured on SECTOR Imager 6000 (Meso Scale Diagnostics, LLC). SOFTmax PRO (Molecular Devices) was used to calculate concentrations of the soluble antigen in murine plasma.

The results of comparing the blood levels of MRAH-mFa55/MRAL-mk0, H0002-mFa55/L1058-ml0, H0041-mFa55/L1088-ml0, and H0052-mFa55/L1083-ml0 in normal mice and hIL6R-tgm are shown in FIG. 67, FIG. 68, FIG. 69, and FIG. 70, respectively.

MRAH-mFa55/MRAL-mk0, a non-switch antibody, exhibited a faster elimination in hIL6R-tgm which systemically expresses hIL6R, compared to that in normal mice (FIG. 67). This result seemed to be caused by the fact that the non-switch antibody was bound to membrane-type hIL6R expressed in the normal tissues of the whole body, and disappeared through hIL6R.

On the other hand, remarkably rapid losses of the antibody concentration were not observed for the switch antibodies H0002-mFa55/L1058-ml0, H0041-mFa55/L1088-ml0, and H0052-mFa55/L1083-ml0 in hIL6R-tgm, like the non-switch antibody, as compared to that in the normal mice. The results suggest that in contrast to the result of the non-switch antibody, switch antibodies do not bind to systemically expressed membrane-type hIL6R, and they do not cause hIL6R-mediated elimination.

Compared with the switch antibodies H0002-mFa55/L1058-ml0, H0041-mFa55/L1088-ml0, and H0052-mFa55/L1083-ml0, only H0052-mFa55/L1083-ml0 showing stronger binding at low ATP concentrations resulted in accelerated loss of the antibody in hIL6R-tgm relative to normal mice.

These results suggest that extracellular ATP concentrations in normal tissues are low for switch antibodies to bind to hIL6R.

Then, the plasma concentrations of soluble hIL6R in hIL6R-tgm were compared after the respective antibodies were administered. The results are shown in FIG. 71.

Compared with soluble hIL6R concentrations in mice receiving the isotype control IC17HdK-mFa55/IC17L-mk1, soluble hIL6R concentrations in mice receiving the non-switch antibody, MRAH-mFa55/MRAL-mk0, were observed to accumulate. This was thought to be caused by binding of the non-switch antibody to the soluble form of hIL6R, preventing normal metabolic pathways.

On the other hand, no significant antigen accumulation like that of the non-switch antibody was observed in mice receiving the switch antibodies H0002-mFa55/L1058-ml0, H0041-mFa55/L1088-ml0, and H0052-mFa55/L1083-ml0. When the switch antibodies H0002-mFa55/L1058-ml0, H0041-mFa55/L1088-ml0, and H0052-mFa55/L1083-ml0 were compared, the tendency for antigen accumulation was observed for antibodies showing stronger binding at low ATP concentrations.

These results suggest that extracellular ATP concentrations in normal tissues and blood are low for switch antibodies to bind to the membrane and soluble forms of hIL6R.

Example 15: Simultaneous Assessment of Antitumor Effects and Systemic Effects of Anti-hIL6R Antibodies Having ATP-Dependent Binding Properties Antitumor effects and systemic effects were simultaneously evaluated to assess the systemic effects of anti-hIL6R antibodies having ATP-dependent binding properties in the presence of a tumor. For this assessment, the hIL6R-Hepal-6-transplanted hIL6R-tgm model was used, and the antibodies described in Table 67 were administered.

An anti-asialo GM1 antibody (Wako Pure Chemical Industries) was dissolved in 1 mL of distilled water (Otsuka Pharmaceutical Factory) and then diluted with 4 mL of PBS. The anti-asialo GM1 antibody prepared this way was administered intraperitoneally to 83 hIL6R-tgm mice at a dose of 0.1 mL per mouse. One day later, a mixed solution was prepared in which the same volume of Matrigel Matrix (Corning) was added to a cell suspension of hIL6R-Hepal-6 suspended to $1 \times 10^8$/mL in Hanks' Balanced Salt solution (Sigma). The mixed solution was injected subcutaneously into 83 hIL6R-tgm at a dose of 0.2 ml per mouse, and the cells were implanted. The tumor diameter of the mice was measured by calipers, and the tumor volume was defined as (major axis)×(minor axis)×(minor axis)× (1/2). Measurement of the tumor diameter was performed by an individual unaware of the contents of the drug solution administered to each mouse. The tumor diameters and body weights of 83 of the above hIL6R-tgm were measured on the 10th day after cell transplantation. Based on this value, randomization of the mice was performed, and the mice were divided into four groups of 10 animals, each group receiving tail-vein administration of the respective antibody solution from four out of the solutions of antibodies shown in Table 67, except H0052-mFa55/L1083-ml0. The dosage (mL) of the antibody solution administered was calculated as (0.01 (mL/g))× (body weight (g) of each mouse).

Subsequently, the tumor diameters and body weights of hIL6R-tgm grouped above were measured in the same manner on the 13th, 17th, and 20th day post-transplantation. On the 17th day after transplantation, solutions of four antibodies among the antibodies shown in Table 67, excluding H0052-mFa55/L1083-ml0, were administered to the corresponding groups via tail vein at the dosage defined by the same calculation formula described above based on the measured body weight data. The mean tumor volume in each antibody treatment group on each day of measurement was calculated, and it served as an index for evaluating the in vivo antitumor activity of each antibody.

In the above experiments, blood was collected by orbital blood sampling from hIL6R-tgm divided into the above groups under isoflurane anesthesia one hour, 1, 2, 3 and 7 days after the initial administration of the antibody solutions. The collected blood was transferred to a series of eight tubes per individual number and left to stand on ice. After centrifugation of the series of eight tubes at 1900× g for 10 minutes at 4° C., the supernatant after centrifugation was obtained as a plasma component, and transferred to another series of eight tubes per individual number and stored at −30° C.

Concentration of each antibody in plasma was measured by the electrochemiluminescence (ECL) method. The hIL6R solution was added to MULTI-ARRAY PR Plate (Meso Scale Diagnostics, LLCs), left to stand at 37° C. for one hour, and hIL6R was immobilized to the plate. For the calibration curve, MRAH-mFa55/MRAL-mk0 and H0041-mFa55/L1088-ml0 were prepared at plasma concentrations of 8, 4, 2, 1, 0.5, 0.25, and 0.125 μg/mL; and H0002-mFa55/L1058-ml0 was prepared at plasma concentrations of 64, 32, 16, 8, 4, 2, and 1 μg/mL. After addition of 1 M Tris-HCl solution, pH 8.0, containing 0.05% Tween20 and 1% BSA to the hIL6R-immobilized plate, plasma samples diluted 250 fold in 0.3 M acetic acid solution, as well as calibration curve samples were added quickly, and an ATP solution was further added and mixed. After the plate was left to stand for one hour at room temperature, a biotin-labeled anti-mouse IgG antibody (Southern Biotechnology Associates, Inc) was added, and left to stand at room temperature for one hour. Subsequently, Streptavidin SULFO-TAG Labeled (Meso Scale Diagnostics, LLC) was added, and the plate was left to stand at room temperature for one hour, followed by addition of Read buffer T (Meso Scale Diagnostics, LLC), and the reaction was measured with SECTOR Imager 6000 (Meso Scale Diagnostics, LLC). SOFTmax PRO (Molecular Devices) was used to calculate the antibody levels in mouse plasma.

Similarly, an anti-asialo GM1 antibody (Wako Pure Chemical Industries) was dissolved in 1 mL of distilled water (Otsuka Pharmaceutical Factory) and then diluted with 4 mL of PBS. The anti-asialo GM1 antibody prepared this way was administered intraperitoneally to 91 hIL6R-tgm at a dose of 0.1 mL per mouse. One day later, a mixed solution was prepared in which the same volume of Matrigel Matrix (Corning) was added to a cell suspension of hIL6R-Hepa1-6 suspended to 1×10$^8$/mL in Hanks' Balanced Salt solution (Sigma). The mixed solution was injected subcutaneously into 91 hIL6R-tgm at a dose of 0.2 ml per mouse, and the cells were implanted. The tumor diameter of the mice was measured by calipers, and the tumor volume was defined as (major axis)×(minor axis)× (minor axis)×(1/2). Measurement of the tumor diameter was performed by an individual unaware of the contents of the drug solution administered to each mouse. The tumor diameters and body weights of 91 of the above hIL6R-tgm were measured on the 10th day after cell transplantation. Based on this value, randomization of the mice was performed, and the mice were divided into four groups of 6 animals, each group receiving tail-vein administration of the respective antibody solution from four out of the solutions of antibodies shown in Table 67, except H0002-mFa55/L1058-ml0. The dosage (mL) of the antibody solution administered was calculated as (0.01 (mL/g))×(body weight (g) of each mouse). Subsequently, the tumor diameters and body weights of hIL6R-tgm grouped above were measured in the same manner on the 13th, 17th, and 20th day post-transplantation. On the 17th day after transplantation, four antibody solutions among the solutions of antibodies shown in Table 67, excluding H0002-mFa55/L1058-ml0, were administered to the corresponding groups via tail vein at the dosage defined by the same calculation formula described above based on the measured body weight data. The mean tumor volume in each antibody treatment group on each day of measurement was calculated, and it served as an index for evaluating the in vivo antitumor activity of each antibody.

In the above experiments, blood was collected by orbital blood sampling from hIL6R-tgm divided into the above groups under isoflurane anesthesia one hour, 3, and 7 days after the initial administration of the antibody solutions. The collected blood was transferred to a series of eight tubes per individual number and left to stand on ice. After centrifugation of the series of eight tubes at 1900× g for 10 minutes at 4° C., the supernatant after centrifugation was obtained as a plasma component, and transferred to another series of eight tubes per individual number and stored at −30° C.

Concentration of each antibody in plasma was measured by the electrochemiluminescence (ECL) method. The hIL6R solution was added to MULTI-ARRAY PR Plate (Meso Scale Diagnostics, LLCs), left to stand at 37° C. for one hour, and hIL6R was immobilized to the plate. For the calibration curve, MRAH-mFa55/MRAL-mk0, H0041-mFa55/L1088-ml0, and H0052-mFa55/L1083-ml0 were prepared at plasma concentrations of 8, 4, 2, 1, 0.5, 0.25, and 0.125 μg/mL. After addition of 1 M Tris-HCl solution, pH 8.0, containing 0.05% Tween20 and 1% BSA to the hIL6R-immobilized plate, plasma samples diluted 250 fold in 0.3 M acetic acid solution, as well as calibration curve samples were added quickly, and an ATP solution was further added and mixed. After the plate was left to stand for one hour at room temperature, a biotin-labeled anti-mouse IgG antibody (Southern Biotechnology Associates, Inc) was added and left to stand at room temperature for one hour. Subsequently, Streptavidin SULFO-TAG Labeled (Meso Scale Diagnostics, LLC) was added, and the plate was left to stand at room temperature for one hour, followed by addition of Read buffer T (Meso Scale Diagnostics, LLC), and the reaction was measured with SECTOR Imager 6000 (Meso Scale Diagnostics, LLC). SOFTmax PRO (Molecular Devices) was used to calculate the antibody levels in mouse plasma.

The soluble antigen concentration in plasma was measured by ECL. Murine plasma samples diluted 50 fold were mixed with a SULFO-TAG (Meso Scale Diagnostics, LLC)-labeled anti-human IL6R antibody (R&D Systems), a biotin-labeled anti-human IL6R antibody (R&D Systems), and excessive anti-human IL6R antibody tocilizumab (in-house manufactured product), and the mixture was incubated overnight at 37° C. After the mixture was added to the blocked Streptavidin-coated standard 96-well plate (Meso Scale Diagnostics, LLC), followed by addition of Read buffer, the reaction was measured on SECTOR Imager 6000 (Meso Scale Diagnostics, LLC). SOFTmax PRO (Molecular Devices) was used to calculate concentrations of the soluble antigen in murine plasma.

First, the antitumor effects, plasma antibody concentrations, and plasma antigen concentrations of IC17HdK-mFa55/IC17L-mk1, MRAH-mFa55/MRAL-mk0, H0002-mFa55/L1058-ml0, and H0041-mFa55/L1088-ml0 were compared. The results are shown in FIGS. 72, 73, and 74, respectively.

In this study, compared with the group receiving the isotype control IC17HdK-mFa55/IC17L-mk1, the groups receiving MRAH-mFa55/MRAL-mk0 and H0002-mFa55/L1058-ml0 did not show greater rates of tumor growth inhibition (TGI). On the other hand, greater TGI was observed in the group receiving the switch antibody H0041-mFa55/L1088-ml0 (FIG. 72). A weaker drug efficacy was observed in the group of mice receiving MRAH-mFa55/MRAL-mk0 compared with that of H0041-mFa55/L1088-ml0, suggesting that MRAH-mFa55/MRAL-mk0 was cleared faster than H0041-mFa55/L1088-ml0 and it was unable to maintain a concentration sufficient for demonstrating drug efficacy (FIG. 73).

Also, accumulation of soluble hIL6R was not observed in the H0002-mFa55/L1058-ml0-treated group. In the H0041-mFa55/L1083-ml0-treated group, accumulation of soluble IL6R occurred at fewer amount than that in the MRAH-mFa55/MRAL-mk0 treated group (FIG. 74).

Next, the antitumor effects, plasma antibody concentrations, and plasma antigen concentrations of IC17HdK-mFa55/IC17L-mk1, MRAH-mFa55/MRAL-mk0, H0041-mFa55/L1088-ml0, and H0052-mFa55/L1083-ml0 were compared. The results are shown in FIGS. 75, 76, and 77, respectively.

In this study, compared with the group receiving the isotype control IC17HdK-mFa55/IC17L-mk1, the groups receiving MRAH-mFa55/MRAL-mk0, H0041-mFa55/L1088-ml0, and H0052-mFa55/L1083-ml0 showed greater rates of tumor growth inhibition (TGI) (FIG. 75). On the other hand, in comparison of their plasma concentrations, MRAH-mFa55/MRAL-mk0 showed a faster elimination than H0052-mFa55/L1083-ml0, and a lower blood concentration was observed (FIG. 76).

Also, compared to MRAH-mFa55/MRAL-mk0, H0052-mFa55/L1083-ml0 only accumulated fewer soluble IL6R (FIG. 77).

These results suggest that in the tumor-bearing mice, switch antibodies have similar or stronger antitumor effects than non-switch antibodies; however, unlike non-switch antibodies, switch antibodies do not bind to hIL6R in normal tissues. The results suggest that even if cancer was present, extracellular ATP concentrations in normal tissues and blood are not elevated enough to stimulate binding of switch antibodies.

Example 16: ATP-Dependent Neutralizing Activity of Anti-PD1 Antibodies Having ATP-Dependent Binding Properties The heavy chains and light chains were combined as shown in Table 68 to express and purify anti-PD-1 antibodies by methods known to those skilled in the art.

Combinations of heavy chains and light chains of antibodies

TABLE 68

| Antibody name | VH | CH | VL | CL |
|---|---|---|---|---|
| mPD1F2VH-mF18/ mPD1F2VL-mkl | mPD1F2VH SEQ ID NO: 201 | mF18 SEQ ID NO: 203 | mPD1F2VL SEQ ID NO: 202 | mkl SEQ ID NO: 185 |
| H5029-mFa31/ L3021-ml0 | H5029 SEQ ID NO: 204 | mFa31 SEQ ID NO: 208 | L3021 SEQ ID NO: 205 | ml0 SEQ ID NO: 212 |
| H5041-mFa31/ | H5041 | | L3023 | |

TABLE 68-continued

| Antibody name | VH | CH | VL | CL |
|---|---|---|---|---|
| L3023-ml0 | SEQ ID NO: 206 | | SEQ ID NO: 207 | |

The neutralizing activity of the antibodies described in Table 68 for the PDL1-PD1 interaction was evaluated according to the methods below.

Initially, for antigens, mPD1-G1CH2 (SEQ ID NO: 209) and mPDL1-G1dCH2His (SEQ ID NO: 210) were genetically synthesized and inserted into plasmids for animal expression. Antigenic proteins were expressed and purified using the methods below. The prepared plasmids were introduced by the lipofection method into the human fetal kidney cell-derived FreeStyle 293-F line (Invitrogen) suspended in the FreeStyle 293 Expression Medium (Invitrogen) at an appropriate density and seeded in flasks. Antigens were purified from culture supernatants of cells cultured in a $CO_2$ incubator (37° C., 8% $CO_2$, 125 rpm) for four days in a manner known to those skilled in the art. Spectrophotometers were used to measure the absorbance at 280 nm of the purified antigen solutions. Concentrations of the purified antigens were calculated using absorption coefficients calculated by the PACE method from the measured values obtained (Protein Science (1995) 4, 2411-2423).

mPD1-G1CH2 (SEQ ID NO: 209), which is Fc-fused murine PD1, was diluted to 5 µg/mL (55 nM) with 0.1 M $NaHCO_3$, 0.05% $NaN_3$, and 100 µL of the diluted solution was added to a 96-well plate, left to stand overnight at 4° C., and immobilized on the plate surfaces. After the wells were washed three times with TBS and 0.1% Tween20, 250 µL of the BSA solution diluted to 2% with TBS was added to each well to block the plate surfaces. The wash was then performed three times. mPDL1-G1dCH2His (SEQ ID NO: 210), which is mouse PDL1 fused with an antibody Fc and a His tag, diluted in TBS to a final concentration of 55 nM; a solution of the antibodies described in Table 68 diluted to final concentrations of 6.25, 1.56, 0.390, 0.0977, 0.0061, and 0 µg/mL; and an ATP solution diluted to final concentrations of 0, 1, 10, and 100 µM were mixed to a total of 100 µL. The mixture was then added to each well and left to stand at 37° C. for one hour. Each well was then washed three times with 0.1% Tween20 and TBS, which had been prepared to contain the same ATP concentration as the ATP concentration of the solutions added to each well. Anti-His-tag mAb-HRP-Direct (MBL Life Science) was diluted 10,000 fold in blocking buffer to contain the same ATP concentration as the ATP concentration of the solutions added to each well, of which 100 µL was added to each well, and it was left to stand at 37° C. for one hour. Each well was then washed three times with 0.1% Tween20 and TBS, which had been prepared to contain the same ATP concentration as the ATP concentration of the solutions added to each well. Then, 100 µL of the TMB solution was added to each well, and the plate was left to stand at 37° C. for one hour, and 50 µL of 1M $H_2SO_4$ was added to each well to stop the reaction. The absorbance of each well at 450 nm was then detected on an absorbance microplate reader (Wako Sunrise).

The absorbance value of the antibody-free well under the same ATP concentration conditions was set as 100% of PD1-PDL1 binding, and the extent to which the rate of binding was reduced by antibody addition was evaluated. The results are shown in FIGS. 78 and 79.

The results showed that the neutralizing activity of mPD1F2VH-mF18/mPD1F2VL-mkl on the interaction of PD1/PDL-1 was not affected by ATP concentrations, whereas the neutralizing activities of H5029-mFa31/L3021-ml0 and H5041-mFa31/L3021-ml0 became stronger with a higher ATP concentration in the assays. The results confirmed that H5029-mFa31/L3021-ml0 and H5041-mFa31/L3021-ml0 have ATP-dependent binding activities and neutralizing activities.

A luciferase assay system (Promega) was used for measurement of the in vitro neutralizing activity. For the effector cell, hPDL1-CHO accessory to the PD-1/PD-L1 Blockade Bioassay, Core Kit (Promega) was used. For the target cell, the Jurkat-NFAT-Luc2-mPD1 cells produced in-house were used. First, the gene of the fusion protein of extracellular mPD1 and intracellular hPD1 (SEQ ID NO: 214) was introduced into Jurkat-NFAT-Luc2 cells (Promega) in a manner known to those skilled in the art to produce Jurkat-NFAT-Luc2-mPD1 cells. The interaction of hPDL1 on hPDL1-CHO with the fusion protein of extracellular mPD1 and intracellular hPD1 on Jurkat-NFAT-Luc2-mPD1 was used as the PD-1/PDL-1 interaction for assessment of the in vitro neutralizing activity.

To each well of a 96-well plate was added 100 µL of the kit accessory hPDL1-CHO, which was prepared to a concentration of $4 \times 10^5$/mL with the medium, and the plate was left to stand overnight at 37° C. For the culture medium, 90% Ham's F-12, 10% FBS, 250 µg Geneticin, and 200 µg Hygromycin was used. Supernatants from each well were aspirated; and 20 µL of a solution of the antibodies described in Table 68 diluted with the assay buffer to a final concentration of 7.5 µg/mL was mixed with 20 µL of an AMP solution diluted with assay buffer to final concentrations of 0, 1, 10, and 100 µM, and 40 µL of the NFAT-Luc2-hPD1-mPD1-Jurkat cell solution prepared with the assay buffer to achieve a cell number of $5 \times 10^4$/well. The mixture was added to each well and left to stand at 37° C. for four hours. For the assay buffer, 98% RPMI 1640 and 2% FBS was used. The plates were then left to stand at room temperature for 10 minutes, and 80 µL of the Bio-Glo reagent was added to each well. The Bio-glo Luciferase Assay System (Buffer and Substrate) was used for the Bio-Glo reagent. Luminescence of each well was then measured with a plate reader.

The value of the luminescence of each well under each AMP concentration condition divided by the value of the luminescence of the antibody-free well was the fold of induction, and it served as an index for evaluating the activity of each antibody to neutralize the PD-1/PDL-1 interaction. The results are shown in FIG. 80. In the figure, fold of induction is denoted as relative light unit (RLU).

ATP was also tested in the same manner as AMP, and 100 ml of hPDL1-CHO prepared at a concentration of $4 \times 10^5$/mL with the medium was added to each well of a 96-well plate, and the plate was left at 37° C. overnight. 90% Ham's F-12, 10% FBS, 250 µg Geneticin, and 200 µg Hygromycin was used for the culture medium. Supernatants from each well were aspirated; and 20 µL of the solution of antibodies described in Table 68 diluted with the assay buffer to a final concentration of 10 µg/mL was mixed with 20 µL of an ATP solution diluted with the assay buffer to final concentrations of 0, 12.5, and 125 µM, and 40 µL of the NFAT-Luc2-hPD1-mPD1-Jurkat cell solution prepared with the assay buffer to achieve a cell number of $5 \times 10^4$/well, and mixture was added to each well and left to stand at 37° C. for four hours. For the assay buffer, 98% RPMI 1640, 2% FBS was used. The plates were then left at room temperature for 10 minutes, and 80 µL of the Bio-Glo reagent was added to each well. The Bio-glo Luciferase Assay System (Buffer and Substrate) was used for the Bio-Glo reagent. Luminescence of each well was then measured with a plate reader.

The value of the luminescence of each well under each AMP concentration condition divided by the value of the luminescence of the antibody-free well was the fold of induction, and it served as an index for evaluating the activity of each antibody to neutralize the PD-1/PDL-1 interaction. These results are shown in FIG. 81. In the figure, fold of induction is denoted as relative light unit (RLU).

Example 17: ATP-Dependent ADCC-Mediated Antitumor Activity of Anti-PD1 Antibodies Having ATP-Dependent Binding Properties The heavy chains and light chains were combined as shown in Table 69 to express and purify anti-PD-1 antibodies in a manner known to those skilled in the art.

Combinations of heavy chains and light chains of antibodies

TABLE 69

| Antibody name | VH | CH | VL | CL |
| --- | --- | --- | --- | --- |
| IC17HdK-mFa55/<br>IC17L-mk1 | IC17HdK<br>SEQ ID NO: 187 | mFa55<br>SEQ ID<br>NO: 184 | IC17L<br>SEQ ID NO:<br>188 | mk1<br>SEQ ID NO:<br>185 |
| mPD1F2VH-<br>mFa55/<br>mPD1F2VL-mk1 | mPD1F2VH<br>SEQ ID NO: 201 | | mPD1F2VL<br>SEQ ID NO:<br>202 | |
| H5041-mFa55/<br>L3023-ml0 | H5041<br>SEQ ID NO: 206 | | L3023<br>SEQ ID NO:<br>207 | ml0<br>SEQ ID NO:<br>212 |

The heavy-chain constant regions of these antibodies were modified to mFa55 which has enhanced ADCC activity through addition of FcγRIV binding-enhancing modifications to mIgG2a. Therefore, it is considered possible to exert the ADCC activity on PD-1-expressing cells and remove the PD-1-expressing cells. The antibodies were used to evaluate the in vivo antitumor activity and to assess the elimination of PD-1-expressing cells according to the methods below.

The murine colorectal cancer line Colon38 (NCI) was implanted at $5 \times 10^6$ with Matrigel (Corning) subcutaneously in the right abdomen of C57BL/6J mice (Japan Charles River) to form solid tumors. On the fourteenth day after implantation, IC17HdK-mFa55/IC17L-mk1 was administered intravenously (i.v.) at 15 mg/kg, mPD1F2VH-mFa55/mPD1F2VL-mk1 at 1.5, 5, and 15 mg/kg, and H5041-mFa55/L3023-ml0 at 25.5 and 100 mg/kg, respectively (n=7 per group). In addition, on the 17th day post-transplantation, the H5041-mFa55/L3023-ml0 group received the same antibodies intravenously (i.v.) at 25.5 and 100 mg/kg, respectively. As a result, an anti-tumor effect was observed in all antibody administration groups except the negative control group (FIG. 82).

The elimination of PD1-expressing cells in tumor tissue after administration of the respective antibodies was assessed using flow cytometry. Solid tumors of Colon38 were allowed to form as described above, and on the 14th day after implantation, IC17HdK-mFa55/IC17L-mk1 (isotype control) was administered intravenously (i.v.) at 15 mg/kg, mPD1F2VH-mFa55/mPD1F2VL-mk1 at 1.5, 5, and 15 mg/kg, and H5041-mFa55/L3023-ml0 at 25.5 and 100 mg/kg, respectively (n=3 per group). Spleen and tumor tissues of each mouse were collected three days after antibody administration. The spleens were minced using tweezers, 10% FBS-supplemented RPMI 1640 was added, and centrifuged at 400×g for 5 minutes, after which the supernatant was removed. 2 mL of ACK Lysing Buffer (Thermo Fisher Scientific) was added, and after it was left to stand at room temperature for 2.5 minutes, the hemolyzed sample was used as spleen cells for flow cytometry analysis. The tumor tissue was minced using scissors followed by addition of enzymes according to the Tumor Dissociation Kit (Miltenyi) protocol, and further minced by the gentle MACS Dissociator (Miltenyi Biotec). With the addition of 10% FBS-supplemented RPMI-1640, it was centrifuged at 400×g for 5 minutes, and the supernatant was removed and used for flow cytometry analysis as tumor cells. Spleen cells and tumor cells were transferred to V bottom plate (Corning), centrifuged at 400×g for 5 minutes, and the supernatant was removed. Cells were resuspended in 100 μL of the FcR blocking reagent (Miltenyi Biotec) diluted 10 fold in PBS (FACS buffer) containing 1% FBS and 2 mM EDTA (Sigma). After incubation of the cells at room temperature for 10 minutes, 0.4 μL of BUV737 Anti-Mouse CD3e (BD), 0.1 μL of Zombie Aqua (Biolegend), 0.4 μL of PerCP/Cy5.5 Anti-Mouse CD8a (Biolegend), 0.4 μL of PE/Cy7 Anti-Mouse CD4 (Biolegend), 0.2 μL of APC-R700 Anti-mouse CD45 (BD), 0.4 μL of FITC anti-human/mouse/rat CD278 (Biolegend), 0.4 μL of APC/Fire™ 750 anti-mouse CD25 (Biolegend), and 0.4 μL of APC anti-mouse CD279 (Biolegend), which has already been confirmed not to compete with each of the administered PD1 antibodies, were added to each well, and FACS Buffer was added at 20 4/well. After 30 minutes of incubation at 4° C., 100 μL of the FACS buffer was added, centrifuged at 400×g for 5 minutes, and the supernatant was removed. Based on the protocol in the Foxp3/Transcription Factor Staining Buffer Set (eBioscience), the Fixation/Permeabilization Concentrate and Fixation/Permeabilization Diluent were mixed, and 200 μL of the mixture was added to each well. After incubation at 4° C. for 30 minutes and centrifugation at 400×g for 5 minutes, the supernatant was removed. Permeabilization buffer was added at 200 μL, and after centrifugation at 400×g for 5 minutes, the supernatant was removed. This washing procedure was performed once more. eFluor450 Anti-Mouse/Rat Foxp3 (eBioscience) at 0.4 μL and PE Anti-Mouse CD152 (BD) at 0.4 μL were added to each well, and the FACS Buffer was added at 20 4/well. After incubation at 4° C. for 30 minutes, 100 μL of the FACS buffer was added and after centrifugation at 400×g for 5 minutes, the supernatant was removed. Permeabilization buffer was added to each well at 200 μL, and after centrifugation at 400×g for 5 minutes, the supernatant was removed. Samples were resuspended with 200 μL of the FACS buffer, and measured on the FACS Fortessa flow cytometer (BD). For the expression analysis, the FlowJo software was used. CD4-positive cells were gated on the population of cells to be analyzed to analyze the expression of Foxp3 and PD1. The level of PD1 expression in the population of CD4⁺ Foxp3⁻ cells was calculated from the fluorescence intensity. As a result, the PD1 expression level in both spleen cells and tumor cells tended to be decreased in the groups administered with 5 and 15 mg/kg of mPD1F2VH-mFa55/mPD1F2VL-mk1, but in the groups administered with 25.5 and 100 mg/kg of H5041-mFa55/L3023-ml0, the PD1 expression level tended to be decreased only in tumor cells (FIGS. 83A and B). It was confirmed that all of the switch antibodies that bind to PD1 in an ATP-dependent manner exhibited drug efficacy against the tumor, while the systemic response (reduction in the PD1 expression level) did not occur, and it was confirmed that the switch antibodies had the property of showing specific activity at the tumor site.

Example 18: Crystal Structure Analysis of hIL6R-Binding Antibodies Having ATP-Dependent Binding Properties X-ray crystallographic analysis of the complex of ATP, hIL6R extracellular domain (shIL6R), and the Fab fragment of human IL6 receptor (hIL6R)-binding antibody H0041L1088 (an ATP switch) obtained in Example 13 was performed.

(18-1) Preparation of H0041L1088 Full-Length Antibodies

Preparation and purification of H0041L1088 full-length antibodies (VH: SEQ ID NO: 194; CH: SEQ ID NO: 217, VL: SEQ ID NO: 195, CL: SEQ ID NO: 189) having the human IgG1 format were performed by methods known to those skilled in the art.

(18-2) Preparation of H0041L1088 Fab Fragments.

The H0041L1088 full-length antibody sample was fragmented into Fab and Fc using Papain (SIGMA-ALDRICH, 10108014001) under conditions of 35° C., about 18 hours, and then subjected to column purification on HiTrap SP HP 1 mL (GE Healthcare) and HiTrap MabSelect SuRe 1 mL (GE Healthcare) and SEC purification by HiLoad 16/600 Superdex 200 pg (GE Healthcare) to prepare Fab samples.

(18-3) Preparation of shIL6R

Based on the amino acid sequence of UniProtKB: P08887 (IL6RA HUMAN) (SEQ ID NO: 213), its domains 2 and 3 (amino acids 111-320) were genetically synthesized and incorporated into expression vectors. For gene synthesis, a signal sequence for secretion expression was added at the N terminus, a FLAG tag+His×8 tag was added at the C-terminus for purification, and the C193S modification was introduced to address the imperfection of Cys-Cys pairs which results from the removal of domain 1. Protein expression by the Expi293™ Expression System (Thermo Fisher Scientific) was performed in the presence of Kifunensine (Santa Cruz Biotechnology) by using the obtained expression plasmids, and an expression culture supernatant containing the protein of interest was obtained. From this, a shIL6R sample was prepared through affinity purification by cOmplete™ His-Tag Purification Column 5 mL (SIGMA-ALDRICH) as well as SEC purification by HiLoad 16/600 Superdex 200 pg (GE Healthcare).

(18-4) Preparation of the H0041L1088 Fab-shIL6R-ATP Ternary Complex

The shIL6R sample was added with Endoglycosidase F1 (EndoF1) for N-type sugar chain cleavage and Enterokinase (SIGMA-ALDRICH, 11334115001) for His×8 tag cleavage, and after it was left to stand at room temperature for one day, through-treatment by HisTrap EXCEL 1 mL (GE Healthcare) and SEC purification by Superdex 200 Increase 10/300

GL (GE Healthcare) was carried out. Following addition of the H0041L1088 Fab sample, the resulting purified fraction was enriched by ultrafiltration, and SEC purification by Superdex 200 Increase 10/300 GL (GE Healthcare) using 20 mM HEPES, pH 7.3, 100 mM NaCl, 0.5 mM ATP as buffer to prepare the complex (Complex) samples. The complex samples for crystallization were prepared by ultrafiltration enrichment of the obtained purified fractions.

(18-5) Preparation of H0041L1088 Fab-shIL6R-ATP Ternary Complex Crystals

Crystallization by the sitting drop vapor diffusion method was performed under the 21° C. condition using complex samples for crystallization, and with reservoir conditions of 60 mM Tris, pH 7.5, 12.0% w/v polyethylene glycol 1500 (Polyethylene glycol 1,500), 60 mM ammonium sulfate (Ammonium sulfate), crystals suitable for X-ray crystallographic analysis were obtained.

(18-6) Measurement of X-Ray Diffraction Data from the H0041L1088 Fab-shIL6R-ATP Ternary Complex Crystals and Determination of Crystal Structures The resulting crystals were immersed in a solution of 68 mM Tris, pH 7.5, 13.6% w/v polyethylene glycol 1500 (Polyethylene glycol 1,500), 68 mM ammonium sulfate (Ammonium sulfate), 14.6% ethylene glycol (Ethylen Glycol), and 0.375 mM ATP, and then frozen in liquid nitrogen. The X-ray diffractometry data were measured in the radiation light facility of High Energy Accelerator Research Organization, Photon Factory BL-17A. During measurement, the crystals were constantly placed under a nitrogen flow of −178° C. to maintain a frozen state. The resulting diffracted images were processed using autoPROC (Acta Cryst. D 67:293-302 (2011)), and diffraction-intensity data up to 2.76 Angstrom resolution were acquired.

Using the obtained X-ray diffraction-intensity data, the initial structure was determined by the molecular replacement method using Phaser (J. Appl. Cryst. (2007) 40, 658-674), using the crystal structures of a known Fab and shIL6R of PDB ID=1N26 as search models. Subsequently, model building and refinement by coot (Acta Cryst. D 66: 486-501 (2010)) and refmac5 (Acta Cryst. D 67: 355-367 (2011)) as well as phenix.refine (Acta Cryst. D 68: 352-367 (2012)) were repeated, resulting in the final refined coordinates. The crystallographic statistics are shown in Table 70. Note that among the coordinates of the crystal structure, the residue numbers of the amino acids in Fab were given based on the Kabat numbering scheme, and the residue numbers of the amino acids in the antigen, shIL6R, were given to match the residue numbers of the amino acids of UniProtKB: P08887 (IL6RA HUMAN). Although there are two complexes in the asymmetric units of this crystal, specialized dimerization called domain swapping was observed in domain 2 of shIL6R. Such dimers are not found in the crystal structures of shIL6R of PDB ID=1N26, making them unique to the shIL6R constructs used here.

TABLE 70

| <Data Measurement> | |
| --- | --- |
| Measurement wavelength (Angstrom) | 0.98 |
| Number of crystals measured | 1 |
| Space group | C222 |
| Cell constant | |
| a b c (Angstrom) | 103.043 185.612 152.085 |
| α β γ (°) | 90.00 90.00 90.00 |
| Number of complexes in asymmetric unit | 2 |
| Resolution (Angstrom) | 90.09-2.757 (2.86-2.76) |

TABLE 70-continued

| <Data Measurement> | |
| --- | --- |
| Number of observed reflections/ Number of unique reflections | 508114/38008 |
| Redundancy | 13.37 (13.66) |
| Completeness (%) | 99.99 (100.00) |
| Diffraction intensity S/N ratio | 18.9 (3.1) |
| Rmerge | 0.106 (0.868) |
| <Refinement> | |
| Rwork/Rfree | 0.1923/0.2656 |
| Number of atoms | 9244 |
| Other than water molecules | 9181 |
| Water molecules | 63 |
| RMSD (root-mean-square deviation) from theoretical value | |
| Bond distance (Angstrom) | 0.008 |
| Bond angle (°) | 1.05 |
| Ramachandran plot | |
| Preferred region (%) | 95.95 |
| Allowed region (%) | 3.72 |
| Disallowed region (%) | 0.34 |

The values in parentheses are the values at the outermost resolution.

(18-7) Interaction Between H0041L1088 and ATP

As shown in FIG. 84, ATP is recognized primarily by the heavy chain of the antibody. Specifically, the adenine ring moiety of ATP is recognized by each side chain of the antibody heavy-chain CDR1: T33, CDR3: Y95, L98, N100B, and W100C, and each main chain of G96, L100A, and W100C. In particular, hydrogen bonds are formed between the carbonyl oxygen of the backbone of G96 and L100A and the position-6 $NH_2$ of ATP, and between the backbone amide NH group of W100C and the position-1 N of ATP; and interactions such as CH-pi ($\pi$) and $\pi$-$\pi$ are formed between the side chains of Y95, L98, and W100C and the adenine ring moiety. The antibody robustly recognizes the adenine ring moiety of ATP. The ribose moiety is recognized by van der Waals interactions with the respective side chains of heavy chain CDR1: T33 and CDR2: H56 and Y58. The triphosphoric group moiety is recognized by the side chains of the heavy-chain CDR2: S52, S52A, Y55, and H56, and the main chain of S52A and Q53. In particular, the S52 side chain and S52A side chain, as well as the main-chain NH group and the Q53 main-chain NH group form a tight hydrogen-bonding network with the triphosphoric group moiety, which play crucial roles in recognizing the triphosphoric group moiety.

(18-8) Interaction Between H0041L1088 and hIL6R

Based on the present crystal structure, amino acid residues of shIL6R containing one or more non-hydrogen atoms located at distances within 4.2 Angstrom from either H0041L1088 Fab or ATP were selected as epitope residues, and they are shown on the shIL6R amino acid sequence (FIG. 85). Details of the interactions of these epitope residues with the antibody are shown in FIGS. 86 and 87. These epitope residues form van der Waals interactions, hydrogen bonding, electrostatic interactions, etc. with the residues of light-chain CDR1: D27B, G28, D29, A31, and Y32, and CDR3: R91, S92, P93, G94, and P95, and heavy-chain CDR2: H56 and Y58 and CDR3: L98, Y99, N100B, and W100C of the antibody; and they are tightly bound to the antibody.

(18-9) ATP-Dependent Antigen-Binding Mechanism

In addition, in the H0041L1088 Fab-shIL6R binding as shown in FIGS. 86 and 87, a large intermolecular contact is formed between F298 of shIL6R and ATP which binds to H0041L1088 Fab. Since this interaction is lost in the ATP-unbound state, this direct interaction between the antigen and ATP which binds to H0041L1088 Fab is presumed to be a major factor in ATP-dependent binding. Structurally, ATP is thought to contribute to the structural stabilization of heavy-chain CDR3 through hydrogen bonding and van der Waals interactions with heavy-chain CDR3 residues. Stabilization of the heavy-chain CDR3 structure in its antigen-bound form by ATP binding is thought to lead to substantial strengthening of the direct interaction of heavy-chain CDR3: L98 or Y99 with shIL6R, thus contributing to ATP-dependent binding.

Example 19: Enhancement of Agonist Activity by Modified Anti-CD137 Antibodies (19-1) Preparation of Antibodies for Evaluation Regarding the case where various amino acid modifications for increasing pI were introduced to the heavy-chain constant region with increased binding activity to FcγRIIb, the effect of such amino acid modifications on CD137 agonist activity and on the plasma kinetics and drug efficacy in hCD137KI/mFcγR2bKO/hFcγR2bTg#90 mice was evaluated. Firstly, as described in Example 7-1, Example 7-2, and Example 7-3, A375-MY201aPh/B167-Lamlib, A375-SCF041aPh/B167-Lamlib, A375-SCF057aPh/B167-Lamlib, and IC17HdK-MY201aPh/IC17L-k0 were prepared.

(19-2) Assessment of the In Vitro ATP-Dependent CD137 Agonist Activity of the Modified Anti-Human CD137 Antibodies Using the 4-1BB Jurkat Reporter Gene Assay Regarding the case where various amino acid modifications for increasing pI were introduced to the heavy-chain constant region with increased binding activity to FcγRIIb, in order to assess the effect of such amino acid modifications on CD137 agonist activity, the CD137 agonist activity of A375-MY201aPh/B167-Lamlib, A375-SCF041aPh/B167-Lamlib, A375-SCF057aPh/B167-Lamlib, and IC17HdK-MY201aPh/IC17L-k0 were assessed.

The GloResponse™ NF-κB-Luc2/4-1BB Jurkat cell line (Promega, CS196004) was used for measuring the in vitro activity of the produced antibodies. To each well of a 96-well plate, 200 μL of FcγRIIB CHO-K1 Cells (Promega) prepared at a concentration of $5\times10^4$/mL with a culture medium was added, and the plate was allowed to stand overnight in a 5% $CO_2$ incubator at 37° C. CHO culture medium (90% Ham's F12, 10% FBS) was used for the culture medium. Next, all of the culture medium was removed by suction, and then 25 μL of a GloResponse™ NF-κB-Luc2/4-1BB Jurkat cell line prepared at $2\times10^6$/mL with an assay medium (99% RPMI, 1% FBS) was added to each well. Next, 25 μL of each antibody solution diluted with an assay medium was added at a final concentration of 0, 0.001, 0.01, 0.1, 1, and 10 μg/mL. Lastly, 25 μL of an ATP solution diluted with an assay medium to make a final concentration of 250 μM was added. The plate was allowed to stand for 6 hours in a 5% $CO_2$ incubator at 37° C., and then allowed to stand for 15 minutes at room temperature, and 75 μL of a Bio-Glo reagent was added to each well. The Bio-Glo Luciferase Assay System (Buffer and Substrate) was used for the Bio-Glo reagent. Thereafter, the relative light unit of each well was determined using a plate reader. The value of the luminescence of each well divided by the value of the luminescence of the well without antibody addition was defined as "relative light unit", and it served as an indicator for evaluating the CD137 agonist activity of each antibody.

The results are shown in FIG. 88. The results showed that CD137 agonist activity is increased by introducing various amino acid modifications for increasing pt.

(19-3) Pharmacokinetic Study of Modified Anti-Human CD137 Antibodies in Mouse (19-3-1) Generation of hCD137KI/mFcγR2bKO/hFcγR2bTg#90 Mouse First, a human CD137 knock-in mouse was generated in which the mouse CD137 gene was replaced with a human CD137 gene, by introducing a human CD137 gene substitution vector into mouse embryonic stem cells (ES cells) together with a Zinc Finger Nuclease (ZFN) that targets mouse CD137. Next, ZFN mRNA that targets the mouse Fcgr2b gene was microinjected to mouse fertilized eggs, and mouse Fcgr2b knock-out mice were generated by selecting those introduced with the mutation at the target site. Further, a BAC vector in which the human FCGR2B gene was cloned was microinjected to mouse fertilized eggs, and by selecting from the mice obtained therefrom those introduced with the genome region of the human FCGR2B gene, a human FCGR2B transgenic mouse was generated (Iwayanagi. et al., J Immunol, 2015, 195, 3198-3205).

By crossing mice of the above three lines, a "human CD137 knock-in Fcgr2b knock-out human FCGR2B transgenic mouse" was established. This mouse is referred to as hCD137KI/mFcγR2bKO/hFcγR2bTg#90 mouse.

(19-3-2) Measurement of Anti-Human CD137 Antibody Concentration in Plasma in the hCD137KI/mFcγR2bKO/hFcγR2bTg#90 Mouse Model The respective anti-human CD137 antibodies were administered intravenously at a single dose to the CD137KI/mFcγR2bKO/hFcγR2bTg#90 mice as shown in Table 71. Blood was collected multiple times over time from 5 minutes to 28 days after administration. The obtained blood was centrifuged to separate plasma. Plasma was stored in a freezer set below −20° C. until measurement.

TABLE 71

| Group | Number of animals | Pharmaceutical agent | Dose [mg/kg] |
|---|---|---|---|
| 1 | 3 | A375-MY201aPh/B167-Lamlib | 7.5 Single administration |
| 2 | 3 | A375-SCF041aPh/B167-Lamlib | 7.5 Single administration |

The concentration of each anti-human CD137 antibody in plasma was measured by the electrochemiluminescence (ECL) method. hCD137 (Sino Biological Inc.) was diluted with PBS(−) and added to a MULTI-ARRAY 96-well Plate (Meso Scale Diagnostics, LLC). The plate added with hCD137 was shaken for 1 hour at room temperature and hCD137 was immobilized to the plate. For blocking, a PBS solution containing 1 mM ADP, 1% BSA, and 0.05% Tween-20 was then added and the plate was shaken for 1 hour at room temperature. Calibration curves for the respective anti-human CD137 antibodies were prepared at plasma concentrations of 640, 320, 160, 80, 40, 20, and 10 ng/mL. Plasma samples diluted with a PBS solution containing 1 mM ADP, 1% BSA, and 0.05% Tween-20 and calibration curve samples were added to the hCD137-immobilized plate. The plate was then shaken for 1 hour at room temperature, and then an antibody described in WO 2019112027 which specifically recognizes the constant regions of the anti-human CD137 antibodies was added as a secondary antibody. The plate was further shaken for 1 hour at room temperature and SULFO-TAG Labeled Goat Anti- Rabbit Antibody (Meso Scale Diagnostics, LLC) was then added thereto. The plate was further shaken for 1 hour at room temperature and Read buffer T (Meso Scale Diagnostics, LLC) diluted two-fold and containing 1 mM ADP was added thereto. Concentration of each antibody in mouse plasma was measured by detecting SULFO-TAG with SECTOR Imager (Meso Scale Diagnostics, LLC). Concentration of each antibody in mouse plasma was calculated using SOFTmax PRO (Molecular Devices).

The results are shown in FIG. 89. A375-SCF041aPh/B167-Lamlib showed a faster elimination than A375-MY201aPh/B167-Lamlib. This is thought to be because the heavy-chain constant region of A375-SCF041aPh/B167-Lamlib is introduced with amino acid modifications that increase pI.

(19-4) Drug Efficacy Assessment of Modified Anti-Human CD137 Antibodies in Mouse (19-4-1) Generation of Cell Lines and a Syngeneic Tumor Line Transplanted Mouse Model As the cells, the LLC1/OVA/GPC3 clone C5 (LLC1/OVA/GPC3) cell line, produced by introducing the expression plasmids for chicken ovalbumin (OVA) and human Glypican-3 (GPC3) into the mouse lung cancer cell-derived cell line LLC1 [LL/2 (alias: LLC1), distributor: ATCC, catalog number: CRL-16421, was used. The hCD137KI/mFcγR2bKO/hFcγR2bTg#90 mouse (11 weeks old, female) described above in (19-3-1) was used as the mouse. The LLC1/OVA/GPC3 cell line was maintained and passaged in an RPMI1640 medium (Sigma-Aldrich, Co. LLC.) containing 9.8% Fetal Bovine Serum (Sigma-Aldrich, Co. LLC.), 0.44 mg/mL G418 (Nacalai Tesque, Inc.), and 0.88 mg/mL Zeocin (Thermo Fisher Scientific, Inc.). The LLC1/OVA/GPC3 cell line was transplanted subcutaneously to the abdomen of a mouse, and the model was deemed as being formed when the tumor volume reached about 250-500 mm³. After the model was formed, the LLC1/OVA/GPC3 cell line-transplanted mice were grouped and then administered with the vehicle and respective anti-human CD137 antibodies.

(19-4-2) Preparation and Administration of the Pharmaceutical Agents to be Administered and Tumor Measurement A375-MY201aPh/B167-Lamlib or A375-SCF041aPh/B167-Lamlib, prepared to the dosages shown in Table 72 with PBS containing 0.05% Tween-20, was administered to the LLC1/OVA/GPC3 cell line-transplanted model on day 11 and day 14 after tumor transplantation. PBS containing 0.05% Tween-20 was administered to the vehicle group. The prepared administration liquid was administered at a dose of 10 mL/kg through the tail vein.

Measurement of antitumor effect in LLC1/OVA/GPC3 cell line-transplanted model

TABLE 72

| Group | Number of animals | Pharmaceutical agent | Dose | Method of administration | Day of administration |
|---|---|---|---|---|---|
| 1 | 5 | PBS containing 0.05% Tween-20 | — | Tail vain | Day 11 and Day 14 after transplantation |
| 2 | 5 | A375-MY201aPh/B167-Lamlib | 2.50 mg/kg | Tail vain | Day 11 and Day 14 after transplantation |
| 3 | 5 | A375-SCF041aPh/B167-Lamlib | 2.50 mg/kg | Tail vain | Day 11 and Day 14 after transplantation |

For evaluating antitumor effect, tumor volume was measured at a frequency of 1 to 2 times per week. Tumor volume was calculated by the following equation.

Tumor volume (mm³)=the length (mm)×the width (mm)×the width (mm)/2

As a result, the results of Example (19-3-2) revealed that the change in blood concentration in A375-SCF041aPh/B167-Lamlib administered mice was smaller compared to that for A375-MY201aPh/B167-Lamlib; however, A375-SCF041aPh/B167-Lamlib exhibited stronger antitumor effect than A375-MY201aPh/B167-Lamlib (FIG. 90).

Based on the above results in the present mouse model, the antitumor effect of an anti-human CD137 antibody was increased by introducing amino acid modifications that increase pI to the heavy-chain constant region.

Example 20: Enhancement of Agonist Activity by Modified Anti-Human CD3 Antibodies Increasing the agonist activity of an anti-CD3 antibody by combining amino acid modifications for increasing pI and a heavy-chain constant region with increased binding activity for FcγRIIb was examined.

SCF057aPh was used, which was produced by introducing the amino acid modification Q311R/P343R for increasing pI to MY201aPh and MY201aPh, which are heavy-chain constant regions with increased binding activity for FcγRIIb produced in Example 7-1. Further, as the constant region of native human IgG1, G1T6 (SEQ ID NO: 223) was used. Respective anti-human CD3 antibodies were produced by using TR01H113 (SEQ ID NO: 224) as the heavy chain variable region; MY201aPh, SCF057aPh, or G1T6 as the heavy-chain constant region; and L0011-k0 (SEQ ID NO: 225) as the light chain of the anti-human CD3 antibodies. IC17HdK-MY201aPh/IC17L-k0 was used as the negative control.

T cell activation Bioassay (NFAT) (Promega, CS176401) was used for measuring the in vitro activity of the produced antibodies. To each well of a 96-well plate, 200 μL of FcγRIIB CHO-K1 Cells (Promega) prepared at a concentration of 5×10⁴/mL with a culture medium was added, and the plate was allowed to stand overnight in a 5% CO₂ incubator at 37° C. CHO culture medium (90% Ham's F12, 10% FBS) was used for the culture medium. Next, all of the culture medium was removed by suction, and then 25 μL of NFAT-RE-Luc2 cells prepared at 2×10⁶/mL with an assay medium (99% RPMI, 1% FBS) was added to each well. Next, 25 μL of each antibody solution diluted with an assay medium was added at a final concentration of 0, 0.0001, 0.001, 0.01, 0.1, 1, and 10 μg/mL. The plate was allowed to stand for 6 hours in a 5% CO₂ incubator at 37° C., and then allowed to stand for 15 minutes at room temperature, and 75 μL of a Bio-Glo reagent was added to each well. The Bio-Glo Luciferase Assay System (Buffer and Substrate) was used for the Bio-Glo reagent. Thereafter, the relative light unit of each well was determined using a plate reader. The value of the luminescence of each well divided by the value of the luminescence of the well without antibody addition was defined as "relative light unit", and it served as an indicator for evaluating the CD3 agonist activity of each antibody.

The results are shown in FIG. 91. Compared with TR01H113-G1T6/L0011-k0 having the constant region of native human IgG1, TR01H113-MY201aPh/L0011-k0 which has enhanced binding to FcγRIIb showed higher CD3 agonist activity. TR01H113-SCF057aPh/L0011-k0 introduced with amino acid modifications that increase pI showed higher CD3 agonist activity compared to TR01H113-MY201aPh/L0011-k0 which is before introduction of the amino acid modifications.

INDUSTRIAL APPLICABILITY

The disclosed anti-CD137 antigen binding molecules and methods of using them are applicable to the development, manufacturing, provision, and use of pharmaceuticals that possess an immune cell-activating effect, a cytotoxic effect, or an anti-tumor effect, but have low effects on non-tumor tissues such as normal tissues and few side effects.

The invention claimed is:

1. An anti-CD137 antigen-binding molecule comprising a combination of HVR-H1, HVR-H2, HVR-H3, HVR-L1, HVR-L2, and HVR-L3 selected from (a) to (m) below:
(a) HVR-H1 comprising the amino acid sequence of SEQ ID NO: 7, HVR-H2 comprising the amino acid sequence of SEQ ID NO: 8, HVR-H3 comprising the amino acid sequence of SEQ ID NO: 17, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;
(b) HVR-H1 comprising the amino acid sequence of SEQ ID NO: 7, HVR-H2 comprising the amino acid sequence of SEQ ID NO: 9, HVR-H3 comprising the amino acid sequence of SEQ ID NO: 17, HVR-L1 comprising the amino acid sequence of SEQ ID NO: 22, HVR-L2 comprising the amino acid sequence of SEQ ID NO: 26, and HVR-L3 comprising the amino acid sequence of SEQ ID NO: 27;
(c) HVR-H1 comprising the amino acid sequence of SEQ ID NO: 7, HVR-H2 comprising the amino acid sequence of SEQ ID NO: 10, HVR-H3 comprising the amino acid sequence of SEQ ID NO: 17, HVR-L1 comprising the amino acid sequence of SEQ ID NO: 22, HVR-L2 comprising the amino acid sequence of SEQ ID NO: 26, and HVR-L3 comprising the amino acid sequence of SEQ ID NO: 27;
(d) HVR-H1 comprising the amino acid sequence of SEQ ID NO: 7, HVR-H2 comprising the amino acid sequence of SEQ ID NO: 11, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;
(e) HVR-H1 comprising the amino acid sequence of SEQ ID NO: 7, HVR-H2 comprising the amino acid sequence of SEQ ID NO: 8, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27;
(f) HVR-H1 comprising the amino acid sequence of SEQ ID NO: 7, HVR-H2 comprising the amino acid sequence of SEQ ID NO: 12, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 28;
(g) HVR-H1 comprising the amino acid sequence of SEQ ID NO: 7, HVR-H2 comprising the amino acid sequence of SEQ ID NO: 13, HVR-H3 comprising the amino acid sequence of SEQ ID NO: 18, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 29;
(h) HVR-H1 comprising the amino acid sequence of SEQ ID NO: 7, HVR-H2 comprising the amino acid sequence of SEQ ID NO: 14, HVR-H3 comprising the amino acid sequence of SEQ ID NO: 19, HVR-L1 comprising the amino acid sequence of SEQ ID NO: 23, HVR-L2 comprising the amino acid sequence of SEQ ID NO: 26, and HVR-L3 comprising the amino acid sequence of SEQ ID NO: 27;
(i) HVR-H1 comprising the amino acid sequence of SEQ ID NO: 7, HVR-H2 comprising the amino acid sequence of SEQ ID NO: 15, HVR-H3 comprising the amino acid sequence of SEQ ID NO: 20, HVR-L1 comprising the amino acid sequence of SEQ ID NO: 24, HVR-L2 comprising the amino acid sequence of SEQ ID NO: 26, and HVR-L3 comprising the amino acid sequence of SEQ ID NO: 27;
(j) HVR-H1 comprising the amino acid sequence of SEQ ID NO: 7, HVR-H2 comprising the amino acid sequence of SEQ ID NO: 15, HVR-H3 comprising the amino acid sequence of SEQ ID NO: 20, HVR-L1 comprising the amino acid sequence of SEQ ID NO: 25, HVR-L2 comprising the amino acid sequence of SEQ ID NO: 26, and HVR-L3 comprising the amino acid sequence of SEQ ID NO: 27;
(k) HVR-H1 comprising the amino acid sequence of SEQ ID NO: 7, HVR-H2 comprising the amino acid sequence of SEQ ID NO: 16, HVR-H3 comprising the amino acid sequence of SEQ ID NO: 20, HVR-L1 comprising the amino acid sequence of SEQ ID NO: 25, HVR-L2 comprising the amino acid sequence of SEQ ID NO: 26, and HVR-L3 comprising the amino acid sequence of SEQ ID NO: 27;
(l) HVR-H1 comprising the amino acid sequence of SEQ ID NO: 7, HVR-H2 comprising the amino acid sequence of SEQ ID NO: 14, HVR-H3 comprising the amino acid sequence of SEQ ID NO: 19, HVR-L1 comprising the amino acid sequence of SEQ ID NO: 24, HVR-L2 comprising the amino acid sequence of SEQ ID NO: 26, and HVR-L3 comprising the amino acid sequence of SEQ ID NO: 27; and
(m) HVR-H1 comprising the amino acid sequence of SEQ ID NO: 7, HVR-H2 comprising the amino acid sequence of SEQ ID NO: 14, HVR-H3 comprising the amino acid sequence of SEQ ID NO: 17, HVR-L1 comprising the amino acid sequence of SEQ ID NO: 21, HVR-L2 comprising the amino acid sequence of SEQ ID NO: 26, and HVR-L3 comprising the amino acid sequence of SEQ ID NO: 27.

2. The anti-CD137 antigen-binding molecule of claim 1, which comprises an altered Fc region, wherein the altered Fc region comprises any one combination of amino acid alterations selected from the following:
L235W/G236N/H268D/Q295L/K326T/A330K/P343R/D413K;
K214R/L235W/G236N/H268D/Q295L/K326T/A330K/P343R/D413K;
L234Y/P238D/T250V/V264I/T307P/A330K/P343R/D413K;
L234Y/P238D/V264I/A330K/P343R/D413K;
L234Y/G237D/P238D/T250V/T307P/A330K/P343R/D413K;
L234Y/G237D/P238D/A330K/P343R/D413K;
L235W/G236N/H268D/Q295L/K326T/A330K/Q311R/P343R;
L234Y/P238D/T250V/V264I/T307P/A330K/Q311R/P343R;
L234Y/P238D/V264I/A330K/Q311R/P343R;
L234Y/G237D/P238D/T250V/T307P/A330K/Q311R/P343R;
L234Y/G237D/P238D/A330K/Q311R/P343R;
L235W/G236N/H268D/Q295L/K326T/A330K/P343R;
K214R/L235W/G236N/H268D/Q295L/K326T/A330K/P343R;
L235W/G236N/H268D/Q295L/K326T/A330K/D413K;
K214R/G236N/H268D/A330K/P343R;
K214R/L235W/G236N/H268D/A330K/P343R;
K214R/G236N/H268D/A330K/D413K;
K214R/G236N/H268D/A330K/P343R/D413K;
K214R/L235W/G236N/H268D/A330K/P343R/D413K;
K214R/G236N/H268D/A330K/Q311R;
K214R/L235W/G236N/H268D/A330K/Q311R;
K214R/G236N/H268D/A330K/Q311R/P343R;
K214R/L235W/G236N/H268D/A330K/Q311R/P343R;
K214R/G236N/H268D/A330K/Q311R/D413K;
K214R/L235W/G236N/H268D/A330K/Q311R/D413K; and
K214R/L235W/G236N/H268D/Q295L/K326T/A330K/Q311R.

3. The anti-CD137 antigen-binding molecule of claim 1, which comprises a heavy chain constant region comprising any one of the amino acid sequences of SEQ ID NOs: 64 to 85.

4. An isolated nucleic acid encoding the anti-CD137 antigen-binding molecule of claim 1.

5. A vector comprising the nucleic acid of claim 4.

6. A host cell comprising the nucleic acid of claim 4.

7. A method for producing an anti-CD137 antigen-binding molecule, which comprises culturing a host cell comprising a nucleic acid encoding the anti-CD137 antigen-binding molecule of claim 1 such that the anti-CD137 antigen-binding molecule is produced.

8. An immunoconjugate comprising the anti-CD137 antigen-binding molecule of claim 1 and a cytotoxic agent.

9. A pharmaceutical formulation comprising the anti-CD137 antigen-binding molecule of claim 1 and a pharmaceutically acceptable carrier.

10. A method of treating an individual having a solid tumor into which CD137 expressing immune cells have infiltrated comprising administering an effective amount of the anti-CD137 antigen-binding molecule of claim 1 to the individual.

11. A method of activating immune cells in an individual comprising administering an effective amount of the anti- CD137 antigen-binding molecule of claim 1 to the individual, wherein the immune cells are B cells, dendritic cells, natural killer cells, macrophages, and/or T cells.

12. The anti-CD137 antigen-binding molecule of claim 1, which comprises a HVR-H1 comprising the amino acid sequence of SEQ ID NO: 7, HVR-H2 comprising the amino acid sequence of SEQ ID NO: 15, HVR-H3 comprising the amino acid sequence of SEQ ID NO: 20, HVR-L1 comprising the amino acid sequence of SEQ ID NO: 25, HVR-L2 comprising the amino acid sequence of SEQ ID NO: 26, and HVR-L3 comprising the amino acid sequence of SEQ ID NO: 27.

13. The anti-CD137 antigen-binding molecule of claim 1, which comprises a variable region that comprises a heavy chain variable domain (VH) and a light chain variable domain (VL) selected from (a) to (m) below:
(a) an antibody variable region that comprises a heavy chain variable domain (VH) of SEQ ID NO: 43, and a light chain variable domain (VL) of SEQ ID NO: 54;
(b) an antibody variable region that comprises a heavy chain variable domain (VH) of SEQ ID NO: 44, and a light chain variable domain (VL) of SEQ ID NO: 55;
(c) an antibody variable region that comprises a heavy chain variable domain (VH) of SEQ ID NO: 45, and a light chain variable domain (VL) of SEQ ID NO: 55;
(d) an antibody variable region that comprises a heavy chain variable domain (VH) of SEQ ID NO: 46, and a light chain variable domain (VL) of SEQ ID NO: 54;
(e) an antibody variable region that comprises a heavy chain variable domain (VH) of SEQ ID NO: 47, and a light chain variable domain (VL) of SEQ ID NO: 54;
(f) an antibody variable region that comprises a heavy chain variable domain (VH) of SEQ ID NO: 48, and a light chain variable domain (VL) of SEQ ID NO: 56;
(g) an antibody variable region that comprises a heavy chain variable domain (VH) of SEQ ID NO: 49, and a light chain variable domain (VL) of SEQ ID NO: 57;
(h) an antibody variable region that comprises a heavy chain variable domain (VH) of SEQ ID NO: 50, and a light chain variable domain (VL) of SEQ ID NO: 58;
(i) an antibody variable region that comprises a heavy chain variable domain (VH) of SEQ ID NO: 51, and a light chain variable domain (VL) of SEQ ID NO: 59;
(j) an antibody variable region that comprises a heavy chain variable domain (VH) of SEQ ID NO: 51, and a light chain variable domain (VL) of SEQ ID NO: 60;
(k) an antibody variable region that comprises a heavy chain variable domain (VH) of SEQ ID NO: 52, and a light chain variable domain (VL) of SEQ ID NO: 60;
(l) an antibody variable region that comprises a heavy chain variable domain (VH) of SEQ ID NO: 50, and a light chain variable domain (VL) of SEQ ID NO: 59; and
(m) an antibody variable region that comprises a heavy chain variable domain (VH) of SEQ ID NO: 53, and a light chain variable domain (VL) of SEQ ID NO: 54.

14. The anti-CD137 antigen-binding molecule of claim 1, which comprises an antibody variable region that comprises a heavy chain variable domain (VH) of SEQ ID NO: 51 and a light chain variable domain (VL) of SEQ ID NO: 60.

15. An antibody comprising an antibody variable region that comprises a heavy chain variable domain (VH) of SEQ ID NO: 51 and a light chain variable domain (VL) of SEQ ID NO: 60.

16. The antibody of claim 15, which comprises a VH comprising the amino acid sequence of SEQ ID NO: 51, a heavy chain constant region (CH) comprising the amino acid sequence of SEQ ID NO: 72, a VL comprising the amino acid sequence of SEQ ID NO: 60, and a light chain constant region (CL) comprising the amino acid sequence of SEQ ID NO: 63.

17. The antibody of claim 15, which comprises a VH comprising the amino acid sequence of SEQ ID NO: 51, a heavy chain constant region (CH) comprising the amino acid sequence of SEQ ID NO: 74, a VL comprising the amino acid sequence of SEQ ID NO: 60, and a light chain constant region (CL) comprising the amino acid sequence of SEQ ID NO: 63.

18. The antibody of claim 15, which comprises a VH comprising the amino acid sequence of SEQ ID NO: 51, a heavy chain constant region (CH) comprising the amino acid sequence of SEQ ID NO: 75, a VL comprising the amino acid sequence of SEQ ID NO: 60, and a light chain constant region (CL) comprising the amino acid sequence of SEQ ID NO: 63.

19. The antibody of claim 15, which comprises a VH comprising the amino acid sequence of SEQ ID NO: 51, a heavy chain constant region (CH) comprising the amino acid sequence of SEQ ID NO: 77, a VL comprising the amino acid sequence of SEQ ID NO: 60, and a light chain constant region (CL) comprising the amino acid sequence of SEQ ID NO: 63.

20. The antibody of claim 15, which comprises a VH comprising the amino acid sequence of SEQ ID NO: 51, a heavy chain constant region (CH) comprising the amino acid sequence of SEQ ID NO: 78, a VL comprising the amino acid sequence of SEQ ID NO: 60, and a light chain constant region (CL) comprising the amino acid sequence of SEQ ID NO: 63.

21. The antibody of claim 15, which comprises a VH comprising the amino acid sequence of SEQ ID NO: 51, a heavy chain constant region (CH) comprising the amino acid sequence of SEQ ID NO: 79, a VL comprising the amino acid sequence of SEQ ID NO: 60, and a light chain constant region (CL) comprising the amino acid sequence of SEQ ID NO: 63.

22. The antibody of claim 15, which comprises a VH comprising the amino acid sequence of SEQ ID NO: 51, a heavy chain constant region (CH) comprising the amino acid sequence of SEQ ID NO: 80, a VL comprising the amino acid sequence of SEQ ID NO: 60, and a light chain constant region (CL) comprising the amino acid sequence of SEQ ID NO: 63.

23. The antibody of claim 15, which comprises a VH comprising the amino acid sequence of SEQ ID NO: 51, a heavy chain constant region (CH) comprising the amino acid sequence of SEQ ID NO: 81, a VL comprising the amino acid sequence of SEQ ID NO: 60, and a light chain constant region (CL) comprising the amino acid sequence of SEQ ID NO: 63.

24. The antibody of claim 15, which comprises a VH comprising the amino acid sequence of SEQ ID NO: 51, a heavy chain constant region (CH) comprising the amino acid sequence of SEQ ID NO: 82, a VL comprising the amino acid sequence of SEQ ID NO: 60, and a light chain constant region (CL) comprising the amino acid sequence of SEQ ID NO: 63.

25. The antibody of claim 15, which comprises a VH comprising the amino acid sequence of SEQ ID NO: 51, a heavy chain constant region (CH) comprising the amino acid sequence of SEQ ID NO: 83, a VL comprising the amino acid sequence of SEQ ID NO: 60, and a light chain constant region (CL) comprising the amino acid sequence of SEQ ID NO: 63.

26. The antibody of claim 15, which comprises a VH comprising the amino acid sequence of SEQ ID NO: 51, a heavy chain constant region (CH) comprising the amino acid sequence of SEQ ID NO: 84, a VL comprising the amino acid sequence of SEQ ID NO: 60, and a light chain constant region (CL) comprising the amino acid sequence of SEQ ID NO: 63.

27. The antibody of claim 15, which comprises a VH comprising the amino acid sequence of SEQ ID NO: 51, a heavy chain constant region (CH) comprising the amino acid sequence of SEQ ID NO: 85, a VL comprising the amino acid sequence of SEQ ID NO: 60, and a light chain constant region (CL) comprising the amino acid sequence of SEQ ID NO: 63.

* * * * *